(12) United States Patent
Dequeant et al.

(10) Patent No.: US 11,857,574 B2
(45) Date of Patent: *Jan. 2, 2024

(54) GENETICALLY ENGINEERED T CELLS WITH REGNASE-1 AND/OR TGFBRII DISRUPTION HAVE IMPROVED FUNCTIONALITY AND PERSISTENCE

(71) Applicant: CRISPR Therapeutics AG, Zug (CH)

(72) Inventors: Mary-Lee Dequeant, Cambridge, MA (US); Demetrios Kalaitzidis, Cambridge, MA (US); Mohammed Ghonime, Cambridge, MA (US)

(73) Assignee: CRISPR Therapeutics AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/054,521

(22) Filed: Nov. 10, 2022

(65) Prior Publication Data

US 2023/0263828 A1 Aug. 24, 2023

Related U.S. Application Data

(63) Continuation of application No. 17/493,280, filed on Oct. 4, 2021, now Pat. No. 11,497,773, which is a continuation of application No. 17/483,100, filed on Sep. 23, 2021.

(60) Provisional application No. 63/225,673, filed on Jul. 26, 2021, provisional application No. 63/124,429, filed on Dec. 11, 2020, provisional application No. 63/082,357, filed on Sep. 23, 2020.

(51) Int. Cl.

| | | |
|---|---|---|
| *A61K 35/17* | (2015.01) | |
| *C07K 14/705* | (2006.01) | |
| *C12N 5/0783* | (2010.01) | |
| *C12N 9/22* | (2006.01) | |
| *C12N 15/01* | (2006.01) | |
| *C07K 14/725* | (2006.01) | |
| *C07K 16/28* | (2006.01) | |
| *C12N 5/16* | (2006.01) | |
| *C12N 15/113* | (2010.01) | |
| *C12N 15/86* | (2006.01) | |
| *A61K 38/00* | (2006.01) | |
| *C12N 15/11* | (2006.01) | |

(52) U.S. Cl.
CPC .......... *A61K 35/17* (2013.01); *C07K 14/7051* (2013.01); *C07K 14/70521* (2013.01); *C07K 14/70575* (2013.01); *C07K 14/70578* (2013.01); *C07K 14/70596* (2013.01); *C07K 16/2803* (2013.01); *C07K 16/2875* (2013.01); *C07K 16/2878* (2013.01); *C12N 5/0636* (2013.01); *C12N 5/16* (2013.01); *C12N 9/22* (2013.01); *C12N 15/111* (2013.01); *C12N 15/113* (2013.01); *C12N 15/86* (2013.01); *A61K 38/00* (2013.01); *C07K 2317/622* (2013.01); *C12N 2310/20* (2017.05); *C12N 2310/315* (2013.01); *C12N 2310/321* (2013.01); *C12N 2510/00* (2013.01)

(58) Field of Classification Search
CPC .............. A61K 35/17; C07K 14/70575; C07K 14/70578; C07K 14/70596; C12N 5/0636; C12N 9/22; C12N 15/111; C12N 2310/20
USPC ...................................................... 424/93.71
See application file for complete search history.

(56) References Cited

U.S. PATENT DOCUMENTS

| | | | |
|---|---|---|---|
| 10,166,255 B2 | 1/2019 | Moriarity et al. | |
| 10,729,725 B2 | 8/2020 | Terrett et al. | |
| 10,736,919 B2 | 8/2020 | Terrett et al. | |
| 10,857,184 B2 | 12/2020 | Terrett et al. | |
| 10,881,689 B2 | 1/2021 | Terrett et al. | |
| 11,071,755 B1 | 7/2021 | Terrett et al. | |
| 11,135,247 B2 | 10/2021 | Terrett et al. | |
| 11,166,985 B2 | 11/2021 | Terrett et al. | |
| 11,191,783 B2 | 12/2021 | Terrett et al. | |
| 11,608,500 B2* | 3/2023 | Benson | A61K 39/001188 |
| 2017/0211075 A1* | 7/2017 | Lee | C12N 15/52 |
| 2018/0112198 A1 | 4/2018 | Liu et al. | |
| 2019/0284553 A1 | 9/2019 | Benson et al. | |
| 2021/0139850 A1* | 5/2021 | Yu | C07K 14/70521 |

FOREIGN PATENT DOCUMENTS

| | | |
|---|---|---|
| EP | 3854877 A1 | 7/2021 |
| JP | WO 2017/002928 A1 | 4/2018 |
| WO | WO 2010/098429 A1 | 9/2010 |
| WO | WO 2014/153114 A1 | 9/2014 |

(Continued)

OTHER PUBLICATIONS

Liu et al. (2016; Cell Res. Jan. 2017; 27(1): 154-157) (Year: 2017).*
Liu et al._Supplementary Data_(2016; Cell Res. Jan. 2017; 27(1): 154-157) (Year: 2017).*
Tang et al. (JCI Insight. 2020;5(4):e133977, pp. 1-17; Published Feb. 27, 2020) (Year: 2020).*
Wei et al. (2019, Nature, vol. 576, 19/26, pp. 471-499) (Year: 2019).*

(Continued)

*Primary Examiner* — Janet L Epps-Smith
(74) *Attorney, Agent, or Firm* — McDermott Will & Emery LLP

(57) ABSTRACT

A population of genetically engineered T cells, comprising a disrupted Reg1 gene and/or a disrupted TGFBRII gene. Such genetically engineered T cells may comprise further genetic modifications, for example, a disrupted CD70 gene. The population of genetically engineered T cells exhibit one or more of (a) improved cell growth activity; (b) enhanced persistence; and (c) reduced T cell exhaustion, (d) enhanced cytotoxicity activity, (e) resistant to inhibitory effects induced by TGF-b, and (f) resistant to inhibitory effects by fibroblasts and/or inhibitory factors secreted thereby, as compared to non-engineered T cell counterparts.

21 Claims, 54 Drawing Sheets

Specification includes a Sequence Listing.

(56) References Cited

FOREIGN PATENT DOCUMENTS

| WO | WO-2014153114 A1 * | 9/2014 | ........... A61K 38/177 |
|----|----|----|----|
| WO | WO 2019/089884 A2 | 5/2019 | |
| WO | WO 2019/097305 A1 | 5/2019 | |
| WO | WO-2019089884 A2 * | 5/2019 | ......... A61K 39/0011 |
| WO | WO 2019/178421 A1 | 9/2019 | |
| WO | WO 2019/215500 A1 | 11/2019 | |
| WO | WO-2019215500 A1 * | 11/2019 | ............. A61K 35/17 |
| WO | WO 2019/235581 A1 | 12/2019 | |
| WO | WO 2020/032160 A1 | 2/2020 | |
| WO | WO 2020/095107 A1 | 5/2020 | |

OTHER PUBLICATIONS

Dempsey, Regnase-1 in the TME. Nat Immunol. Feb. 2020;21(2):103.

Eyquem et al., Targeting a CAR to the TRAC locus with CRISPR/Cas9 enhances tumour rejection. Nature. Mar. 2, 2017;543(7643):113-117. Epub Feb. 22, 2017.

Heaton et al., Frontiers in antiviral therapy and immunotherapy. Clin Transl Immunology. Feb. 19, 2020;9(2):e1115.

Liu et al., CRISPR screen in mechanism and target discovery for cancer immunotherapy. Biochim Biophys Acta Rev Cancer. Aug. 2020;1874(1):188378(1-15). Epub May 13, 2020.

Liu et al., CRISPR-Cas9-mediated multiplex gene editing in CAR-T cells. Cell Res. Jan. 2017;27(1):154-157. Epub Dec. 2, 2016. Supplemental Information included. 10 pages total.

Oh et al., Monocyte chemotactic protein-induced protein-1 enhances DR5 degradation and negatively regulates DR5 activation-induced apoptosis through its deubiquitinase function. Oncogene. Jun. 2018;37(25):3415-3425. Epub Mar. 19, 2018.

Reina-Campos et al., Antitumour T cells stand the test of time. Nature. Dec. 11, 2019;576:392-3.

Roth, Editing of Endogenous Genes in Cellular Immunotherapies. Curr Hematol Malig Rep. Aug. 2020;15(4):235-240.

Tang et al., TGF-β inhibition via CRISPR promotes the long-term efficacy of CAR T cells against solid tumors. JCI Insight. Feb. 27, 2020;5(4):e133977(1-17).

Wei et al., Targeting Regnase-1 programs long-lived effector T cells for cancer therapy. Nature. Dec. 11, 2019;576(7787):471-476. Supplemental Information included. 29 pages total.

Yoshinaga et al., Post-transcriptional control of immune responses and its potential application. Clin Transl Immunology. Jun. 17, 2019;8(6):e1063(1-13).

[No Author Listed], addgene Sequence Analyzer: lentiGuide-Puro Seqeuncing Result. 2019. 1 page. Accessible at addgene.org/browse/sequence/331247.

[No Author Listed], *Homo sapiens* zinc finger CCCH-type containing 12A (ZC3H12A), transcript variant 1, mRNA. NCBI Reference Sequence: NM_025079.3. May 23, 2023. 5 pages.

[No Author Listed], Human Reg1 sgRNA designer. 2019. 1 page. Accessible through portals.broadinstitute.org/gpp/public/analysis-tools/sgrna-design.

[No Author Listed], Mouse Reg1 sgRNA sequence information. 2019. 1 page. Accessible through portals.broadinstitute.org/gpp/public/analysis-tools/sgrna-design.

[No Author Listed], NCBI ZC3H12A—zinc finger CCCH-type containing 12A : NCBI Orthologs. 2023. 4 pages. Accessible athttps://www.ncbi.nlm.nih.gov/gene/80149/ortholog/?scope=7776.

Basila et al., Minimal 2'-O-methyl phosphorothioate linkage modification pattern of synthetic guide RNAs for increased stability and efficient CRISPR-Cas9 gene editing avoiding cellular toxicity. PLoS One. Nov. 27, 2017;12(11):e0188593(20 pages).

Jinek et al., A programmable dual-RNA-guided DNA endonuclease in adaptive bacterial immunity. Science. Aug. 17, 2012;337(6096):816-21. Epub Jun. 28, 2012.

Safari et al., CRISPR Cpf1 proteins: structure, function and implications for genome editing. Cell Biosci. May 9, 2019;9:36(21 pages).

* cited by examiner

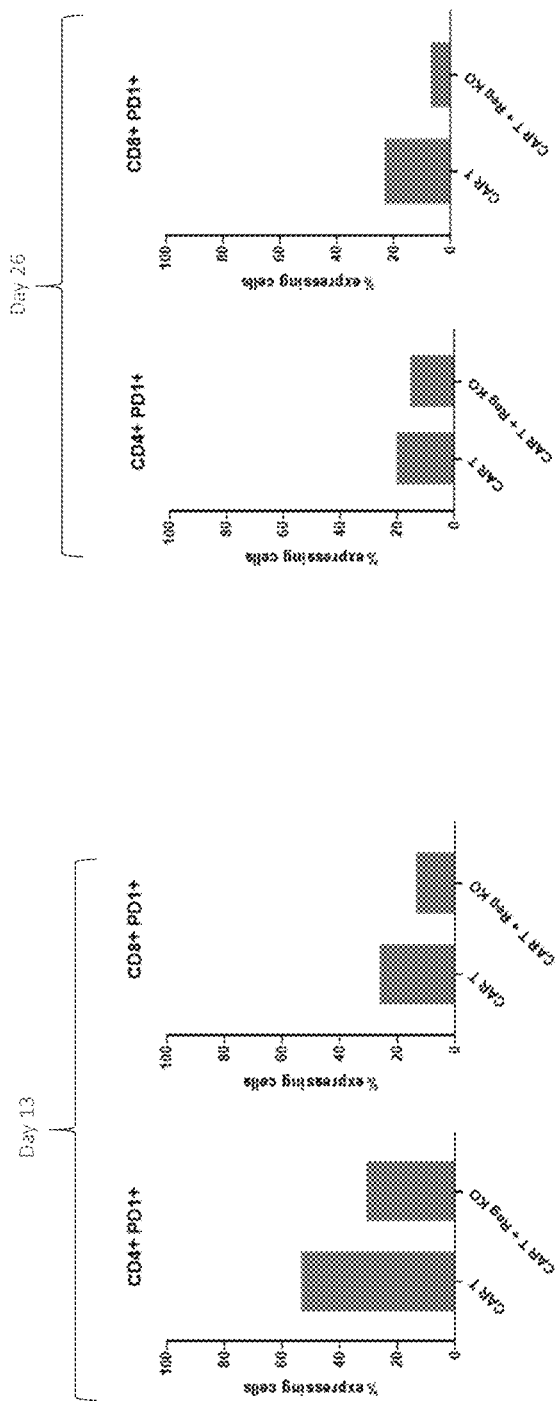
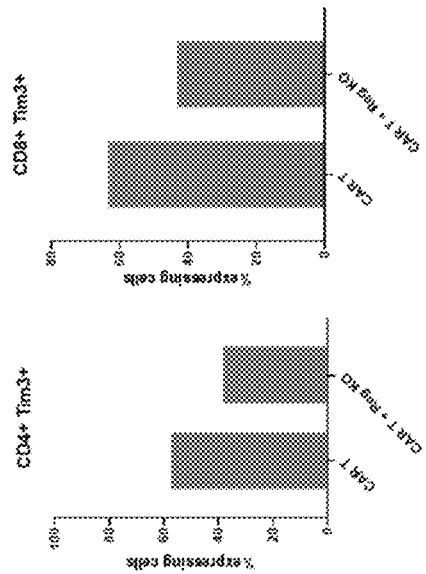
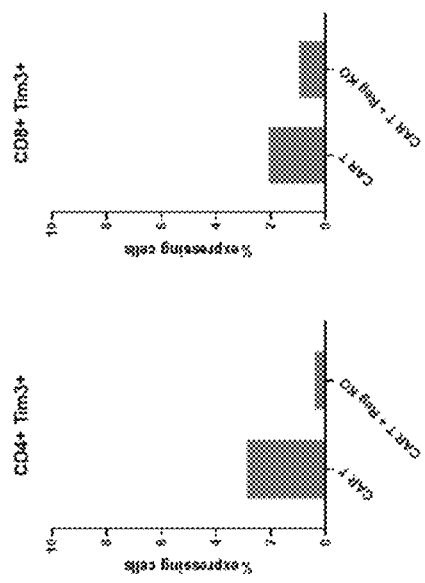
FIG. 3A, FIG. 3B, FIG. 3C, FIG. 3D

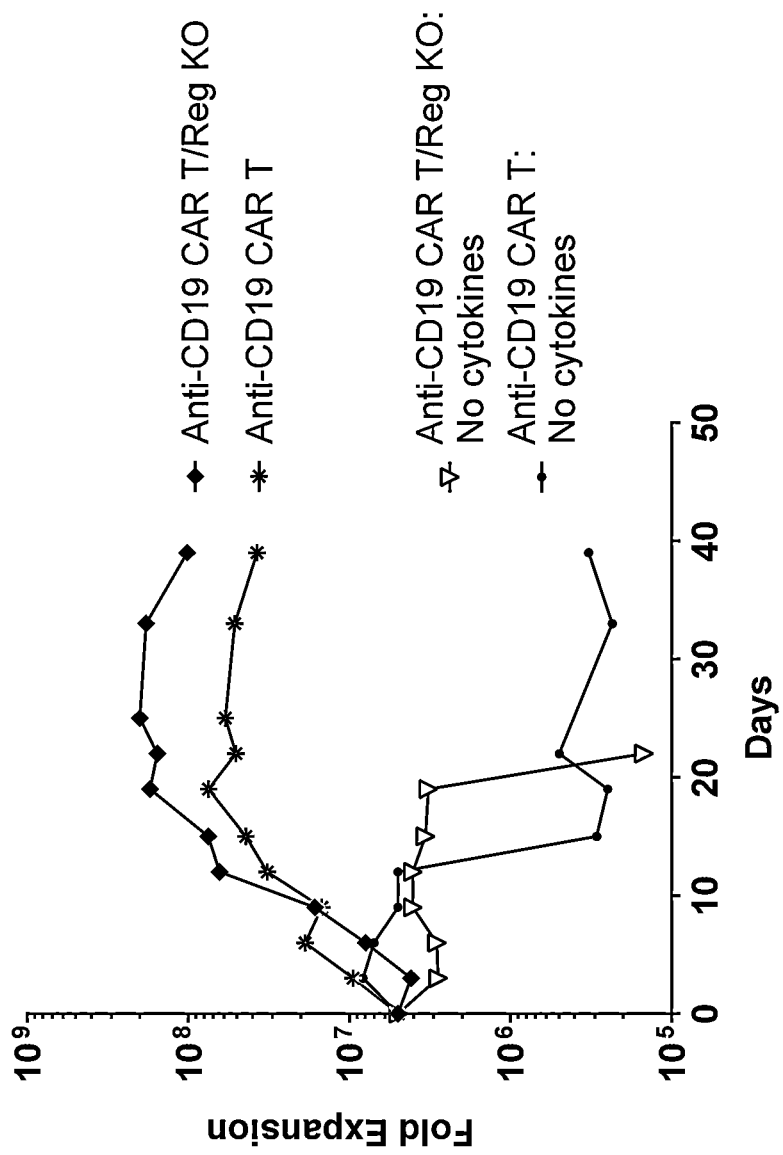

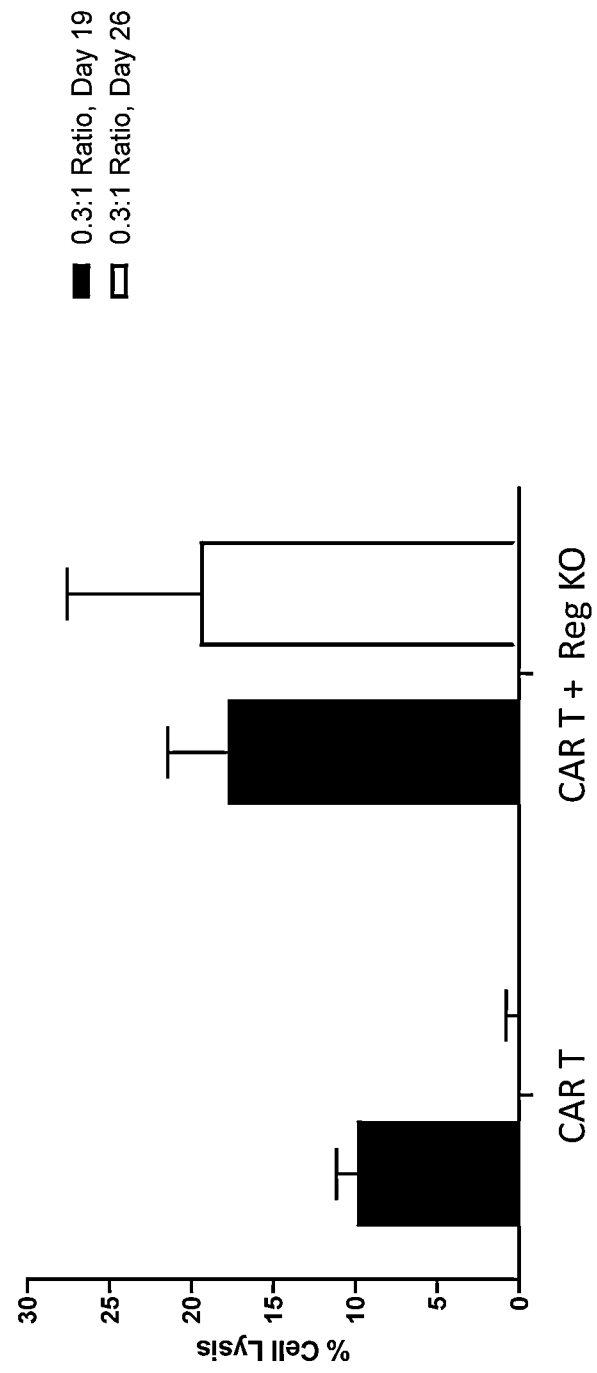

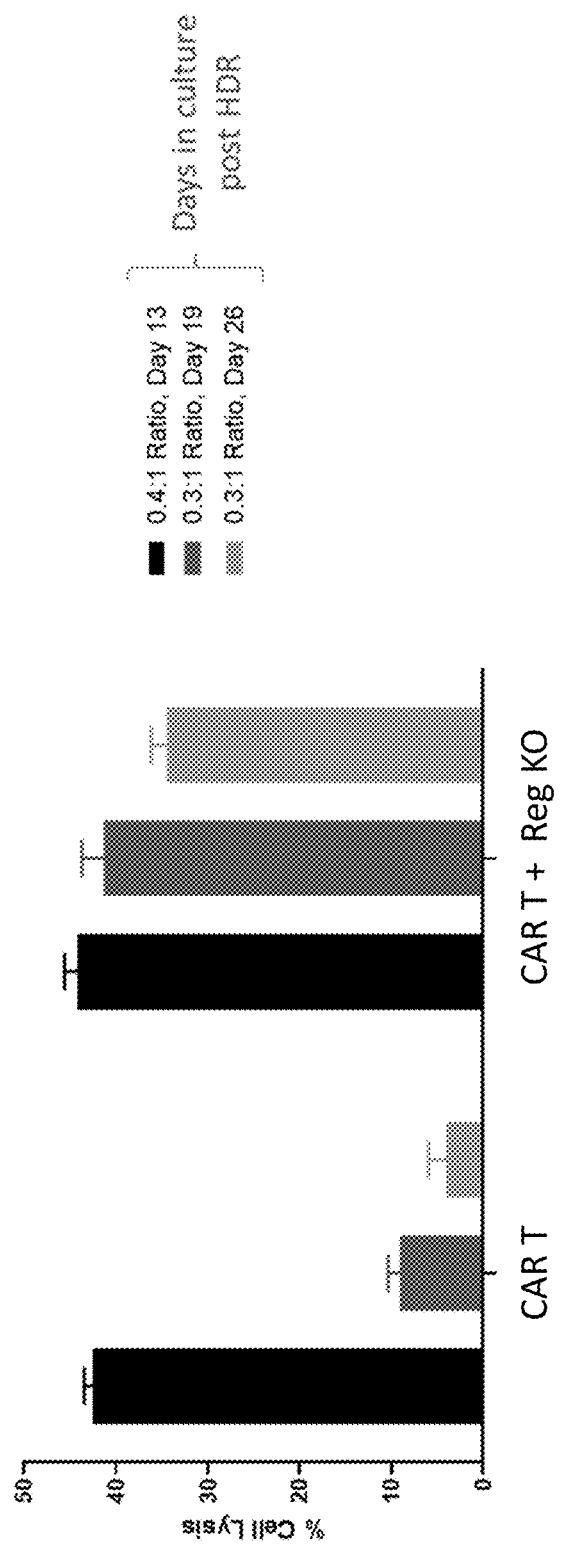

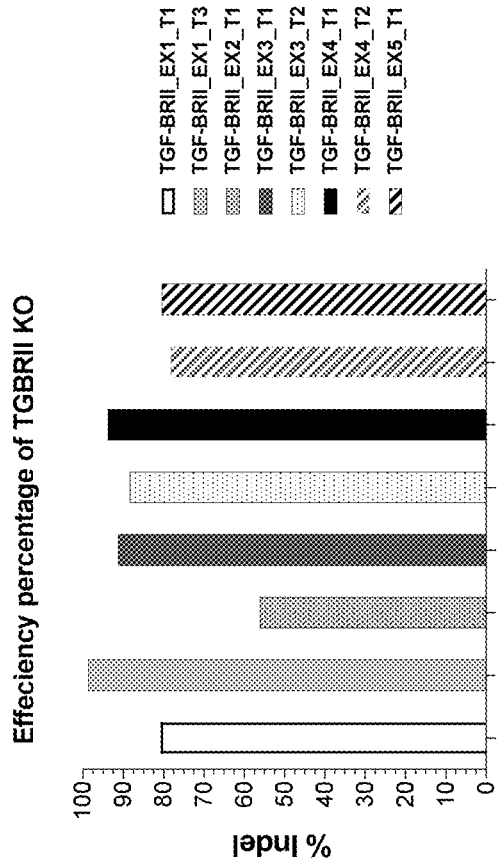
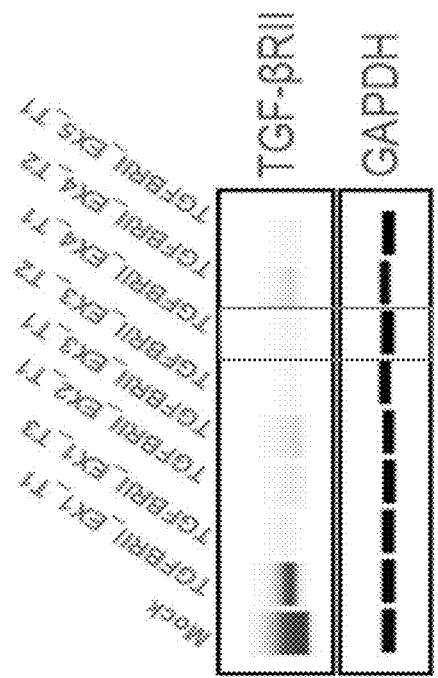
FIG. 7A
FIG. 7B

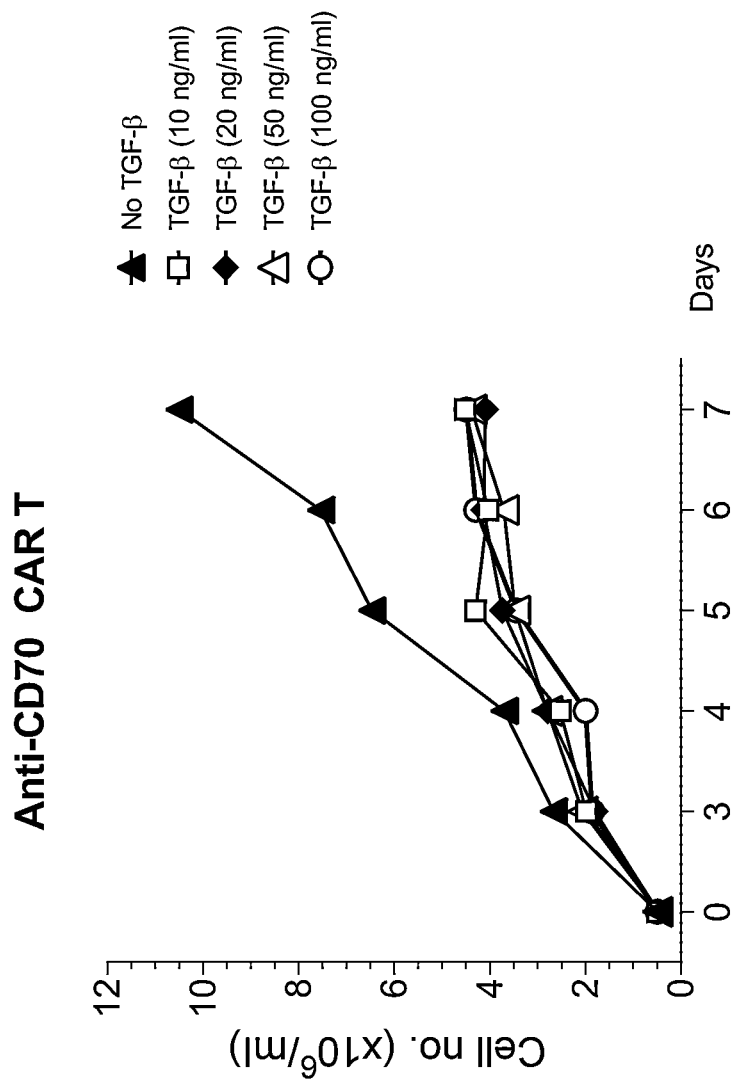

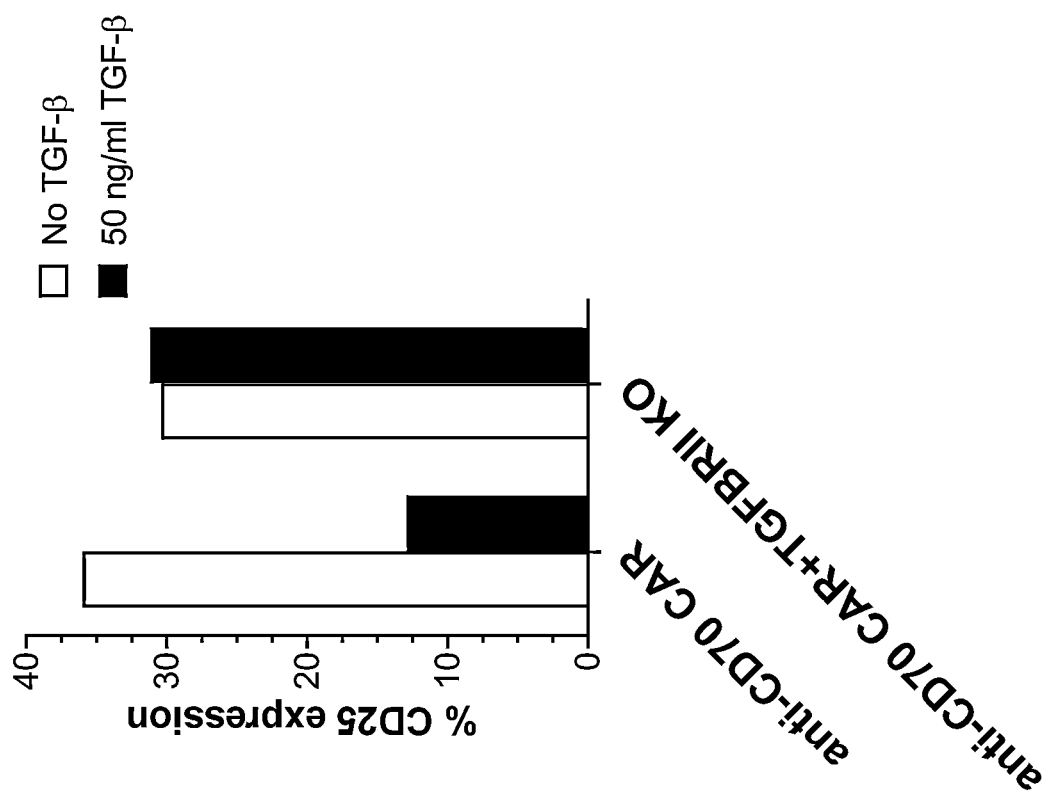

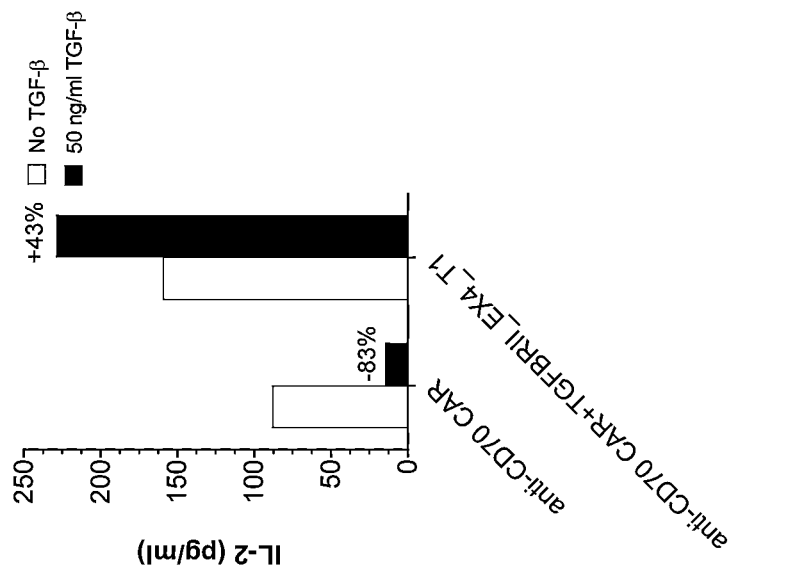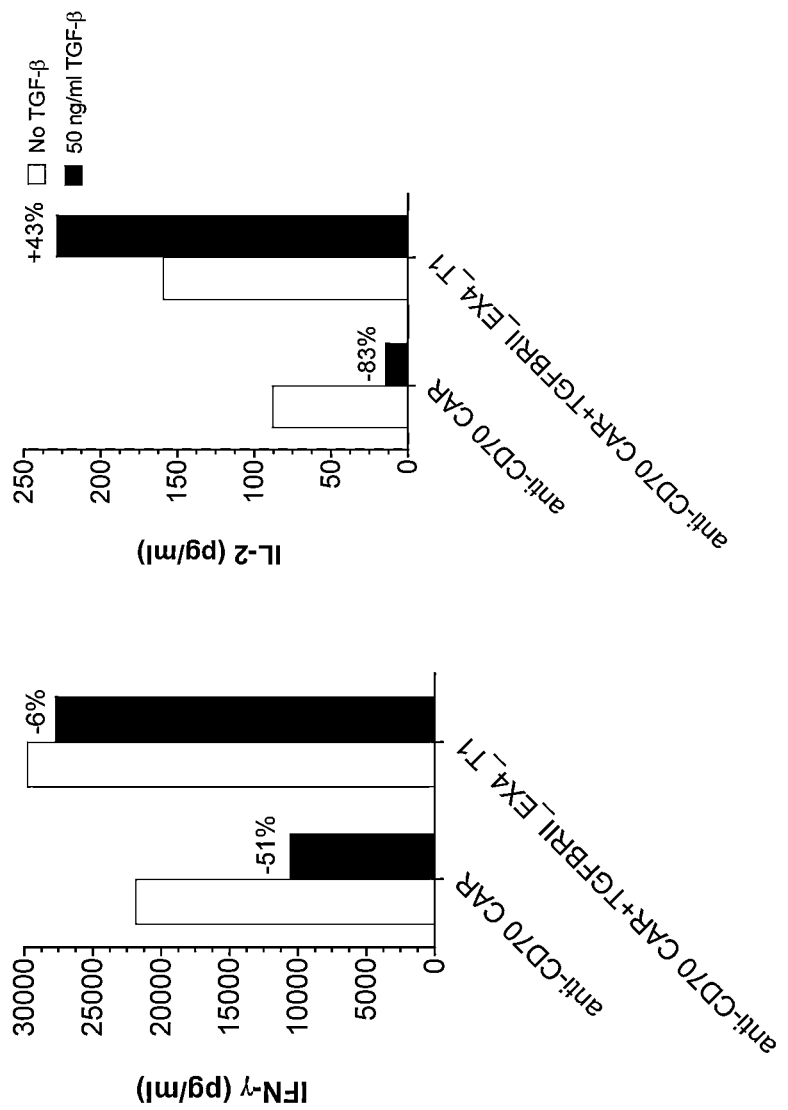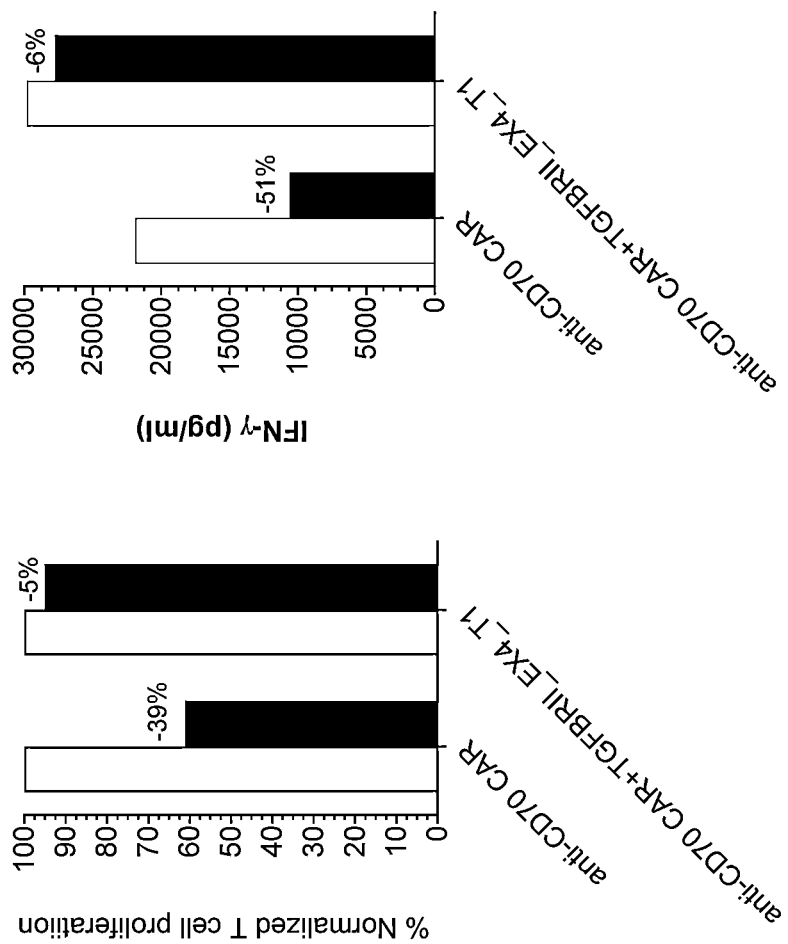

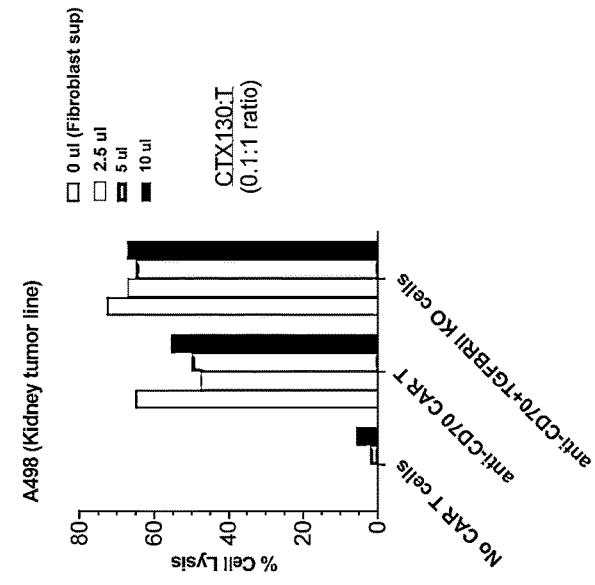
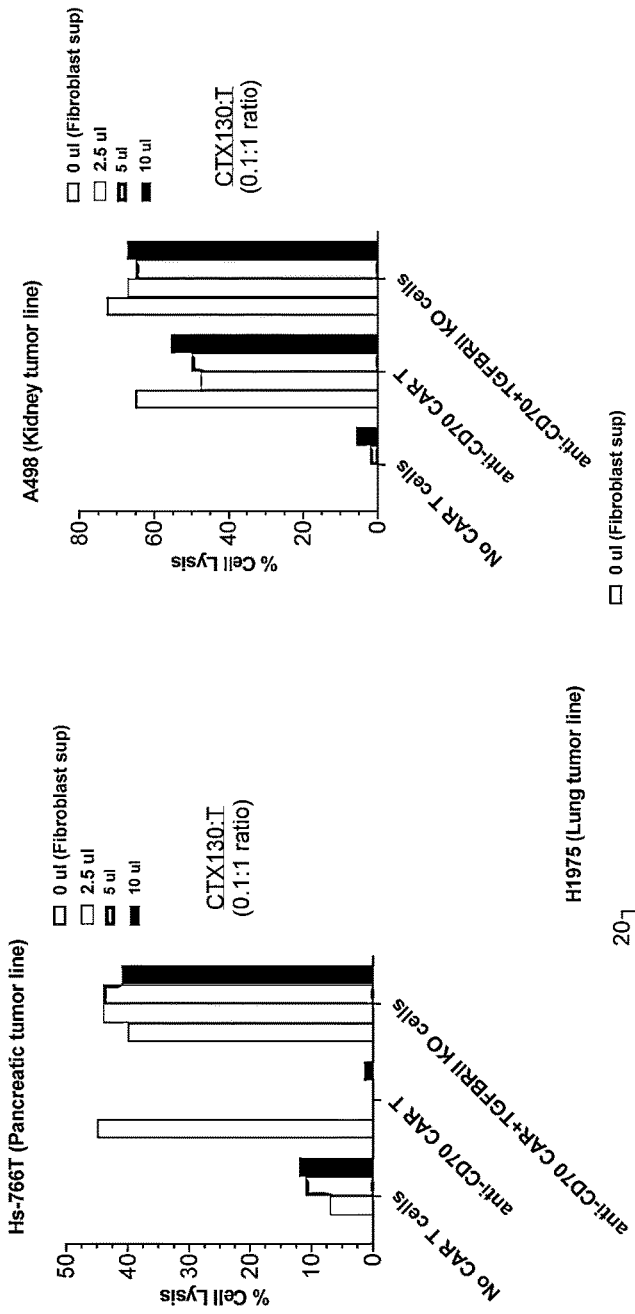
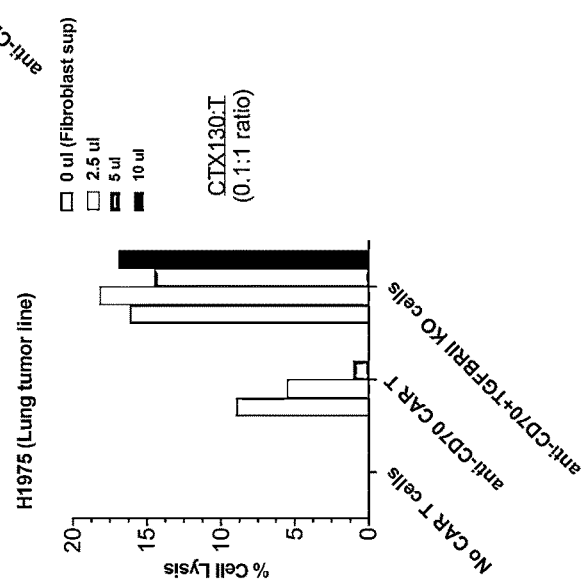
FIG. 15A
FIG. 15B
FIG. 15C

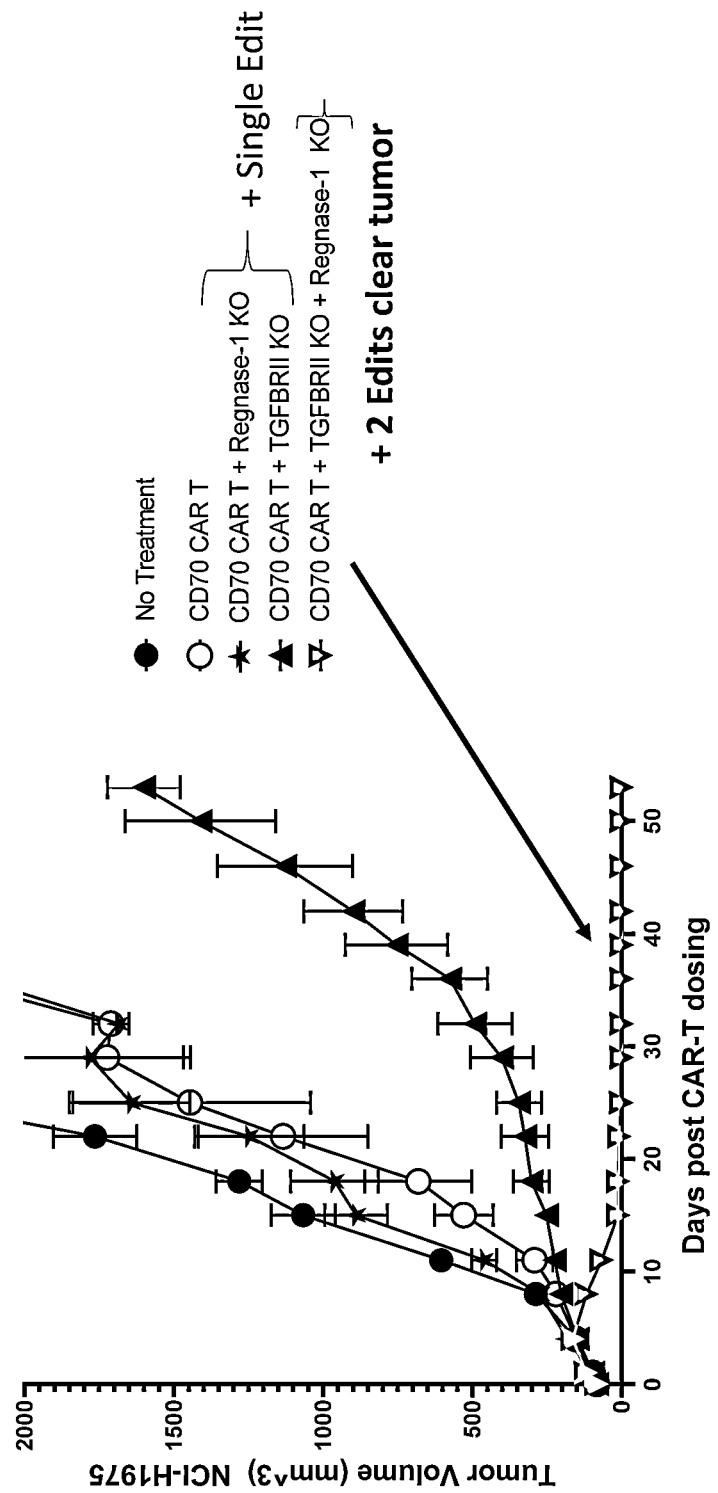

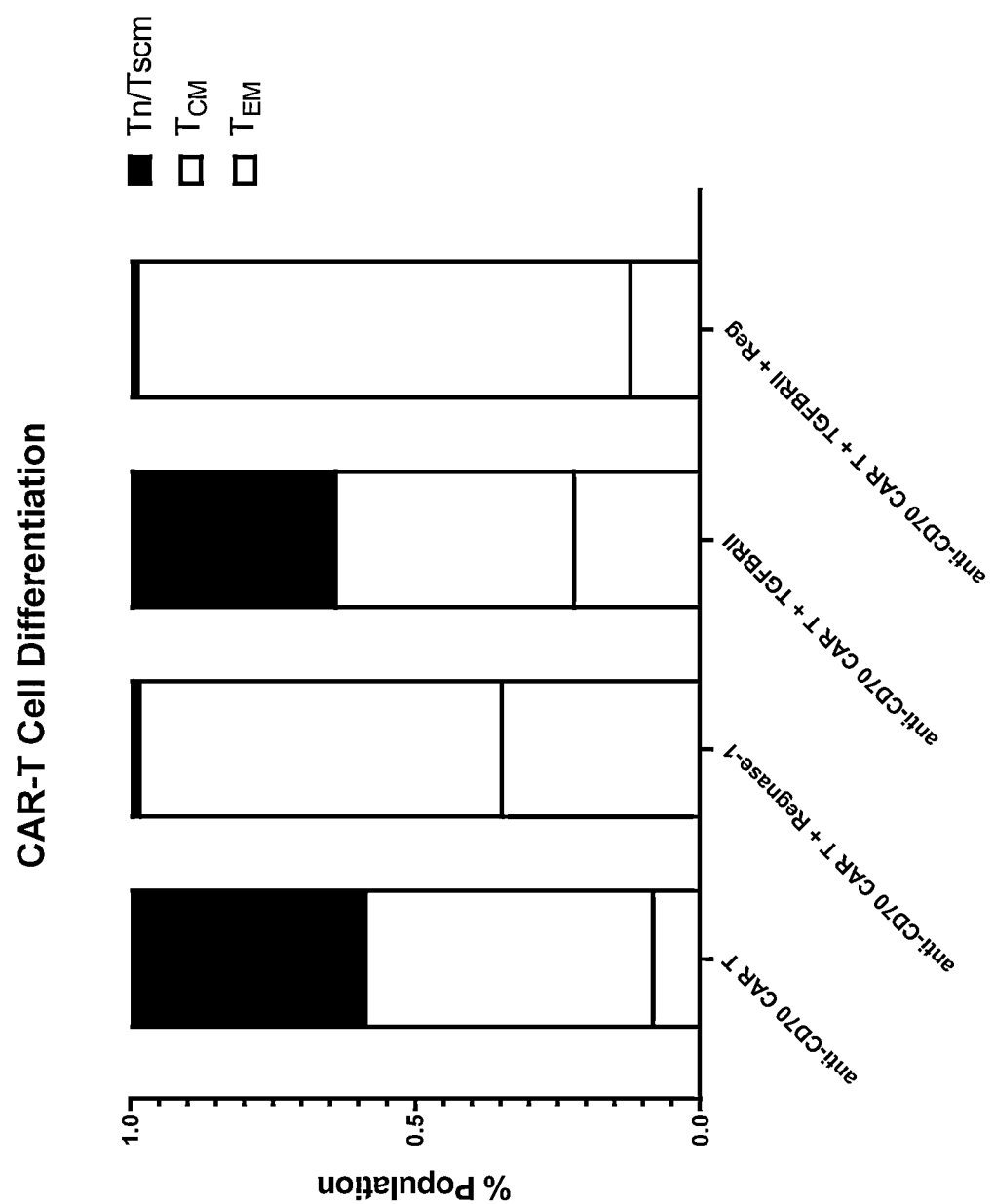

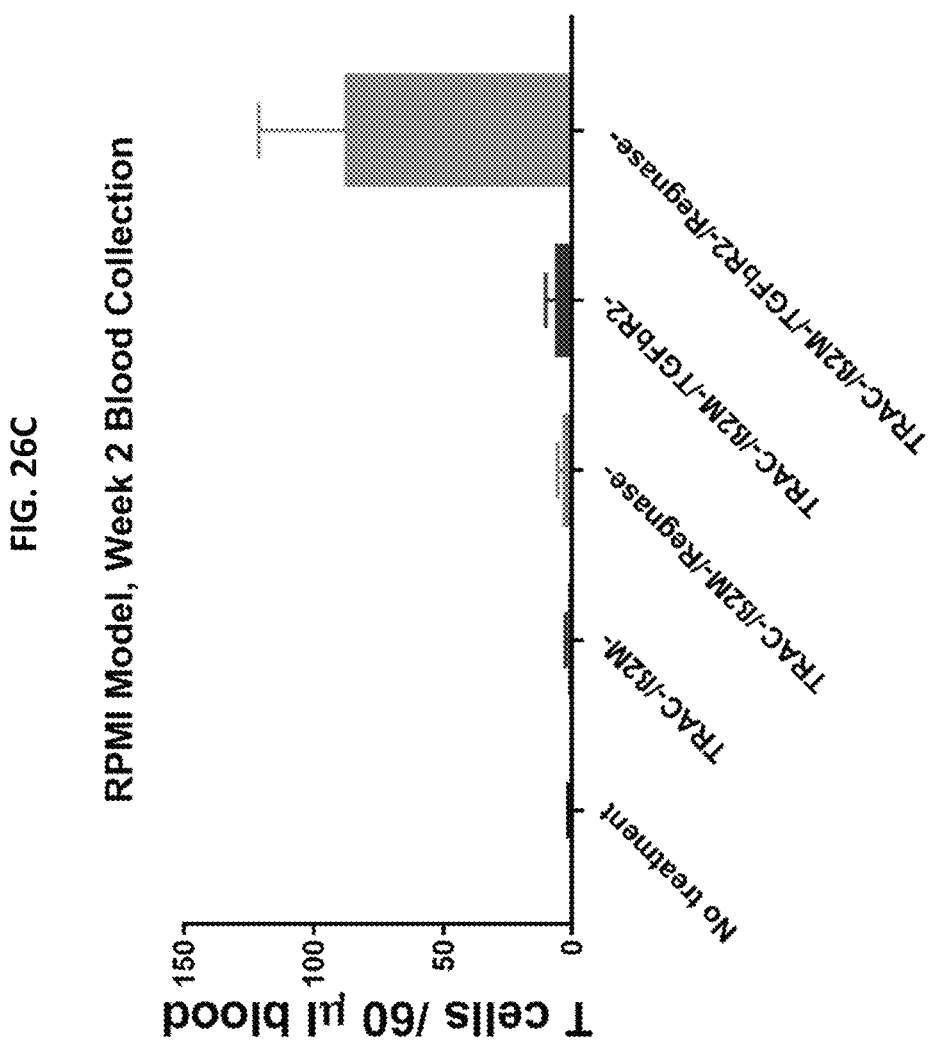

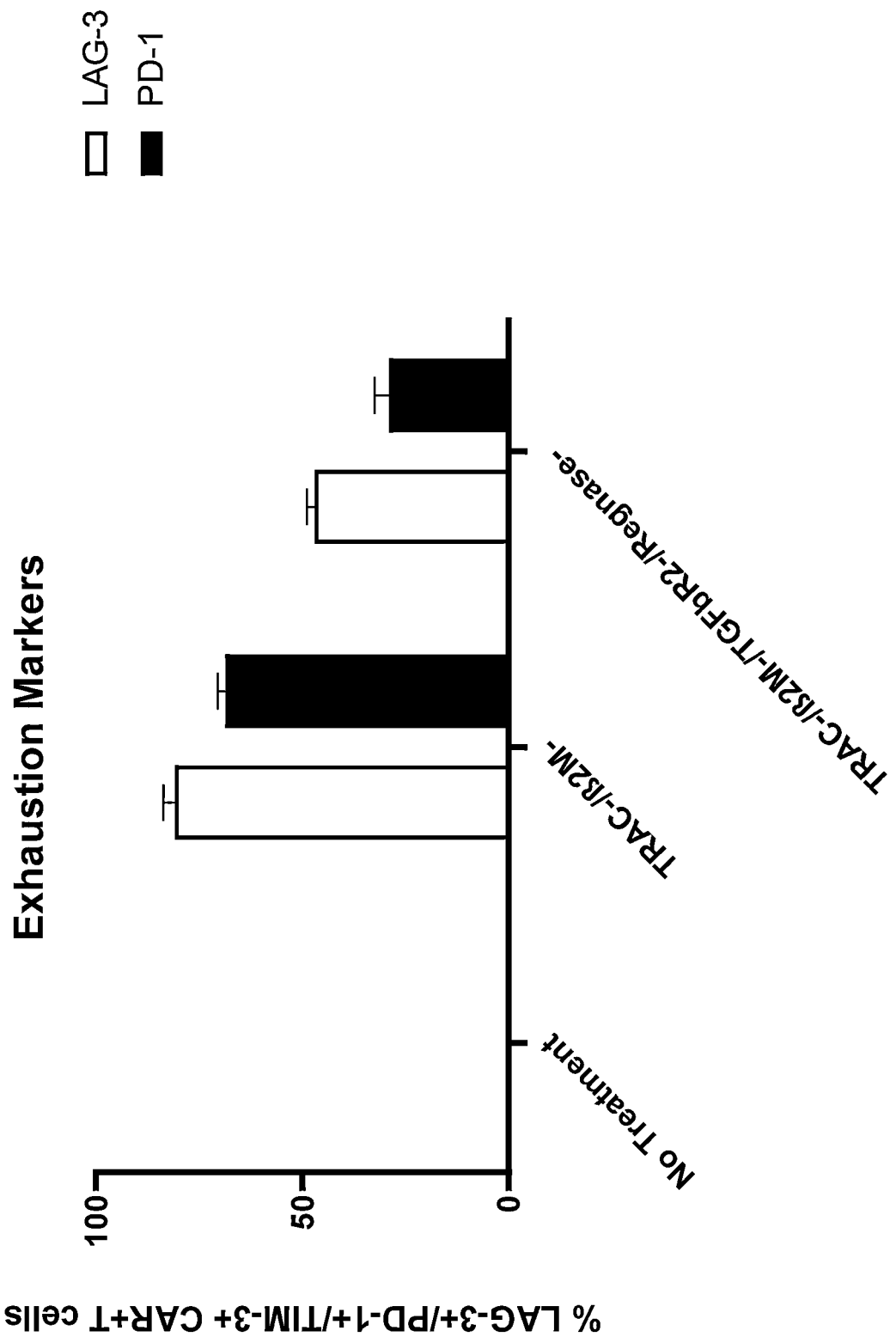

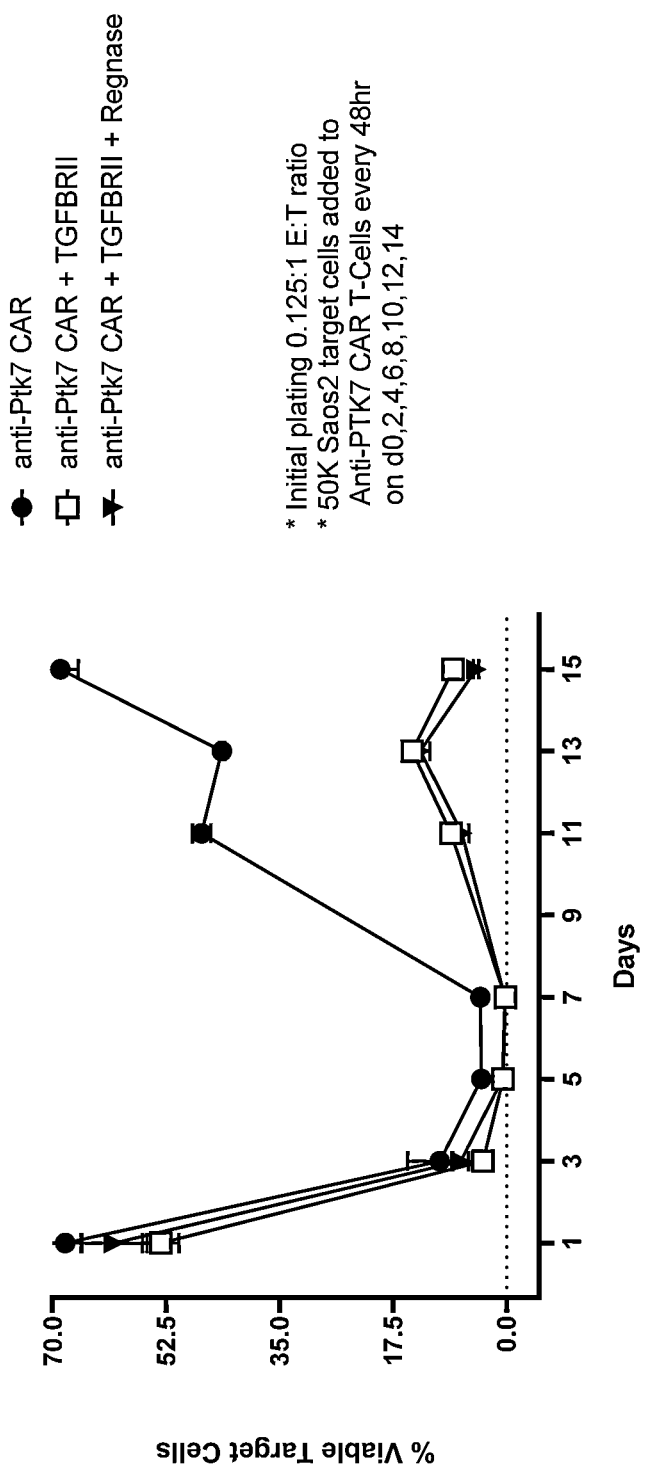

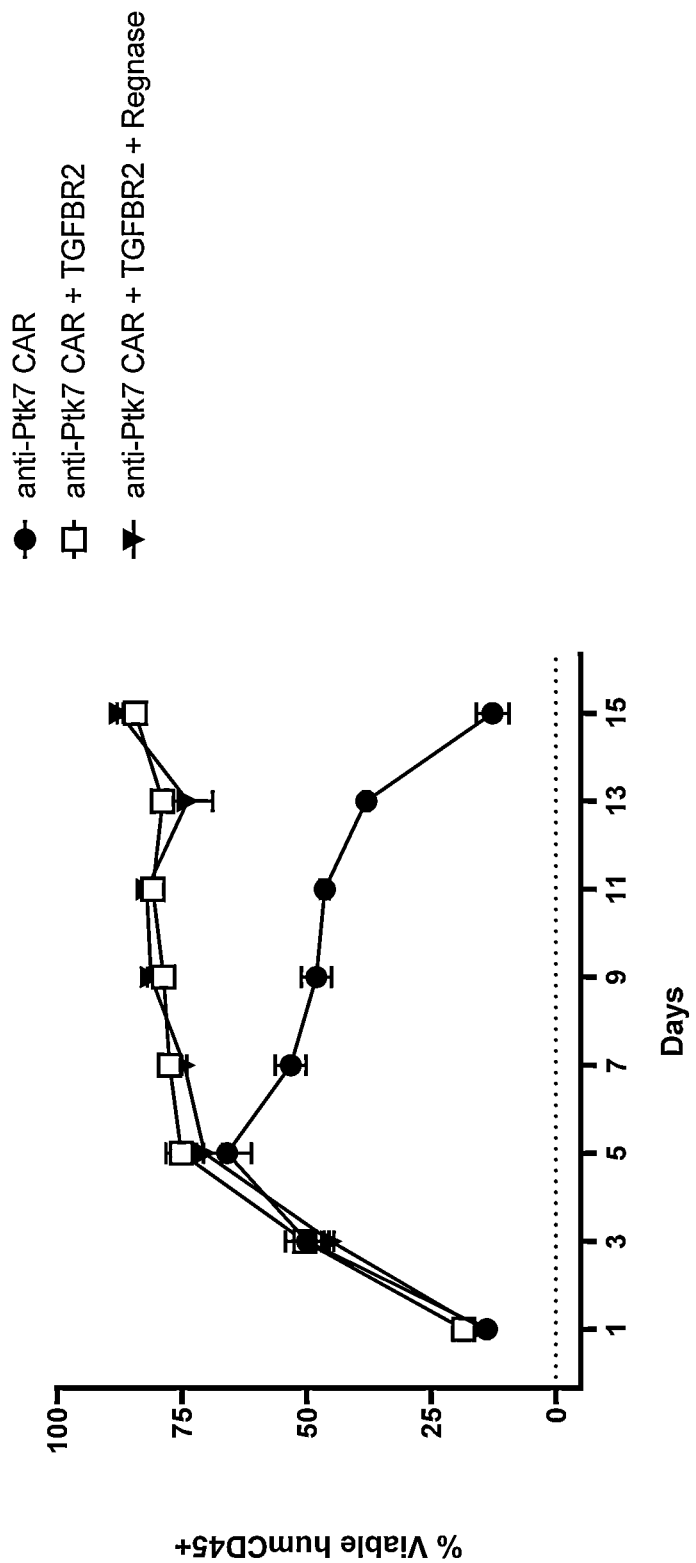

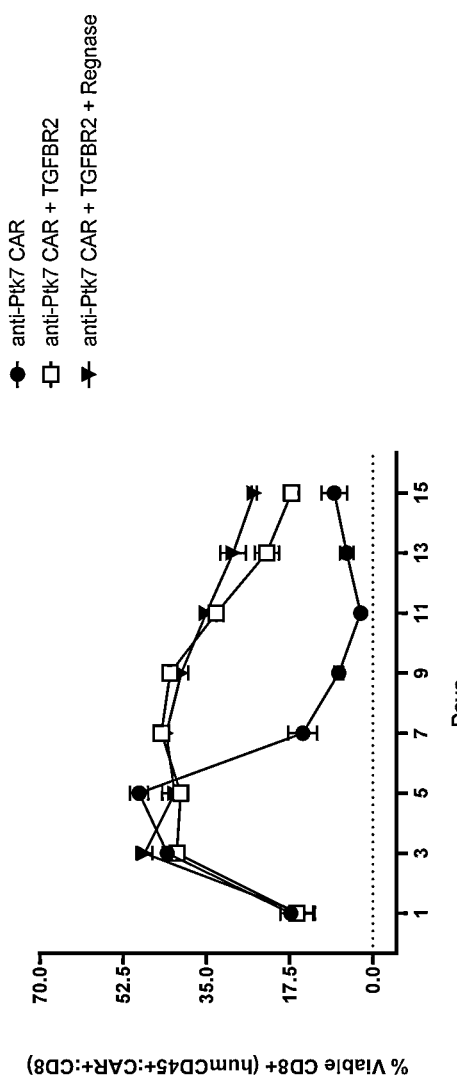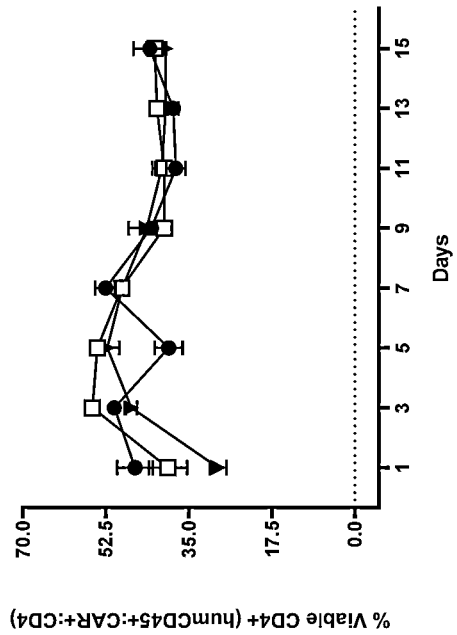
FIG. 29C
FIG. 29D

GENETICALLY ENGINEERED T CELLS WITH REGNASE-1 AND/OR TGFBRII DISRUPTION HAVE IMPROVED FUNCTIONALITY AND PERSISTENCE

CROSS REFERENCE TO RELATED APPLICATIONS

This application is a continuation of, and claims the benefit of and priority to, U.S. patent application Ser. No. 17/493,280 filed Oct. 4, 2021, which is a continuation of, and claims the benefit of and priority to, U.S. patent application Ser. No. 17/483,100 filed Sep. 23, 2021, which claims the benefit of the filing dates of U.S. Provisional Application No. 63/082,357, filed Sep. 23, 2020, U.S. Provisional Application No. 63/124,429, filed Dec. 11, 2020, and U.S. Provisional Application No. 63/225,673, filed Jul. 26, 2021. The entire contents of each of the prior applications are incorporated by reference herein.

REFERENCE TO SEQUENCE LISTING

The application contains a Sequence Listing that has been filed electronically in XML format, created Nov. 8, 2022, and named "095136-0725_Sequence Listing.xml" (675,953 bytes), the contents of which are incorporated by reference herein in their entirety.

BACKGROUND OF THE INVENTION

Chimeric antigen receptor (CAR) T-cell therapy uses genetically modified T cells to more specifically and efficiently target and kill cancer cells. After T cells have been collected from the blood, the cells are engineered to include CARs on their surface. The CARs may be introduced into the T cells using CRISPR/Cas9 gene editing technology. When these allogeneic CAR T cells are injected into a patient, the receptors enable the T cells to kill cancer cells.

T cells having improved persistence in culture are desired in CAR T therapy. Such T cells live longer in both in vitro and in vivo, thereby conferring benefits in CAR T cell manufacturing and clinical applications. However, it remains challenging to improve persistence of T cells in culture.

SUMMARY OF THE INVENTION

The present disclosure is based, at least in part, on the development of genetically edited T cells carrying a disrupted Regnase 1 (Reg1) gene (e.g., "Reg1 Knockout T cells"), a disrupted TGFBRII gene (e.g., "TGFBRII Knockout T cells", or genetically edited T cells carrying both a disrupted Reg1 gene and a disrupted TGFBRII gene, and effective methods of producing such genetically edited T cells via CRISPR/Cas-mediated gene editing using guide RNAs, for example, those targeting specific sites within the Reg1 gene with high on-target editing efficiency and low off-target editing efficiency, and/or those targeting specific sites within the TGFBRII gene with high on-target editing efficiency and low off-target editing efficiency.

Such genetically engineered T cells exhibits at least one of the following advantageous features: (a) improved cell growth activity; (b) enhanced persistence; (c) reduced T cell exhaustion; (d) resistant to inhibitory effects induced by TGF-β; (e) enhanced cell killing capacity; and (f) resistant to inhibitory effects by fibroblasts and/or inhibitory factors secreted thereby.

The Reg1 disrupted T cells, the TGFBRII disrupted T cells, or the Reg1/TGFBRII double disrupted T cells disclosed herein can further be genetically engineered to express a chimeric antigen receptor (CAR) targeting an antigen of interest, e.g., an antigen associated with an undesired cell such as a cancer cell, and to comprise one or more additional disrupted genes, for example, TRAC, β2M, CD70, or a combination thereof. The resultant CAR-expressing, Reg1 disrupted T cells exhibit enhanced cytotoxic activity against target cells and anti-tumor activity as compared with CAR-T cells having a wild-type Reg1 gene.

In some aspects, the current disclosure is related to the development of genetically engineered CAR T cells that comprise a disrupted Reg1 gene. The genetically engineered CAR T cells, in certain aspects, are further genetically engineered to comprise a disrupted cluster of differentiation 70 (CD70) gene. In some aspects, the CAR T cells described herein may express anti-CD70 CAR, anti-cluster of differentiation 19 (CD19) CAR or anti-B-cell maturation antigen (anti-BCMA) CAR.

The genetically edited T cells disclosed herein showed enhanced cell expansion, longevity and proliferation capacity in culture, enhanced potency (e.g., enhanced cytotoxicity), and enhanced CAR-T efficacy in animal models (via, e.g., longer persistence). Further, the genetically edited T cells showed cytokine-dependent growth, indicating safety. In addition, disrupting both the Reg1 and TGFBRII genes exhibited synergistic effects in anti-tumor activity and CAR-T cell expansion and persistence as observed in animal models.

Accordingly, the present disclosure provides, in some aspects, a population of genetically engineered T cells, comprising: (i) a disrupted Regnase-1 (Reg1) gene; and/or (ii) a disrupted Transforming Growth Factor Beta Receptor II (TGFBRII) gene. In some embodiments, the population of genetically engineered T cells comprises (i). In some embodiments, population of genetically engineered T cells comprises (ii). In other embodiments, the population of genetically engineered T cells comprises both (i) and (ii). Any of the genetically engineered T cells may be further engineered to express a chimeric antigen receptor (CAR).

The population of genetically engineered T cells disclosed herein, as compared to non-engineered T cell counterparts, has one or more of the following features: (a) improved cell growth activity; (b) enhanced persistence; (c) reduced T cell exhaustion; (d) resistant to inhibitory effects induced by TGF-β; (e) enhanced cell killing capacity; and (f) resistant to inhibitory effects by fibroblasts and/or inhibitory factors secreted thereby.

In some embodiments, the disrupted Reg1 gene is genetically edited in exon 1, exon 2, exon 3, or exon 4. In some examples, the disrupted Reg1 gene is genetically edited in exon 2 and/or exon 4. Alternatively or in addition, the disrupted TGFBRII gene is genetically edited in exon 1, exon 2, exon 3, exon 4, or exon 5. In some examples, the disrupted TGFBRII gene is genetically edited in exon 4. In other examples, the disrupted TGFBRII gene is genetically edited in exon 5. The disrupted Reg1 gene, the disrupted TGFBRII gene, or both can be genetically edited by a CRISPR/Cas-mediated gene editing system.

In some instances, the CRISPR/Cas-mediated gene editing comprises a guide RNA (gRNA) targeting a site in the Reg1 gene that comprises a nucleotide sequence listed in Table 22 (with or without PAM) (e.g., SEQ ID NO: 320, 322, 323, or 327, or the corresponding ones with PAM). For example, the gRNA targeting the Reg1 gene comprises a spacer that comprises the nucleotide sequence of listed in Table 22 (e.g., SEQ ID NO: 24, 32, 36, or 52). In some examples, the disrupted Reg1 gene comprises a nucleotide sequence selected from those listed in Tables 29-38 (e.g., Table 31, 33, 34, or 38).

In some instances, the CRISPR/Cas-mediated gene editing system comprises a guide RNA (gRNA) targeting a site in the TGFBRII gene that comprises a nucleotide sequence listed in Table 39 (with or without PAM). For example, the gRNA targeting the TGFBRII gene comprises a spacer listed in Table 39, for example, having a nucleotide sequence of any one of SEQ ID NOs: 270, 302, 308, and 312. In some examples, the disrupted TGFBRII gene may comprise a nucleotide sequence selected from those listed in Tables 40-48 (e.g., Table 43).

Any of the gRNAs disclosed herein may further comprise a scaffold sequence. For example, the gRNA targeting the Reg1 gene comprises any of the nucleotide sequences listed in Table 22. Examples include 22, 23, 30, 31, 34, 35, 50, and 51. Alternatively or in addition, the gRNA targeting the TGFBRII gene may comprise any of the nucleotide sequences provided in Table 39. Examples include SEQ ID NOs: 270, 271, 300, 301, 306, 307, 312, and 313.

Any of the populations of genetically engineered T cells disclosed herein may further comprise: (iii) a disrupted T cell receptor alpha chain constant region (TRAC) gene, (iv) a disrupted beta-2-microglobulin (β2M) gene, (v) a disrupted CD70 gene, or (vi) a combination of any of (iii)-(v). In some embodiments, the T cells comprise a disrupted T cell receptor alpha chain constant region (TRAC) gene. Alternatively or in addition, the T cells comprise a disrupted beta-2-microglobulin (β2M) gene. Any of the T cells disclosed herein may also comprise a disrupted CD70 gene. In some examples, the disrupted TRAC gene, the disrupted) β2M gene, and/or the disrupted CD70 gene is genetically edited by one or more CRISPR/Cas-mediated gene editing system In some embodiments, the genetically engineered T cells may comprise a nucleic acid encoding the CAR, and wherein the nucleic acid is inserted in the genome of the T cells. In some instances, the nucleic acid encoding the CAR is inserted in the disrupted Reg1 gene, the disrupted TGFBRII gene, the disrupted TRAC gene, the disrupted β2M, or the disrupted CD70 gene. In some examples, the nucleic acid encoding the CAR is inserted in the disrupted TRAC gene. In specific examples, the nucleic acid encoding the CAR may replace the deleted fragment comprising SEQ ID NO: 69 in the TRAC gene. In some examples, the disrupted Reg1 gene may comprise a nucleotide sequence listed in Tables 29-38 (e.g., Table 31, 33, 34, or 38). In some examples, the disrupted TGFBRII gene may comprise a nucleotide sequence selected from those listed in Tables 40-48 (e.g., Table 43). In some examples, the disrupted TRAC gene may comprise a nucleotide sequence of any one of SEQ ID NOs: 75-82 (see Table 24). In some examples, the disrupted β2M may comprise a nucleotide sequence of any one of SEQ ID NOs: 83-88 (see Table 25). In some examples, the disrupted CD70 gene may comprise a nucleotide sequence of any one of SEQ ID NOs: 89-94 (see Table 26).

Any of the CAR constructs disclosed herein may comprise an extracellular antigen binding domain specific to a tumor antigen, a co-stimulatory signaling domain of 4-1BB or CD28, and a cytoplasmic signaling domain of CD3ζ. In some examples, the tumor antigen is CD19. In some examples, the tumor antigen is BCMA. In some examples, the tumor antigen is CD70. In some examples, the tumor antigen is CD33. In some examples, the tumor antigen is PTK7.

In some embodiments, the CAR binds CD19 (anti-CD19 CAR). The extracellular antigen binding domain in the anti-CD19 CAR can be a single chain variable fragment (scFv) that binds CD19 (anti-CD19 scFv). In some instances, the anti-CD19 scFv may comprise (i) a heavy chain variable region ($V_H$) that comprises the same heavy chain complementary determining regions (CDRs) as those in SEQ ID NO: 124; and (ii) a light chain variable region ($V_L$) that comprises the same light chain CDRs as those in SEQ ID NO: 125. In some examples, the $V_H$ comprises the amino acid sequence of SEQ ID NO: 124 and the $V_L$ comprises the amino acid sequence of SEQ ID NO: 125. In one example, the anti-CD19 scFv comprises the amino acid sequence of SEQ ID NO: 120. In one specific example, the anti-CD19 CAR comprises the amino acid sequence of SEQ ID NO: 118 (with an N-terminal signal peptide) or SEQ ID NO:353 (without N-terminal signal peptide).

In some embodiments, the CAR binds CD70 (anti-CD70 CAR). The extracellular antigen binding domain in the anti-CD70 CAR can be a single chain variable fragment (scFv) that binds CD70 (anti-CD70 scFv). In some instances, the anti-CD70 scFv comprises (i) a heavy chain variable region ($V_H$) that comprises the same heavy chain complementary determining regions (CDRs) as those in SEQ ID NO: 143; and (ii) a light chain variable region ($V_L$) that comprises the same light chain CDRs as those in SEQ ID NO: 144. In some examples, the $V_H$ comprises the amino acid sequence of SEQ ID NO: 143 and the $V_L$ comprises the amino acid sequence of SEQ ID NO: 144. In one example, the anti-CD70 scFv comprises the amino acid sequence of SEQ ID NO: 140 or 142. In one specific example, the anti-CD70 CAR comprises the amino acid sequence of SEQ ID NO: 138 (with an N-terminal signal peptide) or SEQ ID NO:354 (without N-terminal signal peptide).

In some embodiments, the CAR binds BCMA (anti-BCMA CAR). The extracellular antigen binding domain in the anti-BCMA CAR can be a single chain variable fragment (scFv) that binds BCMA (anti-BCMA CAR). In some instances, the anti-BCMA scFv comprises (i) a heavy chain variable region ($V_H$) that comprises the same heavy chain complementary determining regions (CDRs) as those in SEQ ID NO: 149; and (ii) a light chain variable region ($V_L$) that comprises the same light chain CDRs as those in SEQ ID NO: 150. In some examples, the $V_H$ comprises the amino acid sequence of SEQ ID NO: 149 and the $V_L$ comprises the amino acid sequence of SEQ ID NO: 150. In one example, the anti-BCMA scFv comprises the amino acid sequence of SEQ ID NO: 148. In one specific example, the anti-BCMA CAR comprises the amino acid sequence of SEQ ID NO: 146 (with an N-terminal signal peptide) or SEQ ID NO:355 (without N-terminal signal peptide).

The genetically engineered T cells disclosed herein may be derived from primary T cells of one or more human donors. In some instances, the genetically engineered T cells show cytokine-dependent growth.

In other aspects, the present disclosure provides a method for preparing any of the populations of genetically engineered T cells disclosed herein. In some instances, the method may comprise: (a) providing a plurality of cells, which are T cells or precursor cells thereof; (b) genetically editing the Reg1 gene and/or the TGFBRII gene; and (c) producing the population of genetically engineered T cells having disrupted Reg1 gene and/or the TGFBRII gene. In some examples, the T cells of step (a) are derived from primary T cells of one or more human donors. In some examples, step (b) comprises genetically editing the Reg1 gene. In some examples, step (b) comprises genetically editing the TGFBRII gene. In some examples, step (b) comprises genetically editing both the Reg1 gene and the TGFBRII gene.

In some embodiments, step (b) is performed by one or more CRISPR/Cas-mediated gene editing systems. For example, step (b) can be performed by delivering to the plurality of cells an RNA-guided nuclease and a gRNA targeting the Reg1 gene. In some instances, the gRNA targeting the Reg1 gene may be specific to an exon of the Reg1 gene, e.g., exon 2 or exon 4. In some examples, the gRNA targeting the Reg1 gene comprises a spacer that comprises a nucleotide sequence listed in Table 22 (e.g., SEQ ID NO: 24, 32, 36, or 52).

Alternatively or in addition, step (b) can be performed, inter alia, by delivering to the plurality of cells an RNA-guided nuclease and a gRNA targeting the TGFBRII gene. For example, the gRNA targeting the TGFBRII gene may be specific to an exon of the TGFBRII gene, e.g., exon 1, exon 2, exon 3, exon 4, and exon 5. In one example, the gRNA targeting the TGFBRII gene is specific to exon 4. In another example, the gRNA targeting the TGFBRII gene is specific to exon 5. In some instances, the gRNA targeting the TGFBRII gene comprises a spacer listed in Table 39. Examples include SEQ ID NOs: 272, 302, 308, and 314.

Any of the gRNAs disclosed herein may further comprise a scaffold sequence. For example, the gRNA targeting the Reg1 gene may comprise any of the nucleotide sequences listed in Table 22. Examples include SEQ ID NO: 22, 23, 30, 31, 34, 35, 50, and 51. Alternatively or in addition, the gRNA targeting the TGFBRII gene may comprise any of the nucleotide sequences provided in Table 39. Examples include SEQ ID NOs: 270, 271, 300, 301, 306, 307, 312, and 313.

In any of the methods disclosed herein, the plurality of T cells in step (a) comprises one or more of the following genetic modifications: (i) engineered to express a chimeric antigen receptor (CAR); (ii) has a disrupted T cell receptor alpha chain constant region (TRAC) gene; (iii) has a disrupted β2M gene; and (iv) has a disrupted CD70 gene.

Alternatively, any of the methods disclosed herein may further comprise:
(i) delivering to the T cells a nucleic acid encoding a chimeric antigen receptor (CAR);
(ii) genetically editing a TRAC gene to disrupt its expression;
(iii) genetically editing a β2M gene to disrupt its expression;
(iv) genetically editing a CD70 gene to disrupt its expression; or
(v) a combination thereof.

In some embodiments, one or more of (i)-(iv) are performed by one or more CRISPR/Cas-mediated gene editing system comprising one or more RNA-guided nucleases and one or more gRNAs targeting the TRAC gene, the β2M gene, and/or the CD70 gene. In some examples, the gRNA targeting the TRAC gene comprises a spacer that comprises the nucleotide sequence of SEQ ID NO: 61. In some examples, the gRNA targeting the β2M gene comprises a spacer that comprises the nucleotide sequence of SEQ ID NO: 65. In some examples, the gRNA targeting the CD70 gene comprises a spacer that comprises the nucleotide sequence of SEQ ID NO: 57. See Table 23.

In some embodiments, the method disclosed herein may comprise delivering to the T cells one or more ribonucleoprotein particles (RNP), which may comprise the RNA-guided nuclease, one or more of the gRNAs, and the nucleic acid encoding the CAR. In some examples, the RNA-guided nuclease is a Cas9 nuclease, for example, a *S. pyogenes* Cas9 nuclease.

In some embodiments, the nucleic acid encoding the CAR is in an AAV vector. In some instances, the nucleic acid encoding the CAR comprises a left homology arm and a right homology arm flanking the nucleotide sequence encoding the CAR. The left homology arm and the right homology arm are homologous to a genomic locus in the T cells, allowing for insertion of the nucleic acid into the genomic locus. In some examples, the genomic locus is in the Reg1 gene. In some examples, the genomic locus is in the TGFBRII gene. In some examples, the genomic locus is in the TRAC gene. In some examples, the genomic locus is in the β2M gene. In some examples, the genomic locus is in the CD70 gene.

In some examples, the method comprising disrupting the TRAC gene by a CRISPR/Cas-mediated gene editing system comprising a gRNA comprising the nucleotide sequence of SEQ ID NO: 59 and the nucleic acid encoding the CAR is inserted at the site targeted by the gRNA. Alternatively or in addition, the method may comprise delivering to the T cells a nucleic acid encoding a CAR, which is specific to CD70, and genetically editing the CD70 gene to disrupt its expression.

Any population of the genetically engineered T cells prepared by a method disclosed herein is also within the scope of the present disclosure.

Further, the present disclosure provides a method for eliminating undesired cells in a subject, the method comprising administering to a subject in need thereof any of the populations of genetically engineered T cells disclosed herein. In some embodiments, the undesired cells are cancer cells, for example, hematopoietic cancer cells or solid tumor cells. In some embodiments, the undesired cells are CD19$^+$. In some embodiments, the undesired cells are BCMA$^+$. In some embodiments, the undesired cells are CD70$^+$. In some embodiments, the undesired cells are CD33$^+$. In some embodiments, the undesired cells are PTK7$^+$.

In yet other aspects, provided herein is a guide RNA (gRNA) targeting a Reg1 gene, comprising a nucleotide sequence specific to a fragment in exon 2 or exon 4 of the Reg1 gene. In some embodiments, the gRNA comprises a spacer listed in Table 22 (e.g., SEQ ID NO: 24, 32, 36 or 52). Such a gRNA may further comprise a scaffold sequence. Alternatively or in addition, the gRNA comprises one or more modified nucleotides. For example, the gRNA comprises one or more 2'-O-methyl phosphorothioate residues at the 5' and/or 3' terminus of the gRNA. Examples of gRNAs targeting Reg1 include any of those listed in Table 22 (e.g., SEQ ID NO: 22, 23, 30, 31, 34, 35, 50, or 51; see also disclosures herein).

In still other aspects, provided herein is a guide RNA (gRNA) targeting a TGFBRII gene, comprising a nucleotide sequence specific to a fragment in exon 1, exon 2, exon 3, exon 4, or exon5 of the TGFBRII gene. In some examples, the gRNA comprises a nucleotide sequence specific to exon 4 of the TGFBRII gene. In other examples, the gRNA comprises a nucleotide sequence specific to exon 5 of the TGFBRII gene. In some instances, the gRNA comprises a spacer having the nucleotide sequence listed in Table 39 (e.g., SEQ ID NOs: 272, 302, 308, and 314). Such a gRNA may further comprise a scaffold sequence. Alternatively or in addition, the gRNA comprises one or more modified nucleotides. For example, the gRNA comprises one or more 2'-O-methyl phosphorothioate residues at the 5' and/or 3' terminus of the gRNA. Examples of gRNAs targeting the TGFBRII gene include any of those listed in Table 39 (e.g., SEQ ID NOs: 270, 271, 300, 301, 306, 307, 312, and 313).

Also within the scope of the present disclosure are any of the genetically engineered T cells, gRNAs targeting Reg1, or gRNAs targeting TGFBRII for use in treating a target disease as disclosed herein (e.g., cancer such as those disclosed herein), or uses of such for manufacturing a medicament for the intended therapeutic purposes The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 1A: Proliferation of anti-CD70 CAR T cells (CAR T) with Reg1 KO using one of the 10 guides (Z01-Z10) targeting Reg1 as indicated. CAR T indicates anti-CD70 CAR T cells with an unedited (wild-type) Reg1 gene. FIG. 1B: Proliferation of anti-CD70 CAR T cells with Reg1 KO using guide REG1-Z10 (Z10) up to 52 days post HDR. Anti-CD70 CAR T cells with an unedited Reg1 gene are also shown (CAR T). (A) and (B) refer to duplicative assays.

FIG. 2A: Cell lysis of ACHN cells by anti-CD70 CAR T cells with Reg1 KO, using Regnase guides Z03 or Z10, relative to CAR T cells with an unedited (wild-type) Reg1 gene (CAR T). Cell lysis was measured after 24 h co-culture at day 12 post HDR. FIG. 2B: Cell lysis of ACHN cells by anti-CD70 CAR T cells with Regnase 1 KO using Regnase guides Z05 or Z06 relative to CAR T cells with an unedited Reg1 gene. Cell lysis was measured after 24 h co-culture at day 12 post HDR. FIG. 2C: Cell lysis of ACHN cells by anti-CD70 CAR T cells with Regnase 1 KO, using Regnase guides Z03, Z05, Z06 or Z10 relative to CAR T cells with an unedited Reg1 gene. Cell lysis was measured after 24 h co-culture at day 27 post HDR. FIG. 2D: Cell lysis of caki-1 cells by anti-CD70 CAR T cells with Regnase 1 KO using Regnase guides Z03, Z05, Z06 or Z10 relative to CAR T cells with an unedited Reg1 gene. Cell lysis was measured after 24 h co-culture at day 27 post HDR. FIG. 2E: Cell lysis of 769P cells by anti-CD70 CAR T cells with Regnase 1 KO using Regnase guides Z03, Z05, Z06 or Z10 relative to CAR T cells with an unedited Reg1 gene. Cell lysis was measured after 24 h co-culture at day 27 post HDR.

FIGS. 3A-3D include diagrams showing that exemplary CAR T cells (anti-CD70 CAR T cells) with Reg1 KO (CAR T+Reg KO, using Z10 guide as an example) express lower levels of T cell exhaustion markers in vitro relative to Reg1 wild-type counterparts (CAR T). FIG. 3A: Day 13 post HDR PD1 expression in CD4+ and CD8+ anti-CD70 CAR T cells with Reg1 KO (+Reg KO) relative to wild-type counterparts. FIG. 3B: Day 26 post HDR PD1 expression in CD4+ and CD8+ anti-CD70 CAR T cells with Reg1 KO (+Reg KO) relative to wild-type counterparts. FIG. 3C: Day 13 post HDR Tim3 expression in CD4+ and CD8+ anti-CD70 CAR T cells with Reg1 KO (+Reg KO) relative to wild-type counterparts. FIG. 3D: Day 26 post HDR Tim3 expression in CD4+ and CD8+ anti-CD70 CAR T cells with Reg1 KO (+Reg KO) relative to wild-type counterparts.

FIG. 4 is a diagram showing that exemplary CAR T cells (anti-CD19 CAR T cells) with Reg1 KO showed enhanced expansion in the presence of cytokines in vitro and continue to depend on cytokines for in vitro expansion. Anti-CD19 CAR T cells with a Reg1 KO (Anti-CD19 CAR T/Reg KO) and anti-CD19 CAR T cells with a wild-type Reg1 gene (Anti-CD19 CAR T) were cultured in the presence and absence (No cytokines) of cytokines for 40 days.

FIG. 5A: Probability of survival of untreated mice, mice dosed with 4e6 anti-CD19 CAR T cells, and 4e6 anti-CD19 CAR T/Reg KO cells. FIG. 5B: Probability of survival of untreated mice, mice dosed with 8e6 anti-CD19 CAR T cells, and 8e6 anti-CD19 CAR T/Reg KO cells. FIG. 5C: Bioluminescence signal from bioluminescent model leukemia cells in mice treated with 4e6 anti-CD19 CAR T cells or 4e6 anti-CD/9 CAR T/Reg KO cells. FIG. 5D: Bioluminescence signal from bioluminescent model leukemia cells in mice treated with 8e6 anti-CD/9 CAR T cells or 8e6 anti-CD19 CAR T/Reg KO cells.

FIGS. 6A-6B include diagrams showing that exemplary CAR T cells (anti-CD70 CAR T cells) with Reg1 KO (CAR T+Reg KO) exhibit superior in vitro potency against tumor cell lines relative to Reg1 wild-type counterparts (CAR T). FIG. 6A: Cell lysis of ACHN cells by anti-CD70 CAR T cells with Reg1 KO using guide REG1-Z10 (CAR T+Reg KO) relative to Reg1 wild-type counterparts (CAR T). Cell lysis was measured after 24 h co-culture at day 19 and 26 post HDR. FIG. 6B: Cell lysis of caki-1 cells by anti-CD70 CAR T cells with Reg1 KO using guide REG1-Z10 (CAR T+Reg KO) relative to Reg1 wild-type counterparts (CAR T). Cell lysis was measured after 24 h co-culture at day 13, 19 and 26 post HDR.

FIGS. 7A and 7B include diagrams showing knock out of TGFBRII using various guide RNAs as indicated. FIG. 7A: Indel rates of edited TGFBRII gene by eight gRNAs that target different TGFBRII gene exons as indicated. From left to right, EX1_T1, EX1_T3, EX2_T1, EX3_T1, EX3_T2, EX4_T1, EX4_T2, and EX5_T1, the nucleotide sequence of each of which is provided in Table 32. FIG. 7B: immunoblot of TGFBRII expression in gene-edited T cells. GAPDH was used as a loading control. The mock sample is unedited T cells with wild-type TGFBRII.

FIGS. 8A-8K include diagrams showing the effect of TGF-β on CAR T cell expansion. Anti-CD70 CAR T cells were exposed to different concentrations of recombinant human TGF-β (10, 20, 50, 100 ng/ml) and cell number was recorded at different time points (FIG. 8A). T cells with or without TGFBRII knock-out, generated using different TGFBRII gRNAs as indicated, were incubated with 0 or 50 ng/ml of TGFB-β and cell expansion was recorded over time (FIGS. 8B-8K).

FIG. 11 is a graph showing the effect of TGFBRII KO on CAR T cell phenotype. Anti-CD70 CAR T cells with or without TGFBRII KO were exposed to 50 ng/ml recombinant human TGF-β and the expression of CD25 was assessed by flow cytometry. TGFBRII KO protects CAR T from TGF-β inhibitory effect on cell phenotype.

FIGS. 13A-13C include diagrams showing that TGFBRII KO anti-CD70 CAR T cells are resistant to TGF-β inhibitory effects on effector function. Anti-CD70 CAR T cells were co-cultured with target cells (A498) with TGF-β (50 ng/ml) or without TGF-β and compared to anti-CD70 CAR T with TGFBRII KO (e.g.: anti-CD70 CAR+TGFBRII_EX4_T1) in their ability to kill target cells. T cell proliferation (FIG. 13A) and effector cytokine secretion was assessed by Luminx (FIGS. 13B and 13C).

FIGS. 15A-15C include graphs showing that TGFBRII KO protects CAR-T cells against the inhibitory effect of fibroblasts. Anti-CD70 CAR T was co-cultured with target cells (A498) at 0.1:1 (E:T) in presence of different volumes of conditioned media from CCL-190 (2.5, 5, 10 μL) and the cell kill capacity was evaluated and compared to cells with TGFBRII KO. The ability of anti-CD70 CAR T cells (with or without TGFBRII KO) to kill target cells is shown in Hs-766T pancreatic tumor cells (FIG. 15A), A498 kidney tumor cells (FIG. 15B), and H1975 lung tumor cells (FIG. 15C).

FIG. 16A: improved potency. FIG. 16B: improved CAR expansion.

FIGS. 17A-17B include diagrams showing synergistic effects of disrupting both TGFBRII and Regnase genes in cancer xenograph models. FIG. 17A: CAKI-1 renal cell carcinoma xenograph model with anti-CD70 CAR T cells. FIG. 17B: H1975 lung cancer xenograph model with anti-CD70 CAR T cells.

FIG. 18A: reduction in RCC (A498) tumor size. FIG. 18B: inhibition of RCC tumor cell growth following rechallenge with ACHN cells.

FIG. 19A-19B include diagrams showing impact of Reg1 and/or TGFBRII disruption on CAR-T cell differentiation and expansion in vivo. FIG. 19A: CAR-T cell differentiation. FIG. 19B: CAR-T cell expansion.

FIG. 20A: reduction in tumor size. FIG. 20B: Survival rates.

FIG. 22A shows CAR T cell expansion in the Jeko-1 xenograph model. FIG. 22B shows CAR T cell expansion in the nalm-6 xenograph model.

FIG. 23A: levels of TCR$^-$ cells. FIG. 23B: levels of β2M$^-$ cells. FIG. 23C: levels of CAR$^+$ cells. FIG. 23D: ratio of CD4$^+$/CD8$^+$ cells.

FIG. 24A: TGFBRII disruption efficiency. FIG. 24B: Reg-1 disruption efficiency.

FIGS. 25A-25B: cytotoxicity against β2M1s (multiple myeloma cell line) cells (25A) relative to K562 cells (25B). FIGS. 25C-25D: cytotoxicity against JeKo-1 cells (mantle cell lymphoma cell line) (25C) relative to K562 cells (25D).

FIGS. 26A-26C include diagrams showing that the combined disruption of Regnase-1 and TGFBRII improved anti-BCMA CAR-T activity against murine multiple myeloma in an animal model. FIG. 26A: tumor volume reduction. FIG. 26B: survival rate. FIG. 26C: CAR-T cell expansion in peripheral blood.

FIGS. 27A-27F include diagrams showing that the combined disruption of Regnase and TGFBRII improves anti-BCMA CAR-T activity against murine mantle cell lymphoma in an animal model. FIG. 27A: tumor volume reduction. FIG. 27B: survival rate. FIG. 27C: CAR-T cell expansion in peripheral blood. FIG. 27D: PD-1 and LAG-3 levels in CAR T cells. FIG. 27E: levels of circulating T cells at three weeks post CAR-T injection. FIG. 27F: levels of exhaustion markers (LAG-3 and PD-1) on circulating T cells at three weeks post CAR-T injection.

FIGS. 29A-29D include diagrams showing impact of TGFBRII disruption, optionally in combination with Reg-1 disruption, in long-term in vitro rechallenge assays. FIG. 29A: TGFBRII disruption alone improves anti-PTK7 CAR T-cell potency in a long-term in vitro rechallenge assay. FIG. 29B: TGFBRII disruption improves anti-PTK7 CAR T-cell persistence and expansion in a long-term in vitro rechallenge assay as measured by humCD45+ cells. FIG. 29C: TGFBRII disruption enhances cytotoxic CD8+ T cells expressing the anti-PTK7 CAR. FIG. 29D: CD4+ cells expressing the anti-PTK7 CAR remains consistent regardless of TGFBRII disruption.

FIG. 30A: effect of treatment on tumor volume. FIG. 30B: effect of treatment on body weight. • Group 1: no treatment. ○: Group 2: anti-PTK7 CAR-T cells, 5×10$^6$ cells/mouse (iv) Day 1. □: Group 3: anti-PTK7 CAR/TGFBRII KO T cells, 5×10$^6$ cells/mouse (iv) Day 1. UTA chow was administered 9 days prior to CAR-T cell treatment to applicable groups.

FIG. 31A: number of humCD45+ cells/ul in murine blood at Day 47 post dose. FIG. 31B: CAR-T cell differentiation at Day 47 post dose.

DETAILED DESCRIPTION OF THE INVENTION

Figure 1A:
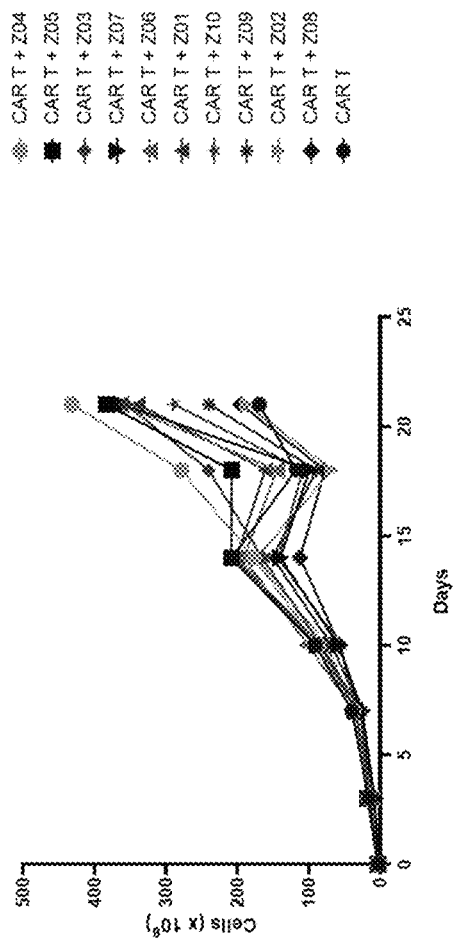
FIGS. 1A and 1B include diagrams showing that exemplary CAR T cells (anti-CD70 CAR T cells) with Reg1 KO exhibit superior in vitro expansion

The present disclosure aims at establishing genetically engineered T cells having improved growth activity, persistence, reduced T cell exhaustion, and enhanced potency, a long-felt need in CAR-T therapy. Such a T cell may use bona fide T cells as the starting material, for example, non-transformed T cells, terminally differentiated T cells, T cells having stable genome, and/or T cells that depend on cytokines and growth factors for proliferation and expansion. Alternatively, such a T cell may use T cells generated from precursor cells such as hematopoietic stem cells (e.g., iPSCs), e.g., in vitro culture. The T cells disclosed herein may confer one or more benefits in both CAR-T cell manufacturing and clinical applications.

Conventional allogenic CAR T cells are produced wherein a single donor leukopak is edited in most cases so that the cells can avoid components of the patient immune system and thus do not cause GvHD. The process of expanding these CAR T cells can yield 10s to 100s of vialed drug product. Patients may receive a single dose or multiple doses. During the manufacturing process, these CAR T cells lose potential due to various mechanisms, for example, apoptosis, exhaustion, replicative senescence, and other processes where the cells become less fit.

The genetically engineered T cells having a disrupted TGFBRII gene, a disrupted Reg1 gene, or a combination thereof, and optionally one or more additional genetic edits, for example, a disrupted TRAC gene, a disrupted β2M gene, a disrupted CD70 gene, and/or an inserted nucleic acid coding for a chimeric antigen receptor (CAR), or a combination thereof.

Unexpectedly, the present disclosure reports that knocking out Reg1 in T cells led to various advantageous features in T cell-mediated cell therapy such as CAR-T therapy. Examples include, but are not limited to: improved cell culture growth and in vitro expansion including faster expansion, longer viability, faster proliferation and/or increased resistance to apoptosis, which are beneficial for manufacturing and production of therapeutic T-cell based products such as CAR-T cells; T cell potency advantages related to maintaining therapeutic T cells (e.g., CAR-T cells) in vitro and in vivo potency and activity (target cell killing) for a more effective and persistent T-cell based therapeutic products; production and/or retention of more central memory cells; lower expression of T cell exhaustion markers (such as, PD-1, Tim-3); improved efficacy of T cell therapeutics in vivo, related to decreasing tumor burden and increasing survival of CAR T treated subjects.

Further, unexpectedly, T cells having a disrupted TGFBRII gene showed advantageous features, including improved cell growth and expansion, enhanced cytotoxicity activity, resistant to the inhibitory effect mediated by TGFβ, and/or mediated by fibroblasts. Given such advantageous features, the genetically engineered T cells (e.g., CAR-T cells) disclosed herein, having a disrupted TGFBRII gene and optionally other genetic edits as disclosed herein, would be expected to exhibit superior therapeutic effects, for example, superior anti-tumor effects, e.g., in TME of a solid tumor.

Moreover, CAR-T cells having both a disrupted Reg1 gene and a disrupted TGFBRII gene showed much higher anti-tumor activities, as well as CAR-T cell expansion in animal models as relative to CAR-T cells having a disrupted Reg1 gene or a disrupted TGFBRII gene.

Other unlimited advantageous features of the T cells provided herein include:
 (a) Improved quality and consistency of CAR-T cell-based therapeutics.
 (b) Greater potency and longer-lived potency of CAR-T cells produced from the T cells in human patients.
 (c) Reduced dosage requirement. Because the T cells disclosed herein have enhanced proliferation and expansion capacities, they can live longer in vivo. As such, a lower dose relative to standard CAR-T therapy may be used to achieve substantially similar therapeutic effects relative to a high dose of conventional CAR-T cell therapy.
 (d) Increased efficacy resulting from enhanced proliferation and expansion of the CAR-T cells disclosed herein, enhanced cytotoxicity, and prolonged persistence in vivo. Further, the T cells would provide the benefit of titratable dosing in patients to optimize safety and efficacy as noted above.
 (e) Extended therapeutic effects due to reduced exhaustion and/or replicative senescence and prolonged persistence of the T cells both in vitro and in vivo.
 (f) Enhanced anti-tumor activity, e.g., reduction of tumor size and/or elongated survival rates.

Accordingly, provided herein are T cells having improved persistence in culture, methods of producing such T cells, and methods of using such T cells for producing therapeutic T cells such as CAR-T cells. Components and processes (e.g., the CRISPR approach for gene editing and components used therein) for making the T cells disclosed herein are also within the scope of the present disclosure.

I. Genetically Engineered T Cells Having Enhanced Features

The T cells disclosed herein comprises genetically engineered T cells having enhanced persistence in culture. Such genetically engineered T cells may have genetic editing of the Reg1 gene or genetic editing of the TGFBRII gene. In some instances, such genetically engineered T cells may have genetic editing of both the Reg1 gene and the TGFBRII gene.

In some embodiments, the genetically engineered T cells may have genetic editing in one or more additional genes involved in T cell exhaustion, such as CD70. As shown by the studies disclosed herein, such genetically engineered T cells show one or more of the following superior features as relative to the T cell counterparts having a wild-type Regnase 1 gene: enhanced expansion capacity in culture (e.g., expandable in culture for at least 4 weeks, e.g., at least 6 weeks; and/or at least 10-fold expandable, for example, at least 15-fold expandable, relative to the non-edited counterpart), enhanced longevity, enhanced proliferation capacity, greater T cell activation, enhanced potency, enhanced expression of central memory T cell markers, and reduced expression of T cell exhaustion markers.

The genetically engineered T cells may be derived from parent T cells (e.g., non-edited wild-type T cells) obtained from a suitable source, for example, one or more mammal donors. In some examples, the parent T cells are primary T cells (e.g., non-transformed and terminally differentiated T cells) obtained from one or more human donors. Alternatively, the parent T cells may be differentiated from precursor T cells obtained from one or more suitable donor or stem cells such as hematopoietic stem cells or inducible pluripotent stem cells (iPSC), which may be cultured in vitro.

In some embodiments, the genetically engineered T cells carry a disrupted Reg1 gene, and optionally, one or more disrupted genes involved in cell exhaustion (e.g., CD70). Such genetically engineered T cells may further comprise one or more disrupted genes, for example, TRAC or β2M. Such genetically engineered T cells may further express a chimeric antigen receptor (CAR), which may be capable of binding to an antigen of interest, for example, a tumor associated antigen (e.g., CD19, BCMA, CD70, CD33, or PTK7).

In some embodiments, the genetically engineered T cells carry a disrupted TGFBRII gene, and optionally, one or more disrupted genes involved in cell exhaustion (e.g., CD70). Such genetically engineered T cells may further comprise one or more disrupted genes, for example, TRAC or β2M. Such genetically engineered T cells may further express a chimeric antigen receptor (CAR), which may be capable of binding to an antigen of interest, for example, a tumor associated antigen (e.g., CD19, BCMA, CD70, CD33, or PTK7). In some examples, the genetically engineered T cells may express an anti-PTK7 CAR such as those disclosed herein. In some instances, such genetically engineered T cells may have a wild-type endogenous Reg-1 gene.

In some embodiments, the genetically engineered T cells carry a disrupted Reg1 gene and a disrupted TGFBRII gene, and optionally, one or more disrupted genes involved in cell exhaustion (e.g., CD70). Such genetically engineered T cells may further comprise one or more disrupted genes, for example, TRAC or β2M. Such genetically engineered T cells may further express a chimeric antigen receptor (CAR), which may be capable of binding to an antigen of interest, for example, a tumor associated antigen (e.g., CD19, BCMA, CD70, CD33, or PTK7).

Any of the genetically engineered T cells may be generated via gene editing (including genomic editing), a type of genetic engineering in which nucleotide(s)/nucleic acid(s) is/are inserted, deleted, and/or substituted in a DNA sequence, such as in the genome of a targeted cell. Targeted gene editing enables insertion, deletion, and/or substitution at pre-selected sites in the genome of a targeted cell (e.g., in a targeted gene or targeted DNA sequence). When a sequence of an endogenous gene is edited, for example by deletion, insertion or substitution of nucleotide(s)/nucleic acid(s), the endogenous gene comprising the affected sequence may be knocked-out due to the sequence alteration. Therefore, targeted editing may be used to disrupt endogenous gene expression. "Targeted integration" refers to a process involving insertion of one or more exogenous sequences, with or without deletion of an endogenous sequence at the insertion site. Targeted integration can result from targeted gene editing when a donor template containing an exogenous sequence is present.

(a) Genetically Edited Genes

In some aspects, the present disclosure provides genetically engineered T cells that may comprise a disrupted Reg1 gene, a disrupted TGFBRII gene, or a combination thereof. In some embodiments, the genetically engineered T cells provided herein comprise both a disrupted Reg1 gene and a disrupted TGFBRII gene. In some instances, the genetically engineered T cells disclosed herein may further comprise a disrupted CD70 gene, a disrupted β2M gene, a disrupted TRAC gene, or a combination thereof.

As used herein, a "disrupted gene" refers to a gene comprising an insertion, deletion or substitution relative to an endogenous gene such that expression of a functional protein from the endogenous gene is reduced or inhibited. As used herein, "disrupting a gene" refers to a method of inserting, deleting or substituting at least one nucleotide/nucleic acid in an endogenous gene such that expression of a functional protein from the endogenous gene is reduced or inhibited. Methods of disrupting a gene are known to those of skill in the art and described herein.

In some embodiments, a cell that comprises a disrupted gene does not express (e.g., at the cell surface) a detectable level (e.g., in an immune assay using an antibody binding to the encoded protein or by flow cytometry) of the protein encoded by the gene. A cell that does not express a detectable level of the protein may be referred to as a knockout cell.

Reg1 Gene Editing

In some embodiments, the genetically engineered T cells may comprise a disrupted gene involved in mRNA decay. Such a gene may be Reg1. Reg1 contains a zinc finger motif, binds RNA and exhibits ribonuclease activity. Reg1 plays roles in both immune and non-immune cells and its expression can be rapidly induced under diverse conditions including microbial infections, treatment with inflammatory cytokines and chemical or mechanical stimulation. Human Reg1 gene is located on chromosome 1p34.3. Additional information can be found in GenBank under Gene ID: 80149.

In some examples, the genetically engineered T cells may comprise a disrupted Reg1 gene such that the expression of Reg1 in the T cells is substantially reduced or eliminated completely. The disrupted Reg1 gene may comprise one or more genetic edits at one or more suitable target sites (e.g., in coding regions or in non-coding regulatory regions such as promoter regions) that disrupt expression of the Reg1 gene. Such target sites may be identified based on the gene editing approach for use in making the genetically engineered T cells. Exemplary target sites for the genetic edits may include exon 1, exon 2, exon 3, exon 4, exon 5, exon 6, or a combination thereof. In some examples, one or more genetic editing may occur in exon 2 or exon 4. Such genetic editing may be induced by the CRISPR/Cas technology using a suitable guide RNA, for example, those listed in Table 22. The resultant edited Reg1 gene using a gRNA listed in Table 22 may comprise one or more edited sequences provided in Tables 29-38 below.

TGFBRII Gene Editing

In some embodiments, the genetically engineered T cells may comprise a disrupted TGFBRII gene, which encodes Transforming Growth Factor Receptor Type II (TGFBRII). TGFBRII receptors are a family of serine/threonine kinase receptors involved in the TGFβ signaling pathway. These receptors bind growth factor and cytokine signaling proteins in the TGFβ family, for example, TGFβs (TGFβ1, TGFβ2, and TGFβ3), bone morphogenetic proteins (BMPs), growth differentiation factors (GDFs), activin and inhibin, myostatin, anti-Müllerian hormone (AMH), and NODAL.

In some examples, the genetically engineered T cells may comprise a disrupted TGFBRII gene such that the expression of TGFBRII in the T cells is substantially reduced or eliminated completely. The disrupted TGFBRII gene may comprise one or more genetic edits at one or more suitable target sites (e.g., in coding regions or in non-coding regulatory regions such as promoter regions) that disrupt expression of the TGFBRII gene. Such target sites may be identified based on the gene editing approach for use in making the genetically engineered T cells. Exemplary target sites for the genetic edits may include exon 1, exon 2, exon 3, exon 4, exon 5, or a combination thereof. In some examples, one or more genetic editing may occur in exon 4 and/or exon 5. Such genetic editing may be induced by a gene editing technology, (e.g., the CRISPR/Cas technology) using a suitable guide RNA, for example, those listed in Table 39. The resultant edited TGFBRII gene using a gRNA listed in Table 39 may comprise one or more edited sequences provided in Tables 40-48 below.

CD70 Gene Editing

T cell exhaustion is a process of stepwise and progressive loss of T cell functions, which may be induced by prolonged antigen stimulation or other factors. Genes involved in T cell exhaustion refer to those that either positively regulate or negatively regulate this biological process. The genetically engineered T cells disclosed herein may comprise genetic editing of a gene that positively regulates T cell exhaustion to disrupt its expression. Alternatively or in addition, the genetically engineered T cells may comprise genetic editing of a gene that negatively regulates T cell exhaustion to enhance its expression and/or biologic activity of the gene product.

In some embodiments, the genetically engineered T cells may comprise an edited gene involved in T cell exhaustion, e.g., disruption of a gene that positively regulates T cell exhaustion. Such a gene may be a Cluster of Differentiation 70 (CD70) gene. CD70 is a member of the tumor necrosis factor superfamily and its expression is restricted to activated T and B lymphocytes and mature dendritic cells. CD70 is implicated in tumor cell and regulatory T cell survival through interaction with its ligand, CD27. CD70 and its receptor CD27 have multiple roles in immune function in multiple cell types including T cells (activated and $T_{reg}$ cells), and B cells.

It was also found that disrupting the CD70 gene in immune cells engineered to express an antigen targeting moiety enhanced anti-tumor efficacy against large tumors and induced a durable anti-cancer memory response. Specifically, the anti-cancer memory response prevented tumor growth upon re-challenge. Further, it has been demonstrated disrupting the CD70 gene results in enhanced cytotoxicity of immune cells engineered to express an antigen targeting moiety at lower ratios of engineered immune cells to target cells, indicating the potential efficacy of low doses of engineered immune cells. See, e.g., WO2019/215500, the relevant disclosures of which are incorporated by reference for the purpose and subject matter referenced herein.

Structures of CD70 genes are known in the art. For example, human CD70 gene is located on chromosome 19p13.3. The gene contains four protein encoding exons. Additional information can be found in GenBank under Gene ID: 970.

In some examples, the genetically engineered T cells may comprise a disrupted CD70 gene such that the expression of CD70 in the T cells is substantially reduced or eliminated completely. The disrupted CD70 gene may comprise one or more genetic edits at one or more suitable target sites (e.g., in coding regions or in non-coding regulatory regions such as promoter regions) that disrupt expression of the CD70 gene. Such target sites may be identified based on the gene editing approach for use in making the genetically engineered T cells. Exemplary target sites for the genetic edits may include exon 1, exon 2, exon 3, exon 4, or a combination thereof. See also WO2019/215500, the relevant disclosures of which are incorporated by reference for the purpose and subject matter referenced herein.

In some embodiments, the gRNA targeting CD70 listed in Table 23 (CD70-7) may be used for disrupting the CD70 gene via CRISPR/Cas9 gene editing. In some examples, an edited CD70 gene may comprise a nucleotide sequence selected from the following sequences in Table 26.

β2M Gene Edit

In some embodiments, the genetically engineered T cells disclosed herein may further comprise a disrupted β2M gene. β2M is a common (invariant) component of MHC I complexes. Disrupting its expression by gene editing will prevent host versus therapeutic allogeneic T cells responses leading to increased allogeneic T cell persistence. In some embodiments, expression of the endogenous β2M gene is eliminated to prevent a host-versus-graft response.

In some embodiments, an edited β2M gene may comprise a nucleotide sequence selected from the following sequences in Table 25. It is known to those skilled in the art that different nucleotide sequences in an edited gene such as an edited β2M gene (e.g., those in Table 25) may be generated by a single gRNA such as the one listed in Table 23 (β2M-1). See also WO2019097305, the relevant disclosures of which are incorporated by reference for the subject matter and purpose referenced herein.

The genetically engineered T cells disclosed herein may further comprise one or more additional gene edits (e.g., gene knock-in or knock-out) to improve T cell function. Examples include knock-in or knock-out genes to improve target cell lysis, knock-in or knock-out genes to enhance performance of therapeutic T cells such as CAR-T cells prepared from the genetically engineered T cells.

TRAC Gene Edit

In some embodiments, the genetically engineered T cells as disclosed herein may further comprise a disrupted TRAC gene. This disruption leads to loss of function of the TCR and renders the engineered T cell non-alloreactive and suitable for allogeneic transplantation, minimizing the risk of graft versus host disease. In some embodiments, expression of the endogenous TRAC gene is eliminated to prevent a graft-versus-host response. See also WO2019097305, the relevant disclosures of which are incorporated by reference herein for the purpose and subject matter referenced herein.

In some embodiments, an edited TRAC gene may comprise a nucleotide sequence selected from the following sequences in Table 24. It is known to those skilled in the art that different nucleotide sequences in an edited gene such as an edited TRAC gene (e.g., those in Table 24) may be generated by a single gRNA such as the one listed in Table 23 (TA-1).

It should be understood that more than one suitable target site/gRNA can be used for each target gene disclosed herein, for example, those known in the art or disclosed herein. Additional examples can be found in, e.g., WO2019097305, the relevant disclosures of which are incorporated by reference herein for the purpose and subject matter referenced herein.

(b) Exemplary Improved Features of Genetically Engineered T Cells Disclosed Herein Any of the genetically engineered T cell having a disrupted Reg1 gene, and optionally one or more additional genetic edits, for example, a disrupted CD70 gene, a disrupted TRAC gene, a disrupted β2M gene, a CAR-coding nucleic acid insertion, or a combination thereof, may be expandable in culture for greater than 4 weeks, for example, greater than 5 weeks, greater than 6 weeks, greater than 8 weeks, and greater than 10 weeks. In some examples, the genetically engineered T cells comprise a disrupted Reg1 (optionally, disruptions in CD70) and are expandable after 6 weeks (e.g., after 7 weeks, after 8 weeks, after 9 weeks, or after 10 weeks) in culture. Such genetically engineered T cells may maintain the ability to be activated after 6 weeks (e.g., after 7 weeks, after 8 weeks, after 9 weeks, or after 10 weeks) in culture. Further, such genetically engineered T cells have an increased expansion capacity, which can be at least 10-fold (e.g., at least 15-fold) higher than the non-engineered counterparts, i.e., T cells having the same genetic background as the engineered T cells disclosed herein except that the counterpart T cells have a wild-type Reg1 gene.

Further, the genetically engineered T cells disclosed herein may exhibit enhanced T cell persistence. "T cell persistence" as used herein refers to the tendency of T cells to continue to grow, proliferate, self-renew, expand, and maintain healthy activity in culture. In some instances, T cell persistence can be represented by the longevity that T cells can grow and expand in vitro, which can be measured by conventional methods and/or assays described herein. In other instances, T cell persistence can be represented by the reduction of cell death (e.g., apoptosis) or reduction in cell states characterized by exhaustion or replicative senescence. In yet other instances, T cell persistence can be presented by the maintenance of T cell activation capacity in culture.

Alternatively or in addition, the genetically engineered T cells disclosed may grow faster and longer than the non-engineered T cells, for example, as observed in vitro cell culture. In some instances, the genetically engineered T cells may grow at least 50% (e.g., at least 1-fold, at least 2-fold, at least 5-fold, or more) than the non-engineered T cells in a conventional in vitro T cell culture (e.g., as described in Examples below). In other instances, the genetically engineered T cells may maintain a high growth rate (e.g., having substantially the same growth rate or with only a slight reduction) in vitro for at least 20 days (e.g., at least 25 days, at least 30 days, at least 35 days, at least 40 days, at least 45 days, at least 50 days, or longer).

In addition, the genetically engineered T cells may exhibit a reduced level of cell exhaustion as relative to the non-engineered T cell counterpart. In some instances, a reduced level of cell exhaustion is reflected by a higher level of central memory T cells in the whole T cell population. The population of genetically engineered T cells disclosed may comprise a higher number of central memory T cells as compared to non-engineered T cell counterparts. For example, in some instances the population of genetically engineered T cells include a higher number of central memory T cells that are characterized by enhanced expression of CD27 and/or CD45RO as compared to non-engineered T cell counterparts. In some instances, the population of genetically engineered T cells disclosed exhibit reduced T cell exhaustion, which is characterized, for example, by reduced expression of PD-1 and/or TIM3 as compared to non-engineered T cell counterparts.

Any of the genetically engineered T cell having a disrupted TGFBRII gene, and optionally one or more additional genetic edits, for example, a disrupted CD70 gene, a disrupted TRAC gene, a disrupted β2M gene, a CAR-coding nucleic acid insertion, or a combination thereof, may have improved growth and expansion activities, both in vitro and in vivo, as compared with the non-engineered counterpart, which refers to T cells having the same genetic background except for an undisrupted TGFBRII gene. Further, such genetically engineered T cells (e.g., CAR-T cells) may exhibit enhanced cytotoxicity activity, for example, against undesired cells (e.g., tumor cells) expressing an antigen targeted by the CAR expressed in the CAR-T cells, as compared with the non-engineered counterpart. Such genetically engineered T cells (e.g., CAR-T cells) may also be resistant to inhibitory effects mediated by the TGFβ signaling and/or by fibroblast (e.g., in TME). For example, the genetically engineered T cells with a disrupted TGFBRII gene may be resistant to inhibitory factors secreted by fibroblasts.

In some embodiments, the genetically engineered T cells may further comprise one or more disrupted genes (e.g., CD70, Reg1, or a combination thereof) to improve T cell persistency. "T cell persistence" as used herein refers to the tendency of T cells to continue to grow, proliferate, self-renew, expand, and maintain healthy activity in culture. In some instances, T cell persistence can be represented by the longevity that T cells can grow and expand in vitro, which can be measured by conventional methods and/or assays described herein. In other instances, T cell persistence can be represented by the reduction of cell death (e.g., apoptosis) or reduction in cell states characterized by exhaustion or replicative senescence. In yet other instances, T cell persistence can be presented by the maintenance of T cell activation capacity in culture.

For example, such genetically engineered T cells may be expandable in culture for greater than 4 weeks, for example, greater than 5 weeks, greater than 6 weeks, greater than 8 weeks, and greater than 10 weeks. In some examples, the genetically engineered T cells comprise a disrupted TGFBRII gene, and a disrupted CD70 gene, Reg1 gene, or both may be expandable after 6 weeks (e.g., after 7 weeks, after 8 weeks, after 9 weeks, or after 10 weeks) in culture. Such genetically engineered T cells may maintain the ability to be activated after 6 weeks (e.g., after 7 weeks, after 8 weeks, after 9 weeks, or after 10 weeks) in culture. Such genetically engineered T cells may exhibit more improved growth and expansion capacity relative to the T cells having the same genetic background except for an undisrupted TGFBRII gene, and an undisrupted CD70 gene and/or Reg1 gene.

In addition, any of the genetically engineered T cell having a disrupted TGFBRII gene and a disrupted Reg1 gene, and optionally one or more additional genetic edits, for example, a disrupted CD70 gene, a disrupted TRAC gene, a disrupted β2M gene, a CAR-coding nucleic acid insertion, or a combination thereof, may have expansion advantage (e.g., in vivo) over counterpart T cells, i.e., having the disrupted TGFBRII gene or the disrupted Reg1 gene (but not both), as well as the other additional genetic edits. CAR-T cells having disruptions of both the TGFBRII gene and the Reg1 gene were found to be more potent in cancer treatment than the counterpart T cells as observed in xenograft mouse models. Accordingly, CAR-T cells having disruptions of both the TGFBRII gene and the Reg1 gene would be expected to show superior cancer treatment efficacy.

(c) Methods of Making Genetically Engineered T Cells

The genetically engineered T cells disclosed herein can be prepared by genetic editing of parent T cells or precursor cells thereof via a conventional gene editing method or those described herein.

(a) T Cells

In some embodiments, T cells can be derived from one or more suitable mammals, for example, one or more human donors. T cells can be obtained from a number of sources, including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In some examples, T cells can be isolated from a mixture of immune cells (e.g., those described herein) to produce an isolated T cell population. For example, after isolation of peripheral blood mononuclear cells (PBMC), both cytotoxic and helper T lymphocytes can be sorted into naive, memory, and effector T cell subpopulations either before or after activation, expansion, and/or genetic modification.

A specific subpopulation of T cells, expressing one or more of the following cell surface markers: TCRab, CD3, CD4, CD8, CD27 CD28, CD38 CD45RA, CD45RO, CD62L, CD127, CD122, CD95, CD197, CCR7, KLRG1, MCH-I proteins and/or MCH-II proteins, can be further isolated by positive or negative selection techniques. In some embodiments, a specific subpopulation of T cells, expressing one or more of the markers selected from the group consisting of TCRab, CD4 and/or CD8, is further isolated by positive or negative selection techniques. In some embodiments, subpopulations of T cells may be isolated by positive or negative selection prior to genetic engineering and/or post genetic engineering.

An isolated population of T cells may express one or more of the T cell markers, including, but not limited to a CD3+, CD4+, CD8+, or a combination thereof. In some embodiments, the T cells are isolated from a donor, or subject, and first activated and stimulated to proliferate in vitro prior to undergoing gene editing.

In some instances, the T cell population comprises primary T cells isolated from one or more human donors. Such T cells are terminally differentiated, not transformed, depend on cytokines and/or growth factors for growth, and/or have stable genomes.

Alternatively, the T cells may be derived from stem cells (e.g., HSCs or iPSCs) via in vitro differentiation.

T cells from a suitable source can be subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041. In some embodiments, T cells can be activated and expanded for about 1 day to about 4 days, about 1 day to about 3 days, about 1 day to about 2 days, about 2 days to about 3 days, about 2 days to about 4 days, about 3 days to about 4 days, or about 1 day, about 2 days, about 3 days, or about 4 days prior to introduction of the genome editing compositions into the T cells.

In some embodiments, T cells are activated and expanded for about 4 hours, about 6 hours, about 12 hours, about 18 hours, about 24 hours, about 36 hours, about 48 hours, about 60 hours, or about 72 hours prior to introduction of the gene editing compositions into the T cells. In some embodiments, T cells are activated at the same time that genome editing compositions are introduced into the T cells. In some instances, the T cell population can be expanded and/or activated after the genetic editing as disclosed herein. T cell populations or isolated T cells generated by any of the gene editing methods described herein are also within the scope of the present disclosure.

(b) Gene Editing Methods

Any of the genetically engineered T cells can be prepared using conventional gene editing methods or those described herein to edit one or more of the target genes disclosed herein (targeted editing). Targeted editing can be achieved either through a nuclease-independent approach, or through a nuclease-dependent approach. In the nuclease-independent targeted editing approach, homologous recombination is guided by homologous sequences flanking an exogenous polynucleotide to be introduced into an endogenous sequence through the enzymatic machinery of the host cell. The exogenous polynucleotide may introduce deletions, insertions or replacement of nucleotides in the endogenous sequence.

Alternatively, the nuclease-dependent approach can achieve targeted editing with higher frequency through the specific introduction of double strand breaks (DSBs) by specific rare-cutting nucleases (e.g., endonucleases). Such nuclease-dependent targeted editing also utilizes DNA repair mechanisms, for example, non-homologous end joining (NHEJ), which occurs in response to DSBs. DNA repair by NHEJ often leads to random insertions or deletions (indels) of a small number of endogenous nucleotides. In contrast to NHEJ mediated repair, repair can also occur by a homology directed repair (HDR). When a donor template containing exogenous genetic material flanked by a pair of homology arms is present, the exogenous genetic material can be introduced into the genome by HDR, which results in targeted integration of the exogenous genetic material.

In some embodiments, gene disruption may occur by deletion of a genomic sequence using two guide RNAs. Methods of using CRISPR-Cas gene editing technology to create a genomic deletion in a cell (e.g., to knock out a gene in a cell) are known (Bauer D E et al. Vis. Exp. 2015; 95:e52118).

Available endonucleases capable of introducing specific and targeted DSBs include, but not limited to, zinc-finger nucleases (ZFN), transcription activator-like effector nucleases (TALEN), and RNA-guided CRISPR-Cas9 nuclease (CRISPR/Cas9; Clustered Regular Interspaced Short Palindromic Repeats Associated 9). Additionally, DICE (dual integrase cassette exchange) system utilizing phiC31 and Bxb1 integrases may also be used for targeted integration. Some exemplary approaches are disclosed in detail below.

CRISPR-Cas9 Gene Editing System

The CRISPR-Cas9 system is a naturally-occurring defense mechanism in prokaryotes that has been repurposed as an RNA-guided DNA-targeting platform used for gene editing. It relies on the DNA nuclease Cas9, and two noncoding RNAs, crisprRNA (crRNA) and trans-activating RNA (tracrRNA), to target the cleavage of DNA. CRISPR is an abbreviation for Clustered Regularly Interspaced Short Palindromic Repeats, a family of DNA sequences found in the genomes of bacteria and archaea that contain fragments of DNA (spacer DNA) with similarity to foreign DNA previously exposed to the cell, for example, by viruses that have infected or attacked the prokaryote. These fragments of DNA are used by the prokaryote to detect and destroy similar foreign DNA upon re-introduction, for example, from similar viruses during subsequent attacks. Transcription of the CRISPR locus results in the formation of an RNA molecule comprising the spacer sequence, which associates with and targets Cas (CRISPR-associated) proteins able to recognize and cut the foreign, exogenous DNA. Numerous types and classes of CRISPR/Cas systems have been described (see, e.g., Koonin et al., (2017) Curr Opin Microbiol 37:67-78).

crRNA drives sequence recognition and specificity of the CRISPR-Cas9 complex through Watson-Crick base pairing typically with a 20 nucleotide (nt) sequence in the target DNA. Changing the sequence of the 5' 20 nt in the crRNA allows targeting of the CRISPR-Cas9 complex to specific loci. The CRISPR-Cas9 complex only binds DNA sequences that contain a sequence match to the first 20 nt of the crRNA, if the target sequence is followed by a specific short DNA motif (with the sequence NGG) referred to as a protospacer adjacent motif (PAM).

tracrRNA hybridizes with the 3' end of crRNA to form an RNA-duplex structure that is bound by the Cas9 endonuclease to form the catalytically active CRISPR-Cas9 complex, which can then cleave the target DNA.

Once the CRISPR-Cas9 complex is bound to DNA at a target site, two independent nuclease domains within the Cas9 enzyme each cleave one of the DNA strands upstream of the PAM site, leaving a double-strand break (DSB) where both strands of the DNA terminate in a base pair (a blunt end).

After binding of CRISPR-Cas9 complex to DNA at a specific target site and formation of the site-specific DSB, the next key step is repair of the DSB. Cells use two main DNA repair pathways to repair the DSB: non-homologous end joining (NHEJ) and homology-directed repair (HDR).

NHEJ is a robust repair mechanism that appears highly active in the majority of cell types, including non-dividing cells. NHEJ is error-prone and can often result in the removal or addition of between one and several hundred nucleotides at the site of the DSB, though such modifications are typically <20 nt. The resulting insertions and deletions (indels) can disrupt coding or noncoding regions of genes. Alternatively, HDR uses a long stretch of homologous donor DNA, provided endogenously or exogenously, to repair the DSB with high fidelity. HDR is active only in dividing cells, and occurs at a relatively low frequency in most cell types. In many embodiments of the present disclosure, NHEJ is utilized as the repair operant.

Endonuclease for Use in CRISPR

In some embodiments, the Cas9 (CRISPR associated protein 9) endonuclease is used in a CRISPR method for making the genetically engineered T cells as disclosed herein. The Cas9 enzyme may be one from *Streptococcus pyogenes*, although other Cas9 homologs may also be used. It should be understood, that wild-type Cas9 may be used or modified versions of Cas9 may be used (e.g., evolved versions of Cas9, or Cas9 orthologues or variants), as provided herein. In some embodiments, Cas9 may be substituted with another RNA-guided endonuclease, such as Cpf1 (of a class II CRISPR/Cas system).

In some embodiments, the CRISPR/Cas system comprises components derived from a Type-I, Type-II, or Type-III system. Updated classification schemes for CRISPR/Cas loci define Class 1 and Class 2 CRISPR/Cas systems, having Types I to V or VI (Makarova et al., (2015) Nat Rev Microbiol, 13(11):722-36; Shmakov et al., (2015) Mol Cell, 60:385-397). Class 2 CRISPR/Cas systems have single protein effectors. Cas proteins of Types II, V, and VI are single-protein, RNA-guided endonucleases, herein called "Class 2 Cas nucleases." Class 2 Cas nucleases include, for example, Cas9, Cpf1, C2c1, C2c2, and C2c3 proteins. The Cpf1 nuclease (Zetsche et al., (2015) Cell 163:1-13) is homologous to Cas9, and contains a RuvC-like nuclease domain.

In some embodiments, the Cas nuclease is from a Type-II CRISPR/Cas system (e.g., a Cas9 protein from a CRISPR/Cas9 system). In some embodiments, the Cas nuclease is from a Class 2 CRISPR/Cas system (a single-protein Cas nuclease such as a Cas9 protein or a Cpf1 protein). The Cas9 and Cpf1 family of proteins are enzymes with DNA endonuclease activity, and they can be directed to cleave a desired nucleic acid target by designing an appropriate guide RNA, as described further herein.

In some embodiments, a Cas nuclease may comprise more than one nuclease domain. For example, a Cas9 nuclease may comprise at least one RuvC-like nuclease domain (e.g., Cpf1) and at least one HNH-like nuclease domain (e.g., Cas9). In some embodiments, the Cas9 nuclease introduces a DSB in the target sequence. In some embodiments, the Cas9 nuclease is modified to contain only one functional nuclease domain. For example, the Cas9 nuclease is modified such that one of the nuclease domains is mutated or fully or partially deleted to reduce its nucleic acid cleavage activity. In some embodiments, the Cas9 nuclease is modified to contain no functional RuvC-like nuclease domain. In other embodiments, the Cas9 nuclease is modified to contain no functional HNH-like nuclease domain. In some embodiments in which only one of the nuclease domains is functional, the Cas9 nuclease is a nickase that is capable of introducing a single-stranded break (a "nick") into the target sequence. In some embodiments, a conserved amino acid within a Cas9 nuclease domain is substituted to reduce or alter a nuclease activity. In some embodiments, the Cas nuclease nickase comprises an amino acid substitution in the RuvC-like nuclease domain. Exemplary amino acid substitutions in the RuvC-like nuclease domain include D10A (based on the *S. pyogenes* Cas9 nuclease). In some embodiments, the nickase comprises an amino acid substitution in the HNH-like nuclease domain. Exemplary amino acid substitutions in the HNH-like nuclease domain include E762A, H840A, N863A, H983A, and D986A (based on the *S. pyogenes* Cas9 nuclease).

```
Amino acid sequence of Cas9 nuclease (SEQ ID NO:
1):
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLIP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNEDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL
```

-continued
TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD

In some embodiments, the Cas nuclease is from a Type-I CRISPR/Cas system. In some embodiments, the Cas nuclease is a component of the Cascade complex of a Type-I CRISPR/Cas system. For example, the Cas nuclease is a Cas3 nuclease. In some embodiments, the Cas nuclease is derived from a Type-III CRISPR/Cas system. In some embodiments, the Cas nuclease is derived from Type-IV CRISPR/Cas system. In some embodiments, the Cas nuclease is derived from a Type-V CRISPR/Cas system. In some embodiments, the Cas nuclease is derived from a Type-VI CRISPR/Cas system.

Guide RNAs (gRNAs)

The CRISPR technology involves the use of a genome-targeting nucleic acid that can direct the endonuclease to a specific target sequence within a target gene for gene editing at the specific target sequence. The genome-targeting nucleic acid can be a RNA. A genome-targeting RNA is referred to as a "guide RNA" or "gRNA" herein. A guide RNA comprises at least a spacer sequence that hybridizes to a target nucleic acid sequence within a target gene for editing, and a CRISPR repeat sequence.

In Type II systems, the gRNA also comprises a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex binds a site-directed polypeptide, such that the guide RNA and site-direct polypeptide form a complex. In some embodiments, the genome-targeting nucleic acid provides target specificity to the complex by virtue of its association with the site-directed polypeptide. The genome-targeting nucleic acid thus directs the activity of the site-directed polypeptide.

As is understood by the person of ordinary skill in the art, each guide RNA is designed to include a spacer sequence complementary to its genomic target sequence. See Jinek et al., Science, 337, 816-821 (2012) and Deltcheva et al., Nature, 471, 602-607 (2011).

In some embodiments, the genome-targeting nucleic acid (e.g., gRNA) is a double-molecule guide RNA. In some embodiments, the genome-targeting nucleic acid (e.g., gRNA) is a single-molecule guide RNA.

A double-molecule guide RNA comprises two strands of RNA molecules. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA (referred to as a "sgRNA") in a Type II system comprises, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins. A single-molecule guide RNA in a Type V system comprises, in the 5' to 3' direction, a minimum CRISPR repeat sequence and a spacer sequence.

A spacer sequence in a gRNA is a sequence (e.g., a 20 nucleotide sequence) that defines the target sequence (e.g., a DNA target sequences, such as a genomic target sequence) of a target gene of interest. In some embodiments, the spacer sequence range from 15 to 30 nucleotides. For example, the spacer sequence may contain 15, 16, 17, 18, 19, 29, 21, 22, 23, 24, 25, 26, 27, 28, 29, or 30 nucleotides. In some embodiments, a spacer sequence contains 20 nucleotides.

The "target sequence" is in a target gene that is adjacent to a PAM sequence and is the sequence to be modified by an RNA-guided nuclease (e.g., Cas9). The "target sequence" is on the so-called PAM-strand in a "target nucleic acid," which is a double-stranded molecule containing the PAM-strand and a complementary non-PAM strand. One of skill in the art recognizes that the gRNA spacer sequence hybridizes to the complementary sequence located in the non-PAM strand of the target nucleic acid of interest. Thus, the gRNA spacer sequence is the RNA equivalent of the target sequence. For example, if the target sequence is 5'-AGAGCAACAGTGCTGTGGCC-3' (SEQ ID NO: 69), then the gRNA spacer sequence is 5'-AGAGCAACAGUGCUGUGGCC-3' (SEQ ID NO: 61). The spacer of a gRNA interacts with a target nucleic acid of interest in a sequence-specific manner via hybridization (i.e., base pairing). The nucleotide sequence of the spacer thus varies depending on the target sequence of the target nucleic acid of interest.

In a CRISPR/Cas system herein, the spacer sequence is designed to hybridize to a region of the target nucleic acid that is located 5' of a PAM recognizable by a Cas9 enzyme used in the system. The spacer may perfectly match the target sequence or may have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence has 20 nucleotides in length. In some embodiments, the target nucleic acid has less than 20 nucleotides in length. In some embodiments, the target nucleic acid has more than 20 nucleotides in length. In some embodiments, the target nucleic acid has at least: 5, 10, 15, 16, 17, 18, 19, 20, 21, 22, 23, 24, 25, 30 or more nucleotides in length. In some embodiments, the target nucleic acid has at most: 5, 10, 15, 16, 17, 18, 19, 20, 21, 22, 23, 24, 25, 30 or more nucleotides in length. In some embodiments, the target nucleic acid sequence has 20 bases immediately 5' of the first nucleotide of the PAM. For example, in a sequence comprising 5'-NNNNNNNNNNNNNNNNNNNNNRG-3', the target nucleic acid can be the sequence that corresponds to the Ns, wherein N can be any nucleotide, and the underlined NRG sequence is the *S. pyogenes* PAM.

The guide RNA disclosed herein may target any sequence of interest via the spacer sequence in the crRNA. In some embodiments, the degree of complementarity between the spacer sequence of the guide RNA and the target sequence in the target gene can be about 60%, 65%, 70%, 75%, 80%, 85%, 90%, 95%, 97%, 98%, 99%, or 100%. In some embodiments, the spacer sequence of the guide RNA and the target sequence in the target gene is 100% complementary. In other embodiments, the spacer sequence of the guide RNA and the target sequence in the target gene may contain up to 10 mismatches, e.g., up to 9, up to 8, up to 7, up to 6, up to 5, up to 4, up to 3, up to 2, or up to 1 mismatch.

For any of the gRNA sequences provided herein, those that do not explicitly indicate modifications are meant to encompass both unmodified sequences and sequences having any suitable modifications.

The length of the spacer sequence in any of the gRNAs disclosed herein may depend on the CRISPR/Cas9 system and components used for editing any of the target genes also disclosed herein. For example, different Cas9 proteins from different bacterial species have varying optimal spacer sequence lengths. Accordingly, the spacer sequence may have 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the spacer sequence may have 18-24 nucleotides in length. In some embodiments, the targeting sequence may have 19-21 nucleotides in length. In some embodiments, the spacer sequence may comprise 20 nucleotides in length.

In some embodiments, the gRNA can be an sgRNA, which may comprise a 20 nucleotide spacer sequence at the 5' end of the sgRNA sequence. In some embodiments, the sgRNA may comprise a less than 20 nucleotide spacer sequence at the 5' end of the sgRNA sequence. In some embodiments, the sgRNA may comprise a more than 20 nucleotide spacer sequence at the 5' end of the sgRNA sequence. In some embodiments, the sgRNA comprises a variable length spacer sequence with 17-30 nucleotides at the 5' end of the sgRNA sequence. Examples are provided in Table 23 below. In these exemplary sequences, the fragment of "n" refers to the spacer sequence at the 5' end.

In some embodiments, the sgRNA comprises comprise no uracil at the 3' end of the sgRNA sequence. In other embodiments, the sgRNA may comprise one or more uracil at the 3' end of the sgRNA sequence. For example, the sgRNA can comprise 1-8 uracil residues, at the 3' end of the sgRNA sequence, e.g., 1, 2, 3, 4, 5, 6, 7, or 8 uracil residues at the 3' end of the sgRNA sequence.

Any of the gRNAs disclosed herein, including any of the sgRNAs, may be unmodified. Alternatively, it may contain one or more modified nucleotides and/or modified backbones. For example, a modified gRNA such as an sgRNA can comprise one or more 2'-O-methyl phosphorothioate nucleotides, which may be located at either the 5' end, the 3' end, or both.

In certain embodiments, more than one guide RNAs can be used with a CRISPR/Cas nuclease system. Each guide RNA may contain a different targeting sequence, such that the CRISPR/Cas system cleaves more than one target nucleic acid. In some embodiments, one or more guide RNAs may have the same or differing properties such as activity or stability within the Cas9 RNP complex. Where more than one guide RNA is used, each guide RNA can be encoded on the same or on different vectors. The promoters used to drive expression of the more than one guide RNA is the same or different.

In some embodiments, the gRNAs disclosed herein target a Reg1 gene, for example, target a site within exon 1, exon 2, exon 3, exon 4, exon 5, or exon 6 of the Reg1 gene. Such a gRNA may comprise a spacer sequence complementary (complete or partially) to the target sequences in exon 2 or exon 4 of a Reg1 gene, or a fragment thereof. Exemplary target sequences of Reg1 and exemplary gRNA sequences are provided in Table 22 below.

In some embodiments, the gRNAs disclosed herein target a TGFBRII gene, for example, target a site within exon 1, exon 2, exon 3, exon 4, exon 5, or exon 6 of the TGFBRII gene. Such a gRNA may comprise a spacer sequence complementary (complete or partially) to the target sequences in exon 4 or exon 5 of a TGFBRII gene, or a fragment thereof. Exemplary target sequences of TGFBRII and exemplary gRNA sequences are provided in Table 39 below.

In some embodiments, the gRNAs disclosed herein target a CD70 gene, for example, target a site within exon 1 or exon 3 of a CD70 gene. Such a gRNA may comprise a spacer sequence complementary (complete or partially) to the target sequences in exon 1 or exon 3 of a CD70 gene, or a fragment thereof. Exemplary target sequences in a CD70 gene and exemplary gRNAs specific to the CD70 gene are provided in Table 23 below.

In some embodiments, the gRNAs disclosed herein target a β2M gene, for example, target a suitable site within a β2M gene. See also WO2019097305, the relevant disclosures of which are incorporated by reference herein for the purpose and subject matter referenced herein. Other gRNA sequences may be designed using the β2M gene sequence located on Chromosome 15 (GRCh38 coordinates: Chromosome 15: 44,711,477-44,718,877; Ensembl: ENSG00000166710). In some embodiments, gRNAs targeting the β2M genomic region and RNA-guided nuclease create breaks in the β2M genomic region resulting in Indels in the β2M gene disrupting expression of the mRNA or protein.

In some embodiments, the gRNAs disclosed herein target a TRAC gene. See also WO2019097305, the relevant disclosures of which are incorporated by reference herein for the subject matter and purpose referenced herein. Other gRNA sequences may be designed using the TRAC gene sequence located on chromosome 14 (GRCh38: chromosome 14: 22,547,506-22,552,154; Ensembl; ENSG00000277734). In some embodiments, gRNAs targeting the TRAC genomic region and RNA-guided nuclease create breaks in the TRAC genomic region resulting Indels in the TRAC gene disrupting expression of the mRNA or protein.

Exemplary spacer sequences and gRNAs targeting a β2M gene or TRAC gene are provided in Table 23 below.

By way of illustration, guide RNAs used in the CRISPR/Cas/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

In some examples, the gRNAs of the present disclosure can be are produced in vitro transcription (IVT), synthetic and/or chemical synthesis methods, or a combination thereof. Enzymatic (IVT), solid-phase, liquid-phase, combined synthetic methods, small region synthesis, and ligation methods are utilized. In one embodiment, the gRNAs are made using IVT enzymatic synthesis methods. Methods of making polynucleotides by IVT are known in the art and are described in WO2013/151666. Accordingly, the present disclosure also includes polynucleotides, e.g., DNA, constructs and vectors are used to in vitro transcribe a gRNA described herein.

Various types of RNA modifications can be introduced during or after chemical synthesis and/or enzymatic generation of RNAs, e.g., modifications that enhance stability, reduce the likelihood or degree of innate immune response, and/or enhance other attributes, as described in the art. In some embodiments, non-natural modified nucleobases can be introduced into any of the gRNAs disclosed herein during synthesis or post-synthesis. In certain embodiments, modifications are on internucleoside linkages, purine or pyrimidine bases, or sugar. In some embodiments, a modification is introduced at the terminal of a gRNA with chemical synthesis or with a polymerase enzyme. Examples of modified nucleic acids and their synthesis are disclosed in WO2013/052523. Synthesis of modified polynucleotides is also described in Verma and Eckstein, Annual Review of Biochemistry, vol. 76, 99-134 (1998).

In some embodiments, enzymatic or chemical ligation methods can be used to conjugate polynucleotides or their regions with different functional moieties, such as targeting or delivery agents, fluorescent labels, liquids, nanoparticles, etc. Conjugates of polynucleotides and modified polynucleotides are reviewed in Goodchild, Bioconjugate Chemistry, vol. 1(3), 165-187 (1990).

In some embodiments of the present disclosure, a CRISPR/Cas nuclease system for use in genetically editing any of the target genes disclosed here may include at least one guide RNA. In some examples, the CRISPR/Cas nuclease system may contain multiple gRNAs, for example, 2, 3, or 4 gRNAs. Such multiple gRNAs may target different sites in a same target gene. Alternatively, the multiple gRNAs may target different genes. In some embodiments, the guide RNA(s) and the Cas protein may form a ribonucleoprotein (RNP), e.g., a CRISPR/Cas complex. The guide RNA(s) may guide the Cas protein to a target sequence(s) on one or more target genes as those disclosed herein, where the Cas protein cleaves the target gene at the target site. In some embodiments, the CRISPR/Cas complex is a Cpf1/guide RNA complex. In some embodiments, the CRISPR complex is a Type-II CRISPR/Cas9 complex. In some embodiments, the Cas protein is a Cas9 protein. In some embodiments, the CRISPR/Cas9 complex is a Cas9/guide RNA complex.

In some embodiments, the indel frequency (editing frequency) of a particular CRISPR/Cas nuclease system, comprising one or more specific gRNAs, may be determined using a TIDE analysis, which can be used to identify highly efficient gRNA molecules for editing a target gene. In some embodiments, a highly efficient gRNA yields a gene editing frequency of higher than 80%. For example, a gRNA is considered to be highly efficient if it yields a gene editing frequency of at least 80%, at least 85%, at least 90%, at least 95%, or 100%.

Delivery of Guide RNAs and Nucleases to T Cells

The CRISPR/Cas nuclease system disclosed herein, comprising one or more gRNAs and at least one RNA-guided nuclease, optionally a donor template as disclosed below, can be delivered to a target cell (e.g., a T cell) for genetic editing of a target gene, via a conventional method. In some embodiments, components of a CRISPR/Cas nuclease system as disclosed herein may be delivered to a target cell separately, either simultaneously or sequentially. In other embodiments, the components of the CRISPR/Cas nuclease system may be delivered into a target together, for example, as a complex. In some instances, gRNA and a RNA-guided nuclease can be pre-complexed together to form a ribonucleoprotein (RNP), which can be delivered into a target cell.

RNPs are useful for gene editing, at least because they minimize the risk of promiscuous interactions in a nucleic acid-rich cellular environment and protect the RNA from degradation. Methods for forming RNPs are known in the art. In some embodiments, an RNP containing an RNA-guided nuclease (e.g., a Cas nuclease, such as a Cas9 nuclease) and one or more gRNAs targeting one or more genes of interest can be delivered a cell (e.g., a T cell). In some embodiments, an RNP can be delivered to a T cell by electroporation.

In some embodiments, an RNA-guided nuclease can be delivered to a cell in a DNA vector that expresses the RNA-guided nuclease in the cell. In other examples, an RNA-guided nuclease can be delivered to a cell in an RNA that encodes the RNA-guided nuclease and expresses the nuclease in the cell. Alternatively or in addition, a gRNA targeting a gene can be delivered to a cell as a RNA, or a DNA vector that expresses the gRNA in the cell.

Delivery of an RNA-guided nuclease, gRNA, and/or an RNP may be through direct injection or cell transfection using known methods, for example, electroporation or chemical transfection. Other cell transfection methods may be used.

Other Gene Editing Methods

Besides the CRISPR method disclosed herein, additional gene editing methods as known in the art can also be used in making the genetically engineered T cells disclosed herein. Some examples include gene editing approaching involve zinc finger nuclease (ZFN), transcription activator-like effector nucleases (TALEN), restriction endonucleases, meganucleases homing endonucleases, and the like.

ZFNs are targeted nucleases comprising a nuclease fused to a zinc finger DNA binding domain (ZFBD), which is a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but not limited to, C2H2 zinc fingers, C3H zinc fingers, and C4 zinc fingers. A designed zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A selected zinc finger domain is a domain not found in nature whose production results primarily from an empirical process such as phage display, interaction trap or hybrid selection. ZFNs are described in greater detail in U.S. Pat. Nos. 7,888,121 and 7,972,854. The most recognized example of a ZFN is a fusion of the FokI nuclease with a zinc finger DNA binding domain.

A TALEN is a targeted nuclease comprising a nuclease fused to a TAL effector DNA binding domain. A "transcription activator-like effector DNA binding domain", "TAL effector DNA binding domain", or "TALE DNA binding domain" is a polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940. The most recognized example of a TALEN in the art is a fusion polypeptide of the FokI nuclease to a TAL effector DNA binding domain.

Additional examples of targeted nucleases suitable for use as provided herein include, but are not limited to, Bxb1, phiC31, R4, PhiBT1, and Wβ/SPBc/TP901-1, whether used individually or in combination.

Any of the nucleases disclosed herein may be delivered using a vector system, including, but not limited to, plasmid vectors, DNA minicircles, retroviral vectors, lentiviral vectors, adenovirus vectors, poxvirus vectors; herpesvirus vectors and adeno-associated virus vectors, and combinations thereof.

Conventional viral and non-viral based gene transfer methods can be used to introduce nucleic acids encoding nucleases and donor templates in cells (e.g., T cells). Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell.

Methods of non-viral delivery of nucleic acids include electroporation, lipofection, microinjection, biolistics, virosomes, liposomes, immunoliposomes, polycation or lipid: nucleic acid conjugates, naked DNA, naked RNA, capped RNA, artificial virions, and agent-enhanced uptake of DNA. Sonoporation using, e.g., the Sonitron 2000 system (Rich-Mar) can also be used for delivery of nucleic acids. Some specific examples are provided below.

II. Genetically Engineered T Cells Expression a Chimeric Antigen Receptor (CAR)

The genetically engineered T cells having a disrupted Reg1 gene, a disrupted TGFBRII gene, or a combination of disrupted Reg1 gene and disrupted TGFBRII gene. Optionally, such genetically engineered T cells may comprise one or more of additional disrupted genes, e.g., β2M, TRAC, CD70, or a combination thereof as disclosed herein, may further express a chimeric antigen receptor (CAR) targeting an antigen of interest or cells expressing such an antigen.

(a) Chimeric Antigen Receptor (CAR)

A chimeric antigen receptor (CAR) refers to an artificial immune cell receptor that is engineered to recognize and bind to an antigen expressed by undesired cells, for example, disease cells such as cancer cells. A T cell that expresses a CAR polypeptide is referred to as a CAR T cell. CARs have the ability to redirect T-cell specificity and reactivity toward a selected target in a non-MHC-restricted manner. The non-MHC-restricted antigen recognition gives CAR-T cells the ability to recognize an antigen independent of antigen processing, thus bypassing a major mechanism of tumor escape. Moreover, when expressed on T-cells, CARs advantageously do not dimerize with endogenous T-cell receptor (TCR) alpha and beta chains.

There are various generations of CARs, each of which contains different components. First generation CARs join an antibody-derived scFv to the CD3zeta (ζ or z) intracellular signaling domain of the T-cell receptor through hinge and transmembrane domains. Second generation CARs incorporate an additional co-stimulatory domain, e.g., CD28, 4-1BB (41BB), or ICOS, to supply a costimulatory signal. Third-generation CARs contain two costimulatory domains (e.g., a combination of CD27, CD28, 4-1BB, ICOS, or OX40) fused with the TCR CD3ζ chain. Maude et al., *Blood.* 2015; 125(26):4017-4023; Kakarla and Gottschalk, *Cancer J.* 2014; 20(2):151-155). Any of the various generations of CAR constructs is within the scope of the present disclosure.

Generally, a CAR is a fusion polypeptide comprising an extracellular domain that recognizes a target antigen (e.g., a single chain fragment (scFv) of an antibody or other antibody fragment) and an intracellular domain comprising a signaling domain of the T-cell receptor (TCR) complex (e.g., CD3ζ) and, in most cases, a co-stimulatory domain. (Enblad et al., Human Gene Therapy. 2015; 26(8):498-505). A CAR construct may further comprise a hinge and transmembrane domain between the extracellular domain and the intracellular domain, as well as a signal peptide at the N-terminus for surface expression. Examples of signal peptides include SEQ ID NO: 95 and SEQ ID NO: 96 as provided in Table 27 below. Other signal peptides may be used.

(i) Antigen Binding Extracellular Domain

The antigen-binding extracellular domain is the region of a CAR polypeptide that is exposed to the extracellular fluid when the CAR is expressed on cell surface. In some instances, a signal peptide may be located at the N-terminus to facilitate cell surface expression. In some embodiments, the antigen binding domain can be a single-chain variable fragment (scFv, which may include an antibody heavy chain variable region ($V_H$) and an antibody light chain variable region ($V_L$) (in either orientation). In some instances, the $V_H$ and $V_L$ fragment may be linked via a peptide linker. The linker, in some embodiments, includes hydrophilic residues with stretches of glycine and serine for flexibility as well as stretches of glutamate and lysine for added solubility. The scFv fragment retains the antigen-binding specificity of the parent antibody, from which the scFv fragment is derived. In some embodiments, the scFv may comprise humanized $V_H$ and/or $V_L$ domains. In other embodiments, the $V_H$ and/or $V_L$ domains of the scFv are fully human.

The antigen-binding extracellular domain may be specific to a target antigen of interest, for example, a pathologic antigen such as a tumor antigen. In some embodiments, a tumor antigen is a "tumor associated antigen," referring to an immunogenic molecule, such as a protein, that is generally expressed at a higher level in tumor cells than in non-tumor cells, in which it may not be expressed at all, or only at low levels. In some embodiments, tumor-associated structures, which are recognized by the immune system of the tumor-harboring host, are referred to as tumor-associated antigens. In some embodiments, a tumor-associated antigen is a universal tumor antigen, if it is broadly expressed by most types of tumors. In some embodiments, tumor-associated antigens are differentiation antigens, mutational antigens, overexpressed cellular antigens or viral antigens. In some embodiments, a tumor antigen is a "tumor specific antigen" or "TSA," referring to an immunogenic molecule, such as a protein, that is unique to a tumor cell. Tumor specific antigens are exclusively expressed in tumor cells, for example, in a specific type of tumor cells.

In some embodiments, the antigen-binding extracellular domain can be a single-chain variable fragment (scFv) that binds a tumor antigen as disclosed herein. The scFv may comprise an antibody heavy chain variable region ($V_H$) and an antibody light chain variable region ($V_L$), which optionally may be connected via a flexible peptide linker. In some instances, the scFv may have the $V_H$ to $V_L$ orientation (from N-terminus to C-terminus). Alternatively the scFv may have the $V_L$ to $V_H$ orientation (from N-terminus to C-terminus).

Exemplary tumor antigens include, but are not limited to, CD19, BCMA, CD70, CD33, and PTK7. Any known antibodies specific to such tumor antigens, for example, those approved for marketing and those in clinical trials, can be used for making the CAR constructs disclosed herein. Non-limiting examples of CAR constructs are provided in WO2019097305 and WO2019215500, WO2020/095107, and International Patent Application No. PCT/IB2021/053849, the relevant disclosures of which are herein incorporated by reference for the purposes and subject matter referenced herein.

In some examples, the antigen-binding extracellular domain can be a single-chain variable fragment (scFv) that binds human CD19. In some instances, the anti-CD19 scFv may comprises (i) a heavy chain variable region ($V_H$) that comprises the same heavy chain complementary determining regions (CDRs) as those in SEQ ID NO: 124; and (ii) a light chain variable region ($V_L$) that comprises the same light chain CDRs as those in SEQ ID NO: 125. In some specific examples, the anti-CD19 antibody discloses herein may comprise the heavy chain CDR1, heavy chain CDR2, and heavy chain CDR3 set forth as SEQ ID NOs: 108-110, respectively as determined by the Kabat method. Alternatively or in addition, the anti-CD19 antibody discloses herein may comprise the light chain CDR1, light chain CDR2, and light chain CDR3 set forth as SEQ ID NOs: 105-107 as determined by the Kabat method. Alternatively, the anti-CD19 antibody discloses herein may comprise the heavy chain CDR1, heavy chain CDR2, and heavy chain CDR3 set forth as SEQ ID NOs: 114-116, respectively as determined by the Chothia method. Alternatively or in addition, the anti-CD19 antibody discloses herein may comprise the light chain CDR1, light chain CDR2, and light chain CDR3 set forth as SEQ ID NOs:111-113 as determined by the Chothia method. In one specific example, the anti-CD19 scFv may comprise a $V_H$ comprising the amino acid sequence of SEQ ID NO: 124 and a $V_L$ comprises the amino acid sequence of SEQ ID NO: 125. See Sequence Table 27 below.

In some examples, the antigen-binding extracellular domain can be a single-chain variable fragment (scFv) that binds human CD70. In some instances, the anti-CD70 scFv may comprises (i) a heavy chain variable region ($V_H$) that comprises the same heavy chain complementary determining regions (CDRs) as those in SEQ ID NO: 143; and (ii) a light chain variable region ($V_L$) that comprises the same light chain CDRs as those in SEQ ID NO: 144. In some specific examples, the anti-CD70 antibody discloses herein may comprise the heavy chain CDR1, heavy chain CDR2, and heavy chain CDR3 set forth as SEQ ID NOs: 132, 134, and 136, respectively as determined by the Kabat method. Alternatively or in addition, the anti-CD70 antibody discloses herein may comprise the light chain CDR1, light chain CDR2, and light chain CDR3 set forth as SEQ ID NOs:127, 129, and 130, respectively as determined by the Kabat method. Alternatively, the anti-CD70 antibody discloses herein may comprise the heavy chain CDR1, heavy chain CDR2, and heavy chain CDR3 set forth as SEQ ID NOs: 133, 135, and 137, respectively as determined by the Chothia method. Alternatively or in addition, the anti-CD70 antibody discloses herein may comprise the light chain CDR1, light chain CDR2, and light chain CDR3 set forth as SEQ ID NO:128, LAS, and SEQ ID NO:131, respectively as determined by the Chothia method. In one specific example, the anti-CD70 scFv may comprise a $V_H$ comprising the amino acid sequence of SEQ ID NO: 143 and a $V_L$ comprises the amino acid sequence of SEQ ID NO: 144. See Sequence Table 27 below.

In some examples, the antigen-binding extracellular domain can be a single-chain variable fragment (scFv) that binds human BCMA. In some instances, the anti-BCMA scFv may comprises (i) a heavy chain variable region ($V_H$) that comprises the same heavy chain complementary determining regions (CDRs) as those in SEQ ID NO: 149; and (ii) a light chain variable region ($V_L$) that comprises the same light chain CDRs as those in SEQ ID NO: 150. In some specific examples, the anti-BCMA antibody discloses herein may comprise the heavy chain CDR1, heavy chain CDR2, and heavy chain CDR3 set forth as SEQ ID NOs: 155, 157, and 159, respectively as determined by the Kabat method. Alternatively or in addition, the anti-BCMA antibody discloses herein may comprise the light chain CDR1, light chain CDR2, and light chain CDR3 set forth as SEQ ID NOs:151, 152, and 153, respectively as determined by the Kabat method. Alternatively, the anti-BCMA antibody discloses herein may comprise the heavy chain CDR1, heavy chain CDR2, and heavy chain CDR3 set forth as SEQ ID NOs: 156, 158, and 160, respectively as determined by the Chothia method. Alternatively or in addition, the anti-BCMA antibody discloses herein may comprise the light chain CDR1, light chain CDR2, and light chain CDR3 set forth as SEQ ID NOs:151, 152, and 154, respectively as determined by the Chothia method. In one specific example, the anti-BCMA scFv may comprise a $V_H$ comprising the amino acid sequence of SEQ ID NO: 149 and a $V_L$ comprises the amino acid sequence of SEQ ID NO: 150. See Sequence Table 27 below.

In some examples, the antigen-binding extracellular domain can be a single-chain variable fragment (scFv) that binds human CD33. Exemplary anti-CD33 scFv and anti-CD33 CAR constructs can be found, for example, in Sequence Table 27 below and in WO2020/095107, the relevant disclosures of which are incorporated by reference for the subject matter and purpose noted herein.

In some examples, the antigen-binding extracellular domain can be a single-chain variable fragment (scFv) that binds human CD33. In some instances, the anti-CD33 scFv may comprises (i) a heavy chain variable region ($V_H$) that comprises the same heavy chain complementary determining regions (CDRs) as those in SEQ ID NO: 334; and (ii) a light chain variable region ($V_L$) that comprises the same light chain CDRs as those in SEQ ID NO: 335. In some specific examples, the anti-CD33 antibody discloses herein may comprise the heavy chain CDR1, heavy chain CDR2, and heavy chain CDR3 set forth as SEQ ID NOs: 328-330, respectively as determined by the Kabat method. Alternatively or in addition, the anti-CD33 antibody discloses herein may comprise the light chain CDR1, light chain CDR2, and light chain CDR3 set forth as SEQ ID NOs: 331-333, respectively as determined by the Kabat method. In one specific example, the anti-BCMA scFv may comprise a $V_H$ comprising the amino acid sequence of SEQ ID NO: 149 and a $V_L$ comprises the amino acid sequence of SEQ ID NO: 150. See Sequence Table 27 below.

In some examples, the antigen-binding extracellular domain can be a single-chain variable fragment (scFv) that binds human PTK7. In some instances, the anti-PTK7 scFv may comprises (i) a heavy chain variable region ($V_H$) that comprises the same heavy chain complementary determining regions (CDRs) as those in SEQ ID NO: 346; and (ii) a light chain variable region ($V_L$) that comprises the same light chain CDRs as those in SEQ ID NO: 347. In some specific examples, the anti-PTK7 antibody discloses herein may comprise the heavy chain CDR1, heavy chain CDR2, and heavy chain CDR3 set forth as SEQ ID NOs: 340-342, respectively as determined by the Kabat method. Alternatively or in addition, the anti-PTK7 antibody discloses herein may comprise the light chain CDR1, light chain CDR2, and light chain CDR3 set forth as SEQ ID NOs: 343-345, respectively as determined by the Kabat method. In one specific example, the anti-BCMA scFv may comprise a $V_H$ comprising the amino acid sequence of SEQ ID NO: 346 and a $V_L$ comprises the amino acid sequence of SEQ ID NO: 347. See Sequence Table 27 below.

Two antibodies having the same $V_H$ and/or $V_L$ CDRs means that their CDRs are identical when determined by the same approach (e.g., the Kabat approach, the Chothia approach, the AbM approach, the Contact approach, or the IMGT approach as known in the art. See, e.g., bioinf.org.uk/abs/ or abysis.org/abysis/sequence_input).

(ii) Transmembrane Domain

The CAR polypeptide disclosed herein may contain a transmembrane domain, which can be a hydrophobic alpha helix that spans the membrane. As used herein, a "transmembrane domain" refers to any protein structure that is thermodynamically stable in a cell membrane, preferably a eukaryotic cell membrane. The transmembrane domain can provide stability of the CAR containing such.

In some embodiments, the transmembrane domain of a CAR as provided herein can be a CD8 transmembrane domain. In other embodiments, the transmembrane domain can be a CD28 transmembrane domain. In yet other embodiments, the transmembrane domain is a chimera of a CD8 and CD28 transmembrane domain. Other transmembrane domains may be used as provided herein. In some embodiments, the transmembrane domain is a CD8a transmembrane domain containing the sequence of SEQ ID NO: 97 as provided below in Table 27. Other transmembrane domains may be used.

(iii) Hinge Domain

In some embodiments, a hinge domain may be located between an extracellular domain (comprising the antigen binding domain) and a transmembrane domain of a CAR, or between a cytoplasmic domain and a transmembrane domain of the CAR. A hinge domain can be any oligopeptide or polypeptide that functions to link the transmembrane domain to the extracellular domain and/or the cytoplasmic domain in the polypeptide chain. A hinge domain may function to provide flexibility to the CAR, or domains thereof, or to prevent steric hindrance of the CAR, or domains thereof.

In some embodiments, a hinge domain may comprise up to 300 amino acids (e.g., 10 to 100 amino acids, or 5 to 20 amino acids). In some embodiments, one or more hinge domain(s) may be included in other regions of a CAR. In some embodiments, the hinge domain may be a CD8 hinge domain. Other hinge domains may be used.

(iv) Intracellular Signaling Domains

Any of the CAR constructs contain one or more intracellular signaling domains (e.g., CD3ζ, and optionally one or more co-stimulatory domains), which are the functional end of the receptor. Following antigen recognition, receptors cluster and a signal is transmitted to the cell.

CD3ζ is the cytoplasmic signaling domain of the T cell receptor complex. CD3ζ contains three (3) immunoreceptor tyrosine-based activation motif (ITAM)s, which transmit an activation signal to the T cell after the T cell is engaged with a cognate antigen. In many cases, CD3ζ provides a primary T cell activation signal but not a fully competent activation signal, which requires a co-stimulatory signaling.

In some embodiments, the CAR polypeptides disclosed herein may further comprise one or more co-stimulatory signaling domains. For example, the co-stimulatory domains of CD28 and/or 4-1BB may be used to transmit a full proliferative/survival signal, together with the primary signaling mediated by CD3ζ. In some examples, the CAR disclosed herein comprises a CD28 co-stimulatory molecule. In other examples, the CAR disclosed herein comprises a 4-1BB co-stimulatory molecule. In some embodiments, a CAR includes a CD3ζ signaling domain and a CD28 co-stimulatory domain. In other embodiments, a CAR includes a CD3ζ signaling domain and 4-1BB co-stimulatory domain. In still other embodiments, a CAR includes a CD3ζ signaling domain, a CD28 co-stimulatory domain, and a 4-1BB co-stimulatory domain.

Table 27 provides examples of signaling domains derived from 4-1BB, CD28 and CD3-zeta that may be used herein.

In specific examples, the anti-CD19 CAR disclosed herein may comprise the amino acid sequence of SEQ ID NO: 118, which may be encoded by the nucleotide sequence of SEQ ID NO: 117. Alternatively, the anti-CD19 CAR may be a mature form without the N-terminal signal peptide, e.g., comprising the amino acid sequence of SEQ ID NO:353.

In other examples, the anti-BCMA CAR disclosed herein may comprise the amino acid sequence of SEQ ID NO: 146, which may be encoded by the nucleotide sequence of SEQ ID NO: 145. Alternatively, the anti-CDBCMA CAR may be a mature form without the N-terminal signal peptide, e.g., comprising the amino acid sequence of SEQ ID NO:355.

In other examples, the anti-CD70 CAR disclosed herein may comprise the amino acid sequence of SEQ ID NO: 138, which may be encoded by the nucleotide sequence of SEQ ID NO: 141. Alternatively, the anti-CD70 CAR may be a mature form without the N-terminal signal peptide, e.g., comprising the amino acid sequence of SEQ ID NO:354.

In some examples, the anti-CD33 CAR disclosed herein may comprise the amino acid sequence of SEQ ID NO: 338 or 339. Alternatively, the anti-CD33 CAR may be a mature form without the N-terminal signal peptide, e.g., comprising the amino acid sequence of SEQ ID NO:356 or 357.

In some examples, the anti-PTK7 CAR disclosed herein may comprise the amino acid sequence of SEQ ID NO: 349 or 350. Alternatively, the anti-PTK7 CAR may be a mature form without the N-terminal signal peptide, e.g., comprising the amino acid sequence of SEQ ID NO:358 or 359.

See sequence Table 27 provided below.

(b) Delivery of CAR Construct to T Cells

In some embodiments, a nucleic acid encoding a CAR can be introduced into any of the genetically engineered T cells disclosed herein by methods known to those of skill in the art. For example, a coding sequence of the CAR may be cloned into a vector, which may be introduced into the genetically engineered T cells for expression of the CAR. A variety of different methods known in the art can be used to introduce any of the nucleic acids or expression vectors disclosed herein into an immune effector cell. Non-limiting examples of methods for introducing nucleic acid into a cell include: lipofection, transfection (e.g., calcium phosphate transfection, transfection using highly branched organic compounds, transfection using cationic polymers, dendrimer-based transfection, optical transfection, particle-based transfection (e.g., nanoparticle transfection), or transfection using liposomes (e.g., cationic liposomes)), microinjection, electroporation, cell squeezing, sonoporation, protoplast fusion, impalefection, hydrodynamic delivery, gene gun, magnetofection, viral transfection, and nucleofection.

In specific examples, a nucleic acid encoding a CAR construct can be delivered to a cell using an adeno-associated virus (AAV). AAVs are small viruses which integrate site-specifically into the host genome and can therefore deliver a transgene, such as CAR. Inverted terminal repeats (ITRs) are present flanking the AAV genome and/or the transgene of interest and serve as origins of replication. Also present in the AAV genome are rep and cap proteins which, when transcribed, form capsids which encapsulate the AAV genome for delivery into target cells. Surface receptors on these capsids which confer AAV serotype, which determines which target organs the capsids will primarily bind and thus what cells the AAV will most efficiently infect. There are twelve currently known human AAV serotypes. In some embodiments, the AAV for use in delivering the CAR-coding nucleic acid is AAV serotype 6 (AAV6).

Adeno-associated viruses are among the most frequently used viruses for gene therapy for several reasons. First, AAVs do not provoke an immune response upon administration to mammals, including humans. Second, AAVs are effectively delivered to target cells, particularly when consideration is given to selecting the appropriate AAV serotype. Finally, AAVs have the ability to infect both dividing and non-dividing cells because the genome can persist in the host cell without integration. This trait makes them an ideal candidate for gene therapy.

A nucleic acid encoding a CAR can be designed to insert into a genomic site of interest in the host T cells. In some embodiments, the target genomic site can be in a safe harbor locus.

In some embodiments, a nucleic acid encoding a CAR (e.g., via a donor template, which can be carried by a viral vector such as an adeno-associated viral (AAV) vector) can be designed such that it can insert into a location within a TRAC gene to disrupt the TRAC gene in the genetically engineered T cells and express the CAR polypeptide. Disruption of TRAC leads to loss of function of the endogenous TCR. For example, a disruption in the TRAC gene can be created with an endonuclease such as those described herein and one or more gRNAs targeting one or more TRAC genomic regions. Any of the gRNAs specific to a TRAC gene and the target regions disclosed herein can be used for this purpose.

In some examples, a genomic deletion in the TRAC gene and replacement by a CAR coding segment can be created by homology directed repair or HDR (e.g., using a donor template, which may be part of a viral vector such as an adeno-associated viral (AAV) vector). In some embodiments, a disruption in the TRAC gene can be created with an endonuclease as those disclosed herein and one or more gRNAs targeting one or more TRAC genomic regions, and inserting a CAR coding segment into the TRAC gene.

In some embodiments, a nucleic acid encoding a CAR (e.g., via a donor template, which can be carried by a viral vector such as an adeno-associated viral (AAV) vector) can be designed such that it can insert into a location within a β2M gene to disrupt the β2M gene in the genetically engineered T cells and express the CAR polypeptide. Disruption of β2M leads to loss of function of the endogenous MHC Class I complexes. For example, a disruption in the β2M gene can be created with an endonuclease such as those described herein and one or more gRNAs targeting one or more β2M genomic regions. Any of the gRNAs specific to a β2M gene and the target regions disclosed herein can be used for this purpose.

In some examples, a genomic deletion in the β2M gene and replacement by a CAR coding segment can be created by homology directed repair or HDR (e.g., using a donor template, which may be part of a viral vector such as an adeno-associated viral (AAV) vector). In some embodiments, a disruption in the β2M gene can be created with an endonuclease as those disclosed herein and one or more gRNAs targeting one or more β2M genomic regions, and inserting a CAR coding segment into the β2M gene.

In some embodiments, a nucleic acid encoding a CAR (e.g., via a donor template, which can be carried by a viral vector such as an adeno-associated viral (AAV) vector) can be designed such that it can insert into a location within a CD70 gene to disrupt the CD70 gene in the genetically engineered T cells and express the CAR polypeptide. Disruption of CD70 leads to loss of function of the endogenous CD70 protein. For example, a disruption in the CD70 gene can be created with an endonuclease such as those described herein and one or more gRNAs targeting one or more CD70 genomic regions. Any of the gRNAs specific to a CD70 gene and the target regions disclosed herein can be used for this purpose.

In some examples, a genomic deletion in the CD70 gene and replacement by a CAR coding segment can be created by homology directed repair or HDR (e.g., using a donor template, which may be part of a viral vector such as an adeno-associated viral (AAV) vector). In some embodiments, a disruption in the CD70 gene can be created with an endonuclease as those disclosed herein and one or more gRNAs targeting one or more CD70 genomic regions, and inserting a CAR coding segment into the CD70 gene.

In some embodiments, a nucleic acid encoding a CAR (e.g., via a donor template, which can be carried by a viral vector such as an adeno-associated viral (AAV) vector) can be designed such that it can insert into a location within a Reg1 gene to disrupt the Reg1 gene in the genetically engineered T cells and express the CAR polypeptide. Disruption of Reg1 leads to loss of function of the endogenous Reg1 protein. For example, a disruption in the Reg1 gene can be created with an endonuclease such as those described herein and one or more gRNAs targeting one or more Reg1 genomic regions. Any of the gRNAs specific to a Reg1 gene and the target regions disclosed herein can be used for this purpose.

In some examples, a genomic deletion in the Reg1 gene and replacement by a CAR coding segment can be created by homology directed repair or HDR (e.g., using a donor template, which may be part of a viral vector such as an adeno-associated viral (AAV) vector). In some embodiments, a disruption in the Reg1 gene can be created with an endonuclease as those disclosed herein and one or more gRNAs targeting one or more Reg1 genomic regions, and inserting a CAR coding segment into the Reg1 gene.

In some embodiments, a nucleic acid encoding a CAR (e.g., via a donor template, which can be carried by a viral vector such as an adeno-associated viral (AAV) vector) can be designed such that it can insert into a location within a TGFBRII gene to disrupt the TGFBRII gene in the genetically engineered T cells and express the CAR polypeptide. Disruption of Reg1 leads to loss of function of the endogenous TGFBRII receptor. For example, a disruption in the TGFBRII gene can be created with an endonuclease such as those described herein and one or more gRNAs targeting one or more TGFBRII genomic regions. Any of the gRNAs specific to a TGFBRII gene and the target regions disclosed herein can be used for this purpose.

In some examples, a genomic deletion in the TGFBRII gene and replacement by a CAR coding segment can be created by homology directed repair or HDR (e.g., using a donor template, which may be part of a viral vector such as an adeno-associated viral (AAV) vector). In some embodiments, a disruption in the TGFBRII gene can be created with an endonuclease as those disclosed herein and one or more gRNAs targeting one or more TGFBRII genomic regions, and inserting a CAR coding segment into the TGFBRII gene.

A donor template as disclosed herein can contain a coding sequence for a CAR. In some examples, the CAR-coding sequence may be flanked by two regions of homology to allow for efficient HDR at a genomic location of interest, for example, at a TRAC gene using a gene editing method known in the art. In some examples, a CRISPR-based method can be used. In this case, both strands of the DNA at the target locus can be cut by a CRISPR Cas9 enzyme guided by gRNAs specific to the target locus. HDR then occurs to repair the double-strand break (DSB) and insert the donor DNA coding for the CAR. For this to occur correctly, the donor sequence is designed with flanking residues which are complementary to the sequence surrounding the DSB site in the target gene (hereinafter "homology arms"), such as the TRAC gene. These homology arms serve as the template for DSB repair and allow HDR to be an essentially error-free mechanism. The rate of homology directed repair (HDR) is a function of the distance between the mutation and the cut site so choosing overlapping or nearby target sites is important. Templates can include extra sequences flanked by the homologous regions or can contain a sequence that differs from the genomic sequence, thus allowing sequence editing.

Alternatively, a donor template may have no regions of homology to the targeted location in the DNA and may be integrated by NHEJ-dependent end joining following cleavage at the target site.

A donor template can be DNA or RNA, single-stranded and/or double-stranded, and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl. Acad. Sci. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor template can be introduced into a cell as part of a vector molecule having additional sequences such as, for example, replication origins, promoters and genes encoding antibiotic resistance. Moreover, a donor template can be introduced into a cell as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

A donor template, in some embodiments, can be inserted at a site nearby an endogenous prompter (e.g., downstream or upstream) so that its expression can be driven by the endogenous promoter. In other embodiments, the donor template may comprise an exogenous promoter and/or enhancer, for example, a constitutive promoter, an inducible promoter, or tissue-specific promoter to control the expression of the CAR gene. In some embodiments, the exogenous promoter is an EF1α promoter, see, e.g., SEQ ID NO: 167 provided in Table 28 below. Other promoters may be used.

Furthermore, exogenous sequences may also include transcriptional or translational regulatory sequences, for example, promoters, enhancers, insulators, internal ribosome entry sites, sequences encoding 2A peptides and/or polyadenylation signals.

When needed, additional gene editing (e.g., gene knock-in or knock-out) can be introduced into therapeutic T cells as disclosed herein to improve T cell function and therapeutic efficacy. For example, if β2M disruption can be performed to reduce the risk of or prevent a host-versus-graft response. Other examples include knock-in or knock-out genes to improve target cell lysis, knock-in or knock-out genes to enhance performance of therapeutic T cells such as CAR-T cells.

In some embodiments, a donor template for delivering an anti-CD19 CAR may be an AAV vector inserted with a nucleic acid fragment comprising the coding sequence of the anti-CD19 CAR, and optionally regulatory sequences for expression of the anti-CD19 CAR (e.g., a promoter such as the EF1a promoter provided in the sequence Table), which can be flanked by homologous arms for inserting the coding sequence and the regulatory sequences into a genomic locus of interest. In some examples, the nucleic acid fragment is inserted in the endogenous TRAC gene locus, thereby disrupting expression of the TRAC gene. In specific examples, the nucleic acid may replace a fragment in the TRAC gene, for example, a fragment comprising the nucleotide sequence of SEQ ID NO: 69. In some specific examples, the donor template for delivering the anti-CD19 CAR may comprise a nucleotide sequence of SEQ ID NO: 117, which can be inserted into a disrupted TRAC gene, for example, replacing the fragment of SEQ ID NO: 69.

In some embodiments, a donor template for delivering an anti-BCMA CAR may be an AAV vector inserted with a nucleic acid fragment comprising the coding sequence of the anti-BCMA CAR, and optionally regulatory sequences for expression of the anti-BCMA CAR (e.g., a promoter such as the EF1a promoter provided in the sequence Table), which can be flanked by homologous arms for inserting the coding sequence and the regulatory sequences into a genomic locus of interest. In some examples, the nucleic acid fragment is inserted in the endogenous TRAC gene locus, thereby disrupting expression of the TRAC gene. In specific examples, the nucleic acid may replace a fragment in the TRAC gene, for example, a fragment comprising the nucleotide sequence of SEQ ID NO: 69. In some specific examples, the donor template for delivering the anti-BCMA CAR may comprise a nucleotide sequence of SEQ ID NO: 145, which can be inserted into a disrupted TRAC gene, for example, replacing the fragment of SEQ ID NO: 69.

In some embodiments, a donor template for delivering an anti-CD70 CAR may be an AAV vector inserted with a nucleic acid fragment comprising the coding sequence of the anti-CD70 CAR, and optionally regulatory sequences for expression of the anti-CD70 CAR (e.g., a promoter such as the EF1a promoter provided in the sequence Table), which can be flanked by homologous arms for inserting the coding sequence and the regulatory sequences into a genomic locus of interest. In some examples, the nucleic acid fragment is inserted in the endogenous TRAC gene locus, thereby disrupting expression of the TRAC gene. In specific examples, the nucleic acid may replace a fragment in the TRAC gene, for example, a fragment comprising the nucleotide sequence of SEQ ID NO: 69. In some specific examples, the donor template for delivering the anti-CD70 CAR may comprise a nucleotide sequence of SEQ ID NO: 139, which can be inserted into a disrupted TRAC gene, for example, replacing the fragment of SEQ ID NO: 69.

The genetically engineered T cells having a disrupted Reg1 gene, additional disrupted genes, e.g., β2M, TRAC, CD70, and further expressing a chimeric antigen receptor (CAR) can be produced by sequential targeting of the genes of interest. For example, in some embodiments, the Reg1 gene may be disrupted first, followed by disruption of TRAC and β2M genes and CAR insertion. In other embodiments, TRAC and β2M genes may be disrupted first, followed by CAR insertion and disruption of the Reg1 gene. Accordingly, in some embodiments, the genetically engineered T cells disclosed herein may be produced by multiple, sequential electroporation events with multiple RNPs targeting the genes of interest, e.g., Reg1, β2M, TRAC, CD70, etc.

In other embodiments, the genetically engineered CAR T cells disclosed herein may be produced by a single electroporation event with an RNP complex comprising an RNA-guided nuclease and multiple gRNAs targeting the genes of interest, e.g., Reg1, β2M, TRAC, CD70, etc.

(c) Exemplary Genetically Engineered T Cells Expression a Chimeric Antigen Receptor It should be understood that gene disruption encompasses gene modification through gene editing (e.g., using CRISPR/Cas gene editing to insert or delete one or more nucleotides). A disrupted gene may contain one or more mutations (e.g., insertion, deletion, or nucleotide substitution, etc.) relative to the wild-type counterpart so as to substantially reduce or completely eliminate the activity of the encoded gene product. The one or more mutations may be located in a non-coding region, for example, a promoter region, a regulatory region that regulates transcription or translation; or an intron region. Alternatively, the one or more mutations may be located in a coding region (e.g., in an exon). In some instances, the disrupted gene does not express or expresses a substantially reduced level of the encoded protein. In other instances, the disrupted gene expresses the encoded protein in a mutated form, which is either not functional or has substantially reduced activity. In some embodiments, a disrupted gene is a gene that does not encode functional protein. In some embodiments, a cell that comprises a disrupted gene does not express (e.g., at the cell surface) a detectable level (e.g. by antibody, e.g., by flow cytometry) of the protein encoded by the gene. A cell that does not express a detectable level of the protein may be referred to as a knockout cell. For example, a cell having a β2M gene edit may be considered a β2M knockout cell if β2M protein cannot be detected at the cell surface using an antibody that specifically binds β2M protein.

In some embodiments, a population of genetically engineered T cells disclosed herein express a CAR (e.g., anti-CD19, anti-BCMA, or anti-CD70 CAR), a disrupted Reg1 gene, a disrupted TGFBRII gene, a disrupted TRAC gene, and optionally a disrupted β2M gene, and optionally a disrupted CD70 gene. The nucleotide sequence encoding the CAR may be inserted in the disrupted TRAC gene (e.g., replacing the site targeted by a sgRNA such as TA-1). In some examples, such a population of genetically engineered T cells may comprise about 70-99% Reg1⁻ cells, for example about 90-97% Reg1⁻ cells, about 70-99% TGFBRII⁻ cells, e.g., for example about 80-89% TGFBRII⁻ cells, about 70-99% TCR⁻ cells, for example about 90-99% TCR⁻ cells, and/or optionally about 60-99% β2M⁻ cells, for example about 60-82% β2M⁻ cells, and/or optionally about 70-99% CD70⁻ cells, for example about 90-99% CD70⁻ cells. The cell population may also contain at least about 30%-50% (e.g., at least 60%) cells expressing the CAR.

i. Anti-CD19 CAR T Cells Having Reg1 and/or TGFBRII Gene Disruption

Also provided herein is population of genetically engineered immune cells (e.g., T cells such as human T cells) comprising a disrupted Reg1 gene, a disrupted TGFBRII gene, or a combination thereof, and expressing an anti-CD19 CAR, e.g., those disclosed herein. In some instances, the population of genetically engineered immune cells (e.g., T cells such as human T cells) comprising both a disrupted Reg1 gene and a disrupted TGFBRII gene, and expressing an anti-CD19 CAR, e.g., those disclosed herein. In some examples, the anti-CD19 CAR-T cells disclosed herein, which express any of the anti-CD19 CAR disclosed herein (e.g., the anti-CD19 CAR comprising the amino acid sequence of SEQ ID NO: 106), may also comprise a disrupted TRAC gene and/or a disrupted β2M gene as also disclosed herein.

In some examples, the population of genetically engineered T cells are anti-CD19 CAR cells that further comprise a disrupted Regnanse-1 gene. In some examples, anti-CD19 CAR cells are CD19-directed T cells having disrupted TRAC gene and β2M gene. The nucleic acid encoding the anti-CD19 CAR can be inserted in the disrupted TRAC gene at the site of SEQ ID NO: 69, which is replaced by the nucleic acid encoding the anti-CD19 CAR, thereby disrupting expression of the TRAC gene. The disrupted TRAC gene in the anti-CD19 CAR cells may comprise the nucleotide sequence of SEQ ID NO: 119.

Anti-CD19 CAR T cells that comprise a disrupted Reg1 gene can be produced via ex vivo genetic modification using the CRISPR/Cas9 (Clustered Regularly Interspaced Short Palindromic Repeats/CRISPR associated protein 9) technology to disrupt targeted genes (Reg1, optionally TRAC and/or β2M genes), and adeno-associated virus (AAV) transduction to deliver the anti-CD19 CAR construct. CRISPR-Cas9-mediated gene editing involves at least a sgRNA targeting Reg1 (e.g., REG1-Z03 (SEQ ID NO: 22), REG1-Z05 (SEQ ID NO: 30), REG1-Z06 (SEQ ID NO: 34) or REG1-Z10 (SEQ ID NO: 50)), and optionally TA-1 sgRNA (SEQ ID NO: 59), which targets the TRAC locus, and β2M-1 sgRNA (SEQ ID NO: 63), which targets the β2M locus. For any of the gRNA sequences provided herein, those that do not explicitly indicate modifications are meant to encompass both unmodified sequences and sequences having any suitable modifications.

Anti-CD19 CAR T cells that comprise a disrupted TGFBRII gene can be produced via ex vivo genetic modification using the CRISPR/Cas9 (Clustered Regularly Interspaced Short Palindromic Repeats/CRISPR associated protein 9) technology to disrupt targeted genes (TGFBRII, optionally TRAC and/or β2M genes), and adeno-associated virus (AAV) transduction to deliver the anti-CD19 CAR construct. CRISPR-Cas9-mediated gene editing involves at least a sgRNA targeting TGFBRII (e.g., those listed in Table 39, for example, TGFBRII_EX1_T2, TGFBRII_EX4_T1, TGFBRII_EX4_T2, TGFBRII_EX5_T1), and optionally TA-1 sgRNA (SEQ ID NO: 59), which targets the TRAC locus, and β2M-1 sgRNA (SEQ ID NO: 63), which targets the β2M locus.

Anti-CD19 CAR T cells that comprise both a disrupted TGFBRII gene and a disrupted Reg1 gene can be produced via ex vivo genetic modification using the CRISPR/Cas9 (Clustered Regularly Interspaced Short Palindromic Repeats/CRISPR associated protein 9) technology to disrupt targeted genes (TGFBRII and Reg1, optionally TRAC and/or 62M genes), and adeno-associated virus (AAV) transduction to deliver the anti-CD19 CAR construct. CRISPR-Cas9-mediated gene editing involves at least a sgRNA targeting TGFBRII (e.g., those listed in Table 39) and a sgRNA targeting Reg1 (e.g., those listed in Table 22), optionally TA-1 sgRNA (SEQ ID NO: 59), which targets the TRAC locus, and β2M-1 sgRNA (SEQ ID NO: 63), which targets the β2M locus.

The anti-CD19 CAR T cells are composed of an anti-CD19 single-chain antibody fragment (scFv, which may comprise the amino acid sequence of SEQ ID NO: 120), followed by a CD8 hinge and transmembrane domain (e.g., comprising the amino acid sequence of SEQ ID NO: 97) that is fused to an intracellular co-signaling domain of CD28 (e.g., SEQ ID NO: 101) and a CD3ζ signaling domain (e.g., SEQ ID NO: 103). In specific examples, the anti-CD19 CAR T cells comprises the amino acid sequence of SEQ ID NO: 118.

In some embodiments, at least 30% of a population of anti-CD19 CAR T cells express a detectable level of the anti-CD19 CAR. For example, at least 40%, at least 50%, at least 60%, at least 70%, at least 75%, at least 80%, at least 85%, at least 90%, or at least 95% of the anti-CD19 CAR T cells express a detectable level of the anti-CD19 CAR.

In some embodiments, at least 50% of a population of anti-CD19 CAR T cells may not express a detectable level of β2M surface protein. For example, at least 55%, at least 60%, at least 70%, at least 75%, at least 80%, at least 85%, at least 90%, or at least 95% of the anti-CD19 CAR T cells may not express a detectable level of β2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of β2M surface protein.

Alternatively or in addition, at least 50% of a population of anti-CD19 CAR T cells may not express a detectable level of TRAC surface protein. For example, at least 55%, at least 60%, at least 70%, at least 75%, at least 80%, at least 85%, at least 90%, or at least 95% of the anti-CD19 CAR T cells may not express a detectable level of TRAC surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of TRAC surface protein. In specific examples, more than 90% (e.g., more than 99.5%) of the anti-CD19 CAR T cells do not express a detectable TRAC surface protein.

In some embodiments, a substantial percentage of the population of anti-CD19 CAR T cells may comprise more than one gene edit, which results in a certain percentage of cells not expressing more than one gene and/or protein.

For example, at least 50% of a population of anti-CD19 CAR T cells may not express a detectable level of two surface proteins, e.g., does not express a detectable level of β2M and TRAC proteins. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the anti-CD19 CAR T cells do not express a detectable level of TRAC and β2M surface proteins. In another example, at least 50% of a population of the anti-CD19 CAR T cells do not express a detectable level of TRAC and β2M surface proteins.

In some embodiments, the population of anti-CD19 CAR T cells may comprise more than one gene edit (e.g., in more than one gene), which may be an edit described herein. For example, the population of anti-CD19 CAR T cells may comprise a disrupted TRAC gene via the CRISPR/Cas technology using the TA-1 TRAC gRNA. In some examples, the anti-CD19 CAR T cells may comprise a deletion in the TRAC gene relative to unmodified T cells. For example, the anti-CD19 CAR T cells may comprise a deletion of the fragment AGAGCAACAGTGCTGTGGCC (SEQ ID NO: 69) in the TRAC gene. This fragment can be replaced by the nucleic acid encoding the anti-CD19 CAR (e.g., SEQ ID NO: 117). Alternatively or in addition, the population of anti-CD19 CAR T cells may comprise a disrupted β2M gene via CRISPR/Cas9 technology using the gRNA of β2M-1. Such anti-CD19 CAR T cells may comprise Indels in the β2M gene, which comprise one or more of the nucleotide sequences of SEQ ID NOs: 83-88. In specific examples, anti-CD19 CAR T cells comprise ≥30% CAR⁺ T cells, ≤50% β2M⁺ cells, and ≤30% TCRαβ⁺ cells. In additional specific examples, anti-CD19 CAR T cells comprise ≥30% CAR⁺ T cells, ≤30% β2M⁺ cells, and ≤0.5% TCRαβ⁺ cells.

See also WO 2019/097305A2, and WO2019215500, the relevant disclosures of each of which are incorporated by reference for the subject matter and purpose referenced herein.

In specific examples, the genetically engineered T cell population may be the anti-CD19 CAR T cells disclosed herein that further comprise a disrupted Reg1 gene. The disrupted Reg 1 gene may comprise any of the sequences provided in Tables 29-38 below. In some examples, the anti-CD19 CAR T cells may comprise at least 80% Reg1⁻ cells, for example, at least 85%, at least 90%, at least 95%, at least 98% or above Reg1⁻ cells.

In specific examples, the genetically engineered T cell population may be the anti-CD19 CAR T cells disclosed herein that further comprise a disrupted TGFBRII gene. In some examples, the disrupted TGFBRII gene may comprise a nucleotide sequence selected from those listed in Tables 40-48 below. In some examples, the anti-CD19 CAR T cells may comprise at least 80% TGFBRII⁻ cells, for example, at least 85%, at least 90%, at least 95%, at least 98% or above TGFBRII⁻ cells.

In specific examples, the genetically engineered T cell population may be the anti-CD19 CAR T cells disclosed herein that further comprise a disrupted TGFBRII gene and a disrupted Reg1 gene. The disrupted Reg 1 gene may comprise any of the sequences provided in Tables 29-38 below. Alternatively or in addition, the disrupted TGFBRII gene may comprise a nucleotide sequence selected from those listed in Tables 40-48 below. In some examples, the anti-CD19 CAR T cells may comprise at least 80% TGFBRII⁻ cells, for example, at least 85%, at least 90%, at least 95%, at least 98% or above TGFBRII⁻ cells. Alternatively or in addition, the anti-CD19 CAR T cells may comprise at least 80% Reg1⁻ cells, for example, at least 85%, at least 90%, at least 95%, at least 98% or above Reg⁻ cells. In some examples, the anti-CD19 CAR T cells may comprise at least 60% Reg1⁻/TGFBRII⁻ cells, for example, at least 65%, at least 70%, at least 75%, at least 80%, at least 85%, at least 90%, at least 95%, at least 98% or above Reg1⁻/TGFBRII⁻ cells.

In some examples, such a population of genetically engineered T cells may comprise about 90-97% Reg1⁻ cells, about 80-89% TGFBRII⁻ cells, about 90-99% TCR⁻ cells, and/or about 60-82% β2M⁻ cells. The cell population may also contain at least 50% (e.g., at least 60%) cells expressing the anti-CD19 CAR.

ii Anti-BCMA CAR-T Cells Having Reg1 and/or TGFBRII Gene Disruption

Also provided herein is population of genetically engineered immune cells (e.g., T cells such as human T cells) comprising a disrupted Reg1 gene and expressing an anti-BCMA CAR, e.g., those disclosed herein. In some examples, the anti-BCMA CAR T cells disclosed herein, which express any of the anti-BCMA CAR disclosed herein (e.g., the anti-BCMA CAR comprising the amino acid sequence of SEQ ID NO: 146), may also comprise a disrupted TRAC gene and/or a disrupted β2M gene as also disclosed herein.

In some examples, the population of genetically engineered T cells are anti-BCMA CAR T cells that further comprise a disrupted Reg1 gene, a disrupted TGFBRII gene, or a combination thereof. In some instances, the population of genetically engineered immune cells (e.g., T cells such as human T cells) comprising both a disrupted Reg1 gene and a disrupted TGFBRII gene, and expressing an anti-BCMA CAR, e.g., those disclosed herein. In some examples anti-BCMA CAR T cells are anti-BCMA CAR T cells having disrupted TRAC gene and β2M gene. The nucleic acid encoding the anti-BCMA CAR can be inserted in the disrupted TRAC gene at the site of SEQ ID NO: 69, which is replaced by the nucleic acid encoding the anti-BCMA CAR, thereby disrupting expression of the TRAC gene. The disrupted TRAC gene in the anti-BCMA CAR T cells may comprise the nucleotide sequence of SEQ ID NO: 145.

Anti-BCMA CAR T cells that comprise a disrupted Reg1 gene can be produced via ex vivo genetic modification using the CRISPR/Cas9 (Clustered Regularly Interspaced Short Palindromic Repeats/CRISPR associated protein 9) technology to disrupt targeted genes (Reg1, and optionally TRAC and β2M genes), and adeno-associated virus (AAV) transduction to deliver the anti-BCMA CAR construct. CRISPR-Cas9-mediated gene editing involves at least three guide RNAs (sgRNAs), as described above for anti-CD19 CAR T cells.

Anti-BCMA CAR T cells that comprise a disrupted TGFBRII gene can be produced via ex vivo genetic modification using the CRISPR/Cas9 (Clustered Regularly Interspaced Short Palindromic Repeats/CRISPR associated protein 9) technology to disrupt targeted genes (TGFBRII, and optionally TRAC and β2M genes), and adeno-associated virus (AAV) transduction to deliver the anti-BCMA CAR construct. CRISPR-Cas9-mediated gene editing involves at least three guide RNAs (sgRNAs), as described above for anti-BCMA CAR T cells.

Anti-BCMA CAR T cells that comprise a disrupted Reg1 gene and a disrupted TGFBRII gene can be produced via ex vivo genetic modification using the CRISPR/Cas9 (Clustered Regularly Interspaced Short Palindromic Repeats/CRISPR associated protein 9) technology to disrupt targeted genes (TGFBRII and Reg1, and optionally TRAC and β2M genes), and adeno-associated virus (AAV) transduction to deliver the anti-BCMA CAR construct. CRISPR-Cas9-mediated gene editing involves at least three guide RNAs (sgRNAs), as described above for anti-BCMA CAR T cells.

The anti-BCMA CAR T cells are composed of an anti-BCMA single-chain antibody fragment (scFv, which may comprise the amino acid sequence of SEQ ID NO: 148), followed by a CD8 hinge and transmembrane domain (e.g., comprising the amino acid sequence of SEQ ID NO: 97) that is fused to an intracellular co-signaling domain of CD28 (e.g., SEQ ID NO: 101) and a CD3ζ signaling domain (e.g., SEQ ID NO: 103). In specific examples, the anti-BCMA CAR T cells comprises the amino acid sequence of SEQ ID NO: 146.

In some embodiments, at least 30% of a population of anti-BCMA CAR T cells express a detectable level of the anti-BCMA CAR. For example, at least 40%, at least 50%, at least 60%, at least 70%, at least 75%, at least 80%, at least 85%, at least 90%, or at least 95% of the anti-BCMA CAR T cells express a detectable level of the anti-BCMA CAR.

In some embodiments, at least 50% of a population of anti-BCMA CAR T cells may not express a detectable level of β2M surface protein. For example, at least 55%, at least 60%, at least 70%, at least 75%, at least 80%, at least 85%, at least 90%, or at least 95% of the anti-BCMA CAR T cells may not express a detectable level of β2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of β2M surface protein.

Alternatively or in addition, at least 50% of a population of anti-BCMA CAR T cells may not express a detectable level of TRAC surface protein. For example, at least 55%, at least 60%, at least 70%, at least 75%, at least 80%, at least 85%, at least 90%, or at least 95% of the anti-BCMA CAR T cells may not express a detectable level of TRAC surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of TRAC surface protein. In specific examples, more than 90% (e.g., more than 99.5%) of the anti-BCMA CAR T cells do not express a detectable TRAC surface protein.

In some embodiments, a substantial percentage of the population of anti-BCMA CAR T cells may comprise more than one gene edit, which results in a certain percentage of cells not expressing more than one gene and/or protein.

For example, at least 50% of a population of anti-BCMA CAR T cells may not express a detectable level of two surface proteins, e.g., does not express a detectable level of β2M and TRAC proteins. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the anti-BCMA CAR T cells do not express a detectable level of TRAC and β2M surface proteins. In another example, at least 50% of a population of anti-BCMA CAR T cells do not express a detectable level of TRAC and β2M surface proteins.

In some embodiments, the population of anti-BCMA CAR T cells may comprise more than one gene edit (e.g., in more than one gene), which may be an edit described herein. For example, the population of anti-BCMA CAR T cells may comprise a disrupted TRAC gene via the CRISPR/Cas technology using the TA-1 TRAC gRNA. In some examples, the anti-BCMA CAR T cells may comprise a deletion in the TRAC gene relative to unmodified T cells. For example, the anti-CD19 CAR T cells may comprise a deletion of the fragment AGAGCAACAGTGCTGTGGCC (SEQ ID NO: 69) in the TRAC gene. This fragment can be replaced by the nucleic acid encoding the anti-BCMA CAR (e.g., SEQ ID NO: 145). Alternatively or in addition, the population of anti-BCMA CAR T cells may comprise a disrupted β2M gene via CRISPR/Cas9 technology using the gRNA of β2M-1. Such anti-BCMA CAR T cells may comprise Indels in the β2M gene, which comprise one or more of the nucleotide sequences of SEQ ID NOs: 83-88. In specific examples, anti-BCMA CAR T cells comprise ≥30% CAR$^+$ T cells, ≤50% (β2M$^+$ cells, and ≤30% TCRαβ$^+$ cells. In additional specific examples, anti-BCMA CAR T cells comprise ≥30% CAR$^+$ T cells, ≤30% β2M$^+$ cells, and ≤0.5% TCRαβ$^+$ cells.

See also WO 2019/097305A2, and WO2019215500, the relevant disclosures of each of which are incorporated by reference for the subject matter and purpose referenced herein.

In specific examples, the genetically engineered T cell population may be the anti-BCMA CAR T cells disclosed herein that further comprise a disrupted Reg1 gene. The disrupted Regnase 1 (Reg1) gene may comprise any of the sequences provided in Tables 29-38 below. In some examples, the anti-BCMA CAR T cells may comprise at least 80% Reg1$^-$ cells, for example, at least 85%, at least 90%, at least 95%, at least 98% or above Reg1$^-$ cells.

In specific examples, the genetically engineered T cell population may be the anti-BCMA CAR T cells disclosed herein that further comprise a disrupted TGFBRII gene. In some examples, the disrupted TGFBRII gene may comprise a nucleotide sequence selected from those listed in Tables 40-48 below. In some examples, the anti-BCMA CAR T cells may comprise at least 80% TGFBRII$^-$ cells, for example, at least 85%, at least 90%, at least 95%, at least 98% or above TGFBRII$^-$ cells.

In specific examples, the genetically engineered T cell population may be the anti-BCMA CAR T cells disclosed herein that further comprise a disrupted TGFBRII gene and a disrupted Reg1 gene. The disrupted Reg 1 gene may comprise any of the sequences provided in Tables 29-38 below. Alternatively or in addition, the disrupted TGFBRII gene may comprise a nucleotide sequence selected from those listed in Tables 40-48 below. In some examples, the anti-BCMA CAR T cells may comprise at least 80% TGFBRII$^-$ cells, for example, at least 85%, at least 90%, at least 95%, at least 98% or above TGFBRII$^-$ cells. Alternatively or in addition, the anti-BCMA CAR T cells may comprise at least 80% Reg1$^-$ cells, for example, at least 85%, at least 90%, at least 95%, at least 98% or above Reg$^-$ cells. In some examples, the anti-BCMA CAR T cells may comprise at least 60% Reg1$^-$/TGFBRII$^-$ cells, for example, at least 65%, at least 70%, at least 75%, at least 80%, at least 85%, at least 90%, at least 95%, at least 98% or above Reg1$^-$/TGFBRII$^-$ cells.

iii. Anti-CD70 CAR-T Cells Having Reg1 and/or TGFBRII Gene Disruption

Also provided herein is population of genetically engineered immune cells (e.g., T cells such as human T cells) comprising a disrupted Reg1 gene, a disrupted TRFBRII gene, or a combination thereof, and expressing anti-CD70 CAR, e.g., those disclosed herein. In some instances, the population of genetically engineered immune cells (e.g., T cells such as human T cells) comprising both a disrupted Reg1 gene and a disrupted TGFBRII gene, and expressing an anti-CD70 CAR, e.g., those disclosed herein. In some examples, the anti-CD70 CAR T cells disclosed herein, which express any of the anti-CD70 CAR disclosed herein (e.g., the anti-CD70 CAR comprising the amino acid sequence of SEQ ID NO: 138), may also comprise a disrupted TRAC gene, a disrupted β2M gene, and/or a disrupted CD70 gene as also disclosed herein.

In some examples anti-CD70 CAR T cells are anti-CD70 CAR T cells having disrupted TRAC gene, a disrupted β2M gene, and a disrupted CD70 gene. The nucleic acid encoding the anti-CD70 CAR can be inserted in the disrupted TRAC gene at the site of SEQ ID NO: 69, which is replaced by the nucleic acid encoding the anti-CD70 CAR, thereby disrupting expression of the TRAC gene. The disrupted TRAC gene in the anti-CD70 CAR T cells may comprise the nucleotide sequence of SEQ ID NO: 139.

Anti-CD70 CAR T cells that comprise a disrupted Reg1 gene can be produced via ex vivo genetic modification using the CRISPR/Cas9 (Clustered Regularly Interspaced Short Palindromic Repeats/CRISPR associated protein 9) technology to disrupt targeted genes (Reg1, and optionally TRAC, β2M and/or CD70 genes), and adeno-associated virus (AAV) transduction to deliver the anti-CD70 CAR construct. CRISPR-Cas9-mediated gene editing involves at least an sgRNA targeting the Reg 1 gene as those disclosed herein (see, e.g., Table 22), and optionally an sgRNA (SEQ ID NO: 55) which targets the CD70 locus, TA-1 sgRNA (SEQ ID NO: 59) which targets the TRAC locus, and (β2M-1 sgRNA (SEQ ID NO: 63) which targets the β2M locus.

Anti-CD70 CAR T cells that comprise a disrupted TGFBRII gene can be produced via ex vivo genetic modification using the CRISPR/Cas9 (Clustered Regularly Interspaced Short Palindromic Repeats/CRISPR associated protein 9) technology to disrupt targeted genes (TGFBRII, and optionally, TRAC, β2M, and/or CD70 genes), and adeno-associated virus (AAV) transduction to deliver the anti-CD70 CAR construct. CRISPR-Cas9-mediated gene editing involves at least an sgRNA targeting the TGFBRII gene as those disclosed herein (see, e.g., Table 39), and optionally an sgRNA (SEQ ID NO: 43) which targets the CD70 locus, TA-1 sgRNA (SEQ ID NO: 59) which targets the TRAC locus, and (β2M-1 sgRNA (SEQ ID NO: 63) which targets the β2M locus.

Anti-CD70 CAR T cells that comprise a disrupted TGFBRII gene and a disrupted Reg1 gene can be produced via ex vivo genetic modification using the CRISPR/Cas9 (Clustered Regularly Interspaced Short Palindromic Repeats/CRISPR associated protein 9) technology to disrupt targeted genes (TGFBRII and Reg1, and optionally, TRAC, β2M, and/or CD70 genes), and adeno-associated virus (AAV) transduction to deliver the anti-CD70 CAR construct. CRISPR-Cas9-mediated gene editing involves at least an sgRNA targeting the TGFBRII gene as those disclosed herein (see, e.g., Table 39), and an sgRNA targeting the Reg1 gene as those disclosed herein (see, e.g., Table 22), and optionally an sgRNA (SEQ ID NO: 55) which targets the CD70 locus, TA-1 sgRNA (SEQ ID NO: 59) which targets the TRAC locus, and β2M-1 sgRNA (SEQ ID NO: 63) which targets the β2M locus.

The anti-CD70 CAR T cells are composed of an anti-CD70 CAR single-chain antibody fragment (scFv, which may comprise the amino acid sequence of SEQ ID NO: 138), followed by a CD8 hinge and transmembrane domain (e.g., comprising the amino acid sequence of SEQ ID NO: 97) that is fused to an intracellular co-signaling domain of CD28 (e.g., SEQ ID NO: 101) and a CD3ζ signaling domain (e.g., SEQ ID NO: 103). In specific examples, the anti-CD70 CAR T cells comprise the amino acid sequence of SEQ ID NO: 138.

In some embodiments, at least 30% of a population of anti-CD70 CAR T cells express a detectable level of the anti-CD70 CAR. For example, at least 40%, at least 50%, at least 60%, at least 70%, at least 75%, at least 80%, at least 85%, at least 90%, or at least 95% of the anti-CD70 CAR T cells express a detectable level of the anti-CD70 CAR.

In some embodiments, at least 50% of a population of anti-CD70 CAR T cells may not express a detectable level of β2M surface protein. For example, at least 55%, at least 60%, at least 70%, at least 75%, at least 80%, at least 85%, at least 90%, or at least 95% of the anti-CD70 CAR T cells may not express a detectable level of β2M surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of β2M surface protein.

Alternatively or in addition, at least 50% of a population of anti-CD70 CAR T cells may not express a detectable level of TRAC surface protein. For example, at least 55%, at least 60%, at least 70%, at least 75%, at least 80%, at least 85%, at least 90%, or at least 95% of the anti-CD70 CAR T cells may not express a detectable level of TRAC surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of TRAC surface protein. In specific examples, more than 90% (e.g., more than 99.5%) of the anti-CD70 CAR T cells do not express a detectable TRAC surface protein.

In some embodiments, at least 50% of a population of the anti-CD70 CAR T cells may not express a detectable level of CD70 surface protein. For example, at least 55%, at least 60%, at least 70%, at least 75%, at least 80%, at least 85%, at least 90%, at least 95%, or at least 98% of the engineered T cells of a population may not express a detectable level of CD70 surface protein. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, 90%-100%, or 95%-100% of the engineered T cells of a population does not express a detectable level of CD70 surface protein.

In some embodiments, a substantial percentage of the population of anti-CD70 CAR T cells may comprise more than one gene edit, which results in a certain percentage of cells not expressing more than one gene and/or protein.

For example, at least 50% of a population of anti-CD70 CAR T cells may not express a detectable level of two surface proteins, e.g., does not express a detectable level of β2M and TRAC proteins, β2M and CD70 proteins, or TRAC and CD70 proteins. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of two surface proteins. In another example, at least 50% of a population of the CTX130 cells may not express a detectable level of all of the three target surface proteins β2M, TRAC, and CD70 proteins. In some embodiments, 50%-100%, 50%-90%, 50%-80%, 50%-70%, 50%-60%, 60%-100%, 60%-90%, 60%-80%, 60%-70%, 70%-100%, 70%-90%, 70%-80%, 80%-100%, 80%-90%, or 90%-100% of the engineered T cells of a population does not express a detectable level of β2M, TRAC, and CD70 surface proteins.

In some embodiments, the population of anti-CD70 CAR T cells may comprise more than one gene edit (e.g., in more than one gene), which may be an edit described herein. For example, the population of anti-CD70 CAR T cells may comprise a disrupted TRAC gene via the CRISPR/Cas technology using the TA-1 TRAC gRNA. In some examples, the anti-CD70 CAR T cells may comprise a deletion in the TRAC gene relative to unmodified T cells. For example, the anti-CD70 CAR T cells may comprise a deletion of the fragment AGAGCAACAGTGCTGTGGCC (SEQ ID NO: 69) in the TRAC gene. This fragment can be replaced by the nucleic acid encoding the anti-CD70 CAR (e.g., SEQ ID NO: 139). Alternatively or in addition, the population of anti-CD70 CAR T cells may comprise a disrupted β2M gene via CRISPR/Cas9 technology using the gRNA of β2M-1. Such anti-CD70 CAR T cells may comprise indels in the β2M gene, which comprise one or more of the nucleotide sequences of SEQ ID NOs: 83-88. In specific examples, anti-CD70 CAR T cells comprise ≥30% CAR$^+$ T cells, ≤50% (β2M$^+$ cells, and ≤30% TCRαβ$^+$ cells. In additional specific examples, anti-CD70 CAR T cells comprise ≥30% CAR$^+$ T cells, ≤30% β2M$^+$ cells, and ≤0.5% TCRαβ$^+$ cells.

See also WO 2019/097305A2, and WO2019215500, the relevant disclosures of each of which are incorporated by reference for the subject matter and purpose referenced herein.

In specific examples, the genetically engineered T cell population may be the anti-CD70 CAR T cells disclosed herein that further comprise a disrupted Reg1 gene. The disrupted Regnase 1 gene may comprise any of the sequences provided in Tables 22-31 below. Such a genetically engineered T cells may have ≥30% CAR+ T cells, ≤0.4% TCR$^+$ T cells, ≤30% β2M$^+$ T cells, and ≤2% CD70$^+$ T cells. In some examples, the anti-CD70 CAR T cells may comprise at least 80% Reg1$^-$ cells, for example, at least 85%, at least 90%, at least 95%, at least 98% or above Reg1$^-$ cells.

In specific examples, the genetically engineered T cell population may be the anti-CD70 CAR T cells disclosed herein that further comprise a disrupted TGFBRII gene. Such a genetically engineered T cells may have ≥30% CAR+ T cells, ≤0.4% TCR$^+$ T cells, ≤30% β2M$^+$ T cells, and ≤2% CD70+ T cells. In some examples, the anti-CD70 CAR T cells may comprise at least 80% TGFBRII$^-$ cells, for example, at least 85%, at least 90%, at least 95%, at least 98% or above TGFBRII$^-$ cells.

In specific examples, the genetically engineered T cell population may be the anti-CD70 CAR T cells disclosed herein that further comprise a disrupted TGFBRII gene and a disrupted Reg1 gene. The disrupted Regnase 1 gene may comprise any of the sequences provided in Tables 29-38 below. Alternatively or in addition, the disrupted TGFBRII gene may comprise a nucleotide sequence selected from those listed in Tables 40-48 below. Such a genetically engineered T cells may have ≥30% CAR+ T cells, ≤0.4% TCR$^+$ T cells, ≤30% β2M$^+$ T cells, and ≤2% CD70$^+$ T cells. In some examples, the anti-CD70 CAR T cells may comprise at least 80% TGFBRII$^-$ cells, for example, at least 85%, at least 90%, at least 95%, at least 98% or above TGFBRII$^-$ cells. In some examples, the anti-CD70 CAR T cells may comprise at least 60% Reg1$^-$/TGFBRII$^-$ cells, for example, at least 65%, at least 70%, at least 75%, at least 80%, at least 85%, at least 90%, at least 95%, at least 98% or above Reg1$^-$/TGFBRII$^-$ cells.

III. Therapeutic Applications

The therapeutic T cells generated using the genetically engineered T cells disclosed herein would be expected to maintain T cell health enabled by the disruption of the Reg1 gene, the disruption of the TGFBRII gene, the disruption of the CD70 gene, or a combination thereof. For example, maintaining T cell health may extend expansion during manufacturing, thereby increasing yield and consistency. In another example, maintaining T cell health may rescue exhausted/unhealthy T cells, thereby enabling potentially lower doses in patients and more robust responses. Further, the disruption of the Reg1 gene and the TGFBRII gene showed synergistic effects in enhancing CAR-T cell potency and in vivo expansion.

The therapeutic T cells disclosed herein can be administered to a subject for therapeutic purposes, for example, treatment of a solid tumor targeted by the CAR construct expressed by the therapeutic T cells.

The step of administering may include the placement (e.g., transplantation) of the therapeutic T cells into a subject by a method or route that results in at least partial localization of the therapeutic T cells at a desired site, such as a tumor site, such that a desired effect(s) can be produced. Therapeutic T cells can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, i.e., long-term engraftment. For example, in some aspects described herein, an effective amount of the therapeutic T cells can be administered via a systemic route of administration, such as an intraperitoneal or intravenous route.

In some embodiments, the therapeutic T cells are administered systemically, which refers to the administration of a population of cells other than directly into a target site, tissue, or organ, such that it enters, instead, the subject's circulatory system and, thus, is subject to metabolism and other like processes. Suitable modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous.

A subject may be any subject for whom diagnosis, treatment, or therapy is desired. In some embodiments, the subject is a mammal. In some embodiments, the subject is a human.

In some instances, the therapeutic T cells may be autologous ("self") to the subject, i.e., the cells are from the same subject. Alternatively, the therapeutic T cells can be non-autologous ("non-self," e.g., allogeneic, syngeneic or xenogeneic) to the subject. "Allogeneic" means that the therapeutic T cells are not derived from the subject who receives the treatment but from different individuals (donors) of the same species as the subject. A donor is an individual who is not the subject being treated. A donor is an individual who is not the patient. In some embodiments, a donor is an individual who does not have or is not suspected of having the cancer being treated. In some embodiments, multiple donors, e.g., two or more donors, are used.

In some embodiments, an engineered T cell population being administered according to the methods described herein comprises allogeneic T cells obtained from one or more donors. Allogeneic refers to a cell, cell population, or biological samples comprising cells, obtained from one or more different donors of the same species, where the genes at one or more loci are not identical to the recipient (e.g., subject). For example, an engineered T cell population, being administered to a subject can be derived from one or more unrelated donors, or from one or more non-identical siblings. In some embodiments, syngeneic cell populations may be used, such as those obtained from genetically identical donors, (e.g., identical twins). In some embodiments, the cells are autologous cells; that is, the engineered T cells are obtained or isolated from a subject and administered to the same subject, i.e., the donor and recipient are the same.

An effective amount refers to the amount of a population of engineered T cells needed to prevent or alleviate at least one or more signs or symptoms of a medical condition (e.g., cancer), and relates to a sufficient amount of a composition to provide the desired effect, e.g., to treat a subject having a medical condition. An effective amount also includes an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate effective amount can be determined by one of ordinary skill in the art using routine experimentation.

Because of the enhanced persistence and efficacy of the therapeutic T cells disclosed herein, the dose of the therapeutic T cells provided herein would be lower than the standard dose of CAR-T cells prepared by conventional approaches (e.g., using T cells that do not have one or more of the genetic editing events disclosed herein, including a disrupted Reg1 gene and/or a disrupted CD70 gene). In some examples, the effective amount of the therapeutic T cells disclosed herein may be at least 2-fold lower, at least 5-fold lower, at least 10-fold lower, at least 20-fold lower, at least 50-fold lower, or at least 100-fold lower than a standard dose of a CAR-T therapy. In some examples, an effective amount of the therapeutic T cells disclosed herein may be less than $10^6$ cells, e.g., $10^5$ cells, $5\times10^4$ cells, $10^4$ cells, $5\times10^3$ cells, or $10^3$ cells. In some examples described herein, the cells are expanded in culture prior to administration to a subject in need thereof.

The efficacy of a treatment using the therapeutic T cells disclosed herein can be determined by the skilled clinician. A treatment is considered "effective", if any one or all of the signs or symptoms of, as but one example, levels of functional target are altered in a beneficial manner (e.g., increased by at least 10%), or other clinically accepted symptoms or markers of disease (e.g., cancer) are improved or ameliorated. Efficacy can also be measured by failure of a subject to worsen as assessed by hospitalization or need for medical interventions (e.g., progression of the disease is halted or at least slowed). Methods of measuring these indicators are known to those of skill in the art and/or described herein. Treatment includes any treatment of a disease in subject and includes: (1) inhibiting the disease, e.g., arresting, or slowing the progression of symptoms; or (2) relieving the disease, e.g., causing regression of symptoms; and (3) preventing or reducing the likelihood of the development of symptoms.

Combination therapies are also encompassed by the present disclosure. For example, the therapeutic T cells disclosed herein may be co-used with other therapeutic agents, for treating the same indication, or for enhancing efficacy of the therapeutic T cells and/or reducing side effects of the therapeutic T cells.

IV. Kits

The present disclosure also provides kits for use in producing the genetically engineered T cells, the therapeutic T cells, and for therapeutic uses, In some embodiments, a kit provided herein may comprise components for performing genetic edit of one or more of Reg1 gene, TGFBRII gene, and CD70 gene, and optionally a population of immune cells to which the genetic editing will be performed (e.g., a leukopak). A leukopak sample may be an enriched leukapheresis product collected from peripheral blood. It typically contains a variety of blood cells including monocytes, lymphocytes, platelets, plasma, and red cells. The components for genetically editing one or more of the target genes may comprise a suitable endonuclease such as an RNA-guided endonuclease and one or more nucleic acid guides, which direct cleavage of one or more suitable genomic sites by the endonuclease. For example, the kit may comprise a Cas enzyme such as Cas 9 and one or more gRNAs targeting a Reg1 gene, a TGFBRII gene, and/or a CD70 gene. Any of the gRNAs specific to these target genes can be included in the kit. Such a kit may further comprise components for further gene editing, for example, gRNAs and optionally additional endonucleases for editing other target genes such as β2M and/or TRAC.

In some embodiments, a kit provided herein may comprise a population of genetically engineered T cells as disclosed herein, and one or more components for producing the therapeutic T cells as also disclosed herein. Such components may comprise an endonuclease suitable for gene editing and a nucleic acid coding for a CAR construct of interest. The CAR-coding nucleic acid may be part of a donor template as disclosed herein, which may contain homologous arms flanking the CAR-coding sequence. In some instances, the donor template may be carried by a viral vector such as an AAV vector.

The kit may further comprise gRNAs specific to a TRAC gene for inserting the CAR-coding sequence into the TRAC gene. In other examples, the kit may further comprise gRNAs specific to a β2M gene for inserting the CAR-coding sequence into the β2M gene. In other examples, the kit may further comprise gRNAs specific to a CD70 gene for inserting the CAR-coding sequence into the CD70 gene. In yet other examples, the kit may further comprise gRNAs specific to a Reg1 gene for inserting the CAR-coding sequence into the Reg1 gene. In still other examples, the kit may further comprise gRNAs specific to a TGFBRII gene for inserting the CAR-coding sequence into the TGFBRII gene.

In yet other embodiments, the kit disclosed herein may comprise a population of therapeutic T cells as disclosed for the intended therapeutic purposes.

Any of the kit disclosed herein may further comprise instructions for making the therapeutic T cells, or therapeutic applications of the therapeutic T cells. In some examples, the included instructions may comprise a description of using the gene editing components to genetically engineer one or more of the target genes (e.g., Reg1, TGFBRII, CD70, or a combination thereof). In other examples, the included instructions may comprise a description of how to introduce a nucleic acid encoding a CAR construction into the T cells for making therapeutic T cells.

Alternatively, the kit may further comprise instructions for administration of the therapeutic T cells as disclosed herein to achieve the intended activity, e.g., eliminating disease cells targeted by the CAR expressed on the therapeutic T cells. The kit may further comprise a description of selecting a subject suitable for treatment based on identifying whether the subject is in need of the treatment. The instructions relating to the use of the therapeutic T cells described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the therapeutic T cells are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an infusion device for administration of the therapeutic T cells. A kit may have a sterile access port (for example, the container may be an intravenous solution bag or a vial having a stopper pierceable by a hypodermic injection needle). The container may also have a sterile access port.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (1RL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Screening of Reg1 Targeting Site by CRISPR/Cas-Mediated Gene Editing (A) Efficient Disruption of Reg1 by Cas9:sgRNA RNPs in T Cells The Reg1 gene was efficiently edited in primary human T cells ex vivo using CRISPR/Cas9 gene editing. Genomic segments of the Reg1 gene containing the six (6) protein coding exons were used as input in gRNA design software. Desired gRNAs were those that would lead to insertions or deletions in the coding sequence, disrupting the amino acid sequence of Reg1, leading to out of frame/loss of function allele(s) (referred to as "Reg1 knockout (KO)" alleles or "Reg1 disrupted alleles"). All ten (10) in silico-identified gRNA spacer sequences targeting the Reg1 gene were synthesized, and the gRNAs were specifically modified, as indicated in Table 1. While the gRNAs used in this example were modified with 2'-O-methyl phosphorothioate modifications, unmodified gRNAs, or gRNAs with other modifications, may be used. The target sequences and gRNA sequences of the Reg1 guides Z01-Z10 are provided in Table 22 below.

TABLE 1

Indel Rate of Reg1 Gene by Ten gRNAs

| Guide Name | Indel Efficiency (TIDE) |
|---|---|
| REG1-Z01 | 98.3% |
| REG1-Z02 | 97.2% |
| REG1-Z03 | 96.8% |
| REG1-Z04 | 92.7% |
| REG1-Z05 | 98.5% |
| REG1-Z06 | 95% |
| REG1-Z07 | 94.8% |
| REG1-Z08 | 71% |
| REG1-Z09 | 88.2% |
| REG1-Z10 | 94.9% |

Primary human T cells were transfected (electroporated) with a ribonucleoprotein particle (RNP) containing Cas9 nuclease and a synthetic modified sgRNA targeting the Reg1 gene (sequences in Table 22) or controls (no Cas9, no gRNA). Four (4) days post transfection, cells were subjected to a TIDE analysis to assess indel frequency.

Ten (10) gRNAs yielded measurable data by TIDE analysis, as indicated in Table 1. Eight (8) gRNA sequences yielded indel percentages (editing frequencies) above 90%, indicating highly efficient gene editing.

Four gRNAs which target either exon 2 or 4 were selected for subsequent studies (REG1-Z03, REG1-Z05, REG1-Z06 and REG1-Z10, which showed 96.8%, 98.5%, 95% and 94.9% editing rate of Reg1, respectively as shown in (Table 1).

(B) On-Target and Off-Target Editing of REG1 Guide RNAs

On-target and off-target editing efficiencies of various REG1-targeting gRNAs noted above were examined following the method disclosed in the above section. Briefly, activated T cells were transfected (electroporated) with a ribonucleoprotein particle (RNP) containing Cas9 nuclease and a synthetic modified sgRNA targeting the Reg1 gene (sequences in Table 22 below) or controls (no Cas9, no gRNA).

For genomic on- and off-target assessment, these electroporation methods were used to generate two cell populations of edited cells from two different donor T cells (termed 1 and 2). Cells were gene edited with each of the ten guides noted above, and then collected ten (10) days post transfection. These samples were analyzed with hybrid capture, a homology-dependent method to enrich on- and off-target sites, combined with next-generation sequencing. Briefly, on- and off-target sites with homology to each gRNA target site were identified computationally, single-stranded RNA probes were used to enrich these sites from bulk genomic DNA, these enriched sites were sequenced with next-generation sequencing, and the data were analyzed for insertions and deletions (indels) indicating repair following CRISPR editing.

(i) Analysis of On-Target Indel Profiles in T Cells

The data used to quantify off-target editing were also used to quantify and summarize the most frequent on-target indels for all Reg1 guides listed in Table 22. This data was generated from hybrid capture of the Reg1 locus combined with next-generation sequencing in two donors (termed Donor 1 and Donor 2).

Following gene editing, hybrid capture analysis of the Reg1 locus in a population of T cells following CRISPR/Cas9 gene editing to produce Reg1 KO T cells results in specific indel frequencies and edited gene sequences at the Reg1 locus (Tables 29-38; deletions as dashes and insertions in bold).

For the purposes of individual sequence quantification from hybrid capture data, sequence reads aligning across the Regnase 1 on-target site, 20 bp upstream and downstream of the cut site, were selected and considered for indel sequence quantification. From the selected reads, the sequence within 10 bp upstream and downstream of each putative cut site (~3 bp upstream of the PAM (Jinek, et al., Science 2012) was quantified as a representative region of on-target non-homologous end joining (NHEJ) editing.

Table 2 below shows the on and off target editing results (from two donors) of exemplary Reg1 gRNAs obtained by the hybrid capture assay disclosed herein.

TABLE 2

On and Off Target Results by Hybrid Capture

| Guide | Number of predicted off target sites tested | On-target mean editing hyb cap | Detected off-targets |
|---|---|---|---|
| REG1-Z01 | 35 | 97.0% | 1 0.75% off-target; 1 0.25% off-target |

TABLE 2-continued

On and Off Target Results by Hybrid Capture

| Guide | Number of predicted off target sites tested | On-target mean editing hyb cap | Detected off-targets |
|---|---|---|---|
| REG1-Z02 | 27 | 97.7% | No off-target editing detected |
| REG1-Z03 | 52 | 99.0% | 1 5.0% off-target; 1 0.6% off-target; 1 0.4% off-target; 1 0.3% off-target; 1 0.2% off-target |
| REG1-Z04 | 6 | 97.0% | No off-target editing detected |
| REG1-Z05 | 14 | 98.6% | No off-target editing detected |
| REG1-Z06 | 1 | 94.2% | No off-target editing detected |
| REG1-Z07 | 16 | 94.2% | 1 0.2% off-target |
| REG1-Z08 | 6 | 53.8% | No off-target editing detected |
| REG1-Z)9 | 6 | 86.2% | No off-target editing detected |
| REG1-Z10 | 14 | 98.2% | No off-target editing detected |

On-target gene edited sequences by the exemplary Reg 1 gRNAs are presented in Tables 29-38 below, with the frequencies of these sequences representing the percent of all sequences spanning the on-target site within 20 bp upstream and downstream of each cut site. The indels for each guide are shown relative to an on-target reference sequence in Tables 29-38. The reference sequence is centered on the cleavage site with 10 bp in either direction, ending 4 bp 3' of the PAM.

Example 2: Regnase 1 Disruption Improves CAR-T Cell Expansion

Using T cells expressing an anti-CD70 CAR disclosed herein as an example, this study demonstrated that knocking out Reg1 in the CAR-T cells resulted in enhanced in vitro CAR-T cell culture expansion.

Allogeneic human T cells that lack expression of the TRAC gene, β2M gene, CD70 gene, and Regnase-1 gene, and express a chimeric antigen receptor (CAR) targeting CD70 were produced. Briefly, activated human T cells were first isolated and then Cas9:sgRNA RNPs (1 µM Cas9, 5 µM gRNA) were delivered to the activated human T cells by electroporation, followed by incubation with recombinant adeno-associated adenoviral vectors (AAVs), serotype 6 (AAV6) (MOI 50,000). The nucleofection mix contained the Nucleofector™ Solution, 5×10⁶ cells, 1 µM Cas9, and 5 µM gRNA (as described in Hendel et al., Nat Biotechnol. 2015; 33(9):985-989, PMID: 26121415). The RNP complex comprised Cas9 and sgRNA targeting the TRAC, B2M, and CD70 (shown in Table 23) and optionally Regnase-1 genes (using the REG1-Z01 to REG1-Z10 sgRNAs shown in Table 22). The rAAV vector included the nucleotide sequence encoding an anti-CD70 CAR (the donor template in SEQ ID NO: 169, encoding an anti-CD70 CAR amino acid sequence of SEQ ID NO: 138).

To assess the ability of anti-CD70 CAR T cells to expand in cytokine containing media (IL-2+IL-7), anti-CD70 CAR T cells were utilized. Specifically, 2.5 to 3.8×10⁶ total anti-CD70 CAR T cells comprising a quadruple disruption (TRAC-/β2M-/CD70-/Reg1-) were generated and compared to anti-CD70 CAR T cells with unedited Reg1 (TRAC-/β2M-/CD70-).

Cells were plated and allowed to grow in flasks with cytokine containing media. Every 3-4 days the total number of cells were enumerated and re-plated as needed. This process was repeated each week for a total of 21 days. Allogeneic anti-CD70 CAR-T cells containing a disruption in the Reg1 gene show an increase in cell expansion after 21 days (FIG. 1A). Reg1 guides REG1-Z01, REG1-Z03, REG1-Z07, REG1-Z09, and REG1-Z10 appear to have a greater effect on cell expansion than cells made using Reg1 guides REG1-Z02 or REG1-Z08.

Figure 1B:
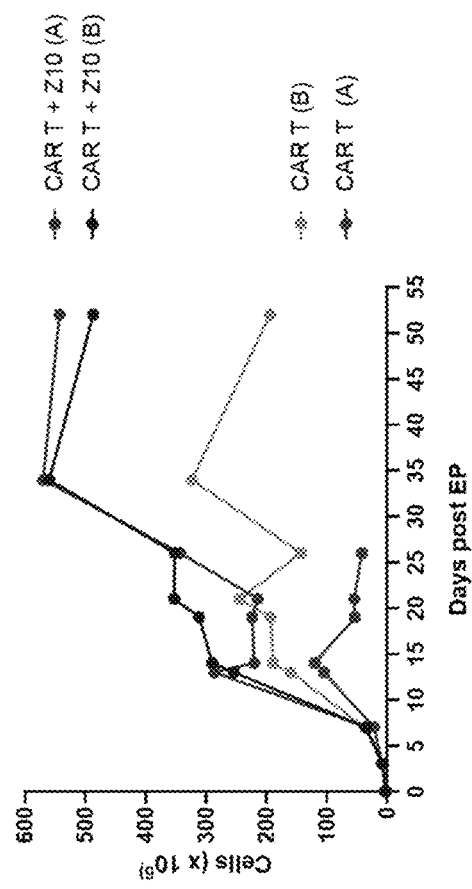

In a second experiment, Reg1 guide REG1-Z10 was used in CAR T cells made from a different T cell donor in replicates by two operators (labelled A and B). The effect of increased cell culture expansion was demonstrated again. The increase in cell expansion can be seen as early as day 13 and continues throughout the experiment to day 52 (FIG. 1B). Furthermore, anti-CD70 CAR-T cells containing a Reg1 disruption are maintained over a longer time in culture (at least up to day 52) as compared to anti-CD70 CAR-T cells with an unedited Regnase 1 gene, one of which was no longer viable on day 26. Collectively, these data show that disruption of the Reg1 gene results in greater cell culture yields and longer cell maintenance in culture as compared to CAR T cells with an unedited Reg1 gene.

Example 3: Cell Killing Function of Anti-CD70 CAR T Cells with Reg1 Disruption Allogeneic human T cells that lack expression of the TRAC gene, β2M gene and CD70 gene, and express a chimeric antigen receptor (CAR) targeting CD70 were produced. The edited CAR T cells further comprised knock out of Reg1 gene. As in the examples above, activated human T cells we electroporated with Cas9:sgRNA RNPs (1 µM Cas9, 5 µM gRNA), followed by incubation with a recombinant adeno-associated adenoviral vectors, serotype 6 (AAV6) (MOI 50,000).

Recombinant AAV comprised the nucleotide sequence of SEQ ID NO: 169 (encoding anti-CD70 CAR comprising the amino acid sequence of SEQ ID NO: 138). The following sgRNAs were used: TRAC (SEQ ID NO: 58), β2M (SEQ ID NO: 62), CD70 (SEQ ID NO: 54), and optionally Reg1 (e.g., REG1-Z03, Z05, Z06, and Z10; see Table 22 and FIGS. 2A to 2E).

At time points of one week and one month post-electroporation, T cells were checked for CAR expression by flow cytometry. Both anti-CD70 CAR T cells and anti-CD70 CAR T cells that lack Reg1 (using four gRNAs REG1-Z03, Z05, Z06, Z10) expressed nearly equivalent amount of CAR on their surface at day 7 (85.6% and 81.8%, 80%, 84.4%, 85.6%) and day 32 (97.6% and 90.7%, 91.5%, 92.6%, 93.2%) post HDR.

Cell Killing Function of Anti-CD70 CAR T Cells with Regnase-1 (Reg1) Disruption

A cell killing assay was used to assess the ability of the TRAC-/β2M-/CD70-/Reg1-/anti-CD70 CAR+ cells to kill CD70+ adherent renal cell carcinoma (RCC)-derived cell lines (ACHN, Caki-1, and/or 769P cell lines). Adherent cells were seeded in 96-well plates at 50,000 cells per well and incubated overnight at 37° C. The next day edited anti-CD70 CAR T cells (cultured until day 12 post HDR or day 27 post HDR) were added to the wells containing target cells at 1:1, 2:1 or 1.5:1 CAR T:Target cell ratios. After 24 hours co-culture, CAR T cells were removed from the culture by aspiration and 100 µL Cell titer-Glo (Promega) was added to each well of the plate to assess the number of remaining viable target cells. The amount of light emitted per well was then quantified using a plate reader.

Figure 2B:
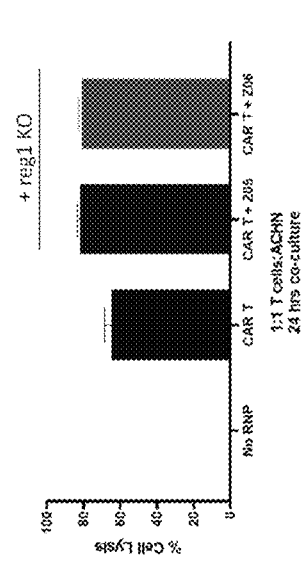
FIGS. 2A-2E include diagrams showing that exemplary CAR T cells (anti-CD70 CAR T cells) with Reg1 KO (+reg1 KO) exhibit superior in vitro potency against tumor cell lines relative to CAR T cells with an unedited Reg1 gene (CAR T).
Figure 2A:
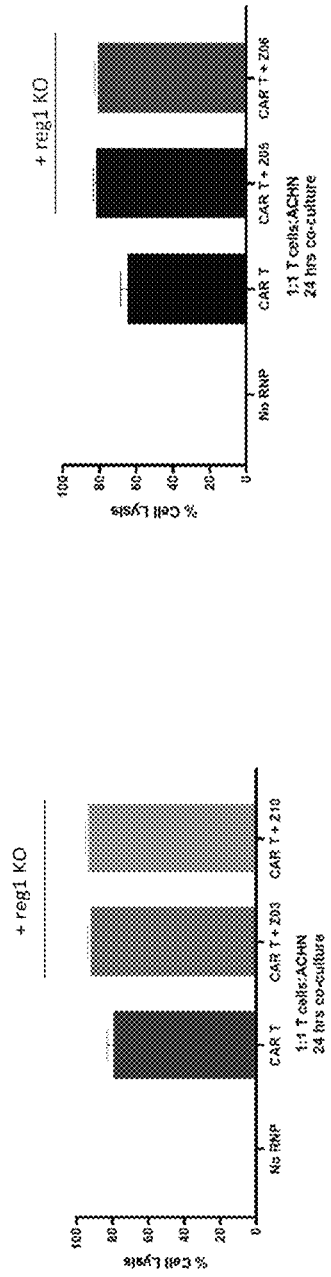
Figure 2E:
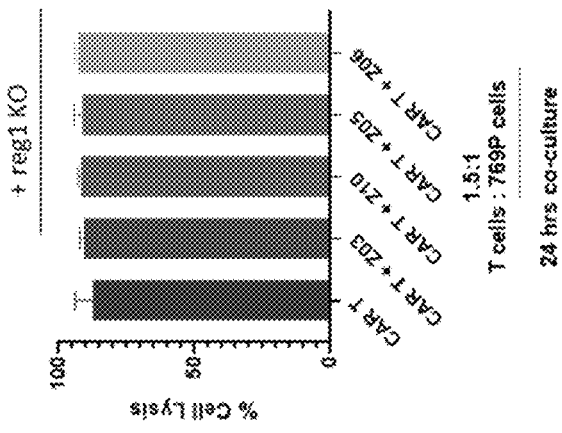
Figure 2D:
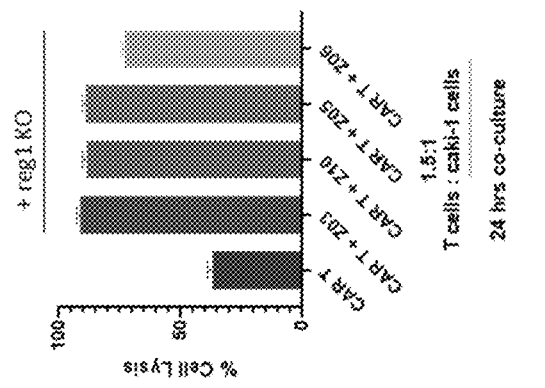
Figure 2C:
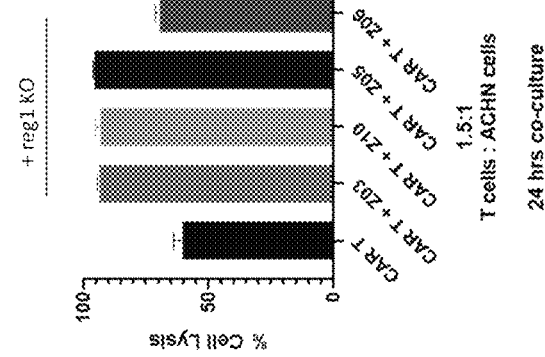

Cells with Reg1 disruption exhibited a more potent cell killing of RCC-derived cells following 24-hour co-incubation. The anti-CD70 CAR T cells at day 12 post HDR (FIGS. 2A and 2B) demonstrated slightly higher potency when Reg1 was knocked out, and much higher potency at day 27 post HDR (FIGS. 2C, 2D, and 2E). This suggests that knocking-out the Reg1 gene gives a maintained/persistent higher cell kill potency to anti-CD70 CAR+ T cells over time post HDR. This finding was consistent across the three tumor lines from Renal cell carcinoma tumor lines. CD70 CAR+ T cells with Reg1 disruption using gRNAs REG1-Z03, REG1-Z05, REG1-Z10 gave a higher persistent potency than when using gRNA REG1-Z06. CAR-T cells with Reg1 disruption demonstrated a visible increased in potency after 24 h co-culture with caki-1 (FIGS. 2A, 2B, and 2C) and ACHN (FIG. 2D), and after 6 hours co-culture with 769P (difference not visible anymore after 24 h) (FIG. 2E).

While CAR-T cells with or without the Regnase KO show similar efficacy at Day 13 post HDR, efficacy appears to be diminished in older cells (Day 19 and Day 26) without the Regnase KO. Surprisingly, TRAC−/β2M−/CD70−/Reg1−/anti-CD70 CAR+ cells still retain the ability to kill with similar activity ACHN and Caki-1 cells in culture (FIGS. 6A and 6B).

This suggests that disrupting the Reg1 gene gives a persistent activity and higher cell kill potency to CAR+ T cells over a longer period of time post HDR editing.

Example 4. Effect of Regnase-1 (Reg1) Disruption on Exhaustion Marker Expression The levels of the T cell exhaustion markers were assessed on TRAC−/β2M−/CD70−/anti-CD70 CAR+ and TRAC−/β2M−/CD70−/Reg1−/anti-CD70 CAR+ cells. CD4+ and CD8+ T cells were assessed for PD-1 expression (FIGS. 3A and 3B) and TIM3 expression (FIGS. 3C and 3D) by flow cytometry at Day 13 (FIGS. 3A and 3C) and Day 26 (FIGS. 3B and 3D) post HDR.

The data demonstrate that Reg1 KO (using Z10 guide as an example) reduces exhaustion marker expression in CAR T cells at all time points measured. The data demonstrate that knocking out Reg1 could reduce the potential exhaustion of CD8+ and CD4+ gene edited populations of CAR+ T cells leading to better therapeutics.

Example 5. Regnase-1 (Reg1) Disruption Increases the Proportion of Central Memory Cells in CAR T Cells Population Upon activation of antigen peptides presented by antigen-presenting cells, native T cells differentiate to various types of T cells in the order of T stem cell memory ($T_{SCM}$), T central memory cell ($T_{CM}$), T effector memory cell ($T_{EM}$), and T effector cell ($T_{EFF}$). Exemplary surface markers of T cells at different differentiation stages are provided below. $T_{CM}$ cells have been associated with T cell long term persistence in vivo: CD8+ clones isolated from $T_{CM}$ cells were shown to persist long term in vivo during adoptive T cell transfer in non-human primates while clones isolated from effector cells did not. (Berger et al., J. Clin. Investig. (2008) 118:294-305). Representative cell surface markers of the various types of T cells are provided in Table 3 below.

TABLE 3

Representative Cell Surface Markers of Various Types of T Cells

|  | Naïve | Stem Central Memory | Central Memory | Effector Memory |
|---|---|---|---|---|
| CD27 | + | + | + | − |
| CD45RO | − | − | + | + |
| CD45RA | + | + | − | − |
| CD62L | + | + | + | − |
| CD95 | − | + | + | + |

The levels of CD27 and CD45 RO T central memory T cell markers were assessed on TRAC−/β2M−/CD70−/anti-CD70 CAR+ and TRAC−/β2M−/CD70−/Reg1−/anti-CD70 CAR+ cells. Cells were stained using commercial antibodies for CD27 (Biolegend, clone M-T271) and CD45 RO (Biolegend, clone UCHL1) and analyzed by flow cytometry.

CAR-T cells with Reg1 knock out were more likely to exhibit central memory T cell identity (double positive for CD27 and CD45 RO) and less likely to exhibit effector memory cell identity (identified as CD27− and CD45 RO+), as shown in Table 4.

TABLE 4

Central memory and effector memory T cell markers in cells with and without Reg1 KO

| Experiment | Cells | CD27+/CD45 RO+ Central memory cells | CD27−/CD45 RO+ Effector memory cells |
|---|---|---|---|
| 1 | TRAC−/β2M−/anti-CD70 CAR+ | 62.3% | 30% |
|  | TRAC−/β2M−/CD70−/Reg1−/anti-CD70 CAR+ | 82.3% | 15.1% |
| 2 | TRAC−/β2M−/anti-CD70 CAR+ | 61.8% | 27.5% |
|  | TRAC−/β2M−/CD70−/Reg1−/anti-CD70 CAR+ | 74.3% | 22.2% |

The results obtained from this study indicate that Reg1 disruption led to an enhanced level of $T_{CM}$ cells in the total T cell population compared to the Reg1 WT counterparts, indicating that Reg1 disruption could increase T cell long term persistence in vivo, which would benefit CAR-T therapy.

Example 6. Reg1 Disruption does not Affect Cytokine Dependency of CAR T Cells

To determine whether the gene editing resulted in unwanted off-target editing that could generate cells with adverse properties, such as uncontrolled cell growth, the ability of TRAC−/β2M−/anti-CD19 CAR+ and TRAC−/β2M−/Reg1−/anti-CD19 CAR+ cells to grow in the absence of cytokines and/or serum was assessed. $5 \times 10^6$ cells were plated approximately 2 weeks post cell production (Day 0) in 10 mL of full media containing IL2, IL7 and human serum, or in serum-containing media lacking cytokines (IL-2 and IL-7). Fresh full media or media lacking cytokines were added to the respective cultures once per week. The volume of media added allowed for the cultures to maintain a density of approximately 1-2 million cells/mL. If the cell density was below 1 million cells/mL, media was not added to the cultures. The number of viable cells were enumerated twice weekly until 40 days post plating. TRAC−/β2M−/anti-CD19 CAR+ or TRAC−/β2M−/Reg1−/anti-CD19 CAR+ were no longer detectable at 40 days in the cultures that lacked cytokines, indicating that any potential off-target effects due to genome editing did not induce growth factor independent growth/proliferation to the cells (FIG. 4). The cells only proliferated in the presence of cytokines (full media that contains cytokines) and did not proliferate in the presence of serum alone. Thus, genome editing did not induce any adverse events that allow the cells to grow in the absence of cytokine, growth factor or antigen stimulation.

Example 7: In Vivo Effect of Reg1 KO on Allogeneic CAR T Cells in the Intravenous Disseminated Nalm-6 Human Acute Lymphoblastic Leukemia Tumor Xenograft Model A disseminated mouse model was utilized to further assess the in vivo efficacy of allogeneic CAR T cells lacking β2M and TRAC, as well as Reg1. The intravenous disseminated model (disseminated model) utilized CD19+B-ALL derived Nalm-6 Human Acute Lymphoblastic Leukemia tumor cell line in NOG mice to demonstrate the efficacy of TRAC−/β2M−/anti-CD19 CAR+ T cells (anti-CD19 CAR T cells) with or without editing of the Reg1 locus. The Reg1 gene was edited via CRISPR/Cas-mediated gene editing using REG1-Z10 guide RNA (see Table 22). The anti-CD19 CAR T cells express an anti-CD19 CAR comprising the amino acid sequence of SEQ ID NO: 118. See also the sequence Tables 27 and 28 below, and WO2019/097305, the relevant disclosures of which are incorporated by reference for the subject matter and purpose referenced herein.

Efficacy of the anti-CD19 CAR T cells was evaluated in the disseminated model using methods employed by Translations Drug Development, LLC (Scottsdale, AZ) and described herein. In brief, 25, 5-8 week old female CIEA NOG (NOD.Cg-PrkdcscidIl2rgtm1Sug/JicTac) mice were individually housed in ventilated microisolator cages, maintained under pathogen-free conditions, 5-7 days prior to the start of the study. At the start of the study, the mice were divided into 5 treatment groups as shown in Table 5. The mice were inoculated with Nalm6-Fluc-GFP (Nalm6-Fluc-Neo/eGFP—Puro) cells intravenously to model disseminated disease. On Day 1, all mice received an intravenous injection of $0.5 \times 10^6$ Nalm6 cells/mouse. On Day 4, Groups 2-5 received an intravenous injection of CAR T cells ($4 \times 10^6$ CAR+ cells/mouse) as indicated in Table 5.

TABLE 5

Treatment groups for intravenous disseminated disease study

| Group | Nalm6 tumor cells $0.5 \times 10^6$ cells/mouse | CAR T cells (i.v.) $4 \times 10^6$ cells/mouse | N |
|---|---|---|---|
| 1 | X | NA | 5 |
| 2 | X | anti-CD19 CAR/TRAC−/β2M− (4e6 CAR+) | 5 |
| 3 | X | anti-CD19 CAR/TRAC−/β2M− (8e6 CAR+) | 5 |
| 4 | X | anti-CD19 CAR/TRAC−/β2M−/Reg1− (4e6 CAR+) | 5 |
| 5 | X | anti-CD19 CAR/TRAC−/β2M−/Reg1− (8e6 CAR+) | 5 |

During the course of the study, the mice were monitored daily and body weight was measured two times weekly. Bioluminescence (BLI; total ROI, photon/s) was measured twice weekly beginning on Day 4 of the study. A significant endpoint was the time to peri-morbidity and the effect of T-cell engraftment was also assessed. The percentage of animal mortality and time to death were recorded for every group in the study. Mice were euthanized prior to reaching a moribund state. Mice may be defined as moribund and sacrificed if one or more of the following criteria were met:

Loss of body weight of 20% or greater sustained for a period of greater than 1 week;

Tumors that inhibit normal physiological function such as eating, drinking, mobility and ability to urinate and or defecate;

Prolonged, excessive diarrhea leading to excessive weight loss (>20%); or

Persistent wheezing and respiratory distress.

Animals were also considered moribund if there was prolonged or excessive pain or distress as defined by clinical observations such as: prostration, hunched posture, paralysis/paresis, distended abdomen, ulcerations, abscesses, seizures and/or hemorrhages.

In Vivo Survival Rate

Figure 5A:
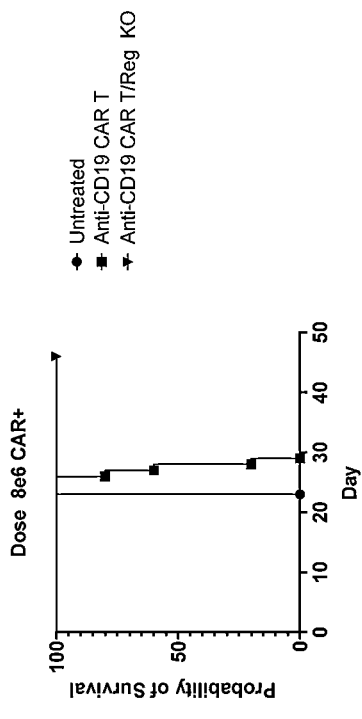
FIGS. 5A-5D include diagrams showing that exemplary CAR T cells (anti-CD19 CAR T cells) with Reg1 KO (Anti-CD19 CAR T/Reg KO) provide superior in vivo survival and decreased tumor burden relative to Reg1 wild-type counterparts (Anti-CD19 CAR T) in the intravenous disseminated Nalm-6 human acute lymphoblastic leukemia tumor xenograft mouse model.
Figure 5B:
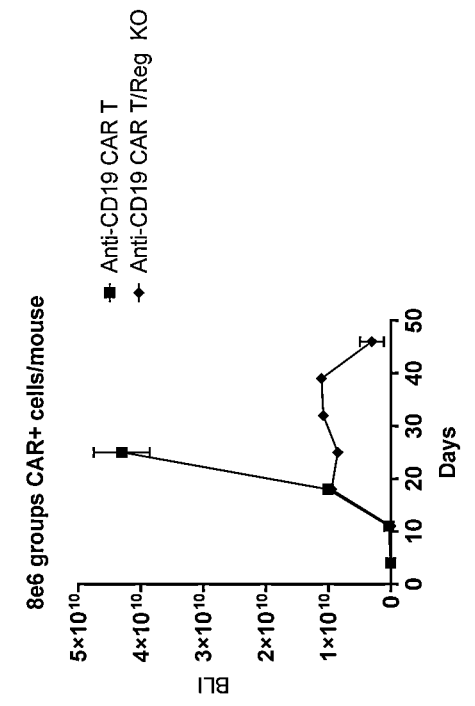
Figure 5C:
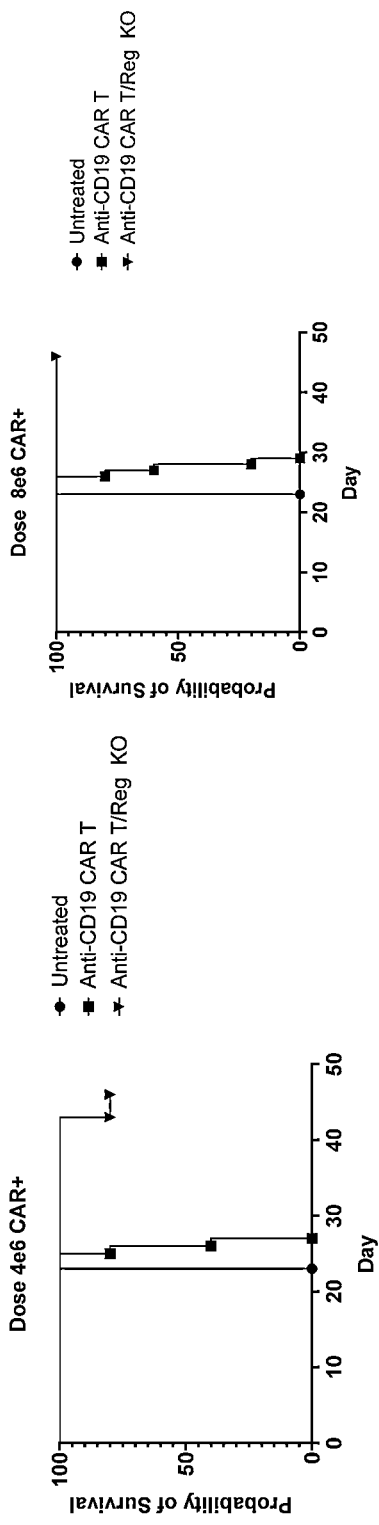
Figure 5D:
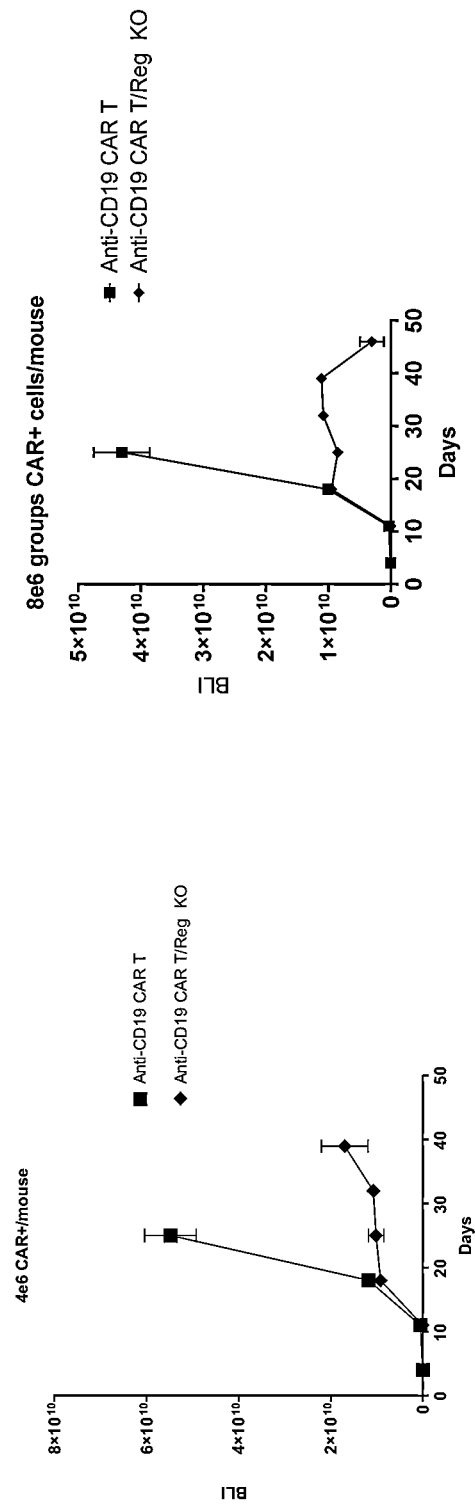

Mice in groups receiving TRAC−/β2M−/anti-CD19 CAR+ T cells with or without an additional Reg1 disruption exhibited an increase in survival relative to mice in the untreated group (Group 1). Mice receiving either dose of TRAC−/β2M−/Reg1−/anti-CD19 CAR+ T cells exhibited increased survival in comparison to TRAC−/β2M−/anti-CD19 CAR+ T cells at each respective dose (FIGS. 5A and 5B). In addition, mice receiving either dose of TRAC−/β2M−/Reg1−/anti-CD19 CAR+ T cells had reduced leukemia burdens as indicated by diminished bioluminescence signal in comparison to TRAC−/β2M−/anti-CD19 CAR+ T cells at each respective dose (FIGS. 5C and 5D).

These data demonstrate that the Reg1 disruption in CAR T cells increases efficacy of CAR T cells in vivo, decreasing tumor burden and increasing survival.

Example 8: Efficient Disruption of TGFBRII by Cas9:sgRNA RNPs in T Cells

This example describes efficient editing of the TGFBRII gene in primary human T cells ex vivo using CRISPR/Cas9 gene editing. Genomic segments of the TGFBRII gene containing the first five (5) protein coding exons were used as input in gRNA design software. The genomic segments also included flanking splice site acceptor/donor sequences. Desired gRNAs were those that would lead to insertions or deletions in the coding sequence, disrupting the amino acid sequence of TFBRII, leading to out of frame/loss of function allele(s) (referred to as "TGFBRII knockout alleles" or "TGFBRII disrupted alleles"). Eight (8) in silico-identified gRNA spacer sequences targeting the CD70 gene were synthesized, and the gRNAs were specifically modified, as indicated in Table 39 and FIGS. 7A and 7B. While the modified gRNAs in Table 39 were modified with 2'-O-methyl phosphorothioate modifications, unmodified gRNAs, or gRNAs with other modifications, can be used.

Primary human T cells were transfected (electroporated) with a ribonucleoprotein particle (RNP) containing Cas9 nuclease and a synthetic modified sgRNA targeting the TGFBRII gene (sequences in Table 39) or controls (no Cas9, no gRNA). Four to six (4-6) days post transfection, cells were: (1) subjected to a TIDE analysis to assess indel frequency, and (2) processed by western blot (primary antibody: anti-human TGFBRII antibody, clone #16H2L4) to assess TGFBRII expression levels at the cell surface (FIG. 7B).

Eight (8) gRNAs yielded measurable data by TIDE analysis, as indicated in FIG. 7A. Seven (7) gRNA sequences and a synthetic modified sgRNA targeting the TGFBRII gene (sequences in Table 39 below) or controls (no Cas9, no gRNA).

For genomic on- and off-target assessment, these electroporation methods were used to generate two cell populations of edited cells from two different donor T cells. Cells were gene edited with each of the nine guides noted in Table 39 and then collected ten (10) days post transfection. These samples were analyzed with hybrid capture, a homology-dependent method to enrich on- and off-target sites, combined with next-generation sequencing. Briefly, on- and off-target sites with homology to each gRNA target site were identified computationally, single-stranded RNA probes were used to enrich these sites from bulk genomic DNA, these enriched sites were sequenced with next-generation sequencing, and the data were analyzed for insertions and deletions (indels) indicating repair following CRISPR editing.

Five (5) gRNAs showed no off-target effect with an on-target editing rate greater than 85%, which includes TGFBRII_Ex1_T1, TGFBRII-Ex1-T2, TGFBRII_Ex1_T3, TGFBRII_Ex2_T1 and TGFBRII_Ex5_T1 as shown in Table 6 below.

TABLE 6

On-Targeting Editing Efficiency and Off-Target Effects of Anti-TGFBRII gRNAs

| Guide | gRNA target sequence + (PAM) | Number of predicted off-target sites tested | On-target mean editing hyb cap | Detected off-targets |
|---|---|---|---|---|
| TGFBRII-Ex1-T1 | CCGACTTCTGAACGTGCGGT (GGG)(SEQ ID NO: 2) | 7 | 86.80% | None |
| TGFBRII-Ex1-T2 | TGCTGGCGATACGCGTCCAC (AGG)(SEQ ID NO: 3) | 8 | 98.30% | None |
| TGFBRII-Ex1-T3 | TCGGTCTATGACGAGCAGCG (GGG)(SEQ ID NO: 4) | 7 | 99.60% | None |
| TGFBRII-Ex2-T1 | ATGGGCAGTCCTATTACAGC (TGG)(SEQ ID NO: 5) | 82 | 96.00% | None |
| TGFBRII-Ex3-T1 | ATTGTTCACTTGTTAGCCCC (AGG)(SEQ ID NO: 6) | 83 | 98.50% | One <1% off-target |
| TGFBRII-Ex3-T2 | GCTGAAGAACTGCCTCTATA (TGG)(SEQ ID NO: 7) | 133 | 98.10% | One 1-10% off-target |
| TGFBRII-Ex4-T1 | GCAGGATTTCTGGTTGTCAC (AGG)(SEQ ID NO: 8) | 222 | 98.80% | One <1% off-target |
| TGFBRII-Ex4-T2 | CTCCATCTGTGAGAAGCCAC (AGG)(SEQ ID NO: 9) | 255 | 99.40% | Four <1% off-targets |
| TGFBRII-Ex5-T1 | CCCCTACCATGACTTTATTC (TGG)(SEQ ID NO: 10) | 85 | 94.20% | None | yielded indel percentages (editing frequencies) above 80% indicating highly efficient gene editing (FIG. 7A). The level of TGFBRII protein expression was assessed by western blot to confirm the TIDE analysis data and GAPDH was used as a loading control. Seven (7) of the gRNAs showed nearly complete knock out of TGFBRII on the T cells (FIG. 7B).

On-Target and Off-Target Editing of TGFBRII Guide RNAs

On-target and off-target editing efficiencies of various TGFBRII-targeting gRNAs noted above were examined following the method disclosed in the above section. Briefly, activated T cells were transfected (electroporated) with a ribonucleoprotein particle (RNP) containing Cas9 nuclease Tables 29-38 list potential indel sequences that may be generated by the gRNAs disclosed herein (deletions as dashes and insertions in bold).

Example 9: Generation of Genetically Modified T Cells That Lack TGFBRII Expression and Are Resistant to TGF-β

This example describes the production of CAR T cells that lack expression of TGFBRII and the assessment of the effect of TGF-β on CAR T cell expansion with TGFBRII KO cells grown in complete media (X-Vivo 15 supplemented with IL-2 and IL-7).

Briefly, human T cells were first isolated and Cas9: sgRNA RNPs (1 µM Cas9, 5 µM gRNA) were delivered to activated human T cells by electroporation, followed by incubation with the recombinant adeno-associated adenoviral vectors (AAVs), serotype 6 (AAV6) (MOI 50,000). The nucleofection mix contained the Nucleofector™ Solution, 5×10⁶ cells, 1 µM Cas9, and 5 µM gRNA (as described in Hendel et al., Nat Biotechnol. 2015; 33(9):985-989, PMID: 26121415). The RNP complex comprised Cas9 and sgRNA targeting the TRAC, B2M, CD70, and optionally TGFBRII genes (sgRNA sequences are shown in Table 23 and Tables 39, SEQ ID NOs: 58, 62, 54, and 301, respectively). The rAAV vector included the nucleotide sequence encoding an anti-CD70 CAR (the donor template in SEQ ID NO: 169 and the anti-CD70 CAR amino acid sequence of SEQ ID NO: 138.

Figure 8C:
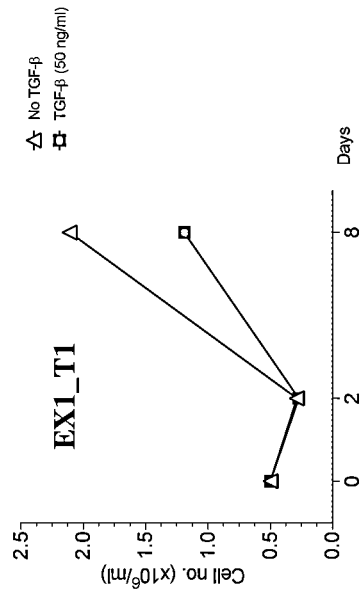
Figure 8E:
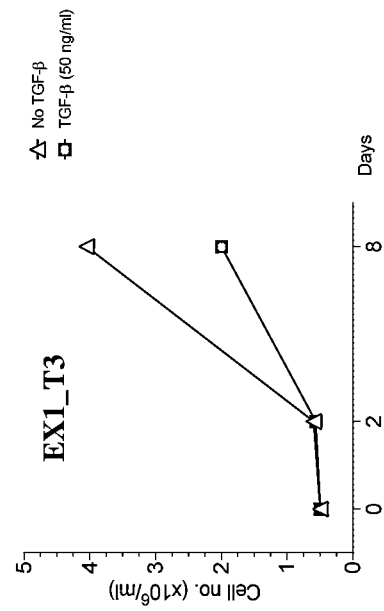

About one week post-electroporation, CAR T cells with an intact (i.e.: wild-type or non-engineered counterpart) TGFBRII gene were exposed to varying amounts recombinant human TGF-β (10, 20, 50 and 100 ng/ml) and cell expansion was recorded over time. TGF-β significantly inhibited CAR T expansion, a concentration as low as 10 ng/ml was sufficient to reduce CAR T expansion in cells with an intact TGFBRII gene (FIG. 8A).

Figure 8B:
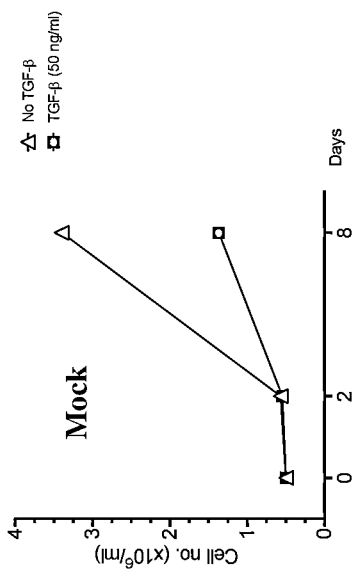
Figure 8D:
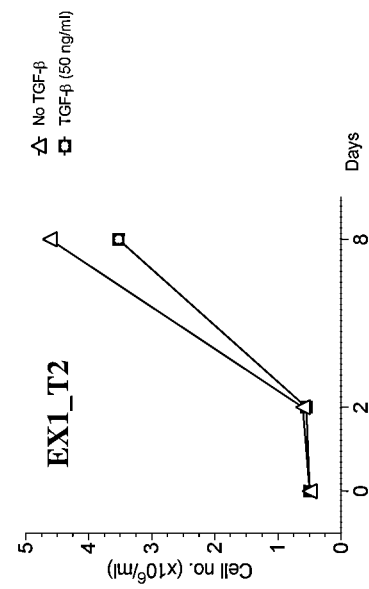
Figure 8F:
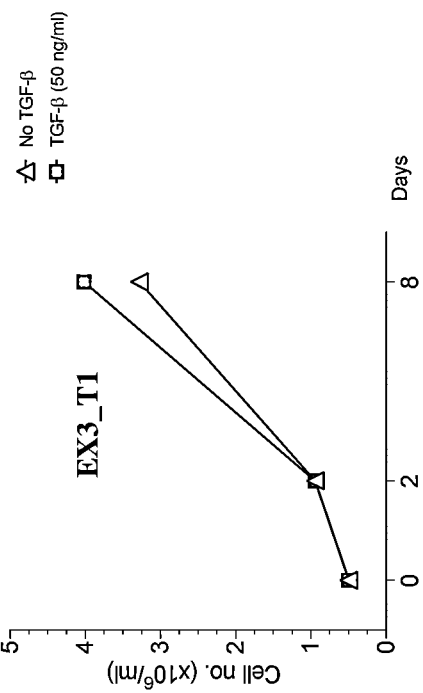
Figure 8G:
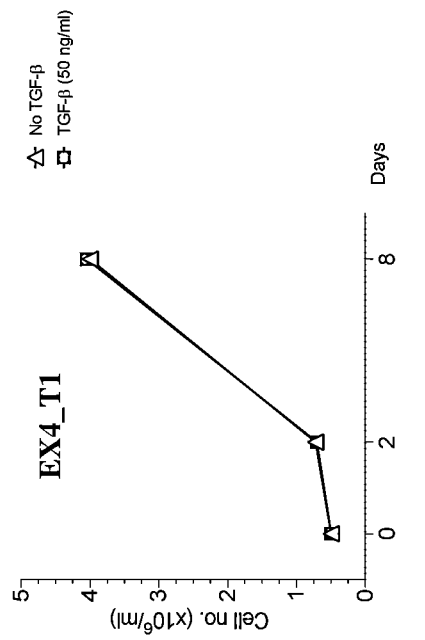
Figure 8H:
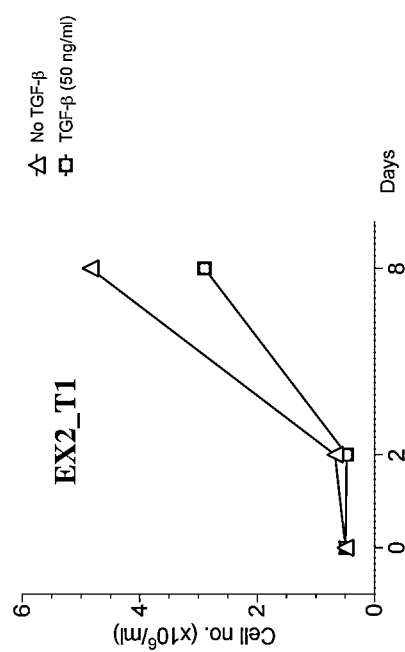
Figure 8I:
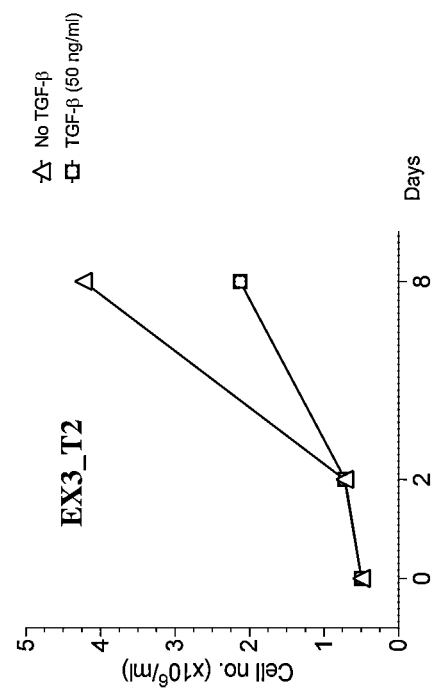
Figure 8J:
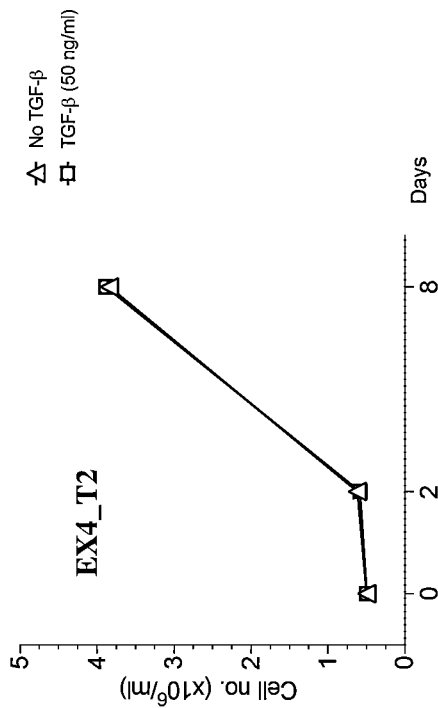
Figure 8K:
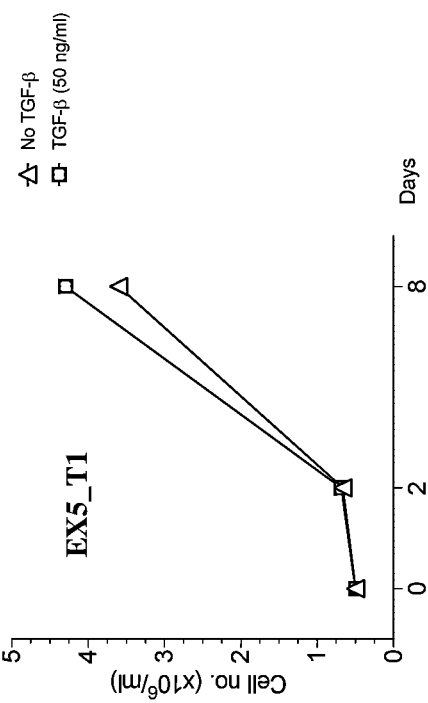

In another study, anti-CD70 CAR T cells with TGFBRII disruption were incubated with or without 50 ng/ml of recombinant human TGF-β, and the T cell expansion was monitored at day 2 and day 8 post-incubation with TGF-β and compared to mock cells. Mock cells (FIG. 8B) were anti-CD70 CAR T cells that did not have a disrupted TGFBRII gene. As shown in FIGS. 8C-8K, T cells with TGFBRII knocked-out were protected against the inhibitory effect of TGF-β on T cell expansion. The extent of protection varied with the sgRNA used to disrupt the TGFBRII gene. T cells that were transfected with gRNA targeting exon 1, 4 and 5 (TGFBRII_EX1_T2, TGFBRII_EX4_T1, TGFBRII_EX4_T2, TGFBRII_EX5_T1) showed the most resistance against a TGF-β inhibitory effect. Sequences of these gRNAs are provided in Table 39 below.

Example 10: Cell Killing Function of Anti-CD70 CAR T Cells with TGFBRII Disruption This example describes the production of allogeneic human T cells that lack expression of the TRAC gene, β2M gene and CD70 gene, and express a chimeric antigen receptor (CAR) targeting CD70. The edited CAR T cells further comprised knock out of the TGFBRII gene. As in the examples above, activated human T cells were electroporated with Cas9:sgRNA RNPs (1 µM Cas9, 5 µM gRNA), followed by incubation with a recombinant adeno-associated adenoviral vectors, serotype 6 (AAV6) (MOI 50,000).

Recombinant AAV comprised the nucleotide sequence of SEQ ID NO: 169 (encoding anti-CD70 CAR comprising the amino acid sequence of SEQ ID NO: 138). The following sgRNAs were used: TRAC (SEQ ID NO: 58), β2M (SEQ ID NO: 62), CD70 (SEQ ID NO: 54) and TGFBRII (SEQ ID NO: 301).

About one week post-electroporation, T cells were checked for CAR expression by flow cytometry. Both anti-CD70 CAR T cells and anti-CD70 CAR T cells lacking TGFBRII expressed nearly equivalent amount of CAR on their surface (71.5% CAR⁺ cells versus 73.7% CAR⁺ cells).

Figure 9:
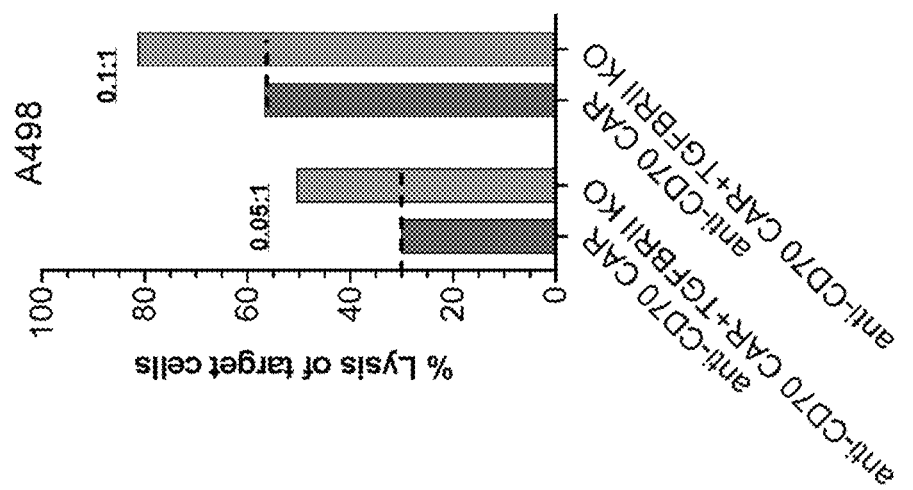
FIG. 9 is a diagram showing the effect of TGFBRII KO on CAR T cell killing ability against A498 cells at various E:T ratios as indicated. TGFBRII KO improves cytotoxicity of CAR-T cells.
Figure 10C:
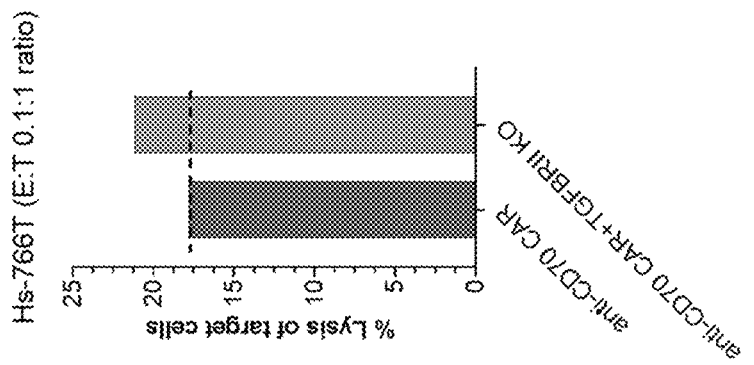
FIGS. 10A-10E include diagrams showing the effect of TGFBRII KO on CAR T cell kill ability against multiple tumor cell lines. The cell kill capacity of anti-CD70 CAR T cells was compared to anti-CD70 CAR T cells with TGFBRII KO. Cell killing activity of the CAR T cells was assessed against CAKI-1 (FIG. 10A) H1975 (FIG. 10B), Hs-766T (FIG. 10C), 786-O (FIG. 10D) and SK-OV3 (FIG. 10E). TGFBRII KO improves cytotoxicity of CAR-T cells.
Figure 10B:
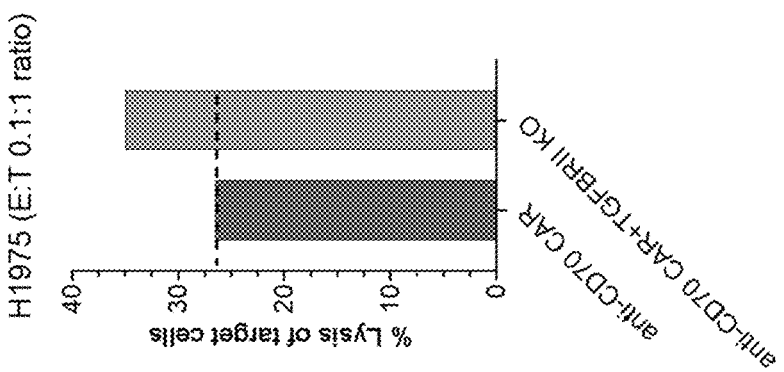
Figure 10A:
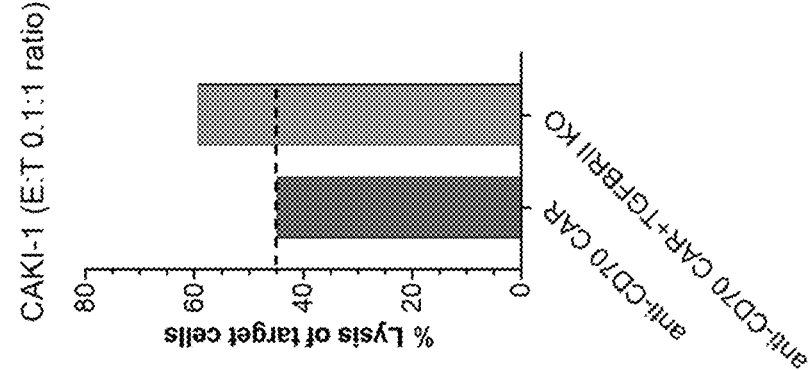
Figure 10E:
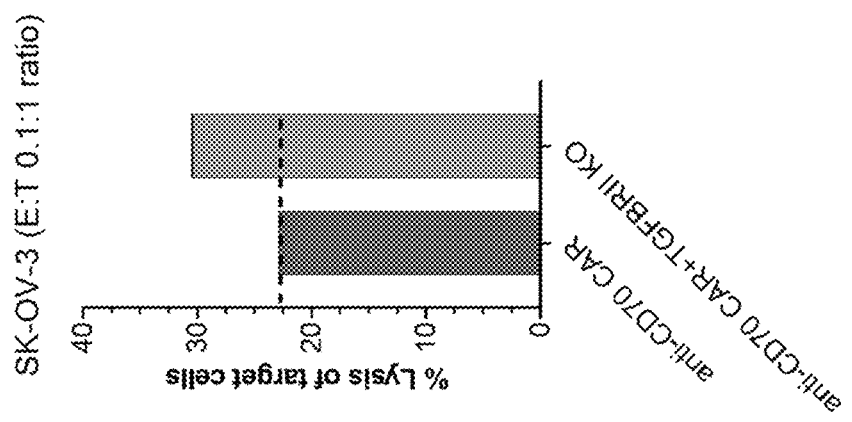
Figure 10D:
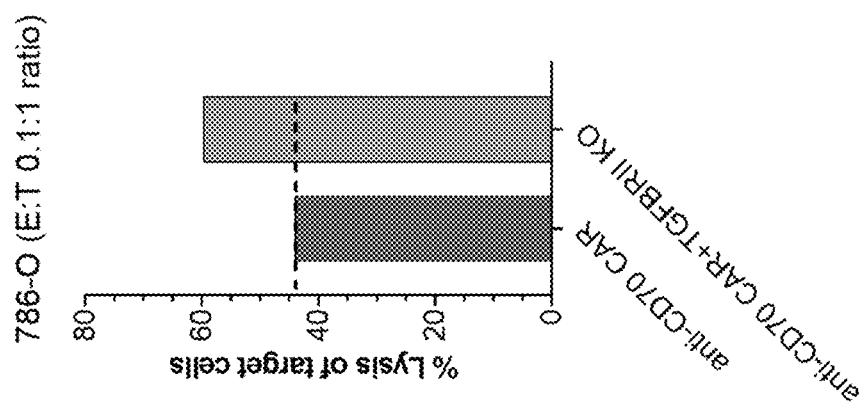

A cell killing assay was used to assess the ability of the TRAC−/β2M−/CD70−/TGFBRII−/anti-CD70 CAR+ cells to kill a CD70+ adherent renal cell carcinoma (RCC)-derived cell line (A498 cells). Adherent cells were seeded in 96-well plates at 50,000 cells per well and left overnight at 37° C. The next day edited anti-CD70 CAR T cells were added to the wells containing target cells at 0.05:1 or 0.1:1 CAR T:T cell (E:T) ratios. After the indicated incubation period, CAR T cells were removed from the culture by aspiration and 100 µL Cell titer-Glo (Promega) was added to each well of the plate to assess the number of remaining viable cells. The amount of light emitted per well was then quantified using a plate reader. Cells with TGFBRII knock out exhibited a more potent cell killing of RCC-derived cells following 24-hour co-incubation. The anti-CD70 CAR T cells demonstrated higher potency when TGFBRII was knocked out, which is clearly visible at two T cell: A498 ratios (0.05:1 and 0.1:1) (FIG. 9). This suggests that knocking-out the TGFBRII gene gives a higher cell kill potency to anti-CD70 CAR+ T cells. This finding was consistent across a wide panel of tumor lines from different tissues as shown in FIGS. 10A-10E. Knocking-out the TGFBRII gene enhances the cell killing capacity of anti-CD70 CAR T cells against 786-O and CAKI-1 (Renal cell carcinoma tumor lines), H1975 (Non-small cell lung cancer), Hs-766T (Pancreatic carcinoma) and SK-OV3 (Ovarian cancer) (FIGS. 10A-10E).

In another study, anti-CD70 CAR T was incubated with 50 ng/ml of recombinant human TGF-β for 24 hours and the expression of CD25 (IL-2R) on cell surface was assessed by flow cytometry. As shown in FIG. 11, anti-CD70 CAR T cells are susceptible to the inhibitory effect of TGF-β that causes downregulation of CD25. CD25 is an activation marker and involved in T cell proliferation. When the TGFBRII gene was knocked out, these cells become resistant to TGF-β and the CAR T cells retain activity and CD25 expression.

Figure 12:
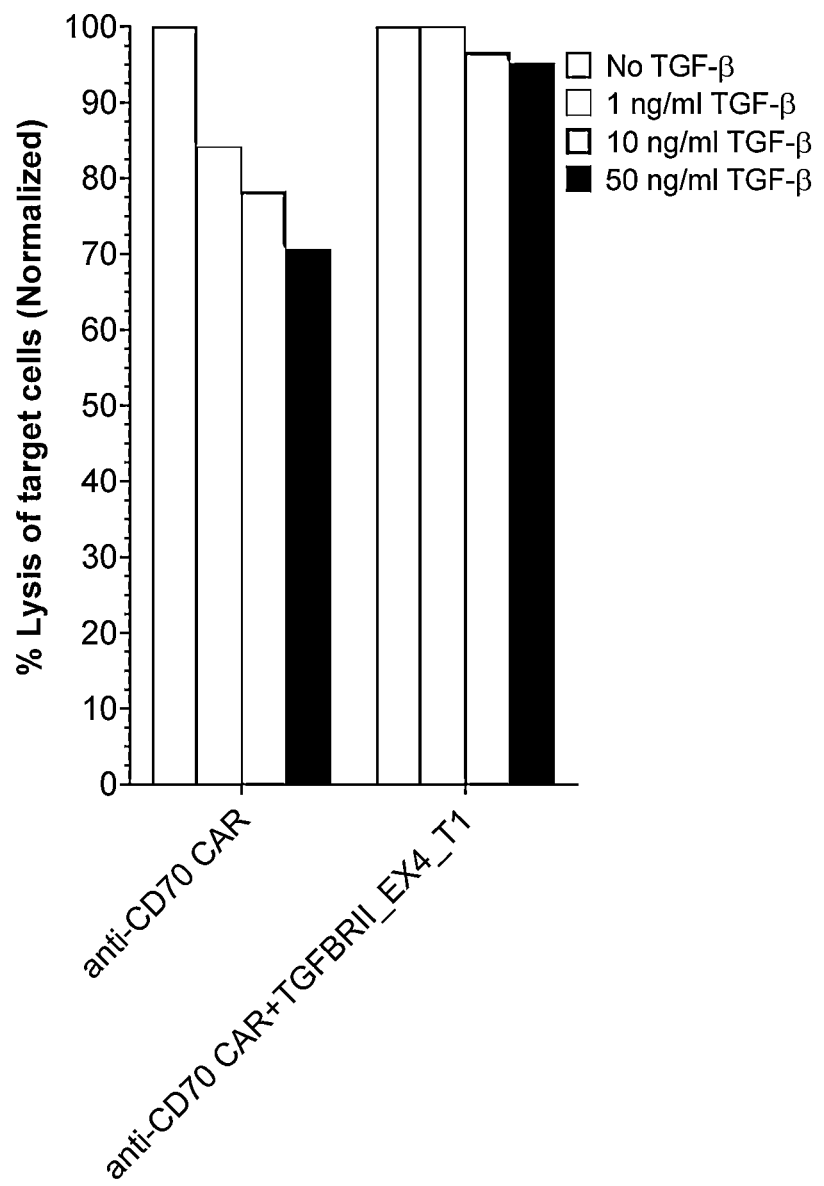
FIG. 12 is a graph showing that TGFBRII KO protects CAR T cells against TGF-β inhibitory effect on cytotoxicity. Anti-CD70 CAR T cells was co-cultured with target tumor cells (A498) in the presences or absence of TGF-β (0, 1, 10, 50 ng/ml) The ability of anti-CD70 CAR T cells with unedited TGFBRII to kill target cells, were compared to anti-CD70 CAR T with TGFBRII KO using an exemplary guide RNA as indicated.

Also, when the cell kill of target cells (A498) was repeated in presence of 1, 10 and 50 ng/ml of recombinant human TGF-β. Anti-CD70 CAR T cells were adversely affected by presence of TGF-β as demonstrated by reduction in the cell kill capacity by CAR T cells with an intact TGFBRII gene (FIG. 12). However, anti-CD70 CAR T cells with a TGFBRII KO (anti-CD70 CAR+TGFBRII_EX4_T1) did not exhibit reduced cell killing ability in the presence of TGF-β (FIG. 12). In addition, T cell proliferation upon exposure to target antigen and effector cytokines production (IFN-γ and IL-2) were reduced in the presence of TGF-β (FIGS. 13A-13C). However, when the cells lacked the expression of TGFBRII, they we were completely protected against TGF-β inhibitory effects, also shown in FIGS. 13A-13C. This suggests that knocking out TGFBRII on the surface of CAR T cells protects the CAR T cells from the adverse effect of TGF-β in the tumor microenvironment.

Example 11: Generation of Anti-CD70 CAR T Cells That Lack TGFBRII Expression and are Resistant to the Inhibitory Effect of Fibroblasts This example describes the production of allogeneic human T cells that lack expression of the TRAC gene, β2M gene and CD70 gene, and express a chimeric antigen receptor (CAR) targeting CD70 and how they are susceptible to the inhibitory effect of fibroblasts, which are a major component of solid tumor microenvironment (TME). The edited CAR T cells further comprised knock out of the TGFBRII gene. As in the examples above, activated human T cells we electroporated with a recombinant adeno-associated adenoviral vectors, serotype 6 (AAV6) (MOI 50,000), and Cas9: sgRNA RNPs (1 µM Cas9, 5 µM gRNA).

Recombinant AAV comprised the nucleotide sequence of SEQ ID NO: 169 (encoding anti-CD70 CAR comprising the amino acid sequence of SEQ ID NO: 138). The following sgRNAs were used: TRAC (SEQ ID NO: 58), β2M (SEQ ID NO: 62), CD70 (SEQ ID NO: 54) and TGFBRII (SEQ ID NO: 301).

Figure 14:
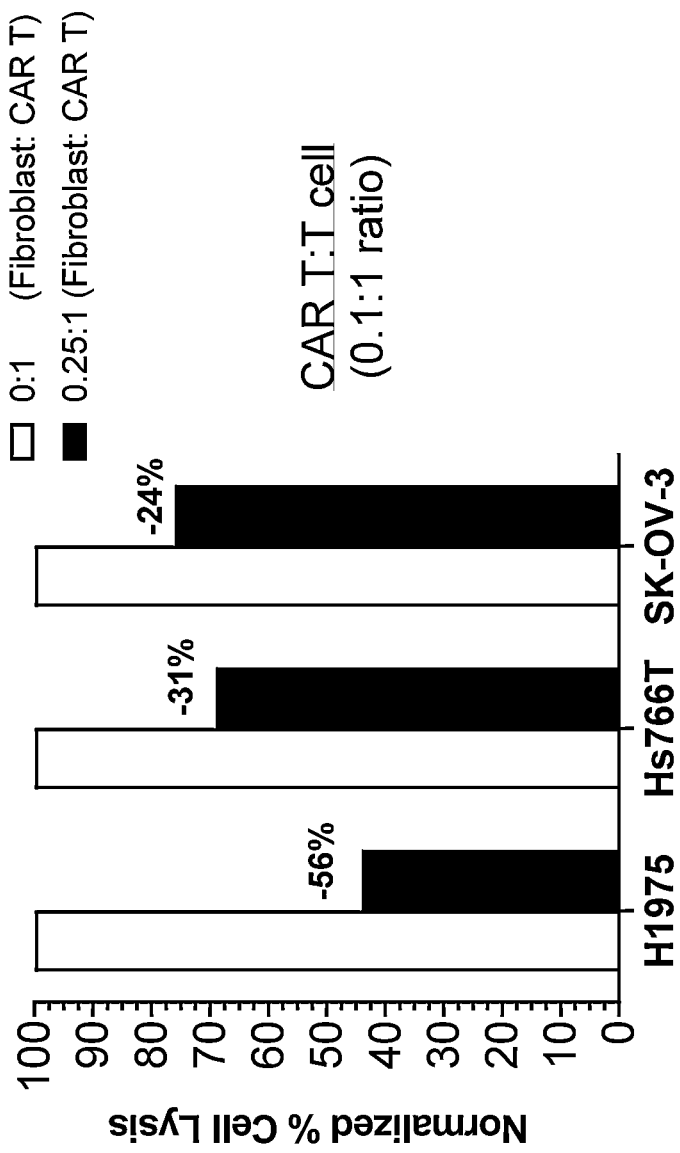
FIG. 14 is a graph showing fibroblasts reduce CAR-T cell cytolytic activity. Anti-CD70 CAR T was co-cultured with target cells (A498) with or without fibroblast (CCL-190) placed in a transwell plate at 0.25:1, fibroblast:anti-CD70 CAR T.

A cell killing assay was used to assess the inhibitory effect of fibroblast on anti-CD70 CAR T cells to kill CD70+ adherent tumor cell lines: H1975 (Non-small cell lung cancer), Hs-766T (Pancreatic carcinoma), or SK-OV3 (Ovarian cancer). The cell kill assay was performed as described in example 3. Briefly, Adherent cells were seeded in 96-well plates at 50,000 cells per well and left overnight at 37° C. and the fibroblast cells (LL 86 (LeSa) ATCC® CCL-190™) were added to the top chamber of a transwell plate without direct contact with target cells. The next day edited anti-CD70 CAR T cells were added to the wells containing target cells. After the indicated incubation period, CAR T cells were removed from the culture by aspiration and 100 μL Cell titer-Glo (Promega) was added to each well of the plate to assess the number of remaining viable cells. The amount of light emitted per well was then quantified using a plate reader. As shown in FIG. 14, the presence of the fibroblast cells on the top chamber led to a decrease of the cell kill capacity of anti-CD70 CAR T cells against the target cells which might suggest that these fibroblast secreted a factor that decrease anti-CD70 CAR T killing effect.

This finding was confirmed when this experiment was repeated with the presence of conditioned media from the fibroblast instead on the cells and similar inhibition was observed. Briefly, 1×10$^6$ CCL-190 fibroblast cells we seeded/0.5 ml in a 24 well plate and incubated overnight and supernatants were collected. A cell kill assay as previously described was carried out with anti-CD70 CAR T cells and tumors cells at a ratio of 0.1:1 effector to target cell ratio, in the presence or absence of fibroblast supernatant and incubated overnight. Cell kill was measured using the CellTiter-Glo® Luminescent Cell Viability Assay. This experiment confirms that fibroblasts secrete a factor that causes a reduction in the killing capacity of anti-CD70 CAR T cells. Disruption of the TGFBRII gene on the surface of anti-CD70 CAR T protected these cells against this inhibitory effect. The TGFBRII KO improved the cell killing ability of anti-CD70 CAR T cells against pancreatic tumor cells, Hs-766T (FIG. 15A), kidney tumor cells, A498 (FIG. 15B), and lung tumor cells, H1975 (FIG. 15C) in the presence of fibroblasts. These data suggest that fibroblasts are contributing to the TGF-β production in TME and reduce the cell kill capacity of anti-CD70 CAR T cells and this could be avoided by disrupting TGFBRII on the surface of the CAR T cell.

Example 12: Generation of CAR T Cells with Disrupted TGFBRII and Regnase-1 Genes Allogeneic human T cells that lack expression of the TRAC gene, β2M gene, CD70 gene, TGFBRII gene and Regnase-1 gene, and express a chimeric antigen receptor (CAR) targeting CD70 were produced. Activated human T cells were electroporated with Cas9:sgRNA RNPs (1 μM Cas9, 5 μM gRNA), followed by incubation with a recombinant adeno-associated adenoviral vectors, serotype 6 (AAV6) (MOI 50,000).

Recombinant AAV comprised the nucleotide sequence of SEQ ID NO: 169 (encoding anti-CD70 CAR comprising the amino acid sequence of SEQ ID NO: 138). The following sgRNAs were used: TRAC (SEQ ID NO: 58), β2M (SEQ ID NO: 62), CD70 (SEQ ID NO:54), TGFBRII (SEQ ID NO: 313) and REG-1 (SEQ ID NO: 51). The sgRNAs, which form RNPs with the Cas9 enzyme, can be introduced into the T cells in a single electroporation event to produce the resulting modified cell populations shown in Table 7 below. Alternatively, they can be introduced into the T cells in two sequential electroporation events to produce the resulting cell populations. After the electroporation, the cells were transduced with the recombinant AAVs to introduce the donor template encoding for the anti-CD70 CAR.

TABLE 7

Genetically Engineered CAR-T Cell Populations

| Population | Edits |
|---|---|
| Anti-CD70 CAR T cells | anti-CD70 CAR+/TRAC-/B2M-/CD70- |
| Anti-CD70 CAR T + Reg KO cells | anti-CD70 CAR+/TRAC-/B2M-/CD70-/Reg- |
| Anti-CD70 CAR T + TGBBRII KO cells | anti-CD70 CAR+/TRAC-/B2M-/CD70-/TGFBRII- |
| Anti-CD70 CAR T + Reg KO + TGFBRII KO cells | anti-CD70 CAR+/TRAC-/B2M-/CD70-/Reg-/TGFBRII- |

At 7 days post-electroporation, T cells were checked for CAR expression by flow cytometry. Both anti-CD70 CAR T cells and anti-CD70 CAR T cells that lack Regnase expressed nearly equivalent amount of CAR on their surface at day 7 post HDR. The results are provided in Table 7A below.

TABLE 7A

CAR Expression Levels in Genetically Engineered Anti-CD70 CAR T Cells

| Population | Edits | CAR % |
|---|---|---|
| Anti-CD70 CAR T cells | anti-CD70 CAR+/TRAC-/B2M-/CD70- | 82.2 |
| Anti-CD70 CAR T + Reg KO cell | anti-CD70 CAR+/TRAC-/B2M-/CD70-/Reg- | 83.1 |
| Anti-CD70 CAR T + TGIFBRII KO cells | anti-CD70 CAR+/TRAC-/B2M-/CD70-/TGFBRII- | 79.7 |
| Anti-CD70 CAR T + Reg KO + TGFBRII KO cells | anti-CD70 CAR+/TRAC-/B2M-/CD70-/Reg-/TGFBRII- | 81.8 |

Example 13: Disruption of Regnase-1 and TGFBRII Increases CAR T Cell Killing Upon Serial Rechallenge In Vitro The anti-CD70 CAR$^+$ T cells generated above were serially rechallenged with CD70+ kidney cancer cell line, ACHN, and evaluated for their ability to kill the CD70+ kidney cancer cell line ACHN.

The anti-CD70 CAR$^+$ T cells used in this experiment contained the following edits:
- Anti-CD70 CAR T cells: anti-CD70 CAR+/TRAC-/B2M-/CD70-
- Anti-CD70 CAR T+Reg KO cells: anti-CD70 CAR+/TRAC-/B2M-/CD70-/Reg-
- Anti-CD70 CAR T+TGFBRII KO cells: anti-CD70 CAR+/TRAC-/B2M-/CD70-/TGFBRII-
- Anti-CD70 CAR T+Reg KO+TGFBRII KO cells: anti-CD70 CAR+/TRAC-/B2M-/CD70-/Reg-/TGFBRII- In a 96-well plate format, CAR T cells were first co-cultured with ACHN cells (4,000 CAR T cells, 16,000 tumor cells) on D0 and re-challenged with tumor cells as follows: 16,000 tumor cells on D2 and D4; 40,000 cells on D7; 50,000 cells on D9; 50,000 cells on D11).

Analysis of tumor cell and CAR T cell number was performed at D1, D3, D6, D8, D10 and D12 using flow cytometry (method adapted from Wang et al., JoVE 2019). The following antibodies in Table 8 were used at 1:100 dilution.

TABLE 8

Antibody Information

| Antibody | Flour | cat # | Dilution | Vendor |
| --- | --- | --- | --- | --- |
| CD4 | BV510 | 344718 | 1:100 | Biolegend |
| CD8 | PacBlue | 300546 | 1:100 | Biolegend |
| CD70 | FITC | 355106 | 1:100 | Biolegend |

TABLE 8-continued

Antibody Information

| Antibody | Flour | cat # | Dilution | Vendor |
| --- | --- | --- | --- | --- |
| CD62L | BV605 | 304833 | 1:100 | Biolegend |
| human CD45 | BV785 | 304048 | 1:100 | Biolegend |
| PD1 | APC/Cy7 | 329922 | 1:100 | Biolegend |
| CD45RO | PE/Cy7 | 304230 | 1:100 | Biolegend |
| Streptavidin | APC | 405207 | 1:100 | Biolegend |
| Tim3 | PE | 345006 | 1:100 | Biolegend |
| Live/Dead | 7AAD | BDB559925 | 1:500 | BD |

Figure 16A:
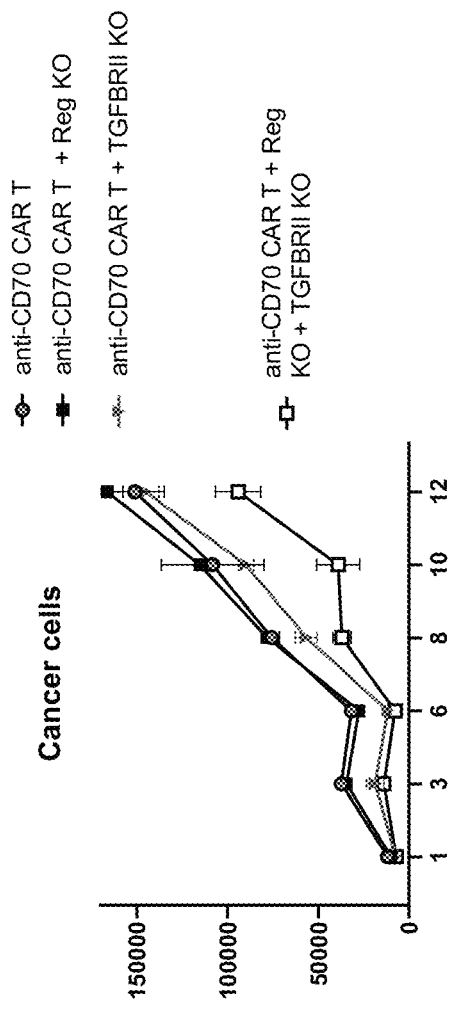
FIG. 16A-16B include diagrams showing synergistic effects of TGFBRII and Regnase double disruptions with in vitro rechallenge of CAR T Cells with ACHN.
Figure 16B:
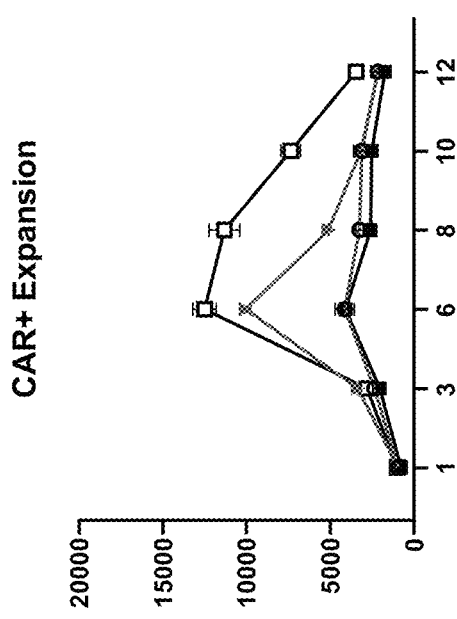

The results demonstrate that disrupting both the TGFBRII gene and the Regnase gene improved potency (FIG. 16A) and CAR+ T cell expansion (FIG. 16B) when CAR T cells are repeatedly challenged with CD70+ positive target cells. Potency and expansion is improved compared to CAR T cells that have neither, or only one (i.e.: TGFBRII or Regnase), of the genes disrupted.

Example 14: Treatment Efficacy of Anti-CD70 CAR T Cells with Multiple Gene Disruptions in the Subcutaneous Renal Cell Carcinoma Tumor Xenograft Model Treatment in the Renal Cell Carcinoma Tumor Model The ability of T cells expressing a CD70 CAR with TGFBRII and/or Regnase gene edits to eliminate renal cell carcinoma cells that express medium levels of CD70 was evaluated in vivo using a subcutaneous renal cell carcinoma (CAKI-1) tumor xenograft mouse model. Anti-CD70 CAR+ T cells were produced as described above. See, e.g., Example 13.

The ability of these anti-CD70 CAR+ T cells to ameliorate disease caused by a CD70+ renal carcinoma cell line was evaluated in NSG mice using methods employed by Translational Drug Development, LLC (Scottsdale, AZ). In brief, 20, 5-8 week old female, NSG mice were individually housed in ventilated microisolator cages, maintained under pathogen-free conditions, 5-7 days prior to the start of the study. Mice received a subcutaneous inoculation of $5 \times 10^6$ Caki-1 renal cell carcinoma cells/mouse in the right hind flank. When mean tumor size reached target of ~70 mm$^3$, the mice were further divided into 5 treatment groups as shown in Table 9. On Day 1, treatment four groups received a single 200 µl intravenous dose of $1 \times 10^7$ anti-CD70 CAR+ T cells according to Table 9.

TABLE 9

Treatment groups

| Group | CAR-T | Caki-1 cells | CAR-T cell treatment (i.v.) | N |
| --- | --- | --- | --- | --- |
| 1 | None | $5 \times 10^6$ cells/mouse | None | 4 |
| 2 | Anti-CD70 CAR T cells: anti-CD70 CAR+/TRAC−/B2M−/CD70− | $5 \times 10^6$ cells/mouse | $1 \times 10^7$ cells/mouse | 4 |
| 3 | Anti-CD70 CAR T + Reg KO cells: anti-CD70 CAR+/TRAC−/B2M−/CD70−/Reg− | $5 \times 10^6$ cells/mouse | $1 \times 10^7$ cells/mouse | 4 |
| 4 | Anti-CD70 CAR T + TGFBRII KO cells: anti-CD70 CAR+/TRAC−/B2M−/CD70−/TGFBRII− | $5 \times 10^6$ cells/mouse | $1 \times 10^7$ cells/mouse | 4 |
| 5 | Anti-CD70 CAR T + Reg KO + TGFBRII KO cells: anti-CD70 CAR+/TRAC−/B2M−/CD70−/Reg−/TGFBRII− | $5 \times 10^6$ cells/mouse | $1 \times 10^7$ cells/mouse | 4 |

Figure 17A:
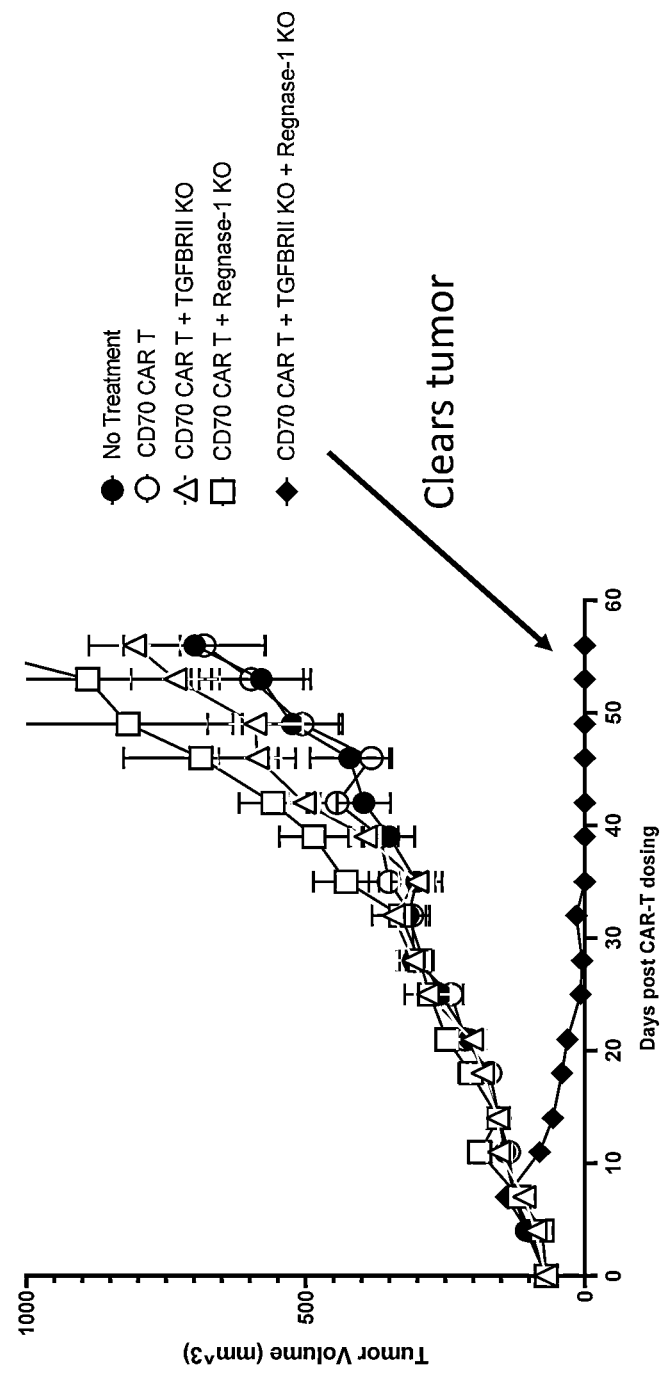

Tumor volume was measured 2 times weekly (~every 3-4 days) from day of treatment initiation. By day 11 post-injection, anti-CD70 CAR T cells with both TGFBRII and Regnase genes KO began to show a significant effect on reducing tumor volume compared to other treatment groups. Approximately one month later the anti-CD70 CAR T+Reg KO+TGFBRII KO cells had completely eliminated tumor growth in the subcutaneous CAKI-1 model (FIG. 17A).

These results demonstrated that disrupting both the TGFBRII and Regnase genes in CAR T cells increased the potency of the CAR T Cells and effectively cleared tumors in the subcutaneous CAKI-1 renal cell carcinoma tumor xenograft model.

Treatment in the Non-Small Cell Lung Carcinoma (NSCLC) Tumor Model

The ability of T cells expressing a CD70 CAR with TGFBRII and/or Regnase gene edits to eliminate lung adenocarcinoma cells that express moderate levels of CD70 was evaluated in vivo using a subcutaneous lung carcinoma (NCI-H1975) tumor xenograft mouse model. Anti-CD70 CAR+ T cells were produced as described herein. See, e.g., Example 13.

The ability of these anti-CD70 CAR+ T cells to ameliorate disease caused by a CD70+ lung carcinoma cell line was evaluated in NSG mice using methods employed by Translational Drug Development, LLC (Scottsdale, AZ). In brief, 20, 5-8 week old female, NSG mice were individually housed in ventilated microisolator cages, maintained under pathogen-free conditions, 5-7 days prior to the start of the study. Mice received a subcutaneous inoculation of $5 \times 10^6$ NCI-H1975 lung carcinoma cells/mouse in the right hind flank. When mean tumor size reached target of ~85 mm$^3$, the mice were further divided into 5 treatment groups as shown in Table 10. On Day 1, treatment four groups received a single 200 μl intravenous dose of 1×10⁷ anti-CD70 CAR+ T cells according to Table 10.

TABLE 10

Treatment groups

| Group | CAR-T | NCI-H1975 cells | CAR+ T cell treatment (i.v.) | N |
|---|---|---|---|---|
| 1 | None | 5 × 10⁶ cells/mouse | None | 4 |
| 2 | Anti-CD70 CAR T cells: anti-CD70 CAR+/TRAC−/B2M−/CD70− | 5 × 10⁶ cells/mouse | 1 × 10⁷ cells/mouse | 4 |
| 3 | Anti-CD70 CAR T + Reg KO cells: anti-CD70 CAR+/TRAC−/B2M−/CD70−/Reg− | 5 × 10⁶ cells/mouse | 1 × 10⁷ cells/mouse | 4 |
| 4 | Anti-CD70 CAR T + TGFBRII KO cells: anti-CD70 CAR+/TRAC−/B2M−/CD70−/TGFBRII− | 5 × 10⁶ cells/mouse | 1 × 10⁷ cells/mouse | 4 |
| 5 | Anti-CD70 CAR T + Reg KO + TGFBRII KO cells: anti-CD70 CAR+/TRAC−/B2M−/CD70−/Reg−/TGFBRII− | 5 × 10⁶ cells/mouse | 1 × 10⁷ cells/mouse | 4 |

Tumor volume was measured 2 times weekly from day of treatment initiation. By day 12 post-injection, animal treated with anti-CD70 CAR T cells having the TGFBRII edit exhibited attenuated tumor growth. Tumors treated with anti-CAR T cells with both TGFBRII and Regnase genes disrupted began to show a decrease in tumor volume by day 8 post-injection and cleared tumors by day 29 in 4 mice out of 4. This complete regression of tumors in treated animals continued through day 53 post injection. Treatment with anti-CD70 CAR+/TRAC−/B2M−/CD70−/Reg−/TGFBRII− T cells resulted in potent activity against established H1975 lung cancer xenografts through 53 days post injection (FIG. 17B). These data demonstrate that disrupting TGFBRII alone or TGFBRII and Regnase-1 in CAR T cells have potent activity against human CD70+ lung cancer tumors in vivo.

Example 15: Tumor Re-Challenge Model Renal Cell Carcinoma Large Tumor Xenograft Model The efficacy of anti-CD70 CAR T cells having TGFBRII and/or Regnase-1 genes disrupted (see, e.g., Example 10) were tested in a subcutaneous A498 xenograft model with an ACHN re-challenge. In brief, five million A498 cells were injected subcutaneously in the right flank of NSG mice. Tumors were allowed to grow to an average size of approximately 425 mm³ after which the tumor-bearing mice were randomized in five groups (N=5/group). Group 1 was left untreated (no treatment) while Groups 2-5 received one of the anti-CD70 CAR T cell treatments shown Table 11.

TABLE 11

Treatment Conditions

| Group | CAR-T | A498 cells | CAR+ T cell treatment (i.v.) | N |
|---|---|---|---|---|
| 2 | Anti-CD70 CAR T cells: anti-CD70 CAR+/TRAC−/B2M−/CD70− | 5 × 10⁶ cells/mouse | 8 × 10⁶ cells/mouse | 5 |
| 3 | Anti-CD70 CAR T + Reg KO cells: anti-CD70 CAR+/TRAC−/B2M−/CD70−/Reg− | 5 × 10⁶ cells/mouse | 8 × 10⁶ cells/mouse | 5 |
| 4 | Anti-CD70 CAR T + TGFBRII KO cells: anti-CD70 CAR+/TRAC−/B2M−/CD70−/TGFBRII− | 5 × 10⁶ cells/mouse | 8 × 10⁶ cells/mouse | 5 |
| 5 | Anti-CD70 CAR T + Reg KO + TGFBRII KO cells: anti-CD70 CAR+/TRAC−/B2M−/CD70−/Reg−/TGFBRII− | 5 × 10⁶ cells/mouse | 8 × 10⁶ cells/mouse | 5 |

On Day 56, a tumor re-challenge was initiated whereby 1×10⁷ ACHN cells were injected into the left flank of treated mice and into a new control group (no treatment).

Figure 18A:
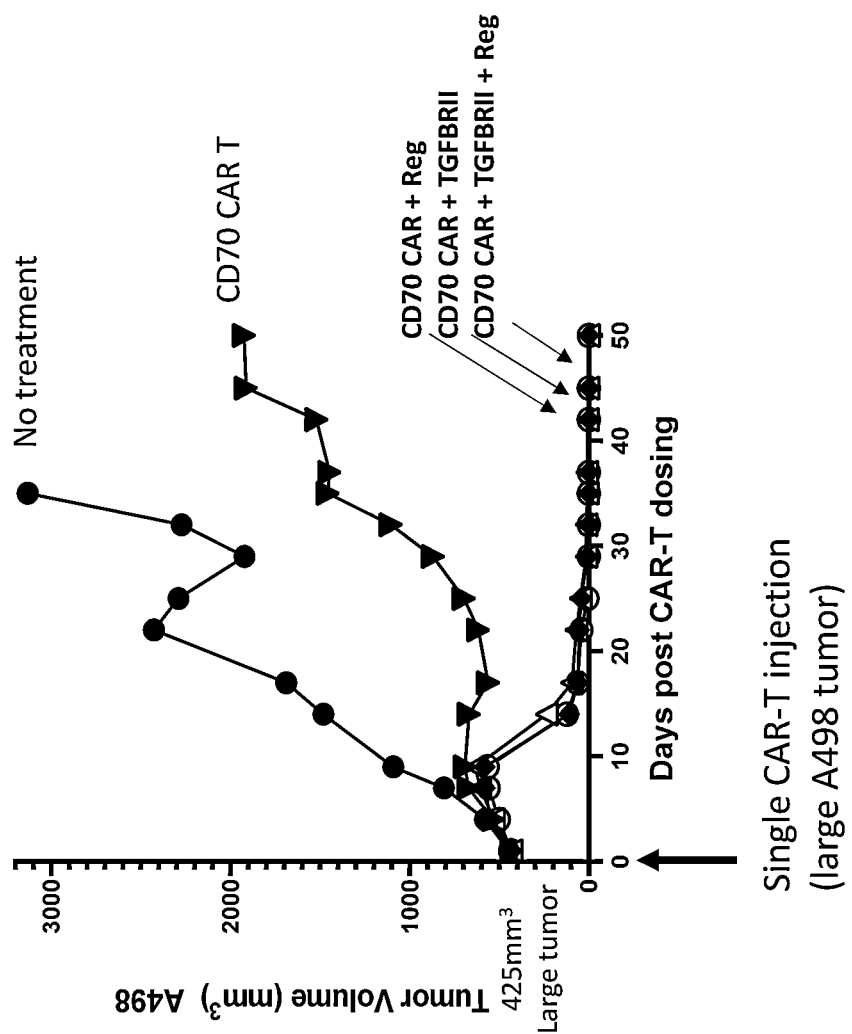
FIGS. 18A-18B include diagrams showing synergistic effects of disrupting both TGFBRII and Regnase genes in an RCC rechallenge xenograph model.
Figure 18B:
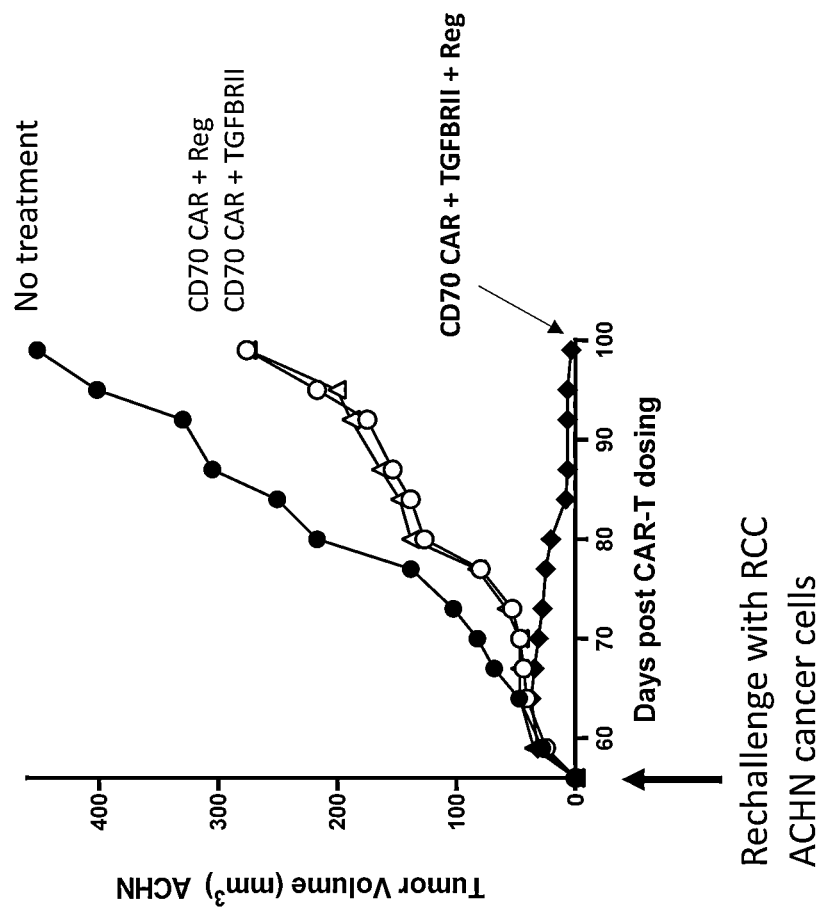

As shown in FIG. 18A, all mice treated with all CAR T cell populations having a disrupted TGFBRII and/or Regnase gene showed complete clearance of the A498 tumor by day 50. However, when mice were rechallenged with a new RCC tumor cell (ACHN) only CAR T Cells with both Regnase and TGFBRII edits were able to clear the tumor compared to cells with either Regnase-1 or TGFBRII disruptions alone (FIG. 18B).

Example 16: Analysis of T Cell Fraction in Renal Cell Carcinoma (CAKI-1) Tumor Xenograft Model Blood samples were taken from mice with CAKI-1 RCC tumors, 44 days after CAR T administration. Briefly, 100 ul of mouse whole blood was collected via submandibular vein. Red blood cell lysis buffer was used to achieve optimal lysis of erythrocytes with minimal effect on lymphocytes. Human CD45 and mouse CD45 were used as a biomarker to separate human and mouse cells by FACS. The blood samples were evaluated by flow cytometry looking for absolute CAR T counts as well as memory T cell subsets. An anti-CD70 CAR anti-idiotype antibody was used to detect CAR T cells and CD45RO+CD27+ to define central memory T cells. See U.S. Patent Application No. 63/069,889, the relevant disclosures of which are incorporated by reference for the subject matter and purpose referenced herein.

Figure 19B:
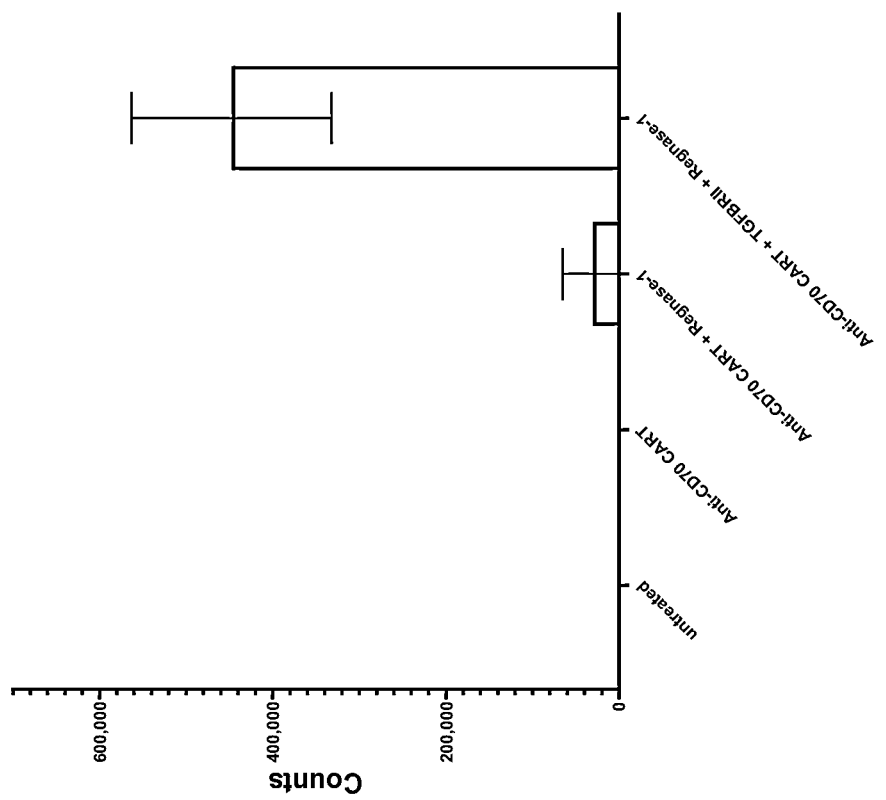

The results demonstrate that the addition of the TGFBRII and Regnase-1 gene edit significantly enhanced the population of central memory T cells compared to the edit of either TFGBRII or Regnase-1 alone, which correlates with massive expansion of CAR T cells (FIG. 19A) seen in these animals. And the TGFBRII edit further promoted the potential of CAR T cell proliferation in vivo, suggesting a robust synergistic effect along with the Regnase edit (FIG. 19B).

Example 17: Assessment of Anti-CD19 CAR-T Cells Having TGFBRII and/or Regnase-1 Gene Disruptions in an Intravenous Disseminated Models in NOG Mice Intravenous Disseminated Nalm-6 Human Acute Lymphoblastic Leukemia Tumor Xenograft Model The Intravenous Disseminated Model (Disseminated Model) using the Nalm-6 Human Acute Lymphoblastic Leukemia tumor cell line in NOG mice was used to further demonstrate the efficacy of anti-CD19 CAR T cells with TGFBRII and/or Regnase-1 gene edits. Efficacy of various anti-CD19 CAR T populations were evaluated in the Disseminated Model using methods employed by Translations Drug Development, LLC (Scottsdale, AZ) and described herein. In brief, 24, 5-8 week old female CIEA NOG (NOD.Cg-Prkdc$^{scid}$I12rg$^{tm1Sug}$/JicTac) mice were individually housed in ventilated microisolator cages, maintained under pathogen-free conditions, 5-7 days prior to the start of the study. At the start of the study, the mice were divided into 5 treatment groups as shown in Table 12. On Day 1 mice in Groups 2-4 received an intravenous injection of 0.5×10$^6$ Nalm6 cells/mouse. The mice were inoculated intravenously to model disseminated disease. On Day 4 (3 days post injection with the Nalm6 cells), treatment Groups 2-4 received a single 200 µl intravenous dose of CAR+ T cells per Table 12.

TABLE 12

Treatment groups.

| Group | CAR T | Nalm6 Cells (i.v.) | anti-CD19 CAR T Treatment (i.v.) | N |
|---|---|---|---|---|
| 1 | Untreated | 0.5 × 10$^6$ cells/mouse | None | 5 |
| 2 | Anti-CD19 CAR T cells: anti-CD19 CAR+/TRAC−/B2M− | 0.5 × 10$^6$ cells/mouse | 4 × 10$^6$ CAR-T positive cells/mouse | 5 |
| 3 | Anti-CD19 CAR T + Reg KO cells: anti-CD19 CAR+/TRAC−/B2M−/Reg− | 0.5 × 10$^6$ cells/mouse | 4 × 10$^6$ CAR-T positive cells/mouse | 5 |
| 4 | Anti-CD19 CAR T + TGFBRII KO cells: anti-CD19 CAR+/TRAC−/B2M−/TGFBRII− | 0.5 × 10$^6$ cells/mouse | 4 × 10$^6$ CAR-T positive cells/mouse | 5 |
| 5 | Anti-CD19 CAR T + Reg KO + TGFBRII KO cells: anti-CD19 CAR+/TRAC−/B2M−/Reg− | 0.5 × 10$^6$ cells/mouse | 4 × 10$^6$ CAR-T positive cells/mouse | 5 |

During the course of the study mice were monitored daily and body weight was measured two times weekly as described above.

Figure 20A:
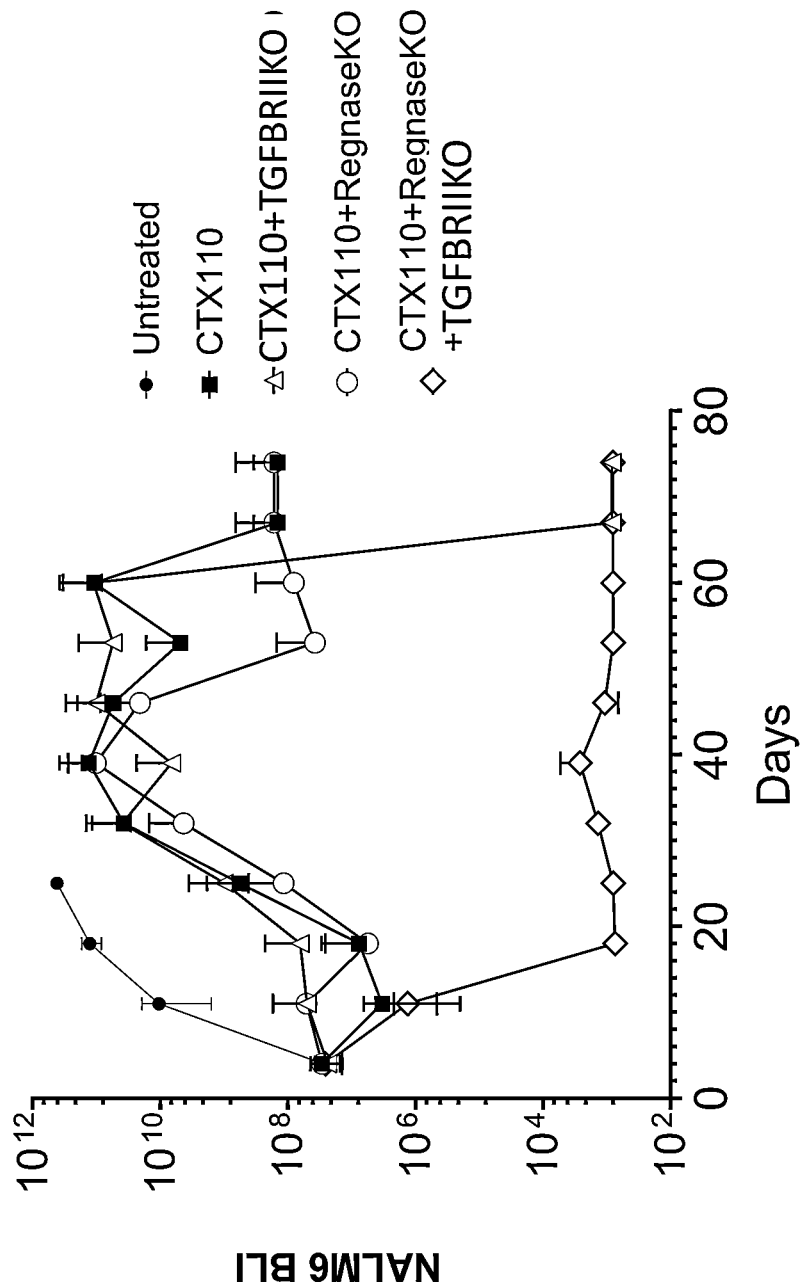
FIGS. 20A-20B include diagrams showing synergistic effects of TGFBRII and Regnase double knock-out in a Nalm6-leukemia (B-ALL) mouse model.

TGFBRII gene editing combined with Regnase editing induced a maintained NALM6 tumor regression at an early time point (day 18) post tumor inoculation, compared to either edit alone. This reduction in tumor size was maintain (FIG. 20A). The sharp decline in tumor size in the TGFBRII KO group at day 74 post tumor inoculation represents only 5 of 15 mince. Ten of the 15 mice in TGFBRIIKO group had already reached the tumor BLI endpoint.

Figure 20B:
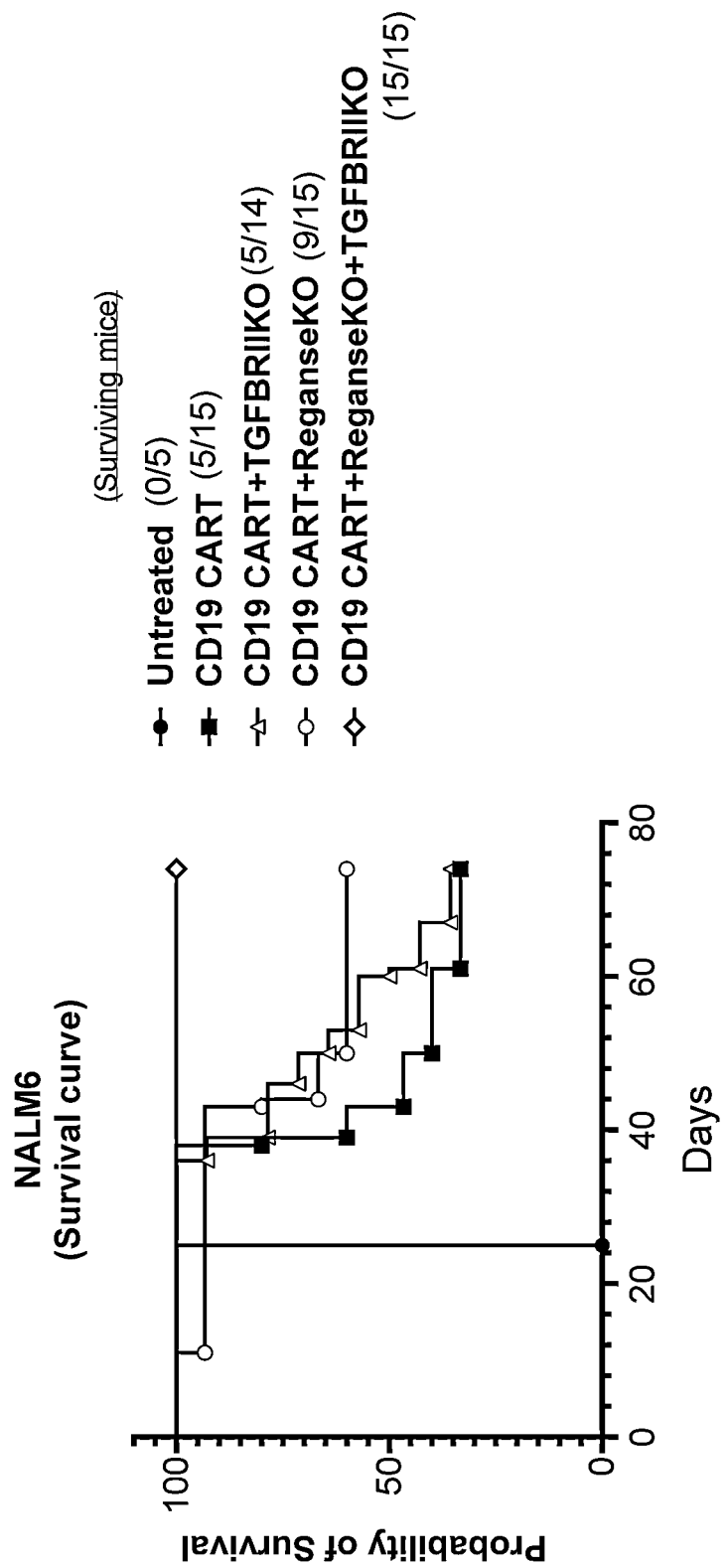

While disruption of either TGFBRII or Regnase showed some survival advantage in the Nalm6 Model mice treated with anti-CD19 CAR+ cells, having both TGFBRII and Regnase gene disruptions exhibited the greatest survival advantage (FIG. 20B).

Intravenous Disseminated JeKo-1 Tumor Xenograft Model

The Intravenous Disseminated Model (Disseminated Model) using the JeKo-1 Human Mantle cell lymphoma (MCL) tumor cell line in NOG mice was used to further demonstrate the efficacy of anti-CD19 CAR T cells with TGFBRII and/or Regnase gene edits. Efficacy of various anti-CD19 CAR T populations were evaluated in the Disseminated Model using methods employed by Translations Drug Development, LLC (Scottsdale, AZ) and described herein. In brief, 24, 5-8 week old female CIEA NOG (NOD.Cg-Prkdc$^{scid}$I12rg$^{tm1Sug}$/JicTac) mice were individually housed in ventilated microisolator cages, maintained under pathogen-free conditions, 5-7 days prior to the start of the study. At the start of the study, the mice were divided into 5 treatment groups as shown in Table 13. On Day 1 mice in Groups 2-4 received an intravenous injection of 0.5×10$^6$ JeKo-1 cells/mouse. The mice were inoculated intravenously to model disseminated disease. On Day 4 (3 days post injection with the JeKo-1 cells), treatment Groups 2-4 received a single 200 µl intravenous dose of CAR T cells per Table 13.

TABLE 13

Treatment groups.

| Group | CAR T | JeKo-1 Cells (i.v.) | anti-CD19 CAR+ T cell Treatment (i.v.) | N |
|---|---|---|---|---|
| 1 | Untreated | 5 × 10$^6$ cells/mouse | None | 5 |
| 2 | Anti-CD19 CAR T cells: anti-CD19 CAR+/TRAC−/B2M− | 5 × 10$^6$ cells/mouse | 4 × 10$^6$ cells/mouse* | 5 |
| 3 | Anti-CD19 CAR T + Reg KO cells: anti-CD19 CAR+/TRAC−/B2M−/Reg− | 5 × 10$^6$ cells/mouse | 4 × 10$^6$ cells/mouse* | 5 |
| 4 | Anti-CD19 CAR T + TGFBRII KO cells: anti-CD19 CAR+/TRAC−/B2M−/TGFBRII− | 5 × 10$^6$ cells/mouse | 4 × 10$^6$ cells/mouse* | 5 |
| 5 | Anti-CD19 CAR T + Reg KO + TGFBRII KO cells: anti-CD19 CAR+/TRAC−/B2M−/Reg−/TGFBRII− | 5 × 10$^6$ cells/mouse | 4 × 10$^6$ cells/mouse* | 5 |

During the course of the study mice were monitored daily and body weight was measured two times weekly as described above.

Figure 21:
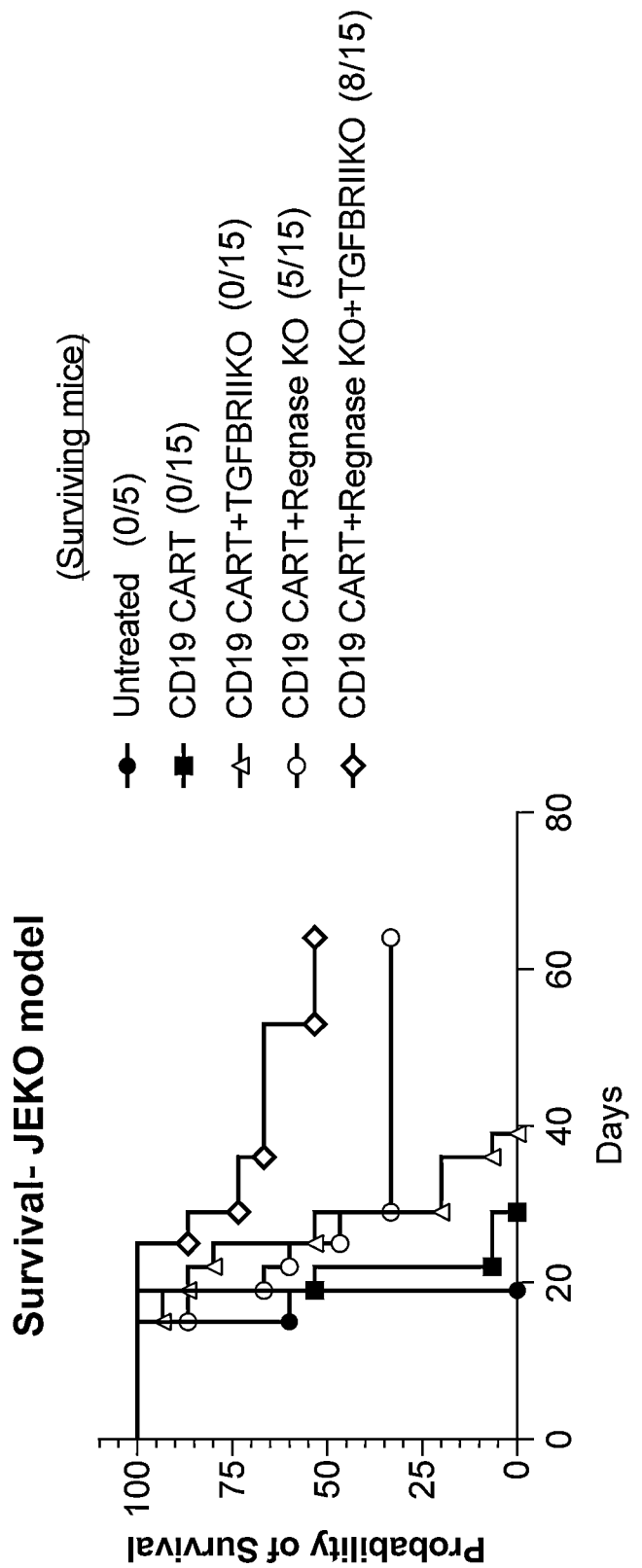
FIG. 21 is a diagram showing survival advantage arising from TGFBRII and Regnase double disruptions in a NOG Mantle cell lymphoma (MCL) tumor xenograft mouse model.

While either TGFBRII or Regnase showed some survival advantage in the JeKo-1 Model, mice treated with anti-CD19 CAR+ cells having both TGFBRII and Regnase gene edits exhibited the greatest survival advantage FIG. 21.

CAR T Cell Expansion In Vivo

CAR T cell expansion was assessed by measuring the CAR copy number by ddPCR of DNA isolated from blood samples collected throughout the Jeko-1 and Nalm-6 studies as described above.

DNA was isolated from mouse tissue using the Qiagen Dneasy blood and tissue kit (Qiagen, Venlo, Netherlands). Total mass of nucleic acid from RBC-lysed samples was quantitated using either Nanodrop (Thermo Fisher Scientific) or DropSense96 (trinean, Gentbrugge, Belgium) machines. Primers and 6-carboxyfluorescein (FAM)-labeled probe sets (provided in Table 14 below) were designed to quantitate the levels of the integrated CAR construct into the human TRAC locus by droplet digital PCR (ddPCR). ddPCR was performed using the Bio-Rad Automated Droplet Generator, Bio-Rad T100 Thermal Cycler, and Bio-Rad QX200 Droplet Reader machine(s) (Bio-rad Laboratories, Hercules, CA). QuantaSoft Version 1.7.4.0917 (Bio-rad Laboratories) software was used to calculate the absolute number of integrated CAR copies per sample. Finally, the number of detected CAR alleles was divided by the input total DNA amount to compute the absolute number of CAR copies per mass of input sample. The ddPCR assay detects the number of copies of integrated CAR transgene per mass of genomic DNA (gDNA) by amplifying an 866 bp amplicon spanning endogenous TRAC sequence and the CAR expression cassette promoter (EF-1α). In brief, qualification of the assay yielded linear data (R$^2$>0.95) within the range tested (2 to 300,000 copies per ug of gDNA) as well as generated a % relative error (% RE) and % coefficient of variation (% CV) within normal ranges (% RE≤100% and % CV≤20%) for conditions ≥LLOQ. The LLOD and LLOQ were calculated based on the available data and the LLOD was set to 5 copies per 0.2 µg of gDNA and the LLOQ was set to 40 copies per 0.2 µg.

TABLE 14

Primers and probes used for ddPCR
CAR primers and probe

| | |
|---|---|
| CTX110-20-30_dd_1 Forward | GGCACCATATTCATTTTGCAGGTGAA (SEQ ID NO: 11) |
| CTX110-20-30_dd_1 Reverse | ATGTGCGCTCTGCCCACTGACGGGC (SEQ ID NO: 12) |
| CTX110-20-30_dd_1 Probe (FAM) | AGACATGAGGTCTATGGACTTCAGGCTCC (SEQ ID NO: 13) |

Figure 22A:
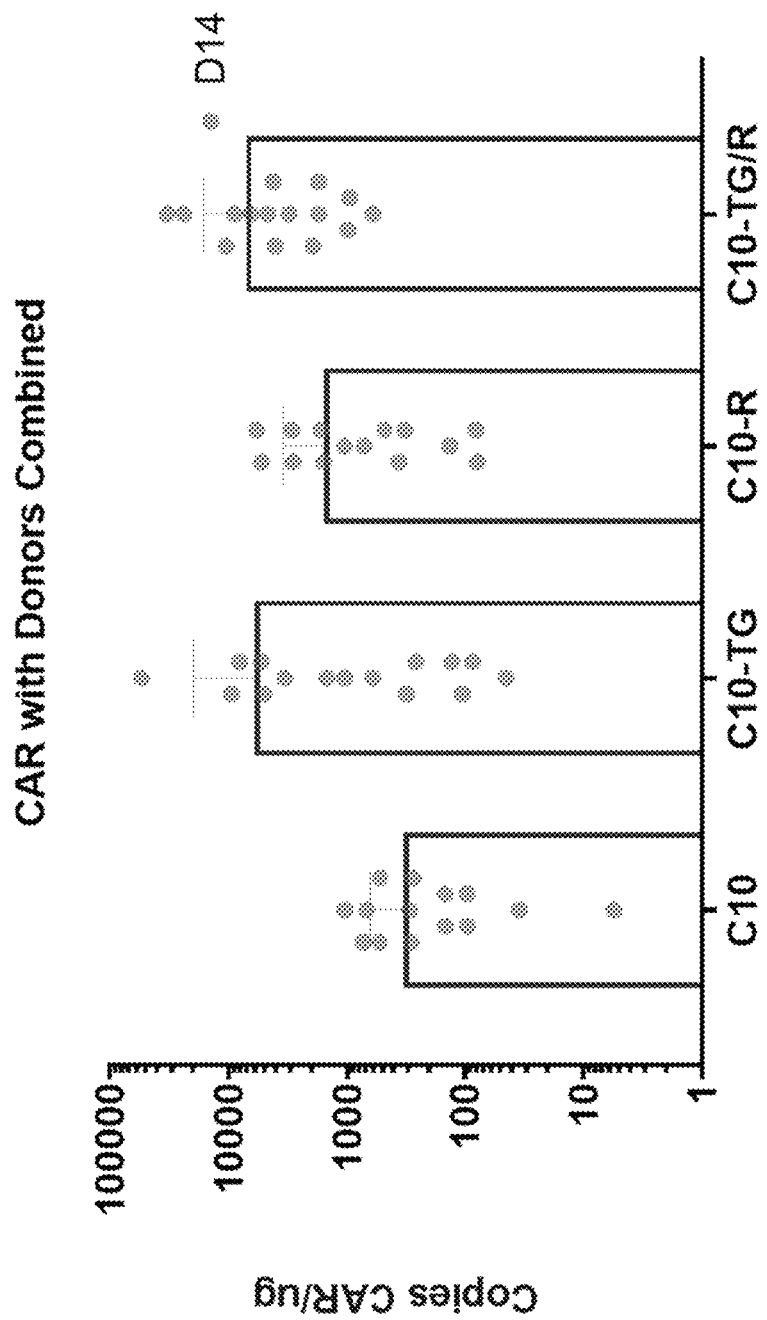
FIGS. 22A-22B include diagrams showing increased in vivo expansion of CAR-T cells having TGFBRII and/or Regnase knock-out.
Figure 22B:
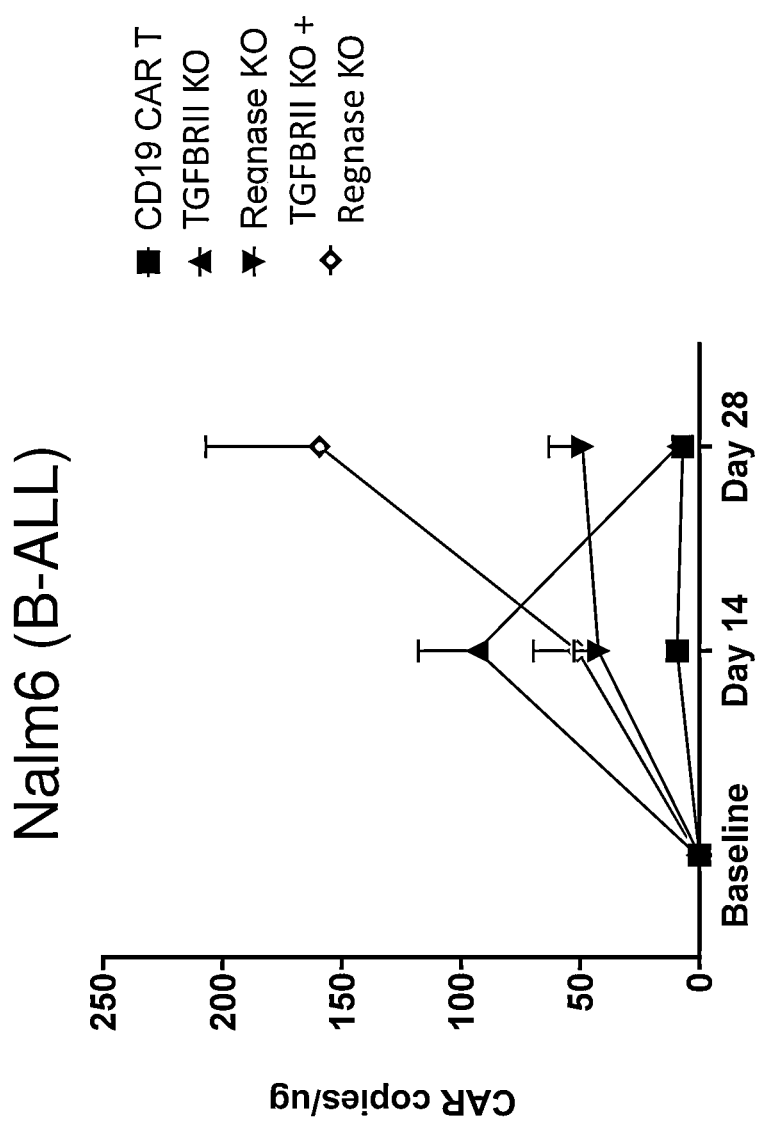

These analysis demonstrate that the addition of either TGFBRII or Regnase-1 KO to allogeneic CAR T cells (TRAC⁻/B2M⁻; Group C-10) allowed the T cells to expand to larger levels in the blood of treated mice (e.g., Groups C10-TG, C10-R, C10-TG/R) compared to groups treated with the allogeneic CAR T cells without those KOs (e.g., Group C10) (FIG. 22A). This expansion was apparent at day 14 of the Jeko-1 study. Loss of both TGFBRII and Regnase-1 (FIG. 22A, C10-TG/R) led to a more uniform expansion relative to TGFBRII (FIG. 22A, C10-TG) or Regnase-1 (FIG. 22A, C10-R) single KOs. In the Nalm-6 study, disruption of both TGFBRII and Regnase-1 had a synergistic effect on CAR T cell expansion at day 28 as shown in FIG. 22B In sum, all groups with loss of either TGFBRII or Regnase-1 had expanded CAR-T cells in the peripheral blood.

Example 18: Generation of CAR T Cells with Multiple Gene Editing and Verification of Gene Edits Activated primary human T cells were electroporated with Cas9/sgRNA RNP complexes (200 pmol Cas9, 1000 pmol gRNA) to generate cells edited for TRAC−/β2M−, TRAC−/β2M−/Regnase-1−, TRAC−/β2M−/TGFBRII− and TRAC−/β2M−/Regnase-1−/TGFBRII−. Sequence encoding anti-BCMA CAR was inserted into the TRAC locus using recombinant AAV6 carrying the DNA sequence for anti-BCMA CAR (SEQ ID NO: 170). The following sgRNAs were used: TRAC (SEQ ID NO: 58), β2M (SEQ ID NO: 62), Reg-1 (SEQ ID NO: 51; REG1-Z10) and TGFBRII (SEQ ID NO: 313).

Flowcytometry was used to verify the editing for TRAC, β2M and the insertion and expression of anti-BCMA CAR. Briefly, about one week post electroporation, cells were stained with anti-human TCR, anti-human β2M and recombinant biotinylated human BCMA/streptavidin-APC to assess the levels of editing for TRAC and β2M, and insertion of the nucleotide sequence encoding anti-BCMA CAR.

Figure 23B:
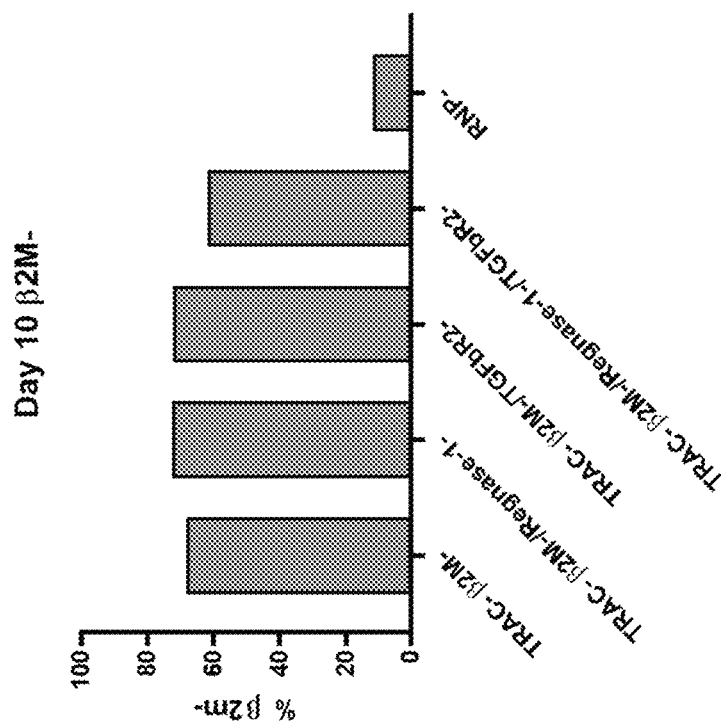
FIGS. 23A-23D include diagrams showing consistent rates of CRISPR/Cas editing in anti-BCMA CAR-T cells with Reg-1 and/or TGFBRII disruption as determined by flowcytometry.
Figure 23A:
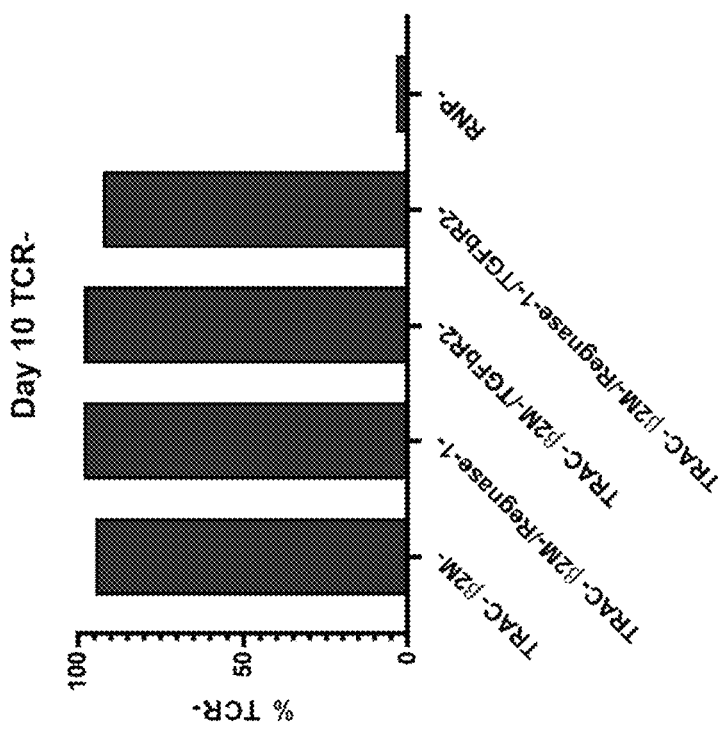
Figure 23C:
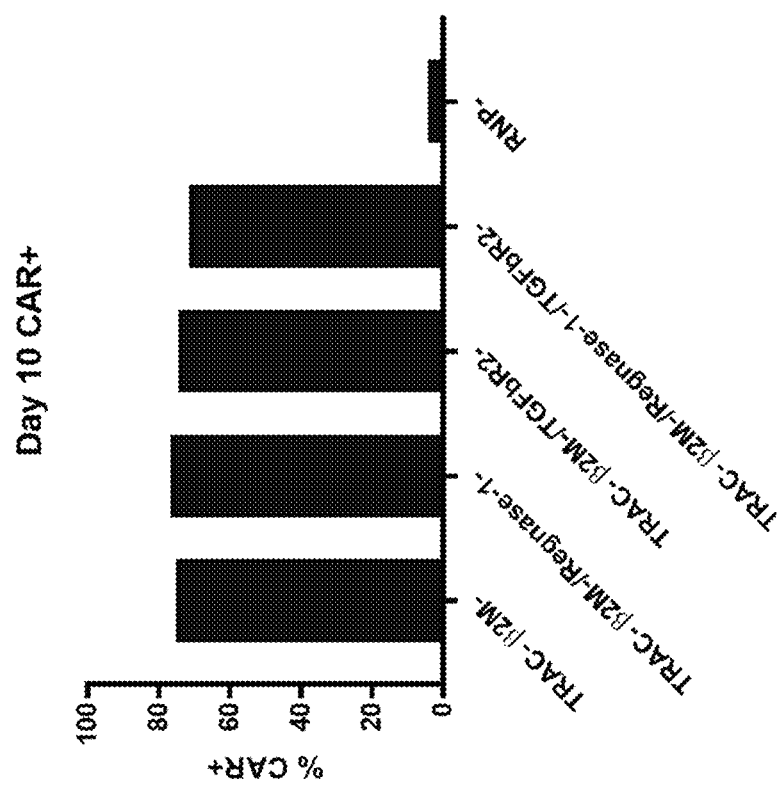
Figure 23D:
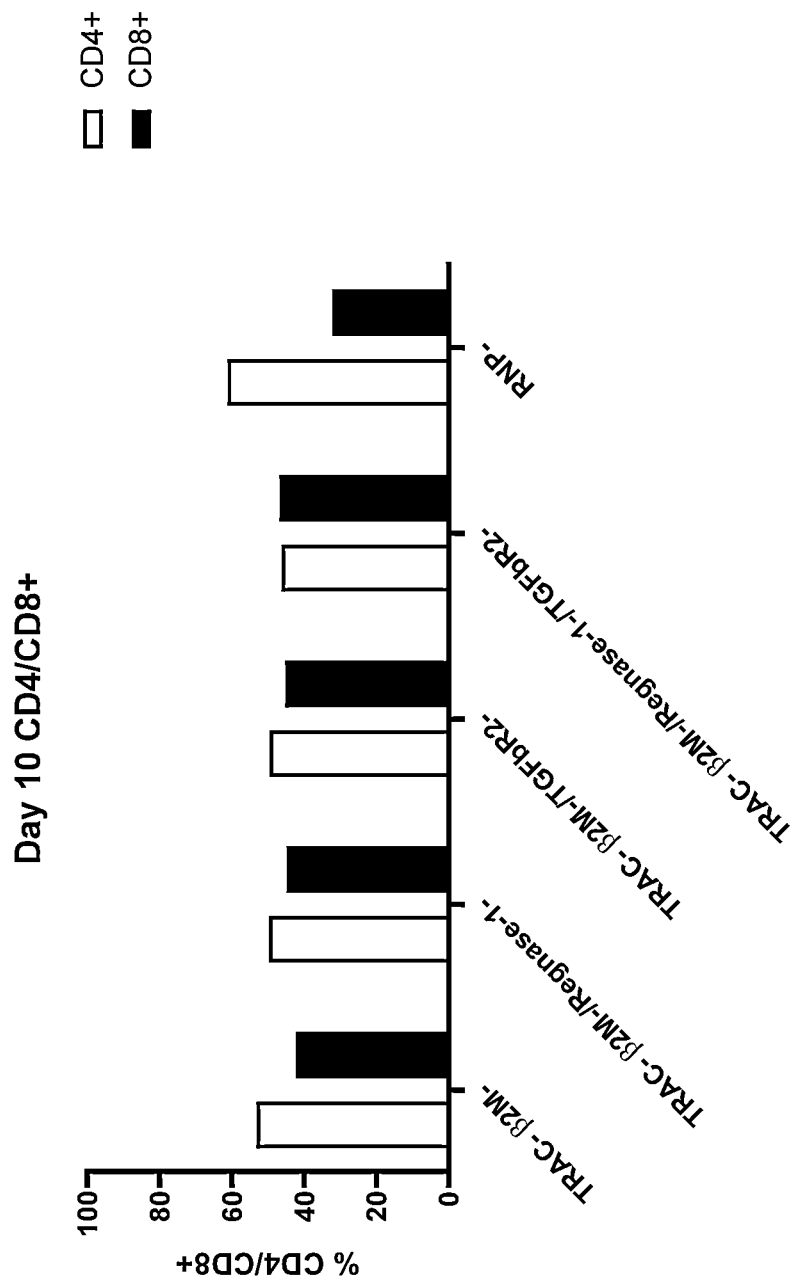

TRAC−/β2M−, TRAC−/β2M−/Reg-1−, TRAC−/β2M−/TGFBRII− and TRAC−/β2M−/Reg-1−/TGFBRII− anti-BCMA CAR+ T-cells show consistent rates of TCR and β2M disruptions at >90% and >60% rates, respectively as determined by flow cytometry (FIGS. 23A and 23B). Anti-BCMA CAR expression was measured flow cytometrically by determining the percentage of cells that bound recombinant biotinylated BCMA/streptavidin-APC conjugate. All the conditions including TRAC−/β2M−, TRAC−/β2M−/Reg-1−, TRAC−/β2M−/TGFBRII− and TRAC−/β2M−/Reg-1−/TGFBRII− anti-BCMA CAR+ T-cells show consistent rates of CAR insertion (>70%), while the unedited RNP− T-cells have no detectable staining for anti-BCMA CAR (FIG. 23C). The ratio of CD4/CD8 T cells as assessed by flow cytometry in the TRAC−/β2M−, TRAC−/β2M−/Reg-1−, TRAC−/β2M−/TGFBRII− and TRAC−/β2M−/Reg-1−/TGFBRII− anti-BCMA CAR+ T-cells were found to be consistent in the range of 55-60%/40-45% across all the samples (FIG. 23D).

TIDE analysis was performed for the verification of editing rates for Reg-1 and TGFBRII genes. Briefly, about one week post electroporation, two million cells from TRAC−/β2M−, TRAC−/β2M−/Reg-1−, TRAC−/β2M−/TGFBRII− and TRAC−/β2M−/Reg-1−/TGFBRII− anti-BCMA CAR+ T-cells and two million unedited T-cells from the same donor were removed from culture and transferred to 1.5 mL microcentrifuge tubes. Cells were spun down in a tabletop microcentrifuge at 300 g for 10 minutes and the resulting supernatant was discarded. The cells were washed twice with 1000 uL 1×PBS and the cell pellets were frozen at −80° C. The frozen cell pellets were then used for the extraction of genomic DNA using QIAamp DNA Blood Mini Kit (Qiagen, catalog #51106). Gene-specific primers were used to amplify the region flanking the cut sites of Reg-1 and TGFBRII (Invitrogen™ Platinum™ SuperFi™ II Green PCR Master Mix; catalog #12369050) and the PCR amplicons derived were subsequently sequenced and analyzed by TIDE to determine the indel patterns/frequencies (editing frequencies).

Figure 24A:
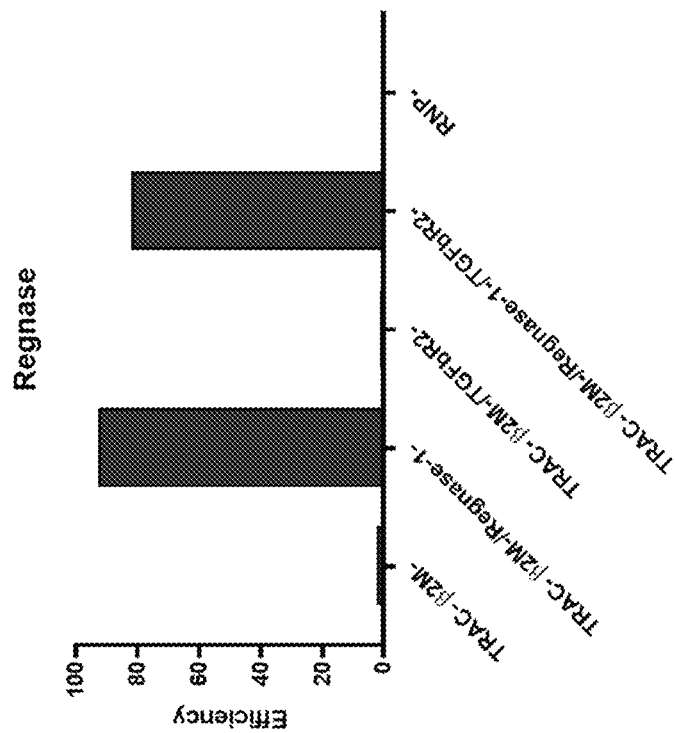
FIGS. 24A-24B include diagrams showing consistent edit editing rates in anti-BCMA CAR-T cells with Reg-1 and/or TGFBRII disruptions.
Figure 24B:
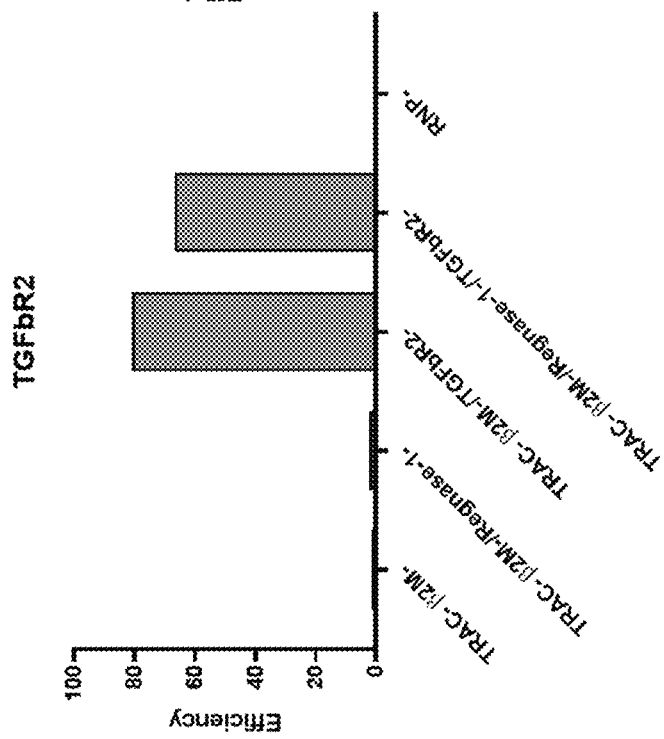

The analyzed indel frequencies were found to be within the expected range of 65-80% for TGF sgRNA and >80% for the Regnase-1 sgRNA, respectively (FIGS. 24A and 24B).

Example 19: Cytotoxicity of Anti-BCMA CAR T Cells with Multiple Gene Edits

A cytotoxicity (cell kill) assay was used to assess the ability of the TRAC−/β2M−, TRAC−/β2M−/Reg-1−, TRAC−/β2M−/TGFBRII− and TRAC−/β2M−/Reg-1−/TGFBRII− anti-BCMA CAR+ T-cells (produced by the methods disclosed herein, see, e.g., Example 18) to cause cell lysis in two target cell lines, MM.1S (multiple myeloma cell line) and JeKo-1 (mantle cell lymphoma cell line). Unedited RNP− cells without CAR were used as a negative control to determine the specific lysis by CAR+ T cells. Briefly, the target cell lines were stained with eBioscience™ Cell Proliferation Dye eFluor™ 670 (Thermofisher Scientific; catalog #65-0840-85) per manufacturer's instructions and seeded into 96-well plates at 50,000 cells per well. Next, CAR T-cells or RNP− T cells were added to the wells containing target cells at ratios of 0, 0.5:1, 1:1, 2:1, or 4:1 (T cell: target cell) and incubated further for approximately 4 hours for MM.1S and 24 hours for JeKo-1. After the respective incubation period, the 96-well plates were spun down at 300 g for 10 minutes and 100 µL of supernatant was removed for cytokine quantification. Cells were then washed once with 1×PBS and stained with 150 ul of 1×PBS supplemented with 0.5% BSA and 5 µg/mL DAPI (Invitrogen; catalog #D3571) and incubated for 15 minutes in dark. Post-incubation, cells were washed-off DAPI, resuspended in 150 µl of 1λPBS supplemented with 0.5% BSA, and acquired and analyzed using a flow cytometer. Target cells were identified via eFluor-based fluorescence and then divided into live and dead cells based on their DAPI fluorescence.

Figure 25A:
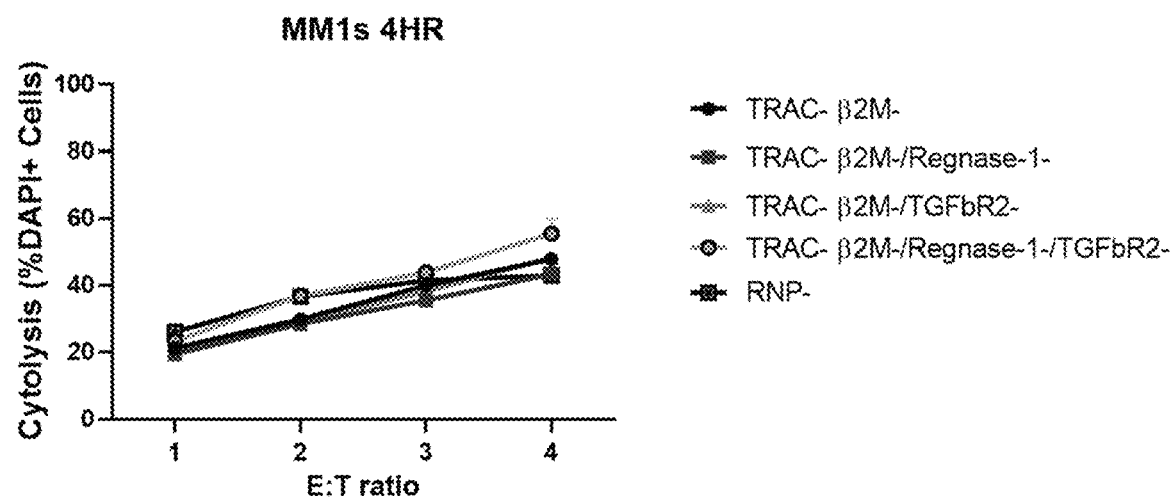
FIGS. 25A-25D include diagrams showing superior cell cytotoxicity of TRAC–/β2M–/Reg-1– TGFBRII– anti-BCMA CAR+ T-cells.
Figure 25B:
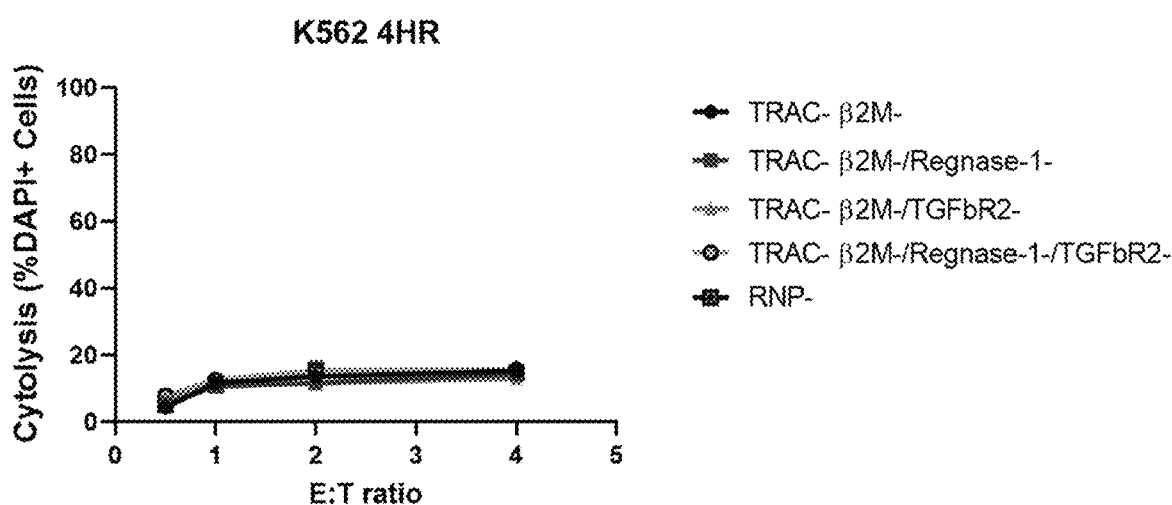
Figure 25C:
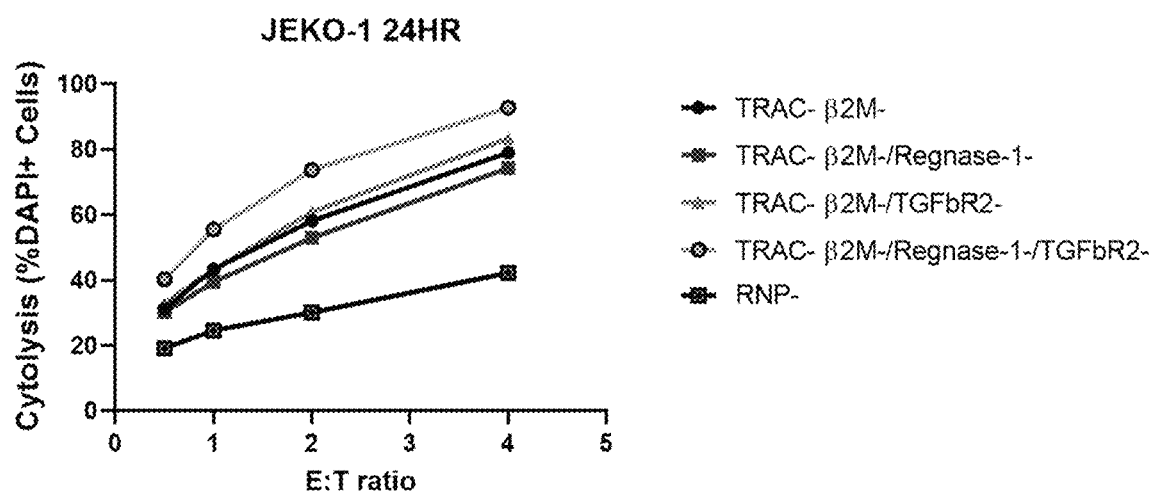
Figure 25D:
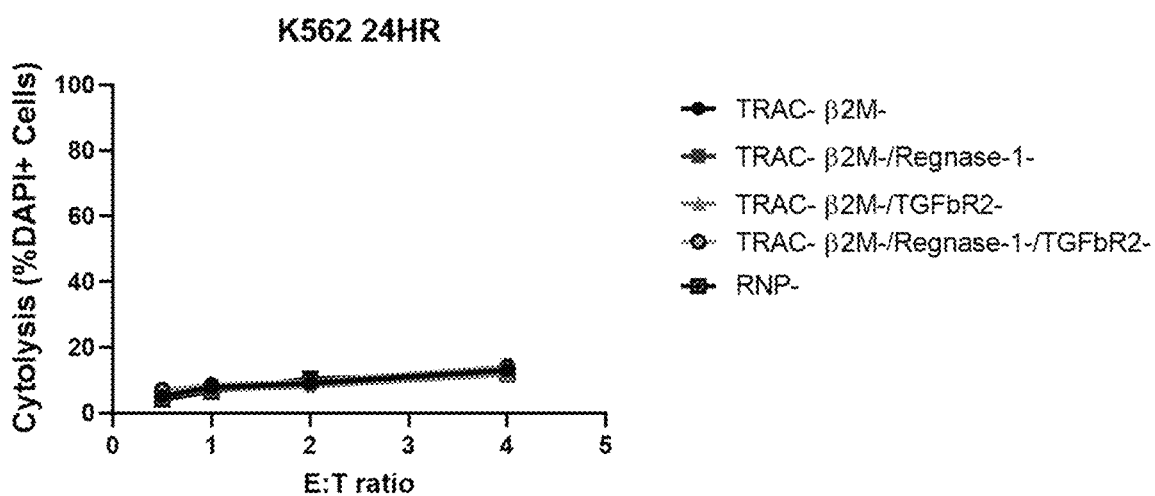

The TRAC−/β2M−/Reg-1−/TGFBRII− anti-BCMA CAR+ T-cells exhibited greater cytotoxicity towards the MM.1S (FIG. 25A) and JeKo-1 cell lines (FIG. 25C) compared to TRAC−/β2M−, TRAC−/β2M−/Regnase-1− or TRAC−/β2M−/TGFBRII− anti-BCMA CAR+ T-cells. Comparative data from K562 cells (as controls) are provided in FIG. 25B and FIG. 25D.

Example 20: In Vivo Effects of TGFBRII+Regnase-1 Disruption on Allogeneic CAR T Cells in the Subcutaneous RPMI-8226 Xenograft Tumor Model A subcutaneous tumor mouse model was utilized to assess the in vivo efficacy of allogeneic anti-BCMA CARs with the following gene disruptions: 1) β2M and TRAC, 2) β2M, TRAC, and TGFBRII, 3) β2M, TRAC, and Reg-1, and 4) β2M, TRAC, TGFBRII, and Reg-1. The subcutaneous tumor mouse model utilized the BCMA+ multiple myeloma derived RPMI-8226 tumor cell line in NSG mice. The TGFBRII gene was edited via CRISPR/Cas-mediated gene editing using the TGFBRII Ex5_T1 guide (SEQ ID NO. 313). The Reg-1 gene was edited via CRISPR/Cas-mediated gene editing using the Z10 guide (SEQ ID NO. 51). The anti-BCMA CAR T cells express an anti-BCMA CAR comprising the amino acid sequence of SEQ ID NO: 146). See also the sequence Tables 22, 23, 27, and 39 below.

Efficacy of the anti-BCMA CAR T cells was evaluated in the subcutaneous xenograft model using methods employed by Translations Drug Development, LLC (Scottsdale, AZ) and described herein. In brief, 25 5-8 week old female NSG mice were individually housed in ventilated microisolator cages, maintained under pathogen-free conditions, 5-7 days prior to the start of the study. On day 1, mice received a subcutaneous inoculation of $1 \times 10^7$ RPMI-8226 cells/mouse in the right hind flank. Nine days later (Day 10), the tumor inoculation sites were inspected to determine if the tumors were palpable. After confirming palpability, the mice were further divided into 5 treatment groups as shown in Table 1. All treatment groups received a single 200 ul intravenous dose of 1e6 anti-BCMA CAR+ T cells.

TABLE 15

Treatment Groups for the RMPI-8226 Xenograft Study

| Group | CAR T cells (i.v.) | N |
| --- | --- | --- |
| 1 | NA | 5 |
| 2 | anti-BCMA CAR/TRAC−/β2M− | 5 |
| 3 | anti-BCMA CAR/TRAC−/β2M−/TGFBRII− | 5 |
| 4 | anti-BCMA CAR/TRAC−/β2M−/TGFBRII−/Regnase− | 5 |
| 5 | anti-BCMA CAR/TRAC−/β2M−/TGFBRII−/Regnase− | 5 |

Throughout the course of the study, the mice were subjected to gross observations daily, while tumor volume and body weight were measured twice weekly (~every 3-4 days) starting on Day 10. A significant endpoint was the time to peri-morbidity and the effect of T-cell engraftment was also assessed. The percentage of animal mortality and time to death were recorded for every group in the study. Mice were euthanized prior to reaching a moribund state. Mice may be defined as moribund and sacrificed if one or more of the following criteria were met:
  Loss of body weight of 20% or greater sustained for a period of greater than 1 week;
  Tumors that inhibit normal physiological function such as eating, drinking, mobility and ability to urinate and or defecate;
  Prolonged, excessive diarrhea leading to excessive weight loss (>20%); or
  Persistent wheezing and respiratory distress.
Animals were also considered moribund if there was prolonged or excessive pain or distress as defined by clinical observations such as: prostration, hunched posture, paralysis/paresis, distended abdomen, ulcerations, abscesses, seizures and/or hemorrhages.

Figure 26A:
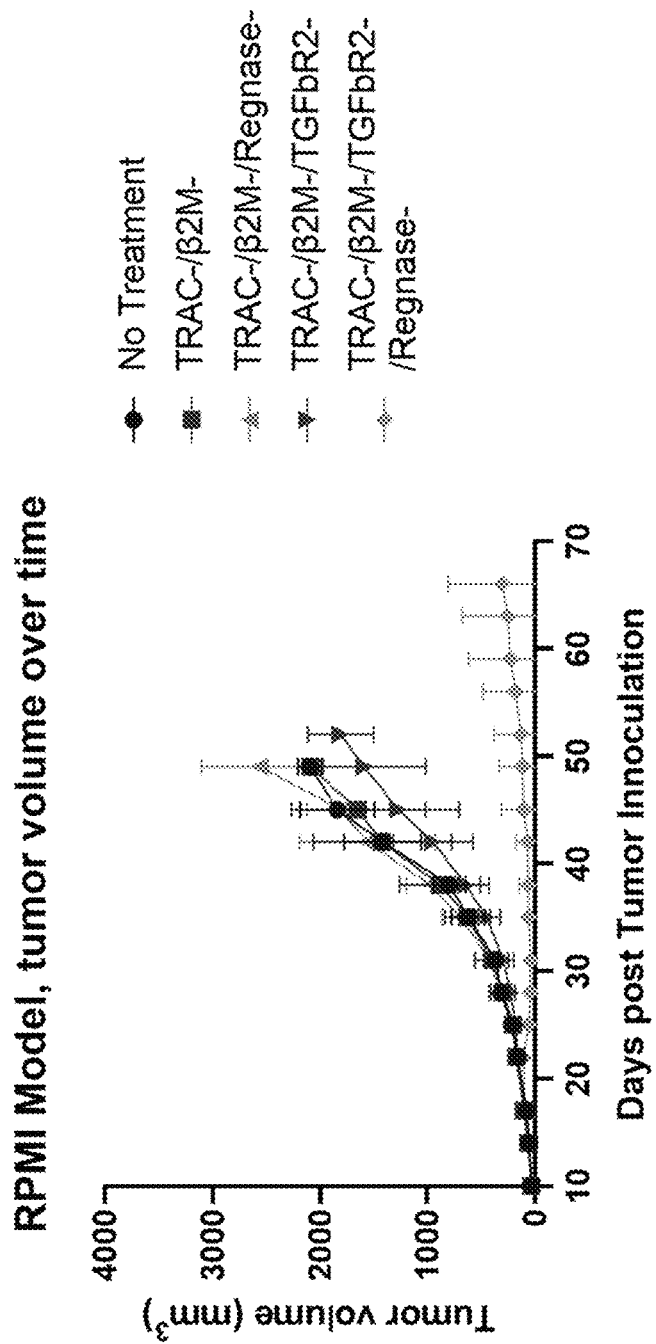
Figure 26B:
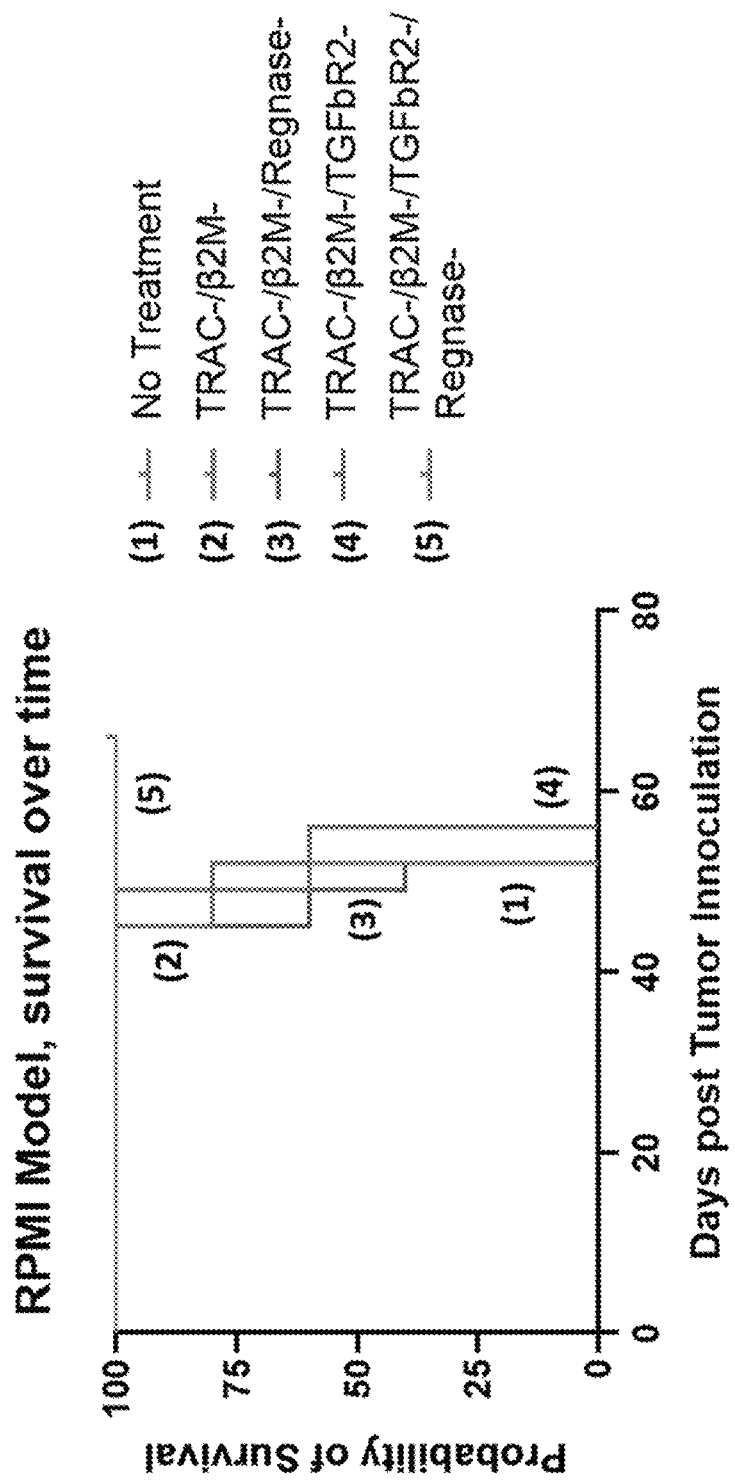

Mice in groups receiving TRAC−/β2M−/TGFBRII−/Reg-1− anti-BCMA CAR+ T-cells saw an increase in survival relative to untreated mice; mice treated TRAC−/β2M− anti-BCMA CAR+ T-cells, TRAC−/β2M−/TGFBRII anti-BCMA CAR+ T-cells, or TRAC−/β2M−/Reg-1− anti-BCMA CAR+ T-cells (FIG. 26B). Mice receiving TRAC−/B2M−/TGFBRII−/Regnase-anti-BCMA CAR+ T cells showed significant tumor regression, while none of the other conditions tested showed significant inhibition of tumor growth (FIG. 26A). These data demonstrate that disruption of TGFBRII and Reg-1 in CAR T cells increases efficacy of CAR T cells in a mouse xenograft tumor model.

Next, small amounts of blood were taken from each mouse for FACS analysis to characterize circulating CAR-T cells and determine drug pharmacokinetics. Approximately 75 uL of blood was drawn 2 weeks post CAR-T dosing via submandibular bleeds. The blood was then transferred into K2 EDTA tubes and shipped overnight to CRISPR Therapeutics on 4 C cold packs. The following day, blood samples were processed with RBC (Red Blood Cell) Lysis Buffer (BioLegend®, catalog #420301) per manufacturer's instructions. The samples then underwent anti-mouse CD16/32 blocking via anti-mouse Trustain FcX™ (BioLegend®, catalog #101320) per manufacturer's instructions. The samples were then processed via flow cytometry to determine prevalence of human CD45 expressing cells, which would represent the circulating CAR-T cells. Blood from mice that had received TRAC−/β2M−/TGFBRII−/Regnase−anti-BCMA CAR+ T-cells showed a high amount of circulating human CD45+ cells, which was not seen in any other treatment groups (FIG. 26C). This indicates that the TGFBRII and Reg-1 knockouts confer superior expansion of CAR-T cells in a multiple myeloma mouse xenograft model.

Example 21: In Vivo Synergistic Effects of TGFBRII+Regnase-1 Disruptions on Allogeneic CAR T Cells in the Subcutaneous JeKo-1 Xenograft Tumor Model A subcutaneous tumor mouse model was utilized to further assess the in vivo efficacy of TRAC−/β2M− anti-BCMA CAR+ T-cells and TRAC−/β2M−/TGFBRII−/Reg-1/anti-BCMA CAR+ T-cells. The subcutaneous tumor mouse model utilized the low BCMA expressing mantle cell lymphoma derived JeKo-1 tumor cell line in NSG mice. The TGFBRII gene was edited via CRISPR/Cas-mediated gene editing using TGFBRII Ex5_T1 guide (SEQ ID NO: 313). The Reg-1 gene was edited via CRISPR/Cas-mediated gene editing using the Z10 guide (SEQ ID NO: 51). The anti-BCMA CAR T cells express an anti-BCMA CAR comprising the amino acid sequence of SEQ ID NO: 146. See also the sequence Tables 22, 23, 27, and 39 below.

Efficacy of the anti-BCMA CAR T cells was evaluated in the subcutaneous xenograft model using methods employed by Translations Drug Development, LLC (Scottsdale, AZ) and described herein. In brief, 15 5-8 week old female NSG mice were individually housed in ventilated microisolator cages, maintained under pathogen-free conditions, 5-7 days prior to the start of the study. On day 1, mice received a subcutaneous inoculation of 5×10⁶ JeKo-1 cells/mouse in the right hind flank. Tumors were then periodically sized in via calipers. Once average tumor size reached an average of 150 mm³ (with an acceptable range of 125-175 mm³), the mice were further divided into 3 treatment groups as shown in Table 1. All treatment groups received a single 200 ul intravenous dose of 10e6 anti-BCMA CAR+ T cells. The day of T-cell injection was marked as Day 1.

TABLE 16

Treatment Groups for the RMPI-8226 Xenograft Study

| Group | CAR T cells (i.v.) | N |
|---|---|---|
| 1 | NA | 5 |
| 2 | anti-BCMA CAR/TRAC−/β2M− | 5 |
| 5 | anti-BCMA CAR/TRAC−/β2M−/TGFBRII−/Regnase− | 5 |

Throughout the course of the study, the mice were subjected to gross observations daily, while tumor volume and body weight were measured twice weekly (~every 3-4 days) starting on Day 1. A significant endpoint was the time to peri-morbidity and the effect of T-cell engraftment was also assessed. The percentage of animal mortality and time to death were recorded for every group in the study. Mice were euthanized prior to reaching a moribund state. Mice may be defined as moribund and sacrificed if one or more of the following criteria were met:

Loss of body weight of 20% or greater sustained for a period of greater than 1 week;

Tumors that inhibit normal physiological function such as eating, drinking, mobility and ability to urinate and or defecate;

Prolonged, excessive diarrhea leading to excessive weight loss (>20%); or

Persistent wheezing and respiratory distress.

Animals were also considered moribund if there was prolonged or excessive pain or distress as defined by clinical observations such as: prostration, hunched posture, paralysis/paresis, distended abdomen, ulcerations, abscesses, seizures and/or hemorrhages.

Figure 27A:
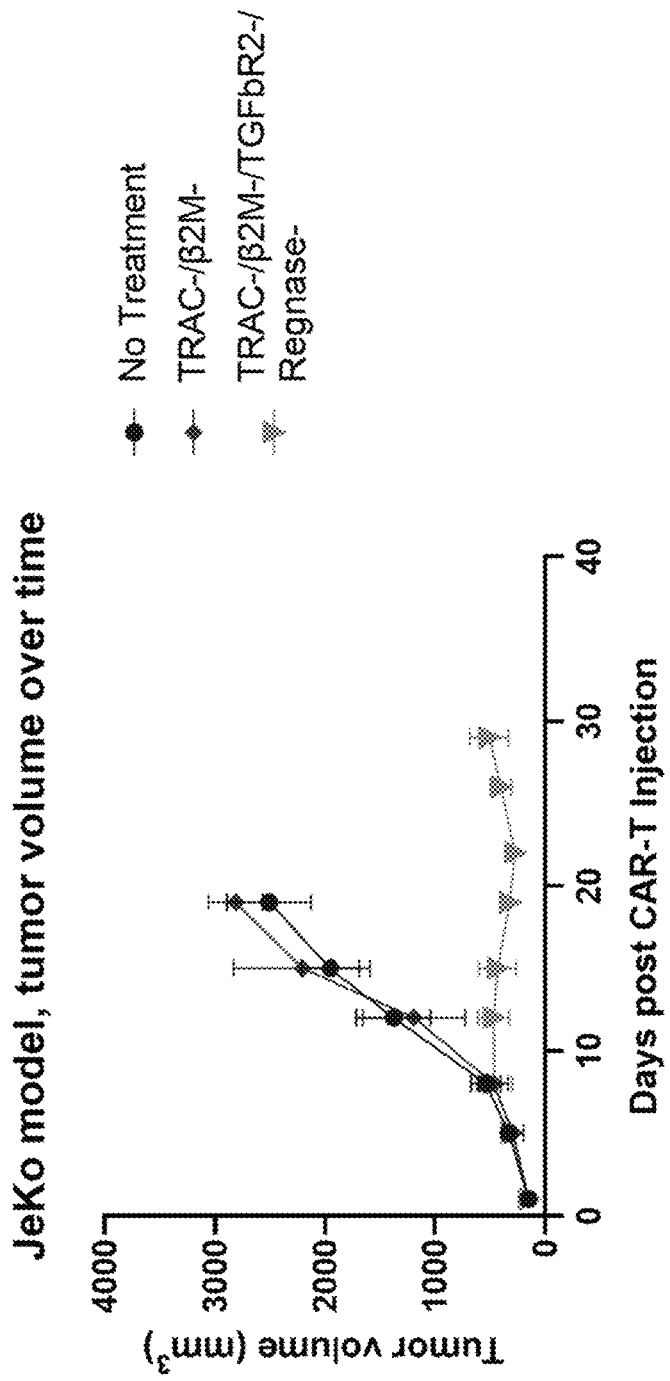
Figure 27B:
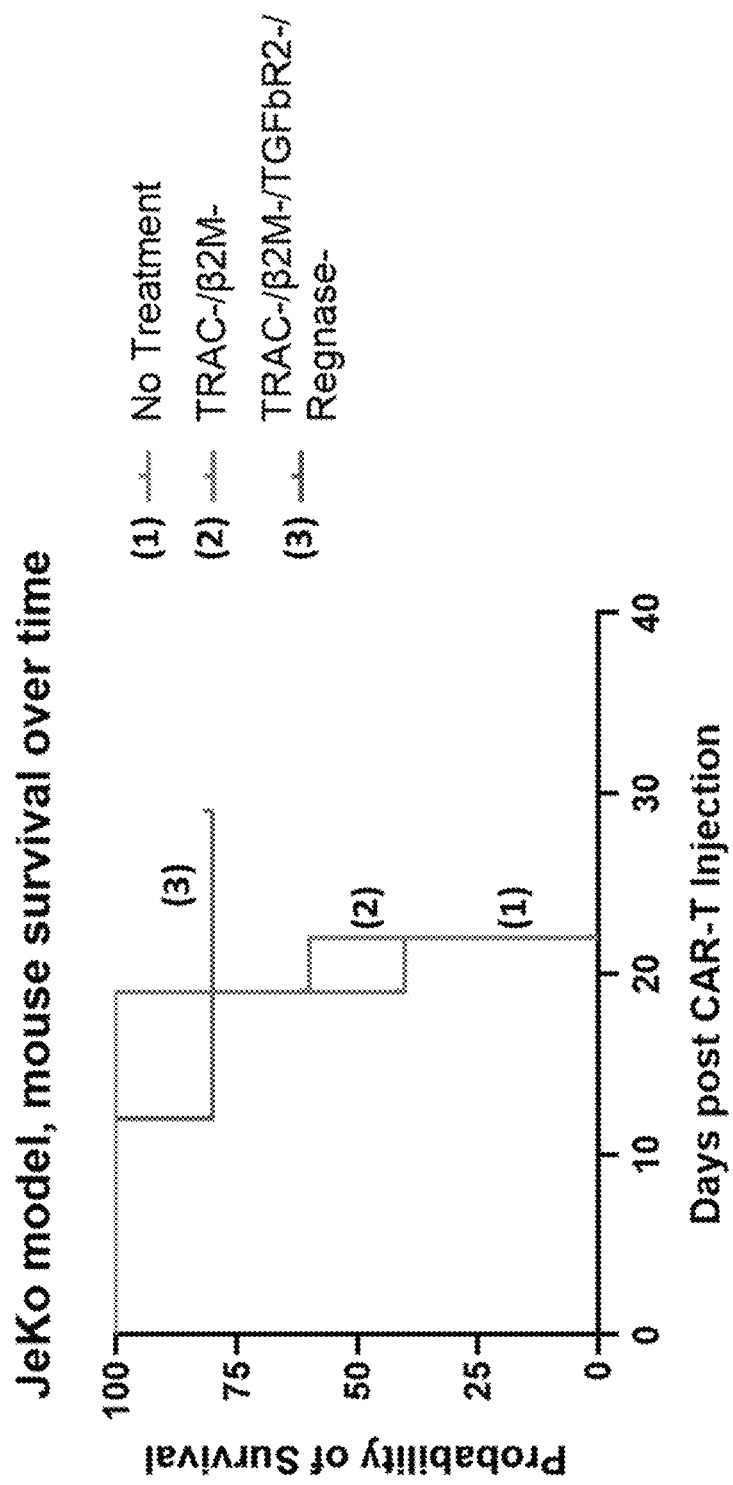

Mice in groups receiving TRAC−/β2M−/TGFBRII−/Reg-1− anti-BCMA CAR+ T-cells saw a significant increase in survival relative to both untreated mice and mice treated TRAC−/β2M− anti-BCMA CAR+ T-cells (FIG. 27B). Mice receiving TRAC−/B2M−/TGFBRII−/Reg-1− anti-BCMA CAR+ T cells arrested tumor growth, while TRAC−/β2M− anti-BCMA CAR+ T-cells did not significant inhibit tumor growth (FIG. 27A). These data demonstrate that disruption of TGFBRII and Reg-1 genes in CAR T cells increases efficacy of CAR-T cells in a mouse xenograft tumor model.

Figure 27C:
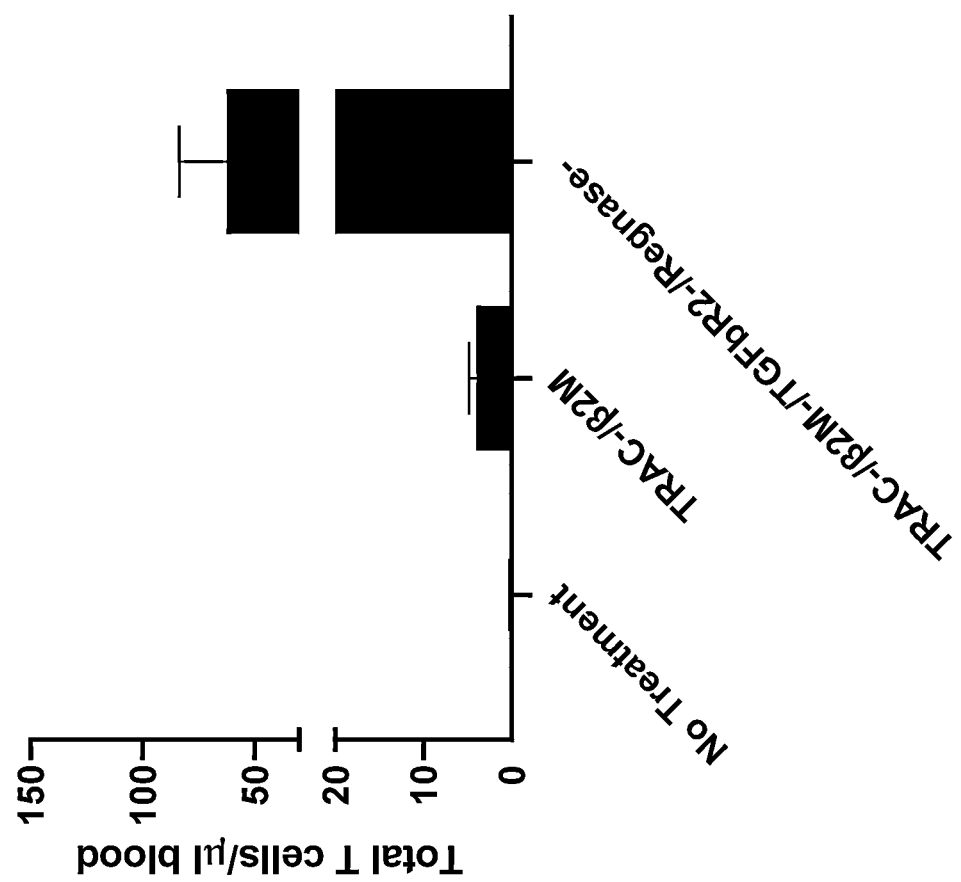

Next, small amounts of blood were taken from each mouse for FACS analysis to characterize circulating CAR-T cells and determine drug pharmacokinetics. Approximately 75 uL of blood was drawn 2 and 3 weeks post CAR-T dosing via submandibular bleeds. The blood was then transferred into K2 EDTA tubes and shipped overnight to CRISPR Therapeutics on 4 C cold packs. The following day, blood samples were processed with RBC (Red Blood Cell) Lysis Buffer (BioLegend®, catalog #420301) per manufacturer's instructions. The samples then underwent anti-mouse CD16/32 blocking via anti-mouse Trustain FcX™ (BioLegend®, catalog #101320) per manufacturer's instructions. To quantify the number of circulating T-cells, the sum of cells positive for human CD4 and CD8 was determined. At the two week timepoint, blood from mice that had received TRAC−/β2M−/TGFBRII−/Reg-1− anti-BCMA CAR+ T-cells showed significantly higher concentrations of human CD4 and human CD8+ expressing cells relative to blood from mice that received TRAC−/β2M-anti-BCMA CAR+ T-cells (FIG. 27C).

Figure 27D:
Figure 27E:
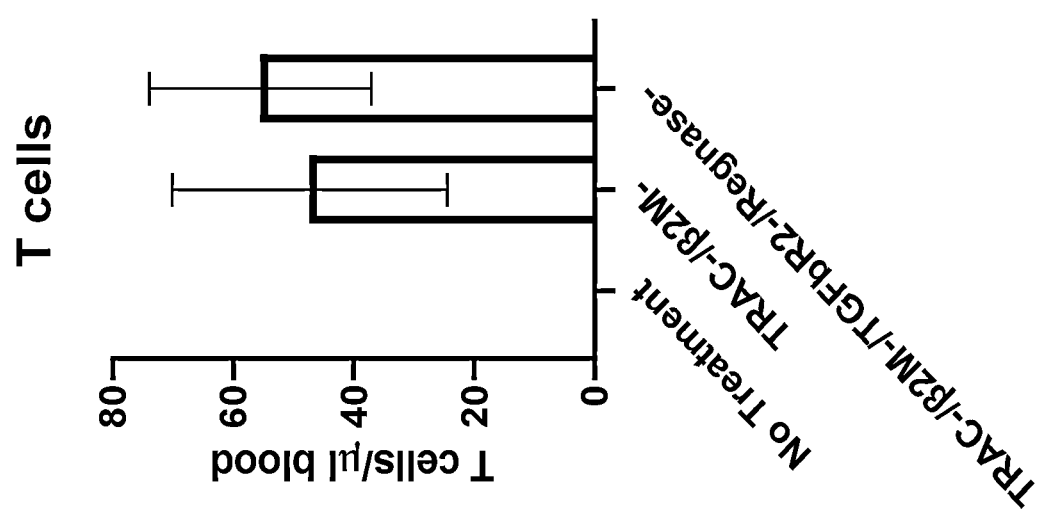

Furthermore, the TRAC−/β2M-TGFBRII−/Reg-1− anti-BCMA CAR+ T-cells showed lower expression of the T-cell exhaustion markers Lag3 and PD1 relative to the TRAC−/β2M− anti-BCMA CAR+ T-cells (FIG. 27D). At the three week timepoint, the overall level of hCD45+ cells in circulation had equalized between groups (FIG. 27E), but the expression of Lag3 and PD1 remained lower in mice treated with TRAC−/β2M-TGFBRII−/Reg-1− anti-BCMA CAR+ T-cells (FIG. 27F). This indicates that CAR-T cells containing the TGFBRII and Regnase knockouts have a superior ability to expand when compared to CAR-T cells lacking those edits while also reducing the expression of T-cell exhaustion markers PD-1 and Lag3.

Example 22: Generation of Anti-PTK7 CAR T Cells with Disrupted TGFBRII and Regnase-1 Genes Allogeneic human T cells that lack expression of the TRAC gene, β2M gene, TGFBRII gene and Reg-1 gene, and express a chimeric antigen receptor (CAR) targeting PTK7 were produced. Activated human T cells were electroporated with Cas9:sgRNA RNPs (1 µM Cas9, 5 µM gRNA), followed by incubation with a recombinant adeno-associated adenoviral vectors, serotype 6 (AAV6) (MOI 50,000).

Recombinant AAV comprised a nucleotide sequence encoding an anti-PTK7 CAR comprising the amino acid sequence of SEQ ID NO: 349. The following sgRNAs were used: TRAC (SEQ ID NO: 58), β2M (SEQ ID NO: 62), TGFBRII (SEQ ID NO: 313) and REGNASE-1 (SEQ ID NO: 51). The sgRNAs, which form RNPs with the Cas9 enzyme, can be introduced into the T cells in a single electroporation event to produce the resulting modified cell populations shown in Table 17 below. After the electroporation, the cells were transduced with the recombinant AAV to introduce the donor template encoding for the anti-PTK7 CAR.

TABLE 17

Genetically Engineered CAR-T Cell Populations

| Population | Edits |
|---|---|
| Anti-PTK7 CAR T cells | anti-PTK7 CAR+/TRAC−/B2M− |
| Anti-PTK7 CAR T + TGFBRII KO cells | anti-PTK7 CAR+/TRAC−/B2M−/TGFBRII− |
| Anti-PTK7 CAR T + TGFBRII KO + Reg KO cells | anti-PTK7 CAR+/TRAC−/B2M−/TGFBRII−/Reg− |

At 7 days post-electroporation, T cells were checked for CAR expression by flow cytometry. Both anti-PTK7 CAR T cells and anti-PTK7 CAR T cells that lack TGFBRII and anti-PTK7 CAR T cells that lack TGFBRII and Regnase expressed nearly equivalent amount of CAR on their surface at day 7 post HDR. The results are provided in Table 18 below.

TABLE 18

Percentage of CAR, TCR, and b2M Expression on Day 7 Post HDR

| Treatment | CAR+ % | TCR+ % | β2M+ % |
|---|---|---|---|
| No RNP | 3.33 | 92 | 93.7 |
| No AAV | 5.16 | 2.63 | 3.87 |
| Anti-Ptk7 CAR | 82.2 | 1.24 | 2.49 |
| Anti-Ptk7 CAR & TGFBRII KO | 83.2 | 0.82 | 2.1 |
| Anti-Ptk7 CAR & TGFBRII/Reg-1 KO | 81.7 | 0.77 | 2 |

Figure 28:
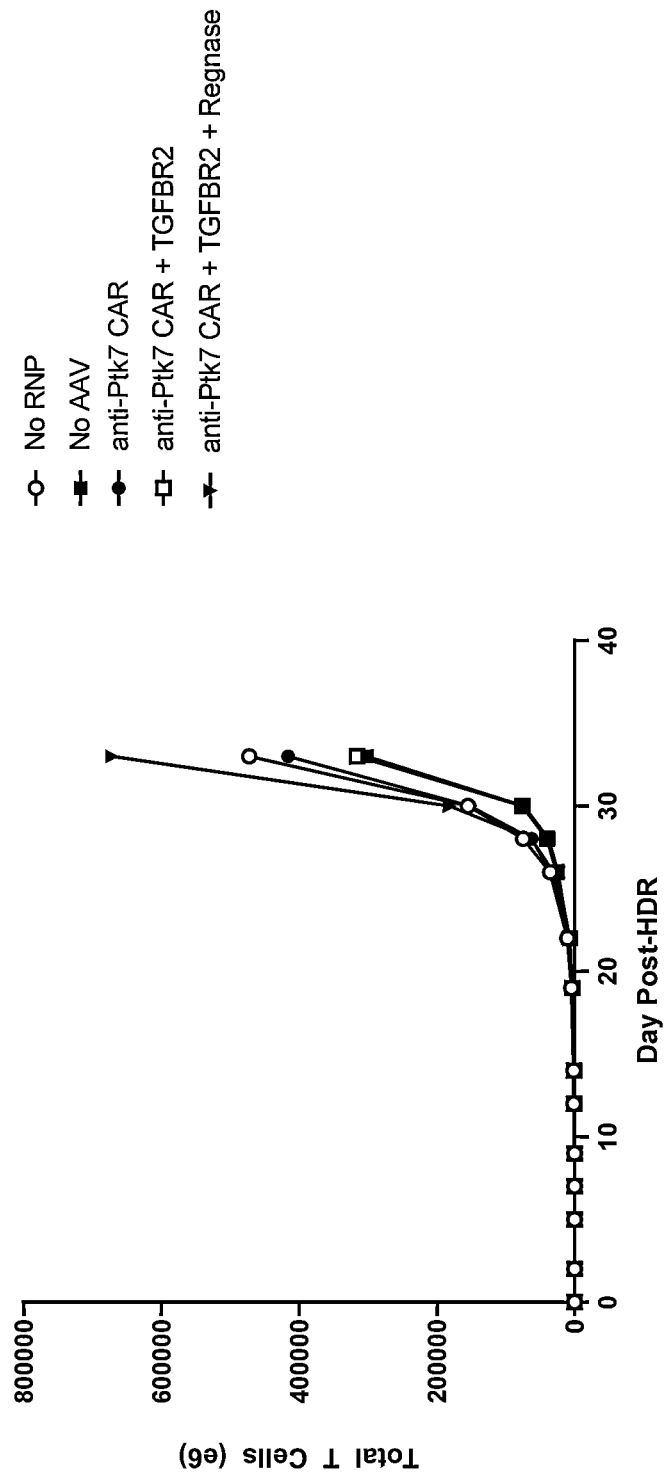
FIG. 28 is a diagram showing disruption of TGFBRII and Reg-1 genes increases proliferation of anti-PTK7 CAR T cells.

Efficient editing of TGFBRII and/or Regnase was achieved in the engineered anti-Ptk7 CAR T cell (Table 19 below) and show an increase in cell proliferation with TGFBRII and Reg-1 disruption (FIG. 28), while cell viability and CD4+/CD8+ T cells ratios remain unchanged.

TABLE 19

Indel Percentage in TGFBRII and Regnase-1 on Day 7 Post HDR

| Treatment | TGFBRII Indel % | Reg-1 Indel % |
|---|---|---|
| No RNP | 1.8 | 1.6 |
| No AAV | 97.75 | 88.8 |
| Anti-Ptk7 CAR | 1.45 | 2.2 |
| Anti-Ptk7 CAR & TGFBRII KO | 97.15 | 3 |
| Anti-Ptk7 CAR & TGFBRII/Reg-1 KO | 97.7 | 92.2 |

In summary, the data presented in this example demonstrated that TGFBRII and/or Reg-1 disruption in anti-Ptk7 CAR T cells (e.g., anti-PTK7 CAR+/TRAC−/B2M−/TGFBRII− or anti-PTK7 CAR+/TRAC−/B2M−/TGFBRII−/Reg-1−), can increase cell proliferation, while not affecting cell viability or CD4/CD8 cell ratios.

Example 23: Disruption of TGFBRII Alone Increases CAR T Cell Killing Upon Serial Rechallenge In Vitro The anti-PTK7 CAR+ T cells generated above were serially rechallenged with PTK7+ osteosarcoma cancer cell line, Saos2, and evaluated for their ability to kill the PTK7+ osteosarcoma cancer cell line Saos2.

The anti-PTK7 CAR+ T cells used in this experiment contained the following edits:

Anti-PTK7 CAR T cells: anti-PTK7 CAR+/TRAC−/B2M−

Anti-PTK7 CAR T+TGFBRII KO cells: anti-PTK7 CAR+/TRAC−/B2M−/TGFBRII−

Anti-PTK7 CAR T+TGFBRII KO+Reg KO cells: anti-PTK7 CAR+/TRAC−/B2M−/TGFBRII−/Reg−

In a 96-well plate format, CAR T cells were first co-cultured with Saos2 cells (6,250 CAR T cells, 50,000 tumor cells) on D0 and re-challenged with 50,000 tumor cells on D2, D4, D6, D8, D10, D12 and D14.

Analysis of tumor cell and CAR T cell number was performed at D1, D3, D5, D7, D9, D11 and D13 using flow cytometry (method adapted from Wang et al., JoVE 2019). The following antibodies in Table 20 were used at 1:100 dilution.

TABLE 20

Antibody Information

| Antibody | Flour | cat # | Dilution | Vendor |
|---|---|---|---|---|
| CD4 | BV510 | 300546 | 1:100 | Biolegend |
| CD8 | FITC | 344704 | 1:100 | Biolegend |
| PTK7 | PE | 130-091-364 | 1:50 | Miltenyi |
| CD62L | BV605 | 304833 | 1:100 | Biolegend |
| human CD45 | BV785 | 304048 | 1:100 | Biolegend |
| PD1 | APC/Cy7 | 329922 | 1:100 | Biolegend |
| CD45RO | PE/Cy7 | 304230 | 1:100 | Biolegend |
| Streptavidin | APC | 405207 | 1:100 | Biolegend |
| Tim3 | BV421 | 345008 | 1:100 | Biolegend |
| Live/Dead | 7AAD | BDB559925 | 1:500 | BD |

The results demonstrate that disrupting the TGFBRII gene improved potency (FIG. 29A) and CAR T cell expansion (FIG. 29B) as measured by hum CD45 staining, when CAR T cells are repeatedly challenged with PTK7+ positive target cells. The addition of Regnase gene disruption does not provide an added advantage in potency over TGFBRII deletion alone. Potency and expansion is improved compared to CAR T cells that have neither, or both (i.e.: TGFBRII and Regnase), of the genes disrupted. In addition, the results demonstrate that cytotoxic CD8+ CAR T cells persist longer during serial rechallenge (FIG. 29C) with tumor cells if the TGFBRII gene is disrupted compared to anti-PTK7 CAR T cells that have neither or both (i.e.: TGFBRII and Regnase) of the genes disrupted. CD4+ CAR T cells remain consistent regardless of whether TGFBRII and/or Regnase genes are disrupted (FIG. 29D).

Example 24: Treatment Efficacy of Anti-PTK7 CAR T Cells with Multiple Gene Disruptions in the Subcutaneous Pancreatic Cell Carcinoma Tumor Xenograft Model Treatment in the Pancreatic Cell Carcinoma Tumor Model The ability of T cells expressing a PTK7 CAR with TGFBRII and/or Reg-1 gene edits to eliminate pancreatic cell carcinoma cells that express medium levels of PTK7 was evaluated in vivo using a subcutaneous renal cell carcinoma (Hs766T) tumor xenograft mouse model. Anti-PTK7 CAR+ T cells were produced as described above. See, e.g., Example 22.

The ability of these anti-PTK7 CAR+ T cells to ameliorate disease caused by a PTK7+ pancreatic carcinoma cell line was evaluated in NSG mice using methods employed by Translational Drug Development, LLC (Scottsdale, AZ). In brief, 20, 5-8 week old female, NSG mice were individually housed in ventilated microisolator cages, maintained under pathogen-free conditions, 5-7 days prior to the start of the study. Mice received a subcutaneous inoculation of 5×10⁶ Hs766T pancreatic cell carcinoma cells/mouse in the right hind flank. When mean tumor size reached target of ~50 mm³, the mice were further divided into 3 treatment groups as shown in Table 21. On Day 1, treatment four groups received a single 200 µl intravenous dose of 0.5×10⁷ anti-PTK7 CAR+ T cells according to Table 21.

TABLE 21

Treatment groups

| Group | CAR-T | Hs766T cells | CAR-T cell treatment (i.v.) | N |
|---|---|---|---|---|
| 1 | None | 5 × 10⁶ cells/mouse | None | 5 |

TABLE 21-continued

Treatment groups

| Group | CAR-T | Hs766T cells | CAR-T cell treatment (i.v.) | N |
|---|---|---|---|---|
| 2 | Anti-PTK7 CAR T cells: anti-PTK7 CAR+/TRAC−/B2M− | 5 × 10⁶ cells/mouse | 0.5 × 10⁷ cells/mouse | 5 |
| 3 | Anti-PTK7 CAR T + TGFBRII KO cells: anti-PTK7 CAR+/TRAC−/B2M−/TGFBRII− | 5 × 10⁶ cells/mouse | 0.5 × 10⁷ cells/mouse | 5 |

Figure 30A:
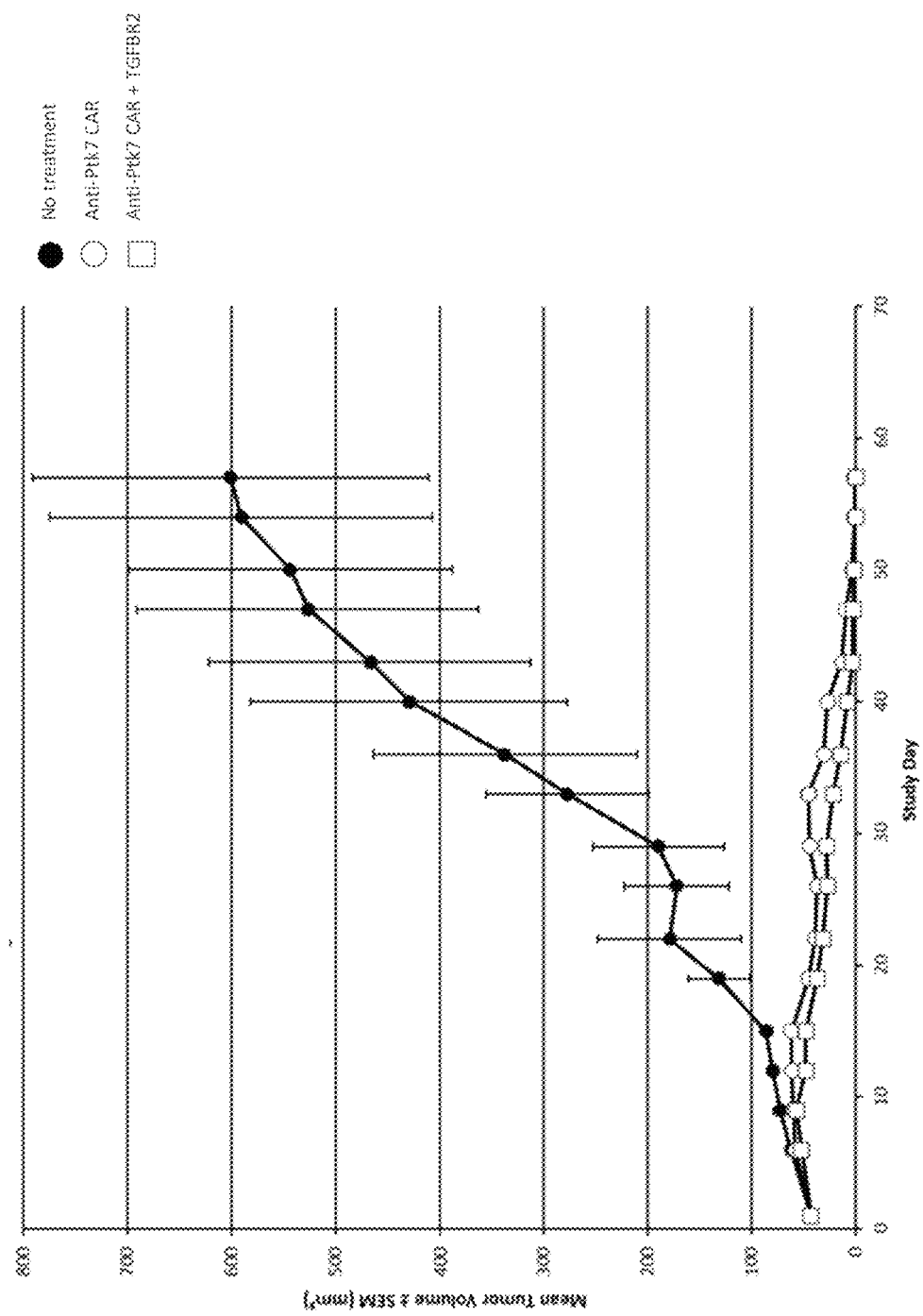
FIGS. 30A-30B include diagrams showing anti-tumor activity of anti-PTK7 CAR T-cells with or without TGFBRII disruption.

Tumor volume was measured 2 times weekly (~every 3-4 days) from day of treatment initiation. By day 11 post-injection, anti-PTK7 CAR T cells with and without TGFBRII gene KO began to show a significant effect on reducing tumor volume compared to no treatment group 1. Approximately one month later the anti-PTK7CAR T with and without TGFBRII KO cells had completely eliminated tumor growth in the subcutaneous Hs766T model (FIG. 30A).

Figure 30B:
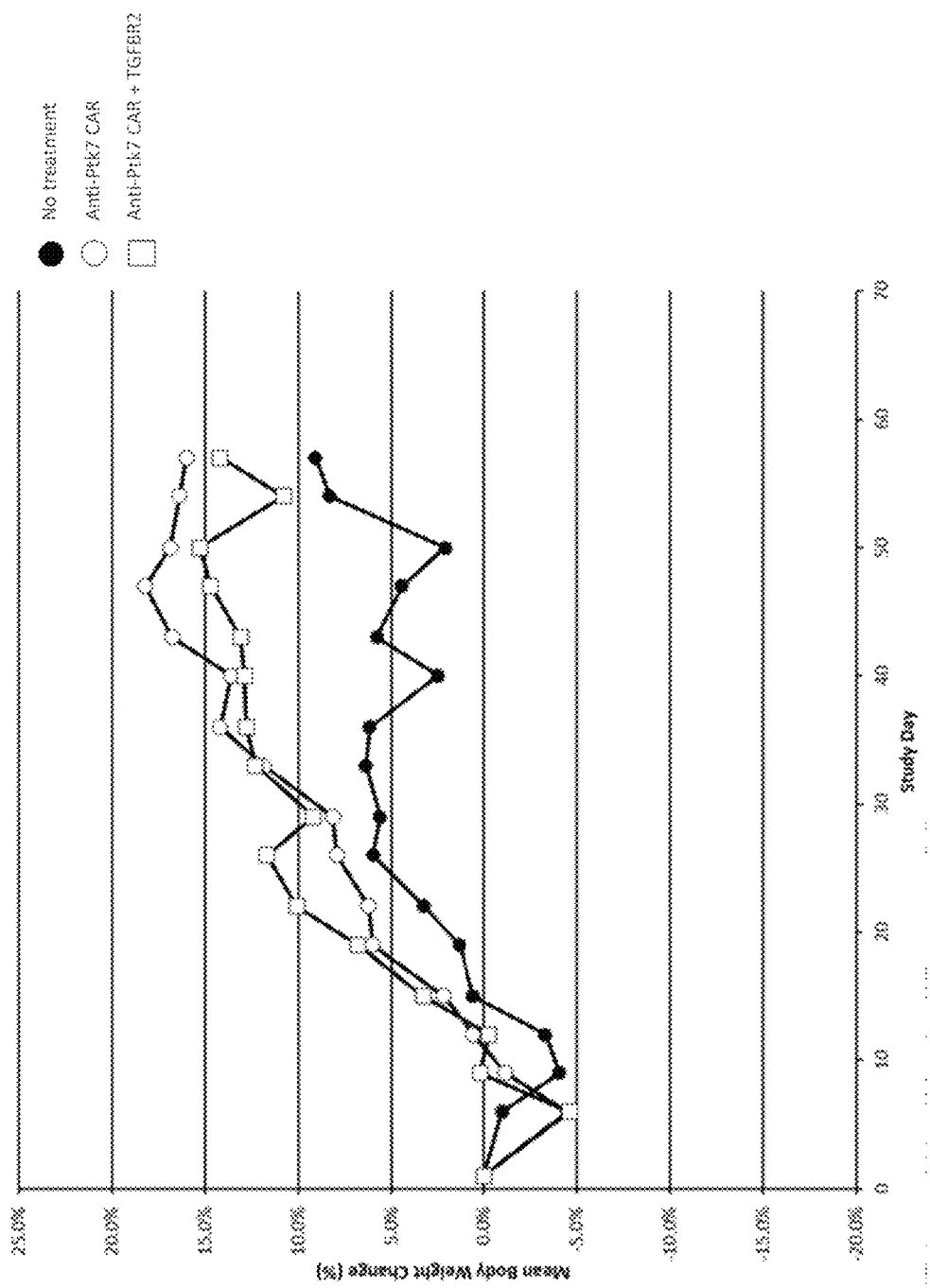

These results demonstrated that disrupting the TGFBRII gene in CAR T cells effectively cleared tumors in the subcutaneous Hs766T renal cell carcinoma tumor xenograft model. No clinical signs of GvHD were observed in anti-PTK7 CAR T cells with and without TGFBRII KO cells (FIG. 30B).

Example 25: Analysis of T Cell Fraction in Pancreatic Cell Carcinoma (Hs766T) Tumor Xenograft Model Blood samples were taken from mice with Hs766T tumors, 47 days after CAR T administration. Briefly, 100 ul of mouse whole blood was collected via submandibular vein. Red blood cell lysis buffer was used to achieve optimal lysis of erythrocytes with minimal effect on lymphocytes. Human CD45 and mouse CD45 were used as a biomarker to separate human and mouse cells by FACS. The blood samples were evaluated by flow cytometry looking for absolute human CD45+ counts as well as memory T cell subsets. Staining for CD45RO+CD27+ was used to define central memory T cells.

Figure 31B:
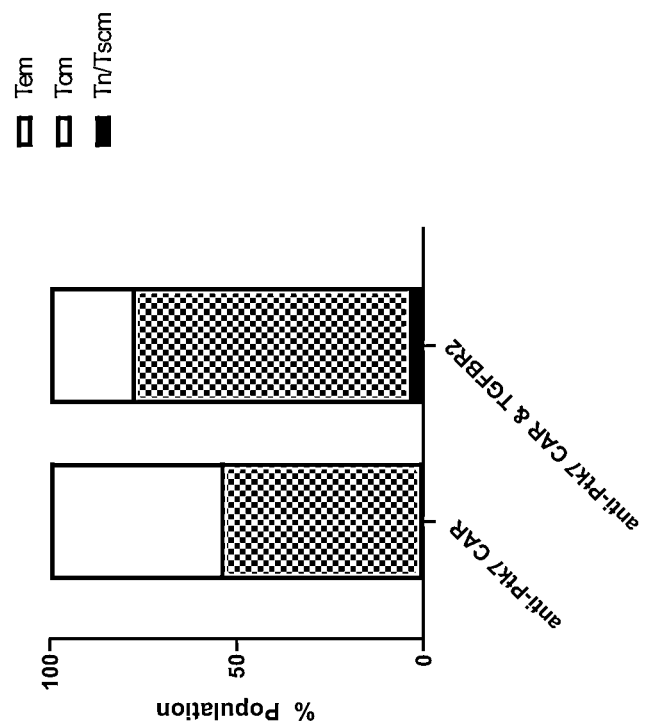
FIGS. 31A-31B include diagrams showing T cell fractions in a pancreatic cell carcinoma (Hs766T) tumor xenograft animal model treated with anti-PTK7 CAR T cells with or without TGFBRII disruption.
Figure 31A:
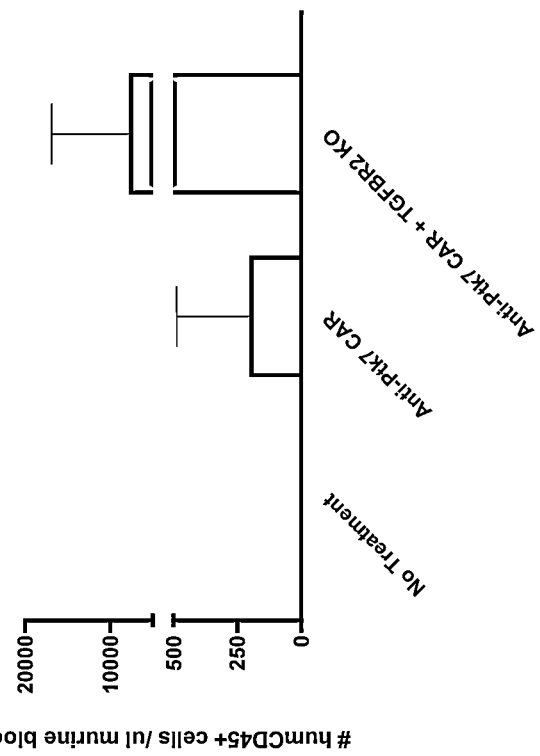

The results demonstrate that the addition of the TGFBRII gene edit significantly enhanced the population of central memory T cells (FIG. 31B) compared to anti-PTK7 CAR T cells without TGFBRII KO which correlates with massive expansion of CAR T cells (FIG. 31A) seen in these animals. And the TGFBRII edit further promoted the potential of CAR T cell proliferation in vivo (FIG. 31B).

Sequence Tables

The following tables provide details for the various nucleotide and amino acid sequences disclosed herein.

TABLE 22 sgRNA Sequences and Target Gene Sequences for Reg1

| Name | Unmodified Sequence | Modified Sequence | Target Sequences (PAM) |
|---|---|---|---|
| REG1-Z01 sgRNA (EX2_T1) | GGUCAUCGAUGGGAGCAACGguuuuagagcuagaaauagcaaguuaaaauaaggcuaguccguuaucaacuugaaaaaguggcaccgagucggugcUUUU (SEQ ID NO: 14) | G*G*U*CAUCGAUGGGAGCAACGguuuuagagcuagaaauagcaaguuaaaauaaggcuaguccguuaucaacuugaaaaaguggcaccgagucggugcU*U*U (SEQ ID NO: 15) | GGTCATCGATGGGAGCAACG (TGG) (SEQ ID NO: 171) GGTCATCGATGGGAGCAACG (SEQ ID NO: 318) |
| REG1-Z01 sgRNA (EX2_T1) spacer | GGUCAUCGAUGGGAGCAACG (SEQ ID NO: 16) | G*G*U*CAUCGAUGGGAGCAACG (SEQ ID NO: 17) | |
| REG1-Z02 sgRNA (EX2_T2) | CACCACCCCGCGGGACUAGAguuuuagagcuagaaauagcaaguuaaaauaaggcuaguccguuaucaacuugaaaaaguggcaccgagucggugcUUUU (SEQ ID NO: 18) | C*A*C*CACCCCGCGGGACUAGAguuuuagagcuagaaauagcaaguuaaaauaaggcuaguccguuaucaacuugaaaaaguggcaccgagucggugcU*U*U (SEQ ID NO: 19) | CACCACCCCGCGGGACTAGA (GGG) (SEQ ID NO: 172) CACCACCCCGCGGGACTAGA (SEQ ID NO: 319) |
| REG1-Z02 sgRNA (EX2_T2) spacer | CACCACCCCGCGGGACUAGA (SEQ ID NO: 20) | mC*mA*mC*CACCCCGCGGGACUAGA (SEQ ID NO: 21) | |
| REG1-Z03 sgRNA (EX2_T3) | GGUCUGGCGCUCCCGCUCGGguuuuagagcuagaaauagcaaguuaaaauaaggcuaguccguuaucaacuugaaaaaguggcaccgagucggugcUUUU (SEQ ID NO: 22) | G*G*U*CUGGCGCUCCCGCUCGGguuuuagagcuagaaauagcaaguuaaaauaaggcuaguccguuaucaacuugaaaaaguggcaccgagucggugcU*U*U (SEQ ID NO: 23) | GGTCTGGCGCTCCCGCTCGG (TGG) (SEQ ID NO: 173) GGTCTGGCGCTCCCGCTCGG (SEQ ID NO: 320) |
| REG1-Z03 sgRNA (EX2_T3) spacer | GGUCUGGCGCUCCCGCUCGG (SEQ ID NO: 24) | mG*mG*mU*CUGGCGCUCCCGCUCGG (SEQ ID NO: 25) | |

TABLE 22-continued sgRNA Sequences and Target Gene Sequences for Reg1

| Name | Unmodified Sequence | Modified Sequence | Target Sequences (PAM) |
|---|---|---|---|
| REG1-Z04 sgRNA (EX4_T1) | UUCACACCAUCACGACGC GUguuuuagagcuagaaa uagcaaguuaaaauaagg cuaguccguuaucaacuu gaaaaaguggcaccgagu cggugcUUUU (SEQ ID NO: 26) | U*U*C*ACACCAUCACGACGCG Uguuuuagagcuagaaauagca aguuaaaauaaggcuaguccgu uaucaacuugaaaaaguggcac cgagucggugcU*U*U*U (SEQ ID NO: 27) | TTCACACCATCACGACGCGT (GGG) (SEQ ID NO: 174) TTCACACCATCACGACGCGT (SEQ ID NO: 321) |
| REG1-Z04 sgRNA (EX4_T1) spacer | UUCACACCAUCACGACGC GU (SEQ ID NO: 28) | U*U*C*ACACCAUCACGACGCG U (SEQ ID NO: 29) | |
| REG1-Z05 sgRNA (EX4_T2) | ACACCAUCACGACGCGUG GGguuuuagagcuagaaa uagcaaguuaaaauaagg cuaguccguuaucaacuu gaaaaaguggcaccgagu cggugcUUUU (SEQ ID NO: 30) | A*C*A*CCAUCACGACGCGUGG Gguuuuagagcuagaaauagca aguuaaaauaaggcuaguccgu uaucaacuugaaaaaguggcac cgagucggugcU*U*U*U (SEQ ID NO: 31) | ACACCATCACGACGCGTGGG (TGG) (SEQ ID NO: 175) ACACCATCACGACGCGTGGG (SEQ ID NO: 322) |
| REG1-Z05 sgRNA (EX4_T2) spacer | ACACCAUCACGACGCGUG GG (SEQ ID NO: 32) | A*C*A*CCAUCACGACGCGUGG G (SEQ ID NO: 33) | |
| REG1-Z06 sgRNA (EX4_T3) | CUACGAGUCUGACGGGAU CGguuuuagagcuagaaa uagcaaguuaaaauaagg cuaguccguuaucaacuu gaaaaaguggcaccgagu cggugcUUUU (SEQ ID NO: 34) | C*U*A*CGAGUCUGACGGGAUC Gguuuuagagcuagaaauagca aguuaaaauaaggcuaguccgu uaucaacuugaaaaaguggcac cgagucggugcU*U*U*U (SEQ ID NO: 35) | CTACGAGTCTGACGGGATCG (TGG) (SEQ ID NO: 176) CTACGAGTCTGACGGGATCG (SEQ ID NO: 323) |
| REG1-Z06 sgRNA (EX4_T3) spacer | CUACGAGUCUGACGGGAU CG (SEQ ID NO: 36) | C*U*A*CGAGUCUGACGGGAUC G (SEQ ID NO: 37) | |
| REG1-Z07 sgRNA (EX4_T4) | UUGCCACCCACGCGUCGU GAguuuuagagcuagaaa uagcaaguuaaaauaagg cuaguccguuaucaacuu gaaaaaguggcaccgagu cggugcUUUU (SEQ ID NO: 38) | U*U*G*CCACCCACGCGUCGUG Aguuuuagagcuagaaauagca aguuaaaauaaggcuaguccgu uaucaacuugaaaaaguggcac cgagucggugcU*U*U*U (SEQ ID NO: 39) | TTGCCACCCACGCGTCGTGA (TGG) (SEQ ID NO: 177) TTGCCACCCACGCGTCGTGA (SEQ ID NO: 324) |
| REG1-Z07 sgRNA (EX4_T4) spacer | UUGCCACCCACGCGUCGU GA (SEQ ID NO: 40) | U*U*G*CCACCCACGCGUCGUG A (SEQ ID NO: 41) | |
| REG1-Z08 sgRNA (EX4_T5) | GUUCACACCAUCACGACG CGguuuuagagcuagaaa uagcaaguuaaaauaagg cuaguccguuaucaacuu gaaaaaguggcaccgagu cggugcUUUU (SEQ ID NO: 42) | G*U*U*CACACCAUCACGACGC Gguuuuagagcuagaaauagca aguuaaaauaaggcuaguccgu uaucaacuugaaaaaguggcac cgagucggugcU*U*U*U (SEQ ID NO: 43) | GTTCACACCATCACGACGCG (TGG) (SEQ ID NO: 178) GTTCACACCATCACGACGCG (SEQ ID NO: 325) |
| REG1-Z08 sgRNA (EX4_T5) spacer | GUUCACACCAUCACGACG CG (SEQ ID NO: 44) | G*U*U*CACACCAUCACGACGC G (SEQ ID NO: 45) | |
| REG1-Z09 sgRNA | CACGAUCCCGUCAGACUC GUguuuuagagcuagaaa uagcaaguuaaaauaagg cuaguccguuaucaacuu gaaaaaguggcaccgagu cggugcUUUU (SEQ ID NO: 46) | C*A*C*GAUCCCGUCAGACUCG Uguuuuagagcuagaaauagca aguuaaaauaaggcuaguccgu uaucaacuugaaaaaguggcac cgagucggugcU*U*U*U (SEQ ID NO: 47) | CACGATCCCGTCAGACTCGT (AGG) (SEQ ID NO: 179) CACGATCCCGTCAGACTCGT (SEQ ID NO: 326) |
| REG1-Z09 sgRNA | CACGAUCCCGUCAGACUC GU (SEQ ID NO: 48) | C*A*C*GAUCCCGUCAGACUCG U (SEQ ID NO: 49) | |

TABLE 22-continued sgRNA Sequences and Target Gene Sequences for Reg1

| Name | Unmodified Sequence | Modified Sequence | Target Sequences (PAM) |
|---|---|---|---|
| (EX4_T6) spacer | | | |
| REG1-Z10 sgRNA (EX4_T7) | ACGACGCGUGGGUGGCAA GCguuuuagagcuagaaa uagcaaguuaaaauaagg cuaguccguuaucaacuu gaaaaaguggcaccgagu cggugcUUUU (SEQ ID NO: 50) | A*C*G*ACGCGUGGGUGGCAAG Cguuuuagagcuagaaauagca aguuaaaauaaggcuaguccgu uaucaacuugaaaaaguggcac cgagucggugcU*U*U*U (SEQ ID NO: 51) | ACGACGCGTGGGTGGCAAGC (GGG) (SEQ ID NO: 180) ACGACGCGTGGGTGGCAAGC (SEQ ID NO: 327) |
| REG1-Z10 sgRNA (EX4_T7) spacer | ACGACGCGUGGGUGGCAA GC (SEQ ID NO: 52) | A*C*G*ACGCGUGGGUGGCAAG C (SEQ ID NO: 53) | |

*indicates a nucleotide with a 2'-O-methyl phosphorothioate modification.

TABLE 23 sgRNA Sequences and Target Gene Sequences for TRAC, β2M, and CD70

| | | sgRNA Sequences | SEQ ID NO: |
|---|---|---|---|
| CD70 sgRNA (CD70-7) | Modified | G*C*U*UUGGUCCCAUUGGUCGCguuuuagagcuagaaauagc aaguuaaaauaaggcuaguccguuaucaacuugaaaaaguggc accgagucggugcU*U*U*U | 54 |
| | Unmodified | GCUUUGGUCCCAUUGGUCGCguuuuagagcuagaaauagcaag uuaaaauaaggcuaguccguuaucaacuugaaaaaguggcacc gagucggugcUUUU | 55 |
| CD70 sgRNA spacer | Modified | G*C*U*UUGGUCCCAUUGGUCGC | 56 |
| | Unmodified | GCUUUGGUCCCAUUGGUCGC | 57 |
| TRAC sgRNA (TA-1) | Modified | A*G*A*GCAACAGUGCUGUGGCCguuuuagagcuagaaauagc aaguuaaaauaaggcuaguccguuaucaacuugaaaaaguggc accgagucggugcU*U*U*U | 58 |
| | Unmodified | AGAGCAACAGUGCUGUGGCCguuuuagagcuagaaauagcaag uuaaaauaaggcuaguccguuaucaacuugaaaaaguggcacc gagucggugcUUUU | 59 |
| TRAC sgRNA spacer | Modified | A*G*A*GCAACAGUGCUGUGGCC | 60 |
| | Unmodified | AGAGCAACAGUGCUGUGGCC | 61 |
| β2M sgRNA (β2M-1) | Modified | G*C*U*ACUCUCUCUUUCUGGCCguuuuagagcuagaaauagc aaguuaaaauaaggcuaguccguuaucaacuugaaaaaguggc accgagucggugcU*U*U*U | 62 |
| | Unmodified | GCUACUCUCUCUUUCUGGCCguuuuagagcuagaaauagcaag uuaaaauaaggcuaguccguuaucaacuugaaaaaguggcacc gagucggugcUUUU | 63 |
| β2M sgRNA spacer | Modified | G*C*U*ACUCUCUCUUUCUGGCC | 64 |
| | Unmodified | GCUACUCUCUCUUUCUGGCC | 65 |
| Target Sequences (PAM) | | | |
| CD70 target sequence with (PAM) | | GCTTTGGTCCCATTGGTCGC (GGG) | 66 |
| CD70 target sequence | | GCTTTGGTCCCATTGGTCGC | 67 |
| TRAC target sequence with (PAM) | | AGAGCAACAGTGCTGTGGCC (TGG) | 68 |
| TRAC target sequence | | AGAGCAACAGTGCTGTGGCC | 69 |
| β2M target sequence with (PAM) | | GCTACTCTCTCTTTCTGGCC (TGG) | 70 |
| β2M target sequence | | GCTACTCTCTCTTTCTGGCC | 71 |

TABLE 23-continued sgRNA Sequences and Target Gene Sequences for TRAC, β2M, and CD70

| sgRNA Sequences | | SEQ ID NO: |
|---|---|---|
| Exemplary sgRNA Formulas | | |
| sgRNA sequence | nnnnnnnnnnnnnnnnnnnnguuuuagagcuagaaauagcaaguuaaaauaaggcuaguccguuaucaacuugaaaaaguggcaccgagucggugcuuuu | 72 |
| sgRNA sequence | nnnnnnnnnnnnnnnnnnnnguuuuagagcuagaaauagcaaguuaaaauaaggcuaguccguuaucaacuugaaaaaguggcaccgagucggugc | 73 |
| sgRNA sequence | n(17-30)guuuuagagcuagaaauagcaaguuaaaauaaggcuaguccguuaucaacuugaaaaaguggcaccgagucggugcu(1-8) | 74 |

*indicates a nucleotide with a 2'-O-methyl phosphorothioate modification.
"n" refers to the spacer sequence at the 5' end.

SEQUENCE TABLE 24

Edited TRAC Gene Sequence.

| Description | Sequence (Deletions indicated by dashes (-); insertions indicated by bold) | SEQ ID NO: |
|---|---|---|
| TRAC gene edit | AA--------------------GAGCAACAAATCTGACT | 75 |
| TRAC gene edit | AAGAGCAACAGTGCTGT-GCCTGGAGCAACAAATCTGACT | 76 |
| TRAC gene edit | AAGAGCAACAGTG-------CTGGAGCAACAAATCTGACT | 77 |
| TRAC gene edit | AAGAGCAACAGT------GCCTGGAGCAACAAATCTGACT | 78 |
| TRAC gene edit | AAGAGCAACAGTG--------------------CTGACT | 79 |
| TRAC gene edit | AAGAGCAACAGTGCTGTGGGCCTGGAGCAACAAATCTGACT | 80 |
| TRAC gene edit | AAGAGCAACAGTGC--TGGCCTGGAGCAACAAATCTGACT | 81 |
| TRAC gene edit | AAGAGCAACAGTGCTGTTGCCTGGAGCAACAAATCTGACT | 82 |

SEQUENCE TABLE 25

Edited β2M Gene Sequence.

| Description | Sequence (Deletions indicated by dashes (-); insertions indicated by bold) | SEQ ID NO: |
|---|---|---|
| β2M gene-edit | CGTGGCCTTAGCTGTGCTCGCGCTACTCTCTCTTTCT-GCCTGGAGGCTATCCAGCGTGAGTCTCTCCTACCCTCCCGCT | 83 |
| β2M gene-edit | CGTGGCCTTAGCTGTGCTCGCGCTACTCTCTCTTTC--GCCTGGAGGCTATCCAGCGTGAGTCTCTCCTACCCTCCCGCT | 84 |
| β2M gene-edit | CGTGGCCTTAGCTGTGCTCGCGCTACTCTCTCTTT-----CTGGAGGCTATCCAGCGTGAGTCTCTCCTACCCTCCCGCT | 85 |
| β2M gene-edit | CGTGGCCTTAGCTGTGCTCGCGCTACTCTCTCTTTCTGGATAGCCTGGAGGCTATCCAGCGTGAGTCTCTCCTACCCTCCCGCT | 86 |
| β2M gene-edit | CGTGGCCTTAGCTGTGCTCGC------------------------GCTATCCAGCGTGAGTCTCTCCTACCCTCCCGCT | 87 |
| β2M gene-edit | CGTGGCCTTAGCTGTGCTCGCGCTACTCTCTCTTTCTGTGGCCTGGAGGCTATCCAGCGTGAGTCTCTCCTACCCTCCCGCT | 88 |

SEQUENCE TABLE 26

Edited CD70 Gene Sequence.

| Description | Sequence (Deletions indicated by dashes (-); insertions indicated by bold) | SEQ ID NO: |
|---|---|---|
| CD70 gene-edit | CACACCACGAGGCAGATCACCAAGCCCGCG--CAATGGGACCAAAGCAGCCCGCAGGACG | 89 |

SEQUENCE TABLE 26-continued

Edited CD70 Gene Sequence.

| Description | Sequence (Deletions indicated by dashes (-); insertions indicated by bold) | SEQ ID NO: |
|---|---|---|
| CD70 gene-edit | CACACCACGAGGCAGATCACCAAGCCCGCGAACCAATGGGACCAAAGCAGCC CGCAGGACG | 90 |
| CD70 gene-edit | CACACCACGAGGCAGATC------------ACCAATGGGACCAAAGCAGCCCGCAGGACG | 91 |
| CD70 gene-edit | CACAccAcGAGGcAGATCACCAAGCCCGCG-CCAATGGGACCAAAGCAGCCCGCAGGACG | 92 |
| CD70 gene-edit | CACACCACGAGGCAGATCACCAAGCCCGC-ACCAATGGGACCAAAGCAGCCCGCAGGACG | 93 |
| CD70 gene-edit | CACACCACGAGGCAGATCACCA------------------------AGCCCGCAGGACG | 94 |

SEQUENCE TABLE 27

Chimeric Antigen Receptor Sequences

| SEQ ID NO | Description | Sequence |
|---|---|---|
| 95 | signal peptide | MLLLVTSLLLCELPHPAFLLIP |
| 96 | signal peptide | MALPVTALLLPLALLLHAARP |
| 97 | CD8a transmembrane domain | IYIWAPLAGTCGVLLLSLVITLY |
| 98 | 4-1BB nucleotide sequence | AAACGGGGCAGAAAGAAACTCCTGTATATATTCAAACAACCATTTATGA GACCAGTACAAACTACTCAAGAGGAAGATGGCTGTAGCTGCCGATTTCC AGAAGAAGAAGAAGGAGGATGTGAACTG |
| 99 | 4-1BB amino acid sequence | KRGRKKLLYIFKQPFMRPVQTTQEEDGCSCRFPEEEEGGCEL |
| 100 | CD28 nucleotide sequence | TCAAAGCGGAGTAGGTTGTTGCATTCCGATTACATGAATATGACTCCTC GCCGGCCTGGGCCGACAAGAAAACATTACCAACCCTATGCCCCCCCACG AGACTTCGCTGCGTACAGGTCC |
| 101 | CD28 amino acid sequence | SKRSRLLHSDYMNMTPRRPGPTRKHYQPYAPPRDFAAYRS |
| 102 | CD3-zeta nucleotide sequence | CGAGTGAAGTTTTCCCGAAGCGCAGACGCTCCGGCATATCAGCAAGGAC AGAATCAGCTGTATAACGAACTGAATTTGGGACGCCGCGAGGAGTATGA CGTGCTTGATAAACGCCGGGGAGAGACCCGGAAATGGGGGTAAACCC CGAAGAAGAATCCCCAAGAAGGACTCTACAATGAACTCCAGAAGGATA AGATGGCGGAGGCCTACTCAGAAATAGGTATGAAGGGCGAACGACGACG GGGAAAAGGTCACGATGGCCTCTACCAAGGGTTGAGTACGGCAACCAAA GATACGTACGATGCACTGCATATGCAGGCCCTGCCTCCCAGA |
| 103 | CD3-zeta amino acid sequence | RVKFSRSADAPAYQQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR |
| 105 | anti-CD19 VL CDR1 (Kabat) | RASQDISKYLN |
| 106 | anti-CD19 VL CDR2 (Kabat) | HTSRLHS |
| 107 | anti-CD19 VL CDR3 (Kabat) | QQGNTLPYT |
| 108 | anti-CD19 VH CDR1 (Kabat) | DYGVS |
| 109 | anti-CD19 VH CDR2 (Kabat) | VIWGSETTYYNSALKS |

SEQUENCE TABLE 27-continued

Chimeric Antigen Receptor Sequences

| SEQ ID NO | Description | Sequence |
|---|---|---|
| 110 | anti-CD19 VH CDR3 (Kabat) | HYYYGGSYAMDY |
| 111 | anti-CD19 VL CDR1 (Chothia) | RASQDISKYLN |
| 112 | anti-CD19 VL CDR2 (Chothia) | HTSRLHS |
| 113 | anti-CD19 VL CDR3 (Chothia) | QQGNTLPYT |
| 114 | anti-CD19 VH CDR1 (Chothia) | GVSLPDY |
| 115 | anti-CD19 VH CDR2 (Chothia) | WGSET |
| 116 | anti-CD19 VH CDR3 (Chothia) | HYYYGGSYAMDY |
| 117 | Anti-CD19 CAR FMC63-28Z (FMC63-CD8[tm]-CD28[co-stimulatory domain]-CD3z) | ATGCTTCTTTTGGTTACGTCTCTGTTGCTTTGCGAACTTCCTCATCCAG CGTTCTTGCTGATCCCCGATATTCAGATGACTCAGACCACCAGTAGCTT GTCTGCCTCACTGGGAGACCGAGTAACAATCTCCTGCAGGGCAAGTCAA GACATTAGCAAATACCTCAATTGGTACCAGCAGAAGCCCGACGGAACGG TAAAACTCCTCATCTATCATACGTCAAGGTTGCATTCCGGAGTACCGTC ACGATTTTCAGGTTCTGGGAGCGGAACTGACTATTCCTTGACTATTTCA AACCTCGAGCAGGAGGACATTGCGACATATTTTTGTCAACAAGGTAATA CCCTCCCTTACACTTTCGGAGGAGGAACCAAACTCGAAATTACCGGGTC CACCAGTGGCTCTGGGAAGCCTGGCAGTGGAGAAGGTTCCACTAAAGGC GAGGTGAAGCTCCAGGAGAGCGGCCCCGGTCTCGTTGCCCCCAGTCAAA GCCTCTCTGTAACGTGCACAGTGAGTGGTGTATCATTGCCTGATTATGG CGTCTCCTGGATAAGGCAGCCCCCGCGAAAGGGTCTTGAATGGCTTGGG GTAATATGGGGCTCAGAGACAACGTATTATAACTCCGCTCTCAAAAGTC GCTTGACGATAATAAAAGATAACTCCAAGAGTCAAGTTTTCCTTAAAAT GAACAGTTTGCAGACTGACGATACCGCTATATATTATTGTGCTAAACAT TATTACTACGGCGGTAGTTACGCGATGGATTATTGGGGGCAGGGGACTT CTGTCACAGTCAGTAGTGCTGCTGCCTTTGTCCCGGTATTTCTCCCAGC CAAACCGACCACGACTCCCGCCCCGCGCCCTCCGACACCCGCTCCCACC ATCGCCTCTCAACCTCTTAGTCTTCGCCCCGAGGGCATGCCGACCCGCCG CCGGGGGTGCTGTTCATACGAGGGGCTTGGACTTCGCTTGTGATATTTA CATTTGGGCTCCGTTGGCGGGTACGTGCGGCGTCCTTTTGTTGTCACTC GTTATTACTTTGTATTGTAATCACAGGAATCGCTCAAAGCGGAGTAGGT TGTTGCATTCCGATTACATGAATATGACTCCTCGCCGGCCTGGGCCGAC AAGAAAACATTACCAACCCTATGCCCCCCCACGAGACTTCGCTGCGTAC AGGTCCCGAGTGAAGTTTTCCCGAAGCGCAGACGCTCCGGCATATATCAGC AAGGACAGAATCAGCTGTATAACGAACTGAATTTGGGACGCCGCGAGGA GTATGACGTGCTTGATAAACGCCGGGGAGAGACCCGGAAATGGGGAGGT AAACCCCGAAGAAAGAATCCCCAAGAAGGACTCTACAATGAACTCCAGA AGGATAAGATGGCGGAGGCCTACTCAGAAATAGGTATGAAGGCGAACG ACGACGGGGAAAAGGTCACGATGGCCTCTACCAAGGGGTTGAGTACGGCA ACCAAAGATACGTACGATGCACTGCATATGCAGGCCCTGCCTCCCAGA |
| 118 | Anti-CD19 CAR FMC63-28Z (FMC63-CD8[tm]-CD28[co-stimulatory domain]-CD3z) Amino Acid with signal peptide | *MLLLVTSLLLCELPHPAFLLIP*DIQMTQTTSSLSASLGDRVTISCRASQ DISKYLNWYQQKPDGTVKLLIYHTSRLHSGVPSRFSGSGSGTDYSLTIS NLEQEDIATYFCQQGNTLPYTFGGGTKLEITGSTSGSGKPGSGEGSTKG EVKLQESGPGLVAPSQSLSVTCTVSGVSLPDYGVSWIRQPPRKGLEWLG VIWGSETTYYNSALKSRLTIIKDNSKSQVFLKMNSLQTDDTAIYYCAKH YYYGGSYAMDYWGQGTSVTVSSAAAFVPVFLPAKTTTPAPRPPTPAPT IASQPLSLRPEACRPAAGGAVHTRGLDFACDIYIWAPLAGTCGVLLLSL VITLYCNHRNRSKRSRLLHSDYMNMTPRRPGPTRKHYQPYAPPRDFAAY RSRVKFSRSADAPAYQQGQNQLYNELNLGRREEYDVLDKRRGRDPEMGG KPRRKNPQEGLYNELQKDKMAEAYSEIGMKGERRRGKGHDGLYQGLSTA TKDTYDALHMQALPPR |
| 353 | Anti-CD19 CAR FMC63-28Z (FMC63-CD8[tm]-CD28[co-stimulatory domain]-CD3z) Amino Acid without signal | DIQMTQTTSSLSASLGDRVTISCRASQDISKYLNWYQQKPDGTVKLLIY HTSRLHSGVPSRFSGSGSGTDYSLTISNLEQEDIATYFCQQGNTLPYTF GGGTKLEITGSTSGSGKPGSGEGSTKGEVKLQESGPGLVAPSQSLSVTC TVSGVSLPDYGVSWIRQPPRKGLEWLGVIWGSETTYYNSALKSRLTIIK DNSKSQVFLKMNSLQTDDTAIYYCAKHYYYGGSYAMDYWGQGTSVTVSS AAAFVPVFLPAKTTTPAPRPPTPAPTIASQPLSLRPEACRPAAGGAVH TRGLDFACDIYIWAPLAGTCGVLLLSLVITLYCNHRNRSKRSRLLHSDY MNMTPRRPGPTRKHYQPYAPPRDFAAYRSRVKFSRSADAPAYQQGQNQL |

SEQUENCE TABLE 27-continued

Chimeric Antigen Receptor Sequences

| SEQ ID NO | Description | Sequence |
|---|---|---|
| | peptide | YNELNLGRREEYDVLDKRRGRDPEMGGKPRRKNPQEGLYNELQKDKMAEAYSEIGMKGERRRGKGHDGLYQGLSTATKDTYDALHMQALPPR |
| 119 | Anti-CD19 scFv coding sequence | GATATTCAGATGACTCAGACCACCAGTAGCTTGTCTGCCTCACTGGGAGACCGAGTAACAATCTCCTGCAGGGCAAGTCAAGACATTAGCAAATACCTCAATTGGTACCAGCAGAAGCCCGACGGAACGGTAAAACTCCTCATCTATCATACGTCAAGGTTGCATTCCGGAGTACCGTCACGATTTTCAGGTTCTGGGAGCGGAACTGACTATTCCTTGACTATTTCAAACCTCGAGCAGGAGGACATTGCGACATATTTTTGTCAACAAGGTAATACCCTCCCTTACACTTTCGGAGGAGGAACCAAACTCGAAATTACCGGGTCCACCAGTGGCTCTGGGAAGCCTGGCAGTGGAGAAGGTTCCACTAAAGGCGAGGTGAAGCTCCAGGAGAGCGGCCCCGGTCTCGTTGCCCCCAGTCAAAGCCTCTCTGTAACGTGCACAGTGAGTGGTGTATCATTGCCTGATTATGGCGTCTCCTGGATAAGGCAGCCCCCGCGAAAGGGTCTTGAATGGCTTGGGGTAATATGGGGCTCAGAGACAACGTATTATAACTCCGCTCTCAAAAGTCGCTTGACGATAATAAAGATAACTCCAAGAGTCAAGTTTTCCTTAAAATGAACAGTTTGCAGACTGACGATACCGCTATATATTATTGTGCTAAACATTATTACTACGGCGGTAGTTACGCGATGGATTATTGGGGGCAGGGGACTTCTGTCACAGTCAGTAGT |
| 120 | Anti-CD19 scFv amino acid sequence Linker underlined | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEITGSTSGSGKPGSGEGSTKGEVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS |
| 121 | CD8a extracellular + CD8a transmembrane + 5' Linker (underlined) | GCTGCTGCCTTTGTCCCGGTATTTCTCCCAGCCAAACCGACCACGACTCCCGCCCCGCGCCCTCCGACACCCGCTCCCACCATCGCCTCTCAACCTCTTAGTCTTCGCCCCGAGGCATGCCGACCCGCCGCCGGGGGTGCTGTTCATACGAGGGGCTTGGACTTCGCTTGTGATATTTACATTTGGGCTCCGTTGGCGGGTACGTGCGGCGTCCTTTTGTTGTCACTCGTTATTACTTTGTATTGTAATCACAGGAATCGC |
| 122 | CD8a extracellular + CD8a transmembrane (without linker) | TTTGTCCCGGTATTTCTCCCAGCCAAACCGACCACGACTCCCGCCCCGCGCCCTCCGACACCCGCTCCCACCATCGCCTCTCAACCTCTTAGTCTTCGCCCCGAGGCATGCCGACCCGCCGCCGGGGGTGCTGTTCATACGAGGGGCTTGGACTTCGCTTGTGATATTTACATTTGGGCTCCGTTGGCGGGTACGTGCGGCGTCCTTTTGTTGTCACTCGTTATTACTTTGTATTGTAATCACAGGAATCGC |
| 123 | CD8a extracellular + CD8a transmembrane | FVPVFLPAKPTTTPAPRPPTPAPTIASQPLSLRPEACRPAAGGAVHTRGLDFACDIYIWAPLAGTCGVLLLSLVITLYCNHRNR |
| 124 | Anti-CD19 VH | EVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS |
| 125 | Anti-CD19 VL | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEIT |
| 126 | CD19 linker | GSTSGSGKPGSGEGSTKG |
| 127 | CD70 VL CDR1 (Kabat) | RASKSVSTSGYSFMH |
| 128 | CD70 VL CDR1 (Chothia) | SKSVSTSGYSF |
| 129 | CD70 VL CDR2 (Kabat) | LASNLES |
| N/A | CD70 VL CDR2 (Chothia) | LAS |
| 130 | CD70 VL CDR3 (Kabat) | QHSREVPWT |
| 131 | CD70 VL CDR3 (Chothia) | SREVPW |
| 132 | CD70 VH CDR1 (Kabat) | NYGMN |

SEQUENCE TABLE 27-continued

Chimeric Antigen Receptor Sequences

| SEQ ID NO | Description | Sequence |
|---|---|---|
| 133 | CD70 VH CDR1 (Chothia) | GYTFTNYGMN |
| 134 | CD70 VH CDR2 (Kabat) | WINTYTGEPTYADAFKG |
| 135 | CD70 VH CDR2 (Chothia) | NTYTGE |
| 136 | CD70 VH CDR3 (Kabat) | DYGDYGMDY |
| 137 | CD70 VH CDR3 (Chothia) | CARDYGDYGMDYWG |
| 138 | CD70 CAR amino acid sequence (CD70B scFv with 41BB) With signal peptide | *MALPVTALLLPLALLLHAARP*QVQLVQSGAEVKKPGASVKVSCKASGYT FTNYGMNWVRQAPGQGLKWMGWINTYTGEPTYADAFKGRVTMTRDTSIS TAYMELSRLRSDDTAVYYCARDYGDYGMDYWGQGTTVTVSSGGGGSGGG GSGGGGSGDIVMTQSPDSLAVSLGERATINCRASKSVSTSGYSFMHWYQ QKPGQPPKLLIYLASNLESGVPDRFSGSGSGTDFTLTISSLQAEDVAVY YCQHSREVPWTFGQGTKVEIKSAAAFVPVFLPAKPTTTPAPRPPTPAPT IASQPLSLRPEACRPAAGGAVHTRGLDFACDIYIWAPLAGTCGVLLLSL VITLYCNHRNRKRGRKKLLYIFKQPFMRPVQTTQEEDGCSCRFPEEEEG GCELRVKFSRSADAPAYQQGQNQLYNELNLGRREEYDVLDKRRGRDPEM GGKPRRKNPQEGLYNELQKDKMAEAYSEIGMKGERRRGKGHDGLYQGLS TATKDTYDALHMQALPPR |
| 354 | CD70 CAR amino acid sequence (CD70B scFv with 41BB) Without signal peptide | QVQLVQSGAEVKKPGASVKVSCKASGYTFTNYGMNWVRQAPGQGLKWMG WINTYTGEPTYADAFKGRVTMTRDTSISTAYMELSRLRSDDTAVYYCAR DYGDYGMDYWGQGTTVTVSSGGGGSGGGGSGGGGSGDIVMTQSPDSLAV SLGERATINCRASKSVSTSGYSFMHWYQQKPGQPPKLLIYLASNLESGV PDRFSGSGSGTDFTLTISSLQAEDVAVYYCQHSREVPWTFGQGTKVEIK SAAAFVPVFLPAKPTTTPAPRPPTPAPTIASQPLSLRPEACRPAAGGAV HTRGLDFACDIYIWAPLAGTCGVLLLSLVITLYCNHRNRKRGRKKLLYI FKQPFMRPVQTTQEEDGCSCRFPEEEEGGCELRVKFSRSADAPAYQQGQ NQLYNELNLGRREEYDVLDKRRGRDPEMGGKPRRKNPQEGLYNELQKDK MAEAYSEIGMKGERRRGKGHDGLYQGLSTATKDTYDALHMQALPPR |
| 139 | Anti-CD70A scFv nucleotide sequence | GATATAGTTATGACCCAATCACCCGATAGTCTTGCGGTAAGCCTGGGGG AGCGAGCAACAATAAACTGTCGGGCATCAAAATCCGTCAGTACAAGCGG GTATTCATTCATGCACTGGTATCAACAGAAACCCGGTCAGCCACCCAAG CTCCTGATTTATCTTGCGTCTAATCTTGAGTCCGGCGTCCCAGACCGGT TTTCCGGCTCCGGGAGCGGCACGGATTTTACTCTTACTATTTCTAGCCT TCAGGCCGAAGATGTGGCGGTATACTACTGCCAGCATTCAAGGGAAGTT CCTTGGACGTTCGGTCAGGGCACGAAAGTGGAAATTAAAGGCGGGGGGG GATCCGGCGGGGAGGGTCTGGAGGAGGTGGCAGTGGTCAGGTCCAACT GGTGCAGTCCGGGGCAGAGGTAAAAAAACCCGGCGCGTCTGTTAAGGTT TCATGCAAGGCCAGTGGATATACTTTCACCAATTACGGAATGAACTGGG TGAGGCAGGCCCCTGGTCAAGGCCTGAAATGGATGGGATGGATAAACAC GTACACCGGTGAACCTACCTATGCCGATGCCTTTAAGGGTCGGGTTACG ATGACGAGAGACACCTCCATATCAACAGCCTACATGGAGCTCAGCAGAT TGAGGAGTGACGATACGGCAGTCTATTACTGTGCAAGAGACTACGGCGA TTATGGCATGGATTACTGGGGCCAGGGCACTACAGTAACCGTTTCCAGC |
| 140 | Anti-CD70A scFv amino acid sequence (linker underlined) | DIVMTQSPDSLAVSLGERATINCRASKSVSTSGYSFMHWYQQKPGQPPK LLIYLASNLESGVPDRFSGSGSGTDFTLTISSLQAEDVAVYYCQHSREV PWTFGQGTKVEIK<u>GGGGSGGGGSGGGGS</u>GQVQLVQSGAEVKKPGASVKV SCKASGYTFTNYGMNWVRQAPGQGLKWMGWINTYTGEPTYADAFKGRVT MTRDTSISTAYMELSRLRSDDTAVYYCARDYGDYGMDYWGQGTTVTVSS |
| 141 | Anti-CD70B scFv nucleotide sequence | CAGGTCCAGTTGGTGCAAAGCGGGGCGGAGGTGAAAAAACCCGGCGCTT CCGTGAAGGTGTCCTGTAAGGCGTCCGGTTATACGTTCACGAACTACGG GATGAATTGGGTTCGCCAAGCGCCGGGGCAGGGACTGAAATGGATGGGG TGGATAAATACCTACACCGGCGAACCTACATACGCCGACGCTTTTAAAG GGCGAGTCACTATGACGCGCGATACCAGCATATCCACCGCATACATGGA GCTGTCCCGACTCCGGTCAGACGACACGGCTGTCTACTATTGTGCTCGG GACTATGGCGATTATGGCATGGACTACTGGGGTCAGGGTACGACTGTAA CAGTTAGTAGTGGTGGAGGCGGCAGTGGCGGGGGGGAAGCGGAGGAGG GGGTTCTGGTGACATAGTTATGACCCAATCCCCAGATAGTTTGGCGGTT TCTCTGGGCGAGAGGGCAACGATTAATTGTCGCGCATCAAAGAGCGTTT CAACGAGCGGATATTCTTTTATGCATTGGTACCAGCAAAAACCCGGACA ACCGCCGAAGCTGCTGATCTACTTGGCTTCAAATCTTGAGTCTGGGGTG CCGGACCGATTTTCTGGTAGTGGAAGCGGAACTGACTTTACGCTCACGA |

SEQUENCE TABLE 27-continued

Chimeric Antigen Receptor Sequences

| SEQ ID NO | Description | Sequence |
|---|---|---|
| | | TCAGTTCACTGCAGGCTGAGGATGTAGCGGTCTATTATTGCCAGCACAG TAGAGAAGTCCCCTGGACCTTCGGTCAAGGCACGAAAGTAGAAATTAAA |
| 142 | Anti-CD70B scFv amino acid sequence (linker underlined) | QVQLVQSGAEVKKPGASVKVSCKASGYTFTNYGMNWVRQAPGQGLKWMG WINTYTGEPTYADAFKGRVTMTRDTSISTAYMELSRLRSDDTAVYYCAR DYGDYGMDYWGQGTTVTVSSGGGGSGGGGSGGGGSGDIVMTQSPDSLAV SLGERATINCRASKSVSTSGYSFMHWYQQKPGQPPKLLIYLASNLESGV PDRFSGSGSGTDFTLTISSLQAEDVAVYYCQHSREVPWTFGQGTKVEIK |
| 143 | Anti-CD70 VH | QVQLVQSGAEVKKPGASVKVSCKASGYTFTNYGMNWVRQAPGQGLKWMG WINTYTGEPTYADAFKGRVTMTRDTSISTAYMELSRLRSDDTAVYYCAR DYGDYGMDYWGQGTTVTVSS |
| 144 | Anti-CD70 VL | DIVMTQSPDSLAVSLGERATINCRASKSVSTSGYSFMHWYQQKPGQPPK LLIYLASNLESGVPDRFSGSGSGTDFTLTISSLQAEDVAVYYCQHSREV PWTFGQGTKVEIK |
| 145 | BCMA CAR nucleotide sequence | ATGGCGCTTCCGGTGACAGCACTGCTCCTCCCCTTGGCGCTGTTGCTCC ACGCAGCAAGGCCGCAGGTGCAGCTGGTGCAGAGCGGAGCCGAGCTCAA GAAGCCCGGAGCCTCCGTGAAGGTGAGCTGCAAGGCCAGCGGCAACACC CTGACCAACTACGTGATCCACTGGGTGAGACAAGCCCCCGGCCAAAGGC TGGAGTGGATGGGCTACATCCTGCCCTACAACGACCTGACCAAGTACAG CCAGAAGTTCCAGGGCAGGGTGACCATCACCAGGGATAAGAGCGCCTCC ACCGCCTATATGGAGCTGAGCAGCCTGAGGAGCGAGGACACCGCTGTGT ACTACTGTACAAGGTGGGACTGGGACGGCTTCTTTGACCCCTGGGGCCA GGGCACAACAGTGACCGTCAGCAGCGGCGGCGAGGCAGCGGCGGCGGC GGCAGCGGCGGAGGCGGAAGCGAAATCGTGATGACCCAGAGCCCCGCCA CACTGAGCGTGAGCCCTGGCGAGAGGGCCAGCATCTCCTGCAGGGCTAG CCAAAGCCTGGTGCACAGCAACGGCAACACCCACCTGCACTGGTACCAG CAGAGACCCGGACAGGCTCCCAGGCTGCTGATCTACAGCGTGAGCAACA GGTTCTCCGAGGTGCCTGCCAGGTTTAGCGGCAGCGGAAGCGGCACCGA CTTTACCCTGACCATCAGCAGCGTGGAGTCCGAGGACTTCGCCGTGTAT TACTGCAGCCAGACCAGCCACATCCCTTACACCTTCGGCGGCGGCACCA AGCTGGAGATCAAAAGTGCTGCTGCCTTTGTCCCGGTATTTCTCCCAGC CAAACCGACCACGACTCCCGCCCCGCGCCCTCCGACACCCGCTCCCACC ATCGCCTCTCAACCTCTTAGTCTTCGCCCCGAGGCATGCCGACCCGCCG CCGGGGGTGCTGTTCATACGAGGGGCTTGGACTTCGCTTGTGATATTTA CATTTGGGCTCCGTTGGCGGGTACGTGCGGCGTCCTTTTGTTGTCACTC GTTATTACTTTGTATTGTAATCACAGGAATCGCAAACGGGGCAGAAAGA AACTTCCTGTATATATTCAAACAACCATTTATGAGACCAGTACAAACTAC TCAAGAGGAAGATGGCTGTAGCTGCCGATTTCCAGAAGAAGAAGAAGGA GGATGTGAACTGCGAGTGAAGTTTTCCCGAAGCGCAGACGCTCCGGCAT ATCAGCAAGGACAGAATCAGCTGTATAACGAACTGAATTTGGGACGCCG CGAGGAGTATGACGTGCTTGATAAACGCCGGGGAGAGACCCGGAAATG GGGGGTAAACCCCGAAGAAAGAATCCCCAAGAAGGACTCTACAATGAAC TCCAGAAGGATAAGATGGCGGAGGCCTACTCAGAAATAGGTATGAAGGG CGAACGACGACGGGGAAAAGGTCACGATGGCCTCTACCAAGGGTTGAGT ACGGCAACCAAAGATACGTACGATGCACTGCATATGCAGGCCCTGCCTC CCAGA |
| 146 | BCMA CAR amino acid sequence With signal peptide | *MALPVTALLLPLALLLHAARP*QVQLVQSGAELKKPGASVKVSCKASGNT LTNYVIHWVRQAPGQRLEWMGYILPYNDLTKYSQKFQGRVTITRDKSAS TAYMELSSLRSEDTAVYYCTRWDWDGFFDPWGQGTTVTVSSGGGGSGGG GSGGGGSEIVMTQSPATLSVSPGERASISCRASQSLVHSNGNTHLHWYQ QRPGQAPRLLIYSVSNRFSEVPARFSGSGSGTDFTLTISSVESEDFAVY YCSQTSHIPYTFGGGTKLEIKSAAAFVPVFLPAKPTTTPAPRPPTPAPT IASQPLSLRPEACRPAAGGAVHTRGLDFACDIYIWAPLAGTCGVLLLSL VITLYCNHRNRKRGRKKLLYIFKQPFMRPVQTTQEEDGCSCRFPEEEEG GCELRVKFSRSADAPAYQQGQNQLYNELNLGRREEYDVLDKRRGRDPEM GGKPRRKNPQEGLYNELQKDKMAEAYSEIGMKGERRRGKGHDGLYQGLS TATKDTYDALHMQALPPR |
| 355 | BCMA CAR amino acid sequence Without signal peptide | QVQLVQSGAELKKPGASVKVSCKASGNTLTNYVIHWVRQAPGQRLEWMG YILPYNDLTKYSQKFQGRVTITRDKSASTAYMELSSLRSEDTAVYYCTR WDWDGFFDPWGQGTTVTVSSGGGGSGGGGSGGGGSEIVMTQSPATLSVS PGERASISCRASQSLVHSNGNTHLHWYQQRPGQAPRLLIYSVSNRFSEV PARFSGSGSGTDFTLTISSVESEDFAVYYCSQTSHIPYTFGGGTKLEIK SAAAFVPVFLPAKPTTTPAPRPPTPAPTIASQPLSLRPEACRPAAGGAV HTRGLDFACDIYIWAPLAGTCGVLLLSVITLYCNHRNRKRGRKKLLYI FKQPFMRPVQTTQEEDGCSCRFPEEEEGGCELRVKFSRSADAPAYQQGQ NQLYNELNLGRREEYDVLDKRRGRDPEMGGKPRRKNPQEGLYNELQKDK MAEAYSEIGMKGERRRGKGHDGLYQGLSTATKDTYDALHMQALPPR |

SEQUENCE TABLE 27-continued

Chimeric Antigen Receptor Sequences

| SEQ ID NO | Description | Sequence |
|---|---|---|
| 147 | BCMA scFv nucleotide sequence | CAGGTGCAGCTGGTGCAGAGCGGAGCCGAGCTCAAGAAGCCCGGAGCCT CCGTGAAGGTGAGCTGCAAGGCCAGCGGCAACACCCTGACCAACTACGT GATCCACTGGGTGAGACAAGCCCCCGGCCAAAGGCTGGAGTGGATGGGC TACATCCTGCCCTACAACGACCTGACCAAGTACAGCCAGAAGTTCCAGG GCAGGGTGACCATCACCAGGGATAAGAGCGCCTCCACCGCCTATATGGA GCTGAGCAGCCTGAGGAGCGAGGACACCGCTGTGTACTACTGTACAAGG TGGGACTGGGACGGCTTCTTTGACCCCTGGGGCCAGGGCACAACAGTGA CCGTCAGCAGCGGCGGCGGAGGCAGCGGCGGCGGCGGCAGCGGCGGAGG CGGAAGCGAAATCGTGATGACCCAGAGCCCCGCCACACTGAGCGTGAGC CCTGGCGAGAGGGCCAGCATCTCCTGCAGGGCTAGCCAAAGCCTGGTGC ACAGCAACGGCAACACCCACCTGCACTGGTACCAGCAGAGACCCGGACA GGCTCCCAGGCTGCTGATCTACAGCGTGAGCAACAGGTTCTCCGAGGTG CCTGCCAGGTTTAGCGGCAGCGGAAGCGGCACCGACTTTACCCTGACCA TCAGCAGCGTGGAGTCCGAGGACTTCGCCGTGTATTACTGCAGCCAGAC CAGCCACATCCCTTACACCTTCGGCGGCGGCACCAAGCTGGAGATCAAA |
| 148 | BCMA scFv amino acid sequence (linker underlined) | QVQLVQSGAELKKPGASVKVSCKASGNTLTNYVIHWVRQAPGQRLEWMG YILPYNDLTKYSQKFQGRVTITRDKSASTAYMELSSLRSEDTAVYYCTR WDWDGFFDPWGQGTTVTVSSGGGGSGGGGSGGGGSEIVMTQSPATLSVS PGERASISCRASQSLVHSNGNTHLHWYQQRPGQAPRLLIYSVSNRFSEV PARFSGSGSGTDFTLTISSVESEDFAVYYCSQTSHIPYTFGGGTKLEIK |
| 149 | BCMA VH | QVQLVQSGAELKKPGASVKVSCKASGNTLTNYVIHWVRQAPGQRLEWMG YILPYNDLTKYSQKFQGRVTITRDKSASTAYMELSSLRSEDTAVYYCTR WDWDGFFDPWGQGTTVTVSS |
| 150 | BCMA VL | EIVMTQSPATLSVSPGERASISCRASQSLVHSNGNTHLHWYQQRPGQAP RLLIYSVSNRFSEVPARFSGSGSGTDFTLTISSVESEDFAVYYCSQTSH IPYTFGGGTKLEIK |
| 151 | BCMA VL CDR1 (Kabat & Chothia) | RASQSLVHSNGNTHLH |
| 152 | BCMA VL CDR2 (Kabat & Chothia) | SVSNRFS |
| 153 | BCMA VL CDR3 (Kabat) | SQTSHIPYT |
| 154 | BCMA VL CDR3 (Chothia) | SQTSHIPYT |
| 155 | BCMA VH CDR1 (Kabat) | NYVIH |
| 156 | BCMA VH CDR1 (Chothia) | GNTLTNY |
| 157 | BCMA VH CDR2 (Kabat) | YILPYNDLTKYSQKFQG |
| 158 | BCMA VH CDR2 (Chothia) | LPYNDL |
| 159 | BCMA VH CDR3 (Kabat) | WDWDGFFDP |
| 160 | BCMA VH CDR3 (Chothia) | WDWDGFFDP |
| 328 | anti-CD33 antibody VH CDR1 (Kabat) | SYYIH |
| 329 | anti-CD33 antibody VH CDR2 (Kabat) | VIYPGNDDISYNQKFQG |
| 330 | anti-CD33 antibody VH CDR3 (Kabat) | EVRLRYFDV |
| 331 | anti-CD33 antibody VL CDR1 (Kabat) | KSSQSVFFSSSQKNYLA |
| 332 | anti-CD33 antibody VL CDR2 (Kabat) | WASTRES |

SEQUENCE TABLE 27-continued

Chimeric Antigen Receptor Sequences

| SEQ ID NO | Description | Sequence |
|---|---|---|
| 333 | anti-CD33 antibody VL CDR3 (Kabat) | <u>HQYLSSRT</u> |
| 334 | anti-CD33 antibody VH | QVQLQQPGAEVVKPGASVKMSCKASGYTFTSYYIHWIKQTPGQGLEWVG VIYPGNDDISYNQKFQGKATLTADKSSTTAYMQLSSLTSEDSAVYYCAR EVRLRYFDVWGQGTTVTVSS |
| 335 | anti-CD33 antibody VL | EIVLTQSPGSLAVSPGERVTMSCKSSQSVFFSSSQKNYLAWYQQIPGQS PRLLIYWASTRESGVPDRFTGSGSGTDFTLTISSVQPEDLAIYYCHQYL SSRTFGQGTKLEIK |
| 336 | Anti-CD33 and anti-CD33b scFv Linker underlined | EIVLTQSPGSLAVSPGERVTMSCKSSQSVFFSSSQKNYLAWYQQIPGQS PRLLIYWASTRESGVPDRFTGSGSGTDFTLTISSVQPEDLAIYYCHQYL SSRTFGQGTKLEIK<u>GGGGGSGGGGSGGGGS</u>QVQLQQPGAEVVKPGASVK MSCKASGYTFTSYYIHWIKQTPGQGLEWVGVIYPGNDDISYNQKFQGKA TLTADKSSTTAYMQLSSLTSEDSAVYYCAREVRLRYFDVWGQGTTVTVS S |
| 337 | Anti-CD33 and anti-CD33b scFv | GAAATCGTCCTCACACAATCCCCGGGGAGCCTCGCAGTCAGTCCTGGGG AACGAGTCACTATGAGCTGCAAATCCAGTCAGAGTGTTTTTTTCTCAAG TAGCCAGAAGAACTACCTCGCATGGTACCAACAAATACCGGGGCAATCT CCCCGCTTGCTTATATACTGGGCAAGTACCCGCGAATCCGGCGTACCGG ATCGATTCACGGGATCTGGGTCAGGTACTGATTTCACTTTGACTATCAG CTCTGTTCAGCCTGAAGATTTGGCAATTTACTACTGTCACCAATACTTG AGTAGCCGAACTTTCGGCCAGGGCACGAAGCTCGAAATCAAGGGCGGAG GGGGAGGTTCTGGTGGGGCGGTTCTGGCGGTGGAGGAAGCCAAGTACA GTTGCAACAGCCAGGGGCGGAGGTCGTAAAACCTGGGGCGTCTGTCAAG ATGAGCTGTAAAGCAAGTGGATACACCTTCACCTCCTACTATATACATT GGATTAAGCAAACTCCGGGTCAGGGGCTGGAATGGGTTGGCGTTATATA CCCCGGGAACGATGATATATCATACAACCAAAAATTTCAAGGCAAGGCG ACTCTGACTGCCGATAAGAGTAGCACAACAGCTTACATGCAGCTTCTT CCCTGACCAGCGAAGATTCAGCAGTTTACTACTGCGCTCGGGAAGTGCG CCTGCGATACTTTGATGTCTGGGGTCAAGGAACTACAGTTACTGTATCA AGC |
| 338 | Anti-CD33 CAR CD28 costim. With signal peptide | *MALPVTALLLPLALLLHAAR*PEIVLTQSPGSLAVSPGERVTMSCKSSQS VFFSSSQKNYLAWYQQIPGQSPRLLIYWASTRESGVPDRFTGSGSGTDF TLTISSVQPEDLAIYYCHQYLSSRTFGQGTKLEIKGGGGSGGGGSGGG GSQVQLQQPGAEVVKPGASVKMSCKASGYTFTSYYIHWIKQTPGQGLEW VGVIYPGNDDISYNQKFQGKATLTADKSSTTAYMQLSSLTSEDSAVYYC AREVRLRYFDVWGQGTTVTVSSSAAAFVPVFLPAKPTTTPAPRPPTPAP TIASQPLSLRPEACRPAAGGAVHTRGLDFACDIYIWAPLAGTCGVLLLS LVITLYCNHRNRSKRSRLLHSDYMNMTPRRPGPTRKHYQPYAPPRDFAA YRSRVKFSRSADAPAYQQGQNQLYNELNLGRREEYDVLDKRRGRDPEMG GKPRRKNPQEGLYNELQKDKMAEAYSEIGMKGERRRGKGHDGLYQGLST ATKDTYDALHMQALPPR |
| 356 | Anti-CD33 CAR CD28 costim. Without signal peptide | EIVLTQSPGSLAVSPGERVTMSCKSSQSVFFSSSQKNYLAWYQQIPGQS PRLLIYWASTRESGVPDRFTGSGSGTDFTLTISSVQPEDLAIYYCHQYL SSRTFGQGTKLEIKGGGGSGGGGSGGGGSQVQLQQPGAEVVKPGASVK MSCKASGYTFTSYYIHWIKQTPGQGLEWVGVIYPGNDDISYNQKFQGKA TLTADKSSTTAYMQLSSLTSEDSAVYYCAREVRLRYFDVWGQGTTVTVS SSAAAFVPVFLPAKPTTTPAPRPPTPAPTIASQPLSLRPEACRPAAGGA VHTRGLDFACDIYIWAPLAGTCGVLLLSLVITLYCNHRNRSKRSRLLHS DYMNMTPRRPGPTRKHYQPYAPPRDFAAYRSRVKFSRSADAPAYQQGQN QLYNELNLGRREEYDVLDKRRGRDPEMGGKPRRKNPQEGLYNELQKDKM AEAYSEIGMKGERRRGKGHDGLYQGLSTATKDTYDALHMQALPPR |
| 339 | Anti-CD33b CAR 41BB costim. With signal peptide | *MALPVTALLLPLALLLHAAR*PEIVLTQSPGSLAVSPGERVTMSCKSSQS VFFSSSQKNYLAWYQQIPGQSPRLLIYWASTRESGVPDRFTGSGSGTDF TLTISSVQPEDLAIYYCHQYLSSRTFGQGTKLEIKGGGGSGGGGSGGGG SQVQLQQPGAEVVKPGASVKMSCKASGYTFTSYYIHWIKQTPGQGLEW VGVIYPGNDDISYNQKFQGKATLTADKSSTTAYMQLSSLTSEDSAVYYC AREVRLRYFDVWGQGTTVTVSSSAAAFVPVFLPAKPTTTPAPRPPTPAP TIASQPLSLRPEACRPAAGGAVHTRGLDFACDIYIWAPLAGTCGVLLLS LVITLYCNHRNRKRGRKKLLYIFKQPFMRPVQTTQEEDGCSCRFPEEEE GGCELRVKFSRSADAPAYQQGQNQLYNELNLGRREEYDVLDKRRGRDPE MGGKPRRKNPQEGLYNELQKDKMAEAYSEIGMKGERRRGKGHDGLYQGL STATKDTYDALHMQALPPR |
| 357 | Anti-CD33b CAR 41BB costim. | EIVLTQSPGSLAVSPGERVTMSCKSSQSVFFSSSQKNYLAWYQQIPGQS PRLLIYWASTRESGVPDRFTGSGSGTDFTLTISSVQPEDLAIYYCHQYL SSRTFGQGTKLEIKGGGGSGGGGSGGGGSQVQLQQPGAEVVKPGASVK |

SEQUENCE TABLE 27-continued

Chimeric Antigen Receptor Sequences

| SEQ ID NO | Description | Sequence |
|---|---|---|
| | Without signal peptide | MSCKASGYTFTSYYIHWIKQTPGQGLEWVGVIYPGNDDISYNQKFQGKA TLTADKSSTTAYMQLSSLTSEDSAVYYCAREVRLRYFDVWGQGTTVTVS SSAAAFVPVFLPAKPTTTPAPRPPTPAPTIASQPLSLRPEACRPAAGGA VHTRGLDFACDIYIWAPLAGTCGVLLLSLVITLYCNHRNRKRGRKKLLY IFKQPFMRPVQTTQEEDGCSCRFPEEEEGGCELRVKFSRSADAPAYQQG QNQLYNELNLGRREEYDVLDKRRGRDPEMGGKPRRKNPQEGLYNELQKD KMAEAYSEIGMKGERRRGKGHDGLYQGLSTATKDTYDALHMQALPPR |
| 340 | Anti-PTK7 VH CDR1 | SYGMH |
| 341 | Anti-PTK7 VH CDR2 | VIWDDGSNKYYVDSVKG |
| 342 | Anti-PTK7 VH CDR3 | DDYYGSGSFNSYYGTDV |
| 343 | Anti-PTK7 VL CDR1 | RASQSVSIYLA |
| 344 | Anti-PTK7 VL CDR2 | DASNRAT |
| 345 | Anti-PTK7 VL CDR3 | QQRSNWPPFT |
| 346 | Anti-PTK7 $V_H$ | QVQLVESGGGVVQPGRSLRLSCAASGFTFSSYGMHWVRQAPGKGL EWVAVIWDDGSNKYYVDSVKGRFTISRDNSKNTLYLQMNSLRAED TAVYYCARDDYYGSGSFNSYYGTDVWGQGTTVTVSS |
| 347 | Anti-PTK7 $V_L$ | EIVLTQSPATLSLSPGERATLSCRASQSVSIYLAWYQQKPGQAPR LLIYDASNRATGIPARFSGSGSGTDFTLTISSLEPEDFAVYYCQQ RSNWPPFTFGPGTKVDIK |
| 348 | Anti-PTK7 scFv (linker underlined) | QVQLVESGGGVVQPGRSLRLSCAASGFTFSSYGMHWVRQAPGKGL EWVAVIWDDGSNKYYVDSVKGRFTISRDNSKNTLYLQMNSLRAED TAVYYCARDDYYGSGSFNSYYGTDVWGQGTTVTVSS<u>GGGGSGGGG SGGGGS</u>EIVLTQSPATLSLSPGERATLSCRASQSVSIYLAWYQQK PGQAPRLLIYDASNRATGIPARFSGSGSGTDFTLTISSLEPEDFA VYYCQQRSNWPPFTFGPGTKVDIK |
| 349 | Anti-PTK7 CAR CD28 co-stim With signal peptide | *MALPVTALLLPLALLLHAARP*QVQLVESGGGVVQPGRSLRLSCAA SGFTFSSYGMHWVRQAPGKGLEWVAVIWDDGSNKYYVDSVKGRFT ISRDNSKNTLYLQMNSLRAEDTAVYYCARDDYGSGSFNSYYGTD VWGQGTIVIVSSGGGGSGGGGSGGGGSEIVLTQSPATLSLSPGER ATLSCRASQSVSIYLAWYQQKPGQAPRLLIYDASNRATGIPARFS GSGSGTDFTLTISSLEPEDFAVYYCQQRSNWPPFTFGPGTKVDIK SAAAFVPVFLPAKPTTTPAPRPPTPAPTIASQPLSLRPEACRPAA GGAVHTRGLDFACDIYIWAPLAGTCGVLLLSLVITLYCNHRNSK RSRLLHSDYMNMTPRRPGPTRKHYQPYAPPRDFAAYRSRVKFSRS ADAPAYQQGQNQLYNELNLGRREEYDVLDKRRGRDPEMGGKPRRK NPQEGLYNELQKDKMAEAYSEIGMKGERRRGKGHDGLYQGLSTAT KDTYDALHMQALPPR |
| 358 | Anti-PTK7 CAR CD28 co-stim Without signal peptide | QVQLVESGGGVVQPGRSLRLSCAASGFTFSSYGMHWVRQAPGKGL EWVAVIWDDGSNKYYVDSVKGRFTISRDNSKNTLYLQMNSLRAED TAVYYCARDDYYGSGSFNSYYGTDVWGQGTTVTVSSGGGGSGGGG SGGGGSEIVLTQSPATLSLSPGERATLSCRASQSVSIYLAWYQQK PGQAPRLLIYDASNRATGIPARFSGSGSGTDFTLTISSLEPEDFA VYYCQQRSNWPPFTFGPGTKVDIKSAAAFVPVFLPAKPTTTPAPR PPTPAPTIASQPLSLRPEACRPAAGGAVHTRGLDFACDIYIWAPL AGTCGVLLLSLVITLYCNHRNSKRSRLLHSDYMNMTPRRPGPTR KHYQPYAPPRDFAAYRSRVKFSRSADAPAYQQGQNQLYNELNLGR REEYDVLDKRRGRDPEMGGKPRRKNPQEGLYNELQKDKMAEAYSE IGMKGERRRGKGHDGLYQGLSTATKDTYDALHMQALPPR |
| 350 | Anti-PTK7 CAR 41BB co-stim With signal peptide | *MALPVTALLLPLALLLHAARP*QVQLVESGGGVVQPGRSLRLSCAA SGFTFSSYGMHWVRQAPGKGLEWVAVIWDDGSNKYYVDSVKGRFT ISRDNSKNTLYLQMNSLRAEDTAVYYCARDDYYGSGSFNSYYGTD VWGQGTTVTVSSGGGGSGGGGSGGGGSEIVLTQSPATLSLSPGER ATLSCRASQSVSIYLAWYQQKPGQAPRLLIYDASNRATGIPARFS GSGSGTDFTLTISSLEPEDFAVYYCQQRSNWPPFTFGPGTKVDIK SAAAFVPVFLPAKPTTTPAPRPPTPAPTIASQPLSLRPEACRPAA GGAVHTRGLDFACDIYIWAPLAGTCGVLLLSLVITLYCNHRNKR GRKKLLYIFKQPFMRPVQTTQEEDGCSCRFPEEEEGGCELRVKFS |

SEQUENCE TABLE 27-continued

Chimeric Antigen Receptor Sequences

| SEQ ID NO | Description | Sequence |
|---|---|---|
| | | RSADAPAYQQGQNQLYNELNLGRREEYDVLDKRRGRDPEMGGKPR RKNPQEGLYNELQKDKMAEAYSEIGMKGERRRGKGHDGLYQGLST ATKDTYDALHMQALPPR |
| 359 | Anti-PTK7 CAR 41BB co-stim Without signal peptide | QVQLVESGGGVVQPGRSLRLSCAASGFTFSSYGMHWVRQAPGKGL EWVAVIWDDGSNKYYVDSVKGRFTISRDNSKNTLYLQMNSLRAED TAVYYCARDDYYGSGSFNSYYGTDVWGQGTTVTVSSGGGGSGGGG SGGGGSEIVLTQSPATLSLSPGERATLSCRASQSVSIYLAWYQQK PGQAPRLLIYDASNRATGIPARFSGSGSGTDFTLTISSLEPEDFA VYYCQQRSNWPPFTFGPGTKVDIKSAAAFVPVFLPAKPTTTPAPR PPTPAPTIASQPLSLRPEACRPAAGGAVHTRGLDFACDIYIWAPL AGTCGVLLLSLVITLYCNHRNRKRGRKKLLYIFKQPFMRPVQTTQ EEDGCSCRFPEEEEGGCELRVKFSRSADAPAYQQGQNQLYNELNL GRREEYDVLDKRRGRDPEMGGKPRRKNPQEGLYNELQKDKMAEAY SEIGMKGERRRGKHDGLYQGLSTATKDTYDALHMQALPPR |

TABLE 28

AAV Donor Template Sequences

| | | |
|---|---|---|
| 161 | Left ITR (5' ITR) | TTGGCCACTCCCTCTCTGCG CGCTCGCTCGCTCACTGAGG CCGGGCGACCAAAGGTCGCC CGACGCCCGGGCTTTGCCCG GGCGGCCTCAGTGAGCGAGC GAGCGCGCAGAGAGGGAGTG GCCAACTCCATCACTAGGGG TTCCT |
| 162 | Left ITR (5' ITR) (alternate) | CCTGCAGGCAGCTGCGCGCT CGCTCGCTCACTGAGGCCGC CCGGGCGTCGGGCGACCTTT GGTCGCCCGGCCTCAGTGAG CGAGCGAGCGCGCAGAGAGG GAGTGGCCAACTCCATCACT AGGGGTTCCT |
| 163 | Right ITR (3' ITR) | AGGAACCCCTAGTGATGGAG TTGGCCACTCCCTCTCTGCG CGCTCGCTCGCTCACTGAGG CCGCCCGGGCAAAGCCCGGG CGTCGGGCGACCTTTGGTCG CCCGGCCTCAGTGAGCGAGC GAGCGCGCAGAGAGGGAGTG GCCAA |
| 164 | Right ITR (3' ITR) (alternate) | AGGAACCCCTAGTGATGGAG TTGGCCACTCCCTCTCTGCG CGCTCGCTCGCTCACTGAGG CCGGGCGACCAAAGGTCGCC CGACGCCCGGGCTTTGCCCG GGCGGCCTCAGTGAGCGAGC GAGCGCGCAGCTGCCTGCAG G |
| 165 | TRAC-LHA (800 bp) | GAGATGTAAGGAGCTGCTGT GACTTGCTCAAGGCCTTATA TCGAGTAAACGGTAGTGCTG GGGCTTAGACGCAGGTGTTC TGATTTATAGTTCAAAACCT CTATCAATGAGAGAGCAATC TCCTGGTAATGTGATAGATT TCCCAACTTAATGCCAACAT ACCATAAACCTCCCATTCTG CTAATGCCCAGCCTAAGTTG GGGAGACCACTCCAGATTCC AAGATGTACAGTTTGCTTTG CTGGGCCTTTTTCCCATGCC TGCCTTTACTCTGCCAGAGT TATATTGCTGGGGTTTTGAA GAAGATCCTATTAAATAAAA GAATAAGCAGTATTATTAAG TAGCCCTGCATTTCAGGTTT CCTTGAGTGGCAGGCCAGGC CTGGCCGTGAACGTTCACTG AAATCATGGCCTCTTGGCCA AGATTGATAGCTTGTGCCTG TCCCTGAGTCCCAGTCCATC ACGAGCAGCTGGTTTCTAAG ATGCTATTTCCCGTATAAAG CATGAGACCGTGACTTGCCA GCCCCACAGAGCCCCGCCCT TGTCCATCACTGGCATCTGG ACTCCAGCCTGGGTTGGGGC AAAGAGGGAAATGAGATCAT GTCCTAACCCTGATCCTCTT GTCCCACAGATATCCAGAAC CCTGACCCTGCCGTGTACCA GCTGAGAGACTCTAAATCCA GTGACAAGTCTGTCTGCCTA TTCACCGATTTTGATTCTCA AACAAATGTGTCACAAAGTA AGGATTCTGATGTGTATATC ACAGACAAAACTGTGCTAGA CATGAGGTCTATGGACTTCA |
| 166 | TRAC-RHA (800 bp) | TGGAGCAACAAATCTGACTT TGCATGTGCAAACGCCTTCA ACAACAGCATTATTCCAGAA GACACCTTCTTCCCCAGCCC AGGTAAGGGCAGCTTTGGTG CCTTCGCAGGCTGTTTCCTT GCTTCAGGAATGGCCAGGTT CTGCCCAGAGCTCTGGTCAA TGATGTCTAAAACTCCTCTG ATTGGTGGTCTCGGCCTTAT CCATTGCCACCAAAACCCTC TTTTTACTAAGAAACAGTGA GCCTTGTTCTGGCAGTCCAG AGAATGACACGGGAAAAAAG CAGATGAAGAGAAGGTGGCA GGAGAGGGCACGTGGCCCAG CCTCAGTCTCTCCAACTGAG TTCCTGCCTGCCTGCCTTTG CTCAGACTGTTTGCCCCTTA CTGCTCTTCTAGGCCTCATT CTAAGCCCCTTCTCCAAGTT GCCTCTCCTTATTTCTCCCT GTCTGCCAAAAAATCTTTCC CAGCTCACTAAGTCAGTCTC ACGCAGTCACTCATTAACCC ACCAATCACTGATTGTGCCG GCACATGAATGCACCAGGTG TTGAAGTGGAGGAATTAAAA |

TABLE 28-continued

AAV Donor Template Sequences

| | | |
|---|---|---|
| | | AGTCAGATGAGGGGTGTGCC |
| | | CAGAGGAAGCACCATTCTAG |
| | | TTGGGGGAGCCCATCTGTCA |
| | | GCTGGGAAAAGTCCAAATAA |
| | | CTTCAGATTGGAATGTGTTT |
| | | TAACTCAGGGTTGAGAAAAC |
| | | AGCTACCTTCAGGACAAAAG |
| | | TCAGGGAAGGGCTCTCTGAA |
| | | GAAATGCTACTTGAAGATAC |
| | | CAGCCCTACCAAGGGCAGGG |
| | | AGAGGACCCTATAGAGGCCT |
| | | GGGACAGGAGCTCAATGAGA |
| | | AAGG |
| 167 | EF1a | GGCTCCGGTGCCCGTCAGTG |
| | | GGCAGAGCGCACATCGCCCA |
| | | CAGTCCCCGAGAAGTTGGGG |
| | | GGAGGGGTCGGCAATTGAAC |
| | | CGGTGCCTAGAGAAGGTGGC |
| | | GCGGGGTAAACTGGGAAAGT |
| | | GATGTCGTGTACTGGCTCCG |
| | | CCTTTTTCCCGAGGGTGGGG |
| | | GAGAACCGTATATAAGTGCA |
| | | GTAGTCGCCGTGAACGTTCT |
| | | TTTTCGCAACGGGTTTGCCG |
| | | CCAGAACACAGGTAAGTGCC |
| | | GTGTGTGGTTCCCGCGGGCC |
| | | TGGCCTCTTTACGGGTTATG |
| | | GCCCTTGCGTGCCTTGAATT |
| | | ACTTCCACTGGCTGCAGTAC |
| | | GTGATTCTTGATCCCGAGCT |
| | | TCGGGTTGGAAGTGGGTGGG |
| | | AGAGTTCGAGGCCTTGCGCT |
| | | TAAGGAGCCCCTTCGCCTCG |
| | | TGCTTGAGTTGAGGCCTGGC |
| | | CTGGGCGCTGGGGCCGCCGC |
| | | GTGCGAATCGGTGGCACCT |
| | | TCGCGCCTGTCTCGCTGCTT |
| | | TCGATAAGTCTCTAGCCATT |
| | | TAAAATTTTTGATGACCTGC |
| | | TGCGACGCTTTTTTTCTGGC |
| | | AAGATAGTCTTGTAAATGCG |
| | | GGCCAAGATCTGCACACTGG |
| | | TATTTCGGTTTTTGGGGCCG |
| | | CGGGCGGCGACGGGGCCCGT |
| | | GCGTCCCAGCGCACATGTTC |
| | | GGCGAGGCGGGGCCTGCGAG |
| | | CGCGGCCACCGAGAATCGGA |
| | | CGGGGGTAGTCTCAAGCTGG |
| | | CCGGCCTGCTCTGGTGCCTG |
| | | GCCTCGCGCCGCCGTGTATC |
| | | GCCCCGCCCTGGGCGGCAAG |
| | | GCTGGCCCGGTCGGCACCAG |
| | | TTGCGTGAGCGGAAAGATGG |
| | | CCGCTTCCCGGCCCTGCTGC |
| | | AGGGAGCTCAAAATGGAGGA |
| | | CGCGGCGCTCGGGAGAGCGG |
| | | GCGGGTGAGTCACCCACACA |
| | | AAGGAAAAGGGCCTTTCCGT |
| | | CCTCAGCCGTCGCTTCATGT |
| | | GACTCCACGGAGTACCGGGC |
| | | GCCGTCCAGGCACCTCGATT |
| | | AGTTCTCGAGCTTTTGGAGT |
| | | ACGTCGTCTTTAGGTTGGGG |
| | | GGAGGGGTTTTATGCGATGG |
| | | AGTTTCCCCACACTGAGTGG |
| | | GTGGAGACTGAAGTTAGGCC |
| | | AGCTTGGCACTTGATGTAAT |
| | | TCTCCTTGGAATTTGCCCTT |
| | | TTTGAGTTTGGATCTTGGTT |
| | | CATTCTCAAGCCTCAGACAG |
| | | TGGTTCAAAGTTTTTTCTT |
| | | CCATTTCAGGTGTCGTGA |
| 168 | CD19 LHA to RHA | GAGATGTAAGGAGCTGCTGT |
| | | GACTTGCTCAAGGCCTTATA |
| | | TCGAGTAAACGGTAGTGCTG |
| | | GGGCTTAGACGCAGGTGTTC |

TABLE 28-continued

AAV Donor Template Sequences

| | | |
|---|---|---|
| | | TGATTTATAGTTCAAAACCT |
| | | CTATCAATGAGAGAGCAATC |
| | | TCCTGGTAATGTGATAGATT |
| | | TCCCAACTTAATGCCAACAT |
| | | ACCATAAACCTCCCATTCTG |
| | | CTAATGCCCAGCCTAAGTTG |
| | | GGGAGACCACTCCAGATTCC |
| | | AAGATGTACAGTTTGCTTTG |
| | | CTGGGCCTTTTTCCCATGCC |
| | | TGCCTTTACTCTGCCAGAGT |
| | | TATATTGCTGGGGTTTTGAA |
| | | GAAGATCCTATTAAATAAAA |
| | | GAATAAGCAGTATTATTAAG |
| | | TAGCCCTGCATTTCAGGTTT |
| | | CCTTGAGTGGCAGGCCAGGC |
| | | CTGGCCGTGAACGTTCACTG |
| | | AAATCATGGCCTCTTGGCCA |
| | | AGATTGATAGCTTGTGCCTG |
| | | TCCCTGAGTCCCAGTCCATC |
| | | ACGAGCAGCTGGTTTCTAAG |
| | | ATGCTATTTCCCGTATAAAG |
| | | CATGAGACCGTGACTTGCCA |
| | | GCCCCACAGAGCCCGCCCT |
| | | TGTCCATCACTGGCATCTGG |
| | | ACTCCAGCCTGGGTTGGGGC |
| | | AAAGAGGGAAATGAGATCAT |
| | | GTCCTAACCCTGATCCTCTT |
| | | GTCCCACAGATATCCAGAAC |
| | | CCTGACCCTGCCGTGTACCA |
| | | GCTGAGAGACTCTAAATCCA |
| | | GTGACAAGTCTGTCTGCCTA |
| | | TTCACCGATTTTGATTCTCA |
| | | AACAAATGTGTCACAAAGTA |
| | | AGGATTCTGATGTGTATATC |
| | | ACAGACAAAACTGTGCTAGA |
| | | CATGAGGTCTATGGACTTCA |
| | | GGCTCCGGTGCCCGTCAGTG |
| | | GGCAGAGCGCACATCGCCCA |
| | | CAGTCCCCGAGAAGTTGGGG |
| | | GGAGGGGTCGGCAATTGAAC |
| | | CGGTGCCTAGAGAAGGTGGC |
| | | GCGGGGTAAACTGGGAAAGT |
| | | GATGTCGTGTACTGGCTCCG |
| | | CCTTTTTCCCGAGGGTGGGG |
| | | GAGAACCGTATATAAGTGCA |
| | | GTAGTCGCCGTGAACGTTCT |
| | | TTTTCGCAACGGGTTTGCCG |
| | | CCAGAACACAGGTAAGTGCC |
| | | GTGTGTGGTTCCCGCGGGCC |
| | | TGGCCTCTTTACGGGTTATG |
| | | GCCCTTGCGTGCCTTGAATT |
| | | ACTTCCACTGGCTGCAGTAC |
| | | GTGATTCTTGATCCCGAGCT |
| | | TCGGGTTGGAAGTGGGTGGG |
| | | AGAGTTCGAGGCCTTGCGCT |
| | | TAAGGAGCCCCTTCGCCTCG |
| | | TGCTTGAGTTGAGGCCTGGC |
| | | CTGGGCGCTGGGGCCGCCGC |
| | | GTGCGAATCGGTGGCACCT |
| | | TCGCGCCTGTCTCGCTGCTT |
| | | TCGATAAGTCTCTAGCCATT |
| | | TAAAATTTTTGATGACCTGC |
| | | TGCGACGCTTTTTTTCTGGC |
| | | AAGATAGTCTTGTAAATGCG |
| | | GGCCAAGATCTGCACACTGG |
| | | TATTTCGGTTTTTGGGGCCG |
| | | CGGGCGGCGACGGGGCCCGT |
| | | GCGTCCCAGCGCACATGTTC |
| | | GGCGAGGCGGGGCCTGCGAG |
| | | CGCGGCCACCGAGAATCGGA |
| | | CGGGGGTAGTCTCAAGCTGG |
| | | CCGGCCTGCTCTGGTGCCTG |
| | | GCCTCGCGCCGCCGTGTATC |
| | | GCCCCGCCCTGGGCGGCAAG |
| | | GCTGGCCCGGTCGGCACCAG |
| | | TTGCGTGAGCGGAAAGATGG |
| | | CCGCTTCCCGGCCCTGCTGC |
| | | AGGGAGCTCAAAATGGAGGA |

TABLE 28-continued

AAV Donor Template Sequences

| | | |
|---|---|---|
| | CGCGGCGCTCGGGAGAGCGG | |
| | GCGGGTGAGTCACCCACACA | |
| | AAGGAAAAGGGCCTTTCCGT | |
| | CCTCAGCCGTCGCTTCATGT | |
| | GACTCCACGGAGTACCGGGC | |
| | GCCGTCCAGGCACCTCGATT | |
| | AGTTCTCGAGCTTTTGGAGT | |
| | ACGTCGTCTTTAGGTTGGGG | |
| | GGAGGGGTTTTATGCGATGG | |
| | AGTTTCCCCACACTGAGTGG | |
| | GTGGAGACTGAAGTTAGGCC | |
| | AGCTTGGCACTTGATGTAAT | |
| | TCTCCTTGGAATTTGCCCTT | |
| | TTTGAGTTTGGATCTTGGTT | |
| | CATTCTCAAGCCTCAGACAG | |
| | TGGTTCAAAGTTTTTTTCTT | |
| | CCATTTCAGGTGTCGTGACC | |
| | ACCATGCTTCTTTTGGTTAC | |
| | GTCTCTGTTGCTTTGCGAAC | |
| | TTCCTCATCCAGCGTTCTTG | |
| | CTGATCCCCGATATTCAGAT | |
| | GACTCAGACCACCAGTAGCT | |
| | TGTCTGCCTCACTGGGAGAC | |
| | CGAGTAACAATCTCCTGCAG | |
| | GGCAAGTCAAGACATTAGCA | |
| | AATACCTCAATTGGTACCAG | |
| | CAGAAGCCCGACGGAACGGT | |
| | AAAACTCCTCATCTATCATA | |
| | CGTCAAGGTTGCATTCCGGA | |
| | GTACCGTCACGATTTTCAGG | |
| | TTCTGGGAGCGGAACTGACT | |
| | ATTCCTTGACTATTTCAAAC | |
| | CTCGAGCAGGAGGACATTGC | |
| | GACATATTTTGTCAACAAG | |
| | GTAATACCCTCCCTTACACT | |
| | TTCGGAGGAGGAACCAAACT | |
| | CGAAATTACCGGGTCCACCA | |
| | GTGGCTCTGGGAAGCCTGGC | |
| | AGTGGAGAAGGTTCCACTAA | |
| | AGGCGAGGTGAAGCTCCAGG | |
| | AGAGCGGCCCCGGTCTCGTT | |
| | GCCCCCAGTCAAAGCCTCTC | |
| | TGTAACGTGCACAGTGAGTG | |
| | GTGTATCATTGCCTGATTAT | |
| | GGCGTCTCCTGGATAAGGCA | |
| | GCCCCCGCGAAAGGGTCTTG | |
| | AATGGCTTGGGGTAATATGG | |
| | GGCTCAGAGACAACGTATTA | |
| | TAACTCCGCTCTCAAAAGTC | |
| | GCTTGACGATAATAAAAGAT | |
| | AACTCCAAGAGTCAAGTTTT | |
| | CCTTAAAATGAACAGTTTGC | |
| | AGACTGACGATACCGCTATA | |
| | TATTATTGTGCTAAACATTA | |
| | TTACTACGGCGGTAGTTACG | |
| | CGATGGATTATTGGGGGCAG | |
| | GGGACTTCTGTCACAGTCAG | |
| | TAGTGCTGCTGCCTTTGTCC | |
| | CGGTATTTCTCCCAGCCAAA | |
| | CCGACCACGACTCCCGCCCC | |
| | GCGCCCTCCGACACCCGCTC | |
| | CCACCATCGCCTCTCAACCT | |
| | CTTAGTCTTCGCCCCGAGGC | |
| | ATGCCGACCCGCCGCCGGGG | |
| | GTGCTGTTCATACGAGGGGC | |
| | TTGGACTTCGCTTGTGATAT | |
| | TTACATTTGGGCTCCGTTGG | |
| | CGGGTACGTGCGGCGTCCTT | |
| | TTGTTGTCACTCGTTATTAC | |
| | TTTGTATTGTAATCACAGGA | |
| | ATCGCTCAAAGCGGAGTAGG | |
| | TTGTTGCATTCCGATTACAT | |
| | GAATATGACTCCTCGCCTGC | |
| | CTGGGCCGACAAGAAAACAT | |
| | TACCAACCCTATGCCCCCCC | |
| | ACGAGACTTCGCTGCGTACA | |
| | GGTCCCGAGTGAAGTTTTCC | |
| | CGAAGCGCAGACGCTCCGGC | |
| 169 | CD70<br>LHA to RHA<br>(CD70B scFV with<br>41BB) | ATATCAGCAAGGACAGAATC |
| | | AGCTGTATAACGAACTGAAT |
| | | TTGGGACGCCGCGAGGAGTA |
| | | TGACGTGCTTGATAAACGCC |
| | | GGGGGAGAGACCCGGAAATG |
| | | GGGGGTAAACCCCGAAGAAA |
| | | GAATCCCCAAGAAGGACTCT |
| | | ACAATGAACTCCAGAAGGAT |
| | | AAGATGGCGGAGGCCTACTC |
| | | AGAAATAGGTATGAAGGGCG |
| | | AACGACGACGGGGAAAAGGT |
| | | CACGATGGCCTCTACCAAGG |
| | | GTTGAGTACGGCAACCAAAG |
| | | ATACGTACGATGCACTGCAT |
| | | ATGCAGGCCCTGCCTCCCAG |
| | | ATAATAATAAAAATCGCTATC |
| | | CATCGAAGATGGATGTGTGT |
| | | TGGTTTTTTGTGTGTGGAGC |
| | | AACAAATCTGACTTTGCATG |
| | | TGCAAACGCCTTCAACAACA |
| | | GCATTATTCCAGAAGACACC |
| | | TTCTTCCCCAGCCCAGGTAA |
| | | GGGCAGCTTTGGTGCCTTCG |
| | | CAGGCTGTTTCCTTGCTTCA |
| | | GGAATGGCCAGGTTCTGCCC |
| | | AGAGCTCTGGTCAATGATGT |
| | | CTAAAACTCCTCTGATTGGT |
| | | GGTCTCGGCCTTATCCATTG |
| | | CCACCAAAACCCTCTTTTTA |
| | | CTAAGAAACAGTGAGCCTTG |
| | | TTCTGGCAGTCCAGAGAATG |
| | | ACACGGGAAAAAAGCAGATG |
| | | AAGAGAAGGTGGCAGGAGAG |
| | | GGCACGTGGCCCAGCCTCAG |
| | | TCTCTCCAACTGAGTTCCTG |
| | | CCTGCCTGCCTTTGCTCAGA |
| | | CTGTTTGCCCCTTACTGCTC |
| | | TTCTAGGCCTCATTCTAAGC |
| | | CCCTTCTCCAAGTTGCCTCT |
| | | CCTTATTTCTCCCTGTCTGC |
| | | CAAAAAATCTTTCCCAGCTC |
| | | ACTAAGTCAGTCTCACGCAG |
| | | TCACTCATTAACCCACCAAT |
| | | CACTGATTGTGCCGGCACAT |
| | | GAATGCACCAGGTGTTGAAG |
| | | TGGAGGAATTAAAAAGTCAG |
| | | ATGAGGGGTGTGCCCAGAGG |
| | | AAGCACCATTCTAGTTGGGG |
| | | GAGCCCATCTGTCAGCTGGG |
| | | AAAAGTCCAAATAACTTCAG |
| | | ATTGGAATGTGTTTTAACTC |
| | | AGGGTTGAGAAAACAGCTAC |
| | | CTTCAGGACAAAAGTCAGGG |
| | | AAGGGCTCTCTGAAGAAATG |
| | | CTACTTGAAGATACCAGCCC |
| | | TACCAAGGGCAGGGAGGAGA |
| | | CCCTATAGAGGCCTGGGACA |
| | | GGAGCTCAATGAGAAAGG |
| | | GAGATGTAAGGAGCTGCTGT |
| | | GACTTGCTCAAGGCCTTATA |
| | | TCGAGTAAACGGTAGTGCTG |
| | | GGGCTTAGACGCAGGTGTTC |
| | | TGATTATAGTTCAAAACCT |
| | | CTATCAATGAGAGAGCAATC |
| | | TCCTGGTAATGTGATAGATT |
| | | TCCCAACTTAATGCAACAT |
| | | ACCATAAACCTCCCATTCTG |
| | | CTAATGCCCAGCCTAAGTTG |
| | | GGGAGACCACTCCAGATTCC |
| | | AAGATGTACAGTTTGCTTTG |
| | | CTGGGCCTTTTTCCCATGCC |
| | | TGCCTTTACTCTGCCAGAGT |
| | | TATATTGCTGGGGTTTTGAA |
| | | GAAGATCCTATTAAATAAAA |
| | | GAATAAGCAGTATTATTAAG |
| | | TAGCCCTGCATTTCAGGTTT |
| | | CCTTGAGTGGCAGGCCAGGC |

TABLE 28-continued

AAV Donor Template Sequences

CTGGCCGTGAACGTTCACTG
AAATCATGGCCTCTTGGCCA
AGATTGATAGCTTGTGCCTG
TCCCTGAGTCCCAGTCCATC
ACGAGCAGCTGGTTTCTAAG
ATGCTATTTCCCGTATAAAG
CATGAGACCGTGACTTGCCA
GCCCCACAGAGCCCCGCCCT
TGTCCATCACTGGCATCTGG
ACTCCAGCTGGGTTGGGGC
AAAGAGGGAAATGAGATCAT
GTCCTAACCCTGATCCTCTT
GTCCCACAGATATCCAGAAC
CCTGACCCTGCCGTGTACCA
GCTGAGAGACTCTAAATCCA
GTGACAAGTCTGTCTGCCTA
TTCACCGATTTTGATTCTCA
AACAAATGTGTCACAAAGTA
AGGATTCTGATGTGTATATC
ACAGACAAAACTGTGCTAGA
CATGAGGTCTATGGACTTCA
GGCTCCGGTGCCCGTCAGTG
GGCAGAGCGCACATCGCCCA
CAGTCCCCGAGAAGTTGGGG
GGAGGGGTCGGCAATTGAAC
CGGTGCCTAGAGAAGGTGGC
GCGGGGTAAACTGGGAAAGT
GATGTCGTGTACTGGCTCCG
CCTTTTTCCCGAGGGTGGGG
GAGAACCGTATATAAGTGCA
GTAGTCGCCGTGAACGTTCT
TTTTCGCAACGGGTTTGCCG
CCAGAACACAGGTAAGTGCC
GTGTGTGGTTCCCGCGGGCC
TGGCCTCTTTACGGGTTATG
GCCCTTGCGTGCCTTGAATT
ACTTCCACTGGCTGCAGTAC
GTGATTCTTGATCCCGAGCT
TCGGGTTGGAAGTGGGTGGG
AGAGTTCGAGGCCTTGCGCT
TAAGGAGCCCCTTCGCCTCG
TGCTTGAGTTGAGGCCTGGC
CTGGGCGCTGGGGCCGCCGC
GTGCGAATCTGGTGGCACCT
TCGCGCCTGTCTCGCTGCTT
TCGATAAGTCTCTAGCCATT
TAAAATTTTTGATGACCTGC
TGCGACGCTTTTTTTCTGGC
AAGATAGTCTTGTAAATGCG
GGCCAAGATCTGCACACTGG
TATTTCGGTTTTTGGGGCCG
CGGGCGGCGACGGGGCCCGT
GCGTCCCAGCGCACATGTTC
GGCGAGGCGGGGCCTGCGAG
CGCGGCCACCGAGAATCGGA
CGGGGGTAGTCTCAAGCTGG
CCGGCCTGCTCTGGTGCCTG
GCCTCGCGCCGCCGTGTATC
GCCCCGCCCTGGGCGGCAAG
GCTGGCCCGGTCGGCACCAG
TTGCGTGAGCGGAAAGATGG
CCGCTTCCCGGCCCTGCTGC
AGGGAGCTCAAAATGGAGGA
CGCGGCGCTCGGGAGAGCGG
GCGGGTGAGTCACCCACACA
AAGGAAAAGGGCCTTTCCGT
CCTCAGCCGTCGCTTCATGT
GACTCCACGGAGTACCGGGC
GCCGTCCAGGCACCTCGATT
AGTTCTCGAGCTTTTGGAGT
ACGTCGTCTTTAGGTTGGGG
GGAGGGGTTTTATGCGATGG
AGTTTCCCCACACTGAGTGG
GTGGAGACTGAAGTTAGGCC
AGCTTGGCACTTGATGTAAT
TCTCCTTGGAATTTGCCCTT
TTTGAGTTTGGATCTTGGTT
CATTCTCAAGCCTCAGACAG

TGGTTCAAAGTTTTTTTCTT
CCATTTCAGGTGTCGTGACC
ACCATGGCGCTTCCGGTGAC
AGCACTGCTCCTCCCCTTGG
CGCTGTTGCTCCACGCAGCA
AGGCCGCAGGTCCAGTTGGT
GCAAAGCGGGGCGGAGGTGA
AAAAACCCGGCGCTTCCGTG
AAGGTGTCCTGTAAGGCGTC
CGGTTATACGTTCACGAACT
ACGGGATGAATTGGGTTCGC
CAAGCGCCGGGGCAGGGACT
GAAATGGATGGGGTGGATAA
ATACCTACACCGGCGAACCT
ACATACGCCGACGCTTTTAA
AGGGCGAGTCACTATGACGC
GCGATACCAGCATATCCACC
GCATACATGGAGCTGTCCCG
ACTCCGGTCAGACGACACGG
CTGTCTACTATTGTGCTCGG
GACTATGGCGATTATGGCAT
GGACTACTGGGGTCAGGGTA
CGACTGTAACAGTTAGTAGT
GGTGGAGGCGGCAGTGGCGG
GGGGGGAAGCGGAGGAGGGG
GTTCTGGTGACATAGTTATG
ACCCAATCCCCAGATAGTTT
GGCGGTTTCTCTGGGCGAGA
GGGCAACGATTAATTGTCGC
GCATCAAAGAGCGTTTCAAC
GAGCGGATATTCTTTTATGC
ATTGGTACCAGCAAAAACCC
GGACAACCGCCGAAGCTGCT
GATCTACTTGGCTTCAAATC
TTGAGTCTGGGGTGCCGGAC
CGATTTTCTGGTAGTGGAAG
CGGAACTGACTTTACGCTCA
CGATCAGTTCACTGCAGGCT
GAGGATGTAGCGGTCTATTA
TTGCCAGCACAGTAGAGAAG
TCCCCTGGACCTTCGGTCAA
GGCACGAAAGTAGAAATTAA
AAGTGCTGCTGCCTTTGTCC
CGGTATTTCTCCCAGCCAAA
CCGACCACGACTCCCGCCCC
GCGCCCTCCGACACCCGCTC
CCACCATCGCCTCTCAACCT
CTTAGTCTTCGCCCCGAGGC
ATGCCGACCCGCCGCCGGGG
GTGCTGTTCATACGAGGGGC
TTGGACTTCGCTTGTGATAT
TTACATTTGGGCTCCGTTGG
CGGGTACGTGCGGCGTCCTT
TTGTTGTCACTCGTTATTAC
TTTGTATTGTAATCACAGGA
ATCGCAAACGGGGCAGAAAG
AAACTCCTGTATATATTCAA
ACAACCATTATGAGACCAG
TACAAACTACTCAAGAGGAA
GATGGCTGTAGCTGCCGATT
TCCAGAAGAAGAAGAAGGAG
GATGTGAACTGCGAGTGAAG
TTTTCCCGAAGCGCAGACGC
TCCGGCATATCAGCAAGGAC
AGAATCAGCTGTATAACGAA
CTGAATTTGGGACGCCGCGA
GGAGTATGACGTGCTTGATA
AACGCCGGGGAGAGACCCG
GAAATGGGGGTAAACCCCG
AAGAAAGAATCCCAAGAAG
GACTCTACAATGAACTCCAG
AAGGATAAGATGGCGGAGGC
CTACTCAGAAATAGGTATGA
AGGGCGAACGACGACGGGA
AAAGGTCACGATGGCCTCTA
CCAAGGGTTGAGTACGGCAA
CCAAAGATACGTACGATGCA
CTGCATATGCAGGCCCTGCC

TABLE 28-continued

AAV Donor Template Sequences

| | | |
|---|---|---|
| | | TCCCAGATAATAATAAAATC |
| | | GCTATCCATCGAAGATGGAT |
| | | GTGTGTTGGTTTTTTGTGTG |
| | | TGGAGCAACAAATCTGACTT |
| | | TGCATGTGCAAACGCCTTCA |
| | | ACAACAGCATTATTCCAGAA |
| | | GACACCTTCTTCCCCAGCCC |
| | | AGGTAAGGGCAGCTTTGGTG |
| | | CCTTCGCAGGCTGTTTCCTT |
| | | GCTTCAGGAATGGCCAGGTT |
| | | CTGCCCAGAGCTCTGGTCAA |
| | | TGATGTCTAAAACTCCTCTG |
| | | ATTGGTGGTCTCGGCCTTAT |
| | | CCATTGCCACCAAAACCCTC |
| | | TTTTTACTAAGAAACAGTGA |
| | | GCCTTGTTCTGGCAGTCCAG |
| | | AGAATGACACGGGAAAAAAG |
| | | CAGATGAAGAGAAGGTGGCA |
| | | GGAGAGGGCACGTGGCCCAG |
| | | CCTCAGTCTCTCCAACTGAG |
| | | TTCCTGCCTGCCTGCCTTTG |
| | | CTCAGACTGTTTGCCCCTTA |
| | | CTGCTCTTCTAGGCCTCATT |
| | | CTAAGCCCCTTCTCCAAGTT |
| | | GCCTCTCCTTATTTCTCCCT |
| | | GTCTGCCAAAAAATCTTTCC |
| | | CAGCTCACTAAGTCAGTCTC |
| | | ACGCAGTCACTCATTAACCC |
| | | ACCAATCACTGATTGTGCCG |
| | | GCACATGAATGCACCAGGTG |
| | | TTGAAGTGGAGGAATTAAAA |
| | | AGTCAGATGAGGGGTGTGCC |
| | | CAGAGGAAGCACCATTCTAG |
| | | TTGGGGGAGCCCATCTGTCA |
| | | GCTGGGAAAAGTCCAAATAA |
| | | CTTCAGATTGGAATGTGTTT |
| | | TAACTCAGGGTTGAGAAAAC |
| | | AGCTACCTTCAGGACAAAAG |
| | | TCAGGGAAGGGCTCTCTGAA |
| | | GAAATGCTACTTGAAGATAC |
| | | CAGCCCTACCAAGGGCAGGG |
| | | AGAGGACCCTATAGAGGCCT |
| | | GGGACAGGAGCTCAATGAGA |
| | | AAGG |
| 170 | BCMA RHA to LHA | GAGATGTAAGGAGCTGCTGT |
| | | GACTTGCTCAAGGCCTTATA |
| | | TCGAGTAAACGGTAGTGCTG |
| | | GGGCTTAGACGCAGGTGTTC |
| | | TGATTTATAGTTCAAAACCT |
| | | CTATCAATGAGAGAGCAATC |
| | | TCCTGGTAATGTGATAGATT |
| | | TCCCAACTTAATGCCAACAT |
| | | ACCATAAACCTCCCATTCTG |
| | | CTAATGCCCAGCCTAAGTTG |
| | | GGGGAGACCACTCCAGATTCC |
| | | AAGATGTACAGTTTGCTTTG |
| | | CTGGGCCTTTTTCCCATGCC |
| | | TGCCTTTACTCTGCCAGAGT |
| | | TATATTGCTGGGGTTTTGAA |
| | | GAAGATCCTATTAAATAAA |
| | | GAATAAGCAGTATTATTAAG |
| | | TAGCCCTGCATTTCAGGTTT |
| | | CCTTGAGTGGCAGGCCAGGC |
| | | CTGGCCGTGAACGTTCACTG |
| | | AAATCATGGCCTCTTGGCCA |
| | | AGATTGATAGCTTGTGCCTG |
| | | TCCCTGAGTCCCAGTCCATC |
| | | ACGAGCAGCTGGTTTCTAAG |
| | | ATGCTATTTCCCGTATAAAG |
| | | CATGAGACCGTGACTTGCCA |
| | | GCCCCACAGAGCCCCGCCCT |
| | | TGTCCATCACTGGCATCTGG |
| | | ACTCCAGCCTGGGTTGGGGC |
| | | AAAGAGGGAAATGAGATCAT |
| | | GTCCTAACCCTGATCCTCTT |
| | | GTCCCACAGATATCCAGAAC |
| | | CCTGACCCTGCCGTGTACCA |

TABLE 28-continued

AAV Donor Template Sequences

| | | |
|---|---|---|
| | | GCTGAGAGACTCTAAATCCA |
| | | GTGACAAGTCTGTCTGCCTA |
| | | TTCACCGATTTTGATTCTCA |
| | | AACAAATGTGTCACAAAGTA |
| | | AGGATTCTGATGTGTATATC |
| | | ACAGACAAAACTGTGCTAGA |
| | | CATGAGGTCTATGGACTTCA |
| | | GGCTCCGGTGCCCGTCAGTG |
| | | GGCAGAGCGCACATCGCCCA |
| | | CAGTCCCCGAGAAGTTGGGG |
| | | GGAGGGGTCGGCAATTGAAC |
| | | CGGTGCCTAGAGAAGGTGGC |
| | | GCGGGGTAAACTGGGAAAGT |
| | | GATGTCGTGTACTGGCTCCG |
| | | CCTTTTTCCCGAGGGTGGGG |
| | | GAGAACCGTATATAAGTGCA |
| | | GTAGTCGCCGTGAACGTTCT |
| | | TTTTCGCAACGGGTTTGCCG |
| | | CCAGAACACAGGTAAGTGCC |
| | | GTGTGTGGTTCCCGCGGGCC |
| | | TGGCCTCTTTACGGGTTATG |
| | | GCCCTTGCGTGCCTTGAATT |
| | | ACTTCCACTGCTGCAGTAC |
| | | GTGATTCTTGATCCCGAGCT |
| | | TCGGGTTGGAAGTGGGTGGG |
| | | AGAGTTCGAGGCCTTGCGCT |
| | | TAAGGAGCCCCTTCGCCTCG |
| | | TGCTTGAGTTGAGGCCTGGC |
| | | CTGGGCGCTGGGGCCGCCGC |
| | | GTGCGAATCTGGTGGCACCT |
| | | TCGCGCCTGTCTCGCTGCTT |
| | | TCGATAAGTCTCTAGCCATT |
| | | TAAAATTTTTGATGACCTGC |
| | | TGCGACGCTTTTTTTCTGGC |
| | | AAGATAGTCTTGTAAATGCG |
| | | GGCCAAGATCTGCACACTGG |
| | | TATTTCGGTTTTTGGGGCCG |
| | | CGGGCGGCGACGGGGCCCGT |
| | | GCGTCCCAGCGCACATGTTC |
| | | GGCGAGGCGGGGCCTGCGAG |
| | | CGCGGCCACCGAGAATCGGA |
| | | CGGGGGTAGTCTCAAGCTGG |
| | | CCGGCCTGCTCTGGTGCCTG |
| | | GCCTCGCGCGCCGTGTATC |
| | | GCCCCGCCCTGGGCGGCAAG |
| | | GCTGGCCCGGTCGGCACCAG |
| | | TTGCGTGAGCGGAAAGATGG |
| | | CCGCTTCCCGGCCCTGCTGC |
| | | AGGGAGCTCAAAATGGAGGA |
| | | CGCGGCGCTCGGGAGAGCGG |
| | | GCGGGTGAGTCACCCACACA |
| | | AAGGAAAAGGGCCTTTCCGT |
| | | CCTCAGCCGTCGCTTCATGT |
| | | GACTCCACGGAGTACCGGGC |
| | | GCCGTCCAGGCACCTCGATT |
| | | AGTTCTCGAGCTTTTGGAGT |
| | | ACGTCGTCTTTAGGTTGGGG |
| | | GGAGGGGTTTTATGCGATGG |
| | | AGTTTCCCCACACTGAGTGG |
| | | GTGGAGACTGAAGTTAGGCC |
| | | AGCTTGGCACTTGATGTAAT |
| | | TCTCCTTGGAATTTGCCCTT |
| | | TTTGAGTTTGGATCTTGGTT |
| | | CATTCTCAAGCCTCAGACAG |
| | | TGGTTCAAAGTTTTTTTCTT |
| | | CCATTTCAGGTGTCGTGACC |
| | | ACCATGGCGCTTCCGGTGAC |
| | | AGCACTGCTCCTCCCCTTGG |
| | | CGCTGTTGCTCCACGCAGCA |
| | | AGGCCGCAGGTGCAGCTGGT |
| | | GCAGAGCGGAGCCGAGCTCA |
| | | AGAAGCCCGGAGCCTCCGTG |
| | | AAGGTGAGCTGCAAGGCCAG |
| | | CGGCAACACCCTGACCAACT |
| | | ACGTGATCCACTGGGTGAGA |
| | | CAAGCCCCCGGCCAAAGGCT |
| | | GGAGTGGATGGGCTACATCC |
| | | TGCCCTACAACGACCTGACC |

TABLE 28-continued

AAV Donor Template Sequences

| | | |
|---|---|---|
| AAGTACAGCCAGAAGTTCCA | | |
| GGGCAGGGTGACCATCACCA | | |
| GGGATAAGAGCGCCTCCACC | | |
| GCCTATATGGAGCTGAGCAG | | |
| CCTGAGGAGCGAGGACACCG | | |
| CTGTGTACTACTGTACAAGG | | |
| TGGGACTGGGACGGCTTCTT | | |
| TGACCCCTGGGGCCAGGGCA | | |
| CAACAGTGACCGTCAGCAGC | | |
| GGCGGCGGAGGCAGCGGCGG | | |
| CGGCGGCAGCGGCGGAGGCG | | |
| GAAGCGAAATCGTGATGACC | | |
| CAGAGCCCCGCCACACTGAG | | |
| CGTGAGCCCTGGCGAGAGGG | | |
| CCAGCATCTCCTGCAGGGCT | | |
| AGCCAAAGCCTGGTGCACAG | | |
| CAACGGCAACACCCACCTGC | | |
| ACTGGTACCAGCAGAGACCC | | |
| GGACAGGCTCCCAGGCTGCT | | |
| GATCTACAGCGTGAGCAACA | | |
| GGTTCTCCGAGGTGCCTGCC | | |
| AGGTTTAGCGGCAGCGGAAG | | |
| CGGCACCGACTTTACCCTGA | | |
| CCATCAGCAGCGTGGAGTCC | | |
| GAGGACTTCGCCGTGTATTA | | |
| CTGCAGCCAGACCAGCCACA | | |
| TCCCTTACACCTTCGGCGGC | | |
| GGCACCAAGCTGGAGATCAA | | |
| AAGTGCTGCTGCCTTTGTCC | | |
| CGGTATTTCTCCCAGCCAAA | | |
| CCGACCACGACTCCCGCCCC | | |
| GCGCCCTCCGACACCCGCTC | | |
| CCACCATCGCCTCTCAACCT | | |
| CTTAGTCTTCGCCCCGAGGC | | |
| ATGCCGACCCGCCGCCGGGG | | |
| GTGCTGTTCATACGAGGGGC | | |
| TTGGACTTCGCTTGTGATAT | | |
| TTACATTTGGGCTCCGTTGG | | |
| CGGGTACGTGCGGCGTCCTT | | |
| TTGTTGTCACTCGTTATTAC | | |
| TTTGTATTGTAATCACAGGA | | |
| ATCGCAAACGGGGCAGAAAG | | |
| AAACTCCTGTATATATTCAA | | |
| ACAACCATTTATGAGACCAG | | |
| TACAAACTACTCAAGAGGAA | | |
| GATGGCTGTAGCTGCCGATT | | |
| TCCAGAAGAAGAAGAAGGAG | | |
| GATGTGAACTGCGAGTGAAG | | |
| TTTTCCCGAAGCGCAGACGC | | |
| TCCGGCATATCAGCAAGGAC | | |
| AGAATCAGCTGTATAACGAA | | |
| CTGAATTTGGGACGCCGCGA | | |
| GGAGTATGACGTGCTTGATA | | |
| AACGCCGGGGAGAGACCCG | | |
| GAAATGGGGGTAAACCCCG | | |
| AAGAAAGAATCCCCAAGAAG | | |
| GACTCTACAATGAACTCCAG | | |
| AAGGATAAGATGGCGGAGGC | | |
| CTACTCAGAAATAGGTATGA | | |
| AGGGCGAACGACGACGGGGA | | |
| AAAGGTCACGATGGCCTCTA | | |
| CCAAGGGTTGAGTACGGCAA | | |
| CCAAAGATACGTACGATGCA | | |
| CTGCATATGCAGGCCCTGCC | | |
| TCCCAGATAATAAAATC | | |
| GCTATCCATCGAAGATGGAT | | |
| GTGTGTTGGTTTTTTGTGTG | | |
| TGGAGCAACAAATCTGACTT | | |
| TGCATGTGCAAACGCCTTCA | | |
| ACAACAGCATTATTCCAGAA | | |
| GACACCTTCTTCCCCAGCCC | | |
| AGGTAAGGGCAGCTTTGGTG | | |
| CCTTCGCAGGCTGTTTCCTT | | |
| GCTTCAGGAATGGCCAGGTT | | |
| CTGCCCAGAGCTCTGGTCAA | | |
| TGATGTCTAAAACTCCTCTG | | |
| ATTGGTGGTCTCGGCCTTAT | | |
| CCATTGCCACCAAAACCCTC | | |
| TTTTTACTAAGAAACAGTGA | | |
| GCCTTGTTCTGGCAGTCCAG | | |
| AGAATGACACGGGAAAAAAG | | |
| CAGATGAAGAGAAGGTGGCA | | |
| GGAGAGGGCACGTGGCCCAG | | |
| CCTCAGTCTCTCCAACTGAG | | |
| TTCCTGCCTGCCTGCCTTTG | | |
| CTCAGACTGTTTGCCCCTTA | | |
| CTGCTCTTCTAGGCCTCATT | | |
| CTAAGCCCCTTCTCCAAGTT | | |
| GCCTCTCCTTATTTCTCCCT | | |
| GTCTGCCAAAAAATCTTTCC | | |
| CAGCTCACTAAGTCAGTCTC | | |
| ACGCAGTCACTCATTAACCC | | |
| ACCAATCACTGATTGTGCCG | | |
| GCACATGAATGCACCAGGTG | | |
| TTGAAGTGGAGGAATTAAAA | | |
| AGTCAGATGAGGGGTGTGCC | | |
| CAGAGGAAGCACCATTCTAG | | |
| TTGGGGGAGCCCATCTGTCA | | |
| GCTGGGAAAAGTCCAAATAA | | |
| CTTCAGATTGGAATGTGTTT | | |
| TAACTCAGGGTTGAGAAAAC | | |
| AGCTACCTTCAGGACAAAAG | | |
| TCAGGGAAGGGCTCTCTGAA | | |
| GAAATGCTACTTGAAGATAC | | |
| CAGCCCTACCAAGGGCAGGG | | |
| AGAGGACCCTATAGAGGCCT | | |
| GGGACAGGAGCTCAATGAGA | | |
| AAGG | | |
| | 351 Anti-CD33 CAR Donor LHA to RHA CD28 costim. | GAGATGTAAGGAGCTGCTGT GACTTGCTCAAGGCCTTATA TCGAGTAAACGGTAGTGCTG GGGCTTAGACGCAGGTGTTC TGATTTATAGTTCAAAACCT CTATCAATGAGAGAGCAATC TCCTGGTAATGTGATAGATT TCCCAACTTAATGCCAACAT ACCATAAACCTCCCATTCTG CTAATGCCCAGCCTAAGTTG GGGAGACCACTCCAGATTCC AAGATGTACAGTTTGCTTTG CTGGGCCTTTTTCCCATGCC TGCCTTTACTCTGCCAGAGT TATATTGCTGGGGTTTTGAA GAAGATCCTATTAAATAAAA GAATAAGCAGTATTATTAAG TAGCCCTGCATTTCAGGTTT CCTTGAGTGGCAGGCCAGGC CTGGCCGTGAACGTTCACTG AAATCATGGCCTCTTGGCCA AGATTGATAGCTTGTGCCTG TCCCTGAGTCCCAGTCCATC ACGAGCAGCTGGTTCTAAG ATGCTATTTCCCGTATAAAG CATGAGACCGTGACTTGCCA GCCCCACAGAGCCCCGCCCT TGTCCATCACTGGCATCTGG ACTCCAGCCTGGGTTGGGGC AAAGAGGGAAATGAGATCAT GTCCTAACCCTGATCCTCTT GTCCCACAGATATCCAGAAC CCTGACCCTGCCGTGTACCA GCTGAGAGACTCTAAATCCA GTGACAAGTCTGTCTGCCTA TTCACCGATTTTGATTCTCA AACAAATGTGTCACAAAGTA AGGATTCTGATGTGTATATC ACAGACAAAACTGTGCTAGA CATGAGGTCTATGGACTTCA ggctccggtgcccgtcagtg ggcagagcgcacatcgccca cagtcccccgagaagttgggg ggaggggtcggcaattgaac cggtgcctagagaaggtggc gcggggtaaactgggaaagt gatgtcgtgtactggctccg |

TABLE 28-continued

AAV Donor Template Sequences ccttttcccgagggtgggg
gagaaccgtatataagtgca
gtagtcgccgtgaacgttct
ttttcgcaacgggtttgccg
ccagaacacaggtaagtgcc
gtgtgtggttcccgcgggcc
tggcctctttacgggttatg
gcccttgcgtgccttgaatt
acttccactggctgcagtac
gtgattcttgatcccgagct
tcgggttggaagtgggtggg
agagttcgaggcttgcgct
taaggagcccttcgcctcg
tgcttgagttgaggcctggc
ctgggcgctggggccgccgc
gtgcgaatctggtggcacct
tcgcgcctgtctcgctgctt
tcgataagtctctagccatt
taaaattttttgatgacctgc
tgcgacgcttttttttctggc
aagatagtcttgtaaatgcg
ggccaagatctgcacactgg
tatttcggttttttggggccg
cgggcggcgacggggcccgt
gcgtcccagcgcacatgttc
ggcgaggcggggcctgcgag
cgcggccaccgagaatcgga
cgggggtagtctcaagctgg
ccggcctgctctggtgcctg
gcctcgcgccgccgtgtatc
gccccgccctgggcggcaag
gctggcccggtcggcaccag
ttgcgtgagcggaaagatgg
ccgcttcccggccctgctgc
agggagctcaaaatggagga
cgcggcgctcgggagagcgg
gcgggtgagtcacccacaca
aaggaaaagggcctttccgt
cctcagccgtcgcttcatgt
gactccacggagtaccgggc
gccgtccaggcacctcgatt
agttctcgagcttttggagt
acgtcgtctttaggttgggg
ggaggggttttatgcgatgg
agtttccccacactgagtgg
gtggagactgaagttaggcc
agcttggcacttgatgtaat
tctccttggaatttgcccctt
tttgagtttggatcttggtt
cattctcaagcctcagacag
tggttcaaagttttttttctt
ccatttcaggtgtcgtgaCC
ACCATGGCGCTTCCGGTGAC
AGCACTGCTCCTCCCCTTGG
CGCTGTTGCTCCACGCAGCA
AGGCCGGAAATCGTCCTCAC
ACAATCCCCGGGGAGCCTCG
CAGTCAGTCCTGGGGAACGA
GTCACTATGAGCTGCAAATC
CAGTCAGAGTGTTTTTTTCT
CAAGTAGCCAGAAGAACTAC
CTCGCATGGTACCAACAAAT
ACCGGGGCAATCTCCCCGCT
TGCTTATATACTGGGCAAGT
ACCCGCGAATCCGGCGTACC
GGATCGATTCACGGGATCTG
GGTCAGGTACTGATTTCACT
TTGACTATCAGCTCTGTTCA
GCCTGAAGATTTGGCAATTT
ACTACTGTCACCAATACTTG
AGTAGCCGAACTTTCGGCCA
GGGCACGAAGCTCGAAATCA
AGGGCGGAGGGGGAGGTTCT
GGTGGGGCGGTTCTGGCGG
TGGAGGAAGCCAAGTACAGT
TGCAACAGCCAGGGGCGGAG
GTCGTAAAACCTGGGGCGTC
TGTCAAGATGAGCTGTAAAG TABLE 28-continued AAV Donor Template Sequences CAAGTGGATACACCTTCACC
TCCTACTATATACATTGGAT
TAAGCAAACTCCGGGTCAGG
GGCTGGAATGGGTTGGCGTT
ATATACCCCGGGAACGATGA
TATATCATACAACCAAAAAT
TTCAAGGCAAGGCGACTCTG
ACTGCCGATAAGAGTAGCAC
AACAGCTTACATGCAGCTTT
CTTCCCTGACCAGCGAAGAT
TCAGCAGTTTACTACTGCGC
TCGGGAAGTGCGCCTGCGAT
ACTTTGATGTCTGGGGTCAA
GGAACTACAGTTACTGTATC
AAGCAGTGCTGCTGCCTTTG
TCCCGGTATTTCTCCCAGCC
AAACCGACCACGACTCCCGC
CCCGCGCCCTCCGACACCCG
CTCCCACCATCGCCTCTCAA
CCTCTTAGTCTTCGCCCCGA
GGCATGCCGACCCGCCGCCG
GGGGTGCTGTTCATACGAGG
GGCTTGGACTTCGCTTGTGA
TATTTACATTTGGGCTCCGT
TGGCGGGTACGTGCGGCGTC
CTTTTGTTGTCACTCGTTAT
TACTTTGTATTGTAATCACA
GGAATCGCTCAAAGCGGAGT
AGGTTGTTGCATTCCGATTA
CATGAATATGACTCCTCGCC
GGCCTGGGCCGACAAGAAAA
CATTACCAACCCTATGCCCC
CCCACGAGCTTCGCTGCGT
ACAGGTCCCGAGTGAAGTTT
TCCCGAAGCGCAGACGCTCC
GGCATATCAGCAAGGACAGA
ATCAGCTGTATAACGAACTG
AATTTGGGACGCCGCGAGGA
GTATGACGTGCTTGATAAAC
GCCGGGGAGAGACCCGGAA
ATGGGGGGTAAACCCCGAAG
AAAGAATCCCCAAGAAGGAC
TCTACAATGAACTCCAGAAG
GATAAGATGGCGGAGGCCTA
CTCAGAAATAGGTATGAAGG
GCGAACGACGACGGGGAAAA
GGTCACGATGGCCTCTACCA
AGGGTTGAGTACGGCAACCA
AAGATACGTACGATGCACTG
CATATGCAGGCCCTGCCTCC
CAGATAATAATAAAATCGCT
ATCCATCGAAGATGGATGTG
TGTTGGTTTTTTGTGTGTGG
AGCAACAAATCTGACTTTGC
ATGTGCAAACGCCTTCAACA
ACAGCATTATTCCAGAAGAC
ACCTTCTTCCCCAGCCCAGG
TAAGGGCAGCTTTGGTGCCT
TCGCAGGCTGTTTCCTTGCT
TCAGGAATGGCCAGGTTCTG
CCCAGAGCTCTGGTCAATGA
TGTCTAAAACTCCTCTGATT
GGTGGTCTCGGCCTTATCCA
TTGCCACCAAAACCCTCTTT
TTACTAAGAAACAGTGAGCC
TTGTTCTGGCAGTCCAGAGA
ATGACACGGGAAAAAGCAG
ATGAAGAGAAGGTGGCAGGA
GAGGGCACGTGGCCCAGCCT
CAGTCTCTCCAACTGAGTTC
CTGCCTGCCTGCCTTTGCTC
AGACTGTTTGCCCCTTACTG
CTCTTCTAGGCCTCATTCTA
AGCCCCTTCTCCAAGTTGCC
TCTCCTTATTTCTCCCTGTC
TGCCAAAAAATCTTTCCCAG
CTCACTAAGTCAGTCTCACG
CAGTCACTCATTAACCCACC TABLE 28-continued AAV Donor Template Sequences

| | | |
|---|---|---|
| | AATCACTGATTGTGCCGGCA | |
| | CATGAATGCACCAGGTGTTG | |
| | AAGTGGAGGAATTAAAAAGT | |
| | CAGATGAGGGGTGTGCCCAG | |
| | AGGAAGCACCATTCTAGTTG | |
| | GGGGAGCCCATCTGTCAGCT | |
| | GGGAAAAGTCCAAATAACTT | |
| | CAGATTGGAATGTGTTTTAA | |
| | CTCAGGGTTGAGAAAACAGC | |
| | TACCTTCAGGACAAAAGTCA | |
| | GGGAAGGGCTCTCTGAAGAA | |
| | ATGCTACTTGAAGATACCAG | |
| | CCCTACCAAGGGCAGGGAGA | |
| | GGACCCTATAGAGGCCTGGG | |
| | ACAGGAGCTCAATGAGAAAG | |
| | G | |
| 352 | Anti-CD33b CAR Donor LHA to RHA 41BB costim. | GAGATGTAAGGAGCTGCTGT GACTTGCTCAAGGCCTTATA TCGAGTAAACGGTAGTGCTG GGGCTTAGACGCAGGTGTTC TGATTTATAGTTCAAACCTC TATCAATGAGAGAGCAATCT CCTGGTAATGTGATAGATTT CCCAACTTAATGCCAACATA CCATAAACCTCCCATTCTGC TAATGCCCAGCCTAAGTTGG GGAGACCACTCCAGATTCCA AGATGTACAGTTTGCTTTGC TGGGCCTTTTTCCCATGCCT GCCTTTACTCTGCCAGAGTT ATATTGCTGGGGTTTTGAAG AAGATCCTATTAAATAAAAG AATAAGCAGTATTATTAAGT AGCCCTGCATTTCAGGTTTC CTTGAGTGGCAGGCCAGGCC TGGCCGTGAACGTTCACTGA AATCATGGCCTCTTGGCCAA GATTGATAGCTTGTGCCTGT CCCTGAGTCCCAGTCCATCA CGAGCAGCTGGTTTCTAAGA TGCTATTTCCCGTATAAAGC ATGAGACCGTGACTTGCCAG CCCCACAGAGCCCCGCCCTT GTCCATCACTGGCATCTGGA CTCCAGCCTGGGTTGGGGCA AAGAGGGAAATGAGATCATG TCCTAACCCTGATCCTCTTG TCCCACAGATATCCAGAACC CTGACCCTGCCGTGTACCAG CTGAGAGACTCTAAATCCAG TGACAAGTCTGTCTGCCTAT TCACCGATTTTGATTCTCAA ACAAATGTGTCACAAAGTAA GGATTCTGATGTGTATATCA CAGACAAAACTGTGCTAGAC ATGAGGTCTATGGACTTCAg gctccggtgcccgtcagtgg gcagagcgcacatcgcccac agtccccgagaagttggggg gagggggtcggcaattgaacc ggtgcctagagaaggtggcg cggggtaaactgggaaagtg atgtcgtgtactggctccgc cttttttcccgagggtgggg agaaccgtatataagtgcag tagtcgccgtgaacgttctt ttttcgcaacgggtttgccg ccagaacacaggtaagtgcc gtgtgtggttcccgcgggcc tggcctcttacgggttatgg cccttgcgtgccttgaattac ttccactggctgcagtacgt gattcttgatcccgagctt cgggttggaagtgggtggga gagttcgaggccttgcgct taaggagcccttcgcctcgt gcttgagttgaggcctggc | ctgggcgctggggccgccgc gtgcgaatctggtggcacctc tcgcgcctgtctcgctgctt tcgataagtctctagccattt taaaattttttgatgacctgc tgcgacgcttttttttctggc aagatagtcttgtaaatgcg ggccaagatctgcacactgg tatttcggttttttggggccg cgggcggcgacggggcccgt gcgtcccagcgcacatgttc ggcgaggcgggcctgcgag cgcggccaccgagaatcgga cggggtagtctcaagctgg ccggcctgctctggtgcctg gcctcgcgcgccgtgtatc gccccgccctgggcggcaag gctggcccggtcggcaccag ttgcgtgagcggaaagatgg ccgcttcccggccctgctgc agggagctcaaaatggagga cgcggcgctcggagagcgg gcgggtgagtcacccacaca aaggaaaagggcctttccgt cctcagccgtcgcttcatgt gactccacggagtaccgggc gccgtccaggcacctcgatt agttctcgagcttttggagt acgtcgtctttaggtggggg ggaggggttttatgcgatgg agtttccccacactgagtgg gtggagactgaagttaggcc agcttggcacttgatgtaat tctccttggaatttgcccttt tttgagtttggatcttggtt cattctcaagcctcagacag tggttcaaagttttttttctt ccatttcaggtgtcgtgaCC ACCATGGCGCTTCCGGTGAC AGCACTGCTCCTCCCCTTGG CGCTGTTGCTCCACGCAGCA AGGCCGGAAATCGTCCTCAC ACAATCCCCGGGAGCCTCG CAGTCAGTCCTGGGAACGA GTCACTATGAGCTGCAAATC CAGTCAGAGTGTTTTTTCT CAAGTAGCCAGAAGAACTAC CTCGCATGGTACCAACAAAT ACCGGGGCAATCTCCCCGCT TGCTTATATACTGGGCAAGT ACCCGCGAATCCGGCGTACC GGATCGATTCACGGGATCTG GGTCAGGTACTGATTTCACT TTGACTATCAGCTCTGTTCA GCCTGAAGATTTGGCAATTT ACTACTGTCACCAATACTTG AGTAGCCGAACTTTCGGCCA GGGCACGAAGCTCGAAATCA AGGGCGGAGGGGAGGTTCT GGTGGGGCGGTTCTGGCGG TGGAGGAAGCCAAGTACAGT TGCAACAGCCAGGGGCGGAG GTCGTAAAACCTGGGCGTC TGTCAAGATGAGCTGTAAAG CAAGTGGATACACCTTCACC TCCTACTATATACATTGGAT TAAGCAAACTCCGGGTCAGG GGCTGGAATGGGTTGGCGTT ATATACCCCGGGAACGATGA TATATCATACAACCAAAAAT TTCAAGGCAAGGCGACTCTG ACTGCCGATAAGAGTAGCAC AACAGCTTACATGCAGCTTT CTTCCCTGACCAGCGAAGAT TCAGCAGTTTACTACTGCGC TCGGGAAGTGCGCCTGCGAT ACTTTGATGTCTGGGGTCAA GGAACTACAGTTACTGTATC |

TABLE 28-continued

AAV Donor Template Sequences

```
AAGCAGTGCTGCTGCCTTTG
TCCCGGTATTTCTCCCAGCC
AAACCGACCACGACTCCCGC
CCCGCGCCCTCCGACACCCG
CTCCCACCATCGCCTCTCAA
CCTCTTAGTCTTCGCCCCGA
GGCATGCCGACCCGCCGCCG
GGGGTGCTGTTCATACGAGG
GGCTTGGACTTCGCTTGTGA
TATTTACATTTGGGCTCCGT
TGGCGGGTACGTGCGGCGTC
CTTTTGTTGTCACTCGTTAT
TACTTTGTATTGTAATCACA
GGAATCGCAAACGGGGCAGA
AAGAAACTCCTGTATATATT
CAAACAACCATTTATGAGAC
CAGTACAAACTACTCAAGAG
GAAGATGGCTGTAGCTGCCG
ATTTCCAGAAGAAGAAGAAG
GAGGATGTGAACTGCGAGTG
AAGTTTTCCCGAAGCGCAGA
CGCTCCGGCATATCAGCAAG
GACAGAATCAGCTGTATAAC
GAACTGAATTTGGGACGCCG
CGAGGAGTATGACGTGCTTG
ATAAACGCCGGGGAGAGAC
CCGGAAATGGGGGGTAAACC
CCGAAGAAAGAATCCCCAAG
AAGGACTCTACAATGAACTC
CAGAAGGATAAGATGGCGGA
GGCCTACTCAGAAATAGGTA
TGAAGGGCAACGACGACGG
GGAAAAGGTCACGATGGCCT
CTACCAAGGGTTGAGTACGG
CAACCAAAGATACGTACGAT
GCACTGCATATGCAGGCCCT
GCCTCCCAGATAATAATAAA
ATCGCTATCCATCGAAGATG
GATGTGTGTTGGTTTTTTGT
GTGTGGAGCAACAAATCTGA
CTTTGCATGTGCAAACGCCT
TCAACAACAGCATTATTCCA
GAAGACACCTTCTTCCCCAG
CCCAGGTAAGGGCAGCTTTG
GTGCCTTCGCAGGCTGTTTC
CTTGCTTCAGGAATGGCCAG
GTTCTGCCCAGAGCTCTGGT
CAATGATGTCTAAAACTCCT
CTGATTGGTGGTCTCGGCCT
TATCCATTGCCACCAAAACC
CTCTTTTTACTAAGAAACAG
TGAGCCTTGTTCTGGCAGTC
CAGAGAATGACACGGGAAAA
AAGCAGATGAAGAGAAGGTG
GCAGGAGAGGGCACGTGGCC
CAGCCTCAGTCTCTCCAACT
GAGTTCCTGCCTGCCTGCCT
TTGCTCAGACTGTTTGCCCC
TTACTGCTCTTCTAGGCCTC
ATTCTAAGCCCCTTCTCCAA
GTTCCTCTCCTTATTTCTC
CCTGTCTGCCAAAAAATCTT
TCCCAGCTCACTAAGTCAGT
CTCACGCAGTCACTCATTAA
CCCACCAATCACTGATTGTG
CCGGCACATGAATGCACCAG
GTGTTGAAGTGGAGGAATTA
AAAAGTCAGATGAGGGGTGT
GCCCAGAGGAAGCACCATTC
TAGTTGGGGGAGCCCATCTG
TCAGCTGGGAAAAGTCCAAA
TAACTTCAGATTGGAATGTG
TTTTAACTCAGGGTTGAGAA
AACAGCTACCTTCAGGACAA
AAGTCAGGGAAGGGCTCTCT
GAAGAAATGCTACTTGAAGA
TACCAGCCCTACCAAGGGCA
GGGAGAGGACCCTATAGAGG
CCTGGGACAGGAGCTCAATG
AGAAAGG
```

TABLE 29

On-Target Gene Edited Sequences >1% Frequency in At Least One Gene Edited T Cell Donor for the REG1-Z01 gRNA.
Reference on-target sequence[a]:
GATGGGAGCAACG(TGG)CCAT (SEQ ID NO: 104)

| SEQ ID NO: | Gene Edited Sequence[b] | Donor 1 (%) | Donor 2 (%) | Mean (%) | Std. Dev. (%) |
|---|---|---|---|---|---|
| 181 | GATGGGAGCAAACGTGGCCAT | 46.1 | 43.9 | 45.0 | 1.6 |
|  | ------------GTGGCCAT | 6.5 | 4.3 | 5.4 | 1.6 |
| 182 | GATGGGAGC-ACGTGGCCAT | 4.1 | 4.9 | 4.5 | 0.6 |
|  | GA-----------TGGCCAT | 3.5 | 3.9 | 3.7 | 0.3 |
|  | -------------------- | 3.3 | 3.7 | 3.5 | 0.3 |
| 183 | GATGGG---AACGTGGCCAT | 2.6 | 3.6 | 3.1 | 0.7 |
| 184 | GATGGGA--------GCCAT | 3.6 | 2.1 | 2.8 | 1.1 |
|  | -----------------CAT | 2.4 | 1.8 | 2.1 | 0.4 |
|  | -----------CGTGGCCAT | 1.4 | 1.2 | 1.3 | 0.1 |
| 185 | GATG----------GGCCAT | 1.1 | 1.3 | 1.2 | 0.1 |
|  | GAT----------------- | 0.9 | 1.1 | 1.0 | 0.1 |
|  | GATGG--------------- | 0.7 | 1.2 | 1.0 | 0.4 |
| 186 | ----------ACGTGGCCAT | 1.1 | 0.5 | 0.8 | 0.4 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 30

On-Target Gene Edited Sequences >1% Frequency in At Least One Gene Edited T Cell Donor for the REG1-Z02 gRNA.
Reference on-target sequence[a]:
CCGCGGGACTAGA(GGG)AGCT (SEQ ID NO: 268)

| SEQ ID NO: | Gene Edited Sequence[b] | Donor 1 (%) | Donor 2 (%) | Mean (%) | Std. Dev. (%) |
|---|---|---|---|---|---|
| 187 | CCGCGGGACTTAGAGGGAGCT | 49.2 | 39.4 | 44.3 | 6.9 |
| 188 | CCGCGGGA---------GCT | 11.9 | 11.5 | 11.7 | 0.3 |
|  | -------------------- | 2.6 | 4.6 | 3.6 | 1.4 |
|  | CCGCGGG------------- | 2.1 | 3.4 | 2.8 | 0.9 |
|  | -------------------T | 2.1 | 2.0 | 2.0 | 0.1 |
| 189 | CCGCGGGA-TAGAGGGAGCT | 1.7 | 1.8 | 1.8 | 0.1 |
| 190 | CCGCGGGACT---------- | 1.8 | 1.3 | 1.6 | 0.4 |
| 191 | CCGCGGG--TAGAGGGAGCT | 1.0 | 1.6 | 1.3 | 0.4 |

TABLE 30-continued

On-Target Gene Edited Sequences >1% Frequency in At Least One Gene Edited T Cell Donor for the REG1-Z02 gRNA.
Reference on-target sequence[a]:
CCGCGGGACTAGA(GGG)AGCT (SEQ ID NO: 268)

| SEQ ID NO: | Gene Edited Sequence[b] | Donor 1 (%) | Donor 2 (%) | Mean (%) | Std. Dev. (%) |
|---|---|---|---|---|---|
| 192 | CCGCGGG--------GAGCT | 1.1 | 1.3 | 1.2 | 0.1 |
| 193 | CCGCGGGAC-AGAGGGAGCT | 1.0 | 1.2 | 1.1 | 0.1 |
| 194 | CCGCGGGACT-GAGGGAGCT | 1.3 | 0.9 | 1.1 | 0.3 |
| 195 | CCG---------AGGGAGCT | 1.2 | 0.9 | 1.0 | 0.2 |
| 196 | CCGCGGGA-----GGGAGCT | 0.8 | 1.1 | 1.0 | 0.2 |
| 197 | CCG------TAGAGGGAGCT | 0.3 | 1.1 | 0.7 | 0.6 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 31

On-Target Gene Edited Sequences >1% Frequency in At Least One Gene Edited T Cell Donor for the REG1-Z03 gRNA.
Reference on-target sequence[a]:
CGCTCCCGCTCGG(TGG)CTGT (SEQ ID NO: 274)

| SEQ ID NO: | Gene Edited Sequence[b] | Donor 1 (%) | Donor 2 (%) | Mean (%) | Std. Dev. (%) |
|---|---|---|---|---|---|
| 198 | CGCTCCCGCTTCGGTGGCTGT | 41.3 | 38.6 | 40.0 | 1.9 |
|  | C---------------TGT | 7.9 | 7.8 | 7.8 | 0.1 |
|  | CGCTCCCG------------ | 7.9 | 7.5 | 7.7 | 0.3 |
| 199 | CGCTCCCGC-CGGTGGCTGT | 3.3 | 3.7 | 3.5 | 0.3 |
|  | -------------------- | 2.7 | 3.7 | 3.2 | 0.7 |
| 200 | CGCTCCCG-TCGGTGGCTGT | 2.8 | 3.7 | 3.2 | 0.6 |
| 201 | CGCTCCCGC--GGTGGCTGT | 2.3 | 2.8 | 2.6 | 0.4 |
|  | ------------------T | 1.7 | 3.0 | 2.4 | 0.9 |
| 202 | CGCTCCCGCT-GGTGGCTGT | 2.2 | 2.4 | 2.3 | 0.1 |
|  | ---------------GCTGT | 2.3 | 1.7 | 2.0 | 0.4 |
| 203 | CGCTCCC--TCGGTGGCTGT | 1.6 | 1.8 | 1.7 | 0.1 |
| 204 | CGCTCCCGCTTTCGGTGGCTGT | 1.1 | 1.4 | 1.2 | 0.2 |
| 205 | CGCTCCCG-----GTGGCTGT | 1.3 | 0.8 | 1.0 | 0.4 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 32

On-Target Gene Edited Sequences >1% Frequency in At Least One Gene Edited T Cell donor for the REG1-Z04 gRNA.
Reference on-target sequence[a]:
CATCACGACGCGT(GGG)TGGC (SEQ ID NO: 280)

| SEQ ID NO: | Gene Edited Sequence[b] | Donor 1 (%) | Donor 2 (%) | Mean (%) | Std. Dev. (%) |
|---|---|---|---|---|---|
| 206 | CATCACGA--CGTGGGTGGC | 34.0 | 32.9 | 33.4 | 0.8 |
| 207 | CATCA-----CGTGGGTGGC | 7.7 | 6.2 | 7.0 | 1.1 |
|  | -------------------- | 2.9 | 3.8 | 3.4 | 0.6 |
| 208 | CATCACGACGCCGTGGGTGGC | 2.5 | 4.2 | 3.4 | 1.2 |
| 209 | CATCACGAC------GTGGC | 3.1 | 3.6 | 3.4 | 0.4 |
| 210 | CATCACGACGGCGTGGGTGGC | 2.3 | 3.4 | 2.8 | 0.8 |
|  | CATCACGA------------ | 2.3 | 2.4 | 2.3 | 0.1 |
| 211 | ----------CGTGGGTGGC | 1.5 | 1.7 | 1.6 | 0.1 |
| 212 | CATCACGACG---TGGTGGC | 1.8 | 1.2 | 1.5 | 0.4 |
| 213 | CATCACGACGTCGTGGGTGGC | 1.5 | 1.2 | 1.4 | 0.2 |
|  | CATCACGAC----------- | 1.7 | 1.1 | 1.4 | 0.4 |
|  | -------------------C | 1.5 | 1.2 | 1.4 | 0.2 |
|  | --------------GGTGGC | 1.1 | 1.3 | 1.2 | 0.1 |
|  | ----------------TGGC | 1.1 | 1.0 | 1.0 | 0.1 |
| 214 | CATCACGAC----GGGTGGC | 0.7 | 1.3 | 1.0 | 0.4 |
|  | CATCA--------------- | 0.9 | 1.1 | 1.0 | 0.1 |
| 215 | CATCACGAC-----GGTGGC | 1.1 | 0.7 | 0.9 | 0.3 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 33

On-Target Gene Edited Sequences >1% Frequency in At Least One Gene Edited T Cell Donor for the REG1-Z05 gRNA.
Reference on-target sequence[a]:
CACGACGCGTGGG(TGG)CAAG (SEQ ID NO: 286)

| SEQ ID NO: | Gene Edited Sequence[b] | Donor 1 (%) | Donor 2 (%) | Mean (%) | Std. Dev. (%) |
|---|---|---|---|---|---|
| 216 | CACGACGCGTTGGGTGGCAAG | 58.4 | 50.0 | 54.2 | 5.9 |
|  | CACGAC-------------G | 5.5 | 7.8 | 6.6 | 1.6 |
| 217 | CACGACGC--GGGTGGCAAG | 1.7 | 3.7 | 2.7 | 1.4 |
| 218 | CACGAC---------GCAAG | 2.2 | 2.8 | 2.5 | 0.4 |
| 219 | CACGACGC----GTGGCAAG | 2.4 | 1.5 | 2.0 | 0.6 |
| 220 | CACGACGCG-GGGTGGCAAG | 1.6 | 1.9 | 1.8 | 0.2 |
|  | -------------------- | 1.4 | 1.5 | 1.4 | 0.1 |
|  | CACGA--------------- | 1.0 | 1.4 | 1.2 | 0.3 |
|  | CACGACGC------------ | 0.9 | 1.3 | 1.1 | 0.3 |

TABLE 33-continued

On-Target Gene Edited Sequences >1% Frequency in At Least One Gene Edited T Cell Donor for the REG1-Z05 gRNA.
Reference on-target sequence[a]:
CACGACGCGTGGG(TGG)CAAG (SEQ ID NO: 286)

| SEQ ID NO: | Gene Edited Sequence[b] | Donor 1 (%) | Donor 2 (%) | Mean (%) | Std. Dev. (%) |
|---|---|---|---|---|---|

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 34

On-Target Gene Edited Sequences >1% Frequency in At Least One Gene Edited T Cell Donor for the REG1-Z06 gRNA.
Reference on-target sequence[a]:
TCTGACGGGATCG(TGG)TTTC (SEQ ID NO: 292)

| SEQ ID NO: | Gene Edited Sequence[b] | Donor 1 (%) | Donor 2 (%) | Mean (%) | Std. Dev. (%) |
|---|---|---|---|---|---|
| 221 | TCTGACGGGAATCGTGGTTTC | 28.1 | 21.9 | 25.0 | 4.4 |
| 222 | TCTGACG-------GGTTTC | 7.0 | 7.4 | 7.2 | 0.3 |
| 223 | TCTGA------CGTGGTTTC | 7.3 | 7.2 | 7.2 | 0.1 |
| 224 | TCTGACGGGATTCGTGGTTTC | 5.4 | 2.6 | 4.0 | 2.0 |
| 225 | TCTGACGGGA-CGTGGTTTC | 4.2 | 2.8 | 3.5 | 1.0 |
| 226 | TCTG------TCGTGGTTTC | 3.5 | 3.1 | 3.3 | 0.3 |
|  | TCTG---------------- | 2.3 | 3.4 | 2.8 | 0.8 |
|  | -------------------- | 2.4 | 3.1 | 2.8 | 0.5 |
|  | ------------------TC | 2.9 | 2.2 | 2.6 | 0.5 |
| 227 | TCTGAC--------GGTTTC | 2.0 | 2.0 | 2.0 | 0.0 |
|  | TCT----------------- | 1.5 | 2.3 | 1.9 | 0.6 |
| 228 | TCTGACGGG-TCGTGGTTTC | 1.7 | 2.1 | 1.9 | 0.3 |
| 229 | TCTGACGGGAGTCGTGGTTTC | 2.4 | 1.3 | 1.8 | 0.8 |
| 230 | TCTGACGGGACTCGTGGTTTC | 1.5 | 1.8 | 1.6 | 0.2 |
| 231 | ----------TCGTGGTTTC | 1.3 | 1.6 | 1.5 | 0.2 |
|  | -------------------C | 1.0 | 1.5 | 1.2 | 0.4 |
| 232 | TCTGACGG--TCGTGGTTTC | 0.6 | 1.4 | 1.0 | 0.6 |
| 233 | TCTGACGGGA--GTGGTTTC | 1.2 | 0.5 | 0.8 | 0.5 |

[a]On-target sequence centered on cleavage site, with 10 bp in either direction. For comparison, the portion of the gRNA target sequence aligning with the Reference on-target sequence is underlined and the PAM is indicated by parenthesis.
bDeletions indicated by dashes (-); insertions indicated by bold

TABLE 35

On-Target Gene Edited Sequences >1% Frequency in At Least One Gene Edited T Cell Donor for the REG1-Z07 gRNA.
Reference on-target sequence[a]:
CCACGCGTCGTGA(TGG)TGTG (SEQ ID NO: 298)

| SEQ ID NO: | Gene Edited Sequence[b] | Donor 1 (%) | Donor 2 (%) | Mean (%) | Std. Dev. (%) |
|---|---|---|---|---|---|
| 234 | CCACGCGTCGGTGATGGTGTG | 15.1 | 12.9 | 14.0 | 1.6 |
| 235 | CCACGCGTCGTTGATGGTGTG | 12.3 | 8.5 | 10.4 | 2.7 |
|  | -------------------- | 4.4 | 5.1 | 4.8 | 0.5 |
| 236 | CCACGCGT---------GTG | 4.9 | 4.4 | 4.6 | 0.4 |
|  | CCACGCGT-----------G | 3.6 | 3.0 | 3.3 | 0.4 |
| 237 | CCACGCGTCGATGATGGTGTG | 2.9 | 1.4 | 2.2 | 1.1 |
|  | CCACGCGTC----------- | 1.9 | 2.5 | 2.2 | 0.4 |
| 238 | CCACGCGTCG--ATGGTGTG | 2.2 | 2.1 | 2.2 | 0.1 |
| 239 | CCACGCGTC-TGATGGTGTG | 2.0 | 2.2 | 2.1 | 0.1 |
|  | CCAC---------------- | 1.9 | 2.2 | 2.0 | 0.2 |
|  | C------------------- | 2.2 | 1.9 | 2.0 | 0.2 |
| 240 | CCACGCGTCGCTGATGGTGTG | 1.9 | 1.6 | 1.8 | 0.2 |
| 241 | CCACGCGTCG---------- | 2.0 | 1.7 | 1.8 | 0.2 |
| 242 | CCACGCGTCG-----GTGTG | 1.7 | 1.7 | 1.7 | 0.0 |
| 243 | CCACGCGTGG-----GTGTG | 1.8 | 1.5 | 1.6 | 0.2 |
| 244 | CCACGCGT---GATGGTGTG | 1.4 | 1.3 | 1.4 | 0.1 |
|  | CCA----------------- | 1.1 | 1.7 | 1.4 | 0.4 |
| 245 | CCACGCGTCGTG------TG | 1.4 | 1.1 | 1.2 | 0.2 |
| 246 | CCACGCGTCGTGA------- | 1.2 | 1.1 | 1.2 | 0.1 |
|  | CCACGC-------------- | 0.8 | 1.5 | 1.2 | 0.5 |
|  | CCACGCG------------- | 1.1 | 0.9 | 1.0 | 0.1 |
|  | CCACG----------TGTG | 0.8 | 1.2 | 1.0 | 0.3 |
| 247 | CCACGCGTGG-------GTG | 1.1 | 0.7 | 0.9 | 0.3 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 36

On-Target Gene Edited Sequences >1% Frequency in At Least One Gene Edited T Cell Donor for the REG1-Z08 gRNA.
Reference on-target sequence[a]:
CCATCACGACGCG(TGG)GTGG (SEQ ID NO: 304)

| SEQ ID NO: | Gene Edited Sequence[b] | Donor 1 (%) | Donor 2 (%) | Mean (%) | Std. Dev. (%) |
|---|---|---|---|---|---|
| 248 | CCATCACGACCGCGTGGGTGG | 28.0 | 15.4 | 21.7 | 8.9 |
| 249 | CCATCA-----CGTGGGTGG | 8.5 | 3.4 | 6.0 | 3.6 |
| 250 | CCATC---ACGCGTGGGTGG | 4.4 | 2.4 | 3.4 | 1.4 |

TABLE 36-continued

On-Target Gene Edited Sequences >1% Frequency in At Least One Gene Edited T Cell Donor for the REG1-Z08 gRNA.
Reference on-target sequence[a]: CCATCACGACGCG(TGG)GTGG (SEQ ID NO: 304)

| SEQ ID NO: | Gene Edited Sequence[b] | Donor 1 (%) | Donor 2 (%) | Mean (%) | Std. Dev. (%) |
|---|---|---|---|---|---|
|  | -------------------- | 2.3 | 1.8 | 2.0 | 0.4 |
|  | --------------GGTGG | 1.5 | 0.7 | 1.1 | 0.6 |
| 251 | CCATCACGACAGCGTGGGTGG | 1.3 | 0.2 | 0.8 | 0.8 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 37

On-Target Gene Edited Sequences >1% Frequency in At Least One Gene Edited T Cell Donor for the REG1-Z09 gRNA.
Reference on-target sequence[a]: CCGTCAGACTCGT(AGG)CCAG (SEQ ID NO: 310)

| SEQ ID NO: | Gene Edited Sequence[b] | Donor 1 (%) | Donor 2 (%) | Mean (%) | Std. Dev. (%) |
|---|---|---|---|---|---|
|  | CCGTCAG------------- | 13.5 | 9.9 | 11.7 | 2.5 |
| 252 | CCGTCAGACTTCGTAGGCCAG | 11.3 | 8.5 | 9.9 | 2.0 |
| 253 | CCGT---------AGGCCAG | 7.5 | 8.3 | 7.9 | 0.6 |
| 254 | CCGTCAGACT---------- | 6.9 | 6.1 | 6.5 | 0.6 |
| 255 | CCGTCAGAC--------CAG | 4.2 | 4.3 | 4.2 | 0.1 |
|  | -------------------- | 3.9 | 4.2 | 4.0 | 0.2 |
|  | CCGTCA-------------- | 3.6 | 2.3 | 3.0 | 0.9 |
| 256 | CCGTCAGAC--GTAGGCCAG | 2.5 | 2.4 | 2.4 | 0.1 |
| 257 | CCGTCAG--------GCCAG | 1.9 | 2.4 | 2.2 | 0.4 |
|  | CCG-------------CCAG | 1.2 | 2.2 | 1.7 | 0.7 |
| 258 | CCGTCAGAC-CGTAGGCCAG | 1.7 | 1.4 | 1.5 | 0.2 |
|  | ------------TAGGCCAG | 1.0 | 1.4 | 1.2 | 0.3 |
| 259 | CCGTCAGACT-GTAGGCCAG | 1.5 | 1.0 | 1.2 | 0.4 |

TABLE 37-continued

On-Target Gene Edited Sequences >1% Frequency in At Least One Gene Edited T Cell Donor for the REG1-Z09 gRNA.
Reference on-target sequence[a]: CCGTCAGACTCGT(AGG)CCAG (SEQ ID NO: 310)

| SEQ ID NO: | Gene Edited Sequence[b] | Donor 1 (%) | Donor 2 (%) | Mean (%) | Std. Dev. (%) |
|---|---|---|---|---|---|
|  | CCGTCAGA------------ | 1.6 | 0.7 | 1.2 | 0.6 |
|  | CCGTCAGAC----------- | 1.2 | 0.6 | 0.9 | 0.4 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 38

On-Target Gene Edited Sequences >1% Frequency in At Least One Gene Edited T Cell Donor for the REG1-Z10 gRNA.
Reference on-target sequence[a]: GTGGGTGGCAAGC(GGG)TGGT (SEQ ID NO: 316)

| SEQ ID NO: | Gene Edited Sequence[b] | Donor 1 (%) | Donor 2 (%) | Mean (%) | Std. Dev. (%) |
|---|---|---|---|---|---|
| 260 | GTGGGTGGCAAAGCGGGTGGT | 23.8 | 21.7 | 22.8 | 1.5 |
|  | GT-----------GGGTGGT | 20.7 | 22.9 | 21.8 | 1.6 |
|  | -----------GCGGGTGGT | 10.4 | 7.7 | 9.0 | 1.9 |
| 261 | GTGGGTGGC-AGCGGGTGGT | 7.0 | 6.5 | 6.8 | 0.4 |
|  | ----------------GTGGT | 3.3 | 4.3 | 3.8 | 0.7 |
|  | GTG---------------GGT | 2.8 | 4.0 | 3.4 | 0.8 |
|  | ------------CGGGTGGT | 2.6 | 3.3 | 3.0 | 0.5 |
|  | -------------------- | 2.0 | 3.5 | 2.8 | 1.1 |
|  | GTGGGTGGC----------- | 2.4 | 1.8 | 2.1 | 0.4 |
| 262 | GTGGGTGGCATAGCGGGTGGT | 1.8 | 1.8 | 1.8 | 0.0 |
|  | GTGGGTG------------- | 1.6 | 1.5 | 1.6 | 0.1 |
|  | GTGG---------------- | 1.5 | 1.8 | 1.6 | 0.2 |
| 263 | GTGGGTGG--AGCGGGTGGT | 0.9 | 1.1 | 1.0 | 0.1 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold

TABLE 39

TGFBRII gRNA Sequences/Targt Sequences

| Name | Unmodified Sequence | Modified Sequence | Target Sequence (PAM) |
|---|---|---|---|
| TGFBRII sgRNA (EX1_T1) | CCGACUUCUGAACGUGCG GUguuuuagagcuagaaa uagcaaguuaaaauaagg cuaguccguuaucaacuu gaaaaaguggcaccgagu cggugcmUUUU (SEQ ID NO: 264) | C*C*G*ACUUCUGAACGUG CGGUGGGguuuuagagcua gaaauagcaaguuaaaaua aggcuaguccguuaucaac uugaaaaaguggcaccgag ucggugcU*U*U*U (SEQ ID NO: 265) | CCGACUUCUGAACGUGCGGT (GGG) (SEQ ID NO: 2) CCGACTTCTGAACGTGCGGT (SEQ ID NO: 269) |

TABLE 39-continued

TGFBRII gRNA Sequences/Target Sequences

| Name | Unmodified Sequence | Modified Sequence | Target Sequence (PAM) |
|---|---|---|---|
| TGFBRII sgRNA (EX1_T1) spacer | CCGACUUCUGAACGUGCG GU (SEQ ID NO: 266) | C*C*C*GACUUCUGAACGU GCGGU (SEQ ID NO: 267) | |
| TGFBRII sgRNA (EX1_T2) | UGCUGGCGAUACGCGUCC ACguuuuagagcuagaaa uagcaaguuaaaauaagg cuaguccguuaucaacuu gaaaaaguggcaccgagu cggugcmUUUU (SEQ ID NO: 270) | U*G*C*UGGCGAUACGCGU CCACguuuuagagcuagaa auagcaaguuaaaauaagg cuaguccguuaucaacuug aaaaaguggcaccgagucg gugcmU*U*U*U (SEQ ID NO: 271) | TGCTGGCGATACGCGTCCAC (AGG) (SEQ ID NO: 3) TGCTGGCGATACGCGTCCAC (SEQ ID NO: 275) |
| TGFBRII sgRNA (EX1_T2) spacer | UGCUGGCGAUACGCGUCC AC (SEQ ID NO: 272) | U*G*C*UGGCGAUACGCGU CCAC (SEQ ID NO: 273) | |
| TGFBRII sgRNA (EX1_T3) | UCGGUCUAUGACGAGCAG CGguuuuagagcuagaaa uagcaaguuaaaauaagg cuaguccguuaucaacuu gaaaaaguggcaccgagu cggugcUUUU (SEQ ID NO: 276) | U*C*G*GUCUAUGACGAGC AGCGguuuuagagcuagaa auagcaaguuaaaauaagg cuaguccguuaucaacuug aaaaaguggcaccgagucg gugcU*U*U*U (SEQ ID NO: 277) | TCGGTCTATGACGAGCAGCG (GGG) (SEQ ID NO: 4) TCGGTCTATGACGAGCAGCG (SEQ ID NO: 281) |
| TGFBRII sgRNA (EX1_T3) spacer | UCGGUCUAUGACGAGCAG CG (SEQ ID NO: 278) | U*C*G*GUCUAUGACGAGC AGCG (SEQ ID NO: 279) | |
| TGFBRII sgRNA (EX2_T1) | AUGGGCAGUCCUAUUACA GCguuuuagagcuagaaa uagcaaguuaaaauaagg cuaguccguuaucaacuu gaaaaaguggcaccgagu cggugcmUUUU (SEQ ID NO: 282) | A*U*G*GGCAGUCCUAUUA CAGCguuuuagagcuagaa auagcaaguuaaaauaagg cuaguccguuaucaacuug aaaaaguggcaccgagucg gugcU*U*U*U (SEQ ID NO: 283) | ATGGGCAGTCCTATTACAGC (TGG) (SEQ ID NO: 5) ATGGGCAGTCCTATTACAGC (SEQ ID NO: 287) |
| TGFBRII sgRNA (EX2_T1) spacer | AUGGGCAGUCCUAUUACA GC (SEQ ID NO: 284) | A*U*G*GGCAGUCCUAUUA CAGC (SEQ ID NO: 285) | |
| TGFBRII sgRNA (EX3_T1) | AUUGUUCACUUGUUAGCC CCguuuuagagcuagaaa uagcaaguuaaaauaagg cuaguccguuaucaacuu gaaaaaguggcaccgagu cggugcUUUU (SEQ ID NO: 288) | A*U*U*GUUCACUUGUUAG CCCCAGGguuuuagagcua gaaauagcaaguuaaaaua aggcuaguccguuaucaac uugaaaaaguggcaccgag ucggugcU*U*U*U (SEQ ID NO: 289) | ATTGTTCACTTGTTAGCCCC (AGG) (SEQ ID NO: 6) ATTGTTCACTTGTTAGCCCC (SEQ ID NO: 293) |
| TGFBRII sgRNA (EX3_TI) spacer | AUUGUUCACUUGUUAGCC CC (SEQ ID NO: 290) | A*u*U*GUUCACUUGUUAG CCCC (SEQ ID NO: 291) | |
| TGFBRII sgRNA (EX3_T2) | GCUGAAGAACUGCCUCUA UAguuuuagagcuagaaa uagcaaguuaaaauaagg cuaguccguuaucaacuu gaaaaaguggcaccgagu cggugcUUUU (SEQ ID NO: 294) | G*C*U*GAAGAACUGCCUC UAUAguuuuagagcuagaa auagcaaguuaaaauaagg cuaguccguuaucaacuug aaaaaguggcaccgagucg gugcU*U*U*U (SEQ ID NO: 295) | GCTGAAGAACTGCCTCTATA (TGG) (SEQ ID NO: 7) GCTGAAGAACTGCCTCTATA (SEQ ID NO: 299) |
| TGFBRII sgRNA (EX3_T2) spacer | GCUGAAGAACUGCCUCUA UA (SEQ ID NO: 296) | G*C*U*GAAGAACUGCCUC UAUA (SEQ ID NO: 297) | |
| TGFBRII sgRNA (EX4_T1) | GCAGGAUUUCUGGUUGUC ACguuuuagagcuagaaa uagcaaguuaaaauaagg cuaguccguuaucaacuu | G*C*A*GGAUUUCUGGUUG UCACguuuuagagcuagaa auagcaaguuaaaauaagg cuaguccguuaucaacuug | GCAGGATTTCTGGTTGTCAC (AGG) (SEQ ID NO: 8) GCAGGATTTCTGGTTGTCAC (SEQ ID NO: 305) |

TABLE 39-continued

TGFBRII gRNA Sequences/Targt Sequences

| Name | Unmodified Sequence | Modified Sequence | Target Sequence (PAM) |
|---|---|---|---|
| | gaaaaaguggcaccgagu cggugcUUUU (SEQ ID NO: 300) | aaaaaguggcaccgagucg gugcU*U*U*U (SEQ ID NO: 301) | |
| TGFBRII sgRNA (EX4_T1) spacer | GCAGGAUUUCUGGUUGUC AC (SEQ ID NO: 302) | G*C*A*GGAUUUCUGGUUG UCAC (SEQ ID NO: 303) | |
| TGFBRII sgRNA (EX4_T2) | CUCCAUCUGUGAGAAGCC ACguuuuagagcuagaaa uagcaaguuaaaauaagg cuaguccguuaucaacuu gaaaaaguggcaccgagu cggugcUUUU (SEQ ID NO: 306) | C*U*C*CAUCUGUGAGAAG CCACguuuuagagcuagaa auagcaaguuaaaauaagg cuaguccguuaucaacuug aaaaaguggcaccgagucg gugcU*U*U*U (SEQ ID NO: 307) | CTCCATCTGTGAGAAGCCAC (AGG) (SEQ ID NO: 9) CTCCATCTGTGAGAAGCCAC (SEQ ID NO: 311) |
| TGFBRII sgRNA (EX4_T2) spacer | CUCCAUCUGUGAGAAGCC AC (SEQ ID NO: 308) | C*U*C*CAUCUGUGAGAAG CCAC (SEQ ID NO: 309) | |
| TGFBRII sgRNA (EX5_T1) | CCCCUACCAUGACUUUAU UCguuuuagagcuagaaa uagcaaguuaaaauaagg cuaguccguuaucaacuu gaaaaaguggcaccgagu cggugcUUUU (SEQ ID NO: 312) | C*C*C*CUACCAUGACUUU AUUCguuuuagagcuagaa auagcaaguuaaaauaagg cuaguccguuaucaacuug aaaaaguggcaccgagucg gugcU*U*U*U (SEQ ID NO: 313) | CCCCTACCATGACTTTATTC (TGG) (SEQ ID NO: 10) CCCCTACCATGACTTTATTC (SEQ ID NO: 317) |
| TGFBRII sgRNA (EX5_T1) spacer | CCCCUACCAUGACUUUAU UCUGG (SEQ ID NO: 314) | C*C*C*CUACCAUGACUUU AUUC (SEQ ID NO: 315) | |

*2'-O-methyl phosphorothioate residue

TABLE 40

On-Target Gene Edited Sequences >%1 Frequency in At Least One Gene Edited T Cell Donor for the TGFBRII-Ex1-T1 gRNA.
Reference on-target sequence[a]:
<u>CTGAACGTGCGGT</u>(GGG)<u>ATCG</u> (SEQ ID NO: 360)

| SEQ ID NO: | Gene Edited Sequence[b] | Donor 1 (%) | Donor 2 (%) | Mean (%) | Std. Dev. (%) |
|---|---|---|---|---|---|
| 361 | CTGAACGTGC---------- | 28.7 | 29.8 | 29.2 | 0.8 |
| 362 | CTGAACGTG-----GGATCG | 10.7 | 12 | 11.4 | 0.9 |
| | CTGA-------------TCG | 9.8 | 9.3 | 9.6 | 0.4 |
| | -------------------- | 3.7 | 1.3 | 2.5 | 1.7 |
| 363 | CTGAACGTGCCGGTGGGATCG | 1.2 | 3.2 | 2.2 | 1.4 |
| | CTG----------------- | 2.8 | 1.1 | 2 | 1.2 |
| 364 | CTGAACGTG-GGTGGGATCG | 0.8 | 2.1 | 1.5 | 0.9 |
| 365 | ----------GGTGGGATCG | 2.2 | 0.8 | 1.5 | 1 |
| 366 | CTGAACGTG--GTGGGATCG | 1 | 1.6 | 1.3 | 0.4 |
| 367 | CTGAACG----GTGGGATCG | 1.5 | 0.8 | 1.2 | 0.5 |
| | CTGAACG------------- | 1.3 | 1 | 1.2 | 0.2 |
| 368 | CTG--------GTGGGATCG | 1.3 | 0.4 | 0.8 | 0.6 |
| 369 | CTGAACGTGCAGGTGGGATCG | 1.3 | 0.3 | 0.8 | 0.7 |
| 370 | CTGAACGTGCGT--GGATCG | 0 | 1.1 | 0.6 | 0.8 |
| | -----------------TCG | 0 | 1.1 | 0.6 | 0.8 |

[a] On-target sequence centered on cleavage site, with 10 bp in either direction. For comparison, the portion of gRNA target sequence aligning with the Reference on-target sequence is underlined and the PAM is indicated by parenthesis.
[b] Deletions indicated by dashes (-); insertions indicated by bold
[c] Positions of inserted bases in the gene edited sequence indicated by dashes (-) in the Reference Sequence

TABLE 41

On-Target Gene Edited Sequences >1% Frequency in At Least One Gene Edited T Cell Donor for the TGFBR1I-Ex1-T2 gRNA.
Reference on-target sequence[a]:
<u>GATACGCGTCCAC</u>(AGG)ACGA (SEQ ID NO: 371)

| SEQ ID NO: | Gene Edited Sequence[b] | Donor 1 (%) | Donor 2 (%) | Mean (%) | Std. Dev. (%) |
|---|---|---|---|---|---|
| 372 | GATACGCGTC-ACAGGACGA | 15.2 | 15.3 | 15.2 | 0.1 |
|  | GAT-------------- | 8.5 | 10.3 | 9.4 | 1.3 |
|  | GATACGC---------- | 6.7 | 5.9 | 6.3 | 0.6 |
| 373 | GATACGCGTCCCACAGGACGA | 3.7 | 6.1 | 4.9 | 1.7 |
|  | GATACG-----------A | 4.3 | 5.6 | 4.9 | 0.9 |
|  |  | 5.4 | 3.5 | 4.4 | 1.3 |
|  | ---------------ACGA | 3.4 | 3.9 | 3.6 | 0.4 |
|  | -------------AGGACGA | 3.7 | 2.2 | 3 | 1.1 |
| 374 | GATACGCGTCCA--GGACGA | 2.2 | 3.2 | 2.7 | 0.7 |
| 375 | GATACGC----ACAGGACGA | 2.3 | 2.8 | 2.6 | 0.4 |
| 376 | GATAC------ACAGGACGA | 2.8 | 1.7 | 2.2 | 0.8 |
|  | ----------ACAGGACGA | 1.4 | 2.5 | 2 | 0.8 |
|  | GATACGCG----------A | 2.5 | 1.4 | 2 | 0.8 |
| 377 | GATACGCGTCC-------GA | 1.9 | 1.7 | 1.8 | 0.1 |
| 378 | GATACGCGTC--------GA | 1.1 | 2 | 1.6 | 0.6 |
| 379 | GATACGCGTC---AGGACGA | 1.9 | 1.1 | 1.5 | 0.6 |
| 380 | GATAC--------AGGACGA | 1.2 | 1.5 | 1.4 | 0.2 |
| 381 | GATACGC---CACAGGACGA | 1.5 | 0.8 | 1.2 | 0.5 |
| 382 | GATACGCGTC---------- | 1 | 1.3 | 1.2 | 0.2 |
| 383 | GATACGCGTCACACAGGACGA | 1.4 | 0.8 | 1.1 | 0.4 |
| 384 | GATACGC-TGCACAGGACGA | 1.1 | 0.8 | 1 | 0.2 |
| 385 | GATACGC------AGGACGA | 0.8 | 1.3 | 1 | 0.4 |
|  | GATACGCG------------ | 0.6 | 1.1 | 0.8 | 0.4 |
|  | GATACGCGT----------- | 0.6 | 1.1 | 0.8 | 0.4 |
|  | ------------------A | 1.1 | 0.3 | 0.7 | 0.6 |
| 386 | ---ACGC----ACAGGACGA | 1.2 | 0 | 0.6 | 0.8 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 42

On-Target Gene Edited Sequences >1% Frequency in At Least One Gene Edited T Cell Donor for the TGFBRII-Ex1-T3 gRNA.
Reference on-target sequence[a]:
<u>ATGACGAGCAGCG</u>(GGG)TCTG (SEQ ID NO: 387)

| SEQ ID NO: | Gene Edited Sequence[b] | Donor 1 (%) | Donor 2 (%) | Mean (%) | Std. Dev. (%) |
|---|---|---|---|---|---|
| 388 | ATGACGAGCAAGCGGGGTCTG | 66.7 | 65.9 | 66.3 | 0.6 |
| 389 | ATGACG---AGCGGGGTCTG | 4.5 | 5.8 | 5.2 | 0.9 |
|  | ---------------GGTCTG | 2.2 | 2.5 | 2.4 | 0.2 |
| 390 | ATGACGA--AGCGGGGTCTG | 1.9 | 1.9 | 1.9 | 0 |
|  | -------------------- | 2.1 | 1.4 | 1.8 | 0.5 |
|  | ------------GGGGTCTG | 1 | 1.7 | 1.4 | 0.5 |
| 391 | ATG------AGCGGGGTCTG | 1.6 | 1.1 | 1.4 | 0.4 |
| 392 | ATGACGAGCAAAGCGGGGTCTG | 1.8 | 0.6 | 1.2 | 0.8 |
| 393 | ATGA-------CGGGGTCTG | 0.7 | 1.5 | 1.1 | 0.6 |
|  | A-----------------TG | 1.2 | 0.5 | 0.8 | 0.5 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 43

On-Target Gene Edited Sequences >1% Frequency in At Least One Gene Edited T Cell Donor for the TGFBRII-Ex5-T1 gRNA.
Reference on-target sequence[a]:
<u>CATGACTTTATTC</u>(TGG)AAGA (SEQ ID NO: 394)

| SEQ ID NO: | Gene Edited Sequence[b] | Donor 1 (%) | Donor 2 (%) | Mean (%) | Std. Dev. (%) |
|---|---|---|---|---|---|
| 395 | CATGA-------CTGGAAGA | 10.6 | 12.4 | 11.5 | 1.3 |
| 396 | CATGAC----TTCTGGAAGA | 8.8 | 8.9 | 8.9 | 0.1 |
| 397 | CATGACT---TTCTGGAAGA | 7 | 5.4 | 6.2 | 1.1 |
| 398 | CATGACTTTATTTCTGGAAGA | 5 | 6.2 | 5.6 | 0.8 |
| 399 | CATGACTTTAATTCTGGAAGA | 5.1 | 6.2 | 5.6 | 0.8 |
|  | CA-----------TGGAAGA | 3.7 | 3.8 | 3.8 | 0.1 |
| 400 | CATGACTT--TTCTGGAAGA | 3.6 | 3 | 3.3 | 0.4 |
|  | CAT------------GAAGA | 2.2 | 3.2 | 2.7 | 0.7 |
|  | C------------------A | 2.5 | 2.1 | 2.3 | 0.3 |
|  | -------------------- | 2.5 | 1.9 | 2.2 | 0.4 |
|  | CATGA--------------- | 2.6 | 1.8 | 2.2 | 0.6 |
|  | CAT---------------GA | 2 | 2 | 2 | 0 |
| 401 | CA---------TCTGGAAGA | 2 | 2.1 | 2 | 0.1 |
| 402 | CATGACTTT-TTCTGGAAGA | 1.6 | 2.3 | 2 | 0.5 |
| 403 | CATGACTTTA-TCTGGAAGA | 2.1 | 1.4 | 1.8 | 0.5 |

TABLE 43-continued

On-Target Gene Edited Sequences >1% Frequency in At Least One Gene Edited T Cell Donor for the TGFBRII-Ex5-T1 gRNA.
Reference on-target sequence[a]: CATGACTTTATTC(TGG)AAGA (SEQ ID NO: 394)

| SEQ ID NO: | Gene Edited Sequence[b] | Donor 1 (%) | Donor 2 (%) | Mean (%) | Std. Dev. (%) |
|---|---|---|---|---|---|
| 404 | CATGACTTT-------AAGA | 1.1 | 1 | 1 | 0.1 |
| 405 | ----------TTCTGGAAGA | 1.2 | 0.9 | 1 | 0.2 |
| 406 | CATGACTTTA--CTGGAAGA | 1.1 | 0.9 | 1 | 0.1 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 44

On-Target Gene Edited Sequences >1% Frequency in At Least One Gene Edited T Cell Donor for the TGFBRII-Ex2-T1 gRNA.
Reference on-target sequence[a]: GTCCTATTACAGC(TGG)GGCA (SEQ ID NO: 407)

| SEQ ID NO: | Gene Edited Sequence[b] | Donor 1 (%) | Donor 2 (%) | Mean (%) | Std. Dev. (%) |
|---|---|---|---|---|---|
|  | G------------------- | 18.4 | 17.4 | 17.9 | 0.7 |
| 408 | GTCCTATTA--GCTGGGGCA | 6.4 | 13 | 9.7 | 4.7 |
|  | -----------------GCA | 9.2 | 5.7 | 7.4 | 2.5 |
| 409 | GTCCTATTA-AGCTGGGGCA | 7.5 | 7.1 | 7.3 | 0.3 |
| 410 | GTCCTAT---AGCTGGGGCA | 6.8 | 7.5 | 7.2 | 0.5 |
| 411 | GTCCTA----AGCTGGGGCA | 7.3 | 4.6 | 5.9 | 1.9 |
| 412 | GTCCTA-----GCTGGGGCA | 7.5 | 4.2 | 5.8 | 2.3 |
|  | -------------------- | 2.8 | 2.2 | 2.5 | 0.4 |
| 413 | GTCCTATTAC---TGGGGCA | 2 | 1.7 | 1.8 | 0.2 |
|  | G-----------CTGGGGCA | 1 | 2 | 1.5 | 0.7 |
| 414 | GTCC------AGCTGGGGCA | 1 | 1.7 | 1.4 | 0.5 |
| 415 | GTCCTATTACCAGCTGGGGCA | 1.2 | 1.3 | 1.2 | 0.1 |
|  | GTCCTAT------------- | 1.4 | 0.8 | 1.1 | 0.4 |
| 416 | GTCCTATT---GCTGGGGCA | 1.1 | 1.1 | 1.1 | 0 |
| 417 | GTCCTATTAC-GCTGGGGCA | 0.7 | 1.2 | 1 | 0.4 |
| 418 | GTCCT-------- GGGGCA | 1.6 | 0.3 | 1 | 0.9 |
|  | GT------------------ | 1.1 | 0.1 | 0.6 | 0.7 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 45

On-Target Gene Edited Sequences >1% Frequency in At Least One Gene Edited T Cell Donor for the TGFBRII-Ex3-T1 gRNA. Reference on-target sequence[a]: ACTTGTTAGCCCC(AGG)GCCA (SEQ ID NO: 419)

| SEQ ID NO: | Gene Edited Sequence | Donor 1 (%) | Donor 2 (%) | Mean (%) | Std. Dev. (%) |
|---|---|---|---|---|---|
| 420 | ACTTGTTAG--CCAGGGCCA | 26.7 | 22.6 | 24.6 | 2.9 |
| 421 | ACTTGTTAG-CCCAGGGCCA | 5.1 | 9.1 | 7.1 | 2.8 |
|  | -------------------- | 6 | 4.1 | 5 | 1.3 |
| 422 | ACTTGTTAG---CAGGGCCA | 4.9 | 3.7 | 4.3 | 0.8 |
| 423 | ACTTGTTA--------GCCA | 4.6 | 3.1 | 3.8 | 1.1 |
|  | ------------CAGGGCCA | 4.1 | 2.7 | 3.4 | 1 |
| 424 | ACTTGTT------AGGGCCA | 2.1 | 3.3 | 2.7 | 0.8 |
|  | ------------------CA | 3.6 | 1.6 | 2.6 | 1.4 |
| 425 | ACTTGTTAGCCCCCAGGGCCA | 2 | 3.3 | 2.6 | 0.9 |
| 426 | ACTTGTT---CCCAGGGCCA | 1.3 | 3 | 2.2 | 1.2 |
| 427 | ----------CCCAGGGCCA | 2.3 | 1.7 | 2 | 0.4 |
| 428 | ACTTGTTA--CCCAGGGCCA | 2 | 1.8 | 1.9 | 0.1 |
| 429 | ACTTG-----CCCAGGGCCA | 2 | 1.7 | 1.8 | 0.2 |
|  | ACT----------------- | 1.3 | 1.3 | 1.3 | 0 |
| 430 | ACTTGT----CCCAGGGCCA | 0.8 | 1.5 | 1.2 | 0.5 |
| 431 | A-----------CAGGGCCA | 1.6 | 0.7 | 1.2 | 0.6 |
|  | ---------------GGCCA | 1.1 | 1.1 | 1.1 | 0 |
|  | A-----------CAGGGCCA | 0.5 | 1.1 | 0.8 | 0.4 |
| 432 | ACTTG-------CAGGGCCA | 0.2 | 1.2 | 0.7 | 0.7 |
| 433 | ACTTGTTAGC-------CCA | 0.3 | 1.1 | 0.7 | 0.6 |

[a]On-target sequence centered on cleavage site with 10 bp in either direction For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 46

On-Target Gene Edited Sequences >1% Frequency in At Least One Gene Edited T Cell Donor for the TGFBRII-Ex3-T2 gRNA. Reference on-target sequence[a]: AACTGCCTCTATA(TGG)TGTG (SEQ ID NO: 434)

| SEQ ID NO: | Gene Edited Sequence | Donor 1 (%) | Donor 2 (%) | Mean (%) | Std. Dev. (%) |
|---|---|---|---|---|---|
| 435 | AACTGCCTCTTATATGGTGTG | 37.1 | 41.7 | 39.4 | 3.3 |
|  | AAC----------------- | 7 | 6 | 6.5 | 0.7 |
|  | -------------------- | 7.2 | 5 | 6.1 | 1.6 |
| 436 | AACTGCCT--ATATGGTGTG | 2.9 | 4.1 | 3.5 | 0.8 |
| 437 | AACTGCCTCTAT--GGTGTG | 3 | 3 | 3 | 0 |

TABLE 46-continued

On-Target Gene Edited Sequences >1% Frequency in At Least One Gene Edited T Cell Donor for the TGFBRII-Ex3-T2 gRNA. Reference on-target sequence[a]: AACTGCCTCTATA(TGG)TGTG (SEQ ID NO: 434)

| SEQ ID NO: | Gene Edited Sequence | Donor 1 (%) | Donor 2 (%) | Mean (%) | Std. Dev. (%) |
|---|---|---|---|---|---|
|  | AACTG--------------- | 2.7 | 2.3 | 2.5 | 0.3 |
| 438 | AACTGCCTC-ATATGGTGTG | 2 | 2.4 | 2.2 | 0.3 |
| 439 | AACTG----TATATGGTGTG | 1.6 | 2.4 | 2 | 0.6 |
| 440 | AACTGC---TATATGGTGTG | 1.6 | 1.8 | 1.7 | 0.1 |
| 441 | AACT------ATATGGTGTG | 1.1 | 1.8 | 1.5 | 0.5 |
|  | AACTGCC-------------- | 1.2 | 1.5 | 1.4 | 0.2 |
|  | A------------------- | 1.8 | 0.9 | 1.4 | 0.6 |
| 442 | AACTGCCT-TATATGGTGTG | 1.1 | 1.3 | 1.2 | 0.1 |
| 443 | AACTGCCTCT---------- | 1.5 | 1 | 1.2 | 0.4 |
| 444 | ---------TATATGGTGTG | 1.1 | 0.9 | 1 | 0.1 |
|  | AACTG------------TG | 0.8 | 1.1 | 1 | 0.2 |
|  | AACTGCCTC----------- | 0.6 | 1.4 | 1 | 0.6 |
|  | AACT---------------- | 1.1 | 1 | 1 | 0.1 |
| 445 | AACTGCCTCTA--------- | 1.1 | 0.7 | 0.9 | 0.3 |
| 446 | AACTGCCTCT-TATGGTGTG | 0.7 | 1.1 | 0.9 | 0.3 |
| 447 | AACTG----------GTGTG | 1.1 | 0.7 | 0.9 | 0.3 |

[a]On-target sequence centered on cleavage site with 10 bp in either direction For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

TABLE 47

On-Target Gene Edited Sequences >1% Frequency in At Least One Gene Edited T Cell Donor for the TGFBRII-Ex4-T1 gRNA. Reference on-target sequence[a]: TTCTGGTTGTCAC(AGG)TGGA (SEQ ID NO: 448)

| SEQ ID NO: | Gene Edited Sequence | Donor 1 (%) | Donor 2 (%) | Mean (%) | Std. Dev. (%) |
|---|---|---|---|---|---|
| 449 | TTCTGGTTGTTCACAGGTGGA | 31.3 | 33.1 | 32.2 | 1.3 |
| 450 | TTCTGGT----------GGA | 11.2 | 11.5 | 11.4 | 0.2 |
| 451 | TTC----------AGGTGGA | 5.2 | 4 | 4.6 | 0.8 |
|  | ----------------TGGA | 4.2 | 3.7 | 4 | 0.4 |
| 452 | TTCTGGTT--CACAGGTGGA | 3.5 | 3.5 | 3.5 | 0 |
| 453 | TTCTGGTTGTTTCACAGGTGGA | 2.1 | 2.7 | 2.4 | 0.4 |
| 454 | TTCTGGTTG---------GA | 2.3 | 2.2 | 2.2 | 0.1 |
|  | TTCTGG-------------A | 1.9 | 1.6 | 1.8 | 0.2 |
| 455 | TTCTGGTTGTCCACAGGTGGA | 1.6 | 1.9 | 1.8 | 0.2 |
| 456 | TTC-------CACAGGTGGA | 1.4 | 2.1 | 1.8 | 0.5 |

TABLE 47-continued

On-Target Gene Edited Sequences >1% Frequency in At Least One Gene Edited T Cell Donor for the TGFBRII-Ex4-T1 gRNA.
Reference on-target sequence[a]: TTCTGGTTGTCAC(AGG)TGGA (SEQ ID NO: 448)

| SEQ ID NO: | Gene Edited Sequence | Donor 1 (%) | Donor 2 (%) | Mean (%) | Std. Dev. (%) |
|---|---|---|---|---|---|
| 457 | TTCTGGTT-TCACAGGTGGA | 1.4 | 2 | 1.7 | 0.4 |
|  | -------------------- | 2 | 1.1 | 1.6 | 0.6 |
| 458 | TTCTGGTTG-CACAGGTGGA | 1.1 | 1.4 | 1.2 | 0.2 |
| 459 | TTCTGGTTGTACACAGGTGGA | 1.1 | 1.2 | 1.2 | 0.1 |
|  | TTCT---------------- | 1.4 | 0.7 | 1 | 0.5 |
| 460 | TTCTGGTTG----------A | 1.1 | 1 | 1 | 0.1 |
| 461 | TTCTGGTTGT-ACAGGTGGA | 0.7 | 1.2 | 1 | 0.4 |

[a] On-target sequence centered on cleavage site, with 10 bp in either direction. For comparison, the portion of the gRNA target sequence aligning with the Reference on-target sequence is underlined and the PAM is indicated by parenthesis.
[b] Deletions indicated by dashes (-); insertions indicated by bold
[c] Positions of inserted bases in the gene edited sequence indicated by dashes (-) in the Reference Sequence

TABLE 48

On-Target Gene Edited Sequences >1% Frequency in At Least One Gene Edited T Cell Donor for the TGFBRII-Ex4-T2 gRNA.
Reference on-target sequence[a]: TGTGAGAAGCCAC(AGG)AAGT (SEQ ID NO: 462)

| SEQ ID NO: | Gene Edited Sequence | Donor 1 (%) | Donor 2 (%) | Mean (%) | Std. Dev. (%) |
|---|---|---|---|---|---|
| 463 | TGTGA----------GAAGT | 22.3 | 17.3 | 19.8 | 3.5 |
| 464 | TGTGAGAAG-CACAGGAAGT | 9.9 | 12.7 | 11.3 | 2 |
|  | -------------------T | 11.8 | 8.2 | 10 | 2.5 |
| 465 | TGTGAGAAGCCCACAGGAAGT | 4.8 | 8.1 | 6.4 | 2.3 |
| 466 | TGTG---------AGGAAGT | 3.1 | 3.5 | 3.3 | 0.3 |
| 467 | TGTGAGAAGC--CAGGAAGT | 3 | 3.1 | 3 | 0.1 |
| 468 | TGTGAGA------AGGAAGT | 3 | 2.8 | 2.9 | 0.1 |
| 469 | ----------CACAGGAAGT | 2.5 | 2.7 | 2.6 | 0.1 |
| 470 | TGTGAGAAGCACACAGGAAGT | 1.2 | 2.3 | 1.8 | 0.8 |
| 471 | TGTGAGAAG---CAGGAAGT | 1.6 | 1.6 | 1.6 | 0 |
|  | ------------CAGGAAGT | 1.3 | 1.8 | 1.6 | 0.4 |
| 472 | TGTG------CACAGGAAGT | 1.2 | 1.8 | 1.5 | 0.4 |
|  | -------------------- | 1.7 | 1 | 1.4 | 0.5 |
| 473 | ---------CCACAGGAAGT | 1.5 | 1.4 | 1.4 | 0.1 |
| 474 | TGTGAGA---CACAGGAAGT | 0.7 | 1.4 | 1 | 0.5 |
| 475 | TGTGAG-----ACAGGAAGT | 1.2 | 0.8 | 1 | 0.3 |
|  | TGT------------GAAGT | 1.2 | 0.7 | 1 | 0.4 |
| 476 | TGTGAGAA--CACAGGAAGT | 0.6 | 1.4 | 1 | 0.6 |
| 477 | TGTGAGAAGC---------- | 0.8 | 1.1 | 1 | 0.2 |

TABLE 48-continued

On-Target Gene Edited Sequences >1% Frequency in At Least One Gene Edited T Cell Donor for the TGFBRII-Ex4-T2 gRNA.
Reference on-target sequence[a]: TGTGAGAAGCCAC(AGG)AAGT (SEQ ID NO: 462)

| SEQ ID NO: | Gene Edited Sequence | Donor 1 (%) | Donor 2 (%) | Mean (%) | Std. Dev. (%) |
|---|---|---|---|---|---|
| 478 | TGTGAGAAGCCACACAG-GAAGT | 1.4 | 0.7 | 1 | 0.5 |

[a]On-target sequence centered on cleavage site, with 10 bp in either direction. For comparison, the portion of the gRNA target sequence aligning with the Reference on-target sequence is underlined and the PAM is indicated by parenthesis.
[b]Deletions indicated by dashes (-); insertions indicated by bold
[c]Positions of inserted bases in the gene edited sequence indicated by dashes (-) in the Reference Sequence

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

The term "about" as used herein means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Where particular values are described in the application and claims, unless otherwise stated, the term "about" is implicit and in this context means within an acceptable error range for the particular value.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A population of immune cells, which comprises genetically engineered T cells, wherein the genetically engineered T cells comprise:
   (i) a disrupted Regnase-1 (Reg1) gene;
   (ii) a disrupted Transforming Growth Factor Beta Receptor II (TGFBRII) gene; and
   (iii) a nucleic acid encoding a chimeric antigen receptor (CAR) that binds a tumor antigen.

2. The population of immune cells of claim 1, wherein the disrupted Reg1 gene is genetically edited in exon 2 and/or exon 4; and/or wherein the disrupted TGFBRII gene is genetically edited in exon 4 or exon 5.

3. The population of immune cells of claim 1, wherein the disrupted Reg1 gene, the disrupted TGFBRII gene, or both are genetically edited by a CRISPR/Cas-mediated gene editing system.

4. The population of immune cells of claim 3,
   wherein the CRISPR/Cas-mediated gene editing system comprises a guide RNA (gRNA) targeting a site in the Reg1 gene, wherein the target site comprises a nucleotide selected from the group consisting of SEQ ID NO: SEQ ID NO: 320, 322, 323, and 327; and/or
   wherein the CRISPR/Cas-mediated gene editing system comprises a guide RNA (gRNA) targeting a site in the TGFBRII gene that comprises a nucleotide sequence selected from the group consisting of SEQ ID NOs: 275, 305, 311, and 317.

5. The population of immune cells of claim 4,
   wherein the gRNA targeting the Reg1 gene comprises the nucleotide sequence selected from the group consisting of SEQ ID NO: 22, 30, 34, and 50; and/or
   wherein the gRNA targeting the TGFBRII gene comprises a nucleotide sequence selected from the group consisting of SEQ ID NOs: 270, 300, 306, and 312.

6. The population of immune cells of claim 1, wherein the genetically engineered T cells further comprise:
   (iv) a disrupted T cell receptor alpha chain constant region (TRAC) gene,
   (v) a disrupted beta-2-microglobulin (β2M) gene,
   (vi) a disrupted CD70 gene, or
   (vii) a combination of any of (iv)-(vi).

7. The population of immune cells of claim 6, wherein the genetically engineered T cells comprise a disrupted T cell receptor alpha chain constant region (TRAC) gene and a disrupted beta-2-microglobulin (β2M) gene.

8. The population of immune cells of claim 7, wherein the nucleic acid encoding the CAR is inserted in the disrupted TRAC gene.

9. The population of immune cells of claim 6, wherein:
   (a) at least 40% of the genetically engineered T cells express the CAR that binds CD70;
   (b) at least 50% of the genetically engineered T cells do not express a detectable level of β2M surface protein;
   (c) at least 90% of the genetically engineered T cells do not express a detectable TRAC surface protein;
   (d) at least 50% of the genetically engineered T cells do not express a detectable CD70 surface protein;
   (e) at least 80% of the genetically engineered T cells are Reg1⁻ cells;
   (f) at least 80% of the genetically engineered T cells are TGFBRII⁻ cells; or
   (g) a combination thereof.

10. The population of immune cells of claim 1, wherein the tumor antigen is CD19, BCMA, CD70, CD33, or PTK7.

11. The population of immune cells of claim 1, wherein the genetically engineered T cells are derived from primary T cells of one or more human donors.

12. A pharmaceutical composition comprising the population of immune cells of claim 1 and a pharmaceutically acceptable carrier.

13. A population of immune cells comprising genetically engineered T cells, wherein the genetically engineered T cells comprise:
   (i) a disrupted Regnase-1 (Reg1) gene genetically edited at a Reg1 target site of SEQ ID NO: 327;
   (ii) a disrupted Transforming Growth Factor Beta Receptor II (TGFBRII) gene genetically edited at a TGFBRII target site of SEQ ID NO: 317;
   (iii) a disrupted a disrupted T cell receptor alpha chain constant region (TRAC) gene genetically edited at a TRAC target site of SEQ ID NO: 69;
   (iv) a disrupted beta-2-microglobulin (β2M) gene genetically edited at a β2M target site of SEQ ID NO: 71,
   (v) a disrupted CD70 gene genetically edited at a CD70 target site of SEQ ID NO: 67; and
   (vi) a nucleic acid encoding a chimeric antigen receptor (CAR) that binds CD70,
      wherein the CAR comprises an extracellular antigen binding domain that binds CD70, which comprises a single chain variable fragment (scFv) that comprises the amino acid sequence of SEQ ID NO: 140 or 142; and
      wherein the nucleic acid is inserted in the disrupted TRAC gene.

14. The population of immune cells of claim 13, comprising the amino acid sequence of SEQ ID NO:354 or SEQ ID NO: 138.

15. The population of immune cells of claim 13, wherein the disrupted Reg1 gene, the disrupted TGFBRII gene, the disrupted TRAC gene, the disrupted β2M gene, and disrupted CD70 gene are generated by CRISPR-Cas9 mediated gene editing.

16. The population of immune cells of claim 15, wherein:
(i) the disrupted Reg1 gene is generated by a gRNA comprising a spacer sequence set forth as SEQ ID NO: 52;
(ii) the disrupted TGFBRII gene is generated by a gRNA comprising a spacer sequence set forth as SEQ ID NO: 314;
(iii) the disrupted TRAC gene is generated by a gRNA comprising a spacer sequence set forth as of SEQ ID NO: 61;
(iv) the disrupted β2M gene is generated by a gRNA comprising a spacer sequence set forth as SEQ ID NO: 65, and
(v) the disrupted CD70 gene is generated by a spacer sequence set forth as SEQ ID NO: 57.

17. The population of immune cells of claim 13, wherein the genetically engineered T cell comprises a disrupted TRAC gene, which comprises the nucleotide sequence of SEQ ID NO: 169.

18. The population of immune cells of claim 17, wherein:
(a) at least 40% of the genetically engineered T cells express the CAR that binds CD70;
(b) at least 50% of the genetically engineered T cells do not express a detectable level of β2M surface protein;
(c) at least 90% of the genetically engineered T cells do not express a detectable TRAC surface protein;
(d) at least 50% of the genetically engineered T cells do not express a detectable CD70 surface protein;
(e) at least 80% of the genetically engineered T cells are Reg1$^-$ cells; and
(f) at least 80% of the genetically engineered T cells are TGFBRII$^-$ cells.

19. The population of immune cells of claim 18, wherein the genetically engineered T cells comprise ≥30% CAR$^+$ T cells, ≤0.4% TCR$^+$ T cells, ≤30% β2M$^+$ T cells, ≤2% CD70$^+$ T cells, and ≥60% Reg1$^-$/TGFBRII$^-$ T cells.

20. The population of immune cells of claim 13, wherein the genetically engineered T cells are derived from primary T cells of one or more human donors.

21. A pharmaceutical composition comprising the population of immune cells of claim 13 and a pharmaceutically acceptable carrier.

* * * * *

```
                        SEQUENCE LISTING

Sequence total quantity: 478
SEQ ID NO: 1            moltype = AA   length = 1368
FEATURE                 Location/Qualifiers
REGION                  1..1368
                        note = Synthetic
source                  1..1368
                        mol_type = protein
                        organism = synthetic construct
SEQUENCE: 1
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG 120
NIVDEVAYHE KYPTIYHLRK KLVDSTDKAD LRLIYLALAH MIKFRGHFLI EGDLNPDNSD 180
VDKLFIQLVQ TYNQLFEENP INASGVDAKA ILSARLSKSR RLENLIAQLP GEKKNGLFGN 240
LIALSLGLTP NFKSNFDLAE DAKLQLSKDT YDDDLDNLLA QIGDQYADLF LAAKNLSDAI 300
LLSDILRVNT EITKAPLSAS MIKRYDEHHQ DLTLLKALVR QQLPEKYKEI FFDQSKNGYA 360
GYIDGGASQE EFYKFIKPIL EKMDGTEELL VKLNREDLLR KQRTFDNGSI PHQIHLGELH 420
AILRRQEDFY PFLKDNREKI EKILTFRIPY YVGPLARGNS RFAWMTRKSE ETITPWNFEE 480
VVDKGASAQS FIERMTNFDK NLPNEKVLPK HSLLYEYFTV YNELTKVKYV TEGMRKPAFL 540
SGEQKKAIVD LLFKTNRKVT VKQLKEDYFK KIECFDSVEI SGVEDRFNAS LGTYHDLLKI 600
IKDKDFLDNE ENEDILEDIV LTLTLFEDRE MIEERLKTYA HLFDDKVMKQ LKRRRYTGWG 660
RLSRKLINGI RDKQSGKTIL DFLKSDGFAN RNFMQLIHDD SLTFKEDIQK AQVSGQGDSL 720
HEHIANLAGS PAIKKGILQT VKVVDELVKV MGRHKPENIV IEMARENQTT QKGQKNSRER 780
MKRIEEGIKE LGSQILKEHP VENTQLQNEK LYLYYLQNGR DMYVDQELDI NRLSDYDVDH 840
IVPQSFLKDD SIDNKVLTRS DKNRGKSDNV PSEEVVKKMK NYWRQLLNAK LITQRKFDNL 900
TKAERGGLSE LDKAGFIKRQ LVETRQITKH VAQILDSRMN TKYDENDKLI REVKVITLKS 960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD           1368

SEQ ID NO: 2            moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 2
ccgacttctg aacgtgcggt ggg                                           23

SEQ ID NO: 3            moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 3
tgctggcgat acgcgtccac agg                                           23

SEQ ID NO: 4            moltype = DNA   length = 23
FEATURE                 Location/Qualifiers
misc_feature            1..23
                        note = Synthetic
```

```
source                  1..23
                        mol_type = other DNA
                        organism = synthetic construct
SEQUENCE: 4
tcggtctatg acgagcagcg ggg                                        23

SEQ ID NO: 5            moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 5
atgggcagtc ctattacagc tgg                                        23

SEQ ID NO: 6            moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 6
attgttcact tgttagcccc agg                                        23

SEQ ID NO: 7            moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 7
gctgaagaac tgcctctata tgg                                        23

SEQ ID NO: 8            moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 8
gcaggatttc tggttgtcac agg                                        23

SEQ ID NO: 9            moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 9
ctccatctgt gagaagccac agg                                        23

SEQ ID NO: 10           moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 10
cccctaccat gactttattc tgg                                        23

SEQ ID NO: 11           moltype = DNA   length = 26
FEATURE                 Location/Qualifiers
misc_feature            1..26
                        note = Synthetic
source                  1..26
                        mol_type = other DNA
                        organism = synthetic construct
SEQUENCE: 11
ggcaccatat tcattttgca ggtgaa                                     26

SEQ ID NO: 12           moltype = DNA   length = 25
FEATURE                 Location/Qualifiers
misc_feature            1..25
```

```
                        note = Synthetic
source                  1..25
                        mol_type = other DNA
                        organism = synthetic construct
SEQUENCE: 12
atgtgcgctc tgcccactga cgggc                                             25

SEQ ID NO: 13           moltype = DNA  length = 29
FEATURE                 Location/Qualifiers
misc_feature            1..29
                        note = Synthetic
source                  1..29
                        mol_type = other DNA
                        organism = synthetic construct
SEQUENCE: 13
agacatgagg tctatggact tcaggctcc                                         29

SEQ ID NO: 14           moltype = RNA  length = 100
FEATURE                 Location/Qualifiers
misc_feature            1..100
                        note = Synthetic
source                  1..100
                        mol_type = other RNA
                        organism = synthetic construct
SEQUENCE: 14
ggtcatcgat gggagcaacg gttttagagc tagaaatagc aagttaaaat aaggctagtc       60
cgttatcaac ttgaaaaagt ggcaccgagt cggtgctttt                            100

SEQ ID NO: 15           moltype = RNA  length = 100
FEATURE                 Location/Qualifiers
misc_feature            1..100
                        note = Synthetic
misc_feature            1..4
                        note = modified with 2'-O-methyl phosphorothioate
misc_feature            97..100
                        note = modified with 2'-O-methyl phosphorothioate
source                  1..100
                        mol_type = other RNA
                        organism = synthetic construct
SEQUENCE: 15
ggtcatcgat gggagcaacg gttttagagc tagaaatagc aagttaaaat aaggctagtc       60
cgttatcaac ttgaaaaagt ggcaccgagt cggtgctttt                            100

SEQ ID NO: 16           moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 16
ggtcatcgat gggagcaacg                                                   20

SEQ ID NO: 17           moltype = RNA  length = 20
FEATURE                 Location/Qualifiers
misc_feature            1..20
                        note = Synthetic
misc_feature            1..4
                        note = modified with 2'-O-methyl phosphorothioate
source                  1..20
                        mol_type = other RNA
                        organism = synthetic construct
SEQUENCE: 17
ggtcatcgat gggagcaacg                                                   20

SEQ ID NO: 18           moltype = RNA  length = 100
FEATURE                 Location/Qualifiers
misc_feature            1..100
                        note = Synthetic
source                  1..100
                        mol_type = other RNA
                        organism = synthetic construct
SEQUENCE: 18
caccacccecg cgggactaga gttttagagc tagaaatagc aagttaaaat aaggctagtc      60
cgttatcaac ttgaaaaagt ggcaccgagt cggtgctttt                            100

SEQ ID NO: 19           moltype = RNA  length = 100
FEATURE                 Location/Qualifiers
misc_feature            1..100
```

```
                         note = Synthetic
misc_feature             1..4
                         note = modified with 2'-O-methyl phosphorothioate
misc_feature             97..100
                         note = modified with 2'-O-methyl phosphorothioate
source                   1..100
                         mol_type = other RNA
                         organism = synthetic construct
SEQUENCE: 19
caccaccccg cgggactaga gttttagagc tagaaatagc aagttaaaat aaggctagtc    60
cgttatcaac ttgaaaaagt ggcaccgagt cggtgctttt                         100

SEQ ID NO: 20            moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 20
caccaccccg cgggactaga                                                20

SEQ ID NO: 21            moltype = RNA  length = 20
FEATURE                  Location/Qualifiers
misc_feature             1..20
                         note = Synthetic
misc_feature             1..4
                         note = modified with 2'-O-methyl phosphorothioate
source                   1..20
                         mol_type = other RNA
                         organism = synthetic construct
SEQUENCE: 21
caccaccccg cgggactaga                                                20

SEQ ID NO: 22            moltype = RNA  length = 100
FEATURE                  Location/Qualifiers
misc_feature             1..100
                         note = Synthetic
source                   1..100
                         mol_type = other RNA
                         organism = synthetic construct
SEQUENCE: 22
ggtctggcgc tcccgctcgg gttttagagc tagaaatagc aagttaaaat aaggctagtc    60
cgttatcaac ttgaaaaagt ggcaccgagt cggtgctttt                         100

SEQ ID NO: 23            moltype = RNA  length = 100
FEATURE                  Location/Qualifiers
misc_feature             1..100
                         note = Synthetic
misc_feature             1..4
                         note = modified with 2'-O-methyl phosphorothioate
misc_feature             97..100
                         note = modified with 2'-O-methyl phosphorothioate
source                   1..100
                         mol_type = other RNA
                         organism = synthetic construct
SEQUENCE: 23
ggtctggcgc tcccgctcgg gttttagagc tagaaatagc aagttaaaat aaggctagtc    60
cgttatcaac ttgaaaaagt ggcaccgagt cggtgctttt                         100

SEQ ID NO: 24            moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 24
ggtctggcgc tcccgctcgg                                                20

SEQ ID NO: 25            moltype = RNA  length = 20
FEATURE                  Location/Qualifiers
misc_feature             1..20
                         note = Synthetic
misc_feature             1..4
                         note = modified with 2'-O-methyl phosphorothioate
source                   1..20
                         mol_type = other RNA
                         organism = synthetic construct
```

-continued

```
SEQUENCE: 25
ggtctggcgc tcccgctcgg                                               20

SEQ ID NO: 26           moltype = RNA   length = 100
FEATURE                 Location/Qualifiers
misc_feature            1..100
                        note = Synthetic
source                  1..100
                        mol_type = other RNA
                        organism = synthetic construct
SEQUENCE: 26
ttcacaccat cacgacgcgt gttttagagc tagaaatagc aagttaaaat aaggctagtc   60
cgttatcaac ttgaaaaagt ggcaccgagt cggtgctttt                        100

SEQ ID NO: 27           moltype = RNA   length = 100
FEATURE                 Location/Qualifiers
misc_feature            1..100
                        note = Synthetic
misc_feature            1..4
                        note = modified with 2'-O-methyl phosphorothioate
misc_feature            97..100
                        note = modified with 2'-O-methyl phosphorothioate
source                  1..100
                        mol_type = other RNA
                        organism = synthetic construct
SEQUENCE: 27
ttcacaccat cacgacgcgt gttttagagc tagaaatagc aagttaaaat aaggctagtc   60
cgttatcaac ttgaaaaagt ggcaccgagt cggtgctttt                        100

SEQ ID NO: 28           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 28
ttcacaccat cacgacgcgt                                               20

SEQ ID NO: 29           moltype = RNA   length = 20
FEATURE                 Location/Qualifiers
misc_feature            1..20
                        note = Synthetic
misc_feature            1..4
                        note = modified with 2'-O-methyl phosphorothioate
source                  1..20
                        mol_type = other RNA
                        organism = synthetic construct
SEQUENCE: 29
ttcacaccat cacgacgcgt                                               20

SEQ ID NO: 30           moltype = RNA   length = 100
FEATURE                 Location/Qualifiers
misc_feature            1..100
                        note = Synthetic
source                  1..100
                        mol_type = other RNA
                        organism = synthetic construct
SEQUENCE: 30
acaccatcac gacgcgtggg gttttagagc tagaaatagc aagttaaaat aaggctagtc   60
cgttatcaac ttgaaaaagt ggcaccgagt cggtgctttt                        100

SEQ ID NO: 31           moltype = RNA   length = 100
FEATURE                 Location/Qualifiers
misc_feature            1..100
                        note = Synthetic
misc_feature            1..4
                        note = modified with 2'-O-methyl phosphorothioate
misc_feature            97..100
                        note = modified with 2'-O-methyl phosphorothioate
source                  1..100
                        mol_type = other RNA
                        organism = synthetic construct
SEQUENCE: 31
acaccatcac gacgcgtggg gttttagagc tagaaatagc aagttaaaat aaggctagtc   60
cgttatcaac ttgaaaaagt ggcaccgagt cggtgctttt                        100

SEQ ID NO: 32           moltype = RNA   length = 20
FEATURE                 Location/Qualifiers
```

```
                        155                                            156
                                      -continued misc_feature          1..20
                      note = Synthetic
source                1..20
                      mol_type = other RNA
                      organism = synthetic construct
SEQUENCE: 32
acaccatcac gacgcgtggg                                                      20

SEQ ID NO: 33         moltype = RNA  length = 20
FEATURE               Location/Qualifiers
misc_feature          1..20
                      note = Synthetic
misc_feature          1..4
                      note = modified with 2'-O-methyl phosphorothioate
source                1..20
                      mol_type = other RNA
                      organism = synthetic construct
SEQUENCE: 33
acaccatcac gacgcgtggg                                                      20

SEQ ID NO: 34         moltype = RNA  length = 100
FEATURE               Location/Qualifiers
misc_feature          1..100
                      note = Synthetic
source                1..100
                      mol_type = other RNA
                      organism = synthetic construct
SEQUENCE: 34
ctacgagtct gacgggatcg gttttagagc tagaaatagc aagttaaaat aaggctagtc          60
cgttatcaac ttgaaaaagt ggcaccgagt cggtgctttt                                100

SEQ ID NO: 35         moltype = RNA  length = 100
FEATURE               Location/Qualifiers
misc_feature          1..100
                      note = Synthetic
misc_feature          1..4
                      note = modified with 2'-O-methyl phosphorothioate
misc_feature          97..100
                      note = modified with 2'-O-methyl phosphorothioate
source                1..100
                      mol_type = other RNA
                      organism = synthetic construct
SEQUENCE: 35
ctacgagtct gacgggatcg gttttagagc tagaaatagc aagttaaaat aaggctagtc          60
cgttatcaac ttgaaaaagt ggcaccgagt cggtgctttt                                100

SEQ ID NO: 36         moltype = RNA  length = 20
FEATURE               Location/Qualifiers
misc_feature          1..20
                      note = Synthetic
source                1..20
                      mol_type = other RNA
                      organism = synthetic construct
SEQUENCE: 36
ctacgagtct gacgggatcg                                                      20

SEQ ID NO: 37         moltype = RNA  length = 20
FEATURE               Location/Qualifiers
misc_feature          1..20
                      note = Synthetic
misc_feature          1..4
                      note = modified with 2'-O-methyl phosphorothioate
source                1..20
                      mol_type = other RNA
                      organism = synthetic construct
SEQUENCE: 37
ctacgagtct gacgggatcg                                                      20

SEQ ID NO: 38         moltype = RNA  length = 100
FEATURE               Location/Qualifiers
misc_feature          1..100
                      note = Synthetic
source                1..100
                      mol_type = other RNA
                      organism = synthetic construct
SEQUENCE: 38
ttgccaccca cgcgtcgtga gttttagagc tagaaatagc aagttaaaat aaggctagtc          60
cgttatcaac ttgaaaaagt ggcaccgagt cggtgctttt                                100
```

-continued

```
SEQ ID NO: 39            moltype = RNA   length = 100
FEATURE                  Location/Qualifiers
misc_feature             1..100
                         note = Synthetic
misc_feature             1..4
                         note = modified with 2'-O-methyl phosphorothioate
misc_feature             97..100
                         note = modified with 2'-O-methyl phosphorothioate
source                   1..100
                         mol_type = other RNA
                         organism = synthetic construct
SEQUENCE: 39
ttgccaccca cgcgtcgtga gttttagagc tagaaatagc aagttaaaat aaggctagtc    60
cgttatcaac ttgaaaaagt ggcaccgagt cggtgctttt                         100

SEQ ID NO: 40            moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 40
ttgccaccca cgcgtcgtga                                                20

SEQ ID NO: 41            moltype = RNA   length = 20
FEATURE                  Location/Qualifiers
misc_feature             1..20
                         note = Synthetic
misc_feature             1..4
                         note = modified with 2'-O-methyl phosphorothioate
source                   1..20
                         mol_type = other RNA
                         organism = synthetic construct
SEQUENCE: 41
ttgccaccca cgcgtcgtga                                                20

SEQ ID NO: 42            moltype = RNA   length = 100
FEATURE                  Location/Qualifiers
misc_feature             1..100
                         note = Synthetic
source                   1..100
                         mol_type = other RNA
                         organism = synthetic construct
SEQUENCE: 42
gttcacacca tcacgacgcg gttttagagc tagaaatagc aagttaaaat aaggctagtc    60
cgttatcaac ttgaaaaagt ggcaccgagt cggtgctttt                         100

SEQ ID NO: 43            moltype = RNA   length = 100
FEATURE                  Location/Qualifiers
misc_feature             1..100
                         note = Synthetic
misc_feature             1..4
                         note = modified with 2'-O-methyl phosphorothioate
misc_feature             97..100
                         note = modified with 2'-O-methyl phosphorothioate
source                   1..100
                         mol_type = other RNA
                         organism = synthetic construct
SEQUENCE: 43
gttcacacca tcacgacgcg gttttagagc tagaaatagc aagttaaaat aaggctagtc    60
cgttatcaac ttgaaaaagt ggcaccgagt cggtgctttt                         100

SEQ ID NO: 44            moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 44
gttcacacca tcacgacgcg                                                20

SEQ ID NO: 45            moltype = RNA   length = 20
FEATURE                  Location/Qualifiers
misc_feature             1..20
                         note = Synthetic
misc_feature             1..4
                         note = modified with 2'-O-methyl phosphorothioate
```

```
source                      1..20
                            mol_type = other RNA
                            organism = synthetic construct
SEQUENCE: 45
gttcacacca tcacgacgcg                                                    20

SEQ ID NO: 46               moltype = RNA   length = 100
FEATURE                     Location/Qualifiers
misc_feature                1..100
                            note = Synthetic
source                      1..100
                            mol_type = other RNA
                            organism = synthetic construct
SEQUENCE: 46
cacgatcccg tcagactcgt gttttagagc tagaaatagc aagttaaaat aaggctagtc        60
cgttatcaac ttgaaaaagt ggcaccgagt cggtgctttt                             100

SEQ ID NO: 47               moltype = RNA   length = 100
FEATURE                     Location/Qualifiers
misc_feature                1..100
                            note = Synthetic
misc_feature                1..4
                            note = modified with 2'-O-methyl phosphorothioate
misc_feature                97..100
                            note = modified with 2'-O-methyl phosphorothioate
source                      1..100
                            mol_type = other RNA
                            organism = synthetic construct
SEQUENCE: 47
cacgatcccg tcagactcgt gttttagagc tagaaatagc aagttaaaat aaggctagtc        60
cgttatcaac ttgaaaaagt ggcaccgagt cggtgctttt                             100

SEQ ID NO: 48               moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 48
cacgatcccg tcagactcgt                                                    20

SEQ ID NO: 49               moltype = RNA   length = 20
FEATURE                     Location/Qualifiers
misc_feature                1..20
                            note = Synthetic
misc_feature                1..4
                            note = modified with 2'-O-methyl phosphorothioate
source                      1..20
                            mol_type = other RNA
                            organism = synthetic construct
SEQUENCE: 49
cacgatcccg tcagactcgt                                                    20

SEQ ID NO: 50               moltype = RNA   length = 100
FEATURE                     Location/Qualifiers
misc_feature                1..100
                            note = Synthetic
source                      1..100
                            mol_type = other RNA
                            organism = synthetic construct
SEQUENCE: 50
acgacgcgtg ggtggcaagc gttttagagc tagaaatagc aagttaaaat aaggctagtc        60
cgttatcaac ttgaaaaagt ggcaccgagt cggtgctttt                             100

SEQ ID NO: 51               moltype = RNA   length = 100
FEATURE                     Location/Qualifiers
misc_feature                1..100
                            note = Synthetic
misc_feature                1..4
                            note = modified with 2'-O-methyl phosphorothioate
misc_feature                97..100
                            note = modified with 2'-O-methyl phosphorothioate
source                      1..100
                            mol_type = other RNA
                            organism = synthetic construct
SEQUENCE: 51
acgacgcgtg ggtggcaagc gttttagagc tagaaatagc aagttaaaat aaggctagtc        60
cgttatcaac ttgaaaaagt ggcaccgagt cggtgctttt                             100
```

```
SEQ ID NO: 52            moltype = RNA   length = 20
FEATURE                  Location/Qualifiers
source                   1..20
                         mol_type = other RNA
                         organism = synthetic construct
SEQUENCE: 52
acgacgcgtg ggtggcaagc                                                  20

SEQ ID NO: 53            moltype = RNA   length = 20
FEATURE                  Location/Qualifiers
misc_feature             1..20
                         note = Synthetic
misc_feature             1..4
                         note = modified with 2'-O-methyl phosphorothioate
source                   1..20
                         mol_type = other RNA
                         organism = synthetic construct
SEQUENCE: 53
acgacgcgtg ggtggcaagc                                                  20

SEQ ID NO: 54            moltype = RNA   length = 100
FEATURE                  Location/Qualifiers
misc_feature             1..100
                         note = Synthetic
misc_feature             1..4
                         note = modified with 2'-O-methyl phosphorothioate
misc_feature             97..100
                         note = modified with 2'-O-methyl phosphorothioate
source                   1..100
                         mol_type = other RNA
                         organism = synthetic construct
SEQUENCE: 54
gctttggtcc cattggtcgc gttttagagc tagaaatagc aagttaaaat aaggctagtc      60
cgttatcaac ttgaaaaagt ggcaccgagt cggtgctttt                           100

SEQ ID NO: 55            moltype = RNA   length = 100
FEATURE                  Location/Qualifiers
misc_feature             1..100
                         note = Synthetic
source                   1..100
                         mol_type = other RNA
                         organism = synthetic construct
SEQUENCE: 55
gctttggtcc cattggtcgc gttttagagc tagaaatagc aagttaaaat aaggctagtc      60
cgttatcaac ttgaaaaagt ggcaccgagt cggtgctttt                           100

SEQ ID NO: 56            moltype = RNA   length = 20
FEATURE                  Location/Qualifiers
misc_feature             1..20
                         note = Synthetic
misc_feature             1..4
                         note = modified with 2'-O-methyl phosphorothioate
source                   1..20
                         mol_type = other RNA
                         organism = synthetic construct
SEQUENCE: 56
gctttggtcc cattggtcgc                                                  20

SEQ ID NO: 57            moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 57
gctttggtcc cattggtcgc                                                  20

SEQ ID NO: 58            moltype = RNA   length = 100
FEATURE                  Location/Qualifiers
misc_feature             1..100
                         note = Synthetic
misc_feature             1..4
                         note = modified with 2'-O-methyl phosphorothioate
misc_feature             97..100
                         note = modified with 2'-O-methyl phosphorothioate
source                   1..100
                         mol_type = other RNA
```

```
                        organism = synthetic construct
SEQUENCE: 58
agagcaacag tgctgtggcc gttttagagc tagaaatagc aagttaaaat aaggctagtc    60
cgttatcaac ttgaaaaagt ggcaccgagt cggtgctttt                         100

SEQ ID NO: 59           moltype = RNA  length = 100
FEATURE                 Location/Qualifiers
misc_feature            1..100
                        note = Synthetic
source                  1..100
                        mol_type = other RNA
                        organism = synthetic construct
SEQUENCE: 59
agagcaacag tgctgtggcc gttttagagc tagaaatagc aagttaaaat aaggctagtc    60
cgttatcaac ttgaaaaagt ggcaccgagt cggtgctttt                         100

SEQ ID NO: 60           moltype = RNA  length = 20
FEATURE                 Location/Qualifiers
misc_feature            1..20
                        note = Synthetic
misc_feature            1..4
                        note = modified with 2'-O-methyl phosphorothioate
source                  1..20
                        mol_type = other RNA
                        organism = synthetic construct
SEQUENCE: 60
agagcaacag tgctgtggcc                                                20

SEQ ID NO: 61           moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 61
agagcaacag tgctgtggcc                                                20

SEQ ID NO: 62           moltype = RNA  length = 100
FEATURE                 Location/Qualifiers
misc_feature            1..100
                        note = Synthetic
misc_feature            1..4
                        note = modified with 2'-O-methyl phosphorothioate
misc_feature            97..100
                        note = modified with 2'-O-methyl phosphorothioate
source                  1..100
                        mol_type = other RNA
                        organism = synthetic construct
SEQUENCE: 62
gctactctct ctttctggcc gttttagagc tagaaatagc aagttaaaat aaggctagtc    60
cgttatcaac ttgaaaaagt ggcaccgagt cggtgctttt                         100

SEQ ID NO: 63           moltype = RNA  length = 100
FEATURE                 Location/Qualifiers
misc_feature            1..100
                        note = Synthetic
source                  1..100
                        mol_type = other RNA
                        organism = synthetic construct
SEQUENCE: 63
gctactctct ctttctggcc gttttagagc tagaaatagc aagttaaaat aaggctagtc    60
cgttatcaac ttgaaaaagt ggcaccgagt cggtgctttt                         100

SEQ ID NO: 64           moltype = RNA  length = 20
FEATURE                 Location/Qualifiers
misc_feature            1..20
                        note = Synthetic
misc_feature            1..4
                        note = modified with 2'-O-methyl phosphorothioate
source                  1..20
                        mol_type = other RNA
                        organism = synthetic construct
SEQUENCE: 64
gctactctct ctttctggcc                                                20

SEQ ID NO: 65           moltype = RNA  length = 20
FEATURE                 Location/Qualifiers
misc_feature            1..20
```

```
                              note = Synthetic
source                        1..20
                              mol_type = other RNA
                              organism = synthetic construct
SEQUENCE: 65
gctactctct ctttctggcc                                                    20

SEQ ID NO: 66             moltype = DNA  length = 23
FEATURE                   Location/Qualifiers
misc_feature              1..23
                          note = Synthetic
source                    1..23
                          mol_type = other DNA
                          organism = synthetic construct
SEQUENCE: 66
gctttggtcc cattggtcgc ggg                                                23

SEQ ID NO: 67             moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 67
gctttggtcc cattggtcgc                                                    20

SEQ ID NO: 68             moltype = DNA  length = 23
FEATURE                   Location/Qualifiers
misc_feature              1..23
                          note = Synthetic
source                    1..23
                          mol_type = other DNA
                          organism = synthetic construct
SEQUENCE: 68
agagcaacag tgctgtggcc tgg                                                23

SEQ ID NO: 69             moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 69
agagcaacag tgctgtggcc                                                    20

SEQ ID NO: 70             moltype = DNA  length = 23
FEATURE                   Location/Qualifiers
misc_feature              1..23
                          note = Synthetic
source                    1..23
                          mol_type = other DNA
                          organism = synthetic construct
SEQUENCE: 70
gctactctct ctttctggcc tgg                                                23

SEQ ID NO: 71             moltype = DNA  length = 20
FEATURE                   Location/Qualifiers
misc_feature              1..20
                          note = Synthetic
source                    1..20
                          mol_type = other DNA
                          organism = synthetic construct
SEQUENCE: 71
gctactctct ctttctggcc                                                    20

SEQ ID NO: 72             moltype = RNA  length = 100
FEATURE                   Location/Qualifiers
misc_feature              1..100
                          note = Synthetic
misc_feature              1..20
                          note = n is a, c, g, or u
source                    1..100
                          mol_type = other RNA
                          organism = synthetic construct
SEQUENCE: 72
nnnnnnnnnn nnnnnnnnnn gttttagagc tagaaatagc aagttaaaat aaggctagtc         60
cgttatcaac ttgaaaaagt ggcaccgagt cggtgctttt                              100
```

```
SEQ ID NO: 73         moltype = RNA  length = 96
FEATURE               Location/Qualifiers
misc_feature          1..96
                      note = Synthetic
misc_feature          1..20
                      note = n is a, c, g, or u
source                1..96
                      mol_type = other RNA
                      organism = synthetic construct
SEQUENCE: 73
nnnnnnnnnn nnnnnnnnnn gttttagagc tagaaatagc aagttaaaat aaggctagtc    60
cgttatcaac ttgaaaaagt ggcaccgagt cggtgc                              96

SEQ ID NO: 74         moltype = RNA  length = 114
FEATURE               Location/Qualifiers
misc_feature          1..114
                      note = Synthetic
misc_feature          1..30
                      note = n is a, c, g, or u
misc_feature          18..30
                      note = may be absent
misc_feature          108..114
                      note = may be absent
source                1..114
                      mol_type = other RNA
                      organism = synthetic construct
SEQUENCE: 74
nnnnnnnnnn nnnnnnnnnn nnnnnnnnnn gttttagagc tagaaatagc aagttaaaat    60
aaggctagtc cgttatcaac ttgaaaaagt ggcaccgagt cggtgctttt tttt          114

SEQ ID NO: 75         moltype = DNA  length = 19
FEATURE               Location/Qualifiers
misc_feature          1..19
                      note = Synthetic
source                1..19
                      mol_type = other DNA
                      organism = synthetic construct
SEQUENCE: 75
aagagcaaca aatctgact                                                 19

SEQ ID NO: 76         moltype = DNA  length = 39
FEATURE               Location/Qualifiers
misc_feature          1..39
                      note = Synthetic
source                1..39
                      mol_type = other DNA
                      organism = synthetic construct
SEQUENCE: 76
aagagcaaca gtgctgtgcc tggagcaaca aatctgact                           39

SEQ ID NO: 77         moltype = DNA  length = 33
FEATURE               Location/Qualifiers
misc_feature          1..33
                      note = Synthetic
source                1..33
                      mol_type = other DNA
                      organism = synthetic construct
SEQUENCE: 77
aagagcaaca gtgctggagc aacaaatctg act                                 33

SEQ ID NO: 78         moltype = DNA  length = 34
FEATURE               Location/Qualifiers
misc_feature          1..34
                      note = Synthetic
source                1..34
                      mol_type = other DNA
                      organism = synthetic construct
SEQUENCE: 78
aagagcaaca gtgcctggag caacaaatct gact                                34

SEQ ID NO: 79         moltype = DNA  length = 19
FEATURE               Location/Qualifiers
misc_feature          1..19
                      note = Synthetic
source                1..19
                      mol_type = other DNA
                      organism = synthetic construct
SEQUENCE: 79
```

```
aagagcaaca gtgctgact                                                    19

SEQ ID NO: 80           moltype = DNA   length = 41
FEATURE                 Location/Qualifiers
misc_feature            1..41
                        note = Synthetic
source                  1..41
                        mol_type = other DNA
                        organism = synthetic construct
SEQUENCE: 80
aagagcaaca gtgctgtggg cctggagcaa caaatctgac t                            41

SEQ ID NO: 81           moltype = DNA   length = 38
FEATURE                 Location/Qualifiers
misc_feature            1..38
                        note = Synthetic
source                  1..38
                        mol_type = other DNA
                        organism = synthetic construct
SEQUENCE: 81
aagagcaaca gtgctggcct ggagcaacaa atctgact                                38

SEQ ID NO: 82           moltype = DNA   length = 41
FEATURE                 Location/Qualifiers
misc_feature            1..41
                        note = Synthetic
source                  1..41
                        mol_type = other DNA
                        organism = synthetic construct
SEQUENCE: 82
aagagcaaca gtgctgtgtg cctggagcaa caaatctgac t                            41

SEQ ID NO: 83           moltype = DNA   length = 79
FEATURE                 Location/Qualifiers
misc_feature            1..79
                        note = Synthetic
source                  1..79
                        mol_type = other DNA
                        organism = synthetic construct
SEQUENCE: 83
cgtggcctta gctgtgctcg cgctactctc tctttctgcc tggaggctat ccagcgtgag        60
tctctcctac cctcccgct                                                    79

SEQ ID NO: 84           moltype = DNA   length = 78
FEATURE                 Location/Qualifiers
misc_feature            1..78
                        note = Synthetic
source                  1..78
                        mol_type = other DNA
                        organism = synthetic construct
SEQUENCE: 84
cgtggcctta gctgtgctcg cgctactctc tctttcgcct ggaggctatc cagcgtgagt        60
ctctcctacc ctcccgct                                                     78

SEQ ID NO: 85           moltype = DNA   length = 75
FEATURE                 Location/Qualifiers
misc_feature            1..75
                        note = Synthetic
source                  1..75
                        mol_type = other DNA
                        organism = synthetic construct
SEQUENCE: 85
cgtggcctta gctgtgctcg cgctactctc tctttctgga ggctatccag cgtgagtctc        60
tcctaccctc ccgct                                                        75

SEQ ID NO: 86           moltype = DNA   length = 84
FEATURE                 Location/Qualifiers
misc_feature            1..84
                        note = Synthetic
source                  1..84
                        mol_type = other DNA
                        organism = synthetic construct
SEQUENCE: 86
cgtggcctta gctgtgctcg cgctactctc tctttctgga tagcctggag gctatccagc        60
gtgagtctct cctaccctcc cgct                                              84

SEQ ID NO: 87           moltype = DNA   length = 55
FEATURE                 Location/Qualifiers
misc_feature            1..55
```

```
                        note = Synthetic
source                  1..55
                        mol_type = other DNA
                        organism = synthetic construct
SEQUENCE: 87
cgtggcctta gctgtgctcg cgctatccag cgtgagtctc tcctaccctc ccgct         55

SEQ ID NO: 88           moltype = DNA  length = 82
FEATURE                 Location/Qualifiers
misc_feature            1..82
                        note = Synthetic
source                  1..82
                        mol_type = other DNA
                        organism = synthetic construct
SEQUENCE: 88
cgtggcctta gctgtgctcg cgctactctc tctttctgtg gcctggaggc tatccagcgt    60
gagtctctcc taccctcccg ct                                             82

SEQ ID NO: 89           moltype = DNA  length = 58
FEATURE                 Location/Qualifiers
misc_feature            1..58
                        note = Synthetic
source                  1..58
                        mol_type = other DNA
                        organism = synthetic construct
SEQUENCE: 89
cacaccacga ggcagatcac caagcccgcg caatgggacc aaagcagccc gcaggacg      58

SEQ ID NO: 90           moltype = DNA  length = 61
FEATURE                 Location/Qualifiers
misc_feature            1..61
                        note = Synthetic
source                  1..61
                        mol_type = other DNA
                        organism = synthetic construct
SEQUENCE: 90
cacaccacga ggcagatcac caagcccgcg aaccaatggg accaaagcag cccgcaggac    60
g                                                                    61

SEQ ID NO: 91           moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 91
cacaccacga ggcagatcac caatgggacc aaagcagccc gcaggacg                 48

SEQ ID NO: 92           moltype = DNA  length = 59
FEATURE                 Location/Qualifiers
misc_feature            1..59
                        note = Synthetic
source                  1..59
                        mol_type = other DNA
                        organism = synthetic construct
SEQUENCE: 92
cacaccacga ggcagatcac caagcccgcg ccaatgggac aaagcagcc cgcaggacg      59

SEQ ID NO: 93           moltype = DNA  length = 59
FEATURE                 Location/Qualifiers
misc_feature            1..59
                        note = Synthetic
source                  1..59
                        mol_type = other DNA
                        organism = synthetic construct
SEQUENCE: 93
cacaccacga ggcagatcac caagcccgca ccaatgggac caaagcagcc cgcaggacg     59

SEQ ID NO: 94           moltype = DNA  length = 35
FEATURE                 Location/Qualifiers
misc_feature            1..35
                        note = Synthetic
source                  1..35
                        mol_type = other DNA
                        organism = synthetic construct
SEQUENCE: 94
cacaccacga ggcagatcac caagcccgca ggacg                               35
```

```
SEQ ID NO: 95           moltype = AA  length = 22
FEATURE                 Location/Qualifiers
REGION                  1..22
                        note = Synthetic
source                  1..22
                        mol_type = protein
                        organism = synthetic construct
SEQUENCE: 95
MLLLVTSLLL CELPHPAFLL IP                                              22

SEQ ID NO: 96           moltype = AA  length = 21
FEATURE                 Location/Qualifiers
REGION                  1..21
                        note = Synthetic
source                  1..21
                        mol_type = protein
                        organism = synthetic construct
SEQUENCE: 96
MALPVTALLL PLALLLHAAR P                                               21

SEQ ID NO: 97           moltype = AA  length = 23
FEATURE                 Location/Qualifiers
REGION                  1..23
                        note = Synthetic
source                  1..23
                        mol_type = protein
                        organism = synthetic construct
SEQUENCE: 97
IYIWAPLAGT CGVLLLSLVI TLY                                             23

SEQ ID NO: 98           moltype = DNA  length = 126
FEATURE                 Location/Qualifiers
misc_feature            1..126
                        note = Synthetic
source                  1..126
                        mol_type = other DNA
                        organism = synthetic construct
SEQUENCE: 98
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                               126

SEQ ID NO: 99           moltype = AA  length = 42
FEATURE                 Location/Qualifiers
REGION                  1..42
                        note = Synthetic
source                  1..42
                        mol_type = protein
                        organism = synthetic construct
SEQUENCE: 99
KRGRKKLLYI FKQPFMRPVQ TTQEEDGCSC RFPEEEEGGC EL                        42

SEQ ID NO: 100          moltype = AA  length = 120
FEATURE                 Location/Qualifiers
REGION                  1..120
                        note = Synthetic
source                  1..120
                        mol_type = protein
                        organism = synthetic construct
SEQUENCE: 100
TCAAAGCGGA GTAGGTTGTT GCATTCCGAT TACATGAATA TGACTCCTCG CCGGCCTGGG     60
CCGACAAGAA AACATTACCA ACCCTATGCC CCCCCACGAG ACTTCGCTGC GTACAGGTCC    120

SEQ ID NO: 101          moltype = AA  length = 40
FEATURE                 Location/Qualifiers
REGION                  1..40
                        note = Synthetic
source                  1..40
                        mol_type = protein
                        organism = synthetic construct
SEQUENCE: 101
SKRSRLLHSD YMNMTPRRPG PTRKHYQPYA PPRDFAAYRS                            40

SEQ ID NO: 102          moltype = DNA  length = 336
FEATURE                 Location/Qualifiers
misc_feature            1..336
                        note = Synthetic
source                  1..336
                        mol_type = other DNA
```

```
                        organism = synthetic construct
SEQUENCE: 102
cgagtgaagt tttcccgaag cgcagacgct ccggcatatc agcaaggaca gaatcagctg   60
tataacgaac tgaatttggg acgccgcgag gagtatgacg tgcttgataa acgccggggg  120
agagacccgg aaatgggggg taaacccga agaaagaatc cccaagaagg actctacaat   180
gaactccaga aggataagat ggcggaggcc tactcagaaa taggtatgaa gggcgaacga  240
cgacggggaa aaggtcacga tggcctctac caagggttga gtacggcaac caaagatacg  300
tacgatgcac tgcatatgca ggccctgcct cccaga                            336

SEQ ID NO: 103           moltype = AA   length = 112
FEATURE                  Location/Qualifiers
REGION                   1..112
                         note = Synthetic
source                   1..112
                         mol_type = protein
                         organism = synthetic construct
SEQUENCE: 103
RVKFSRSADA PAYQQGQNQL YNELNLGRRE EYDVLDKRRG RDPEMGGKPR RKNPQEGLYN   60
ELQKDKMAEA YSEIGMKGER RRGKGHDGLY QGLSTATKDT YDALHMQALP PR          112

SEQ ID NO: 104           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 104
gatgggagca acgtggccat                                              20

SEQ ID NO: 105           moltype = AA   length = 11
FEATURE                  Location/Qualifiers
REGION                   1..11
                         note = Synthetic
source                   1..11
                         mol_type = protein
                         organism = synthetic construct
SEQUENCE: 105
RASQDISKYL N                                                       11

SEQ ID NO: 106           moltype = AA   length = 7
FEATURE                  Location/Qualifiers
REGION                   1..7
                         note = Synthetic
source                   1..7
                         mol_type = protein
                         organism = synthetic construct
SEQUENCE: 106
HTSRLHS                                                             7

SEQ ID NO: 107           moltype = AA   length = 9
FEATURE                  Location/Qualifiers
REGION                   1..9
                         note = Synthetic
source                   1..9
                         mol_type = protein
                         organism = synthetic construct
SEQUENCE: 107
QQGNTLPYT                                                           9

SEQ ID NO: 108           moltype = AA   length = 5
FEATURE                  Location/Qualifiers
REGION                   1..5
                         note = Synthetic
source                   1..5
                         mol_type = protein
                         organism = synthetic construct
SEQUENCE: 108
DYGVS                                                               5

SEQ ID NO: 109           moltype = AA   length = 16
FEATURE                  Location/Qualifiers
REGION                   1..16
                         note = Synthetic
source                   1..16
                         mol_type = protein
                         organism = synthetic construct
SEQUENCE: 109
VIWGSETTYY NSALKS                                                  16
```

```
SEQ ID NO: 110           moltype = AA   length = 12
FEATURE                  Location/Qualifiers
REGION                   1..12
                         note = Synthetic
source                   1..12
                         mol_type = protein
                         organism = synthetic construct
SEQUENCE: 110
HYYYGGSYAM DY                                                              12

SEQ ID NO: 111           moltype = AA   length = 11
FEATURE                  Location/Qualifiers
REGION                   1..11
                         note = Synthetic
source                   1..11
                         mol_type = protein
                         organism = synthetic construct
SEQUENCE: 111
RASQDISKYL N                                                               11

SEQ ID NO: 112           moltype = AA   length = 7
FEATURE                  Location/Qualifiers
REGION                   1..7
                         note = Synthetic
source                   1..7
                         mol_type = protein
                         organism = synthetic construct
SEQUENCE: 112
HTSRLHS                                                                     7

SEQ ID NO: 113           moltype = AA   length = 9
FEATURE                  Location/Qualifiers
REGION                   1..9
                         note = Synthetic
source                   1..9
                         mol_type = protein
                         organism = synthetic construct
SEQUENCE: 113
QQGNTLPYT                                                                   9

SEQ ID NO: 114           moltype = AA   length = 7
FEATURE                  Location/Qualifiers
REGION                   1..7
                         note = Synthetic
source                   1..7
                         mol_type = protein
                         organism = synthetic construct
SEQUENCE: 114
GVSLPDY                                                                     7

SEQ ID NO: 115           moltype = AA   length = 5
FEATURE                  Location/Qualifiers
REGION                   1..5
                         note = Synthetic
source                   1..5
                         mol_type = protein
                         organism = synthetic construct
SEQUENCE: 115
WGSET                                                                       5

SEQ ID NO: 116           moltype = AA   length = 12
FEATURE                  Location/Qualifiers
REGION                   1..12
                         note = Synthetic
source                   1..12
                         mol_type = protein
                         organism = synthetic construct
SEQUENCE: 116
HYYYGGSYAM DY                                                              12

SEQ ID NO: 117           moltype = DNA   length = 1518
FEATURE                  Location/Qualifiers
misc_feature             1..1518
                         note = Synthetic
source                   1..1518
                         mol_type = other DNA
                         organism = synthetic construct
SEQUENCE: 117
```

```
atgcttcttt tggttacgtc tctgttgctt tgcgaacttc ctcatccagc gttcttgctg    60
atccccgata ttcagatgac tcagaccacc agtagcttgt ctgcctcact gggagaccga   120
gtaacaatct cctgcagggc aagtcaagac attagcaaat acctcaattg gtaccagcag   180
aagcccgacg gaacggtaaa actcctcatc tatcatacgt caaggttgca ttccggagta   240
ccgtcacgat tttcaggttc tgggagcgga actgactatt ccttgactat ttcaaacctc   300
gagcaggagg acattgcgac atattttgt caacaaggta ataccctccc ttacactttc   360
ggaggaggaa ccaaactcga aattaccggg tccaccagtg gctctgggaa gcctggcagt   420
ggagaaggtt ccactaaagg cgaggtgaag ctccaggaga gcggcccgg tctcgttgcc   480
cccagtcaaa gcctctctgt aacgtgcaca gtgagtggtg tatcattgcc tgattatggc   540
gtctcctgga taaggcagcc cccgcgaaag ggtcttgaat ggcttgggt aatatgggc   600
tcagagacaa cgtattataa ctccgctctc aaaagtcgct tgacgataat aaagataac   660
tccaagagtc aagttttcct taaaatgaac agtttgcaga ctgacgatac cgctatatat   720
tattgtgcta acattatta ctacggcggt agttacgcga tggattattg ggggcagggg   780
acttcgtca cagtcagtag tgctgctgcc tttgtccgg tatttctccc agccaaaccg   840
accacgactc ccgccccgcg ccctccgaca ccgctccca catcgcctc tcaacctctt   900
agtcttcgcc ccgaggcatg ccgacccgcc gccggggtg ctgttcatac gaggggcttg   960
gacttcgctt gtgatattta catttgggct ccgttgcgg gtacgtgcgg cgtccttttg  1020
ttgtcactcg ttattactt gtattgtaat cacaggaatg gctcaaagcg gagtaggttg  1080
ttgcattccg attacatgaa tatgactcct cgccggcctg ggccgacaag aaaacattac  1140
caacccatg ccccccacg agacttgct gcgtacaggt cccgagtgaa gttttcccga  1200
agcgcagacg ctccggcata tcagcaagga cagaatcagc tgtataacga actgaatttg  1260
ggacgccgcg aggagtatga cgtgcttgat aaacgcggg agaggagccc gaaatggggg  1320
ggtaaacccc gaagaaagaa tccccaagaa ggactctaca atgaactcca gaaggataag  1380
atggcggagg cctactcaga aataggtatg aaggcgaac gacgcgggg aaaaggtcac  1440
gatggcctct accaagggtt gagtacggca ccaaagata cgtacgatgc actgcatatg  1500
caggccctgc ctcccaga                                               1518

SEQ ID NO: 118          moltype = AA  length = 506
FEATURE                 Location/Qualifiers
REGION                  1..506
                        note = Synthetic
source                  1..506
                        mol_type = protein
                        organism = synthetic construct
SEQUENCE: 118
MLLLVTSLLL CELPHPAFLL IPDIQMTQTT SSLSASLGDR VTISCRASQD ISKYLNWYQQ    60
KPDGTVKLLI YHTSRLHSGV PSRFSGSGSG TDYSLTISNL EQEDIATYFC QQGNTLPYTF   120
GGGTKLEITG STSGSGKPGS GEGSTKGEVK LQESGPGLVA PSQSLSVTCT VSGVSLPDYG   180
VSWIRQPPRK GLEWLGVIWG SETTYYNSAL KSRLTIIKDN SKSQVFLKMN SLQTDDTAIY   240
YCAKHYYYGG SYAMDYWGQG TSVTVSSAAA FVPVFLPAKP TTTPAPRPPT PAPTIASQPL   300
SLRPEACRPA AGGAVHTRGL DFACDIYIWA PLAGTCGVLL LSLVITLYCN HRNRSKRSRL   360
LHSDYMNMTP RRPGPTRKHY QPYAPPRDFA AYRSRVKFSR SADAPAYQQG QNQLYNELNL   420
GRREEYDVLD KRRGRDPEMG GKPRRKNPQE GLYNELQKDK MAEAYSEIGM KGERRRGKGH   480
DGLYQGLSTA TKDTYDALHM QALPPR                                       506

SEQ ID NO: 119          moltype = DNA  length = 735
FEATURE                 Location/Qualifiers
misc_feature            1..735
                        note = Synthetic
source                  1..735
                        mol_type = other DNA
                        organism = synthetic construct
SEQUENCE: 119
gatattcaga tgactcagac caccagtagc ttgtctgcct cactgggaga ccgagtaaca    60
atctcctgca gggcaagtca agacattagc aaatacctca attgtacca gcagaagcc   120
gacggaacgg taaaactcct catctatcat acgtcaaggt tgcattccgg agtaccgtca   180
cgatttcag ttctgggag cggaactgac tattccttga ctatttcaaa cctcgagcag   240
gaggacattg cgacatattt tgtcaacaa ggtaataccc tccttacac tttcggagga   300
ggaaccaaac tcgaaattac cgggtccacc agtggcctg gaagcctgg cagtggagaa   360
ggttccacta aaggcgaggt gaagctccag gagagcggcc cggtctcgt tgcccccagt   420
caaagcctct ctgtaacgtg cacagtgagt ggtgtatcat tgcctgatta tggcgtctcc   480
tggataaggc agcccccgcg aaagggtctt gaatggcttg ggtaatatg gggctcagag   540
acaacgtatt ataactccgc tctcaaaagt cgcttgacga taataaaga taactccaag   600
agtcaagttt tccttaaaat gaacagtttg cagactgacg ataccgctat atattattgt   660
gctaaacatt attactacgg cggtagttac gcgatggatt attggggca ggggacttct   720
gtcacagtca gtagt                                                   735

SEQ ID NO: 120          moltype = AA  length = 245
FEATURE                 Location/Qualifiers
REGION                  1..245
                        note = Synthetic
source                  1..245
                        mol_type = protein
                        organism = synthetic construct
SEQUENCE: 120
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEITGST SGSGKPGSGE   120
GSTKGEVKLQ ESGPGLVAPS QSLSVTCTVS GVSLPDYGVS WIRQPPRKGL EWLGVIWGSE   180
TTYYNSALKS RLTIIKDNSK SQVFLKMNSL QTDDTAIYYC AKHYYYGGSY AMDYWGQGTS   240
```

VTVSS                                                                                  245

SEQ ID NO: 121          moltype = DNA   length = 261
FEATURE                 Location/Qualifiers
misc_feature            1..261
                        note = Synthetic
source                  1..261
                        mol_type = other DNA
                        organism = synthetic construct
SEQUENCE: 121
gctgctgcct ttgtcccggt atttctccca gccaaaccga ccacgactcc cgccccgcgc   60
cctccgacac ccgctccac catcgcctct caacctctta gtcttcgccc cgaggcatgc   120
cgacccgccg ccggggggtgc tgttcatacg aggggcttgg acttcgcttg tgatatttac  180
atttgggctc cgttggcggg tacgtgcggc gtccttttgt tgtcactcgt tattactttg   240
tattgtaatc acaggaatcg c                                             261

SEQ ID NO: 122          moltype = DNA   length = 252
FEATURE                 Location/Qualifiers
misc_feature            1..252
                        note = Synthetic
source                  1..252
                        mol_type = other DNA
                        organism = synthetic construct
SEQUENCE: 122
tttgtcccgg tatttctccc agccaaaccg accacgactc cgccccgcg ccctccgaca    60
cccgctccac ccatcgcctc tcaacctctt agtcttcgcc ccgaggcatg ccgacccgcc   120
gccgggggtg ctgttcatac gagggggcttg gacttcgctt gtgatattta catttgggct  180
ccgttggcgg gtacgtgcgg cgtccttttg ttgtcactcg ttattacttt gtattgtaat   240
cacaggaatc gc                                                       252

SEQ ID NO: 123          moltype = AA    length = 84
FEATURE                 Location/Qualifiers
REGION                  1..84
                        note = Synthetic
source                  1..84
                        mol_type = protein
                        organism = synthetic construct
SEQUENCE: 123
FVPVFLPAKP TTTPAPRPPT PAPTIASQPL SLRPEACRPA AGGAVHTRGL DFACDIYIWA   60
PLAGTCGVLL LSLVITLYCN HRNR                                          84

SEQ ID NO: 124          moltype = AA    length = 120
FEATURE                 Location/Qualifiers
REGION                  1..120
                        note = Synthetic
source                  1..120
                        mol_type = protein
                        organism = synthetic construct
SEQUENCE: 124
EVKLQESGPG LVAPSQSLSV TCTVSGVSLP DYGVSWIRQP PRKGLEWLGV IWGSETTYYN   60
SALKSRLTII KDNSKSQVFL KMNSLQTDDT AIYYCAKHYY YGGSYAMDYW GQGTSVTVSS   120

SEQ ID NO: 125          moltype = AA    length = 107
FEATURE                 Location/Qualifiers
REGION                  1..107
                        note = Synthetic
source                  1..107
                        mol_type = protein
                        organism = synthetic construct
SEQUENCE: 125
DIQMTQTTSS LSASLGDRVT ISCRASQDIS KYLNWYQQKP DGTVKLLIYH TSRLHSGVPS   60
RFSGSGSGTD YSLTISNLEQ EDIATYFCQQ GNTLPYTFGG GTKLEIT                 107

SEQ ID NO: 126          moltype = AA    length = 18
FEATURE                 Location/Qualifiers
REGION                  1..18
                        note = Synthetic
source                  1..18
                        mol_type = protein
                        organism = synthetic construct
SEQUENCE: 126
GSTSGSGKPG SGEGSTKG                                                 18

SEQ ID NO: 127          moltype = AA    length = 15
FEATURE                 Location/Qualifiers
REGION                  1..15
                        note = Synthetic
source                  1..15
                        mol_type = protein

```
                                        organism = synthetic construct
SEQUENCE: 127
RASKSVSTSG YSFMH                                                            15

SEQ ID NO: 128          moltype = AA  length = 11
FEATURE                 Location/Qualifiers
REGION                  1..11
                        note = Synthetic
source                  1..11
                        mol_type = protein
                        organism = synthetic construct
SEQUENCE: 128
SKSVSTSGYS F                                                                11

SEQ ID NO: 129          moltype = AA  length = 7
FEATURE                 Location/Qualifiers
REGION                  1..7
                        note = Synthetic
source                  1..7
                        mol_type = protein
                        organism = synthetic construct
SEQUENCE: 129
LASNLES                                                                      7

SEQ ID NO: 130          moltype = AA  length = 9
FEATURE                 Location/Qualifiers
REGION                  1..9
                        note = Synthetic
source                  1..9
                        mol_type = protein
                        organism = synthetic construct
SEQUENCE: 130
QHSREVPWT                                                                    9

SEQ ID NO: 131          moltype = AA  length = 6
FEATURE                 Location/Qualifiers
REGION                  1..6
                        note = Synthetic
source                  1..6
                        mol_type = protein
                        organism = synthetic construct
SEQUENCE: 131
SREVPW                                                                       6

SEQ ID NO: 132          moltype = AA  length = 5
FEATURE                 Location/Qualifiers
REGION                  1..5
                        note = Synthetic
source                  1..5
                        mol_type = protein
                        organism = synthetic construct
SEQUENCE: 132
NYGMN                                                                        5

SEQ ID NO: 133          moltype = AA  length = 10
FEATURE                 Location/Qualifiers
REGION                  1..10
                        note = Synthetic
source                  1..10
                        mol_type = protein
                        organism = synthetic construct
SEQUENCE: 133
GYTFTNYGMN                                                                  10

SEQ ID NO: 134          moltype = AA  length = 17
FEATURE                 Location/Qualifiers
REGION                  1..17
                        note = Synthetic
source                  1..17
                        mol_type = protein
                        organism = synthetic construct
SEQUENCE: 134
WINTYTGEPT YADAFKG                                                          17

SEQ ID NO: 135          moltype = AA  length = 6
FEATURE                 Location/Qualifiers
REGION                  1..6
                        note = Synthetic
source                  1..6
```

```
                             mol_type = protein
                             organism = synthetic construct
SEQUENCE: 135
NTYTGE                                                              6

SEQ ID NO: 136           moltype = AA   length = 9
FEATURE                  Location/Qualifiers
REGION                   1..9
                         note = Synthetic
source                   1..9
                         mol_type = protein
                         organism = synthetic construct
SEQUENCE: 136
DYGDYGMDY                                                           9

SEQ ID NO: 137           moltype = AA   length = 14
FEATURE                  Location/Qualifiers
REGION                   1..14
                         note = Synthetic
source                   1..14
                         mol_type = protein
                         organism = synthetic construct
SEQUENCE: 137
CARDYGDYGM DYWG                                                    14

SEQ ID NO: 138           moltype = AA   length = 508
FEATURE                  Location/Qualifiers
REGION                   1..508
                         note = Synthetic
source                   1..508
                         mol_type = protein
                         organism = synthetic construct
SEQUENCE: 138
MALPVTALLL PLALLLHAAR PQVQLVQSGA EVKKPGASVK VSCKASGYTF TNYGMNWVRQ    60
APGQGLKWMG WINTYTGEPT YADAFKGRVT MTRDTSISTA YMELSRLRSD DTAVYYCARD   120
YGDYGMDYWG QGTTVTVSSG GGGSGGGGSG GGGSGDIVMT QSPDSLAVSL GERATINCRA   180
SKSVSTSGYS FMHWYQQKPG QPPKLLIYLA SNLESGVPDR FSGSGSGTDF TLTISSLQAE   240
DVAVYYCQHS REVPWTFGQG TKVEIKSAAA FVPVFLPAKP TTTPAPRPPT PAPTIASQPL   300
SLRPEACRPA AGGAVHTRGL DFACDIYIWA PLAGTCGVLL LSLVITLYCN HRNRKRGRKK   360
LLYIFKQPFM RPVQTTQEED GCSCRFPEEE EGGCELRVKF SRSADAPAYQ QGQNQLYNEL   420
NLGRREEYDV LDKRRGRDPE MGGKPRRKNP QEGLYNELQK DKMAEAYSEI GMKGERRRGK   480
GHDGLYQGLS TATKDTYDAL HMQALPPR                                     508

SEQ ID NO: 139           moltype = DNA   length = 735
FEATURE                  Location/Qualifiers
misc_feature             1..735
                         note = Synthetic
source                   1..735
                         mol_type = other DNA
                         organism = synthetic construct
SEQUENCE: 139
gatatagtta tgacccaatc acccgatagt cttgcggtaa gcctggggga gcgagcaaca    60
ataaactgtc gggcatcaaa atccgtcagt acaagcgggt attcattcat gcactggtat   120
caacagaaac ccggtcagcc acccaagctc ctgatttatc ttgcgtctaa tcttgagtcc   180
ggcgtcccag accggttttc cggctccggg agcggcacgg attttactct tactatttct   240
agccttcagg ccgaagatgt ggcggtatac tactgccagc attcaaggga agttccttgg   300
acgttcggtc agggcacgaa agtggaaatt aaaggcgggg gggatccgg cggggggaggg   360
tctggaggag gtggcagtgg tcaggtccaa ctggtgcagt ccggggcaga ggtaaaaaaa   420
cccggcgcgt ctgttaaggt ttcatgcaag gccagtggat atactttcac caattacgga   480
atgaactggg tgaggcaggc ccctggtcaa ggcctggatg ggatggaatg gataaacacg   540
tacaccggtg aacctaccta tgccgatgcc tttaagggtc gggttacgat gacgagagac   600
acctccatat caacagccta catggagctc agcagattga ggagtgacga tacggcagtc   660
tattactgtg caagagacta cggcgattat ggcatggatt actggggcca gggcactaca   720
gtaaccgttt ccagc                                                   735

SEQ ID NO: 140           moltype = AA   length = 245
FEATURE                  Location/Qualifiers
REGION                   1..245
                         note = Synthetic
source                   1..245
                         mol_type = protein
                         organism = synthetic construct
SEQUENCE: 140
DIVMTQSPDS LAVSLGERAT INCRASKSVS TSGYSFMHWY QQKPGQPPKL LIYLASNLES    60
GVPDRFSGSG SGTDFTLTIS SLQAEDVAVY YCQHSREVPW TFGQGTKVEI KGGGGSGGGG   120
SGGGGSGVQ LVQSGAEVKK PGASVKVSCK ASGYTFTNYG MNWVRQAPGQ GLKWMGWINT   180
YTGEPTYADA FKGRVTMTRD TSISTAYMEL SRLRSDDTAV YYCARDYGDY GMDYWGQGTT   240
VTVSS                                                              245
```

```
SEQ ID NO: 141            moltype = DNA  length = 735
FEATURE                   Location/Qualifiers
misc_feature              1..735
                          note = Synthetic
source                    1..735
                          mol_type = other DNA
                          organism = synthetic construct
SEQUENCE: 141
caggtccagt tggtgcaaag cggggcggag gtgaaaaaac ccggcgcttc cgtgaaggtg    60
tcctgtaagg cgtccggtta tacgttcacg aactacggga tgaattgggt tcgccaagcg   120
ccggggcagg gactgaaatg gatggggtgg ataaatacct acaccggcga acctacatac   180
gccgacgctt ttaaagggcg agtcactatg acgcgcgata ccagcatatc caccgcatac   240
atggagctgt cccgactccg gtcagacgac acggctgtct actattgtgc tcgggactat   300
ggcgattatg gcatggacta ctgggggtcag gtacgactag taacagttag tagtggtgga   360
ggcggcagtg gcggggggggg aagcggagga ggggggttctg gtgacatagt tatgacccaa   420
tccccagata gtttggcggt ttctctgggc gagagggcaa cgattaattg cgcgcatca    480
aagagcgttt caacgagcgg atattctttt atgcattggt accagcaaaa acccggacaa    540
ccgccgaagc tgctgatcta cttggcttca aatcttgagt ctgggtgcc ggaccgattt    600
tctggtagtg gaagcggaac tgactttacg ctcacgatca gttcactgca ggctgaggat    660
gtagcggtct attattgcca gcacagtaga gaagtcccct ggaccttcgg tcaaggcacg    720
aaagtagaaa ttaaa                                                    735

SEQ ID NO: 142            moltype = AA  length = 245
FEATURE                   Location/Qualifiers
REGION                    1..245
                          note = Synthetic
source                    1..245
                          mol_type = protein
                          organism = synthetic construct
SEQUENCE: 142
QVQLVQSGAE VKKPGASVKV SCKASGYTFT NYGMNWVRQA PGQGLKWMGW INTYTGEPTY    60
ADAFKGRVTM TRDTSISTAY MELSRLRSDD TAVYYCARDY GDYGMDYWGQ GTTVTVSSGG   120
GGSGGGGSGG GGSGDIVMTQ SPDSLAVSLG ERATINCRAS KSVSTSGYSF MHWYQQKPGQ   180
PPKLLIYLAS NLESGVPDRF SGSGSGTDFT LTISSLQAED VAVYYCQHSR EVPWTFGQGT   240
KVEIK                                                                245

SEQ ID NO: 143            moltype = AA  length = 118
FEATURE                   Location/Qualifiers
REGION                    1..118
                          note = Synthetic
source                    1..118
                          mol_type = protein
                          organism = synthetic construct
SEQUENCE: 143
QVQLVQSGAE VKKPGASVKV SCKASGYTFT NYGMNWVRQA PGQGLKWMGW INTYTGEPTY    60
ADAFKGRVTM TRDTSISTAY MELSRLRSDD TAVYYCARDY GDYGMDYWGQ GTTVTVSS     118

SEQ ID NO: 144            moltype = AA  length = 111
FEATURE                   Location/Qualifiers
REGION                    1..111
                          note = Synthetic
source                    1..111
                          mol_type = protein
                          organism = synthetic construct
SEQUENCE: 144
DIVMTQSPDS LAVSLGERAT INCRASKSVS TSGYSFMHWY QQKPGQPPKL LIYLASNLES    60
GVPDRFSGSG SGTDFTLTIS SLQAEDVAVY YCQHSREVPW TFGQGTKVEI K            111

SEQ ID NO: 145            moltype = DNA  length = 1524
FEATURE                   Location/Qualifiers
misc_feature              1..1524
                          note = Synthetic
source                    1..1524
                          mol_type = other DNA
                          organism = synthetic construct
SEQUENCE: 145
atggcgcttc cggtgacagc actgctcctc cccttggcgc tgttgctcca cgcagcaagg    60
ccgcaggtgc agctggtgca gagcggagcc gagctcaaga gcccggagc ctccgtgaag    120
gtgagctgca aggccagcgg caacacctg accaactacg tgatccactg ggtgagacaa    180
gcccccggcc aaaggctgga gtggatgggc tacatcctgc cctacaacga cctgaccaag    240
tacagccaga agttccaggg cagggtgacc atcaccaggg ataagagcgc ctccaccgcc    300
tatatggagc tgagcagcct gaggagcgag gacaccgctg tgtactactg tacaaggtgg    360
gactgggacg gcttctttga ccctggggc cagggcacaa cagtgaccgt cagcagcggc    420
ggcggaggaa gcggcggcgg cggaagcggc ggaggaggga gcgaaatcgt gatgacccag    480
agccccgcca cactgagcgt gagccctggc gagagggcca gcatctcctg cagggctagc    540
caaagcctgg tgcacagcaa cggcaacacc cacctgcact ggtaccagca gagacccgga    600
caggctccca ggctgctgat ctacagcgtg agcaacaggt tctccgaggt gcctgccagg    660
tttagcggca gcggaagcgg caccgacttt accctgacca tcagcagcgt ggagtccgag    720
gacttcgccg tgtattactg cagccagacc agccacatcc ttacaccttt cggcggcggc    780
```

```
accaagctgg agatcaaaag tgctgctgcc tttgtcccgg tatttctccc agccaaaccg    840
accacgactc ccgccccgcg ccctccgaca cccgctccca ccatcgcctc tcaacctctt    900
agtcttcgcc ccgaggcatg ccgacccgcc gccggggtg ctgttcatac gaggggcttg    960
gacttcgctt gtgatattta catttgggct ccgttggcgg gtacgtgcgg cgtccttttg   1020
ttgtcactcg ttattacttt gtattgtaat cacaggaatc gcaaacgggg cagaaagaaa   1080
ctcctgtata tattcaaaca accatttatg agaccagtac aaactactca agaggaagat   1140
ggctgtagct gccgatttcc agaagaagaa gaaggaggat gtgaactgcg agtgaagttt   1200
tcccgaagcg cagacgctcc ggcatatcag caaggacaga atcagctgta taacgaactg   1260
aatttgggac gccgcgagga gtatgacgtg cttgataaac gccggggag agacccggag   1320
atgggggta aaccccgaag aaagaatccc caagaaggac tctacaatga actccagaag   1380
gataagatgg cggaggccta ctcagaaata ggtatgaagg gcgaacgacg acggggaaaa   1440
ggtcacgatg gcctctacca agggttgagt acggcaacca agatacgta cgatgcactg   1500
catatgcagg ccctgcctcc caga                                           1524
```

```
SEQ ID NO: 146          moltype = AA   length = 508
FEATURE                 Location/Qualifiers
REGION                  1..508
                        note = Synthetic
source                  1..508
                        mol_type = protein
                        organism = synthetic construct
SEQUENCE: 146
MALPVTALLL PLALLLHAAR PQVQLVQSGA ELKKPGASVK VSCKASGNTL TNYVIHWVRQ     60
APGQRLEWMG YILPYNDLTK YSQKFQGRVT ITRDKSASTA YMELSSLRSE DTAVYYCTRW    120
DWDGFFDPWG QGTTVTVSSG GGGSGGGGSG GGGSEIVMTQ SPATLSVSPG ERASISCRAS    180
QSLVHSNGNT HLHWYQQRPG QAPRLLIYSV SNRFSEVPAR FSGSGSGTDF TLTISSVESE    240
DFAVYYCSQT SHIPYTFGGG TKLEIKSAAA FVPVFLPAKP TTTPAPRPPT PAPTIASQPL    300
SLRPEACRPA AGGAVHTRGL DFACDIYIWA PLAGTCGVLL LSLVITLYCN HRNRKRGRKK    360
LLYIFKQPFM RPVQTTQEED GCSCRFPEEE EGGCELRVKF SRSADAPAYQ QGQNQLYNEL    420
NLGRREEYDV LDKRRGRDPE MGGKPRRKNP QEGLYNELQK DKMAEAYSEI GMKGERRRGK    480
GHDGLYQGLS TATKDTYDAL HMQALPPR                                      508
```

```
SEQ ID NO: 147          moltype = DNA   length = 735
FEATURE                 Location/Qualifiers
misc_feature            1..735
                        note = Synthetic
source                  1..735
                        mol_type = other DNA
                        organism = synthetic construct
SEQUENCE: 147
caggtgcagc tggtgcagag cggagccgag ctcaagaagc ccggagcctc cgtgaaggtg     60
agctgcaagg ccagcggcaa caccctgacc aactacgtga tccactgggt gagacaagcc    120
cccgggcaaa ggctggagtg gatgggctac atcctgcct acaacgacct gaccaagtac    180
agccagaagt tccagggcag ggtgaccatc accaggata gagcgcctc caccgcctat     240
atggagctga gcagcctgag gagcgaggac ccgctgtgt actactgac aaggtgggac    300
tgggacggct tctttgaccc ctggggccag ggcacaacag tgaccgtcag cagcggcggc    360
ggaggcagcg gcggcggcgg cagcggcgga ggcggaagcg aaatcgtgat gacccagagc    420
cccgccacac tgagcgtgag ccctggcgag agggccagca tctcctgcag ggctagccaa    480
agcctggtgc acagcaacgg caacacccac ctgcactggt accagcagag acccggacag    540
gctcccagcc tgctgatcta cagcgtgagc aacaggttct ccgaggtgcc tgccaggttt    600
agcggcagcg gaagcggcac cgactttacc ctgaccatca gcagcgtgga gtccgaggac    660
ttcgccgtgt attactgcag ccagaccagc cacatccctt acaccttcgg cggcggcacc    720
aagctgggaga tcaaa                                                   735
```

```
SEQ ID NO: 148          moltype = AA   length = 245
FEATURE                 Location/Qualifiers
REGION                  1..245
                        note = Synthetic
source                  1..245
                        mol_type = protein
                        organism = synthetic construct
SEQUENCE: 148
QVQLVQSGAE LKKPGASVKV SCKASGNTLT NYVIHWVRQA PGQRLEWMGY ILPYNDLTKY     60
SQKFQGRVTI TRDKSASTAY MELSSLRSED TAVYYCTRWD WDGFFDPWGQ GTTVTVSSGG    120
GGSGGGGSGG GGSEIVMTQS PATLSVSPGE RASISCRASQ SLVHSNGNTH LHWYQQRPGQ    180
APRLLIYSVS NRFSEVPARF SGSGSGTDFT LTISSVESED FAVYYCSQTS HIPYTFGGGT    240
KLEIK                                                               245
```

```
SEQ ID NO: 149          moltype = AA   length = 118
FEATURE                 Location/Qualifiers
REGION                  1..118
                        note = Synthetic
source                  1..118
                        mol_type = protein
                        organism = synthetic construct
SEQUENCE: 149
QVQLVQSGAE LKKPGASVKV SCKASGNTLT NYVIHWVRQA PGQRLEWMGY ILPYNDLTKY     60
SQKFQGRVTI TRDKSASTAY MELSSLRSED TAVYYCTRWD WDGFFDPWGQ GTTVTVSS      118
```

```
SEQ ID NO: 150            moltype = AA  length = 112
FEATURE                   Location/Qualifiers
REGION                    1..112
                          note = Synthetic
source                    1..112
                          mol_type = protein
                          organism = synthetic construct
SEQUENCE: 150
EIVMTQSPAT LSVSPGERAS ISCRASQSLV HSNGNTHLHW YQQRPGQAPR LLIYSVSNRF    60
SEVPARFSGS GSGTDFTLTI SSVESEDFAV YYCSQTSHIP YTFGGGTKLE IK           112

SEQ ID NO: 151            moltype = AA  length = 16
FEATURE                   Location/Qualifiers
REGION                    1..16
                          note = Synthetic
source                    1..16
                          mol_type = protein
                          organism = synthetic construct
SEQUENCE: 151
RASQSLVHSN GNTHLH                                                    16

SEQ ID NO: 152            moltype = AA  length = 7
FEATURE                   Location/Qualifiers
REGION                    1..7
                          note = Synthetic
source                    1..7
                          mol_type = protein
                          organism = synthetic construct
SEQUENCE: 152
SVSNRFS                                                               7

SEQ ID NO: 153            moltype = AA  length = 9
FEATURE                   Location/Qualifiers
REGION                    1..9
                          note = Synthetic
source                    1..9
                          mol_type = protein
                          organism = synthetic construct
SEQUENCE: 153
SQTSHIPYT                                                             9

SEQ ID NO: 154            moltype = AA  length = 9
FEATURE                   Location/Qualifiers
REGION                    1..9
                          note = Synthetic
source                    1..9
                          mol_type = protein
                          organism = synthetic construct
SEQUENCE: 154
SQTSHIPYT                                                             9

SEQ ID NO: 155            moltype = AA  length = 5
FEATURE                   Location/Qualifiers
REGION                    1..5
                          note = Synthetic
source                    1..5
                          mol_type = protein
                          organism = synthetic construct
SEQUENCE: 155
NYVIH                                                                 5

SEQ ID NO: 156            moltype = AA  length = 7
FEATURE                   Location/Qualifiers
REGION                    1..7
                          note = Synthetic
source                    1..7
                          mol_type = protein
                          organism = synthetic construct
SEQUENCE: 156
GNTLTNY                                                               7

SEQ ID NO: 157            moltype = AA  length = 17
FEATURE                   Location/Qualifiers
REGION                    1..17
                          note = Synthetic
source                    1..17
                          mol_type = protein
                          organism = synthetic construct
SEQUENCE: 157
```

YILPYNDLTK YSQKFQG 17

SEQ ID NO: 158        moltype = AA   length = 6
FEATURE               Location/Qualifiers
REGION                1..6
                      note = Synthetic
source                1..6
                      mol_type = protein
                      organism = synthetic construct
SEQUENCE: 158
LPYNDL 6

SEQ ID NO: 159        moltype = AA   length = 9
FEATURE               Location/Qualifiers
REGION                1..9
                      note = Synthetic
source                1..9
                      mol_type = protein
                      organism = synthetic construct
SEQUENCE: 159
WDWDGFFDP 9

SEQ ID NO: 160        moltype = AA   length = 9
FEATURE               Location/Qualifiers
REGION                1..9
                      note = Synthetic
source                1..9
                      mol_type = protein
                      organism = synthetic construct
SEQUENCE: 160
WDWDGFFDP 9

SEQ ID NO: 161        moltype = DNA  length = 145
FEATURE               Location/Qualifiers
misc_feature          1..145
                      note = Synthetic
source                1..145
                      mol_type = other DNA
                      organism = synthetic construct
SEQUENCE: 161
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg    120
gccaactcca tcactagggg ttcct                                          145

SEQ ID NO: 162        moltype = DNA  length = 130
FEATURE               Location/Qualifiers
misc_feature          1..130
                      note = Synthetic
source                1..130
                      mol_type = other DNA
                      organism = synthetic construct
SEQUENCE: 162
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
agggggttcct                                                          130

SEQ ID NO: 163        moltype = DNA  length = 145
FEATURE               Location/Qualifiers
misc_feature          1..145
                      note = Synthetic
source                1..145
                      mol_type = other DNA
                      organism = synthetic construct
SEQUENCE: 163
aggaacccct agtgatggag ttggccactc cctctctgcg cgctcgctcg ctcactgagg     60
ccgcccgggc aaagcccggg cgtcgggcga cctttggtcg cccggcctca gtgagcgagc    120
gagcgcgcag agagggagtg gccaa                                          145

SEQ ID NO: 164        moltype = DNA  length = 141
FEATURE               Location/Qualifiers
misc_feature          1..141
                      note = Synthetic
source                1..141
                      mol_type = other DNA
                      organism = synthetic construct
SEQUENCE: 164
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc    120
gagcgcgcag ctgcctgcag g                                              141

```
SEQ ID NO: 165            moltype = DNA  length = 800
FEATURE                   Location/Qualifiers
misc_feature              1..800
                          note = Synthetic
source                    1..800
                          mol_type = other DNA
                          organism = synthetic construct
SEQUENCE: 165
gagatgtaag gagctgctgt gacttgctca aggccttata tcgagtaaac ggtagtgctg   60
gggcttagac gcaggtgttc tgatttatag ttcaaaacct ctatcaatga gagagcaatc  120
tcctggtaat gtgatagatt tcccaactta atgccaacat accataaacc tcccattctg  180
ctaatgccca gcctaagttg gggagaccac tccagattcc aagatgtaca gtttgctttg  240
ctgggccttt ttcccatgcc tgcctttact ctgccagagt tatattgctg gggttttgaa  300
gaagatccta ttaaataaaa gaataagcag tattattaag tagccctgca tttcaggttt  360
ccttgagtgg caggccaggc ctggccgtga acgttcactg aaatcatggc ctcttggcca  420
agattgatag cttgtgcctg tccctgagtc ccagtccatc acgagcagct ggtttctaag  480
atgctatttc ccgtataaag catgagaccg tgacttgcca gccccacaga gccccgccct  540
tgtccatcac tggcatctgg actccagcct gggttgggc aaagagggaa atgagatcat   600
gtcctaaccc tgatcctctt gtcccacaga tatccagaac cctgaccctg ccgtgtacca  660
gctgagagac tctaaatcca gtgacaagtc tgtctgccta ttcaccgatt ttgattctca  720
aacaaatgtg tcacaaagta aggattctga tgtgtatatc acagacaaaa ctgtgctaga  780
catgaggtct atggacttca                                              800

SEQ ID NO: 166            moltype = DNA  length = 804
FEATURE                   Location/Qualifiers
misc_feature              1..804
                          note = Synthetic
source                    1..804
                          mol_type = other DNA
                          organism = synthetic construct
SEQUENCE: 166
tggagcaaca aatctgactt tgcatgtgca acgccttca acaacagcat tattccagaa    60
gacaccttct tccccagccc aggtaagggc agctttggtg ttctcgcagg ctgtttcctt  120
gcttcaggaa tggccaggtt ctgcccagag ctctggtcaa tgatgtctaa aactcctctg  180
attggtggtc tcggccttat ccattgccac caaaaccctc tttttactaa gaaacagtga  240
gccttgttct ggcagtccag agaatgacac gggaaaaaag cagatgaaga gaaggtggca  300
ggagagggca cgtggcccag cctcagtctc tccaactgag ttcctgcctg cctgcctttg  360
ctcagactgt ttgcccctta ctgctcttct aggcctcatt ctaagcccct tctccaagtt  420
gcctctcctt atttctccct gtctgccaaa aaatctttcc cagctcacta agtcagtctc  480
acgcagtcac tcattaaccc accaatcact gattgtgccg gcacatgaat gcaccaggtg  540
ttgaagtgga ggaattaaaa agtcagatga ggggtgtgcc cagaggaagc accattctag  600
ttggggagc ccatctgtca gctgggaaaa gtccaaataa cttcagattg gaatgtgttt   660
taactcaggg ttgagaaaac agctaccttc aggacaaaag tcaggaagg gctctctgaa   720
gaaatgctac ttgaagatac cagccctacc aagggcaggg agaggaccct atagaggcct  780
gggacaggag ctcaatgaga aagg                                         804

SEQ ID NO: 167            moltype = DNA  length = 1178
FEATURE                   Location/Qualifiers
misc_feature              1..1178
                          note = Synthetic
source                    1..1178
                          mol_type = other DNA
                          organism = synthetic construct
SEQUENCE: 167
ggctccggtg cccgtcagtg ggcagagcgc acatcgccca cagtccccga gaagttgggg   60
ggaggggtcg gcaattgaac cggtgcctag agaaggtggc gcggggtaaa ctgggaaagt  120
gatgtcgtgt actggctccg ccttttccc gagggtgggg gagaaccgta tataagtgca   180
gtagtcgccg tgaacgttct ttttcgcaac gggtttgccg ccagaacaca ggtaagtgcc  240
gtgtgtggtt cccgcgggcc tggcctcttt acgggttatg gcccttgcgt gccttgaatt  300
acttccactg gctgcagtac gtgattcttg atcccgagct tcgggttgga agtgggtggg  360
agagttcgag gccttgcgct taaggagccc cttcgcctcg tgcttgagtt gaggcctggc  420
ctgggcgctg gggccgccgc gtgcgaatct ggtggcacct tcgcgcctgt ctcgctgctt  480
tcgataagtc tctagccatt taaaatttt gatgacctgc tgcgacgtt tttttcgttt    540
aagatagtct tgtaaatgcg ggccaagatc tgcacactgg tatttcggtt tttggggccg  600
cgggcggcga cggggcccgt gcgtcccagc gcacatgttc ggcgaggcgg ggcctgcgag  660
cgcggccacc gagaatcgga cggggtagt ctcaagctgg ccggcctgct ctggtgcctg   720
gcctcgcgc gccgtgtatc gccccgccc gggcggcaag gctggcccgg tcggcaccag    780
ttgcgtgagc ggaaagatgg ccgcttccg gccctgcga aatggagga                840
cgcggcgctc gggagagcgg gcgggtgagt cacccacaca aaggaaaagg gccttttccgt 900
cctcagccgt cgcttcatgt gactccacgg agtaccgggc gccgtccagg cacctcgatt  960
agttctcgag cttttggagt acgtcgtctt taggttgggg ggaggggttt tatgcgatgg 1020
agtttcccca cactgagtgg gtggagactg aagttaggcc agcttggcac ttgatgtaat 1080
tctccttgga atttgccctt tttgagtttg gatcttggtt cattctcaag cctcagacag 1140
tggttcaaag ttttttttctt ccatttcagg tgtcgtga                        1178

SEQ ID NO: 168            moltype = DNA  length = 4358
FEATURE                   Location/Qualifiers
misc_feature              1..4358
```

|  | note = Synthetic |
| --- | --- |
| source | 1..4358 |
|  | mol_type = other DNA |
|  | organism = synthetic construct |

SEQUENCE: 168

```
gagatgtaag gagctgctgt gacttgctca aggccttata tcgagtaaac ggtagtgctg    60
gggcttagac gcaggtgttc tgatttatag ttcaaaacct ctatcaatga gagagcaatc   120
tcctggtaat gtgatagatt tcccaactta atgccaacat accataaacc tcccattctg   180
ctaatgccca gcctaagttg gggagaccac tccagattcc aagatgtaca gtttgctttg   240
ctgggccttt ttcccatgcc tgcctttact ctgccagagt tatattgctg gggttttgaa   300
gaagatccta ttaaataaaa gaataagcag tattattaag tagccctgca tttcaggttt   360
ccttgagtgg caggccaggc ctggccgtga acgttcactg aaatcatggc ctcttggcca   420
agattgatag cttgtgcctg tccctgagtc ccagtccatc acgagcagct ggtttctaag   480
atgctatttc ccgtataaag catgagaccg tgacttgcca gccccacaga gccccgccct   540
tgtccatcac tggcatctgg actccagcct gggttggggc aaagagggaa atgagatcat   600
gtcctaaccc tgatcctctt gtcccacaga tatccagaac cctgaccctg ccgtgtacca   660
gctgagagac tctaaatcca gtgacaagtc tgtctgccta ttcaccgatt ttgattctca   720
aacaaatgtg tcacaaagta aggattctga tgtgtatatc acagacaaaa ctgtgctaga   780
catgaggtct atggacttca ggctccggtg cccgtcagtg ggcagagcgc acatcgccca   840
cagtccccga gaagttgggg ggaggggtcg gcaattgaac cggtgcctag agaaggtggc   900
gcggggtaaa ctgggaaagt gatgtcgtgt actggctccg ccttttttccc gagggtgggg   960
gagaaccgta tataagtgca gtagtcgccg tgaacgttct ttttcgcaac gggtttgccg  1020
ccagaacaca ggtaagtgcc gtgtgtggtt cccgcgggcc tggcctcttt acgggttatg  1080
gcccttgcgt gccttgaatt acttccactg gctgcagtac gtgattcttg atcccgagct  1140
tcgggttgga agtgggtggg agagttcgag gccttgcgct taaggagccc cttcgcctcg  1200
tgcttgagtt gaggcctggc ctgggcgctg gggccgccgc gtcgaatct ggtgcacct  1260
tcgcgcctgt ctcgctgctt tcgataagtc tctagccatt taaaattttt gatgacctgc  1320
tgcgacgctt ttttttctggc aagatagtct tgtaaatgcg ggccaagatc tgcacactgg  1380
tatttcggtt tttggggccg cggcggcga cggggcccgt gcgtcccagc gcacatgttc  1440
ggcgagggcgg ggcctgcgag cgcggccacc gagaatcgga cggggtagt ctcaagctgg  1500
ccggcctgct ctggtgcctg gcctcgcgcc gccgtgtatc gccccgcccct gggcggcaag  1560
gctgcccggg tcggcaccag ttgcgtgagc ggaaagatgg ccgcttccg gccctgctgc  1620
agggagctca aaatggagga cgcggcgctc gggagagcgg gcgggtgagt cacccacaca  1680
aaggaaaagg gccttttccgt cctcagccgt cgcttcatgt gactccacgg agtaccgggc  1740
gccgtccagg cacctcgatt agttctcgag cttttgagtt acgtcgtctt taggttgggg  1800
ggaggggttt tatgcgatgg agtttcccca cactgagtgg gtggagactg aagttaggcc  1860
agcttggcac ttgatgtaat tctccttgga atttgccctt tttgagtttg gatcttggtt  1920
cattctcaag cctcagacag tggttcaaag ttttttttctt ccatttcagg tgtccgtgacc  1980
accatgcttc ttttggttac gtctctgttg ctttgcgaac ttcctcatcc agcgttcttg  2040
ctgatccccg atattcagat gactcagacc accagtagct tgtctgcctc actgggagac  2100
cgagtaacaa tctcctgcag ggcaagtcaa gacattagca aatacctcaa ttggtaccag  2160
cagaagcccg acggaacggt aaaactcctc atctatcata cgtcaaggtt gcattccgga  2220
gtaccgtcac gattttcagg ttctgggagc ggaactgact attccttgac tatttcaaac  2280
ctcgagcagg aggacattgc gacatatttt tgtcaacaag gtaatacct cccttacact  2340
ttcggaggag gaaccaaact cgaaattacc gggtccacca gtggctctgg gaagcctggc  2400
agtggagaag gttccactaa aggcgaggtg aagctccagg agagcggccc cggtctcgtt  2460
gcccccagtc aaagcctctc tgtaacgtgc acagtgagtg gtgtatcatt gcctgattat  2520
ggcgtctcct ggataaggca gccccgcgca aagggtcttg aatggcttgg ggtaatatgg  2580
ggctcagaga caacgtatta taactccgct ctcaaaagtc gcttgacgat aataaaagat  2640
aactccaaga gtcaagtttt ccttaaaatg aacagtttgc agactgacga taccgctata  2700
tattattgtg ctaaacatta ttactacggc ggtagttacg cgatggatta ttgggggcag  2760
gggacttctg tcacagtcag tagtgctgct gcctttgtcc cggtattct cccagccaaa  2820
ccgaccacga ctcccgcccc gcgccctccg acacccgctc ccaccatcgc ctctcaacct  2880
cttagtcttc gccccgaggc atgccgaccc gccgccgggg gtgctgttca tacgaggggc  2940
ttggacttcg cttgtgatat ttacatttgg gctccgttgg cgggtacgtc cggcgtcctt  3000
ttgttgtcac tcgttattac tttgtattgt aatcacagga atcgctcaaa gcggagtagg  3060
ttgttgcatt ccgattacat gaatatgact cctcgccggc ctgggccgac aagaaaacat  3120
taccaaccct atgcccccc acgagacttc gctgcgtaca ggtcccgagt gaagttttcc  3180
cgaagcgcag acgctccggc atatcagcaa ggacagaatc agctgtataa cgaactgaat  3240
ttgggacgcc gcgaggagta tgacgtgctt gataaacgcc ggggagaga cccggaaatg  3300
gggggtaaac cccgaagaaa gaatcccaa aaggactct acaatgaact ccagaaggat  3360
aagatgcgcc aggcctactc agaaataggt atgaagggcg aacgacgacg gggaaaaggt  3420
cacgatggcc tctaccaagg gttgagtacg gcaaccaaag atacgtacga tgcactgcat  3480
atgcaggccc tgcctcccag ataataataa aatcgctatc catcgaagat ggatgtgtgt  3540
tggttttttg tgtgtggagc aacaaatctg actttgcatg tgcaaacgcc ttcaacaaca  3600
gcattattcc agaagacacc ttcttcccca gcccaggtaa gggcagcttt ggtgccttcg  3660
caggctgttt ccttgcttca ggaatggcca ggttctgccc agagctctgg tcaatgatgt  3720
ctaaaactcc tctgattggt ggtctcggcc ttatccattg ccaccaaaac cctcttttta  3780
ctaagaaaca gtgagccttg ttctggcagt ccagagaatg acacgggaaa aaagcagatg  3840
aagagaaggt ggcaggagag ggcacgtggc ccagcctcag tctctccaac tgagttcctg  3900
cctgcctgcc tttgctcaga ctgtttgccc cttactgctc ttctaggcct cattctaagc  3960
ccccttctcca agttgcctct ccttatttct ccctgtctgc caaaaaatct ttcccagctc  4020
actaagtcag tctcacgcag tcactcatta acccaccaat cactgattgt gccggcacat  4080
gaatgcacca ggtgttgaag tggaggaatt aaaaagtcag atgagggtg tgcccagagg  4140
aagcaccatt ctagttgggg gagcccatct gtcagctggg aaaagtccaa ataacttcag  4200
attggaatgt gttttaactc agggttgaga aaacagctac cttcaggaca aaagtcaggg  4260
aagggctctc tgaagaaatg ctacttgaag ataccagccc taccaagggc agggagagga  4320
ccctatagag gcctgggaca ggagctcaat gagaaagg                          4358
```

SEQ ID NO: 169   moltype = DNA   length = 4364
FEATURE          Location/Qualifiers
misc_feature     1..4364
                 note = Synthetic
source           1..4364
                 mol_type = other DNA
                 organism = synthetic construct SEQUENCE: 169
gagatgtaag gagctgctgt gacttgctca aggccttata tcgagtaaac ggtagtgctg   60
gggcttagac gcaggtgttc tgatttatag ttcaaaacct ctatcaatga gagagcaatc   120
tcctggtaat gtgatagatt tcccaactta atgccaacat accataaacc tcccattctg   180
ctaatgccca gcctaagttg gggagaccac tccagattcc aagatgtaca gtttgctttg   240
ctgggccttt ttcccatgcc tgcctttact ctgccagagt tatattgctg gggttttgaa   300
gaagatccta ttaaataaaa gaataagcag tattattaag tagccctgca tttcaggttt   360
ccttgagtgg caggccaggc ctggccgtga acgttcactg aaatcatggc ctcttggcca   420
agattgatag cttgtgcctg tccctgagtc ccagtccatc acgagcagct ggtttctaag   480
atgctatttc ccgtataaag catgagaccg tgacttgcca gccccacaga gccccgccct   540
tgtccatcac tggcatctgg actccagcct gggttgggc aaagagggaa atgagatcat   600
gtcctaaccc tgatcctctt gtcccacaga tatccagaac cctgaccctg ccgtgtacca   660
gctgagagac tctaaatcca gtgacaagtc tgtctgccta ttcaccgatt tgattctca   720
aacaaatgtg tcacaaagta aggattctga tgtgtatatc acagacaaaa ctgtgctaga   780
catgaggtct atggacttca ggctccggtg cccgtcagtg ggcagagcgc acatcgccca   840
cagtccccga gaagttgggg ggaggggtcg gcaattgaac cggtgcctag agaaggtggc   900
gcggggtaaa ctgggaaagt gatgtcgtgt actggctccg cctttttccc gagggtgggg   960
gagaaccgta tataagtgca gtagtcgccg tgaacgttct ttttcgcaac gggtttgccg  1020
ccagaacaca ggtaagtgcc gtgtgtggtt cccgcgggcc tggcctcttt acgggttatg  1080
gcccttgcgt gccttgaatt acttccactg gctgcagtac gtgattcttg atcccgagct  1140
tcggggttgga agtgggtggg agagttcgag gccttgcgct taaggagccc cttcgcctcg  1200
tgcttgagtt gaggcctggc ctgggcgctg gggccgccgc gtgcgaatct ggtggcacct  1260
tcgcgcctgt ctcgctgctt tcgataagtc tctagccatt taaaattttt gatgacctgc  1320
tgcgacgctt ttttctggc aagatagtct tgtaaatgcg ggccaagatc tgcacactgg  1380
tatttcggtt tttggggccg cgggcggcga cggggcccgt gcgtcccagc gcacatgttc  1440
ggcgaggcgg ggcctgcgag cgcggccacc gagaatcgga cggggtagt ctcaagctgg  1500
ccggcctgct ctggtgcctg gcctcgcgcc gccgtgtatc gccccgccct gggcggcaag  1560
gctggcccgg tcggcaccag ttgcgtgagc ggaaagatgg ccgcttccg gccctgctgc  1620
agggagctca aaatggagga cgcggcgctc gggagagcgg gcgggtgagt cacccacaca  1680
aaggaaaagg gcctttccgt cctcagccgt cgcttcatgt gactccacgg agtaccgggc  1740
gccgtccagg cacctcgatt agttctcgag cttttggagt acgtcgtctt taggttgggg  1800
ggaggggttt tatgcgatgg agtttcccca cactgagtgg gtggagactg aagttaggcc  1860
agcttggcac ttgatgtaat tctccttgga atttgccctt tttgagtttg gatcttggtt  1920
cattctcaag cctcagacag tggttcaaag tttttttctt ccatttcagg tgtcgtgacc  1980
accatggcgc ttccggtgac agcactgctc tcccccttgg cgctgttgct ccacgcagca  2040
aggccgacag tccagttggt gcaaagcggg gcggaggtga aaaaacccgg gcttccgtg  2100
aaggtgtcct gtaaggcgtc cggttatacg ttcacgaact acgggatgaa ttgggttcgc  2160
caagcgccgg ggcagggact gaaatggatg gggtggataa atacctacac cggcgaacct  2220
acatacgccg acgcttttaa agggcgagtc actatgacgc gcgataccag catatccacc  2280
gcatacatgg agctgtcccg actccggtca gacgacacgg ctgtctacta ttgtgctcgg  2340
gactatggcg attatggcat ggactactgg ggtcagggta cgactgtaac agttagtagt  2400
ggtgaggcg gcagtggcgg gggggaagc ggaggagggg gttctggtga catagttatg  2460
acccaatccc cagatagttt ggcggttct ctgggcgaga gggcaacgat taattgtcgc  2520
gcatcaaaga gcgtttcaac gagcggatat tctttttatgc attggtacca gcaaaaaccc  2580
ggacaaccgc cgaagctgct gatctacttg gcttcaaatc ttgagtctgg ggtgccggac  2640
cgattttctg gtagtggaag cggaactgac tttacgctca cgatcagttc actgcaggct  2700
gaggatgtag cggtctatta ttgccagcac agtagagaag tccctggac cttcggtcaa  2760
ggcacgaaag tagaaattaa aagtgctgct gcctttgtcc cggtatttct cccagccaaa  2820
ccgaccacga ctcccgcccc gcgccctccg acaccgctc ccaccatcgc ctctcaacct  2880
cttagtcttc gccccgaggc atgccgaccc gccgcggg gtgctgttca tacgagggc  2940
ttggacttcg cttgtgatat ttacatttgg gctccgttgg cgggtacgtg cggcgtcctt  3000
ttgttgtcac tcgttattac tttgtattgt aatcacagga atcgcaaacg gggcagaaag  3060
aaactcctgt atatattcaa acaaccattt atgagaccag tacaaactac tcaaggaa   3120
gatggctgta gctgccgatt tccagaagaa gaagaaggag gatgtgaact gcagtgaag   3180
ttttcccgaa gcgcagacgc tccggcatat cagcaaggac agaatcagct gtataacgaa  3240
ctgaatttgg gacgccgcga ggagtatgac gtgcttgata acgccgggg gagagacccg  3300
gaaatggggg gtaaacccg aagaaagaat ccccaagaag gactctacaa tgaactccag  3360
aaggataaga tggcggaggc ctactcagaa ataggtatga agggcaacg acgacggga  3420
aaaggtcacg atggcctcta ccaagggttg agtacggcaa ccaaagatac gtacgatgca  3480
ctgcatatgc aggccctgcc tcccagataa taataaaatc gctatccatc gaagatggat  3540
gtgtgttggt tttttgtgtg tggagcaaca aatctgactt tgcatgtgca aacgcctca   3600
acaacagcat tattccagaa gacaccttct tccccagccc aggtaagggc agctttggtg  3660
ccttcgcagg ctgtttcctt gcttcaggaa tggccaggtt ctgcccagag ctctggtcaa  3720
tgatgtctaa aactcctctg attggtggtc tcggccttat ccattgccac caaaaccctc  3780
tttttactaa gaaacagtga gccttgttct ggcagtccag agaatgacac gggaaaaaag  3840
cagatgaaga gaaggtggca ggagagggca cgtggcccga cctcagtctc tccaactgag  3900
ttcctgcctg cctgccttta ctcagactgt ttgcccttca tgctcttcc aggcctcatt  3960
ctaagcccct tctccaagtt gcctctcctt atttctccct gtctgccaaa aaatctttcc  4020
cagctcacta agtcagtctc acgcagtcac tcattaaccc accaatcact gattgtgccg  4080
gcacatgaat gcaccaggtg ttgaagtgga ggaattaaaa agtcagatga gggtgtgcc   4140
cagaggaagc accattctag ttgggggagc ccatctgtca gctgggaaaa gtccaaataa  4200
cttcagattg gaatgtgttt taactcaggg ttgagaaaac agctaccttc aggacaaaag  4260

```
tcagggaagg gctctctgaa gaaatgctac ttgaagatac cagccctacc aagggcaggg   4320
agaggaccct atagaggcct gggacaggag ctcaatgaga aagg                   4364

SEQ ID NO: 170         moltype = DNA   length = 4364
FEATURE                Location/Qualifiers
misc_feature           1..4364
                       note = Synthetic
source                 1..4364
                       mol_type = other DNA
                       organism = synthetic construct
SEQUENCE: 170
gagatgtaag gagctgctgt gacttgctca aggcctttata tcgagtaaac ggtagtgctg   60
gggcttagac gcaggtgttc tgatttatag ttcaaaacct ctatcaatga gagagcaatc   120
tcctggtaat gtgatagatt tcccaactta atgccaacat accataaacc tcccattctg   180
ctaatgccca gcctaagttg gggagaccac tccagattcc aagatgtaca gtttgctttg   240
ctgggccttt ttcccatgcc tgcctttact ctgccagagt tatattgctg gggttttgaa   300
gaagatccta ttaaataaaa gaataagcag tattattaag tagccctgca tttcaggttt   360
ccttgagtgg caggccaggc ctggccgtga acgttcactg aaatcatggc tcttggcca    420
agattgatag cttgtgcctg tccctgagtc ccagtccatc acgagcagct ggtttctaag   480
atgctatttc ccgtataaag catgagaccg tgacttgcca gccccacaga gccccgccct   540
tgtccatcac tggcatctgg actccagcct gggttgggc aaagagggaa atgagatcat    600
gtcctaaccc tgatcctctt gtcccacaga tatccagaac ctgacccctg ccgtgtacca   660
gctgagagac tctaaatcca gtgacaagtc tgtctgccta ttcaccgatt ttgattctca   720
aacaaatgtg tcacaaagta aggattctga tgtgtatatc acagacaaaa ctgtgctaga   780
catgaggtct atggacttca ggctccggtg cccgtcagtg ggcagagcgc acatcgccca   840
cagtcccga gaagttgggg gaggggtcg caattgaac cggtgcctag agaaggtggt     900
gcggggtaaa ctgggaaagt gatgtcgtgt actggctccg ccttttccc gagggtgggg    960
gagaaccgta tataagtgca gtagtcgccg tgaacgttct ttttcgcaac gggttttgccg  1020
ccagaacaca ggtaagtgcc gtgtgtggtt cccgcgggcc tggcctcttt acgggttatg   1080
gcccttgcgt gccttgaatt acttccactg gctgcagtac gtgattcttg atcccgagct   1140
tcgggtttga agtgggtggg agagttcgag gccttgcgct taaggagccc cttcgcctcg   1200
tgcttgagtt gaggcctggc ctgggcgctg gggccgccgc gtgcgaatct ggtggcacct   1260
tcgcgcctgt ctcgctgctt tcgataagtc tctagccatt taaaatttt gatgacctgc    1320
tgcgacgctt tttttctggc aagatagtct tgtaaatgcg ggccaagatc tgcacactgg   1380
tatttcggtt tttggggccg cgggcgggcga cggggcccgt gcgtcccagc gcacatgttc   1440
ggcgaggcgg ggcctgcgag cgcggccacc gagaatcgga cggggtagt ctcaagctgg    1500
ccggcctgct ctggtgcctg gcctcgcgcc gccgtgtatc gccccgccct gggcggcaag   1560
gctggcccgg tcggcaccag ttgcgtgagc ggaaagatgg ccgcttcccg gccctgctgc   1620
agggagctca aaatgaggga cgcggccgctc gggagagccg gcgggtgagt cacccacaca   1680
aaggaaaagg gcctttccgt cctcagccgt cgcttcatgt gactccacgg agtaccgggc   1740
gccgtccagg caccttcgatt agttctcgag ctttttggagt acgtcgtctt taggttgggg   1800
ggaggggttt tatgcgatgg agtttcccca cactgagtgg gtggagactg aagttaggcc   1860
agcttgcac ttgatgtaat tctccttgga atttgcccttt tttgagtttg gatcttggtt    1920
cattctcaag cctcagacag tggttcaaag tttttttctt ccatttcagg tgtcgtgacc   1980
accatgcgc ttccggtgac agcactgctc ctcccccttgg cgctgttgct ccacgcagca   2040
aggccgcagg tgcagctggt gcagagcgga gccgagctca agaagcccgg agcctccgtg   2100
aaggtgagct gcaaggccag cggcaacacc ctgaccacct acgtgatcca ctgggtgaga   2160
caagcccccg gccaaaggct ggagtggatg ggctacatcc tgcccctacaa cgacctgacc   2220
aagtacagcc agaagttcca gggcagggtg accatcacca gggataagag cgcctccacc   2280
gcctatatgg agctgagcag cctgaggagc gaggacaccc tgtgtacta ctgtacaagg   2340
tgggactggg acggcttctt tgaccctcgg ggccagggca caacagtgac cgtcagcagc   2400
ggcggcggag gcagcggcgg cggcggcagc ggcggaggcg gaagcgaaat cgtgatgacc   2460
cagagccccg ccacactgag cgtgagccct ggcgagaggg ccagcatctc tgcagggct    2520
agccaaagcc tggtgcacag caacggcaac acccacctgc actggtacca gcagagaccc   2580
ggacaggctc ccaggctgct gatctacagc gtgagcaaca ggttctccga ggtgcctgcc   2640
aggtttagcg gcagcggaag cggcaccgac tttaccctga ccatcagcag cgtggagtcc   2700
gaggacttcg ccgtgtatta ctgcagccag accagccaca tcccttacac cttcggcggc   2760
ggcaccaagc tggagatcaa aagtgctgct gcctttgtcc cggtatttct cccagccaaa   2820
ccgaccacga ctccgcccc gcgccctccg acacccgtgc ccaccatgcgc ctctcaacct   2880
cttagtcttc gccccgaggc atgccgaccc gccgccgggg tgctgttca tacgagggcg   2940
ttggacttcg cttgtgatat ttacatttgg gctccgttgg cgggtacgtg cggcgtcctt   3000
ttgttgtcac tcgttattac tttgtattgt aatcacagga atcgcaaacg gggcagaaag   3060
aaaactcctgt atatattcaa acaaccattt atgagaccag tacaaactac tcaagaggaa   3120
gatggctgta gctgccgatt tccagaagaa gaagaaggag gatgtgaact gcgagtgaa    3180
tttttcccgaa gcgcagacgc tccggcatat cagcaaggac agaatcagct gtataacgaa   3240
ctgaatttgg gacgccgcga ggagtatgac gtgcttgata aaccgcgggg gagagacccg   3300
gaaatggggg gtaaaccccg aagaaagaat cccaagaag gactctacaa tgaactccag   3360
aaggataaga tggcggaggc ctactcagaa ataggtatga agggcaacg acgacgggga   3420
aaaggtcacg atgccctcta ccaaggggttg agtacgccaa ccaaagatac gtacgatgca   3480
ctgcatatgc aggccctgcc tcccagataa taataaaatc gctatccatc gaagatggat   3540
gtgtgttggt ttttttgtgtg tggagcaaca aatctgactt tgcatgtgca aacgccttca   3600
acaacagcat tattccagaa gacaccttct tccccagccc aggtaagggc agctttggtg   3660
ccttcgcagg ctgtttcctt gcttcaggaa tggccaggtt ctgcccagag ctcctggtcaa  3720
tgatgtctaa aactcctctg attggtagtc tcggcctcat ccattgccac caaaccctc    3780
tttttactaa gaaacagtga gccttgttct ggcagtccag agaatgacac gggaaaaaag   3840
cagatgaaga gaaggtggca ggagagggca cgtggcccag cctcagtctc ccaactgag    3900
ttcctgcctg cctgcctttg ctcagactgt ttgcccctta ctgctcttct aggcctcatt   3960
ctaagcccct tctccaagtt gcctctcctt atttctccct gtctgccaaa aaatctttcc   4020
cagctcacta agtcagtctc acgcagtcac tcattaaccc accaatcact gattgtgccg   4080
```

```
gcacatgaat gcaccaggtg ttgaagtgga ggaattaaaa agtcagatga ggggtgtgcc    4140
cagaggaagc accattctag ttggggagc ccatctgtca gctgggaaaa gtccaaataa    4200
cttcagattg gaatgtgttt taactcaggg ttgagaaaac agctaccttc aggacaaaag   4260
tcagggaagg gctctctgaa gaaatgctac ttgaagatac cagccctacc aagggcaggg   4320
agaggaccct atagaggcct gggacaggag ctcaatgaga aagg                     4364

SEQ ID NO: 171          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 171
ggtcatcgat gggagcaacg tgg                                              23

SEQ ID NO: 172          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 172
caccaccccg cgggactaga ggg                                              23

SEQ ID NO: 173          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 173
ggtctggcgc tcccgctcgg tgg                                              23

SEQ ID NO: 174          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 174
ttcacaccat cacgacgcgt ggg                                              23

SEQ ID NO: 175          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 175
acaccatcac gacgcgtggg tgg                                              23

SEQ ID NO: 176          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 176
ctacgagtct gacgggatcg tgg                                              23

SEQ ID NO: 177          moltype = DNA   length = 23
FEATURE                 Location/Qualifiers
misc_feature            1..23
                        note = Synthetic
source                  1..23
                        mol_type = other DNA
                        organism = synthetic construct
SEQUENCE: 177
ttgccaccca cgcgtcgtga tgg                                              23

SEQ ID NO: 178          moltype = DNA   length = 23
FEATURE                 Location/Qualifiers
misc_feature            1..23
```

```
                          note = Synthetic
source                    1..23
                          mol_type = other DNA
                          organism = synthetic construct
SEQUENCE: 178
gttcacacca tcacgacgcg tgg                                          23

SEQ ID NO: 179            moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 179
cacgatcccg tcagactcgt agg                                          23

SEQ ID NO: 180            moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 180
acgacgcgtg ggtggcaagc ggg                                          23

SEQ ID NO: 181            moltype = DNA   length = 21
FEATURE                   Location/Qualifiers
misc_feature              1..21
                          note = Synthetic
source                    1..21
                          mol_type = other DNA
                          organism = synthetic construct
SEQUENCE: 181
gatgggagca aacgtggcca t                                            21

SEQ ID NO: 182            moltype = DNA   length = 19
FEATURE                   Location/Qualifiers
misc_feature              1..19
                          note = Synthetic
source                    1..19
                          mol_type = other DNA
                          organism = synthetic construct
SEQUENCE: 182
gatgggagca cgtggccat                                               19

SEQ ID NO: 183            moltype = DNA   length = 17
FEATURE                   Location/Qualifiers
misc_feature              1..17
                          note = Synthetic
source                    1..17
                          mol_type = other DNA
                          organism = synthetic construct
SEQUENCE: 183
gatgggaacg tggccat                                                 17

SEQ ID NO: 184            moltype = DNA   length = 12
FEATURE                   Location/Qualifiers
misc_feature              1..12
                          note = Synthetic
source                    1..12
                          mol_type = other DNA
                          organism = synthetic construct
SEQUENCE: 184
gatgggagcc at                                                      12

SEQ ID NO: 185            moltype = DNA   length = 10
FEATURE                   Location/Qualifiers
misc_feature              1..10
                          note = Synthetic
source                    1..10
                          mol_type = other DNA
                          organism = synthetic construct
SEQUENCE: 185
gatgggccat                                                         10

SEQ ID NO: 186            moltype = DNA   length = 10
FEATURE                   Location/Qualifiers
```

```
misc_feature              1..10
                          note = Synthetic
source                    1..10
                          mol_type = other DNA
                          organism = synthetic construct
SEQUENCE: 186
acgtggccat                                                                 10

SEQ ID NO: 187            moltype = DNA  length = 21
FEATURE                   Location/Qualifiers
misc_feature              1..21
                          note = Synthetic
source                    1..21
                          mol_type = other DNA
                          organism = synthetic construct
SEQUENCE: 187
ccgcgggact tagagggagc t                                                    21

SEQ ID NO: 188            moltype = DNA  length = 11
FEATURE                   Location/Qualifiers
misc_feature              1..11
                          note = Synthetic
source                    1..11
                          mol_type = other DNA
                          organism = synthetic construct
SEQUENCE: 188
ccgcgggagc t                                                               11

SEQ ID NO: 189            moltype = DNA  length = 19
FEATURE                   Location/Qualifiers
misc_feature              1..19
                          note = Synthetic
source                    1..19
                          mol_type = other DNA
                          organism = synthetic construct
SEQUENCE: 189
ccgcgggata gagggagct                                                       19

SEQ ID NO: 190            moltype = DNA  length = 10
FEATURE                   Location/Qualifiers
misc_feature              1..10
                          note = Synthetic
source                    1..10
                          mol_type = other DNA
                          organism = synthetic construct
SEQUENCE: 190
ccgcgggact                                                                 10

SEQ ID NO: 191            moltype = DNA  length = 18
FEATURE                   Location/Qualifiers
misc_feature              1..18
                          note = Synthetic
source                    1..18
                          mol_type = other DNA
                          organism = synthetic construct
SEQUENCE: 191
ccgcgggtag agggagct                                                        18

SEQ ID NO: 192            moltype = DNA  length = 12
FEATURE                   Location/Qualifiers
misc_feature              1..12
                          note = Synthetic
source                    1..12
                          mol_type = other DNA
                          organism = synthetic construct
SEQUENCE: 192
ccgcggggag ct                                                              12

SEQ ID NO: 193            moltype = DNA  length = 19
FEATURE                   Location/Qualifiers
misc_feature              1..19
                          note = Synthetic
source                    1..19
                          mol_type = other DNA
                          organism = synthetic construct
SEQUENCE: 193
ccgcgggaca gagggagct                                                       19

SEQ ID NO: 194            moltype = DNA  length = 19
```

```
FEATURE                 Location/Qualifiers
misc_feature            1..19
                        note = Synthetic
source                  1..19
                        mol_type = other DNA
                        organism = synthetic construct
SEQUENCE: 194
ccgcgggact gagggagct                                                  19

SEQ ID NO: 195          moltype = DNA  length = 11
FEATURE                 Location/Qualifiers
misc_feature            1..11
                        note = Synthetic
source                  1..11
                        mol_type = other DNA
                        organism = synthetic construct
SEQUENCE: 195
ccgagggagc t                                                          11

SEQ ID NO: 196          moltype = DNA  length = 15
FEATURE                 Location/Qualifiers
misc_feature            1..15
                        note = Synthetic
source                  1..15
                        mol_type = other DNA
                        organism = synthetic construct
SEQUENCE: 196
ccgcgggagg gagct                                                      15

SEQ ID NO: 197          moltype = DNA  length = 14
FEATURE                 Location/Qualifiers
misc_feature            1..14
                        note = Synthetic
source                  1..14
                        mol_type = other DNA
                        organism = synthetic construct
SEQUENCE: 197
ccgtagaggg agct                                                       14

SEQ ID NO: 198          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 198
cgctcccgct tcggtggctg t                                               21

SEQ ID NO: 199          moltype = DNA  length = 19
FEATURE                 Location/Qualifiers
misc_feature            1..19
                        note = Synthetic
source                  1..19
                        mol_type = other DNA
                        organism = synthetic construct
SEQUENCE: 199
cgctcccgcc ggtggctgt                                                  19

SEQ ID NO: 200          moltype = DNA  length = 19
FEATURE                 Location/Qualifiers
misc_feature            1..19
                        note = Synthetic
source                  1..19
                        mol_type = other DNA
                        organism = synthetic construct
SEQUENCE: 200
cgctcccgtc ggtggctgt                                                  19

SEQ ID NO: 201          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 201
cgctcccgcg gtggctgt                                                   18
```

| | | |
|---|---|---|
| SEQ ID NO: 202<br>FEATURE<br>misc_feature<br><br>source | moltype = DNA   length = 19<br>Location/Qualifiers<br>1..19<br>note = Synthetic<br>1..19<br>mol_type = other DNA<br>organism = synthetic construct | |
| SEQUENCE: 202<br>cgctcccgct ggtggctgt | | 19 |
| SEQ ID NO: 203<br>FEATURE<br>misc_feature<br><br>source | moltype = DNA   length = 18<br>Location/Qualifiers<br>1..18<br>note = Synthetic<br>1..18<br>mol_type = other DNA<br>organism = synthetic construct | |
| SEQUENCE: 203<br>cgctccctcg gtggctgt | | 18 |
| SEQ ID NO: 204<br>FEATURE<br>misc_feature<br><br>source | moltype = DNA   length = 22<br>Location/Qualifiers<br>1..22<br>note = Synthetic<br>1..22<br>mol_type = other DNA<br>organism = synthetic construct | |
| SEQUENCE: 204<br>cgctcccgct ttcggtggct gt | | 22 |
| SEQ ID NO: 205<br>FEATURE<br>misc_feature<br><br>source | moltype = DNA   length = 16<br>Location/Qualifiers<br>1..16<br>note = Synthetic<br>1..16<br>mol_type = other DNA<br>organism = synthetic construct | |
| SEQUENCE: 205<br>cgctcccggt ggctgt | | 16 |
| SEQ ID NO: 206<br>FEATURE<br>misc_feature<br><br>source | moltype = DNA   length = 18<br>Location/Qualifiers<br>1..18<br>note = Synthetic<br>1..18<br>mol_type = other DNA<br>organism = synthetic construct | |
| SEQUENCE: 206<br>catcacgacg tgggtggc | | 18 |
| SEQ ID NO: 207<br>FEATURE<br>misc_feature<br><br>source | moltype = DNA   length = 15<br>Location/Qualifiers<br>1..15<br>note = Synthetic<br>1..15<br>mol_type = other DNA<br>organism = synthetic construct | |
| SEQUENCE: 207<br>catcacgtgg gtggc | | 15 |
| SEQ ID NO: 208<br>FEATURE<br>misc_feature<br><br>source | moltype = DNA   length = 21<br>Location/Qualifiers<br>1..21<br>note = Synthetic<br>1..21<br>mol_type = other DNA<br>organism = synthetic construct | |
| SEQUENCE: 208<br>catcacgacg ccgtgggtgg c | | 21 |
| SEQ ID NO: 209<br>FEATURE<br>misc_feature<br><br>source | moltype = DNA   length = 14<br>Location/Qualifiers<br>1..14<br>note = Synthetic<br>1..14<br>mol_type = other DNA<br>organism = synthetic construct | |
| SEQUENCE: 209<br>catcacgacg tggc | | 14 |

-continued

```
SEQ ID NO: 210            moltype = DNA   length = 21
FEATURE                   Location/Qualifiers
misc_feature              1..21
                          note = Synthetic
source                    1..21
                          mol_type = other DNA
                          organism = synthetic construct
SEQUENCE: 210
catcacgacg gcgtgggtgg c                                                   21

SEQ ID NO: 211            moltype = DNA   length = 10
FEATURE                   Location/Qualifiers
misc_feature              1..10
                          note = Synthetic
source                    1..10
                          mol_type = other DNA
                          organism = synthetic construct
SEQUENCE: 211
cgtgggtggc                                                                10

SEQ ID NO: 212            moltype = DNA   length = 17
FEATURE                   Location/Qualifiers
misc_feature              1..17
                          note = Synthetic
source                    1..17
                          mol_type = other DNA
                          organism = synthetic construct
SEQUENCE: 212
catcacgacg tggtggc                                                        17

SEQ ID NO: 213            moltype = DNA   length = 21
FEATURE                   Location/Qualifiers
misc_feature              1..21
                          note = Synthetic
source                    1..21
                          mol_type = other DNA
                          organism = synthetic construct
SEQUENCE: 213
catcacgacg tcgtgggtgg c                                                   21

SEQ ID NO: 214            moltype = DNA   length = 16
FEATURE                   Location/Qualifiers
misc_feature              1..16
                          note = Synthetic
source                    1..16
                          mol_type = other DNA
                          organism = synthetic construct
SEQUENCE: 214
catcacgacg ggtggc                                                         16

SEQ ID NO: 215            moltype = DNA   length = 15
FEATURE                   Location/Qualifiers
misc_feature              1..15
                          note = Synthetic
source                    1..15
                          mol_type = other DNA
                          organism = synthetic construct
SEQUENCE: 215
catcacgacg gtggc                                                          15

SEQ ID NO: 216            moltype = DNA   length = 21
FEATURE                   Location/Qualifiers
misc_feature              1..21
                          note = Synthetic
source                    1..21
                          mol_type = other DNA
                          organism = synthetic construct
SEQUENCE: 216
cacgacgcgt tgggtggcaa g                                                   21

SEQ ID NO: 217            moltype = DNA   length = 18
FEATURE                   Location/Qualifiers
misc_feature              1..18
                          note = Synthetic
source                    1..18
                          mol_type = other DNA
                          organism = synthetic construct
SEQUENCE: 217
```

```
cacgacgcgg gtggcaag                                                        18

SEQ ID NO: 218           moltype = DNA   length = 11
FEATURE                  Location/Qualifiers
misc_feature             1..11
                         note = Synthetic
source                   1..11
                         mol_type = other DNA
                         organism = synthetic construct
SEQUENCE: 218
cacgacgcaa g                                                               11

SEQ ID NO: 219           moltype = DNA   length = 16
FEATURE                  Location/Qualifiers
misc_feature             1..16
                         note = Synthetic
source                   1..16
                         mol_type = other DNA
                         organism = synthetic construct
SEQUENCE: 219
cacgacgcgt ggcaag                                                          16

SEQ ID NO: 220           moltype = DNA   length = 19
FEATURE                  Location/Qualifiers
misc_feature             1..19
                         note = Synthetic
source                   1..19
                         mol_type = other DNA
                         organism = synthetic construct
SEQUENCE: 220
cacgacgcgg ggtggcaag                                                       19

SEQ ID NO: 221           moltype = DNA   length = 21
FEATURE                  Location/Qualifiers
misc_feature             1..21
                         note = Synthetic
source                   1..21
                         mol_type = other DNA
                         organism = synthetic construct
SEQUENCE: 221
tctgacggga atcgtggttt c                                                    21

SEQ ID NO: 222           moltype = DNA   length = 13
FEATURE                  Location/Qualifiers
misc_feature             1..13
                         note = Synthetic
source                   1..13
                         mol_type = other DNA
                         organism = synthetic construct
SEQUENCE: 222
tctgacgggt ttc                                                             13

SEQ ID NO: 223           moltype = DNA   length = 14
FEATURE                  Location/Qualifiers
misc_feature             1..14
                         note = Synthetic
source                   1..14
                         mol_type = other DNA
                         organism = synthetic construct
SEQUENCE: 223
tctgacgtgg tttc                                                            14

SEQ ID NO: 224           moltype = DNA   length = 21
FEATURE                  Location/Qualifiers
misc_feature             1..21
                         note = Synthetic
source                   1..21
                         mol_type = other DNA
                         organism = synthetic construct
SEQUENCE: 224
tctgacggga ttcgtggttt c                                                    21

SEQ ID NO: 225           moltype = DNA   length = 19
FEATURE                  Location/Qualifiers
misc_feature             1..19
                         note = Synthetic
source                   1..19
                         mol_type = other DNA
                         organism = synthetic construct
```

```
SEQUENCE: 225
tctgacggga cgtggtttc                                                19

SEQ ID NO: 226          moltype = DNA  length = 14
FEATURE                 Location/Qualifiers
misc_feature            1..14
                        note = Synthetic
source                  1..14
                        mol_type = other DNA
                        organism = synthetic construct
SEQUENCE: 226
tctgtcgtgg tttc                                                     14

SEQ ID NO: 227          moltype = DNA  length = 12
FEATURE                 Location/Qualifiers
misc_feature            1..12
                        note = Synthetic
source                  1..12
                        mol_type = other DNA
                        organism = synthetic construct
SEQUENCE: 227
tctgacggtt tc                                                       12

SEQ ID NO: 228          moltype = DNA  length = 19
FEATURE                 Location/Qualifiers
misc_feature            1..19
                        note = Synthetic
source                  1..19
                        mol_type = other DNA
                        organism = synthetic construct
SEQUENCE: 228
tctgacgggt cgtggtttc                                                19

SEQ ID NO: 229          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 229
tctgacggga gtcgtggttt c                                             21

SEQ ID NO: 230          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 230
tctgacggga ctcgtggttt c                                             21

SEQ ID NO: 231          moltype = DNA  length = 10
FEATURE                 Location/Qualifiers
misc_feature            1..10
                        note = Synthetic
source                  1..10
                        mol_type = other DNA
                        organism = synthetic construct
SEQUENCE: 231
tcgtggtttc                                                          10

SEQ ID NO: 232          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 232
tctgacggtc gtggtttc                                                 18

SEQ ID NO: 233          moltype = DNA  length = 18
FEATURE                 Location/Qualifiers
misc_feature            1..18
                        note = Synthetic
source                  1..18
                        mol_type = other DNA
```

```
                              organism = synthetic construct
SEQUENCE: 233
tctgacggga gtggtttc                                                       18

SEQ ID NO: 234          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 234
ccacgcgtcg gtgatggtgt g                                                   21

SEQ ID NO: 235          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 235
ccacgcgtcg ttgatggtgt g                                                   21

SEQ ID NO: 236          moltype = DNA  length = 11
FEATURE                 Location/Qualifiers
misc_feature            1..11
                        note = Synthetic
source                  1..11
                        mol_type = other DNA
                        organism = synthetic construct
SEQUENCE: 236
ccacgcgtgt g                                                              11

SEQ ID NO: 237          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 237
ccacgcgtcg atgatggtgt g                                                   21

SEQ ID NO: 238          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 238
ccacgcgtcg atggtgtg                                                       18

SEQ ID NO: 239          moltype = DNA  length = 19
FEATURE                 Location/Qualifiers
misc_feature            1..19
                        note = Synthetic
source                  1..19
                        mol_type = other DNA
                        organism = synthetic construct
SEQUENCE: 239
ccacgcgtct gatggtgtg                                                      19

SEQ ID NO: 240          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 240
ccacgcgtcg ctgatggtgt g                                                   21

SEQ ID NO: 241          moltype = DNA  length = 10
FEATURE                 Location/Qualifiers
misc_feature            1..10
                        note = Synthetic
source                  1..10
```

```
                        mol_type = other DNA
                        organism = synthetic construct
SEQUENCE: 241
ccacgcgtcg                                                              10

SEQ ID NO: 242          moltype = DNA   length = 15
FEATURE                 Location/Qualifiers
misc_feature            1..15
                        note = Synthetic
source                  1..15
                        mol_type = other DNA
                        organism = synthetic construct
SEQUENCE: 242
ccacgcgtcg gtgtg                                                        15

SEQ ID NO: 243          moltype = DNA   length = 15
FEATURE                 Location/Qualifiers
misc_feature            1..15
                        note = Synthetic
source                  1..15
                        mol_type = other DNA
                        organism = synthetic construct
SEQUENCE: 243
ccacgcgtgg gtgtg                                                        15

SEQ ID NO: 244          moltype = DNA   length = 17
FEATURE                 Location/Qualifiers
misc_feature            1..17
                        note = Synthetic
source                  1..17
                        mol_type = other DNA
                        organism = synthetic construct
SEQUENCE: 244
ccacgcgtga tggtgtg                                                      17

SEQ ID NO: 245          moltype = DNA   length = 14
FEATURE                 Location/Qualifiers
misc_feature            1..14
                        note = Synthetic
source                  1..14
                        mol_type = other DNA
                        organism = synthetic construct
SEQUENCE: 245
ccacgcgtcg tgtg                                                         14

SEQ ID NO: 246          moltype = DNA   length = 13
FEATURE                 Location/Qualifiers
misc_feature            1..13
                        note = Synthetic
source                  1..13
                        mol_type = other DNA
                        organism = synthetic construct
SEQUENCE: 246
ccacgcgtcg tga                                                          13

SEQ ID NO: 247          moltype = DNA   length = 13
FEATURE                 Location/Qualifiers
misc_feature            1..13
                        note = Synthetic
source                  1..13
                        mol_type = other DNA
                        organism = synthetic construct
SEQUENCE: 247
ccacgcgtgg gtg                                                          13

SEQ ID NO: 248          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 248
ccatcacgac cgcgtgggtg g                                                 21

SEQ ID NO: 249          moltype = DNA   length = 15
FEATURE                 Location/Qualifiers
misc_feature            1..15
                        note = Synthetic
```

```
source                        1..15
                              mol_type = other DNA
                              organism = synthetic construct
SEQUENCE: 249
ccatcacgtg ggtgg                                                         15

SEQ ID NO: 250                moltype = DNA   length = 17
FEATURE                       Location/Qualifiers
misc_feature                  1..17
                              note = Synthetic
source                        1..17
                              mol_type = other DNA
                              organism = synthetic construct
SEQUENCE: 250
ccatcacgcg tgggtgg                                                       17

SEQ ID NO: 251                moltype = DNA   length = 21
FEATURE                       Location/Qualifiers
misc_feature                  1..21
                              note = Synthetic
source                        1..21
                              mol_type = other DNA
                              organism = synthetic construct
SEQUENCE: 251
ccatcacgac agcgtgggtg g                                                  21

SEQ ID NO: 252                moltype = DNA   length = 21
FEATURE                       Location/Qualifiers
misc_feature                  1..21
                              note = Synthetic
source                        1..21
                              mol_type = other DNA
                              organism = synthetic construct
SEQUENCE: 252
ccgtcagact tcgtaggcca g                                                  21

SEQ ID NO: 253                moltype = DNA   length = 11
FEATURE                       Location/Qualifiers
misc_feature                  1..11
                              note = Synthetic
source                        1..11
                              mol_type = other DNA
                              organism = synthetic construct
SEQUENCE: 253
ccgtaggcca g                                                             11

SEQ ID NO: 254                moltype = DNA   length = 10
FEATURE                       Location/Qualifiers
misc_feature                  1..10
                              note = Synthetic
source                        1..10
                              mol_type = other DNA
                              organism = synthetic construct
SEQUENCE: 254
ccgtcagact                                                               10

SEQ ID NO: 255                moltype = DNA   length = 12
FEATURE                       Location/Qualifiers
misc_feature                  1..12
                              note = Synthetic
source                        1..12
                              mol_type = other DNA
                              organism = synthetic construct
SEQUENCE: 255
ccgtcagacc ag                                                            12

SEQ ID NO: 256                moltype = DNA   length = 18
FEATURE                       Location/Qualifiers
misc_feature                  1..18
                              note = Synthetic
source                        1..18
                              mol_type = other DNA
                              organism = synthetic construct
SEQUENCE: 256
ccgtcagacg taggccag                                                      18

SEQ ID NO: 257                moltype = DNA   length = 12
FEATURE                       Location/Qualifiers
misc_feature                  1..12
```

```
                        note = Synthetic
source                  1..12
                        mol_type = other DNA
                        organism = synthetic construct
SEQUENCE: 257
ccgtcaggcc ag                                                              12

SEQ ID NO: 258          moltype = DNA   length = 19
FEATURE                 Location/Qualifiers
misc_feature            1..19
                        note = Synthetic
source                  1..19
                        mol_type = other DNA
                        organism = synthetic construct
SEQUENCE: 258
ccgtcagacc gtaggccag                                                       19

SEQ ID NO: 259          moltype = DNA   length = 19
FEATURE                 Location/Qualifiers
misc_feature            1..19
                        note = Synthetic
source                  1..19
                        mol_type = other DNA
                        organism = synthetic construct
SEQUENCE: 259
ccgtcagact gtaggccag                                                       19

SEQ ID NO: 260          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 260
gtgggtggca aagcgggtgg t                                                    21

SEQ ID NO: 261          moltype = DNA   length = 19
FEATURE                 Location/Qualifiers
misc_feature            1..19
                        note = Synthetic
source                  1..19
                        mol_type = other DNA
                        organism = synthetic construct
SEQUENCE: 261
gtgggtggca gcgggtggt                                                       19

SEQ ID NO: 262          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 262
gtgggtggca tagcgggtgg t                                                    21

SEQ ID NO: 263          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 263
gtgggtggag cgggtggt                                                        18

SEQ ID NO: 264          moltype = RNA   length = 101
FEATURE                 Location/Qualifiers
misc_feature            1..101
                        note = Synthetic
source                  1..101
                        mol_type = other RNA
                        organism = synthetic construct
SEQUENCE: 264
ccgacttctg aacgtgcggt gttttagagc tagaaatagc aagttaaaat aaggctagtc          60
cgttatcaac ttgaaaaagt ggcaccgagt cggtgcmttt t                             101

SEQ ID NO: 265          moltype = RNA   length = 103
```

```
FEATURE                   Location/Qualifiers
misc_feature              1..103
                          note = Synthetic
misc_feature              1..4
                          note = modified with 2'-O-methyl phosphorothioate
misc_feature              100..103
                          note = modified with 2'-O-methyl phosphorothioate
source                    1..103
                          mol_type = other RNA
                          organism = synthetic construct
SEQUENCE: 265
ccgacttctg aacgtgcggt ggggttttag agctagaaat agcaagttaa aataaggcta   60
gtccgttatc aacttgaaaa agtggcaccg agtcggtgct ttt                    103

SEQ ID NO: 266            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 266
ccgacttctg aacgtgcggt                                               20

SEQ ID NO: 267            moltype = RNA   length = 21
FEATURE                   Location/Qualifiers
misc_feature              1..21
                          note = Synthetic
misc_feature              1..4
                          note = modified with 2'-O-methyl phosphorothioate
source                    1..21
                          mol_type = other RNA
                          organism = synthetic construct
SEQUENCE: 267
cccgacttct gaacgtgcgg t                                             21

SEQ ID NO: 268            moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 268
ccgcgggact agagggagct                                               20

SEQ ID NO: 269            moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 269
ccgacttctg aacgtgcggt                                               20

SEQ ID NO: 270            moltype = RNA   length = 101
FEATURE                   Location/Qualifiers
misc_feature              1..101
                          note = Synthetic
source                    1..101
                          mol_type = other RNA
                          organism = synthetic construct
SEQUENCE: 270
tgctggcgat acgcgtccac gttttagagc tagaaatagc aagttaaaat aaggctagtc   60
cgttatcaac ttgaaaaagt ggcaccgagt cggtgcmttt t                      101

SEQ ID NO: 271            moltype = RNA   length = 101
FEATURE                   Location/Qualifiers
misc_feature              1..101
                          note = Synthetic
misc_feature              1..4
                          note = modified with 2'-O-methyl phosphorothioate
misc_feature              98..101
                          note = modified with 2'-O-methyl phosphorothioate
source                    1..101
                          mol_type = other RNA
                          organism = synthetic construct
SEQUENCE: 271
```

```
tgctggcgat acgcgtccac gttttagagc tagaaatagc aagttaaaat aaggctagtc    60
cgttatcaac ttgaaaaagt ggcaccgagt cggtgcmttt t                        101

SEQ ID NO: 272         moltype = RNA   length = 20
FEATURE                Location/Qualifiers
misc_feature           1..20
                       note = Synthetic
source                 1..20
                       mol_type = other RNA
                       organism = synthetic construct
SEQUENCE: 272
tgctggcgat acgcgtccac                                                20

SEQ ID NO: 273         moltype = RNA   length = 20
FEATURE                Location/Qualifiers
misc_feature           1..20
                       note = Synthetic
misc_feature           1..4
                       note = modified with 2'-O-methyl phosphorothioate
source                 1..20
                       mol_type = other RNA
                       organism = synthetic construct
SEQUENCE: 273
tgctggcgat acgcgtccac                                                20

SEQ ID NO: 274         moltype = DNA   length = 20
FEATURE                Location/Qualifiers
misc_feature           1..20
                       note = Synthetic
source                 1..20
                       mol_type = other DNA
                       organism = synthetic construct
SEQUENCE: 274
cgctcccgct cggtggctgt                                                20

SEQ ID NO: 275         moltype = DNA   length = 20
FEATURE                Location/Qualifiers
misc_feature           1..20
                       note = Synthetic
source                 1..20
                       mol_type = other DNA
                       organism = synthetic construct
SEQUENCE: 275
tgctggcgat acgcgtccac                                                20

SEQ ID NO: 276         moltype = RNA   length = 100
FEATURE                Location/Qualifiers
misc_feature           1..100
                       note = Synthetic
source                 1..100
                       mol_type = other RNA
                       organism = synthetic construct
SEQUENCE: 276
tcggtctatg acgagcagcg gttttagagc tagaaatagc aagttaaaat aaggctagtc    60
cgttatcaac ttgaaaaagt ggcaccgagt cggtgctttt                          100

SEQ ID NO: 277         moltype = RNA   length = 100
FEATURE                Location/Qualifiers
misc_feature           1..100
                       note = Synthetic
misc_feature           1..4
                       note = modified with 2'-O-methyl phosphorothioate
misc_feature           97..100
                       note = modified with 2'-O-methyl phosphorothioate
source                 1..100
                       mol_type = other RNA
                       organism = synthetic construct
SEQUENCE: 277
tcggtctatg acgagcagcg gttttagagc tagaaatagc aagttaaaat aaggctagtc    60
cgttatcaac ttgaaaaagt ggcaccgagt cggtgctttt                          100

SEQ ID NO: 278         moltype = RNA   length = 20
FEATURE                Location/Qualifiers
misc_feature           1..20
                       note = Synthetic
source                 1..20
                       mol_type = other RNA
                       organism = synthetic construct
SEQUENCE: 278
```

```
tcggtctatg acgagcagcg                                               20

SEQ ID NO: 279          moltype = RNA   length = 20
FEATURE                 Location/Qualifiers
misc_feature            1..20
                        note = Synthetic
misc_feature            1..4
                        note = modified with 2'-O-methyl phosphorothioate
source                  1..20
                        mol_type = other RNA
                        organism = synthetic construct
SEQUENCE: 279
tcggtctatg acgagcagcg                                               20

SEQ ID NO: 280          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 280
catcacgacg cgtgggtggc                                               20

SEQ ID NO: 281          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 281
tcggtctatg acgagcagcg                                               20

SEQ ID NO: 282          moltype = RNA   length = 101
FEATURE                 Location/Qualifiers
misc_feature            1..101
                        note = Synthetic
source                  1..101
                        mol_type = other RNA
                        organism = synthetic construct
SEQUENCE: 282
atgggcagtc ctattacagc gttttagagc tagaaatagc aagttaaaat aaggctagtc   60
cgttatcaac ttgaaaaagt ggcaccgagt cggtgcmttt t                      101

SEQ ID NO: 283          moltype = RNA   length = 100
FEATURE                 Location/Qualifiers
misc_feature            1..100
                        note = Synthetic
misc_feature            1..4
                        note = modified with 2'-O-methyl phosphorothioate
misc_feature            97..100
                        note = modified with 2'-O-methyl phosphorothioate
source                  1..100
                        mol_type = other RNA
                        organism = synthetic construct
SEQUENCE: 283
atgggcagtc ctattacagc gttttagagc tagaaatagc aagttaaaat aaggctagtc   60
cgttatcaac ttgaaaaagt ggcaccgagt cggtgctttt                        100

SEQ ID NO: 284          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 284
atgggcagtc ctattacagc                                               20

SEQ ID NO: 285          moltype = RNA   length = 20
FEATURE                 Location/Qualifiers
misc_feature            1..20
                        note = Synthetic
misc_feature            1..4
                        note = modified with 2'-O-methyl phosphorothioate
source                  1..20
                        mol_type = other RNA
                        organism = synthetic construct
```

```
SEQUENCE: 285
atgggcagtc ctattacagc                                               20

SEQ ID NO: 286          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 286
cacgacgcgt gggtggcaag                                               20

SEQ ID NO: 287          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 287
atgggcagtc ctattacagc                                               20

SEQ ID NO: 288          moltype = RNA  length = 100
FEATURE                 Location/Qualifiers
misc_feature            1..100
                        note = Synthetic
source                  1..100
                        mol_type = other RNA
                        organism = synthetic construct
SEQUENCE: 288
attgttcact tgttagcccc gttttagagc tagaaatagc aagttaaaat aaggctagtc   60
cgttatcaac ttgaaaaagt ggcaccgagt cggtgctttt                         100

SEQ ID NO: 289          moltype = RNA  length = 103
FEATURE                 Location/Qualifiers
misc_feature            1..103
                        note = Synthetic
misc_feature            1..4
                        note = modified with 2'-O-methyl phosphorothioate
misc_feature            100..103
                        note = modified with 2'-O-methyl phosphorothioate
source                  1..103
                        mol_type = other RNA
                        organism = synthetic construct
SEQUENCE: 289
attgttcact tgttagcccc agggttttag agctagaaat agcaagttaa aataaggcta   60
gtccgttatc aacttgaaaa agtggcaccg agtcggtgct ttt                     103

SEQ ID NO: 290          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 290
attgttcact tgttagcccc                                               20

SEQ ID NO: 291          moltype = RNA  length = 20
FEATURE                 Location/Qualifiers
misc_feature            1..20
                        note = Synthetic
misc_feature            1..4
                        note = modified with 2'-O-methyl phosphorothioate
source                  1..20
                        mol_type = other RNA
                        organism = synthetic construct
SEQUENCE: 291
attgttcact tgttagcccc                                               20

SEQ ID NO: 292          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 292
```

```
tctgacggga tcgtggtttc                                               20

SEQ ID NO: 293          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 293
attgttcact tgttagcccc                                               20

SEQ ID NO: 294          moltype = RNA   length = 100
FEATURE                 Location/Qualifiers
misc_feature            1..100
                        note = Synthetic
source                  1..100
                        mol_type = other RNA
                        organism = synthetic construct
SEQUENCE: 294
gctgaagaac tgcctctata gttttagagc tagaaatagc aagttaaaat aaggctagtc   60
cgttatcaac ttgaaaaagt ggcaccgagt cggtgctttt                        100

SEQ ID NO: 295          moltype = RNA   length = 100
FEATURE                 Location/Qualifiers
misc_feature            1..100
                        note = Synthetic
misc_feature            1..4
                        note = modified with 2'-O-methyl phosphorothioate
misc_feature            97..100
                        note = modified with 2'-O-methyl phosphorothioate
source                  1..100
                        mol_type = other RNA
                        organism = synthetic construct
SEQUENCE: 295
gctgaagaac tgcctctata gttttagagc tagaaatagc aagttaaaat aaggctagtc   60
cgttatcaac ttgaaaaagt ggcaccgagt cggtgctttt                        100

SEQ ID NO: 296          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 296
gctgaagaac tgcctctata                                               20

SEQ ID NO: 297          moltype = RNA   length = 20
FEATURE                 Location/Qualifiers
misc_feature            1..20
                        note = Synthetic
misc_feature            1..4
                        note = modified with 2'-O-methyl phosphorothioate
source                  1..20
                        mol_type = other RNA
                        organism = synthetic construct
SEQUENCE: 297
gctgaagaac tgcctctata                                               20

SEQ ID NO: 298          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 298
ccacgcgtcg tgatggtgtg                                               20

SEQ ID NO: 299          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 299
gctgaagaac tgcctctata                                               20
```

```
SEQ ID NO: 300          moltype = RNA   length = 100
FEATURE                 Location/Qualifiers
misc_feature            1..100
                        note = Synthetic
source                  1..100
                        mol_type = other RNA
                        organism = synthetic construct
SEQUENCE: 300
gcaggatttc tggttgtcac gttttagagc tagaaatagc aagttaaaat aaggctagtc    60
cgttatcaac ttgaaaaagt ggcaccgagt cggtgctttt                         100

SEQ ID NO: 301          moltype = RNA   length = 100
FEATURE                 Location/Qualifiers
misc_feature            1..100
                        note = Synthetic
misc_feature            1..4
                        note = modified with 2'-O-methyl phosphorothioate
misc_feature            97..100
                        note = modified with 2'-O-methyl phosphorothioate
source                  1..100
                        mol_type = other RNA
                        organism = synthetic construct
SEQUENCE: 301
gcaggatttc tggttgtcac gttttagagc tagaaatagc aagttaaaat aaggctagtc    60
cgttatcaac ttgaaaaagt ggcaccgagt cggtgctttt                         100

SEQ ID NO: 302          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 302
gcaggatttc tggttgtcac                                                20

SEQ ID NO: 303          moltype = RNA   length = 20
FEATURE                 Location/Qualifiers
misc_feature            1..20
                        note = Synthetic
misc_feature            1..4
                        note = modified with 2'-O-methyl phosphorothioate
source                  1..20
                        mol_type = other RNA
                        organism = synthetic construct
SEQUENCE: 303
gcaggatttc tggttgtcac                                                20

SEQ ID NO: 304          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 304
ccatcacgac gcgtgggtgg                                                20

SEQ ID NO: 305          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 305
gcaggatttc tggttgtcac                                                20

SEQ ID NO: 306          moltype = RNA   length = 100
FEATURE                 Location/Qualifiers
misc_feature            1..100
                        note = Synthetic
source                  1..100
                        mol_type = other RNA
                        organism = synthetic construct
SEQUENCE: 306
ctccatctgt gagaagccac gttttagagc tagaaatagc aagttaaaat aaggctagtc    60
cgttatcaac ttgaaaaagt ggcaccgagt cggtgctttt                         100
```

```
SEQ ID NO: 307           moltype = RNA   length = 100
FEATURE                  Location/Qualifiers
misc_feature             1..100
                         note = Synthetic
misc_feature             1..4
                         note = modified with 2'-O-methyl phosphorothioate
misc_feature             97..100
                         note = modified with 2'-O-methyl phosphorothioate
source                   1..100
                         mol_type = other RNA
                         organism = synthetic construct
SEQUENCE: 307
ctccatctgt gagaagccac gttttagagc tagaaatagc aagttaaaat aaggctagtc    60
cgttatcaac ttgaaaaagt ggcaccgagt cggtgctttt                         100

SEQ ID NO: 308           moltype = RNA   length = 20
FEATURE                  Location/Qualifiers
misc_feature             1..20
                         note = Synthetic
source                   1..20
                         mol_type = other RNA
                         organism = synthetic construct
SEQUENCE: 308
ctccatctgt gagaagccac                                                20

SEQ ID NO: 309           moltype = RNA   length = 20
FEATURE                  Location/Qualifiers
misc_feature             1..20
                         note = Synthetic
misc_feature             1..4
                         note = modified with 2'-O-methyl phosphorothioate
source                   1..20
                         mol_type = other RNA
                         organism = synthetic construct
SEQUENCE: 309
ctccatctgt gagaagccac                                                20

SEQ ID NO: 310           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 310
ccgtcagact cgtaggccag                                                20

SEQ ID NO: 311           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 311
ctccatctgt gagaagccac                                                20

SEQ ID NO: 312           moltype = RNA   length = 100
FEATURE                  Location/Qualifiers
misc_feature             1..100
                         note = Synthetic
source                   1..100
                         mol_type = other RNA
                         organism = synthetic construct
SEQUENCE: 312
cccctaccat gactttattc gttttagagc tagaaatagc aagttaaaat aaggctagtc    60
cgttatcaac ttgaaaaagt ggcaccgagt cggtgctttt                         100

SEQ ID NO: 313           moltype = RNA   length = 100
FEATURE                  Location/Qualifiers
misc_feature             1..100
                         note = Synthetic
misc_feature             1..4
                         note = modified with 2'-O-methyl phosphorothioate
misc_feature             97..100
                         note = modified with 2'-O-methyl phosphorothioate
source                   1..100
                         mol_type = other RNA
```

```
                        organism = synthetic construct
SEQUENCE: 313
ccccctaccat gactttattc gttttagagc tagaaatagc aagttaaaat aaggctagtc    60
cgttatcaac ttgaaaaagt ggcaccgagt cggtgctttt                          100

SEQ ID NO: 314          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 314
cccctaccat gactttattc                                                 20

SEQ ID NO: 315          moltype = RNA   length = 20
FEATURE                 Location/Qualifiers
misc_feature            1..20
                        note = Synthetic
misc_feature            1..4
                        note = modified with 2'-O-methyl phosphorothioate
source                  1..20
                        mol_type = other RNA
                        organism = synthetic construct
SEQUENCE: 315
cccctaccat gactttattc                                                 20

SEQ ID NO: 316          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 316
gtgggtggca agcgggtggt                                                 20

SEQ ID NO: 317          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 317
cccctaccat gactttattc                                                 20

SEQ ID NO: 318          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 318
ggtcatcgat gggagcaacg                                                 20

SEQ ID NO: 319          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 319
caccaccccg cgggactaga                                                 20

SEQ ID NO: 320          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 320
ggtctggcgc tcccgctcgg                                                 20

SEQ ID NO: 321          moltype = DNA   length = 20
FEATURE                 Location/Qualifiers
```

```
misc_feature            1..20
                        note = Synthetic
source                  1..20
                        mol_type = other DNA
                        organism = synthetic construct
SEQUENCE: 321
ttcacaccat cacgacgcgt                                               20

SEQ ID NO: 322          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 322
acaccatcac gacgcgtggg                                               20

SEQ ID NO: 323          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 323
ctacgagtct gacgggatcg                                               20

SEQ ID NO: 324          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 324
ttgccaccca cgcgtcgtga                                               20

SEQ ID NO: 325          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 325
gttcacacca tcacgacgcg                                               20

SEQ ID NO: 326          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 326
cacgatcccg tcagactcgt                                               20

SEQ ID NO: 327          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 327
acgacgcgtg ggtggcaagc                                               20

SEQ ID NO: 328          moltype = AA  length = 5
FEATURE                 Location/Qualifiers
REGION                  1..5
                        note = Synthetic
source                  1..5
                        mol_type = protein
                        organism = synthetic construct
SEQUENCE: 328
SYYIH                                                                5

SEQ ID NO: 329          moltype = AA  length = 17
```

```
FEATURE                 Location/Qualifiers
REGION                  1..17
                        note = Synthetic
source                  1..17
                        mol_type = protein
                        organism = synthetic construct
SEQUENCE: 329
VIYPGNDDIS YNQKFQG                                                      17

SEQ ID NO: 330          moltype = AA  length = 9
FEATURE                 Location/Qualifiers
REGION                  1..9
                        note = Synthetic
source                  1..9
                        mol_type = protein
                        organism = synthetic construct
SEQUENCE: 330
EVRLRYFDV                                                               9

SEQ ID NO: 331          moltype = AA  length = 17
FEATURE                 Location/Qualifiers
REGION                  1..17
                        note = Synthetic
source                  1..17
                        mol_type = protein
                        organism = synthetic construct
SEQUENCE: 331
KSSQSVFFSS SQKNYLA                                                      17

SEQ ID NO: 332          moltype = AA  length = 7
FEATURE                 Location/Qualifiers
REGION                  1..7
                        note = Synthetic
source                  1..7
                        mol_type = protein
                        organism = synthetic construct
SEQUENCE: 332
WASTRES                                                                 7

SEQ ID NO: 333          moltype = AA  length = 8
FEATURE                 Location/Qualifiers
REGION                  1..8
                        note = Synthetic
source                  1..8
                        mol_type = protein
                        organism = synthetic construct
SEQUENCE: 333
HQYLSSRT                                                                8

SEQ ID NO: 334          moltype = AA  length = 118
FEATURE                 Location/Qualifiers
REGION                  1..118
                        note = Synthetic
source                  1..118
                        mol_type = protein
                        organism = synthetic construct
SEQUENCE: 334
QVQLQQPGAE VVKPGASVKM SCKASGYTFT SYYIHWIKQT PGQGLEWVGV IYPGNDDISY        60
NQKFQGKATL TADKSSTTAY MQLSSLTSED SAVYYCAREV RLRYFDVWGQ GTTVTVSS         118

SEQ ID NO: 335          moltype = AA  length = 112
FEATURE                 Location/Qualifiers
REGION                  1..112
                        note = Synthetic
source                  1..112
                        mol_type = protein
                        organism = synthetic construct
SEQUENCE: 335
EIVLTQSPGS LAVSPGERVT MSCKSSQSVF FSSSQKNYLA WYQQIPGQSP RLLIYWASTR        60
ESGVPDRFTG SGSGTDFTLT ISSVQPEDLA IYYCHQYLSS RTFGQGTKLE IK               112

SEQ ID NO: 336          moltype = AA  length = 246
FEATURE                 Location/Qualifiers
REGION                  1..246
                        note = Synthetic
source                  1..246
                        mol_type = protein
                        organism = synthetic construct
SEQUENCE: 336
```

```
EIVLTQSPGS LAVSPGERVT MSCKSSQSVF FSSSQKNYLA WYQQIPGQSP RLLIYWASTR    60
ESGVPDRFTG SGSGTDFTLT ISSVQPEDLA IYYCHQYLSS RTFGQGTKLE IKGGGGGSGG   120
GGSGGGGSQV QLQQPGAEVV KPGASVKMSC KASGYTFTSY YIHWIKQTPG QGLEWVGVIY   180
PGNDDISYNQ KFQGKATLTA DKSSTTAYMQ LSSLTSEDSA VYYCAREVRL RYFDVWGQGT   240
TVTVSS                                                             246

SEQ ID NO: 337           moltype = DNA  length = 738
FEATURE                  Location/Qualifiers
misc_feature             1..738
                         note = Synthetic
source                   1..738
                         mol_type = other DNA
                         organism = synthetic construct
SEQUENCE: 337
gaaatcgtcc tcacacaatc cccgggagc ctcgcagtca gtcctgggga cagagtcact    60
atgagctgca aatccagtca gagtgttttt tctcaagta gccagaagaa ctacctcgca   120
tggtaccaac aaataccggg gcaatctccc cgcttgctta tactgggc aagtacccgc    180
gaatccggcg taccggatcg attcacggga tctgggtcag gtactgattt cactttgact   240
atcagctctg ttcagcctga agatttggca atttactact gtcaccaata cttgagtagc   300
cgaactttcg gccagggcac gaagctcgaa atcaagggcg gagggggagg ttctggtggg   360
ggcggttctg gcggtggagg aagccaagta cagttgcaac agccagggc ggaggtcgta    420
aaacctgggg cgtctgtcaa gatgagctgt aaagcaagtt gatacacctt cacctcctac   480
tatatacatt ggattaagca aactccgggt caggggctgg aatggggttgg cgttatatac   540
cccgggaacg atgatatatc atacaaccaa aaatttcaag gcaaggcgac tctgactgcc   600
gataagagta gcacaacagc ttacatgcag ctttcttccc tgaccagcga agattcagca   660
gtttactact gcgctcggga gtgcgcctg cgatactttg atgtctgggg tcaaggaact    720
acagttactg tatcaagc                                                 738

SEQ ID NO: 338           moltype = AA  length = 507
FEATURE                  Location/Qualifiers
REGION                   1..507
                         note = Synthetic
source                   1..507
                         mol_type = protein
                         organism = synthetic construct
SEQUENCE: 338
MALPVTALLL PLALLLHAAR PEIVLTQSPG SLAVSPGERV TMSCKSSQSV FFSSSQKNYL    60
AWYQQIPGQS PRLLIYWAST RESGVPDRFT GSGSGTDFTL TISSVQPEDL AIYYCHQYLS   120
SRTFGQGTKL EIKGGGGSG GGGSGGGGSQ VQLQQPGAEV VKPGASVKMS CKASGYTFTS    180
YYIHWIKQTP GQGLEWVGVI YPGNDDISYN QKFQGKATLT ADKSSTTAYM QLSSLTSEDS   240
AVYYCAREVR LRYFDVWGQG TTVTVSSSAA AFVPVFLPAK PTTTPAPRPP TPAPTIASQP   300
LSLRPEACRP AAGGAVHTRG LDFACDIYIW APLAGTCGVL LLSLVITLYC NHRNRSKRSR   360
LLHSDYMNMT PRRPGPTRKH YQPYAPPRDF AAYRSRVKFS RSADAPAYQQ GQNQLYNELN   420
LGRREEYDVL DKRRGRDPEM GGKPRRKNPQ EGLYNELQKD KMAEAYSEIG MKGERRRGKG   480
HDGLYQGLST ATKDTYDALH MQALPPR                                      507

SEQ ID NO: 339           moltype = AA  length = 509
FEATURE                  Location/Qualifiers
REGION                   1..509
                         note = Synthetic
source                   1..509
                         mol_type = protein
                         organism = synthetic construct
SEQUENCE: 339
MALPVTALLL PLALLLHAAR PEIVLTQSPG SLAVSPGERV TMSCKSSQSV FFSSSQKNYL    60
AWYQQIPGQS PRLLIYWAST RESGVPDRFT GSGSGTDFTL TISSVQPEDL AIYYCHQYLS   120
SRTFGQGTKL EIKGGGGGSG GGSGGGGSQ VQLQQPGAEV VKPGASVKMS CKASGYTFTS    180
YYIHWIKQTP GQGLEWVGVI YPGNDDISYN QKFQGKATLT ADKSSTTAYM QLSSLTSEDS   240
AVYYCAREVR LRYFDVWGQG TTVTVSSSAA AFVPVFLPAK PTTTPAPRPP TPAPTIASQP   300
LSLRPEACRP AAGGAVHTRG LDFACDIYIW APLAGTCGVL LLSLVITLYC NHRNRKRGRK   360
KLLYIFKQPF MRPVQTTQEE DGCSCRFPEE EEGGCELRVK FSRSADAPAY QQGQNQLYNE   420
LNLGRREEYD VLDKRRGRDP EMGGKPRRKN PQEGLYNELQ KDKMAEAYSE IGMKGERRRG   480
KGHDGLYQGL STATKDTYDA LHMQALPPR                                    509

SEQ ID NO: 340           moltype = AA  length = 5
FEATURE                  Location/Qualifiers
REGION                   1..5
                         note = Synthetic
source                   1..5
                         mol_type = protein
                         organism = synthetic construct
SEQUENCE: 340
SYGMH                                                                5

SEQ ID NO: 341           moltype = AA  length = 17
FEATURE                  Location/Qualifiers
REGION                   1..17
                         note = Synthetic
source                   1..17
```

```
                            mol_type = protein
                            organism = synthetic construct
SEQUENCE: 341
VIWDDGSNKY YVDSVKG                                                       17

SEQ ID NO: 342              moltype = AA   length = 17
FEATURE                     Location/Qualifiers
REGION                      1..17
                            note = Synthetic
source                      1..17
                            mol_type = protein
                            organism = synthetic construct
SEQUENCE: 342
DDYYGSGSFN SYYGTDV                                                       17

SEQ ID NO: 343              moltype = AA   length = 11
FEATURE                     Location/Qualifiers
REGION                      1..11
                            note = Synthetic
source                      1..11
                            mol_type = protein
                            organism = synthetic construct
SEQUENCE: 343
RASQSVSIYL A                                                             11

SEQ ID NO: 344              moltype = AA   length = 7
FEATURE                     Location/Qualifiers
REGION                      1..7
                            note = Synthetic
source                      1..7
                            mol_type = protein
                            organism = synthetic construct
SEQUENCE: 344
DASNRAT                                                                   7

SEQ ID NO: 345              moltype = AA   length = 10
FEATURE                     Location/Qualifiers
REGION                      1..10
                            note = Synthetic
source                      1..10
                            mol_type = protein
                            organism = synthetic construct
SEQUENCE: 345
QQRSNWPPFT                                                               10

SEQ ID NO: 346              moltype = AA   length = 126
FEATURE                     Location/Qualifiers
REGION                      1..126
                            note = Synthetic
source                      1..126
                            mol_type = protein
                            organism = synthetic construct
SEQUENCE: 346
QVQLVESGGG VVQPGRSLRL SCAASGFTFS SYGMHWVRQA PGKGLEWVAV IWDDGSNKYY         60
VDSVKGRFTI SRDNSKNTLY LQMNSLRAED TAVYYCARDD YYGSGSFNSY YGTDVWGQGT        120
TVTVSS                                                                  126

SEQ ID NO: 347              moltype = AA   length = 108
FEATURE                     Location/Qualifiers
REGION                      1..108
                            note = Synthetic
source                      1..108
                            mol_type = protein
                            organism = synthetic construct
SEQUENCE: 347
EIVLTQSPAT LSLSPGERAT LSCRASQSVS IYLAWYQQKP GQAPRLLIYD ASNRATGIPA         60
RFSGSGSGTD FTLTISSLEP EDFAVYYCQQ RSNWPPFTFG PGTKVDIK                    108

SEQ ID NO: 348              moltype = AA   length = 249
FEATURE                     Location/Qualifiers
REGION                      1..249
                            note = Synthetic
source                      1..249
                            mol_type = protein
                            organism = synthetic construct
SEQUENCE: 348
QVQLVESGGG VVQPGRSLRL SCAASGFTFS SYGMHWVRQA PGKGLEWVAV IWDDGSNKYY         60
VDSVKGRFTI SRDNSKNTLY LQMNSLRAED TAVYYCARDD YYGSGSFNSY YGTDVWGQGT        120
TVTVSSGGGG SGGGGSGGGG SEIVLTQSPA TLSLSPGERA TLSCRASQSV SIYLAWYQQK        180
```

```
PGQAPRLLIY DASNRATGIP ARFSGSGSGT DFTLTISSLE PEDFAVYYCQ QRSNWPPFTF    240
GPGTKVDIK                                                           249

SEQ ID NO: 349          moltype = AA  length = 510
FEATURE                 Location/Qualifiers
REGION                  1..510
                        note = Synthetic
source                  1..510
                        mol_type = protein
                        organism = synthetic construct
SEQUENCE: 349
MALPVTALLL PLALLLHAAR PQVQLVESGG GVVQPGRSLR LSCAASGFTF SSYGMHWVRQ    60
APGKGLEWVA VIWDDGSNKY YVDSVKGRFT ISRDNSKNTL YLQMNSLRAE DTAVYYCARD    120
DYYGSGSFNS YYGTDVWGQG TTVTVSSGGG GSGGGGSGGG GSEIVLTQSP ATLSLSPGER    180
ATLSCRASQS VSIYLAWYQQ KPGQAPRLLI YDASNRATGI PARFSGSGSG TDFTLTISSL    240
EPEDFAVYYC QQRSNWPPFT FGPGTKVDIK SAAAFVPVFL PAKPTTTPAP RPPTPAPTIA    300
SQPLSLRPEA CRPAAGGAVH TRGLDFACDI YIWAPLAGTC GVLLLSLVIT LYCNHRNRSK    360
RSRLLHSDYM NMTPRRPGPT RKHYQPYAPP RDFAAYRSRV KFSRSADAPA YQQGQNQLYN    420
ELNLGRREEY DVLDKRRGRD PEMGGKPRRK NPQEGLYNEL QKDKMAEAYS EIGMKGERRR    480
GKGHDGLYQG LSTATKDTYD ALHMQALPPR                                    510

SEQ ID NO: 350          moltype = AA  length = 512
FEATURE                 Location/Qualifiers
REGION                  1..512
                        note = Synthetic
source                  1..512
                        mol_type = protein
                        organism = synthetic construct
SEQUENCE: 350
MALPVTALLL PLALLLHAAR PQVQLVESGG GVVQPGRSLR LSCAASGFTF SSYGMHWVRQ    60
APGKGLEWVA VIWDDGSNKY YVDSVKGRFT ISRDNSKNTL YLQMNSLRAE DTAVYYCARD    120
DYYGSGSFNS YYGTDVWGQG TTVTVSSGGG GSGGGGSGGG GSEIVLTQSP ATLSLSPGER    180
ATLSCRASQS VSIYLAWYQQ KPGQAPRLLI YDASNRATGI PARFSGSGSG TDFTLTISSL    240
EPEDFAVYYC QQRSNWPPFT FGPGTKVDIK SAAAFVPVFL PAKPTTTPAP RPPTPAPTIA    300
SQPLSLRPEA CRPAAGGAVH TRGLDFACDI YIWAPLAGTC GVLLLSLVIT LYCNHRNRKR    360
GRKKLLYIFK QPFMRPVQTT QEEDGCSCRF PEEEEGGCEL RVKFSRSADA PAYQQGQNQL    420
YNELNLGRRE EYDVLDKRRG RDPEMGGKPR RKNPQEGLYN ELQKDKMAEA YSEIGMKGER    480
RRGKGHDGLY QGLSTATKDT YDALHMQALP PR                                 512

SEQ ID NO: 351          moltype = DNA  length = 4361
FEATURE                 Location/Qualifiers
misc_feature            1..4361
                        note = Synthetic
source                  1..4361
                        mol_type = other DNA
                        organism = synthetic construct
SEQUENCE: 351
gagatgtaag gagctgctgt gacttgctca aggcctttata tcgagtaaac ggtagtgctg    60
gggcttagac gcaggtgttc tgatttatag ttcaaaacct ctatcaatga gagagcaatc    120
tcctggtaat gtgatagatt tcccaactta atgccaacat accataaacc tcccattctg    180
ctaatgccca gcctaagttg gggagaccac tccagattcc aagatgtaca gtttgcttg    240
ctgggccttt ttcccatgcc tgcctttact ctgccagagt tatattgctg ggttttgaa    300
gaagatccta ttaaataaaa gaataagcag tattattaag tagccctgca tttcaggttt    360
ccttgagtgg caggccaggc ctggccgtga acgttcactg aaatcatggc ctcttggcca    420
agattgatag cttgtgcctg tccctgagtc ccagtccatc acgagcagct ggtttctaag    480
atgctatttc ccgtataaag catgagaccg tgacttgcca gccccacaga gccccgccct    540
tgtccatcac tggcatctgg actccagcct gggttgggc aaagagggaa atgagatcat    600
gtcctaaccc tgatcctctt gtcccacaga tatccagaac cctgaccctg ccgtgtacca    660
gctgagagac tctaaatcca gtgacaagtc tgtctgccta ttcaccgatt ttgattctca    720
aacaaatgtg tcacaaagta aggattctga tgtgtatatc acagacaaaa ctgtgctaga    780
catgaggtct atggacttca ggctccggtt cccgtcagtg gcagagcgc acatcgccca    840
cagtccccga gaagttgggg ggaggggtcg gcaattgaac cggtgcctag agaaggtggc    900
gcggggtaaa ctgggaaagt gatgtcgtgt actggctccg cctttttccc gagggtgggg    960
gagaaccgta tataagtgca gtagtcgccg tgaacgttct ttttcgcaac gggtttgccg    1020
ccagaacaca ggtaagtgcc gtgtgtggtt cccgcgggcc tggcctcttt acgggttatg    1080
gcccttgcgt gccttgaatt acttccactg ctgcagtac gtgattcttg atcccgagct    1140
tcgggttgga agtgggtggg agagttcgag gccttgcgct taaggagccc cttgcctcg    1200
tgcttgagtt gaggcctggc ctgggcgctg gggccgccgc gtgcgaatct ggtggcacct    1260
tcgcgcctgc ctcgctgctt tcgataagtc tctagccatt taaaattttt gatgacctgc    1320
tgcgacgctt ttttctggc aagatagtct tgtaaatgcg gccaagatc tgcacactgg    1380
tatttcggtt tttggggccg cggcggcga cggggcccgt gcgtcccagc gcacatgttc    1440
ggcgaggcg ggcctgcgag gcggccacc gagaatcgga cggggtagt ctcaagctgg    1500
ccggcctgct ctggtgcctg gctcgcgcc gcgtgtatc gccccgccct gggcggcaag    1560
gctgggccca tcggcaccag ttgcgtgagc ggaaagatgg ccgcttccg gcctgctgc    1620
agggagctca aaatggagga cgcggcgctc gggagagcgg gcgggtgagt cacccacaca    1680
aaggaaaagg gcctttccgt cctcagccgt gcttcatgt gactcacgg agtaccgggc    1740
gccgtccagg cacctcgatt agttctcgag cttttggagt acgtcgtctt taggttgggg    1800
gaggggtttt tatgcgatgg agtttcccca cactgagtgg gtgagactg aagttaggcc    1860
agcttggcac ttgatgtaat tctccttgga atttgccctt tttgagtttg gatcttggtt    1920
```

-continued

```
cattctcaag cctcagacag tggttcaaag ttttttttctt ccatttcagg tgtcgtgacc  1980
accatggcgc ttccggtgac agcactgctc ctccccttgg cgctgttgct ccacgcagca  2040
aggccggaaa tcgtcctcac acaatccccg gggagcctcg cagtcagtcc tggggaacga  2100
gtcactatga gctgcaaatc cagtcagagt gttttttttct caagtagcca gaagaactac  2160
ctcgcatggt accaacaaat accggggcaa tctccccgct tgcttatata ctgggcaagt  2220
acccgcgaat ccggcgtacc ggatcgattc acgggatctg ggtcaggtac tgatttcact  2280
ttgactatca gctctgttca gcctgaagat ttggcaattt actactgtca ccaatacttg  2340
agtagccgaa ctttcggcca gggcacgaag ctcgaaatca agggcggagg gggaggttct  2400
ggtggggggc gttctggcgg tggaggaagc caagtacagt tgcaacagcc aggggcggag  2460
gtcgtaaaac ctggggcgtc tgtcaagatg agctgtaaag caagtggata caccttcacc  2520
tcctactata tacattggat taagcaaact ccgggtcagg gctggaatg ggttggcgtt  2580
atatacccccg ggaacgatga tatatcatac aaccaaaaat ttcaaggcaa ggcgactctg  2640
actgccgata agagtagcac aacagcttac atgcagcttt cttccctgac cagcgaagat  2700
tcagcagttt actactgcgc tcgggaagtg cgcctgcaga actttgatgt ctgggtcaa  2760
ggaactacag ttactgtatc aagcagtgct gctgcctttg tcccggtatt tctcccagcc  2820
aaaccgacca cgactcccgc cccgcgccct ccgacacccg ctcccaccat cgcctctcaa  2880
cctcttagtc ttcgccccga ggcatgccga cccgccgccg ggggtgctgt tcatacgagg  2940
ggcttggact tcgcttgtga tatttacatt tgggctccgt tggcgggtac gtgcggcgtc  3000
cttttgttgt cactcgttat tactttgtat tgtaatcaca ggaatcgctc aaagcggagt  3060
aggttgttgc attccgatta catgaatatg actcctcgcc ggcctgggcc gacaagaaaa  3120
cattccaac cctatgcccc cccacgagac ttcgctgcgt acaggtcccg agtgaagttt  3180
tcccgaagcg cagacgctcc ggcatatcag caaggacaga atcagctgta taacgaactg  3240
aatttgggac gccgcgagga gtatgacgtg cttgataaac gccggggag agacccggaa  3300
atgggggta aaccccgaag aaagaatccc caagaaggac tctacaatga actccagaag  3360
gataagatgc cggaggccta ctcagaaata ggtatgaagg cgaacgacg acgggaaaa  3420
ggtcacgatg gcctctacca agggtgagt acggcaacca aagatacgta cgatgcactg  3480
catatcagg ccctgcctcc cagataataa taaaatcgct atccatcgaa gatggatgtg  3540
tgttggtttt ttgtgtgtgg agcaacaaat ctgactttgc atgtgcaaac gccttcaaca  3600
acagcattat tccagaagac accttcttcc ccagcccagg taagggcagc tttggtgcct  3660
tcgcaggctg tttccttgct tcaggaatgg ccaggttctg cccagagctc tggtcaatga  3720
tgtctaaaac tcctctgatt ggtggtctcg gccttatcca ttgccaccaa acccctcttt  3780
ttactaagaa acagtgagcc ttgttctggc agtccagaga atgacacggg aaaaaagcag  3840
atgaagagaa ggtggcagga gagggcacgt ggcccagcct cagtctctcc aactgagttc  3900
ctgcctgcct gcctttgctc agactgtttc cccttactg ctcttctagg cctcattcta  3960
agcccccttct ccaagttgcc tctccttatt tctccctgc tgccaaaaaa tcttttcccag  4020
ctcactaagt cagtctcacg cagtcactca ttaacccacc aatcactgat tgtgccggca  4080
catgaatgca ccaggtgttg aagtggagga attaaaaagt cagatgaggg gtgtgcccag  4140
aggaagcacc attctagttg ggggagccca tctgtcagct gggaaaagtc caaataactt  4200
cagattggaa tgtgttttaa ctcagggttg agaaaacagc taccttcagg acaaaagtca  4260
gggaagggct ctctgaagaa atgctacttg aagataccag ccctaccaag ggcagggaga  4320
ggaccctata gaggcctggg acaggagctc aatgagaaag g            4361

SEQ ID NO: 352            moltype = DNA  length = 4367
FEATURE                   Location/Qualifiers
misc_feature              1..4367
                          note = Synthetic
source                    1..4367
                          mol_type = other DNA
                          organism = synthetic construct
SEQUENCE: 352
gagatgtaag gagctgctgt gacttgctca aggcctttata tcgagtaaac ggtagtgctg  60
gggcttagac gcaggtgttc tgatttatag ttcaaaacct ctatcaatga gagagcaatc  120
tcctggtaat gtgatagatt tcccaactta atgccaacat accataaacc tcccattctg  180
ctaatgccca gcctaagttg gggagaccac tccagattcc aagatgtaca gtttgctttg  240
ctgggcctt ttcccatgcc tgcctttact ctgccagagt tatattgccg gggtttttgaa  300
gaagatccta ttaaataaaa gaataagcag tattattaag tagccctgca tttcaggttt  360
ccttgagtgg caggccaggc ctggccgtga acgttcactg aaatcatggc ctcttggcca  420
agattgatag cttgtgcctg tccctgagtc ccagtccatc acgagcagct ggtttctaag  480
atgctatttc ccgtataaag catgagaccg tgacttgcca gccccacaga gccccgccct  540
tgtccatcac tggcatctgt actccagcct gggttgggc aaagagggaa atgagatcat  600
gtcctaaccc tgatcctctt gtcccacaga tatccagaac cctgaccctg ccgtgtacca  660
gctgagagac tctaaatcca gtgacaagtc tgtctgccta ttcaccgatt tgattctca  720
aacaaatgtg tcacaaagta aggattctga tgtgtatatc acagacaaaa ctgtgctaga  780
catgaggtct atggacttca ggctccggtg ccgtcagtga cagcagagcg acatcgccca  840
cagtccccga gaagttgggg ggaggggtcg gcaattgaac cggtgcctag agaaggggc  900
gcgggtaaa ctgggaaagt gatgtcgtgt actggctccg ccttttttccc gagggtgggg  960
gagaaccgta tataagtgca gtagtcgccg tgaacgttct ttttcgcaac gggttttgccg  1020
ccagaacaca ggtaagtgcc gtgtgtggtt cccgcgggcc tggcctctt acggggtatg  1080
gcccttgcgt gccttgaatt acttccactg gctgcagtac gtgattcttg atcccgagct  1140
tcggggttgga agtgggtggg agagttcgag gccttgcgct taaggagccc cttcgcctcg  1200
tgcttgagtt gaggcctggc ctgggcgctg ggccgccgc gtgcgaatct ggtggcacct  1260
tcgcgcctgc ctcgctgctt tcgataagtc tctagccatt taaaattttt gatgacctgc  1320
tgcgacgctt tttttctggc aagatagtct tgtaaatgcg ggccaagatc tgcacactgg  1380
tatttcggtt tttggggccg cgggcggcga cggggcccgt gcgtcccagc gcacatgttc  1440
ggcgaggcgg ggcctgcgag cgcggccacc gagaatgcaa cggggtagt ctcaagctgg  1500
ccggcctgct ctggtgcctg gcctcgcgcc gccgtgtatc gccccgccct gggcggcaag  1560
gctgcccgg tcggcaccag ttgcgtgagc ggaaagatgg ccgcttccg gccctgctgc  1620
agggagctca aatgggagga gcggcgctc gggagagcgg gcgggtgagt cacccacaca  1680
aaggaaaagg gcctttccgt cctcagccgt cgcttcatgt gactccacgg agtaccgggc  1740
```

```
gccgtccagg cacctcgatt agttctcgag cttttggagt acgtcgtctt taggttgggg     1800
ggagggttt tatgcgatgg agtttcccca cactgagtgg gtggagactg aagttaggcc     1860
agcttggcac ttgatgtaat tctccttgga atttgccctt tttgagtttg gatcttggtt     1920
cattctcaag cctcagacag tggttcaaag ttttttttctt ccatttcagg tgtcgtgacc    1980
accatggcgc ttccggtgac agcactgctc ctccccttgg cgctgttgct ccacgcagca    2040
aggccggaaa tcgtcctcac acaatccccg gggagcctcg cagtcagtcc tggggaacga    2100
gtcactatga gctgcaaatc cagtcagagt gttttttttct caagtagcca gaagaactac   2160
ctcgcatggt accaacaaat accggggcaa tctcccgct tgcttatata ctgggcaagt     2220
acccgcgaat ccggcgtacc ggatcgattc acgggatgtc ggtcaggtac tgatttcact    2280
ttgactatca gctctgttca gcctgaagat ttggcaattt actactgtca ccaatacttg    2340
agtagccgaa ctttcggcca gggcacgaag ctcgaaatca agggcggagg gggaggttct    2400
ggtggggcg gttctggcgg tggaggaagc caagtacagt tgcaacagcc aggggcggag     2460
gtcgtaaaac ctggggcgtc tgtcaagatg agctgtaaag caagtggata caccttcacc    2520
tcctactata tacattggat taagcaaact ccgggtcagg ggctggaatg ggttggcgtt    2580
atataccccg ggaacgatga tatatcatac aaccaaaaat ttcaaggcaa ggcgactctg    2640
actgccgata agagtagcac aacagcttac atgcagcttt cttccctgac cagcgaagat    2700
tcagcagttt actactgcgc tcgggaagtg cgcctgcgat actttgatgt ctggggtcaa    2760
ggaactacag ttactgtatc aagcagctgct gctgccttttg tcccggtatt tctcccagcc  2820
aaaccgacca cgactcccgc cccgcgcccct ccgacaccccg ctcccaccat cgcctctcaa  2880
cctcttagtc ttcgccccga ggcatgccga cccgccgccg ggggtgctgt tcatacgagg    2940
ggcttggact tcgcttgtga tatttacatt tgggctccgt tggcgggtac gtgcggcgtc    3000
cttttgttgt cactcgttat tacttttgtat tgtaatcaca gaatcgcaa acggggcaga    3060
aagaaactcc tgtatatatt caaacaacca tttatgagac cagtacaaac tactcaagag    3120
gaagatggct gtagctgccg atttccgaaa gaagaagaag gaggatgtga actgcgagtg    3180
aagttttccc gaagcgcaga cgctccggca tatcagcaag gacagaatca gctgtataac    3240
gaactgaatt tgggacgccg cgaggagtat gacgtgcttg ataaacgccg ggggagagaac   3300
ccggaaatgg ggggtaaaacc ccgaagaaag aatccccaag aaggactcta caatgaactc   3360
cagaaggata agatggcgga ggcctactca gaaataggta tgaagggcga acgacgacgg    3420
ggaaaggtc acgatggcct ctaccaaggg ttgagtacgg caaccaaaga tacgtacgat     3480
gcactgcata tgcaggcccct gcctcccaga taataataaa atcgctatcc atcgaagatg   3540
gatgtgtgtt ggttttttgt gtgtggagca acaaatctga ctttgcatgt gcaaacgcct   3600
tcaacaacag cattattcca gaagacacct tcttccccag cccaggtaag ggcagctttg   3660
gtgccttcgc aggctgtttc cttgcttcag gaatggccag ttctgcccca gagctctggt   3720
caatgatgtc taaaactcct ctgattggtg gtctcggcct tatccattgc caccaaaacc   3780
ctcttttttac taagaaacag tgagccttgt tctggcagtc cagagaatga cacgggaaaa  3840
aagcagatga agagaaggtg gcaggagagg gcacgtggcc cagcctcagt ctctccaact    3900
gagttcctgc ctgcctgcct ttgctcagac tgtttgcccc ttactgctct tctaggcctc   3960
attctaagcc ccttctccaa gttgcctctc cttatttctc cctgtctgcc aaaaaatctt    4020
tcccagctca ctaagtcagt ctcacgcagt cactcattaa cccaccaatc actgattgtg   4080
ccggcacatg aatgcaccag gtgttgaagt ggaggaatta aaaagtcaga tgagggggtgt   4140
gcccagagga agcaccattc tagttggggg agcccatctg tcagctggga aaagtccaaa    4200
taacttcaga ttggaatgtg ttttaactca gggttgagaa aacagctacc ttcaggacaa    4260
aagtcaggga agggctctct gaaagaaatgc tacttgaaga taccagcccct accaagggca  4320
gggagaggac cctatagagg cctgggacag gagctcaatg agaaagg                 4367

SEQ ID NO: 353        moltype = AA  length = 484
FEATURE               Location/Qualifiers
REGION                1..484
                      note = Synthetic
source                1..484
                      mol_type = protein
                      organism = synthetic construct
SEQUENCE: 353
DIQMTQTTSS LSASLGDRVT ISCRASQDIS KYLNWYQQKP DGTVKLLIYH TSRLHSGVPS   60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSAAAFV PVFLPAKPTT TPAPRPPTPA PTIASQPLSL RPEACRPAAG GAVHTRGLDF  300
ACDIYIWAPL AGTCGVLLLS LVITLYCNHR NRSKRSRLLH SDYMNMTPRR PGPTRKHYQP  360
YAPPRDFAAY RSRVKFSRSA DAPAYQQGQN QLYNELNLGR REEYDVLDKR RGRDPEMGGK  420
PRRKNPQEGL YNELQKDKMA EAYSEIGMKG ERRRGKGHDG LYQGLSTATK DTYDALHMQA  480
LPPR                                                               484

SEQ ID NO: 354        moltype = AA  length = 487
FEATURE               Location/Qualifiers
REGION                1..487
                      note = Synthetic
source                1..487
                      mol_type = protein
                      organism = synthetic construct
SEQUENCE: 354
QVQLVQSGAE VKKPGASVKV SCKASGYTFT NYGMNWVRQA PGQGLKWMGW INTYTGEPTY   60
ADAFKGRVTM TRDTSISTAY MELSRLRSDD TAVYYCARDY GDYVMDYWGQ GTTVTVSSGG  120
GGSGGGGSGG GGSGDIVMTQ SPDSLAVSLG ERATINCRAS KSVSTSGYSF MHWYQQKPGQ  180
PPKLLIYLAS NLESGVPDRF SGSGSGTDFT LTISSLQAED VAVYYCQHSR EVPWTFGQGT  240
KVEIKSAAAF VPVFLPAKPT TTPAPRPPTP APTIASQPLS LRPEACRPAA GGAVHTRGLD  300
FACDIYIWAP LAGTCGVLLL SLVITLYCNH RNRKRGRKKL LYIFKQPFMR PVQTTQEEDG  360
CSCRFPEEEE GGCELRVKFS RSADAPAYQQ GQNQLYNELN LGRREEYDVL DKRRGRDPEM  420
GGKPRRKNPQ EGLYNELQKD KMAEAYSEIG MKGERRRGKG HDGLYQGLST ATKDTYDALH  480
```

```
MQALPPR                                                                    487

SEQ ID NO: 355          moltype = AA  length = 487
FEATURE                 Location/Qualifiers
REGION                  1..487
                        note = Synthetic
source                  1..487
                        mol_type = protein
                        organism = synthetic construct
SEQUENCE: 355
QVQLVQSGAE LKKPGASVKV SCKASGNTLT NYVIHWVRQA PGQRLEWMGY ILPYNDLTKY    60
SQKFQGRVTI TRDKSASTAY MELSSLRSED TAVYYCTRWD WDGFFDPWGQ GTTVTVSSGG   120
GGSGGGGSGG GGSEIVMTQS PATLSVSPGE RASISCRASQ SLVHSNGNTH LHWYQQRPGQ   180
APRLLIYSVS NRFSEVPARF SGSGSGTDFT LTISSVESED FAVYYCSQTS HIPYTFGGGT   240
KLEIKSAAAF VPVFLPAKPT TTPAPRPPTP APTIASQPLS LRPEACRPAA GGAVHTRGLD   300
FACDIYIWAP LAGTCGVLLL SLVITLYCNH RNRKRGRKKL LYIFKQPFMR PVQTTQEEDG   360
CSCRFPEEEE GGCELRVKFS RSADAPAYQQ GQNQLYNELN LGRREEYDVL DKRRGRDPEM   420
GGKPRRKNPQ EGLYNELQKD KMAEAYSEIG MKGERRRGKG HDGLYQGLST ATKDTYDALH   480
MQALPPR                                                             487

SEQ ID NO: 356          moltype = AA  length = 486
FEATURE                 Location/Qualifiers
REGION                  1..486
                        note = Synthetic
source                  1..486
                        mol_type = protein
                        organism = synthetic construct
SEQUENCE: 356
EIVLTQSPGS LAVSPGERVT MSCKSSQSVF FSSSQKNYLA WYQQIPGQSP RLLIYWASTR    60
ESGVPDRFTG SGSGTDFTLT ISSVQPEDLA IYYCHQYLSS RTFGQGTKLE IKGGGGGSGG   120
GGSGGGGSQV QLQQPGAEVV KPGASVKMSC KASGYTFTSY YIHWIKQTPG QGLEWVGVIY   180
PGNDDISYNQ KFQGKATLTA DKSSTTAYMQ LSSLTSEDSA VYYCAREVRL RYFDVWGQGT   240
TVTVSSSAAA FVPVFLPAKP TTTPAPRPPT PAPTIASQPL SLRPEACRPA AGGAVHTRGL   300
DFACDIYIWA PLAGTCGVLL LSLVITLYCN HRNRSKRSRL HSDYMNMTP RRPGPTRKHY   360
QPYAPPRDFA AYRSRVKFSR SADAPAYQQG QNQLYNELNL GRREEYDVLD KRRGRDPEMG   420
GKPRRKNPQE GLYNELQKDK MAEAYSEIGM KGERRRGKGH DGLYQGLSTA TKDTYDALHM   480
QALPPR                                                              486

SEQ ID NO: 357          moltype = AA  length = 488
FEATURE                 Location/Qualifiers
REGION                  1..488
                        note = Synthetic
source                  1..488
                        mol_type = protein
                        organism = synthetic construct
SEQUENCE: 357
EIVLTQSPGS LAVSPGERVT MSCKSSQSVF FSSSQKNYLA WYQQIPGQSP RLLIYWASTR    60
ESGVPDRFTG SGSGTDFTLT ISSVQPEDLA IYYCHQYLSS RTFGQGTKLE IKGGGGGSGG   120
GGSGGGGSQV QLQQPGAEVV KPGASVKMSC KASGYTFTSY YIHWIKQTPG QGLEWVGVIY   180
PGNDDISYNQ KFQGKATLTA DKSSTTAYMQ LSSLTSEDSA VYYCAREVRL RYFDVWGQGT   240
TVTVSSSAAA FVPVFLPAKP TTTPAPRPPT PAPTIASQPL SLRPEACRPA AGGAVHTRGL   300
DFACDIYIWA PLAGTCGVLL LSLVITLYCN HRNRKRGRKK LLYIFKQPFM RPVQTTQEED   360
GCSCRFPEEE EGGCELRVKF SRSADAPAYQ GQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPR                                                            488

SEQ ID NO: 358          moltype = AA  length = 489
FEATURE                 Location/Qualifiers
REGION                  1..489
                        note = Synthetic
source                  1..489
                        mol_type = protein
                        organism = synthetic construct
SEQUENCE: 358
QVQLVESGGG VVQPGRSLRL SCAASGFTFS SYGMHWVRQA PGKGLEWVAV IWDDGSNKYY    60
VDSVKGRFTI SRDNSKNTLY LQMNSLRAED TAVYYCARDD YYGSGSFNSY YGTDVWGQGT   120
TVTVSSGGGG SGGGGSGGGG SEIVLTQSPA TLSLSPGERA TLSCRASQSV SIYLAWYQQK   180
PGQAPRLLIY DASNRATGIP ARFSGSGSGT DFTLTISSLE PEDFAVYYCQ QRSNWPPFTF   240
GPGTKVDIKS AAAFVPVFLP AKPTTTPAPR PPTPAPTIAS QPLSLRPEAC RPAAGGAVHT   300
RGLDFACDIY IWAPLAGTCG VLLLSLVITL YCNHRNRSKR SRLHSDYMN MTPRRPGPTR   360
KHYQPYAPPR DFAAYRSRVK FSRSADAPAY QQGQNQLYNE LNLGRREEYD VLDKRRGRDP   420
EMGGKPRRKN PQEGLYNELQ KDKMAEAYSE IGMKGERRRG KGHDGLYQGL STATKDTYDA   480
LHMQALPPR                                                           489

SEQ ID NO: 359          moltype = AA  length = 491
FEATURE                 Location/Qualifiers
REGION                  1..491
                        note = Synthetic
source                  1..491
```

```
                    mol_type = protein
                    organism = synthetic construct
SEQUENCE: 359
QVQLVESGGG VVQPGRSLRL SCAASGFTFS SYGMHWVRQA PGKGLEWVAV IWDDGSNKYY    60
VDSVKGRFTI SRDNSKNTLY LQMNSLRAED TAVYYCARDD YYGSGSFNSY YGTDVWGQGT   120
TVTVSSGGGG SGGGGSGGGG SEIVLTQSPA TLSLSPGERA TLSCRASQSV SIYLAWYQQK   180
PGQAPRLLIY DASNRATGIP ARFSGSGSGT DFTLTISSLE PEDFAVYYCQ QRSNWPPFTF   240
GPGTKVDIKS AAAFVPVFLP AKPTTTPAPR PPTPAPTIAS QPLSLRPEAC RPAAGGAVHT   300
RGLDFACDIY IWAPLAGTCG VLLLSLVITL YCNHRNRKRG RKKLLYIFKQ PPMRPVQTTQ   360
EEDGCSCRFP EEEEGGCELR VKFSRSADAP AYQQGQNQLY NELNLGRREE YDVLDKRRGR   420
DPEMGGKPRR KNPQEGLYNE LQKDKMAEAY SEIGMKGERR RGKGHDGLYQ GLSTATKDTY   480
DALHMQALPP R                                                       491

SEQ ID NO: 360         moltype = DNA  length = 20
FEATURE                Location/Qualifiers
misc_feature           1..20
                       note = Synthetic
source                 1..20
                       mol_type = other DNA
                       organism = synthetic construct
SEQUENCE: 360
ctgaacgtgc ggtgggatcg                                               20

SEQ ID NO: 361         moltype = DNA  length = 10
FEATURE                Location/Qualifiers
misc_feature           1..10
                       note = Synthetic
source                 1..10
                       mol_type = other DNA
                       organism = synthetic construct
SEQUENCE: 361
ctgaacgtgc                                                          10

SEQ ID NO: 362         moltype = DNA  length = 15
FEATURE                Location/Qualifiers
misc_feature           1..15
                       note = Synthetic
source                 1..15
                       mol_type = other DNA
                       organism = synthetic construct
SEQUENCE: 362
ctgaacgtgg gatcg                                                    15

SEQ ID NO: 363         moltype = DNA  length = 21
FEATURE                Location/Qualifiers
misc_feature           1..21
                       note = Synthetic
source                 1..21
                       mol_type = other DNA
                       organism = synthetic construct
SEQUENCE: 363
ctgaacgtgc cggtgggatc g                                             21

SEQ ID NO: 364         moltype = DNA  length = 19
FEATURE                Location/Qualifiers
misc_feature           1..19
                       note = Synthetic
source                 1..19
                       mol_type = other DNA
                       organism = synthetic construct
SEQUENCE: 364
ctgaacgtgg gtgggatcg                                                19

SEQ ID NO: 365         moltype = DNA  length = 10
FEATURE                Location/Qualifiers
misc_feature           1..10
                       note = Synthetic
source                 1..10
                       mol_type = other DNA
                       organism = synthetic construct
SEQUENCE: 365
ggtgggatcg                                                          10

SEQ ID NO: 366         moltype = DNA  length = 18
FEATURE                Location/Qualifiers
misc_feature           1..18
                       note = Synthetic
source                 1..18
                       mol_type = other DNA
```

```
                        organism = synthetic construct
SEQUENCE: 366
ctgaacgtgg tgggatcg                                                 18

SEQ ID NO: 367          moltype = DNA  length = 16
FEATURE                 Location/Qualifiers
misc_feature            1..16
                        note = Synthetic
source                  1..16
                        mol_type = other DNA
                        organism = synthetic construct
SEQUENCE: 367
ctgaacggtg ggatcg                                                   16

SEQ ID NO: 368          moltype = DNA  length = 12
FEATURE                 Location/Qualifiers
misc_feature            1..12
                        note = Synthetic
source                  1..12
                        mol_type = other DNA
                        organism = synthetic construct
SEQUENCE: 368
ctggtgggat cg                                                       12

SEQ ID NO: 369          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 369
ctgaacgtgc aggtgggatc g                                             21

SEQ ID NO: 370          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 370
ctgaacgtgc gtggatcg                                                 18

SEQ ID NO: 371          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 371
gatacgcgtc cacaggacga                                               20

SEQ ID NO: 372          moltype = DNA  length = 19
FEATURE                 Location/Qualifiers
misc_feature            1..19
                        note = Synthetic
source                  1..19
                        mol_type = other DNA
                        organism = synthetic construct
SEQUENCE: 372
gatacgcgtc acaggacga                                                19

SEQ ID NO: 373          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 373
gatacgcgtc ccacaggacg a                                             21

SEQ ID NO: 374          moltype = DNA  length = 18
FEATURE                 Location/Qualifiers
misc_feature            1..18
                        note = Synthetic
source                  1..18
```

```
                        mol_type = other DNA
                        organism = synthetic construct
SEQUENCE: 374
gatacgcgtc caggacga                                                            18

SEQ ID NO: 375          moltype = DNA  length = 16
FEATURE                 Location/Qualifiers
misc_feature            1..16
                        note = Synthetic
source                  1..16
                        mol_type = other DNA
                        organism = synthetic construct
SEQUENCE: 375
gatacgcaca ggacga                                                              16

SEQ ID NO: 376          moltype = DNA  length = 14
FEATURE                 Location/Qualifiers
misc_feature            1..14
                        note = Synthetic
source                  1..14
                        mol_type = other DNA
                        organism = synthetic construct
SEQUENCE: 376
gatacacagg acga                                                                14

SEQ ID NO: 377          moltype = DNA  length = 13
FEATURE                 Location/Qualifiers
misc_feature            1..13
                        note = Synthetic
source                  1..13
                        mol_type = other DNA
                        organism = synthetic construct
SEQUENCE: 377
gatacgcgtc cga                                                                 13

SEQ ID NO: 378          moltype = DNA  length = 12
FEATURE                 Location/Qualifiers
misc_feature            1..12
                        note = Synthetic
source                  1..12
                        mol_type = other DNA
                        organism = synthetic construct
SEQUENCE: 378
gatacgcgtc ga                                                                  12

SEQ ID NO: 379          moltype = DNA  length = 17
FEATURE                 Location/Qualifiers
misc_feature            1..17
                        note = Synthetic
source                  1..17
                        mol_type = other DNA
                        organism = synthetic construct
SEQUENCE: 379
gatacgcgtc aggacga                                                             17

SEQ ID NO: 380          moltype = DNA  length = 12
FEATURE                 Location/Qualifiers
misc_feature            1..12
                        note = Synthetic
source                  1..12
                        mol_type = other DNA
                        organism = synthetic construct
SEQUENCE: 380
gatacaggac ga                                                                  12

SEQ ID NO: 381          moltype = DNA  length = 17
FEATURE                 Location/Qualifiers
misc_feature            1..17
                        note = Synthetic
source                  1..17
                        mol_type = other DNA
                        organism = synthetic construct
SEQUENCE: 381
gatacgccac aggacga                                                             17

SEQ ID NO: 382          moltype = DNA  length = 10
FEATURE                 Location/Qualifiers
misc_feature            1..10
                        note = Synthetic
```

```
source                    1..10
                          mol_type = other DNA
                          organism = synthetic construct
SEQUENCE: 382
gatacgcgtc                                                              10

SEQ ID NO: 383            moltype = DNA   length = 21
FEATURE                   Location/Qualifiers
misc_feature              1..21
                          note = Synthetic
source                    1..21
                          mol_type = other DNA
                          organism = synthetic construct
SEQUENCE: 383
gatacgcgtc acacaggacg a                                                 21

SEQ ID NO: 384            moltype = DNA   length = 19
FEATURE                   Location/Qualifiers
misc_feature              1..19
                          note = Synthetic
source                    1..19
                          mol_type = other DNA
                          organism = synthetic construct
SEQUENCE: 384
gatacgctgc acaggacga                                                    19

SEQ ID NO: 385            moltype = DNA   length = 14
FEATURE                   Location/Qualifiers
misc_feature              1..14
                          note = Synthetic
source                    1..14
                          mol_type = other DNA
                          organism = synthetic construct
SEQUENCE: 385
gatacgcagg acga                                                         14

SEQ ID NO: 386            moltype = DNA   length = 13
FEATURE                   Location/Qualifiers
misc_feature              1..13
                          note = Synthetic
source                    1..13
                          mol_type = other DNA
                          organism = synthetic construct
SEQUENCE: 386
acgcacagga cga                                                          13

SEQ ID NO: 387            moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 387
atgacgagca gcggggtctg                                                   20

SEQ ID NO: 388            moltype = DNA   length = 21
FEATURE                   Location/Qualifiers
misc_feature              1..21
                          note = Synthetic
source                    1..21
                          mol_type = other DNA
                          organism = synthetic construct
SEQUENCE: 388
atgacgagca agcggggtct g                                                 21

SEQ ID NO: 389            moltype = DNA   length = 17
FEATURE                   Location/Qualifiers
misc_feature              1..17
                          note = Synthetic
source                    1..17
                          mol_type = other DNA
                          organism = synthetic construct
SEQUENCE: 389
atgacgagcg gggtctg                                                      17

SEQ ID NO: 390            moltype = DNA   length = 18
FEATURE                   Location/Qualifiers
misc_feature              1..18
```

```
                        note = Synthetic
source                  1..18
                        mol_type = other DNA
                        organism = synthetic construct
SEQUENCE: 390
atgacgaagc ggggtctg                                                 18

SEQ ID NO: 391          moltype = DNA   length = 14
FEATURE                 Location/Qualifiers
misc_feature            1..14
                        note = Synthetic
source                  1..14
                        mol_type = other DNA
                        organism = synthetic construct
SEQUENCE: 391
atgagcgggg tctg                                                     14

SEQ ID NO: 392          moltype = DNA   length = 22
FEATURE                 Location/Qualifiers
misc_feature            1..22
                        note = Synthetic
source                  1..22
                        mol_type = other DNA
                        organism = synthetic construct
SEQUENCE: 392
atgacgagca aagcggggtc tg                                            22

SEQ ID NO: 393          moltype = DNA   length = 13
FEATURE                 Location/Qualifiers
misc_feature            1..13
                        note = Synthetic
source                  1..13
                        mol_type = other DNA
                        organism = synthetic construct
SEQUENCE: 393
atgacggggt ctg                                                      13

SEQ ID NO: 394          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 394
catgacttta ttctggaaga                                               20

SEQ ID NO: 395          moltype = DNA   length = 13
FEATURE                 Location/Qualifiers
misc_feature            1..13
                        note = Synthetic
source                  1..13
                        mol_type = other DNA
                        organism = synthetic construct
SEQUENCE: 395
catgactgga aga                                                      13

SEQ ID NO: 396          moltype = DNA   length = 16
FEATURE                 Location/Qualifiers
misc_feature            1..16
                        note = Synthetic
source                  1..16
                        mol_type = other DNA
                        organism = synthetic construct
SEQUENCE: 396
catgacttct ggaaga                                                   16

SEQ ID NO: 397          moltype = DNA   length = 17
FEATURE                 Location/Qualifiers
misc_feature            1..17
                        note = Synthetic
source                  1..17
                        mol_type = other DNA
                        organism = synthetic construct
SEQUENCE: 397
catgactttc tggaaga                                                  17

SEQ ID NO: 398          moltype = DNA   length = 21
FEATURE                 Location/Qualifiers
```

```
                        -continued misc_feature            1..21
                        note = Synthetic
source                  1..21
                        mol_type = other DNA
                        organism = synthetic construct
SEQUENCE: 398
catgacttta tttctggaag a                                              21

SEQ ID NO: 399          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 399
catgacttta attctggaag a                                              21

SEQ ID NO: 400          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 400
catgactttt ctggaaga                                                  18

SEQ ID NO: 401          moltype = DNA   length = 11
FEATURE                 Location/Qualifiers
misc_feature            1..11
                        note = Synthetic
source                  1..11
                        mol_type = other DNA
                        organism = synthetic construct
SEQUENCE: 401
catctggaag a                                                         11

SEQ ID NO: 402          moltype = DNA   length = 19
FEATURE                 Location/Qualifiers
misc_feature            1..19
                        note = Synthetic
source                  1..19
                        mol_type = other DNA
                        organism = synthetic construct
SEQUENCE: 402
catgactttt tctggaaga                                                 19

SEQ ID NO: 403          moltype = DNA   length = 19
FEATURE                 Location/Qualifiers
misc_feature            1..19
                        note = Synthetic
source                  1..19
                        mol_type = other DNA
                        organism = synthetic construct
SEQUENCE: 403
catgacttta tctggaaga                                                 19

SEQ ID NO: 404          moltype = DNA   length = 13
FEATURE                 Location/Qualifiers
misc_feature            1..13
                        note = Synthetic
source                  1..13
                        mol_type = other DNA
                        organism = synthetic construct
SEQUENCE: 404
catgacttta aga                                                       13

SEQ ID NO: 405          moltype = DNA   length = 10
FEATURE                 Location/Qualifiers
misc_feature            1..10
                        note = Synthetic
source                  1..10
                        mol_type = other DNA
                        organism = synthetic construct
SEQUENCE: 405
ttctggaaga                                                           10

SEQ ID NO: 406          moltype = DNA   length = 18
```

```
FEATURE                 Location/Qualifiers
misc_feature            1..18
                        note = Synthetic
source                  1..18
                        mol_type = other DNA
                        organism = synthetic construct
SEQUENCE: 406
catgactttta ctggaaga                                                       18

SEQ ID NO: 407          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 407
gtcctattac agctggggca                                                      20

SEQ ID NO: 408          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 408
gtcctattag ctggggca                                                        18

SEQ ID NO: 409          moltype = DNA  length = 19
FEATURE                 Location/Qualifiers
misc_feature            1..19
                        note = Synthetic
source                  1..19
                        mol_type = other DNA
                        organism = synthetic construct
SEQUENCE: 409
gtcctattaa gctggggca                                                       19

SEQ ID NO: 410          moltype = DNA  length = 17
FEATURE                 Location/Qualifiers
misc_feature            1..17
                        note = Synthetic
source                  1..17
                        mol_type = other DNA
                        organism = synthetic construct
SEQUENCE: 410
gtcctatagc tggggca                                                         17

SEQ ID NO: 411          moltype = DNA  length = 16
FEATURE                 Location/Qualifiers
misc_feature            1..16
                        note = Synthetic
source                  1..16
                        mol_type = other DNA
                        organism = synthetic construct
SEQUENCE: 411
gtcctaagct ggggca                                                          16

SEQ ID NO: 412          moltype = DNA  length = 15
FEATURE                 Location/Qualifiers
misc_feature            1..15
                        note = Synthetic
source                  1..15
                        mol_type = other DNA
                        organism = synthetic construct
SEQUENCE: 412
gtcctagctg gggca                                                           15

SEQ ID NO: 413          moltype = DNA  length = 17
FEATURE                 Location/Qualifiers
misc_feature            1..17
                        note = Synthetic
source                  1..17
                        mol_type = other DNA
                        organism = synthetic construct
SEQUENCE: 413
gtcctattac tggggca                                                         17
```

| | | |
|---|---|---|
| SEQ ID NO: 414<br>FEATURE<br>misc_feature<br>source | moltype = DNA   length = 14<br>Location/Qualifiers<br>1..14<br>note = Synthetic<br>1..14<br>mol_type = other DNA<br>organism = synthetic construct | |
| SEQUENCE: 414<br>gtccagctgg ggca | | 14 |
| SEQ ID NO: 415<br>FEATURE<br>misc_feature<br>source | moltype = DNA   length = 21<br>Location/Qualifiers<br>1..21<br>note = Synthetic<br>1..21<br>mol_type = other DNA<br>organism = synthetic construct | |
| SEQUENCE: 415<br>gtcctattac cagctggggc a | | 21 |
| SEQ ID NO: 416<br>FEATURE<br>misc_feature<br>source | moltype = DNA   length = 17<br>Location/Qualifiers<br>1..17<br>note = Synthetic<br>1..17<br>mol_type = other DNA<br>organism = synthetic construct | |
| SEQUENCE: 416<br>gtcctattgc tggggca | | 17 |
| SEQ ID NO: 417<br>FEATURE<br>misc_feature<br>source | moltype = DNA   length = 19<br>Location/Qualifiers<br>1..19<br>note = Synthetic<br>1..19<br>mol_type = other DNA<br>organism = synthetic construct | |
| SEQUENCE: 417<br>gtcctattac gctggggca | | 19 |
| SEQ ID NO: 418<br>FEATURE<br>misc_feature<br>source | moltype = DNA   length = 11<br>Location/Qualifiers<br>1..11<br>note = Synthetic<br>1..11<br>mol_type = other DNA<br>organism = synthetic construct | |
| SEQUENCE: 418<br>gtcctggggc a | | 11 |
| SEQ ID NO: 419<br>FEATURE<br>misc_feature<br>source | moltype = DNA   length = 20<br>Location/Qualifiers<br>1..20<br>note = Synthetic<br>1..20<br>mol_type = other DNA<br>organism = synthetic construct | |
| SEQUENCE: 419<br>acttgttagc cccagggcca | | 20 |
| SEQ ID NO: 420<br>FEATURE<br>misc_feature<br>source | moltype = DNA   length = 18<br>Location/Qualifiers<br>1..18<br>note = Synthetic<br>1..18<br>mol_type = other DNA<br>organism = synthetic construct | |
| SEQUENCE: 420<br>acttgttagc cagggcca | | 18 |
| SEQ ID NO: 421<br>FEATURE<br>misc_feature<br>source | moltype = DNA   length = 19<br>Location/Qualifiers<br>1..19<br>note = Synthetic<br>1..19<br>mol_type = other DNA<br>organism = synthetic construct | |
| SEQUENCE: 421<br>acttgttagc ccagggcca | | 19 |

| | | |
|---|---|---|
| SEQ ID NO: 422 | moltype = DNA   length = 17 | |
| FEATURE | Location/Qualifiers | |
| misc_feature | 1..17 | |
| | note = Synthetic | |
| source | 1..17 | |
| | mol_type = other DNA | |
| | organism = synthetic construct | |
| SEQUENCE: 422 | | |
| acttgttagc agggcca | | 17 |
| | | |
| SEQ ID NO: 423 | moltype = DNA   length = 12 | |
| FEATURE | Location/Qualifiers | |
| misc_feature | 1..12 | |
| | note = Synthetic | |
| source | 1..12 | |
| | mol_type = other DNA | |
| | organism = synthetic construct | |
| SEQUENCE: 423 | | |
| acttgttagc ca | | 12 |
| | | |
| SEQ ID NO: 424 | moltype = DNA   length = 14 | |
| FEATURE | Location/Qualifiers | |
| misc_feature | 1..14 | |
| | note = Synthetic | |
| source | 1..14 | |
| | mol_type = other DNA | |
| | organism = synthetic construct | |
| SEQUENCE: 424 | | |
| acttgttagg gcca | | 14 |
| | | |
| SEQ ID NO: 425 | moltype = DNA   length = 21 | |
| FEATURE | Location/Qualifiers | |
| misc_feature | 1..21 | |
| | note = Synthetic | |
| source | 1..21 | |
| | mol_type = other DNA | |
| | organism = synthetic construct | |
| SEQUENCE: 425 | | |
| acttgttagc ccccagggcc a | | 21 |
| | | |
| SEQ ID NO: 426 | moltype = DNA   length = 17 | |
| FEATURE | Location/Qualifiers | |
| misc_feature | 1..17 | |
| | note = Synthetic | |
| source | 1..17 | |
| | mol_type = other DNA | |
| | organism = synthetic construct | |
| SEQUENCE: 426 | | |
| acttgttccc agggcca | | 17 |
| | | |
| SEQ ID NO: 427 | moltype = DNA   length = 10 | |
| FEATURE | Location/Qualifiers | |
| misc_feature | 1..10 | |
| | note = Synthetic | |
| source | 1..10 | |
| | mol_type = other DNA | |
| | organism = synthetic construct | |
| SEQUENCE: 427 | | |
| cccagggcca | | 10 |
| | | |
| SEQ ID NO: 428 | moltype = DNA   length = 18 | |
| FEATURE | Location/Qualifiers | |
| misc_feature | 1..18 | |
| | note = Synthetic | |
| source | 1..18 | |
| | mol_type = other DNA | |
| | organism = synthetic construct | |
| SEQUENCE: 428 | | |
| acttgttacc cagggcca | | 18 |
| | | |
| SEQ ID NO: 429 | moltype = DNA   length = 15 | |
| FEATURE | Location/Qualifiers | |
| misc_feature | 1..15 | |
| | note = Synthetic | |
| source | 1..15 | |
| | mol_type = other DNA | |
| | organism = synthetic construct | |
| SEQUENCE: 429 | | |

```
acttgcccag ggcca                                                    15

SEQ ID NO: 430          moltype = DNA  length = 16
FEATURE                 Location/Qualifiers
misc_feature            1..16
                        note = Synthetic
source                  1..16
                        mol_type = other DNA
                        organism = synthetic construct
SEQUENCE: 430
acttgtccca gggcca                                                   16

SEQ ID NO: 431          moltype = DNA  length = 10
FEATURE                 Location/Qualifiers
misc_feature            1..10
                        note = Synthetic
source                  1..10
                        mol_type = other DNA
                        organism = synthetic construct
SEQUENCE: 431
accagggcca                                                          10

SEQ ID NO: 432          moltype = DNA  length = 13
FEATURE                 Location/Qualifiers
misc_feature            1..13
                        note = Synthetic
source                  1..13
                        mol_type = other DNA
                        organism = synthetic construct
SEQUENCE: 432
acttgcaggg cca                                                      13

SEQ ID NO: 433          moltype = DNA  length = 13
FEATURE                 Location/Qualifiers
misc_feature            1..13
                        note = Synthetic
source                  1..13
                        mol_type = other DNA
                        organism = synthetic construct
SEQUENCE: 433
acttgttagc cca                                                      13

SEQ ID NO: 434          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 434
aactgcctct atatggtgtg                                               20

SEQ ID NO: 435          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 435
aactgcctct tatatggtgt g                                             21

SEQ ID NO: 436          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 436
aactgcctat atggtgtg                                                 18

SEQ ID NO: 437          moltype = DNA  length = 18
FEATURE                 Location/Qualifiers
misc_feature            1..18
                        note = Synthetic
source                  1..18
                        mol_type = other DNA
                        organism = synthetic construct
```

```
SEQUENCE: 437
aactgcctct atggtgtg                                                    18

SEQ ID NO: 438         moltype = DNA  length = 19
FEATURE                Location/Qualifiers
misc_feature           1..19
                       note = Synthetic
source                 1..19
                       mol_type = other DNA
                       organism = synthetic construct
SEQUENCE: 438
aactgcctca tatggtgtg                                                   19

SEQ ID NO: 439         moltype = DNA  length = 16
FEATURE                Location/Qualifiers
misc_feature           1..16
                       note = Synthetic
source                 1..16
                       mol_type = other DNA
                       organism = synthetic construct
SEQUENCE: 439
aactgtatat ggtgtg                                                      16

SEQ ID NO: 440         moltype = DNA  length = 17
FEATURE                Location/Qualifiers
misc_feature           1..17
                       note = Synthetic
source                 1..17
                       mol_type = other DNA
                       organism = synthetic construct
SEQUENCE: 440
aactgctata tggtgtg                                                     17

SEQ ID NO: 441         moltype = DNA  length = 14
FEATURE                Location/Qualifiers
misc_feature           1..14
                       note = Synthetic
source                 1..14
                       mol_type = other DNA
                       organism = synthetic construct
SEQUENCE: 441
aactatatgg tgtg                                                        14

SEQ ID NO: 442         moltype = DNA  length = 19
FEATURE                Location/Qualifiers
misc_feature           1..19
                       note = Synthetic
source                 1..19
                       mol_type = other DNA
                       organism = synthetic construct
SEQUENCE: 442
aactgcctta tatggtgtg                                                   19

SEQ ID NO: 443         moltype = DNA  length = 10
FEATURE                Location/Qualifiers
misc_feature           1..10
                       note = Synthetic
source                 1..10
                       mol_type = other DNA
                       organism = synthetic construct
SEQUENCE: 443
aactgcctct                                                             10

SEQ ID NO: 444         moltype = DNA  length = 11
FEATURE                Location/Qualifiers
misc_feature           1..11
                       note = Synthetic
source                 1..11
                       mol_type = other DNA
                       organism = synthetic construct
SEQUENCE: 444
tatatggtgt g                                                           11

SEQ ID NO: 445         moltype = DNA  length = 11
FEATURE                Location/Qualifiers
misc_feature           1..11
                       note = Synthetic
source                 1..11
                       mol_type = other DNA
```

```
                           organism = synthetic construct
SEQUENCE: 445
aactgcctct a                                                              11

SEQ ID NO: 446             moltype = DNA   length = 19
FEATURE                    Location/Qualifiers
misc_feature               1..19
                           note = Synthetic
source                     1..19
                           mol_type = other DNA
                           organism = synthetic construct
SEQUENCE: 446
aactgcctct tatggtgtg                                                      19

SEQ ID NO: 447             moltype = DNA   length = 10
FEATURE                    Location/Qualifiers
misc_feature               1..10
                           note = Synthetic
source                     1..10
                           mol_type = other DNA
                           organism = synthetic construct
SEQUENCE: 447
aactggtgtg                                                                10

SEQ ID NO: 448             moltype = DNA   length = 20
FEATURE                    Location/Qualifiers
misc_feature               1..20
                           note = Synthetic
source                     1..20
                           mol_type = other DNA
                           organism = synthetic construct
SEQUENCE: 448
ttctggttgt cacaggtgga                                                     20

SEQ ID NO: 449             moltype = DNA   length = 21
FEATURE                    Location/Qualifiers
misc_feature               1..21
                           note = Synthetic
source                     1..21
                           mol_type = other DNA
                           organism = synthetic construct
SEQUENCE: 449
ttctggttgt tcacaggtgg a                                                   21

SEQ ID NO: 450             moltype = DNA   length = 10
FEATURE                    Location/Qualifiers
misc_feature               1..10
                           note = Synthetic
source                     1..10
                           mol_type = other DNA
                           organism = synthetic construct
SEQUENCE: 450
ttctggtgga                                                                10

SEQ ID NO: 451             moltype = DNA   length = 10
FEATURE                    Location/Qualifiers
misc_feature               1..10
                           note = Synthetic
source                     1..10
                           mol_type = other DNA
                           organism = synthetic construct
SEQUENCE: 451
ttcaggtgga                                                                10

SEQ ID NO: 452             moltype = DNA   length = 18
FEATURE                    Location/Qualifiers
misc_feature               1..18
                           note = Synthetic
source                     1..18
                           mol_type = other DNA
                           organism = synthetic construct
SEQUENCE: 452
ttctggttca caggtgga                                                       18

SEQ ID NO: 453             moltype = DNA   length = 22
FEATURE                    Location/Qualifiers
misc_feature               1..22
                           note = Synthetic
source                     1..22
```

```
                              mol_type = other DNA
                              organism = synthetic construct
SEQUENCE: 453
ttctggttgt ttcacaggtg ga                                              22

SEQ ID NO: 454        moltype = DNA  length = 11
FEATURE               Location/Qualifiers
misc_feature          1..11
                      note = Synthetic
source                1..11
                      mol_type = other DNA
                      organism = synthetic construct
SEQUENCE: 454
ttctggttgg a                                                          11

SEQ ID NO: 455        moltype = DNA  length = 21
FEATURE               Location/Qualifiers
misc_feature          1..21
                      note = Synthetic
source                1..21
                      mol_type = other DNA
                      organism = synthetic construct
SEQUENCE: 455
ttctggttgt ccacaggtgg a                                               21

SEQ ID NO: 456        moltype = DNA  length = 13
FEATURE               Location/Qualifiers
misc_feature          1..13
                      note = Synthetic
source                1..13
                      mol_type = other DNA
                      organism = synthetic construct
SEQUENCE: 456
ttccacaggt gga                                                        13

SEQ ID NO: 457        moltype = DNA  length = 19
FEATURE               Location/Qualifiers
misc_feature          1..19
                      note = Synthetic
source                1..19
                      mol_type = other DNA
                      organism = synthetic construct
SEQUENCE: 457
ttctggtttc acaggtgga                                                  19

SEQ ID NO: 458        moltype = DNA  length = 19
FEATURE               Location/Qualifiers
misc_feature          1..19
                      note = Synthetic
source                1..19
                      mol_type = other DNA
                      organism = synthetic construct
SEQUENCE: 458
ttctggttgc acaggtgga                                                  19

SEQ ID NO: 459        moltype = DNA  length = 21
FEATURE               Location/Qualifiers
misc_feature          1..21
                      note = Synthetic
source                1..21
                      mol_type = other DNA
                      organism = synthetic construct
SEQUENCE: 459
ttctggttgt acacaggtgg a                                               21

SEQ ID NO: 460        moltype = DNA  length = 10
FEATURE               Location/Qualifiers
misc_feature          1..10
                      note = Synthetic
source                1..10
                      mol_type = other DNA
                      organism = synthetic construct
SEQUENCE: 460
ttctggttga                                                            10

SEQ ID NO: 461        moltype = DNA  length = 19
FEATURE               Location/Qualifiers
misc_feature          1..19
                      note = Synthetic
```

```
                        source              1..19
                                            mol_type = other DNA
                                            organism = synthetic construct
SEQUENCE: 461
ttctggttgt acaggtgga                                                              19

SEQ ID NO: 462          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 462
tgtgagaagc cacaggaagt                                                             20

SEQ ID NO: 463          moltype = DNA   length = 10
FEATURE                 Location/Qualifiers
misc_feature            1..10
                        note = Synthetic
source                  1..10
                        mol_type = other DNA
                        organism = synthetic construct
SEQUENCE: 463
tgtgagaagt                                                                        10

SEQ ID NO: 464          moltype = DNA   length = 19
FEATURE                 Location/Qualifiers
misc_feature            1..19
                        note = Synthetic
source                  1..19
                        mol_type = other DNA
                        organism = synthetic construct
SEQUENCE: 464
tgtgagaagc acaggaagt                                                              19

SEQ ID NO: 465          moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 465
tgtgagaagc ccacaggaag t                                                           21

SEQ ID NO: 466          moltype = DNA   length = 11
FEATURE                 Location/Qualifiers
misc_feature            1..11
                        note = Synthetic
source                  1..11
                        mol_type = other DNA
                        organism = synthetic construct
SEQUENCE: 466
tgtgaggaag t                                                                      11

SEQ ID NO: 467          moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 467
tgtgagaagc caggaagt                                                               18

SEQ ID NO: 468          moltype = DNA   length = 14
FEATURE                 Location/Qualifiers
misc_feature            1..14
                        note = Synthetic
source                  1..14
                        mol_type = other DNA
                        organism = synthetic construct
SEQUENCE: 468
tgtgagaagg aagt                                                                   14

SEQ ID NO: 469          moltype = DNA   length = 10
FEATURE                 Location/Qualifiers
misc_feature            1..10
```

```
                        note = Synthetic
source                  1..10
                        mol_type = other DNA
                        organism = synthetic construct
SEQUENCE: 469
cacaggaagt                                                                 10

SEQ ID NO: 470          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 470
tgtgagaagc acacaggaag t                                                    21

SEQ ID NO: 471          moltype = DNA  length = 17
FEATURE                 Location/Qualifiers
misc_feature            1..17
                        note = Synthetic
source                  1..17
                        mol_type = other DNA
                        organism = synthetic construct
SEQUENCE: 471
tgtgagaagc aggaagt                                                         17

SEQ ID NO: 472          moltype = DNA  length = 14
FEATURE                 Location/Qualifiers
misc_feature            1..14
                        note = Synthetic
source                  1..14
                        mol_type = other DNA
                        organism = synthetic construct
SEQUENCE: 472
tgtgcacagg aagt                                                            14

SEQ ID NO: 473          moltype = DNA  length = 11
FEATURE                 Location/Qualifiers
misc_feature            1..11
                        note = Synthetic
source                  1..11
                        mol_type = other DNA
                        organism = synthetic construct
SEQUENCE: 473
ccacaggaag t                                                               11

SEQ ID NO: 474          moltype = DNA  length = 17
FEATURE                 Location/Qualifiers
misc_feature            1..17
                        note = Synthetic
source                  1..17
                        mol_type = other DNA
                        organism = synthetic construct
SEQUENCE: 474
tgtgagacac aggaagt                                                         17

SEQ ID NO: 475          moltype = DNA  length = 15
FEATURE                 Location/Qualifiers
misc_feature            1..15
                        note = Synthetic
source                  1..15
                        mol_type = other DNA
                        organism = synthetic construct
SEQUENCE: 475
tgtgagacag gaagt                                                           15

SEQ ID NO: 476          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 476
tgtgagaaca caggaagt                                                        18

SEQ ID NO: 477          moltype = DNA  length = 10
FEATURE                 Location/Qualifiers
```

```
misc_feature       1..10
                   note = Synthetic
source             1..10
                   mol_type = other DNA
                   organism = synthetic construct
SEQUENCE: 477
tgtgagaagc                                                                  10

SEQ ID NO: 478     moltype = DNA  length = 22
FEATURE            Location/Qualifiers
misc_feature       1..22
                   note = Synthetic
source             1..22
                   mol_type = other DNA
                   organism = synthetic construct
SEQUENCE: 478
tgtgagaagc cacacaggaa gt                                                    22
```